(12) United States Patent
Caffaro et al.

(10) Patent No.: US 12,344,648 B2
(45) Date of Patent: Jul. 1, 2025

(54) IL-15 CONJUGATES AND USES THEREOF

(71) Applicant: Synthorx, Inc., La Jolla, CA (US)

(72) Inventors: Carolina E. Caffaro, La Jolla, CA (US); Jerod Ptacin, La Jolla, CA (US); Marcos Milla, La Jolla, CA (US)

(73) Assignee: Synthrox, Inc., La Jolla, CA (US)

( * ) Notice: Subject to any disclaimer, the term of this patent is extended or adjusted under 35 U.S.C. 154(b) by 537 days.

(21) Appl. No.: 16/999,638

(22) Filed: Aug. 21, 2020

(65) Prior Publication Data

US 2021/0054040 A1 Feb. 25, 2021

Related U.S. Application Data

(60) Provisional application No. 62/958,177, filed on Jan. 7, 2020, provisional application No. 62/931,663, filed on Nov. 6, 2019, provisional application No. 62/890,741, filed on Aug. 23, 2019.

(51) Int. Cl.
*C07K 14/54* (2006.01)
*C07D 487/12* (2006.01)

(52) U.S. Cl.
CPC ........ *C07K 14/5443* (2013.01); *C07D 487/12* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr. et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Dinh et al. |
| 4,849,513 A | 7/1989 | Smith et al. |
| 4,876,335 A | 10/1989 | Yamane et al. |
| 4,904,582 A | 2/1990 | Tullis |
| 4,910,300 A | 3/1990 | Urdea et al. |
| 4,948,882 A | 8/1990 | Ruth |
| 4,958,013 A | 9/1990 | Letsinger |
| 4,981,957 A | 1/1991 | Lebleu et al. |
| 5,015,733 A | 5/1991 | Smith et al. |
| 5,023,243 A | 6/1991 | Tullis |
| 5,034,506 A | 7/1991 | Summerton et al. |
| 5,082,830 A | 1/1992 | Brakel et al. |
| 5,093,232 A | 3/1992 | Urdea et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |

(Continued)

FOREIGN PATENT DOCUMENTS

| | | |
|---|---|---|
| EP | 0614907 A1 | 9/1994 |
| EP | 0629633 A2 | 12/1994 |

(Continued)

OTHER PUBLICATIONS

Bohringer et al. Synthesis of 5'-deoxy-5'-methylphosphonate linked thymidine oligonucleotides. Tet Lett 34:2723-2726 (1993).

(Continued)

*Primary Examiner* — Brian Gangle
*Assistant Examiner* — Andrea K McCollum
(74) *Attorney, Agent, or Firm* — McNeill PLLC

(57) ABSTRACT

Disclosed herein are interleukin (IL)-15 conjugates and use in the treatment of one or more indications. Also described herein include pharmaceutical compositions and kits comprising one or more of IL-15 conjugates. In some embodiments, at least one amino acid residue in the IL-15 conjugate is replaced by the structure of Formula (I) described herein.

33 Claims, 13 Drawing Sheets

Specification includes a Sequence Listing.

(56) References Cited

U.S. PATENT DOCUMENTS

| | | |
|---|---|---|
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,714,331 A | 2/1998 | Ole Buchardt et al. |
| 5,719,262 A | 2/1998 | Ole Buchardt et al. |
| 5,750,692 A | 5/1998 | Cook et al. |
| 5,763,588 A | 6/1998 | Matteucci et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,525,191 B1 | 2/2003 | Ramasamy |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,955,807 B1 | 10/2005 | Shanafelt et al. |
| 7,034,133 B2 | 4/2006 | Wengel et al. |
| 7,053,207 B2 | 5/2006 | Wengel |
| 7,399,845 B2 | 7/2008 | Seth et al. |
| 7,427,672 B2 | 9/2008 | Imanishi et al. |
| 8,012,465 B2 | 9/2011 | Elias et al. |
| 8,501,805 B2 | 8/2013 | Seth et al. |
| 8,546,556 B2 | 10/2013 | Seth et al. |
| 9,682,934 B2 | 6/2017 | Stafford et al. |
| 9,732,134 B2 | 8/2017 | Gavin et al. |
| 9,840,493 B2 | 12/2017 | Yang et al. |
| 9,861,705 B2 | 1/2018 | Bossard et al. |
| 9,938,516 B2 | 4/2018 | Zimmerman et al. |
| 9,988,619 B2 | 6/2018 | Zimmerman et al. |
| 10,610,571 B2 | 4/2020 | Ptacin et al. |
| 10,851,144 B2 | 12/2020 | Butz et al. |
| 10,960,079 B2 | 3/2021 | Bossard et al. |
| 11,077,195 B2 | 8/2021 | Ptacin et al. |
| 11,622,993 B2 | 4/2023 | Ptacin et al. |
| 11,701,407 B2 | 7/2023 | Ptacin et al. |
| 2004/0171570 A1 | 9/2004 | Allerson et al. |
| 2005/0130923 A1 | 6/2005 | Bhat et al. |
| 2006/0074035 A1 | 4/2006 | Hong et al. |
| 2007/0287831 A1 | 12/2007 | Seth et al. |
| 2008/0039618 A1 | 2/2008 | Allerson et al. |
| 2010/0316595 A1 | 12/2010 | Elias et al. |
| 2017/0260137 A1 | 9/2017 | Stafford et al. |
| 2017/0313753 A1 | 11/2017 | Gavin et al. |
| 2018/0086734 A1 | 3/2018 | Yang et al. |
| 2020/0181220 A1 | 6/2020 | Ptacin et al. |
| 2020/0188484 A1 | 6/2020 | Ptacin et al. |
| 2020/0231644 A1 | 7/2020 | Ptacin et al. |
| 2020/0246467 A1 | 8/2020 | Ptacin et al. |
| 2020/0299349 A1 | 9/2020 | Garcia et al. |
| 2020/0330601 A1 | 10/2020 | Ptacin et al. |
| 2020/0399338 A1 | 12/2020 | Caffaro et al. |
| 2021/0023230 A1 | 1/2021 | Bossard et al. |
| 2021/0024602 A1 | 1/2021 | Sprogøe et al. |
| 2021/0046160 A1 | 2/2021 | Ptacin et al. |
| 2021/0054040 A1 | 2/2021 | Caffaro et al. |
| 2021/0060169 A1 | 3/2021 | Ikeda et al. |
| 2021/0070827 A1 | 3/2021 | Ptacin et al. |
| 2021/0139554 A1 | 5/2021 | Butz et al. |
| 2021/0196796 A1 | 7/2021 | Penaflor-Aspuria et al. |
| 2021/0221863 A1 | 7/2021 | Kang et al. |
| 2021/0338829 A1 | 11/2021 | Caffaro et al. |
| 2022/0016249 A1 | 1/2022 | Ptacin et al. |
| 2022/0016252 A1 | 1/2022 | Abbadessa et al. |
| 2022/0273767 A1 | 9/2022 | Caffaro et al. |
| 2022/0324792 A1 | 10/2022 | Aerni et al. |
| 2023/0277627 A1 | 9/2023 | Caffaro et al. |
| 2023/0302089 A1 | 9/2023 | Caffaro et al. |
| 2023/0416327 A1 | 12/2023 | Caffaro et al. |
| 2024/0082359 A1 | 3/2024 | Ptacin et al. |
| 2024/0226309 A1 | 7/2024 | Abbadessa et al. |
| 2024/0287151 A1 | 8/2024 | Caffaro et al. |

FOREIGN PATENT DOCUMENTS

| | | |
|---|---|---|
| EP | 2382228 B1 | 8/2020 |
| EP | 3280725 B1 | 8/2020 |
| JP | 2019503348 A1 | 2/2019 |
| JP | 2021514974 A1 | 6/2021 |
| RU | 2644671 C2 | 2/2018 |
| WO | 9213869 A1 | 8/1992 |
| WO | 9414226 A1 | 6/1994 |
| WO | 9422890 A1 | 10/1994 |

(56) References Cited

FOREIGN PATENT DOCUMENTS

| | | | | |
|---|---|---|---|---|
| WO | 9735869 | A1 | 10/1997 | |
| WO | 1999014226 | A3 | 8/1999 | |
| WO | 9962923 | A2 | 12/1999 | |
| WO | 0105801 | A1 | 1/2001 | |
| WO | 02070533 | A2 | 9/2002 | |
| WO | 2004007713 | A1 | 1/2004 | |
| WO | 2004106356 | A1 | 12/2004 | |
| WO | 2005021570 | A1 | 3/2005 | |
| WO | 2005026187 | A1 | 3/2005 | |
| WO | 2006049297 | A1 | 5/2006 | |
| WO | 2007015557 | A1 | 2/2007 | |
| WO | 2007066737 | A1 | 6/2007 | |
| WO | 2007090071 | A2 | 8/2007 | |
| WO | 2007134181 | A3 | 1/2008 | |
| WO | 2008101157 | A1 | 8/2008 | |
| WO | 2009006478 | A2 | 1/2009 | |
| WO | 2008150729 | A3 | 3/2009 | |
| WO | 2008154401 | A3 | 3/2009 | |
| WO | 2009123216 | A1 | 10/2009 | |
| WO | 2011043385 | A1 | 4/2011 | |
| WO | 2011139699 | A3 | 7/2013 | |
| WO | 2015021432 | A1 | 2/2015 | |
| WO | WO-2015153753 | A2 * | 10/2015 | ......... A61K 38/2086 |
| WO | 2015157555 | | 3/2016 | |
| WO | 2016115168 | A1 | 7/2016 | |
| WO | 2017106767 | A1 | 6/2017 | |
| WO | WO-2017112528 | A2 * | 6/2017 | ......... A61K 38/2086 |
| WO | 2017223528 | A1 | 12/2017 | |
| WO | 2019014262 | A1 | 1/2019 | |
| WO | 2019014267 | A1 | 1/2019 | |
| WO | 2019028419 | A1 | 2/2019 | |
| WO | WO-2019028425 | A1 * | 2/2019 | ............ A61K 38/00 |
| WO | 2019165453 | A1 | 8/2019 | |
| WO | 2020020783 | A1 | 1/2020 | |
| WO | 2020056066 | A1 | 3/2020 | |
| WO | 2020097325 | A1 | 5/2020 | |
| WO | 2020146221 | A1 | 7/2020 | |
| WO | 2020163532 | A1 | 8/2020 | |
| WO | 2020201095 | A1 | 10/2020 | |
| WO | 2020219943 | A1 | 10/2020 | |
| WO | 2020252418 | A2 | 12/2020 | |
| WO | 2021030374 | A1 | 2/2021 | |
| WO | 2021030483 | A1 | 2/2021 | |
| WO | 2021030602 | A1 | 2/2021 | |
| WO | 2021030706 | A1 | 2/2021 | |
| WO | 2021041206 | A1 | 3/2021 | |
| WO | 2021050554 | A1 | 3/2021 | |
| WO | 2021091986 | A1 | 5/2021 | |
| WO | 2021093633 | A1 | 5/2021 | |
| WO | 2021133839 | A1 | 7/2021 | |
| WO | 2021140416 | A2 | 7/2021 | |
| WO | 2021263026 | A1 | 12/2021 | |
| WO | 2022076853 | A1 | 4/2022 | |
| WO | 2022076859 | A1 | 4/2022 | |
| WO | 2022174101 | A1 | 8/2022 | |
| WO | 202256538 | A1 | 12/2022 | |
| WO | 2023127750 | A1 | 6/2023 | |
| WO | 2023137401 | A1 | 7/2023 | |

OTHER PUBLICATIONS

Braasch et al. Locked nucleic acid (LNA): fine-tuning the recognition of DNA and RNA. Chem Bio 8:1-7 (2001).
Chaturvedi et al. Stabilization of triple-stranded oligonucleotide complexes: use of probes containing alternating phosphodiester and stereo-uniform cationic phosphoramidate linkages. Nucleic Acids Res. 24:2318-2323 (1996).
Chen et al. Phosphonate Analogues of Cytosine Arabinoside Monophosphate. Phosphorus, Sulfur and Silicon 177:1783-1786 (2002).
Chen et al. Selective chemical labeling of proteins. Org. Biomol. Chem. 14:5417 (2016).

Collingwood et al. The Synthesis and Incorporation in Oligonucleotides of a Thymidine Dimer Containing an Internucleoside Phosphinate Linkage. Synlett 7:703-705 (1995).
Crooke et al. Pharmacokinetic properties of several novel oligonucleotide analogs in mice. J Pharmacol Exp Ther 277:923-937 (1996).
De Mesmaeker et al. Amide-Modified Oligonucleotides with Preorganized Backbone and Furanose Rings: Highly Increased Thermodynamic Stability of the Duplexes Formed with their RNA and DNA Complements. Synlett 1997(11) 1287-1290 (1997).
Dhami et al. Systematic exploration of a class of hydrophobic unnatural base pairs yields multiple new candidates for the expansion of the genetic alphabet. Nucleic Acids Res 42:10235-10244 (2014).
Dien et al. Progress Toward a Semi-Synthetic Organism with an Unrestricted Expanded Genetic Alphabet. J Am Chem Soc. 140:16115-16123 (2018).
Dumas et al. Designing logical codon reassignment—Expanding the chemistry in biology. Chem Sci 6:50-69 (2015).
Elayadi et al. Application of PNA and LNA oligomers to chemotherapy. Curr Opinion Invens Drugs 2:558-561 (2001).
Englisch et al. Chemically Modified Oligonucleotides as Probes and Inhibitors. Angew. Chem. Int. Ed. Eng. 30:613-629 (1991).
Eppacher et al. Synthesis and Incorporation of C(5')-Ethynylated Uracil-Derived Phosphoramidites into RNA. Helvetica Chimica Acta 87:3004-3020 (2004).
Fairhurst et al. Synthesis and Hybridisation Properties of Phosphonamidate Ester Modified Nucleic Acid. Synlett 4:467-472 (2001).
Feldman et al. A Tool for the Import of Natural and Unnatural Nucleoside Triphosphates into Bacteria. J Am Chem Soc 140(4):1447-1454 (2018).
Feldman et al. In Vivo Structure-Activity Relationships and Optimization of an Unnatural Base Pair for Replication in a Semi-Synthetic Organism. J Am Chem Soc 139:11427-11433 (2017).
Feldman. Expansion of the Genetic Alphabet: A Chemist's Approach to Synthetic Biology. Ace Chem Res 51 (2):394-403 (2018).
Gallier et al. Ex-Chiral-Pool Synthesis of 13-Hydroxyphosphonate Nucleoside Analogues. Eur J Org Chem 6:925-933 (2007).
Gong et al. Recent advances in bioorthogonal reactions for site-specific protein labeling and engineering. Tetrahedron Letters 56:2123-2131 (2015).
Hampton et al. Design of substrate-site-directed inhibitors of adenylate kinase and hexokinase. Effect of substrate substituents on affinity on affinity for the adenine nucleotide sites. J Med Chem 19:1371-1377 (1976).
Hampton et al. Design of substrate-site-directed irreversible inhibitors of adenosine 5'-phosphate aminohydrolase. Effect of substrate substituents on affinity for the substrate site. J Med Chem 19(8):1029-1033 (1976).
Hampton et al. Synthesis of 6'-cyano-6'-deoxyhomoadenosine-6'-phosphonic acid and its phosphoryl and pyrophosphoryl an hydrides and studies of their interactions with adenine nucleotide utilizing enzymes. J Am Chem Soc 95(13):4404-4414 (1973).
Hutter et al. From Phosphate to Bis(methylene) Sulfone: Non-Ionic Backbone Linkers in DNA. Helvetica Chimica Acta 85:2777-2806 (2002).
Jager et al. Oligonucleotide N-alkylphosphoramidates: synthesis and binding to polyn ucleotides. Biochemistry 27 :724 7-7246 (1988).
Jung et al. Synthesis of phosphonate derivatives of uridine, cytidine, and cytosine arabinoside. Bioorg Med Chem 8:2501-2509 (2000).
Kandimalla et al. Effect of chemical modifications of cytosine and guanine in a CpG-motif of oligonucleotides: structure-immunostimulatory activity relationships. Bioorg. Med. Chem. 9:807-813 (2001).
Kappler et al. Isozyme-specific enzyme inhibitors. 11. L-homocysteine-ATP S-C5' covalent adducts as inhibitors of rat methionine adenosyltransferases. J Med Chem 29:1030-1038 (1986).
Kappler et al. Species—or isozyme-specific enzyme inhibitors. 8. Synthesis of disubstituted two-substrate condensation products as inhibitors of rat adenylate kinases. J Med Chem 25:1179-1184 (1982).

(56) References Cited

OTHER PUBLICATIONS

Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54 (14):3607-3630 (1998).
Kroschwitz, J.I., The Concise Encyclopedia of Polymer Science and Engineering, Ed., John Wiley & Sons pp. 858-859 (1990).
Kumar et al. The First Analogues of LNA (Locked Nucleic Acids): Phosphorothioate LNA and 2'-Thio-LNA. Bioorg Med Chem Lett 8:2219-2222 (1998).
Lavergne et al. Expanding the scope of replicable unnatural DNA: Stepwise optimization of a predominantly hydrophobic base pair. JACS 135:5408-5419 (2013).
Ledbetter et al. Reprograming the Replisome of a Semisynthetic Organism for the Expansion of the Genetic Alphabet. J Am Chem Soc. 140:758-765 (2018).
Letsinger et al. Cholesteryl-conjugated oligonucleotides: Synthesis, properties, and activity as inhibitors of replication of human immunodeficiency virus in cell culture. PNAS 86:6553-6556 (1989).
Malyshev et al. A semi-synthetic organism with an expanded genetic alphabet. Nature 509(7500):385-388 (2014).
Malyshev et al. Efficient and sequence-independent replication of DNA containing a third base pair establishes a functional six-letter genetic alphabet. PNAS USA 109: 12005-12010 (2012).
Manoharan et al. Chemical Modifications to Improve Uptake and Bioavailability of Antisense Oligonucleotides. Ann. N.Y. Acad. Scie 660:306-309 (1992).
Manoharan et al. Cholic Acid-Oligonucleotide Conjugates for Antisense Applications. Bioorg. Med. Chem. Let 4:1053-1060 (1994).
Manoharan et al. Introduction of a Lipophilic Thioether in the Minor Groove of Nucleic Acids for Antisense Applications. Bioorg. Med. Chem. Let 3:2765-2770 (1993).
Manoharan et al. Lipidic Nucleic Acids. Tetrahedron Lett 36:3651-3654 (1995).
Manoharan et al. Oligonucleotide Conjugates: Alteration of the Pharmacokinetic Properties of Antisense Agents. Nucleosides & Nucleotides 14:969-973 (1995).
Matteucci. Oligonucleotide Analogs: an Overview in Oligonucleotides as Therapeutic Agents, (Chadwick and Cardew, ed.) John Wiley and Sons, New York, NY; Zon, 1993, Oligonucleoside Phosphorothioates in Protocols for Oligonucleotides and Analogs, Synthesis and Properties, Humana Press, pp. 165-190 (1997).
Abbadessa et al, Co-pending U.S. Appl. No. 17/357,615, filed Jun. 24, 2021; also cited herein as US 2022/0016252.
Aerni et al, Co-pending U.S. Appl. No. 17/845,495, filed Jun. 21, 2022; also cited herein as US 2022/0324792.
Caffaro et al, Co-pending U.S. Appl. No. 17/313,579, filed May 6, 2021; also cited herein as US 2021/0338829.
Caffaro et al, Co-pending U.S. Appl. No. 17/735,564, filed May 3, 2022; also cited herein as US 2022/0273767.
Ptacin et al, Co-pending U.S. Appl. No. 17/350,672, filed Jun. 17, 2021; also cited herein as US 2022/0016249.
Gupta et al., "Protein PEGylation for cancer therapy: bench to bedside", Journal of Cell Communication and Signaling, vol. 13, No. 3, Nov. 29, 2018, pp. 319-330.
International Search Report and Written Opinion, International Application No. PCT/US2020/047389, dated Nov. 20, 2020, 12 pages.
Micklefield. Backbone Modification of Nucleic Acids: Synthesis, Structure and Therapeutic Applications. Current Medicinal Chemistry 8:1157-1179 (2001).
Mikhailov et al. Substrate Properties of C'-Methylnucleoside and C'-Methyl-2'-deoxynucleoside 5'-Triphosphates in RNA and DNA Synthesis Reactions Catalysed by RNA and DNA Polymerases Nucleosides & Nucleotides 10 (1-3):339-343 (1991).
Miller et al. Conformation and interaction of dinucleoside mono- and diphosphates. V. Syntheses and properties of adenine and thymine nucleoside alkyl phosphotriesters, the neutral analogs of dinucleoside monophosphates. JACS 93:6657-6665 (1971).
Mishra et al. Improved leishmanicidal effect of phosphorotioate antisense oligonucleotides by LDL-mediated delivery. Biochem Biophys Acta 1264:229-237 (1995).
Napolitano et al. Emergent rules for codon choice elucidated by editing rare argine codons in *Escherichia coli*. PNAS 113(38): E5588-5597 (2016).
Nawrot et al. A novel class of DNA analogs bearing 5'-C-phosphonothymidine units: synthesis and physicochemical and biochemical properties. Oligonucleotides16(1):68-82 (2006).
Nelson et al. N3'->PS' Oligodeoxyribonucleotide Phosphoramidates: A New Method of Synthesis Based on a Phosphoramidite Amine-Exchange Reaction. J Org Chem 62:7278-7287 (1997).
Neumann et al. Encoding multiple unnatural amino acids via evolution of a quadruplet-decoding ribosome Nature 464 (7287):441-444 (2010).
Nielsen et al. Sequence-selective recognition of DNA by strand displacement with a thymine-substituted polyamide. Science 254:1497-1500 (1991).
Oberhauser et al. Effective incorporation of 2'-O-methyl-oligoribonucleotides into liposomes and enhanced cell association through modification with thiocholesterol. Nucl. Acids Res. 20:533-538 (1992).
Orum et al. Locked nucleic acids: a promising molecular family for gene-function analysis and antisense drug development. Curr Opinion Mol Ther 3:239-243 (2001).
Ostrov et al. Design, synthesis, and testing toward a 57-codon genome. Science 353(6301): 819-822 (2016).
Peyrottes et al. Oligodeoxynucleoside phosphoramidates (P-NH2): synthesis and thermal stability of duplexes with DNA and RNA targets. Nucleic Acids Res 24:1841-1848 (1996).
Ring et al., "Mechanistic and structural insight into the functional dichotomy between interleukin-2 and interleukin-15", Nat Immunol. Dec. 2012, 13(12): 1187-1195.
Saha et al. 5'-Methyl-DNA—A New Oligonucleotide Analog: Synthesis and Biochemical Properties J Org Chem 60:788-789 (1995).
Saison-Behmoaras et al. Short modified antisense oligonucleotides directed against Ha-ras point mutation induce selective cleavage of the mRNA and inhibit T24 cells proliferation. EMBO J. 10:1111-1118 (1991).
Sanghvi, Chapter 15, Antisense Research and Applications, Crookeand Lebleu Eds., CRC Press, 1993, 273-288.
Schultz et al. Oligo-2'-fluoro-2'-deoxynucleotide N3'- > PS' phosphoramidates: synthesis and properties. Nucleic Acids Res 24:2966-2973 (1996).
Singh et al. LNA (locked nucleic acids): synthesis and high-affinity nucleic acid recognition. Chem Commun 4:455-456 (1998).
Singh et al. Synthesis of 2'-amino-LNA: A novel conformationally restricted high-affinity oligonucleotide analogues with a handle. J Bio Chem 63:10035-10039 (1998).
Srivastava et al. Five- and six-membered conformationally locked 2',4'-carbocyclic ribo-thymidines: synthesis, structure, and biochemical studies. J Am Chem Soc 129(26):8362-8379 (2007).
Svinarchuk et al. Inhibition of HIV proliferation in MT-4 cells by antisense oligonucleotide conjugated to lipophilic groups. Biochimie 75:49-54 (1993).
Vrudhula et al. Isozyme-specific enzyme inhibitors. 13. S-[5'(R)-[(N-triphosphoamino)methyl]adenosyl]-L-homocysteine, a potent inhibitor of rat methionine adenosyltransferases. J Med Chem 30:888-894 (1987).
Wahlestedt et al. Potent and nontoxic antisense oligonucleotides containing locked nucleic acids. PNAS USA 97:5633-5638 (2000).
Wang et al. Biophysical and biochemical properties of oligodeoxynucleotides containing 4'-C-and 5'-C-substituted thymidines. Bioorg Med Chem Lett 9:885-890 (1999).
Wang et al. Synthesis of Azole Nucleoside 5 '-Monophosphate Mimics (P1 Ms) and Their Inhibitory Properties of IMP Dehydrogenases. Nucleosides Nucleotides & Nucleic Acids 23(1 & 2):317-337 (2004).
Wu et al. Functionalization of the sugar moiety of oligoribonucleotides on solid support. Bioconjugate Chem 10:921-924 (1999).
Zhang et al. A semisynthetic organism engineered for the stable expansion of the genetic alphabet. PNAS USA 114 (6):1317-1322 (2017).

(56) References Cited

OTHER PUBLICATIONS

Zhang et al. A Semi-Synthetic Organism that Stores and Retrieves Increased Genetic Information. Nature 551 (7682):644-647 (2017).
Zhou et al. Fine tuning of electrostatics around the internucleotidic phosphate through incorporation of modified 2',4'-carbocyclic-LNAs and—ENAs leads to significant modulation of antisense properties. J Org Chem 74:118-134 (2009).
Zon. Chapter 8: Oligonucleotide Phosphorothioates in Protocols for Oligonucleotides and Analogs, Synthesis and Properties. Humana Press (pp. 165-190) (1993).
Ptacin, J., et al., Co-pending U.S. Appl. No. 16/634,487, filed Jan. 27, 2020; also cited previously as US 2020/0231644.
Ptacin, J., et al., Co-pending U.S. Appl. No. 16/803,816, filed Feb. 27, 2020; also cited previously as US 2020/0188484.
Ptacin, J., et al., Co-pending U.S. Appl. No. 16/918,930, filed Jul. 1, 2020; also cited previously as US 2020/0330601.
Ptacin, J., et al., Co-pending U.S. Appl. No. 16/993,967, filed Aug. 14, 2020.
Caffaro, C., et al., Co-pending U.S. Appl. No. 17/001,965, filed Aug. 25, 2020.
Ptacin, J., et al., Co-pending U.S. Appl. No. 17/016,003, filed Sep. 9, 2020.
Wu et al., Synthesis of 5'-C- and 2'-O-(Bromoalkyl)-Substituted Ribonucleoside Phosphoramidites for the Post-synthetic Functionalization of Oligonucleotides on Solid Support, Helvetica Chimica Acta, vol. 83, pp. 1127-1143, 2000.
Chen X. et al., Fusion protein linkers: property, design and functionality, Advanced drug delivery reviews, 2013, v. 65, n. 10, pp. 1357-1369.
Maeda Y. et al., Engineering of Functional chimeric protein G-Vargula Luciferase, Analytical biochemistry, 1997, v. 249, n. 2, p. 147-152.
Orlando M., Modification of proteins and low molecular weight subtances with hydroxyethyl starch (HES), Inauguraldissertation, Giesen, 2003, p. 14.
Rowley J. et al., Inhibition of tumor growth by NK1. 1+ cells and CD8+ T cells activated by IL-15 through receptor β/common γ signalingin trans, The Journal of Immunology, 2008, v. 181, n. 12, p. 8237-8247.
Treetharmathurot B. et al, Effect of PEG molecular weigh and linking chemistry on the biological activity and thermal stability of PEGylated trypsin, International Journal of Pharmaceutics, 2008, v. 357, pp. 252-259.
Zhou J. et al. Preparation and PEGylation of exendin-4 peptide secreted from yeast Pichia pastoris, European journal of pharmaceutics and biopahrmaceutics, 2009, V. 72, N. 2, p. 412-417.
Abbadessa, et al., Co-pending U.S. Appl. No. 18/524,157, filed Nov. 30, 2023.
Caffaro, et al., Co-pending U.S. Appl. No. 18/179,198, filed Mar. 6, 2023; also cited as US 2023/0302089 A1.
Caffaro, et al., Co-pending U.S. Appl. No. 18/296,710, filed Apr. 6, 2023; also cited as US 2023/0277627 A1.
Caffaro, et al., Co-pending U.S. Appl. No. 18/296,711, filed Apr. 6, 2023; also cited as US 2023/0416327 A1.
Caffaro, et al., Co-pending U.S. Appl. No. 18/415,445, filed Jan. 17, 2024.
Caffaro, et al., Co-pending U.S. Appl. No. 18/424,573, filed Jan. 26, 2024.
Ptacin et al, Co-pending U.S. Appl. No. 18/886,814, filed on Sep. 16, 2024.
Ptacin, et al., Co-pending U.S. Appl. No. 18/327,535, filed Jun. 1, 2023; also cited as US 2024/0082359 A1.
Vanbrunt, M.P. et al., Genetically Encoded Azide Containing Amino Acid in Mammalian Cells Enables Site-Specific Antibody-Drug Conjugates Using Click Cycloaddition Chemistry, Bioconjug. Chem., 2015, vol. 26, pp. 2249-2260.
Colman P.M. et al.: "Effects of amino acid sequence changes on antibody-antigen interations", Research in Immunology, 1994, vol. 145, Issue 1, pp. 33-36.

\* cited by examiner

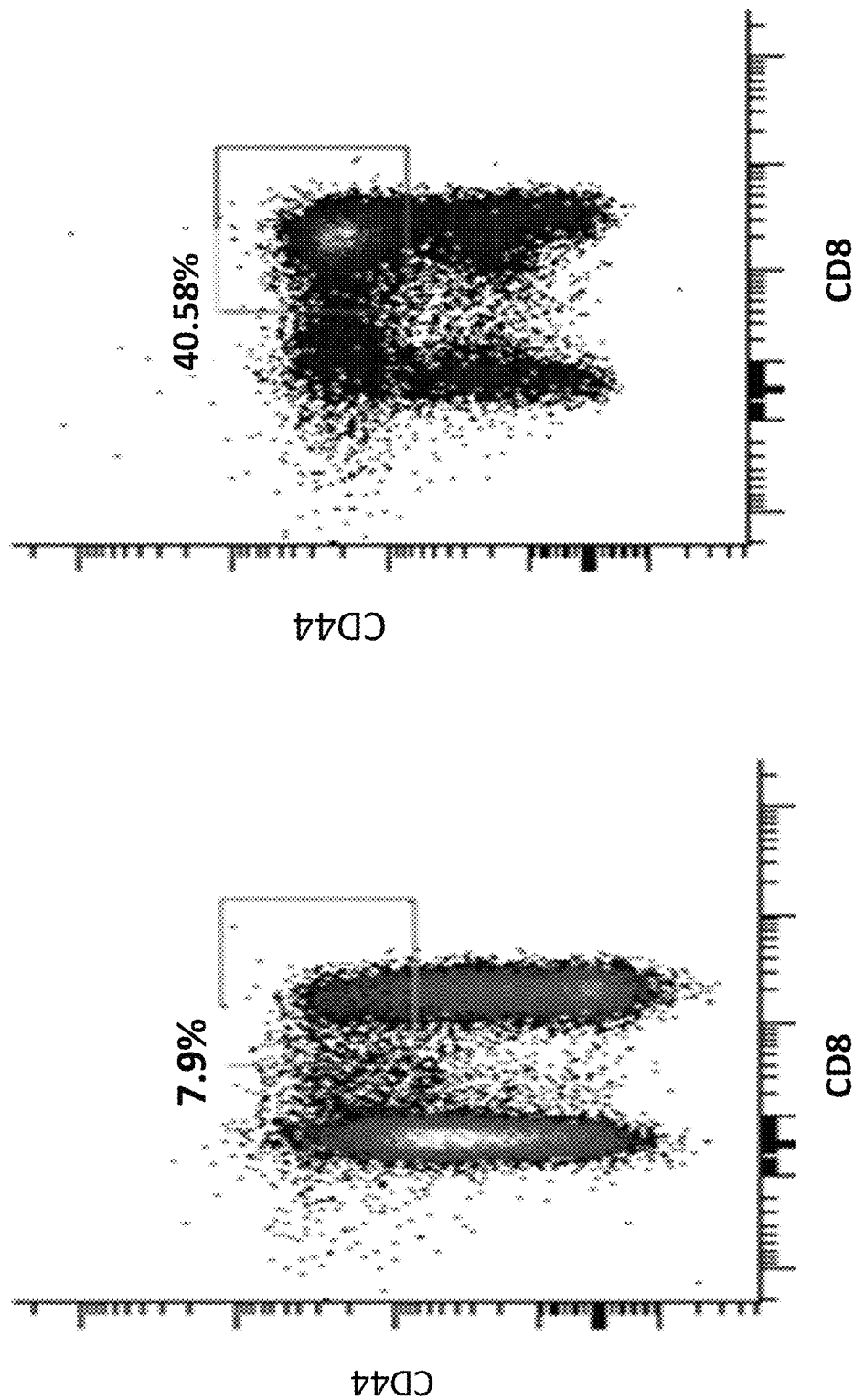

SEQUENCE LISTING

<160> NUMBER OF SEQ ID NOS: 99

<210> SEQ ID NO 1
<211> LENGTH: 114
<212> TYPE: PRT
<213> ORGANISM: Homo sapiens
<220> FEATURE:
<221> NAME/KEY: misc_feature
<223> OTHER INFORMATION: IL-15 (mature form)

<400> SEQUENCE: 1

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 2
<211> LENGTH: 136
<212> TYPE: PRT
<213> ORGANISM: Homo sapiens
<220> FEATURE:
<221> NAME/KEY: misc_feature
<223> OTHER INFORMATION: IL-15 (precursor)

<400> SEQUENCE: 2

Met Asp Phe Gln Val Gln Ile Phe Ser Phe Leu Leu Ile Ser Ala Ser
1               5                   10                  15

Val Ile Met Ser Arg Ala Asn Trp Val Asn Val Ile Ser Asp Leu Lys
            20                  25                  30

Lys Ile Glu Asp Leu Ile Gln Ser Met His Ile Asp Ala Thr Leu Tyr
        35                  40                  45

Thr Glu Ser Asp Val His Pro Ser Cys Lys Val Thr Ala Met Lys Cys
    50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
        115                 120                 125

Val Gln Met Phe Ile Asn Thr Ser
    130                 135

<210> SEQ ID NO 3
<211> LENGTH: 115
<212> TYPE: PRT
<213> ORGANISM: Homo sapiens
<220> FEATURE:
<221> NAME/KEY: misc_feature
<223> OTHER INFORMATION: Met-IL-15 (mature form with N-terminal
      methionine)

<400> SEQUENCE: 3

Met Asn Trp Val Asn Val Ile Ser Asp Leu Lys Lys Ile Glu Asp Leu
1               5                   10                  15

```
Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
 50                  55                  60

Glu Asn Leu Ile Ile Leu Ala Asn Asn Ser Leu Ser Ser Asn Gly Asn
 65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 4
<211> LENGTH: 114
<212> TYPE: PRT
<213> ORGANISM: Artificial Sequence
<220> FEATURE:
<223> OTHER INFORMATION: Synthetic: IL-15_S18X
<220> FEATURE:
<221> NAME/KEY: misc_feature
<222> LOCATION: (18)..(18)
<223> OTHER INFORMATION: Xaa is an unnatural amino acid

<400> SEQUENCE: 4

Asn Trp Val Asn Val Ile Ser Asp Leu Lys Lys Ile Glu Asp Leu Ile
1               5                   10                  15

Gln Xaa Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 5
<211> LENGTH: 114
<212> TYPE: PRT
<213> ORGANISM: Artificial Sequence
<220> FEATURE:
<223> OTHER INFORMATION: Synthetic: IL-15_L25X
<220> FEATURE:
<221> NAME/KEY: misc_feature
<222> LOCATION: (25)..(25)
<223> OTHER INFORMATION: Xaa is an unnatural amino acid

<400> SEQUENCE: 5

Asn Trp Val Asn Val Ile Ser Asp Leu Lys Lys Ile Glu Asp Leu Ile
1               5                   10                  15

Gln Ser Met His Ile Asp Ala Thr Xaa Tyr Thr Glu Ser Asp Val His
            20                  25                  30

Pro Ser Cys Lys Val Thr Ala Met Lys Cys Phe Leu Leu Glu Leu Gln
        35                  40                  45
```

```
                35                  40                  45
Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
            85                  90                  95

Lys Glu Phe Leu Gln Ser Phe Val His Ile Val Gln Met Phe Ile Asn
            100                 105                 110

Thr Ser

<210> SEQ ID NO 6
<211> LENGTH: 114
<212> TYPE: PRT
<213> ORGANISM: Artificial Sequence
<220> FEATURE:
<223> OTHER INFORMATION: Synthetic: IL-15_E46X
<220> FEATURE:
<221> NAME/KEY: misc_feature
<222> LOCATION: (46)..(46)
<223> OTHER INFORMATION: Xaa is an unnatural amino acid

<400> SEQUENCE: 6

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Xaa Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
            85                  90                  95

Lys Glu Phe Leu Gln Ser Phe Val His Ile Val Gln Met Phe Ile Asn
            100                 105                 110

Thr Ser

<210> SEQ ID NO 7
<211> LENGTH: 114
<212> TYPE: PRT
<213> ORGANISM: Artificial Sequence
<220> FEATURE:
<223> OTHER INFORMATION: Synthetic: IL-15_E53X
<220> FEATURE:
<221> NAME/KEY: misc_feature
<222> LOCATION: (53)..(53)
<223> OTHER INFORMATION: Xaa is an unnatural amino acid

<400> SEQUENCE: 7

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Xaa Ser Gly Asp Ala Ser Ile His Asp Thr Val Glu
    50                  55                  60
```

```
Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser
```

<210> SEQ ID NO 8
<211> LENGTH: 114
<212> TYPE: PRT
<213> ORGANISM: Artificial Sequence
<220> FEATURE:
<223> OTHER INFORMATION: Synthetic: IL-15_N77X
<220> FEATURE:
<221> NAME/KEY: misc_feature
<222> LOCATION: (77)..(77)
<223> OTHER INFORMATION: Xaa is an unnatural amino acid

<400> SEQUENCE: 8

```
Asn Trp Val Asn Val Ile Ser Asp Leu Lys Lys Ile Glu Asp Leu Ile
  1               5                  10                  15

Gln Ser Met His Ile Asp Ala Thr Leu Tyr Thr Glu Ser Asp Val His
             20                  25                  30

Pro Ser Cys Lys Val Thr Ala Met Lys Cys Phe Leu Leu Glu Leu Gln
         35                  40                  45

Val Ile Ser Leu Glu Ser Gly Asp Ala Ser Ile His Asp Thr Val Glu
     50                  55                  60

Asn Leu Ile Ile Leu Ala Asn Asn Ser Leu Ser Ser Xaa Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser
```

<210> SEQ ID NO 9
<211> LENGTH: 114
<212> TYPE: PRT
<213> ORGANISM: Artificial Sequence
<220> FEATURE:
<223> OTHER INFORMATION: Synthetic: IL-15_S83X
<220> FEATURE:
<221> NAME/KEY: misc_feature
<222> LOCATION: (83)..(83)
<223> OTHER INFORMATION: Xaa is an unnatural amino acid

<400> SEQUENCE: 9

```
Asn Trp Val Asn Val Ile Ser Asp Leu Lys Lys Ile Glu Asp Leu Ile
  1               5                  10                  15

Gln Ser Met His Ile Asp Ala Thr Leu Tyr Thr Glu Ser Asp Val His
             20                  25                  30

Pro Ser Cys Lys Val Thr Ala Met Lys Cys Phe Leu Leu Glu Leu Gln
         35                  40                  45

Val Ile Ser Leu Glu Ser Gly Asp Ala Ser Ile His Asp Thr Val Glu
     50                  55                  60

Asn Leu Ile Ile Leu Ala Asn Asn Ser Leu Ser Ser Asn Gly Asn Val
 65                  70                  75                  80

Thr Glu Xaa Gly Cys Lys Glu Cys Glu Glu Leu Glu Glu Lys Asn Ile
                 85                  90                  95
```

```
Lys Glu Phe Leu Gln Ser Phe Val His Ile Val Gln Met Phe Ile Asn
            100                 105                 110

Thr Ser

<210> SEQ ID NO 10
<211> LENGTH: 114
<212> TYPE: PRT
<213> ORGANISM: Artificial Sequence
<220> FEATURE:
<223> OTHER INFORMATION: Synthetic: IL-15_S18[AzK]
<220> FEATURE:
<221> NAME/KEY: misc_feature
<222> LOCATION: (18)..(18)
<223> OTHER INFORMATION: Xaa is [AzK] = N6-((2-azidoethoxy)-carbonyl)-L-
      lysine

<400> SEQUENCE: 10

Asn Trp Val Asn Val Ile Ser Asp Leu Lys Lys Ile Glu Asp Leu Ile
1               5                   10                  15

Gln Xaa Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 11
<211> LENGTH: 114
<212> TYPE: PRT
<213> ORGANISM: Artificial Sequence
<220> FEATURE:
<223> OTHER INFORMATION: Synthetic: IL-15_L25[AzK]
<220> FEATURE:
<221> NAME/KEY: misc_feature
<222> LOCATION: (25)..(25)
<223> OTHER INFORMATION: Xaa is [AzK] = N6-((2-azidoethoxy)-carbonyl)-L-
      lysine

<400> SEQUENCE: 11

Asn Trp Val Asn Val Ile Ser Asp Leu Lys Lys Ile Glu Asp Leu Ile
1               5                   10                  15

Gln Ser Met His Ile Asp Ala Thr Xaa Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110
```

Thr Ser

<210> SEQ ID NO 12
<211> LENGTH: 114
<212> TYPE: PRT
<213> ORGANISM: Artificial Sequence
<220> FEATURE:
<223> OTHER INFORMATION: Synthetic: IL-15_E46[AzK]
<220> FEATURE:
<221> NAME/KEY: misc_feature
<222> LOCATION: (46)..(46)
<223> OTHER INFORMATION: Xaa is [AzK] = N6-((2-azidoethoxy)-carbonyl)-L-lysine

<400> SEQUENCE: 12

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Xaa Leu Gln
        35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 13
<211> LENGTH: 114
<212> TYPE: PRT
<213> ORGANISM: Artificial Sequence
<220> FEATURE:
<223> OTHER INFORMATION: Synthetic: IL-15_E53[AzK]
<220> FEATURE:
<221> NAME/KEY: misc_feature
<222> LOCATION: (53)..(53)
<223> OTHER INFORMATION: Xaa is [AzK] = N6-((2-azidoethoxy)-carbonyl)-L-lysine

<400> SEQUENCE: 13

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Xaa Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 14
<211> LENGTH: 114
<212> TYPE: PRT
<213> ORGANISM: Artificial Sequence
<220> FEATURE:
<223> OTHER INFORMATION: Synthetic: IL-15_N77[AzK]
<220> FEATURE:
<221> NAME/KEY: misc_feature
<222> LOCATION: (77)..(77)
<223> OTHER INFORMATION: Xaa is [AzK] = N6-((2-azidoethoxy)-carbonyl)-L-lysine

<400> SEQUENCE: 14

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Xaa Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 15
<211> LENGTH: 114
<212> TYPE: PRT
<213> ORGANISM: Artificial Sequence
<220> FEATURE:
<223> OTHER INFORMATION: Synthetic: IL-15_S83[AzK]
<220> FEATURE:
<221> NAME/KEY: misc_feature
<222> LOCATION: (83)..(83)
<223> OTHER INFORMATION: Xaa is [AzK] = N6-((2-azidoethoxy)-carbonyl)-L-lysine

<400> SEQUENCE: 15

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Xaa Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 16
<211> LENGTH: 114

```
<212> TYPE: PRT
<213> ORGANISM: Artificial Sequence
<220> FEATURE:
<223> OTHER INFORMATION: Synthetic: IL-15_S18[AzK_PEG]
<220> FEATURE:
<221> NAME/KEY: misc_feature
<222> LOCATION: (18)..(18)
<223> OTHER INFORMATION: Xaa is [AzK_PEG] = N6-((2-azidoethoxy)-
      carbonyl)-L-lysine stably-conjugated to PEG

<400> SEQUENCE: 16

Asn Trp Val Asn Val Ile Ser Asp Leu Lys Lys Ile Glu Asp Leu Ile
1               5                   10                  15

Gln Xaa Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 17
<211> LENGTH: 114
<212> TYPE: PRT
<213> ORGANISM: Artificial Sequence
<220> FEATURE:
<223> OTHER INFORMATION: Synthetic: IL-15_L25[AzK_PEG]
<220> FEATURE:
<221> NAME/KEY: misc_feature
<222> LOCATION: (25)..(25)
<223> OTHER INFORMATION: Xaa is [AzK_PEG] = N6-((2-azidoethoxy)-
      carbonyl)-L-lysine stably-conjugated to PEG

<400> SEQUENCE: 17

Asn Trp Val Asn Val Ile Ser Asp Leu Lys Lys Ile Glu Asp Leu Ile
1               5                   10                  15

Gln Ser Met His Ile Asp Ala Thr Xaa Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 18
<211> LENGTH: 114
<212> TYPE: PRT
<213> ORGANISM: Artificial Sequence
<220> FEATURE:
```

<223> OTHER INFORMATION: Synthetic: IL-15_E46[AzK_PEG]
<220> FEATURE:
<221> NAME/KEY: misc_feature
<222> LOCATION: (46)..(46)
<223> OTHER INFORMATION: Xaa is [AzK_PEG] = N6-((2-azidoethoxy)-
      carbonyl)-L-lysine stably-conjugated to PEG

<400> SEQUENCE: 18

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Xaa Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 19
<211> LENGTH: 114
<212> TYPE: PRT
<213> ORGANISM: Artificial Sequence
<220> FEATURE:
<223> OTHER INFORMATION: Synthetic: IL-15_E53[AzK_PEG]
<220> FEATURE:
<221> NAME/KEY: misc_feature
<222> LOCATION: (53)..(53)
<223> OTHER INFORMATION: Xaa is [AzK_PEG] = N6-((2-azidoethoxy)-
      carbonyl)-L-lysine stably-conjugated to PEG

<400> SEQUENCE: 19

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Xaa Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 20
<211> LENGTH: 114
<212> TYPE: PRT
<213> ORGANISM: Artificial Sequence
<220> FEATURE:
<223> OTHER INFORMATION: Synthetic: IL-15_N77[AzK_PEG]
<220> FEATURE:
<221> NAME/KEY: misc_feature
<222> LOCATION: (77)..(77)
<223> OTHER INFORMATION: Xaa is [AzK_PEG] = N6-((2-azidoethoxy)-
      carbonyl)-L-lysine stably-conjugated to PEG

<400> SEQUENCE: 20

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Xaa Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 21
<211> LENGTH: 114
<212> TYPE: PRT
<213> ORGANISM: Artificial Sequence
<220> FEATURE:
<223> OTHER INFORMATION: Synthetic: IL-15_S83[AzK_PEG]
<220> FEATURE:
<221> NAME/KEY: misc_feature
<222> LOCATION: (83)..(83)
<223> OTHER INFORMATION: Xaa is [AzK_PEG] = N6-((2-azidoethoxy)-
      carbonyl)-L-lysine stably-conjugated to PEG

<400> SEQUENCE: 21

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Xaa Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 22
<211> LENGTH: 114
<212> TYPE: PRT
<213> ORGANISM: Artificial Sequence
<220> FEATURE:
<223> OTHER INFORMATION: Synthetic: IL-15_S18[AzK_PEG30]
<220> FEATURE:
<221> NAME/KEY: misc_feature
<222> LOCATION: (18)..(18)
<223> OTHER INFORMATION: Xaa is [AzK_PEG30] = N6-((2-azidoethoxy)-
      carbonyl)-L-lysine stably-conjugated to PEG

<400> SEQUENCE: 22

Asn Trp Val Asn Val Ile Ser Asp Leu Lys Lys Ile Glu Asp Leu Ile
1               5                   10                  15

Gln Xaa Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 23
<211> LENGTH: 114
<212> TYPE: PRT
<213> ORGANISM: Artificial Sequence
<220> FEATURE:
<223> OTHER INFORMATION: Synthetic: IL-15_L25[AzK_PEG30]
<220> FEATURE:
<221> NAME/KEY: misc_feature
<222> LOCATION: (25)..(25)
<223> OTHER INFORMATION: Xaa is [AzK_PEG30] = N6-((2-azidoethoxy)-
      carbonyl)-L-lysine stably-conjugated to PEG

<400> SEQUENCE: 23

Asn Trp Val Asn Val Ile Ser Asp Leu Lys Lys Ile Glu Asp Leu Ile
1               5                   10                  15

Gln Ser Met His Ile Asp Ala Thr Xaa Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 24
<211> LENGTH: 114
<212> TYPE: PRT
<213> ORGANISM: Artificial Sequence
<220> FEATURE:
<223> OTHER INFORMATION: Synthetic: IL-15_E46[AzK_PEG30]
<220> FEATURE:
<221> NAME/KEY: misc_feature
<222> LOCATION: (46)..(46)
<223> OTHER INFORMATION: Xaa is [AzK_PEG30] = N6-((2-azidoethoxy)-
      carbonyl)-L-lysine stably-conjugated to PEG

<400> SEQUENCE: 24

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Xaa Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 25
<211> LENGTH: 114
<212> TYPE: PRT
<213> ORGANISM: Artificial Sequence
<220> FEATURE:
<223> OTHER INFORMATION: Synthetic: IL-15_E53[AzK_PEG30]
<220> FEATURE:
<221> NAME/KEY: misc_feature
<222> LOCATION: (53)..(53)
<223> OTHER INFORMATION: Xaa is [AzK_PEG30] = N6-((2-azidoethoxy)-
      carbonyl)-L-lysine stably-conjugated to PEG

<400> SEQUENCE: 25

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Xaa Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 26
<211> LENGTH: 114
<212> TYPE: PRT
<213> ORGANISM: Artificial Sequence
<220> FEATURE:
<223> OTHER INFORMATION: Synthetic: IL-15_N77[AzK_PEG30]
<220> FEATURE:
<221> NAME/KEY: misc_feature
<222> LOCATION: (77)..(77)
<223> OTHER INFORMATION: Xaa is [AzK_PEG30] = N6-((2-azidoethoxy)-
      carbonyl)-L-lysine stably-conjugated to PEG

<400> SEQUENCE: 26

Asn Trp Val Asn Val Ile Ser Asp Leu Lys Lys Ile Glu Asp Leu Ile
1               5                   10                  15
```

```
Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Xaa Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 27
<211> LENGTH: 114
<212> TYPE: PRT
<213> ORGANISM: Artificial Sequence
<220> FEATURE:
<223> OTHER INFORMATION: Synthetic: IL-15_S83[AzK_PEG30]
<220> FEATURE:
<221> NAME/KEY: misc_feature
<222> LOCATION: (83)..(83)
<223> OTHER INFORMATION: Xaa is [AzK_PEG30] = N6-((2-azidoethoxy)-
      carbonyl)-L-lysine stably-conjugated to PEG

<400> SEQUENCE: 27

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Xaa Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 28
<211> LENGTH: 114
<212> TYPE: PRT
<213> ORGANISM: Artificial Sequence
<220> FEATURE:
<223> OTHER INFORMATION: Synthetic: IL-15_S18[AzK_PEG40]
<220> FEATURE:
<221> NAME/KEY: misc_feature
<222> LOCATION: (18)..(18)
<223> OTHER INFORMATION: Xaa is [AzK_PEG40] = N6-((2-azidoethoxy)-
      carbonyl)-L-lysine stably-conjugated to PEG

<400> SEQUENCE: 28

Asn Trp Val Asn Val Ile Ser Asp Leu Lys Lys Ile Glu Asp Leu Ile
1               5                   10                  15

Gln Xaa Met His Ile Asp Ala Thr Leu Tyr Thr Glu Ser Asp Val His
            20                  25                  30
```

```
Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
            85                  90                  95

Lys Glu Phe Leu Gln Ser Phe Val His Ile Val Gln Met Phe Ile Asn
            100                 105                 110

Thr Ser

<210> SEQ ID NO 29
<211> LENGTH: 114
<212> TYPE: PRT
<213> ORGANISM: Artificial Sequence
<220> FEATURE:
<223> OTHER INFORMATION: Synthetic: IL-15_L25[AzK_PEG40]
<220> FEATURE:
<221> NAME/KEY: misc_feature
<222> LOCATION: (25)..(25)
<223> OTHER INFORMATION: Xaa is [AzK_PEG40] = N6-((2-azidoethoxy)-
      carbonyl)-L-lysine stably-conjugated to PEG

<400> SEQUENCE: 29

Asn Trp Val Asn Val Ile Ser Asp Leu Lys Lys Ile Glu Asp Leu Ile
 1               5                  10                  15

Gln Ser Met His Ile Asp Ala Thr Xaa Tyr Thr Glu Ser Asp Val His
            20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
            85                  90                  95

Lys Glu Phe Leu Gln Ser Phe Val His Ile Val Gln Met Phe Ile Asn
            100                 105                 110

Thr Ser

<210> SEQ ID NO 30
<211> LENGTH: 114
<212> TYPE: PRT
<213> ORGANISM: Artificial Sequence
<220> FEATURE:
<223> OTHER INFORMATION: Synthetic: IL-15_E46[AzK_PEG40]
<220> FEATURE:
<221> NAME/KEY: misc_feature
<222> LOCATION: (46)..(46)
<223> OTHER INFORMATION: Xaa is [AzK_PEG40] = N6-((2-azidoethoxy)-
      carbonyl)-L-lysine stably-conjugated to PEG

<400> SEQUENCE: 30

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Xaa Leu Gln
            35                  40                  45
```

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 31
<211> LENGTH: 114
<212> TYPE: PRT
<213> ORGANISM: Artificial Sequence
<220> FEATURE:
<223> OTHER INFORMATION: Synthetic: IL-15_E53[AzK_PEG40]
<220> FEATURE:
<221> NAME/KEY: misc_feature
<222> LOCATION: (53)..(53)
<223> OTHER INFORMATION: Xaa is [AzK_PEG40] = N6-((2-azidoethoxy)-
      carbonyl)-L-lysine stably-conjugated to PEG

<400> SEQUENCE: 31

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
             35                  40                  45

Val Ile Ser Leu Xaa Ser Gly Asp Ala Ser Ile His Asp Thr Val Glu
        50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 32
<211> LENGTH: 114
<212> TYPE: PRT
<213> ORGANISM: Artificial Sequence
<220> FEATURE:
<223> OTHER INFORMATION: Synthetic: IL-15_N77[AzK_PEG40]
<220> FEATURE:
<221> NAME/KEY: misc_feature
<222> LOCATION: (77)..(77)
<223> OTHER INFORMATION: Xaa is [AzK_PEG40] = N6-((2-azidoethoxy)-
      carbonyl)-L-lysine stably-conjugated to PEG

<400> SEQUENCE: 32

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
             35                  40                  45

Val Ile Ser Leu Glu Ser Gly Asp Ala Ser Ile His Asp Thr Val Glu
        50                  55                  60

```
Asn Leu Ile Ile Leu Ala Asn Asn Ser Leu Ser Ser Xaa Gly Asn Val
 65                  70                  75                  80

Thr Glu Ser Gly Cys Lys Glu Cys Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser
```

<210> SEQ ID NO 33
<211> LENGTH: 114
<212> TYPE: PRT
<213> ORGANISM: Artificial Sequence
<220> FEATURE:
<223> OTHER INFORMATION: Synthetic: IL-15_S83[AzK_PEG40]
<220> FEATURE:
<221> NAME/KEY: misc_feature
<222> LOCATION: (83)..(83)
<223> OTHER INFORMATION: Xaa is [AzK_PEG40] = N6-((2-azidoethoxy)-
      carbonyl)-L-lysine stably-conjugated to PEG

<400> SEQUENCE: 33

```
Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Xaa Gly Cys Lys Glu Cys Glu Leu Glu Glu Lys Asn Ile
                 85                  90                  95

Lys Glu Phe Leu Gln Ser Phe Val His Ile Val Gln Met Phe Ile Asn
                100                 105                 110

Thr Ser
```

<210> SEQ ID NO 34
<211> LENGTH: 114
<212> TYPE: PRT
<213> ORGANISM: Artificial Sequence
<220> FEATURE:
<223> OTHER INFORMATION: Synthetic: IL-15_S18[AzK_L1_PEG]
<220> FEATURE:
<221> NAME/KEY: misc_feature
<222> LOCATION: (18)..(18)
<223> OTHER INFORMATION: Xaa is [AzK_L1_PEG] = N6-((2-azidoethoxy)-
      carbonyl)-L-lysine stably-conjugated to PEG

<400> SEQUENCE: 34

```
Asn Trp Val Asn Val Ile Ser Asp Leu Lys Lys Ile Glu Asp Leu Ile
 1               5                  10                  15

Gln Xaa Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80
```

Thr Glu Ser Gly Cys Lys Glu Cys Glu Glu Leu Glu Glu Lys Asn Ile
            85                  90                  95

Lys Glu Phe Leu Gln Ser Phe Val His Ile Val Gln Met Phe Ile Asn
            100                 105                 110

Thr Ser

<210> SEQ ID NO 35
<211> LENGTH: 114
<212> TYPE: PRT
<213> ORGANISM: Artificial Sequence
<220> FEATURE:
<223> OTHER INFORMATION: Synthetic: IL-15_L25[AzK_L1_PEG]
<220> FEATURE:
<221> NAME/KEY: misc_feature
<222> LOCATION: (25)..(25)
<223> OTHER INFORMATION: Xaa is [AzK_L1_PEG] = N6-((2-azidoethoxy)-
      carbonyl)-L-lysine stably-conjugated to PEG

<400> SEQUENCE: 35

Asn Trp Val Asn Val Ile Ser Asp Leu Lys Lys Ile Glu Asp Leu Ile
1               5                   10                  15

Gln Ser Met His Ile Asp Ala Thr Xaa Tyr Thr Glu Ser Asp Val His
            20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
            85                  90                  95

Lys Glu Phe Leu Gln Ser Phe Val His Ile Val Gln Met Phe Ile Asn
            100                 105                 110

Thr Ser

<210> SEQ ID NO 36
<211> LENGTH: 114
<212> TYPE: PRT
<213> ORGANISM: Artificial Sequence
<220> FEATURE:
<223> OTHER INFORMATION: Synthetic: IL-15_E46[AzK_L1_PEG]
<220> FEATURE:
<221> NAME/KEY: misc_feature
<222> LOCATION: (46)..(46)
<223> OTHER INFORMATION: Xaa is [AzK_L1_PEG] = N6-((2-azidoethoxy)-
      carbonyl)-L-lysine stably-conjugated to PEG

<400> SEQUENCE: 36

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Xaa Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
            85                  90                  95

Lys Glu Phe Leu Gln Ser Phe Val His Ile Val Gln Met Phe Ile Asn
            100                 105                 110

Thr Ser

<210> SEQ ID NO 37
<211> LENGTH: 114
<212> TYPE: PRT
<213> ORGANISM: Artificial Sequence
<220> FEATURE:
<223> OTHER INFORMATION: Synthetic: IL-15_E53[AzK_L1_PEG]
<220> FEATURE:
<221> NAME/KEY: misc_feature
<222> LOCATION: (53)..(53)
<223> OTHER INFORMATION: Xaa is [AzK_L1_PEG] = N6-((2-azidoethoxy)-
      carbonyl)-L-lysine stably-conjugated to PEG

<400> SEQUENCE: 37

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Xaa Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 38
<211> LENGTH: 114
<212> TYPE: PRT
<213> ORGANISM: Artificial Sequence
<220> FEATURE:
<223> OTHER INFORMATION: Synthetic: IL-15_N77[AzK_L1_PEG]
<220> FEATURE:
<221> NAME/KEY: misc_feature
<222> LOCATION: (77)..(77)
<223> OTHER INFORMATION: Xaa is [AzK_L1_PEG] = N6-((2-azidoethoxy)-
      carbonyl)-L-lysine stably-conjugated to PEG

<400> SEQUENCE: 38

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Xaa Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 39
<211> LENGTH: 114
<212> TYPE: PRT
<213> ORGANISM: Artificial Sequence
<220> FEATURE:
<223> OTHER INFORMATION: Synthetic: IL-15_S83[AzK_L1_PEG]
<220> FEATURE:
<221> NAME/KEY: misc_feature
<222> LOCATION: (83)..(83)
<223> OTHER INFORMATION: Xaa is [AzK_L1_PEG] = N6-((2-azidoethoxy)-
      carbonyl)-L-lysine stably-conjugated to PEG

<400> SEQUENCE: 39

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Xaa Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 40
<211> LENGTH: 114
<212> TYPE: PRT
<213> ORGANISM: Artificial Sequence
<220> FEATURE:
<223> OTHER INFORMATION: Synthetic: IL-15_S18[AzK_L1_PEG30]
<220> FEATURE:
<221> NAME/KEY: misc_feature
<222> LOCATION: (18)..(18)
<223> OTHER INFORMATION: Xaa is [AzK_L1_PEG30] = N6-((2-azidoethoxy)-
      carbonyl)-L-lysine stably-conjugated to PEG

<400> SEQUENCE: 40

Asn Trp Val Asn Val Ile Ser Asp Leu Lys Lys Ile Glu Asp Leu Ile
1               5                   10                  15

Gln Xaa Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

```
<210> SEQ ID NO 41
<211> LENGTH: 114
<212> TYPE: PRT
<213> ORGANISM: Artificial Sequence
<220> FEATURE:
<223> OTHER INFORMATION: Synthetic: IL-15_L25[AzK_L1_PEG30]
<220> FEATURE:
<221> NAME/KEY: misc_feature
<222> LOCATION: (25)..(25)
<223> OTHER INFORMATION: Xaa is [AzK_L1_PEG30] = N6-((2-azidoethoxy)-
      carbonyl)-L-lysine stably-conjugated to PEG

<400> SEQUENCE: 41

Asn Trp Val Asn Val Ile Ser Asp Leu Lys Lys Ile Glu Asp Leu Ile
1               5                   10                  15

Gln Ser Met His Ile Asp Ala Thr Xaa Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 42
<211> LENGTH: 114
<212> TYPE: PRT
<213> ORGANISM: Artificial Sequence
<220> FEATURE:
<223> OTHER INFORMATION: Synthetic: IL-15_E46[AzK_L1_PEG30]
<220> FEATURE:
<221> NAME/KEY: misc_feature
<222> LOCATION: (46)..(46)
<223> OTHER INFORMATION: Xaa is [AzK_L1_PEG30] = N6-((2-azidoethoxy)-
      carbonyl)-L-lysine stably-conjugated to PEG

<400> SEQUENCE: 42

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Xaa Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 43
<211> LENGTH: 114
<212> TYPE: PRT
```

<213> ORGANISM: Artificial Sequence
<220> FEATURE:
<223> OTHER INFORMATION: Synthetic: IL-15_E53[AzK_L1_PEG30]
<220> FEATURE:
<221> NAME/KEY: misc_feature
<222> LOCATION: (53)..(53)
<223> OTHER INFORMATION: Xaa is [AzK_L1_PEG30] = N6-((2-azidoethoxy)-
      carbonyl)-L-lysine stably-conjugated to PEG

<400> SEQUENCE: 43

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Xaa Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 44
<211> LENGTH: 114
<212> TYPE: PRT
<213> ORGANISM: Artificial Sequence
<220> FEATURE:
<223> OTHER INFORMATION: Synthetic: IL-15_N77[AzK_L1_PEG30]
<220> FEATURE:
<221> NAME/KEY: misc_feature
<222> LOCATION: (77)..(77)
<223> OTHER INFORMATION: Xaa is [AzK_L1_PEG30] = N6-((2-azidoethoxy)-
      carbonyl)-L-lysine stably-conjugated to PEG

<400> SEQUENCE: 44

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Xaa Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 45
<211> LENGTH: 114
<212> TYPE: PRT
<213> ORGANISM: Artificial Sequence
<220> FEATURE:
<223> OTHER INFORMATION: Synthetic: IL-15_S83[AzK_L1_PEG30]

```
<220> FEATURE:
<221> NAME/KEY: misc_feature
<222> LOCATION: (83)..(83)
<223> OTHER INFORMATION: Xaa is [AzK_L1_PEG30] = N6-((2-azidoethoxy)-
      carbonyl)-L-lysine stably-conjugated to PEG

<400> SEQUENCE: 45

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Xaa Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 46
<211> LENGTH: 114
<212> TYPE: PRT
<213> ORGANISM: Artificial Sequence
<220> FEATURE:
<223> OTHER INFORMATION: Synthetic: IL-15_S18[AzK_L1_PEG40]
<220> FEATURE:
<221> NAME/KEY: misc_feature
<222> LOCATION: (18)..(18)
<223> OTHER INFORMATION: Xaa is [AzK_L1_PEG40] = N6-((2-azidoethoxy)-
      carbonyl)-L-lysine stably-conjugated to PEG

<400> SEQUENCE: 46

Asn Trp Val Asn Val Ile Ser Asp Leu Lys Lys Ile Glu Asp Leu Ile
1               5                   10                  15

Gln Xaa Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 47
<211> LENGTH: 114
<212> TYPE: PRT
<213> ORGANISM: Artificial Sequence
<220> FEATURE:
<223> OTHER INFORMATION: Synthetic: IL-15_L25[AzK_L1_PEG40]
<220> FEATURE:
<221> NAME/KEY: misc_feature
<222> LOCATION: (25)..(25)
```

```
<223> OTHER INFORMATION: Xaa is [AzK_L1_PEG40] = N6-((2-azidoethoxy)-
      carbonyl)-L-lysine stably-conjugated to PEG

<400> SEQUENCE: 47

Asn Trp Val Asn Val Ile Ser Asp Leu Lys Lys Ile Glu Asp Leu Ile
1               5                   10                  15

Gln Ser Met His Ile Asp Ala Thr Xaa Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 48
<211> LENGTH: 114
<212> TYPE: PRT
<213> ORGANISM: Artificial Sequence
<220> FEATURE:
<223> OTHER INFORMATION: Synthetic: IL-15_E46[AzK_L1_PEG40]
<220> FEATURE:
<221> NAME/KEY: misc_feature
<222> LOCATION: (46)..(46)
<223> OTHER INFORMATION: Xaa is [AzK_L1_PEG40] = N6-((2-azidoethoxy)-
      carbonyl)-L-lysine stably-conjugated to PEG

<400> SEQUENCE: 48

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Xaa Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 49
<211> LENGTH: 114
<212> TYPE: PRT
<213> ORGANISM: Artificial Sequence
<220> FEATURE:
<223> OTHER INFORMATION: Synthetic: IL-15_E53[AzK_L1_PEG40]
<220> FEATURE:
<221> NAME/KEY: misc_feature
<222> LOCATION: (53)..(53)
<223> OTHER INFORMATION: Xaa is [AzK_L1_PEG40] = N6-((2-azidoethoxy)-
      carbonyl)-L-lysine stably-conjugated to PEG
```

<400> SEQUENCE: 49

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Xaa Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 50
<211> LENGTH: 114
<212> TYPE: PRT
<213> ORGANISM: Artificial Sequence
<220> FEATURE:
<223> OTHER INFORMATION: Synthetic: IL-15_N77[AzK_L1_PEG40]
<220> FEATURE:
<221> NAME/KEY: misc_feature
<222> LOCATION: (77)..(77)
<223> OTHER INFORMATION: Xaa is [AzK_L1_PEG40] = N6-((2-azidoethoxy)-
      carbonyl)-L-lysine stably-conjugated to PEG

<400> SEQUENCE: 50

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Xaa Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 51
<211> LENGTH: 114
<212> TYPE: PRT
<213> ORGANISM: Artificial Sequence
<220> FEATURE:
<223> OTHER INFORMATION: Synthetic: IL-15_S83[AzK_L1_PEG40]
<220> FEATURE:
<221> NAME/KEY: misc_feature
<222> LOCATION: (83)..(83)
<223> OTHER INFORMATION: Xaa is [AzK_L1_PEG40] = N6-((2-azidoethoxy)-
      carbonyl)-L-lysine stably-conjugated to PEG

<400> SEQUENCE: 51

Asn Trp Val Asn Val Ile Ser Asp Leu Lys Lys Ile Glu Asp Leu Ile

```
              1               5                  10                 15
Gln Ser Met His Ile Asp Ala Thr Leu Tyr Thr Glu Ser Asp Val His
               20                 25                 30
Pro Ser Cys Lys Val Thr Ala Met Lys Cys Phe Leu Leu Glu Leu Gln
               35                 40                 45
Val Ile Ser Leu Glu Ser Gly Asp Ala Ser Ile His Asp Thr Val Glu
     50                 55                 60
Asn Leu Ile Ile Leu Ala Asn Asn Ser Leu Ser Ser Asn Gly Asn Val
 65                 70                 75                 80
Thr Glu Xaa Gly Cys Lys Glu Cys Glu Glu Leu Glu Glu Lys Asn Ile
               85                 90                 95
Lys Glu Phe Leu Gln Ser Phe Val His Ile Val Gln Met Phe Ile Asn
               100                105                110
Thr Ser
```

<210> SEQ ID NO 52
<211> LENGTH: 115
<212> TYPE: PRT
<213> ORGANISM: Artificial Sequence
<220> FEATURE:
<223> OTHER INFORMATION: Synthetic: IL-15_S19X
<220> FEATURE:
<221> NAME/KEY: misc_feature
<222> LOCATION: (19)..(19)
<223> OTHER INFORMATION: Xaa is an unnatural amino acid

<400> SEQUENCE: 52

```
Met Asn Trp Val Asn Val Ile Ser Asp Leu Lys Lys Ile Glu Asp Leu
 1               5                  10                 15
Ile Gln Xaa Met His Ile Asp Ala Thr Leu Tyr Thr Glu Ser Asp Val
               20                 25                 30
His Pro Ser Cys Lys Val Thr Ala Met Lys Cys Phe Leu Leu Glu Leu
               35                 40                 45
Gln Val Ile Ser Leu Glu Ser Gly Asp Ala Ser Ile His Asp Thr Val
     50                 55                 60
Glu Asn Leu Ile Ile Leu Ala Asn Asn Ser Leu Ser Ser Asn Gly Asn
 65                 70                 75                 80
Val Thr Glu Ser Gly Cys Lys Glu Cys Glu Glu Leu Glu Glu Lys Asn
               85                 90                 95
Ile Lys Glu Phe Leu Gln Ser Phe Val His Ile Val Gln Met Phe Ile
               100                105                110
Asn Thr Ser
          115
```

<210> SEQ ID NO 53
<211> LENGTH: 115
<212> TYPE: PRT
<213> ORGANISM: Artificial Sequence
<220> FEATURE:
<223> OTHER INFORMATION: Synthetic: IL-15_L26X
<220> FEATURE:
<221> NAME/KEY: misc_feature
<222> LOCATION: (26)..(26)
<223> OTHER INFORMATION: Xaa is an unnatural amino acid

<400> SEQUENCE: 53

```
Met Asn Trp Val Asn Val Ile Ser Asp Leu Lys Lys Ile Glu Asp Leu
 1               5                  10                 15
Ile Gln Ser Met His Ile Asp Ala Thr Xaa Tyr Thr Glu Ser Asp Val
               20                 25                 30
```

```
His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
 50                  55                  60

Glu Asn Leu Ile Ile Leu Ala Asn Asn Ser Leu Ser Ser Asn Gly Asn
 65                  70                  75                  80

Val Thr Glu Ser Gly Cys Lys Glu Cys Glu Glu Leu Glu Glu Lys Asn
                 85                  90                  95

Ile Lys Glu Phe Leu Gln Ser Phe Val His Ile Val Gln Met Phe Ile
            100                 105                 110

Asn Thr Ser
        115

<210> SEQ ID NO 54
<211> LENGTH: 115
<212> TYPE: PRT
<213> ORGANISM: Artificial Sequence
<220> FEATURE:
<223> OTHER INFORMATION: Synthetic: IL-15_E47X
<220> FEATURE:
<221> NAME/KEY: misc_feature
<222> LOCATION: (47)..(47)
<223> OTHER INFORMATION: Xaa is an unnatural amino acid

<400> SEQUENCE: 54

Met Asn Trp Val Asn Val Ile Ser Asp Leu Lys Lys Ile Glu Asp Leu
 1               5                  10                  15

Ile Gln Ser Met His Ile Asp Ala Thr Leu Tyr Thr Glu Ser Asp Val
             20                  25                  30

His Pro Ser Cys Lys Val Thr Ala Met Lys Cys Phe Leu Leu Xaa Leu
        35                  40                  45

Gln Val Ile Ser Leu Glu Ser Gly Asp Ala Ser Ile His Asp Thr Val
 50                  55                  60

Glu Asn Leu Ile Ile Leu Ala Asn Asn Ser Leu Ser Ser Asn Gly Asn
 65                  70                  75                  80

Val Thr Glu Ser Gly Cys Lys Glu Cys Glu Glu Leu Glu Glu Lys Asn
                 85                  90                  95

Ile Lys Glu Phe Leu Gln Ser Phe Val His Ile Val Gln Met Phe Ile
            100                 105                 110

Asn Thr Ser
        115

<210> SEQ ID NO 55
<211> LENGTH: 115
<212> TYPE: PRT
<213> ORGANISM: Artificial Sequence
<220> FEATURE:
<223> OTHER INFORMATION: Synthetic: IL-15_E54X
<220> FEATURE:
<221> NAME/KEY: misc_feature
<222> LOCATION: (54)..(54)
<223> OTHER INFORMATION: Xaa is an unnatural amino acid

<400> SEQUENCE: 55

Met Asn Trp Val Asn Val Ile Ser Asp Leu Lys Lys Ile Glu Asp Leu
 1               5                  10                  15

Ile Gln Ser Met His Ile Asp Ala Thr Leu Tyr Thr Glu Ser Asp Val
             20                  25                  30

His Pro Ser Cys Lys Val Thr Ala Met Lys Cys Phe Leu Leu Glu Leu
        35                  40                  45
```

Gln Val Ile Ser Leu Xaa Ser Gly Asp Ala Ser Ile His Asp Thr Val
                50                  55                  60

Glu Asn Leu Ile Ile Leu Ala Asn Asn Ser Leu Ser Ser Asn Gly Asn
 65                  70                  75                  80

Val Thr Glu Ser Gly Cys Lys Glu Cys Glu Glu Leu Glu Glu Lys Asn
                 85                  90                  95

Ile Lys Glu Phe Leu Gln Ser Phe Val His Ile Val Gln Met Phe Ile
            100                 105                 110

Asn Thr Ser
        115

<210> SEQ ID NO 56
<211> LENGTH: 115
<212> TYPE: PRT
<213> ORGANISM: Artificial Sequence
<220> FEATURE:
<223> OTHER INFORMATION: Synthetic: IL-15_N78X
<220> FEATURE:
<221> NAME/KEY: misc_feature
<222> LOCATION: (78)..(78)
<223> OTHER INFORMATION: Xaa is an unnatural amino acid

<400> SEQUENCE: 56

Met Asn Trp Val Asn Val Ile Ser Asp Leu Lys Lys Ile Glu Asp Leu
 1               5                  10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
                50                  55                  60

Glu Asn Leu Ile Ile Leu Ala Asn Asn Ser Leu Ser Ser Xaa Gly Asn
 65                  70                  75                  80

Val Thr Glu Ser Gly Cys Lys Glu Cys Glu Glu Leu Glu Glu Lys Asn
                 85                  90                  95

Ile Lys Glu Phe Leu Gln Ser Phe Val His Ile Val Gln Met Phe Ile
            100                 105                 110

Asn Thr Ser
        115

<210> SEQ ID NO 57
<211> LENGTH: 115
<212> TYPE: PRT
<213> ORGANISM: Artificial Sequence
<220> FEATURE:
<223> OTHER INFORMATION: Synthetic: IL-15_S84X
<220> FEATURE:
<221> NAME/KEY: misc_feature
<222> LOCATION: (84)..(84)
<223> OTHER INFORMATION: Xaa is an unnatural amino acid

<400> SEQUENCE: 57

Met Asn Trp Val Asn Val Ile Ser Asp Leu Lys Lys Ile Glu Asp Leu
 1               5                  10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
                50                  55                  60

```
Glu Asn Leu Ile Ile Leu Ala Asn Asn Ser Leu Ser Ser Asn Gly Asn
 65                  70                  75                  80

Val Thr Glu Xaa Gly Cys Lys Glu Cys Glu Glu Leu Glu Glu Lys Asn
             85                  90                  95

Ile Lys Glu Phe Leu Gln Ser Phe Val His Ile Val Gln Met Phe Ile
            100                 105                 110

Asn Thr Ser
        115

<210> SEQ ID NO 58
<211> LENGTH: 115
<212> TYPE: PRT
<213> ORGANISM: Artificial Sequence
<220> FEATURE:
<223> OTHER INFORMATION: Synthetic: IL-15_S19[AzK]
<220> FEATURE:
<221> NAME/KEY: misc_feature
<222> LOCATION: (19)..(19)
<223> OTHER INFORMATION: Xaa is [AzK] = N6-((2-azidoethoxy)-carbonyl)-L-
      lysine

<400> SEQUENCE: 58

Met Asn Trp Val Asn Val Ile Ser Asp Leu Lys Lys Ile Glu Asp Leu
  1               5                  10                  15

Ile Gln Xaa Met His Ile Asp Ala Thr Leu Tyr Thr Glu Ser Asp Val
             20                  25                  30

His Pro Ser Cys Lys Val Thr Ala Met Lys Cys Phe Leu Leu Glu Leu
         35                  40                  45

Gln Val Ile Ser Leu Glu Ser Gly Asp Ala Ser Ile His Asp Thr Val
 50                  55                  60

Glu Asn Leu Ile Ile Leu Ala Asn Asn Ser Leu Ser Ser Asn Gly Asn
 65                  70                  75                  80

Val Thr Glu Ser Gly Cys Lys Glu Cys Glu Glu Leu Glu Glu Lys Asn
             85                  90                  95

Ile Lys Glu Phe Leu Gln Ser Phe Val His Ile Val Gln Met Phe Ile
            100                 105                 110

Asn Thr Ser
        115

<210> SEQ ID NO 59
<211> LENGTH: 115
<212> TYPE: PRT
<213> ORGANISM: Artificial Sequence
<220> FEATURE:
<223> OTHER INFORMATION: Synthetic: IL-15_L26[AzK]
<220> FEATURE:
<221> NAME/KEY: misc_feature
<222> LOCATION: (26)..(26)
<223> OTHER INFORMATION: Xaa is [AzK] = N6-((2-azidoethoxy)-carbonyl)-L-
      lysine

<400> SEQUENCE: 59

Met Asn Trp Val Asn Val Ile Ser Asp Leu Lys Lys Ile Glu Asp Leu
  1               5                  10                  15

Ile Gln Ser Met His Ile Asp Ala Thr Xaa Tyr Thr Glu Ser Asp Val
             20                  25                  30

His Pro Ser Cys Lys Val Thr Ala Met Lys Cys Phe Leu Leu Glu Leu
         35                  40                  45

Gln Val Ile Ser Leu Glu Ser Gly Asp Ala Ser Ile His Asp Thr Val
 50                  55                  60
```

```
Glu Asn Leu Ile Ile Leu Ala Asn Asn Ser Leu Ser Ser Asn Gly Asn
 65                  70                  75                  80

Val Thr Glu Ser Gly Cys Lys Glu Cys Glu Glu Leu Glu Glu Lys Asn
                 85                  90                  95

Ile Lys Glu Phe Leu Gln Ser Phe Val His Ile Val Gln Met Phe Ile
            100                 105                 110

Asn Thr Ser
        115

<210> SEQ ID NO 60
<211> LENGTH: 115
<212> TYPE: PRT
<213> ORGANISM: Artificial Sequence
<220> FEATURE:
<223> OTHER INFORMATION: Synthetic: IL-15_E47[AzK]
<220> FEATURE:
<221> NAME/KEY: misc_feature
<222> LOCATION: (47)..(47)
<223> OTHER INFORMATION: Xaa is [AzK] = N6-((2-azidoethoxy)-carbonyl)-L-
      lysine

<400> SEQUENCE: 60

Met Asn Trp Val Asn Val Ile Ser Asp Leu Lys Lys Ile Glu Asp Leu
 1               5                  10                  15

Ile Gln Ser Met His Ile Asp Ala Thr Leu Tyr Thr Glu Ser Asp Val
             20                  25                  30

His Pro Ser Cys Lys Val Thr Ala Met Lys Cys Phe Leu Leu Xaa Leu
         35                  40                  45

Gln Val Ile Ser Leu Glu Ser Gly Asp Ala Ser Ile His Asp Thr Val
 50                  55                  60

Glu Asn Leu Ile Ile Leu Ala Asn Asn Ser Leu Ser Ser Asn Gly Asn
 65                  70                  75                  80

Val Thr Glu Ser Gly Cys Lys Glu Cys Glu Glu Leu Glu Glu Lys Asn
                 85                  90                  95

Ile Lys Glu Phe Leu Gln Ser Phe Val His Ile Val Gln Met Phe Ile
            100                 105                 110

Asn Thr Ser
        115

<210> SEQ ID NO 61
<211> LENGTH: 115
<212> TYPE: PRT
<213> ORGANISM: Artificial Sequence
<220> FEATURE:
<223> OTHER INFORMATION: Synthetic: IL-15_E54[AzK]
<220> FEATURE:
<221> NAME/KEY: misc_feature
<222> LOCATION: (54)..(54)
<223> OTHER INFORMATION: Xaa is [AzK] = N6-((2-azidoethoxy)-carbonyl)-L-
      lysine

<400> SEQUENCE: 61

Met Asn Trp Val Asn Val Ile Ser Asp Leu Lys Lys Ile Glu Asp Leu
 1               5                  10                  15

Ile Gln Ser Met His Ile Asp Ala Thr Leu Tyr Thr Glu Ser Asp Val
             20                  25                  30

His Pro Ser Cys Lys Val Thr Ala Met Lys Cys Phe Leu Leu Glu Leu
         35                  40                  45

Gln Val Ile Ser Leu Xaa Ser Gly Asp Ala Ser Ile His Asp Thr Val
 50                  55                  60

Glu Asn Leu Ile Ile Leu Ala Asn Asn Ser Leu Ser Ser Asn Gly Asn
```

65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 62
<211> LENGTH: 115
<212> TYPE: PRT
<213> ORGANISM: Artificial Sequence
<220> FEATURE:
<223> OTHER INFORMATION: Synthetic: IL-15_N78[AzK]
<220> FEATURE:
<221> NAME/KEY: misc_feature
<222> LOCATION: (78)..(78)
<223> OTHER INFORMATION: Xaa is [AzK] = N6-((2-azidoethoxy)-carbonyl)-L-
      lysine

<400> SEQUENCE: 62

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Xaa Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 63
<211> LENGTH: 115
<212> TYPE: PRT
<213> ORGANISM: Artificial Sequence
<220> FEATURE:
<223> OTHER INFORMATION: Synthetic: IL-15_S84[AzK]
<220> FEATURE:
<221> NAME/KEY: misc_feature
<222> LOCATION: (84)..(84)
<223> OTHER INFORMATION: Xaa is [AzK] = N6-((2-azidoethoxy)-carbonyl)-L-
      lysine

<400> SEQUENCE: 63

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

```
Val Thr Glu Xaa Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 64
<211> LENGTH: 115
<212> TYPE: PRT
<213> ORGANISM: Artificial Sequence
<220> FEATURE:
<223> OTHER INFORMATION: Synthetic: IL-15_S19[AzK_PEG]
<220> FEATURE:
<221> NAME/KEY: misc_feature
<222> LOCATION: (19)..(19)
<223> OTHER INFORMATION: Xaa is [AzK_PEG] = N6-((2-azidoethoxy)-
      carbonyl)-L-lysine stably-conjugated to PEG

<400> SEQUENCE: 64

Met Asn Trp Val Asn Val Ile Ser Asp Leu Lys Lys Ile Glu Asp Leu
1               5                   10                  15

Ile Gln Xaa Met His Ile Asp Ala Thr Leu Tyr Thr Gly Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 65
<211> LENGTH: 115
<212> TYPE: PRT
<213> ORGANISM: Artificial Sequence
<220> FEATURE:
<223> OTHER INFORMATION: Synthetic: IL-15_L26[AzK_PEG]
<220> FEATURE:
<221> NAME/KEY: misc_feature
<222> LOCATION: (26)..(26)
<223> OTHER INFORMATION: Xaa is [AzK_PEG] = N6-((2-azidoethoxy)-
      carbonyl)-L-lysine stably-conjugated to PEG

<400> SEQUENCE: 65

Met Asn Trp Val Asn Val Ile Ser Asp Leu Lys Lys Ile Glu Asp Leu
1               5                   10                  15

Ile Gln Ser Met His Ile Asp Ala Thr Xaa Tyr Thr Gly Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80
```

```
Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 66
<211> LENGTH: 115
<212> TYPE: PRT
<213> ORGANISM: Artificial Sequence
<220> FEATURE:
<223> OTHER INFORMATION: Synthetic: IL-15_E47[AzK_PEG]
<220> FEATURE:
<221> NAME/KEY: misc_feature
<222> LOCATION: (47)..(47)
<223> OTHER INFORMATION: Xaa is [AzK_PEG] = N6-((2-azidoethoxy)-
      carbonyl)-L-lysine stably-conjugated to PEG

<400> SEQUENCE: 66

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Xaa Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 67
<211> LENGTH: 115
<212> TYPE: PRT
<213> ORGANISM: Artificial Sequence
<220> FEATURE:
<223> OTHER INFORMATION: Synthetic: IL-15_E54[AzK_PEG]
<220> FEATURE:
<221> NAME/KEY: misc_feature
<222> LOCATION: (54)..(54)
<223> OTHER INFORMATION: Xaa is [AzK_PEG] = N6-((2-azidoethoxy)-
      carbonyl)-L-lysine stably-conjugated to PEG

<400> SEQUENCE: 67

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Xaa Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
```

```
                85                  90                  95

Ile Lys Glu Phe Leu Gln Ser Phe Val His Ile Val Gln Met Phe Ile
            100                 105                 110

Asn Thr Ser
        115

<210> SEQ ID NO 68
<211> LENGTH: 115
<212> TYPE: PRT
<213> ORGANISM: Artificial Sequence
<220> FEATURE:
<223> OTHER INFORMATION: Synthetic: IL-15_N78[AzK_PEG]
<220> FEATURE:
<221> NAME/KEY: misc_feature
<222> LOCATION: (78)..(78)
<223> OTHER INFORMATION: Xaa is [AzK_PEG] = N6-((2-azidoethoxy)-
      carbonyl)-L-lysine stably-conjugated to PEG

<400> SEQUENCE: 68

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Xaa Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 69
<211> LENGTH: 115
<212> TYPE: PRT
<213> ORGANISM: Artificial Sequence
<220> FEATURE:
<223> OTHER INFORMATION: Synthetic: IL-15_S84[AzK_PEG]
<220> FEATURE:
<221> NAME/KEY: misc_feature
<222> LOCATION: (84)..(84)
<223> OTHER INFORMATION: Xaa is [AzK_PEG] = N6-((2-azidoethoxy)-
      carbonyl)-L-lysine stably-conjugated to PEG

<400> SEQUENCE: 69

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Xaa Gly Cys Lys Glu Cys Glu Glu Leu Glu Glu Lys Asn
                85                  90                  95
```

```
Ile Lys Glu Phe Leu Gln Ser Phe Val His Ile Val Gln Met Phe Ile
            100                 105                 110

Asn Thr Ser
        115

<210> SEQ ID NO 70
<211> LENGTH: 115
<212> TYPE: PRT
<213> ORGANISM: Artificial Sequence
<220> FEATURE:
<223> OTHER INFORMATION: Synthetic: IL-15_S19[AzK_PEG30]
<220> FEATURE:
<221> NAME/KEY: misc_feature
<222> LOCATION: (19)..(19)
<223> OTHER INFORMATION: Xaa is [AzK_PEG30] = N6-((2-azidoethoxy)-
      carbonyl)-L-lysine stably-conjugated to PEG

<400> SEQUENCE: 70

Met Asn Trp Val Asn Val Ile Ser Asp Leu Lys Lys Ile Glu Asp Leu
1               5                   10                  15

Ile Gln Xaa Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 71
<211> LENGTH: 115
<212> TYPE: PRT
<213> ORGANISM: Artificial Sequence
<220> FEATURE:
<223> OTHER INFORMATION: Synthetic: IL-15_L26[AzK_PEG30]
<220> FEATURE:
<221> NAME/KEY: misc_feature
<222> LOCATION: (26)..(26)
<223> OTHER INFORMATION: Xaa is [AzK_PEG30] = N6-((2-azidoethoxy)-
      carbonyl)-L-lysine stably-conjugated to PEG

<400> SEQUENCE: 71

Met Asn Trp Val Asn Val Ile Ser Asp Leu Lys Lys Ile Glu Asp Leu
1               5                   10                  15

Ile Gln Ser Met His Ile Asp Ala Thr Xaa Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95
```

Ile Lys Glu Phe Leu Gln Ser Phe Val His Ile Val Gln Met Phe Ile
            100                 105                 110

Asn Thr Ser
        115

<210> SEQ ID NO 72
<211> LENGTH: 115
<212> TYPE: PRT
<213> ORGANISM: Artificial Sequence
<220> FEATURE:
<223> OTHER INFORMATION: Synthetic: IL-15_E47[AzK_PEG30]
<220> FEATURE:
<221> NAME/KEY: misc_feature
<222> LOCATION: (47)..(47)
<223> OTHER INFORMATION: Xaa is [AzK_PEG30] = N6-((2-azidoethoxy)-
      carbonyl)-L-lysine stably-conjugated to PEG

<400> SEQUENCE: 72

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Xaa Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 73
<211> LENGTH: 115
<212> TYPE: PRT
<213> ORGANISM: Artificial Sequence
<220> FEATURE:
<223> OTHER INFORMATION: Synthetic: IL-15_E54[AzK_PEG30]
<220> FEATURE:
<221> NAME/KEY: misc_feature
<222> LOCATION: (54)..(54)
<223> OTHER INFORMATION: Xaa is [AzK_PEG30] = N6-((2-azidoethoxy)-
      carbonyl)-L-lysine stably-conjugated to PEG

<400> SEQUENCE: 73

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Xaa Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile

```
                    100                 105                 110

Asn Thr Ser
        115

<210> SEQ ID NO 74
<211> LENGTH: 115
<212> TYPE: PRT
<213> ORGANISM: Artificial Sequence
<220> FEATURE:
<223> OTHER INFORMATION: Synthetic: IL-15_N78[AzK_PEG30]
<220> FEATURE:
<221> NAME/KEY: misc_feature
<222> LOCATION: (78)..(78)
<223> OTHER INFORMATION: Xaa is [AzK_PEG30] = N6-((2-azidoethoxy)-
      carbonyl)-L-lysine stably-conjugated to PEG

<400> SEQUENCE: 74

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Xaa Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 75
<211> LENGTH: 115
<212> TYPE: PRT
<213> ORGANISM: Artificial Sequence
<220> FEATURE:
<223> OTHER INFORMATION: Synthetic: IL-15_S84[AzK_PEG30]
<220> FEATURE:
<221> NAME/KEY: misc_feature
<222> LOCATION: (84)..(84)
<223> OTHER INFORMATION: Xaa is [AzK_PEG30] = N6-((2-azidoethoxy)-
      carbonyl)-L-lysine stably-conjugated to PEG

<400> SEQUENCE: 75

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Xaa Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110
```

Asn Thr Ser
        115

<210> SEQ ID NO 76
<211> LENGTH: 115
<212> TYPE: PRT
<213> ORGANISM: Artificial Sequence
<220> FEATURE:
<223> OTHER INFORMATION: Synthetic: IL-15_S19[AzK_PEG40]
<220> FEATURE:
<221> NAME/KEY: misc_feature
<222> LOCATION: (19)..(19)
<223> OTHER INFORMATION: Xaa is [AzK_PEG40] = N6-((2-azidoethoxy)-
      carbonyl)-L-lysine stably-conjugated to PEG

<400> SEQUENCE: 76

Met Asn Trp Val Asn Val Ile Ser Asp Leu Lys Lys Ile Glu Asp Leu
1               5                   10                  15

Ile Gln Xaa Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 77
<211> LENGTH: 115
<212> TYPE: PRT
<213> ORGANISM: Artificial Sequence
<220> FEATURE:
<223> OTHER INFORMATION: Synthetic: IL-15_L26[AzK_PEG40]
<220> FEATURE:
<221> NAME/KEY: misc_feature
<222> LOCATION: (26)..(26)
<223> OTHER INFORMATION: Xaa is [AzK_PEG40] = N6-((2-azidoethoxy)-
      carbonyl)-L-lysine stably-conjugated to PEG

<400> SEQUENCE: 77

Met Asn Trp Val Asn Val Ile Ser Asp Leu Lys Lys Ile Glu Asp Leu
1               5                   10                  15

Ile Gln Ser Met His Ile Asp Ala Thr Xaa Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 78
<211> LENGTH: 115
<212> TYPE: PRT
<213> ORGANISM: Artificial Sequence
<220> FEATURE:
<223> OTHER INFORMATION: Synthetic: IL-15_E47[AzK_PEG40]
<220> FEATURE:
<221> NAME/KEY: misc_feature
<222> LOCATION: (47)..(47)
<223> OTHER INFORMATION: Xaa is [AzK_PEG40] = N6-((2-azidoethoxy)-
      carbonyl)-L-lysine stably-conjugated to PEG

<400> SEQUENCE: 78

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Xaa Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 79
<211> LENGTH: 115
<212> TYPE: PRT
<213> ORGANISM: Artificial Sequence
<220> FEATURE:
<223> OTHER INFORMATION: Synthetic: IL-15_E54[AzK_PEG40]
<220> FEATURE:
<221> NAME/KEY: misc_feature
<222> LOCATION: (54)..(54)
<223> OTHER INFORMATION: Xaa is [AzK_PEG40] = N6-((2-azidoethoxy)-
      carbonyl)-L-lysine stably-conjugated to PEG

<400> SEQUENCE: 79

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Xaa Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser

```
<210> SEQ ID NO 80
<211> LENGTH: 115
<212> TYPE: PRT
<213> ORGANISM: Artificial Sequence
<220> FEATURE:
<223> OTHER INFORMATION: Synthetic: IL-15_N78[AzK_PEG40]
<220> FEATURE:
<221> NAME/KEY: misc_feature
<222> LOCATION: (78)..(78)
<223> OTHER INFORMATION: Xaa is [AzK_PEG40] = N6-((2-azidoethoxy)-
      carbonyl)-L-lysine stably-conjugated to PEG

<400> SEQUENCE: 80

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Xaa Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 81
<211> LENGTH: 115
<212> TYPE: PRT
<213> ORGANISM: Artificial Sequence
<220> FEATURE:
<223> OTHER INFORMATION: Synthetic: IL-15_S84[AzK_PEG40]
<220> FEATURE:
<221> NAME/KEY: misc_feature
<222> LOCATION: (84)..(84)
<223> OTHER INFORMATION: Xaa is [AzK_PEG40] = N6-((2-azidoethoxy)-
      carbonyl)-L-lysine stably-conjugated to PEG

<400> SEQUENCE: 81

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Xaa Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115
```

<210> SEQ ID NO 82
<211> LENGTH: 115
<212> TYPE: PRT
<213> ORGANISM: Artificial Sequence
<220> FEATURE:
<223> OTHER INFORMATION: Synthetic: IL-15_S19[AzK_L1_PEG]
<220> FEATURE:
<221> NAME/KEY: misc_feature
<222> LOCATION: (19)..(19)
<223> OTHER INFORMATION: [AzK_L1_PEG] = N6-((2-azidoethoxy)-carbonyl)-L-lysine stably-conjugated to PEG

<400> SEQUENCE: 82

```
Met Asn Trp Val Asn Val Ile Ser Asp Leu Lys Lys Ile Glu Asp Leu
1               5                   10                  15

Ile Gln Xaa Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115
```

<210> SEQ ID NO 83
<211> LENGTH: 115
<212> TYPE: PRT
<213> ORGANISM: Artificial Sequence
<220> FEATURE:
<223> OTHER INFORMATION: Synthetic: IL-15_L26[AzK_L1_PEG]
<220> FEATURE:
<221> NAME/KEY: misc_feature
<222> LOCATION: (26)..(26)
<223> OTHER INFORMATION: Xaa is [AzK_L1_PEG] = N6-((2-azidoethoxy)-carbonyl)-L-lysine stably-conjugated to PEG

<400> SEQUENCE: 83

```
Met Asn Trp Val Asn Val Ile Ser Asp Leu Lys Lys Ile Glu Asp Leu
1               5                   10                  15

Ile Gln Ser Met His Ile Asp Ala Thr Xaa Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115
```

```
<210> SEQ ID NO 84
<211> LENGTH: 115
<212> TYPE: PRT
<213> ORGANISM: Artificial Sequence
<220> FEATURE:
<223> OTHER INFORMATION: Synthetic: IL-15_E47[AzK_L1_PEG]
<220> FEATURE:
<221> NAME/KEY: misc_feature
<222> LOCATION: (47)..(47)
<223> OTHER INFORMATION: Xaa is [AzK_L1_PEG] = N6-((2-azidoethoxy)-
      carbonyl)-L-lysine stably-conjugated to PEG

<400> SEQUENCE: 84

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Xaa Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 85
<211> LENGTH: 115
<212> TYPE: PRT
<213> ORGANISM: Artificial Sequence
<220> FEATURE:
<223> OTHER INFORMATION: Synthetic: IL-15_E54[AzK_L1_PEG]
<220> FEATURE:
<221> NAME/KEY: misc_feature
<222> LOCATION: (54)..(54)
<223> OTHER INFORMATION: Xaa is [AzK_L1_PEG] = N6-((2-azidoethoxy)-
      carbonyl)-L-lysine stably-conjugated to PEG

<400> SEQUENCE: 85

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Xaa Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115
```

```
<210> SEQ ID NO 86
<211> LENGTH: 115
<212> TYPE: PRT
<213> ORGANISM: Artificial Sequence
<220> FEATURE:
<223> OTHER INFORMATION: Synthetic: IL-15_N78[AzK_L1_PEG]
<220> FEATURE:
<221> NAME/KEY: misc_feature
<222> LOCATION: (78)..(78)
<223> OTHER INFORMATION: Xaa is [AzK_L1_PEG] = N6-((2-azidoethoxy)-
      carbonyl)-L-lysine stably-conjugated to PEG

<400> SEQUENCE: 86

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Xaa Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 87
<211> LENGTH: 115
<212> TYPE: PRT
<213> ORGANISM: Artificial Sequence
<220> FEATURE:
<223> OTHER INFORMATION: Synthetic: IL-15_S84[AzK_L1_PEG]
<220> FEATURE:
<221> NAME/KEY: misc_feature
<222> LOCATION: (84)..(84)
<223> OTHER INFORMATION: Xaa is [AzK_L1_PEG] = N6-((2-azidoethoxy)-
      carbonyl)-L-lysine stably-conjugated to PEG

<400> SEQUENCE: 87

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Xaa Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 88
```

```
<211> LENGTH: 115
<212> TYPE: PRT
<213> ORGANISM: Artificial Sequence
<220> FEATURE:
<223> OTHER INFORMATION: Synthetic: IL-15_S19[AzK_L1_PEG30]
<220> FEATURE:
<221> NAME/KEY: misc_feature
<222> LOCATION: (19)..(19)
<223> OTHER INFORMATION: Xaa is [AzK_L1_PEG30] = N6-((2-azidoethoxy)-
      carbonyl)-L-lysine stably-conjugated to PEG

<400> SEQUENCE: 88

Met Asn Trp Val Asn Val Ile Ser Asp Leu Lys Lys Ile Glu Asp Leu
1               5                   10                  15

Ile Gln Xaa Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 89
<211> LENGTH: 115
<212> TYPE: PRT
<213> ORGANISM: Artificial Sequence
<220> FEATURE:
<223> OTHER INFORMATION: Synthetic: IL-15_L26[AzK_L1_PEG30]
<220> FEATURE:
<221> NAME/KEY: misc_feature
<222> LOCATION: (26)..(26)
<223> OTHER INFORMATION: Xaa is [AzK_L1_PEG30] = N6-((2-azidoethoxy)-
      carbonyl)-L-lysine stably-conjugated to PEG

<400> SEQUENCE: 89

Met Asn Trp Val Asn Val Ile Ser Asp Leu Lys Lys Ile Glu Asp Leu
1               5                   10                  15

Ile Gln Ser Met His Ile Asp Ala Thr Xaa Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 90
<211> LENGTH: 115
```

```
<212> TYPE: PRT
<213> ORGANISM: Artificial Sequence
<220> FEATURE:
<223> OTHER INFORMATION: Synthetic: IL-15_E47[AzK_L1_PEG30]
<220> FEATURE:
<221> NAME/KEY: misc_feature
<222> LOCATION: (47)..(47)
<223> OTHER INFORMATION: Xaa is [AzK_L1_PEG30] = N6-((2-azidoethoxy)-
      carbonyl)-L-lysine stably-conjugated to PEG

<400> SEQUENCE: 90

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Xaa Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 91
<211> LENGTH: 115
<212> TYPE: PRT
<213> ORGANISM: Artificial Sequence
<220> FEATURE:
<223> OTHER INFORMATION: Synthetic: IL-15_E54[AzK_L1_PEG30]
<220> FEATURE:
<221> NAME/KEY: misc_feature
<222> LOCATION: (54)..(54)
<223> OTHER INFORMATION: Xaa is [AzK_L1_PEG30] = N6-((2-azidoethoxy)-
      carbonyl)-L-lysine stably-conjugated to PEG

<400> SEQUENCE: 91

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Xaa Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 92
<211> LENGTH: 115
<212> TYPE: PRT
```

<213> ORGANISM: Artificial Sequence
<220> FEATURE:
<223> OTHER INFORMATION: Synthetic: IL-15_N78[AzK_L1_PEG30]
<220> FEATURE:
<221> NAME/KEY: misc_feature
<222> LOCATION: (78)..(78)
<223> OTHER INFORMATION: Xaa is [AzK_L1_PEG30] = N6-((2-azidoethoxy)-carbonyl)-L-lysine stably-conjugated to PEG

<400> SEQUENCE: 92

```
Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Xaa Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115
```

<210> SEQ ID NO 93
<211> LENGTH: 115
<212> TYPE: PRT
<213> ORGANISM: Artificial Sequence
<220> FEATURE:
<223> OTHER INFORMATION: Synthetic: IL-15_S84[AzK_L1_PEG30]
<220> FEATURE:
<221> NAME/KEY: misc_feature
<222> LOCATION: (84)..(84)
<223> OTHER INFORMATION: Xaa is [AzK_L1_PEG30] = N6-((2-azidoethoxy)-carbonyl)-L-lysine stably-conjugated to PEG

<400> SEQUENCE: 93

```
Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Xaa Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115
```

<210> SEQ ID NO 94
<211> LENGTH: 115
<212> TYPE: PRT
<213> ORGANISM: Artificial Sequence

```
<220> FEATURE:
<223> OTHER INFORMATION: Synthetic: IL-15_S19[AzK_L1_PEG40]
<220> FEATURE:
<221> NAME/KEY: misc_feature
<222> LOCATION: (19)..(19)
<223> OTHER INFORMATION: Xaa is [AzK_L1_PEG40] = N6-((2-azidoethoxy)-
      carbonyl)-L-lysine stably-conjugated to PEG

<400> SEQUENCE: 94

Met Asn Trp Val Asn Val Ile Ser Asp Leu Lys Lys Ile Glu Asp Leu
1               5                   10                  15

Ile Gln Xaa Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 95
<211> LENGTH: 115
<212> TYPE: PRT
<213> ORGANISM: Artificial Sequence
<220> FEATURE:
<223> OTHER INFORMATION: Synthetic: IL-15_L26[AzK_L1_PEG40]
<220> FEATURE:
<221> NAME/KEY: misc_feature
<222> LOCATION: (26)..(26)
<223> OTHER INFORMATION: Xaa is [AzK_L1_PEG40] = N6-((2-azidoethoxy)-
      carbonyl)-L-lysine stably-conjugated to PEG

<400> SEQUENCE: 95

Met Asn Trp Val Asn Val Ile Ser Asp Leu Lys Lys Ile Glu Asp Leu
1               5                   10                  15

Ile Gln Ser Met His Ile Asp Ala Thr Xaa Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 96
<211> LENGTH: 115
<212> TYPE: PRT
<213> ORGANISM: Artificial Sequence
<220> FEATURE:
```

```
<223> OTHER INFORMATION: Synthetic: IL-15_E47[AzK_L1_PEG40]
<220> FEATURE:
<221> NAME/KEY: misc_feature
<222> LOCATION: (47)..(47)
<223> OTHER INFORMATION: Xaa is [AzK_L1_PEG40] = N6-((2-azidoethoxy)-
      carbonyl)-L-lysine stably-conjugated to PEG

<400> SEQUENCE: 96
```

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Xaa Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

```
<210> SEQ ID NO 97
<211> LENGTH: 115
<212> TYPE: PRT
<213> ORGANISM: Artificial Sequence
<220> FEATURE:
<223> OTHER INFORMATION: Synthetic: IL-15_E54[AzK_L1_PEG40]
<220> FEATURE:
<221> NAME/KEY: misc_feature
<222> LOCATION: (54)..(54)
<223> OTHER INFORMATION: Xaa is [AzK_L1_PEG40] = N6-((2-azidoethoxy)-
      carbonyl)-L-lysine stably-conjugated to PEG

<400> SEQUENCE: 97
```

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Xaa Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

```
<210> SEQ ID NO 98
<211> LENGTH: 115
<212> TYPE: PRT
<213> ORGANISM: Artificial Sequence
<220> FEATURE:
<223> OTHER INFORMATION: Synthetic: IL-15_N78[AzK_L1_PEG40]
```

```
<220> FEATURE:
<221> NAME/KEY: misc_feature
<222> LOCATION: (78)..(78)
<223> OTHER INFORMATION: Xaa is [AzK_L1_PEG40] = N6-((2-azidoethoxy)-
      carbonyl)-L-lysine stably-conjugated to PEG

<400> SEQUENCE: 98
```

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Xaa Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

```
<210> SEQ ID NO 99
<211> LENGTH: 115
<212> TYPE: PRT
<213> ORGANISM: Artificial Sequence
<220> FEATURE:
<223> OTHER INFORMATION: Synthetic: IL-15_S84[AzK_L1_PEG40]
<220> FEATURE:
<221> NAME/KEY: misc_feature
<222> LOCATION: (84)..(84)
<223> OTHER INFORMATION: Xaa is [AzK_L1_PEG40] = N6-((2-azidoethoxy)-
      carbonyl)-L-lysine stably-conjugated to PEG

<400> SEQUENCE: 99
```

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Xaa Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

IL-15 CONJUGATES AND USES THEREOF

This application claims the benefit of priority to U.S. Provisional Application No. 62/890,741, filed Aug. 23, 2019, U.S. Provisional Application No. 62/931,663, filed Nov. 6, 2019, and U.S. Provisional Application No. 62/958,177, filed Jan. 7, 2020, the contents of each of which are incorporated herein by reference in their entirety for all purposes.

SEQUENCE LISTING

This application contains a Sequence Listing which has been submitted electronically in ASCII format and is hereby incorporated by reference in its entirety. Said ASCII copy, created on Aug. 6, 2020, is named 2020-08-21_01183-0074-00PCT_ST25.txt and is 120 KB in size.

INTRODUCTION AND SUMMARY

Distinct populations of T cells modulate the immune system to maintain immune homeostasis and tolerance. For example, regulatory T (Treg) cells prevent inappropriate responses by the immune system by preventing pathological self-reactivity while cytotoxic T cells target and destroy infected cells and/or cancerous cells. In some embodiments, modulation of the different populations of T cells provides an option for treatment of a disease or indication.

Described herein are IL-15 conjugates comprising the amino acid sequence of SEQ ID NO: 1 in which at least one amino acid residue in the IL-15 conjugate is replaced by the structure of Formula (I):

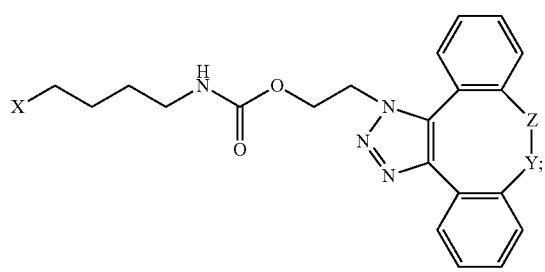

Formula (I)

wherein:
Z is CH$_2$ and Y is

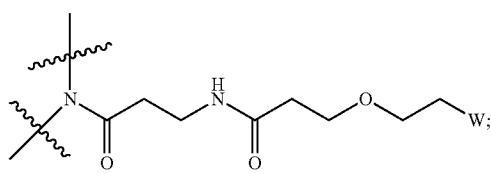

Y is CH$_2$ and Z is

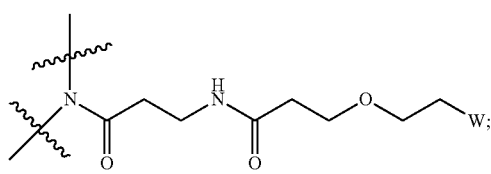

Z is CH$_2$ and Y is

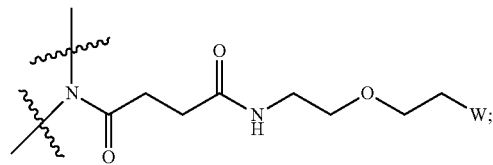

or
Y is CH$_2$ and Z is

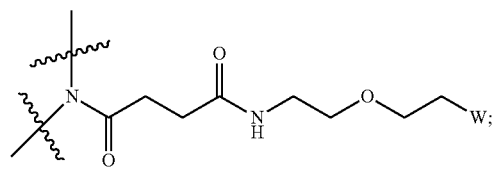

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

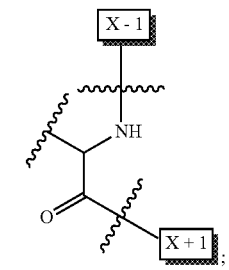

X−1 indicates the point of attachment to the preceding amino acid residue; and

X+1 indicates the point of attachment to the following amino acid residue.

In some embodiments, the IL-15 conjugate is a pharmaceutically acceptable salt, solvate, or hydrate.

Described herein are IL-15 conjugates comprising the amino acid sequence of SEQ ID NO: 3 in which at least one amino acid residue in the IL-15 conjugate is replaced by the structure of Formula (I):

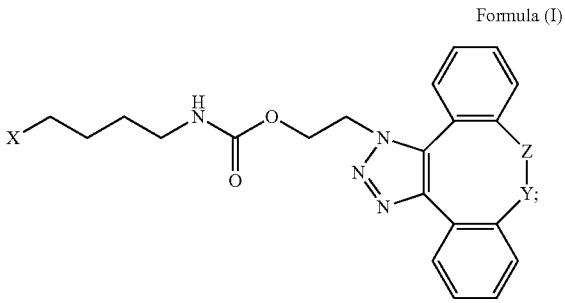

Formula (I)

wherein:
Z is CH₂ and Y is

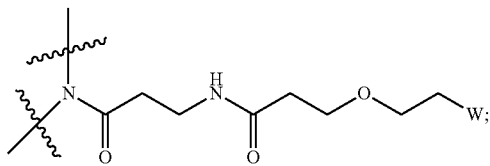

Y is CH₂ and Z is

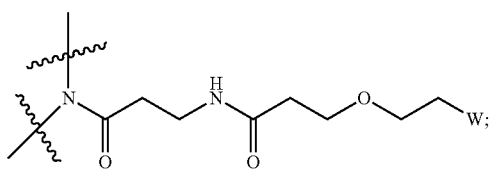

Z is CH₂ and Y is

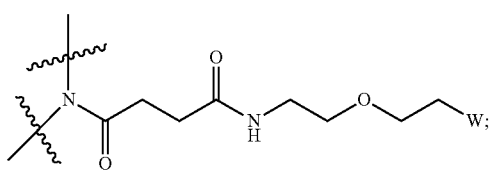

or
Y is CH₂ and Z is

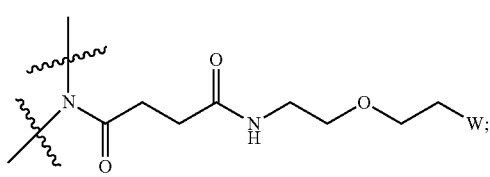

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

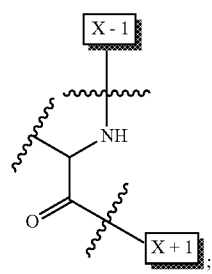

X−1 indicates the point of attachment to the preceding amino acid residue; and
X+1 indicates the point of attachment to the following amino acid residue.

In some embodiments, the IL-15 conjugate is a pharmaceutically acceptable salt, solvate, or hydrate. In some embodiments, Z is CH₂ and Y is

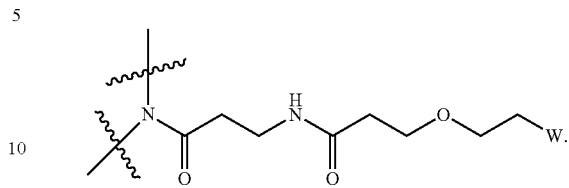

In some embodiments, Y is CH₂ and Z is

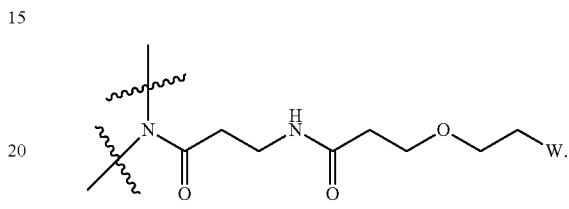

In some embodiments, Z is CH₂ and Y is

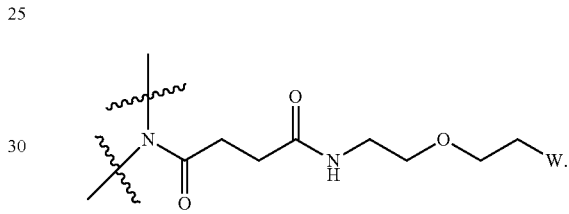

In some embodiments, Y is CH₂ and Z is

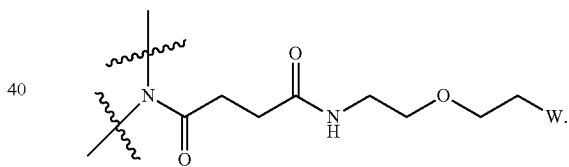

Here and throughout, embodiments of Z and Y also encompass a pharmaceutically acceptable salt, solvate, or hydrate thereof. In some embodiments, the PEG group has an average molecular weight selected from 5 kDa, 10 kDa, 15 kDa, 20 kDa, 25 kDa, 30 kDa, 35 kDa, 40 kDa, and 45 kDa. In some embodiments, the PEG group has an average molecular weight of 5 kDa. In some embodiments, the PEG group has an average molecular weight of 10 kDa. In some embodiments, the PEG group has an average molecular weight of 15 kDa. In some embodiments, the PEG group has an average molecular weight of 20 kDa. In some embodiments, the PEG group has an average molecular weight of 25 kDa. In some embodiments, the PEG group has an average molecular weight of 30 kDa. In some embodiments, the PEG group has an average molecular weight of 35 kDa. In some embodiments, the PEG group has an average molecular weight of 40 kDa. In some embodiments, the PEG group has an average molecular weight of 45 kDa. In some embodiments, the PEG group has an average molecular weight of 50 kDa. In some embodiments, the PEG group has an average molecular weight of 55 kDa. In some embodiments, the PEG group has an average molecular weight of 60 kDa.

In some embodiments, the position of the structure of Formula (I) in the amino acid sequence of the IL-15 conjugate comprising SEQ ID NO: 1 is selected from S18, L25, E46, E53, N77, and S83. In some embodiments, the position of the structure of Formula (I) in the amino acid sequence of the IL-15 conjugate comprising SEQ ID NO: 1 is selected from L25, E53, and N77. In some embodiments, the position of the structure of Formula (I) in the amino acid sequence of the IL-15 conjugate comprising SEQ ID NO: 1 is S18. In some embodiments, the position of the structure of Formula (I) in the amino acid sequence of the IL-15 conjugate comprising SEQ ID NO: 1 is L25. In some embodiments, the position of the structure of Formula (I) in the amino acid sequence of the IL-15 conjugate comprising SEQ ID NO: 1 is E46. In some embodiments, the position of the structure of Formula (I) in the amino acid sequence of the IL-15 conjugate comprising SEQ ID NO: 1 is E53. In some embodiments, the position of the structure of Formula (I) in the amino acid sequence of the IL-15 conjugate comprising SEQ ID NO: 1 is N77. In some embodiments, the position of the structure of Formula (I) in the amino acid sequence of the IL-15 conjugate comprising SEQ ID NO: 1 is S83.

In some embodiments, the position of the structure of Formula (I) in the amino acid sequence of the IL-15 conjugate comprising SEQ ID NO: 3 is selected from S19, L26, E47, E54, N78, and S84. In some embodiments, the position of the structure of Formula (I) in the amino acid sequence of the IL-15 conjugate comprising SEQ ID NO: 3 is selected from L26, E54, and N78. In some embodiments, the position of the structure of Formula (I) in the amino acid sequence of the IL-15 conjugate comprising SEQ ID NO: 3 is S19. In some embodiments, the position of the structure of Formula (I) in the amino acid sequence of the IL-15 conjugate comprising SEQ ID NO: 3 is L26. In some embodiments, the position of the structure of Formula (I) in the amino acid sequence of the IL-15 conjugate comprising SEQ ID NO: 3 is E47. In some embodiments, the position of the structure of Formula (I) in the amino acid sequence of the IL-15 conjugate comprising SEQ ID NO: 3 is E54. In some embodiments, the position of the structure of Formula (I) in the amino acid sequence of the IL-15 conjugate comprising SEQ ID NO: 3 is N78. In some embodiments, the position of the structure of Formula (I) in the amino acid sequence of the IL-15 conjugate comprising SEQ ID NO: 3 is S84.

Described herein are IL-15 conjugates comprising the amino acid sequence of any one of SEQ ID NOS: 16-21, wherein [AzK_PEG] has the structure of Formula (II) or Formula (III), or a mixture of Formula (II) and Formula (I):

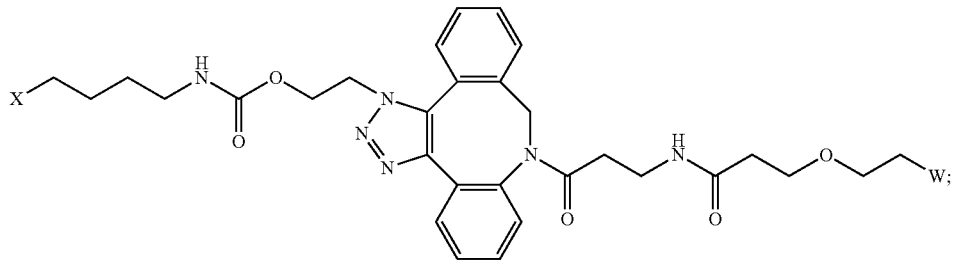

Formula (II)

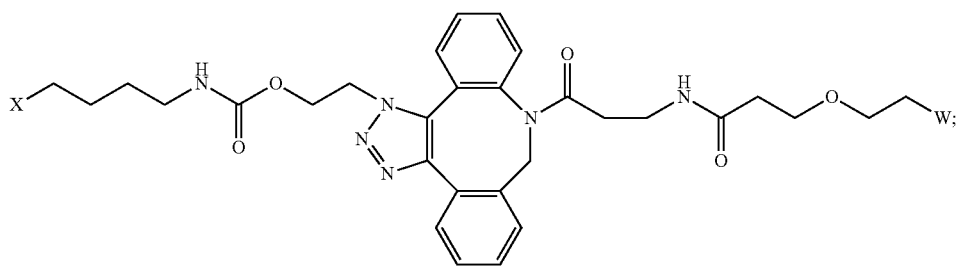

Formula (III)

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

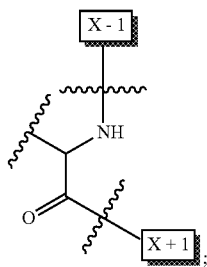

X−1 indicates the point of attachment to the preceding amino acid residue; and

X+1 indicates the point of attachment to the following amino acid residue.

In some embodiments, the IL-15 conjugate is a pharmaceutically acceptable salt, solvate, or hydrate. In some embodiments, the [AzK_PEG] is a mixture of Formula (II) and Formula (III). In some embodiments, the [AzK_PEG] has the structure of Formula (II):

Formula (II)

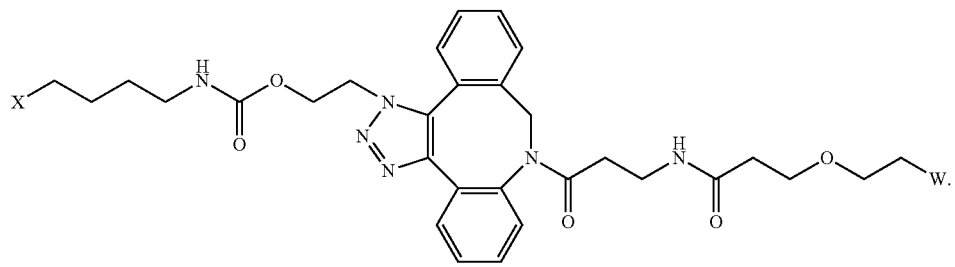

Here and throughout, the structure of Formula (II) encompasses pharmaceutically acceptable salts, solvates, or hydrates thereof. In some embodiments, the IL-15 conjugate has the amino acid sequence of SEQ ID NO: 16. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 17. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 18. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 19. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 20. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 21. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa.

In some embodiments, the [AzK_PEG] has the structure of Formula (III)

Formula (III)

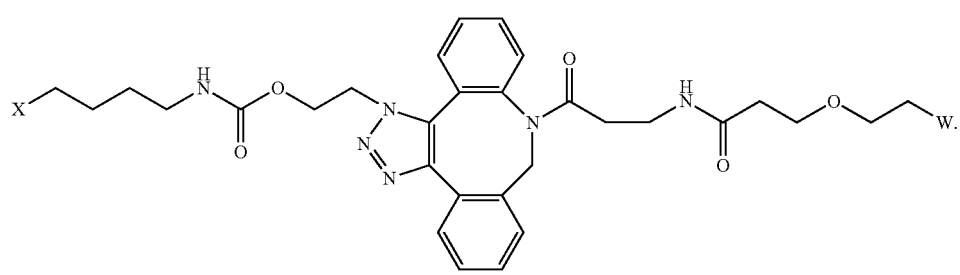

Here and throughout, the structure of Formula (III) encompasses pharmaceutically acceptable salts, solvates, or hydrates thereof. In some embodiments, the IL-15 conjugate has the amino acid sequence of SEQ ID NO: 16. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 17. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 18. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 19. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 20. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 21. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa.

Described herein are IL-15 conjugates comprising the amino acid sequence of any one of SEQ ID NOS: 16-21, wherein [AzK_PEG] is a mixture of the structures of Formula (II) and Formula (III):

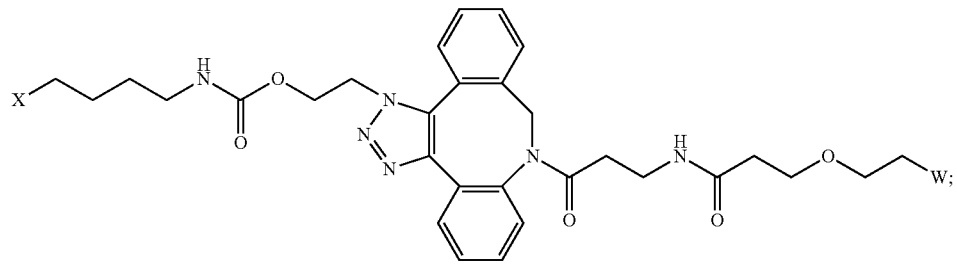

Formula (II)

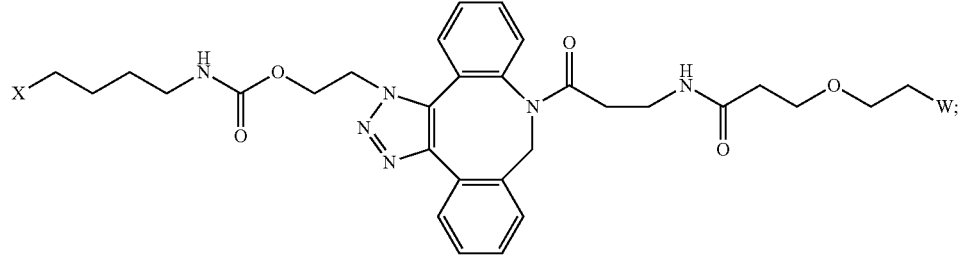

Formula (III)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

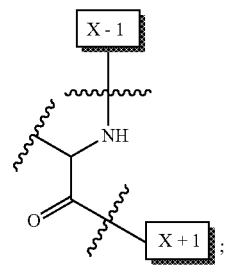

X-1 indicates the point of attachment to the preceding amino acid residue; and
X+1 indicates the point of attachment to the following amino acid residue.

In some embodiments, the IL-15 conjugate is a pharmaceutically acceptable salt, solvate, or hydrate. In some embodiments, the ratio of the amount of the structure of Formula (II) to the amount of the structure of Formula (III) comprising the total amount of [AzK_PEG] in the IL-15 conjugate is about 1:1. In some embodiments, the ratio of the amount of the structure of Formula (II) to the amount of the structure of Formula (III) comprising the total amount of [AzK_PEG] in the IL-15 conjugate is greater than 1:1. In some embodiments, the ratio of the amount of the structure of Formula (II) to the amount of the structure of Formula (III) comprising the total amount of [AzK_PEG] in the IL-15 conjugate is less than 1:1. In some embodiments, W is a linear or branched PEG group. In some embodiments, W is a linear PEG group. In some embodiments, W is a branched PEG group. In some embodiments, W is a methoxy PEG group. In some embodiments, the methoxy PEG group is linear or branched. In some embodiments, the methoxy PEG group is linear. In some embodiments, the methoxy PEG group is branched.

Described herein are IL-15 conjugates comprising the amino acid sequence of any one of SEQ ID NOS: 22-27, wherein [AzK_PEG30] has the structure of Formula (II) or Formula (III), or a mixture of Formula (II) and Formula (III):

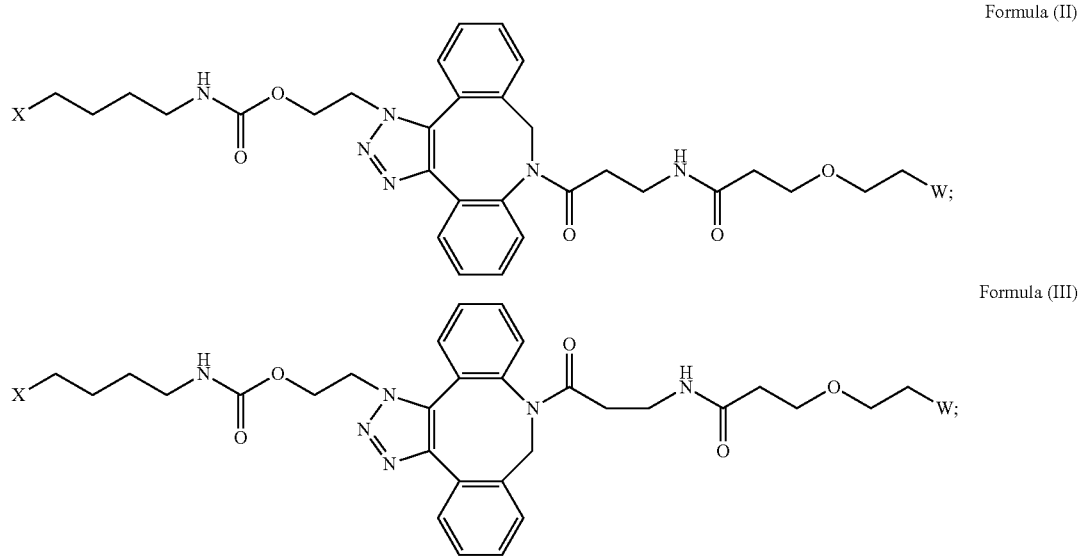

Formula (II)

Formula (III)

wherein:
W is a PEG group having an average molecular weight of 30 kDa; and
X has the structure:

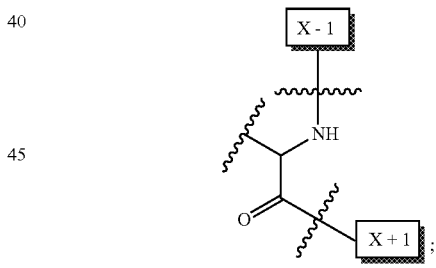

X−1 indicates the point of attachment to the preceding amino acid residue; and
X+1 indicates the point of attachment to the following amino acid residue.

In some embodiments, the IL-15 conjugate is a pharmaceutically acceptable salt, solvate, or hydrate. In some embodiments, the IL-15 conjugate has the amino acid sequence of SEQ ID NO: 22. In some embodiments, the IL-15 conjugate has the amino acid sequence of SEQ ID NO: 23. In some embodiments, the IL-15 conjugate has the amino acid sequence of SEQ ID NO: 24. In some embodiments, the IL-15 conjugate has the amino acid sequence of SEQ ID NO: 25. In some embodiments, the IL-15 conjugate has the amino acid sequence of SEQ ID NO: 26. In some embodiments, the IL-15 conjugate has the amino acid sequence of SEQ ID NO: 27.

In some embodiments, the [AzK_PEG30] has the structure of Formula (II)

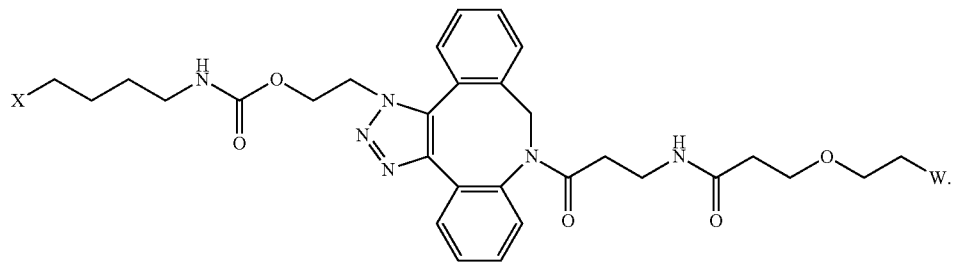

Formula (II)

In some embodiments, the IL-15 conjugate has the amino acid sequence of SEQ ID NO: 22. In some embodiments, the IL-15 conjugate has the amino acid sequence of SEQ ID NO: 23. In some embodiments, the IL-15 conjugate has the amino acid sequence of SEQ ID NO: 24. In some embodiments, the IL-15 conjugate has the amino acid sequence of SEQ ID NO: 25. In some embodiments, the IL-15 conjugate has the amino acid sequence of SEQ ID NO: 26. In some embodiments, the IL-15 conjugate has the amino acid sequence of SEQ ID NO: 27.

In some embodiments, the [AzK_PEG30] has the structure of Formula (III)

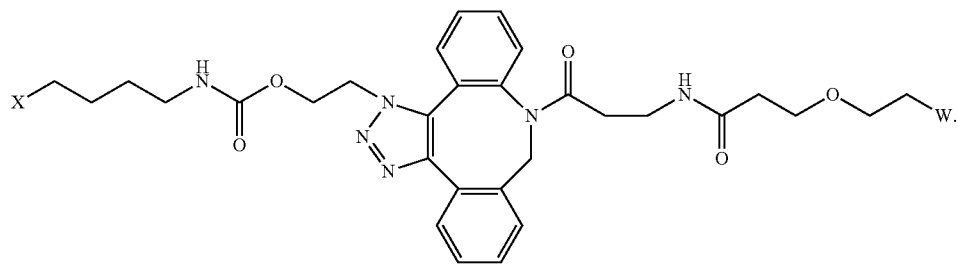

Formula (III)

Here and throughout, the structure of Formula (III) encompasses pharmaceutically acceptable salts, solvates, or hydrates thereof. In some embodiments, the IL-15 conjugate has the amino acid sequence of SEQ ID NO: 22. In some embodiments, the IL-15 conjugate has the amino acid sequence of SEQ ID NO: 23. In some embodiments, the IL-15 conjugate has the amino acid sequence of SEQ ID NO: 24. In some embodiments, the IL-15 conjugate has the amino acid sequence of SEQ ID NO: 25. In some embodiments, the IL-15 conjugate has the amino acid sequence of SEQ ID NO: 26. In some embodiments, the IL-15 conjugate has the amino acid sequence of SEQ ID NO: 27.

Described herein are IL-15 conjugates comprising the amino acid sequence of any one of SEQ ID NOS: 22 to 27, wherein [AzK_PEG30] is a mixture of the structures of Formula (II) and Formula (III):

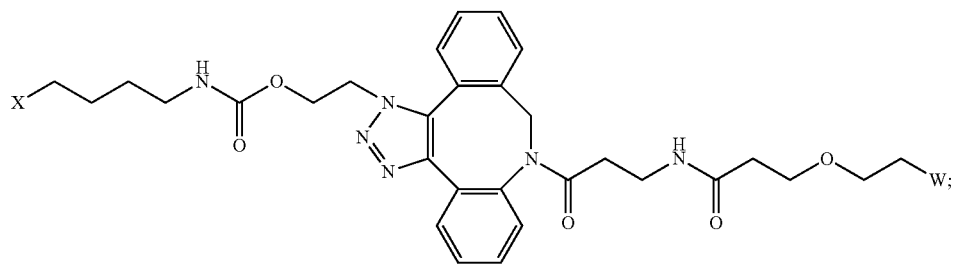

Formula (II)

-continued

Formula (III)

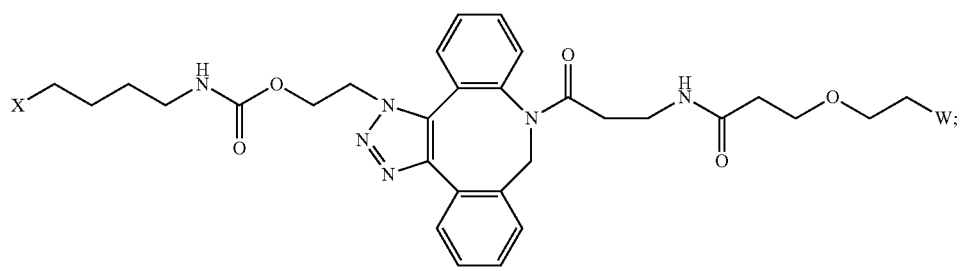

wherein:
W is a PEG group having an average molecular weight of 30 kDa; and
X has the structure:

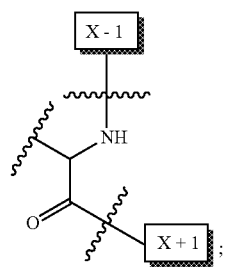

X−1 indicates the point of attachment to the preceding amino acid residue; and
X+1 indicates the point of attachment to the following amino acid residue. In some embodiments, the IL-15 conjugate is a pharmaceutically acceptable salt, solvate, or hydrate.

In some embodiments, the ratio of the amount of the structure of Formula (II) to the amount of the structure of Formula (III) comprising the total amount of [AzK_PEG30] in the IL-15 conjugate is about 1:1. In some embodiments, the ratio of the amount of the structure of Formula (II) to the amount of the structure of Formula (III) comprising the total amount of [AzK_PEG30] in the IL-15 conjugate is greater than 1:1. In some embodiments, the ratio of the amount of the structure of Formula (II) to the amount of the structure of Formula (III) comprising the total amount of [AzK_PEG30] in the IL-15 conjugate is less than 1:1. In some embodiments, W is a linear or branched PEG group. In some embodiments, W is a linear PEG group. In some embodiments, W is a branched PEG group. In some embodiments, W is a methoxy PEG group. In some embodiments, the methoxy PEG group is linear or branched. In some embodiments, the methoxy PEG group is linear. In some embodiments, the methoxy PEG group is branched.

Described herein are IL-15 conjugates comprising the amino acid sequence of any one of SEQ ID NOS: 28-33, wherein [AzK_PEG40] has the structure of Formula (II) or Formula (III), or is a mixture of the structures of Formula (II) and Formula (III):

Formula (II)

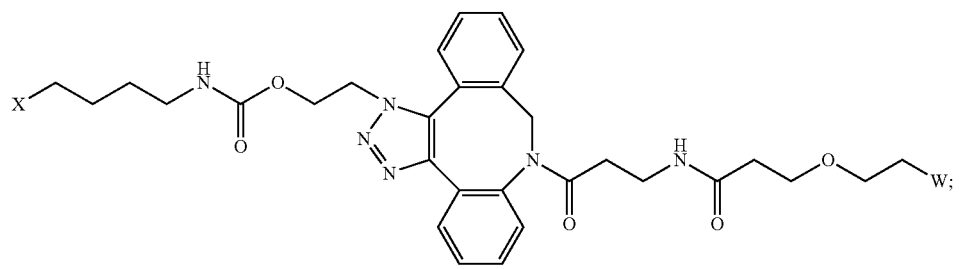

Formula (III)

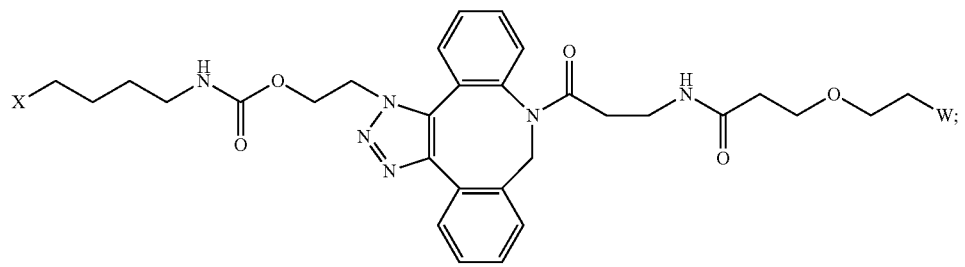

wherein:
W is a PEG group having an average molecular weight of 40 kDa; and
X has the structure:

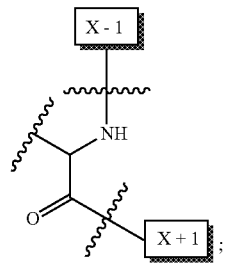

X−1 indicates the point of attachment to the preceding amino acid residue; and
X+1 indicates the point of attachment to the following amino acid residue.

In some embodiments, the IL-15 conjugate is a pharmaceutically acceptable salt, solvate, or hydrate. In some embodiments, the IL-15 conjugate has the amino acid sequence of SEQ ID NO: 28. In some embodiments, the IL-15 conjugate has the amino acid sequence of SEQ ID NO: 29. In some embodiments, the IL-15 conjugate has the amino acid sequence of SEQ ID NO: 30. In some embodiments, the IL-15 conjugate has the amino acid sequence of SEQ ID NO: 31. In some embodiments, the IL-15 conjugate has the amino acid sequence of SEQ ID NO: 32. In some embodiments, the IL-15 conjugate has the amino acid sequence of SEQ ID NO: 33.

In some embodiments, the [AzK_PEG40] has the structure of Formula (II):

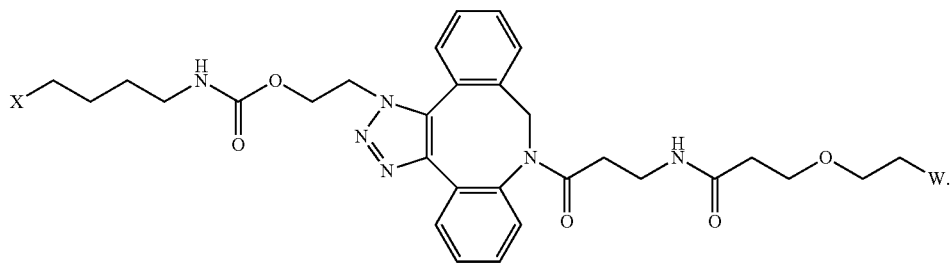

Formula (II)

In some embodiments, the IL-15 conjugate has the amino acid sequence of SEQ ID NO: 28. In some embodiments, the IL-15 conjugate has the amino acid sequence of SEQ ID NO: 29. In some embodiments, the IL-15 conjugate has the amino acid sequence of SEQ ID NO: 30. In some embodiments, the IL-15 conjugate has the amino acid sequence of SEQ ID NO: 31. In some embodiments, the IL-15 conjugate has the amino acid sequence of SEQ ID NO: 32. In some embodiments, the IL-15 conjugate has the amino acid sequence of SEQ ID NO: 33. In some embodiments, the [AzK_PEG40] has the structure of Formula (III)

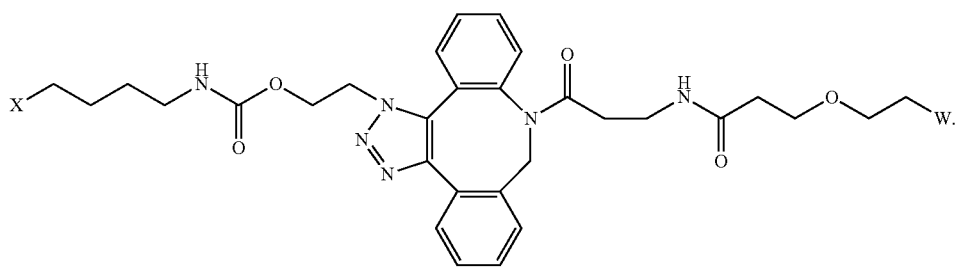

Formula (III)

In some embodiments, the IL-15 conjugate has the amino acid sequence of SEQ ID NO: 28. In some embodiments, the IL-15 conjugate has the amino acid sequence of SEQ ID NO: 29. In some embodiments, the IL-15 conjugate has the amino acid sequence of SEQ ID NO: 30. In some embodiments, the IL-15 conjugate has the amino acid sequence of SEQ ID NO: 31. In some embodiments, the IL-15 conjugate has the amino acid sequence of SEQ ID NO: 32. In some embodiments, the IL-15 conjugate has the amino acid sequence of SEQ ID NO: 33.

Described herein are IL-15 conjugates comprising the amino acid sequence of any one of SEQ ID NOS: 28-33, wherein [AzK_PEG40] is a mixture of the structures of Formula (II) and Formula (III):

X-1 indicates the point of attachment to the preceding amino acid residue; and

X+1 indicates the point of attachment to the following amino acid residue.

In some embodiments, the IL-15 conjugate is a pharmaceutically acceptable salt, solvate, or hydrate. In some embodiments, the ratio of the amount of the structure of Formula (II) to the amount of the structure of Formula (III) comprising the total amount of [AzK_PEG40] in the IL-15 conjugate is about 1:1. In some embodiments, the ratio of the amount of the structure of Formula (II) to the amount of the structure of Formula (III) comprising the total amount of [AzK_PEG40] in the IL-15 conjugate is greater than 1:1. In some embodiments, the ratio of the amount of the structure of Formula (II) to the amount of the structure of Formula (III) comprising the total amount of [AzK_PEG40] in the IL-15 conjugate is less than 1:1. In some embodiments, W is a linear or branched PEG group. In some embodiments, W is a linear PEG group. In some embodiments, W is a branched PEG group. In some embodiments, W is a methoxy PEG group. In some embodiments, the methoxy PEG group is linear or branched. In some embodiments, the methoxy PEG group is linear. In some embodiments, the methoxy PEG group is branched.

Described herein are IL-15 conjugates comprising the amino acid sequence of any one of SEQ ID NOS: 34-39, wherein [AzK_L1_PEG] has the structure of Formula (IV) or Formula (V), or a mixture of Formula (IV) and Formula (V):

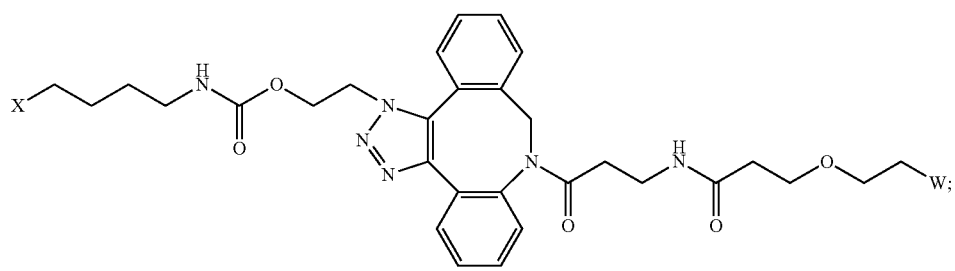

Formula (II)

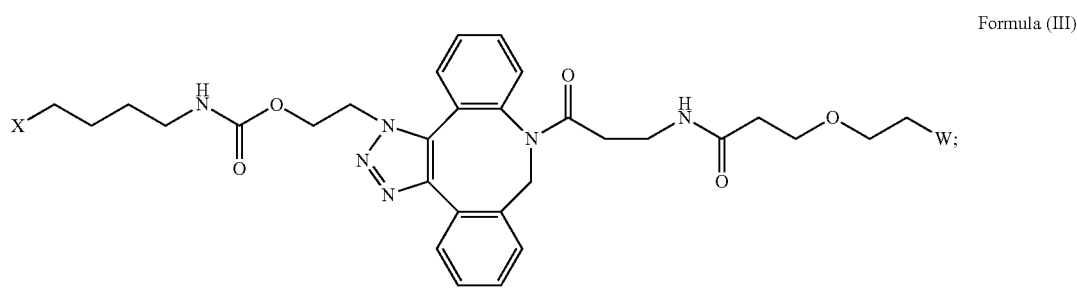

Formula (III)

wherein:

W is a PEG group having an average molecular weight of 40 kDa; and

X has the structure:

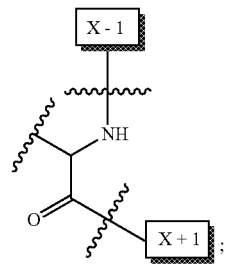

Formula (IV)

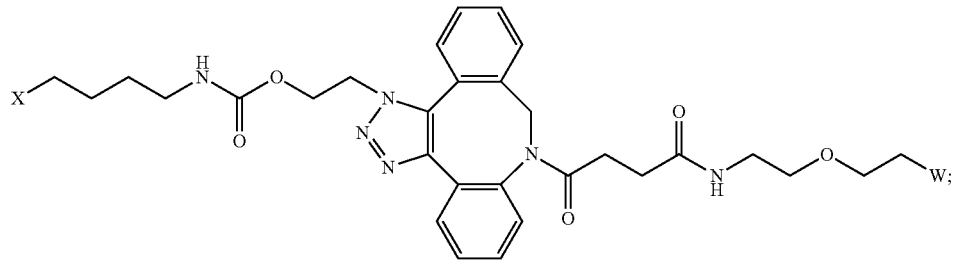

Formula (V)

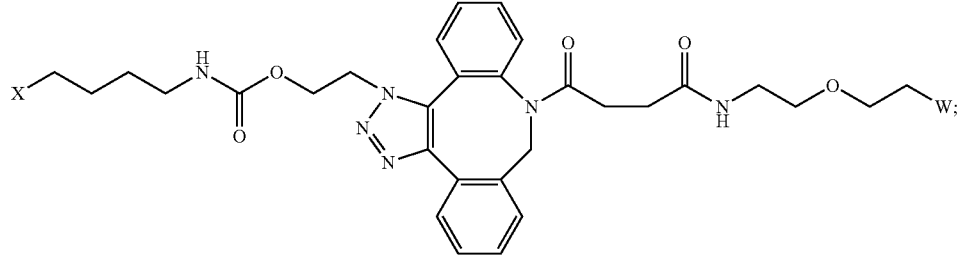

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

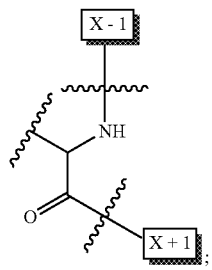

X−1 indicates the point of attachment to the preceding amino acid residue; and
X+1 indicates the point of attachment to the following amino acid residue.

In some embodiments, the IL-15 conjugate is a pharmaceutically acceptable salt, solvate, or hydrate. In some embodiments, the [AzK_L1_PEG] is a mixture of Formula (IV) and Formula (V).

In some embodiments, the [AzK_L1_PEG] has the structure of Formula (IV):

Here and throughout, the structure of Formula (IV) encompasses pharmaceutically acceptable salts, solvates, or hydrates thereof. In some embodiments, the IL-15 conjugate has the amino acid sequence of SEQ ID NO: 34. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 35. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 36. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some Formula (IV)

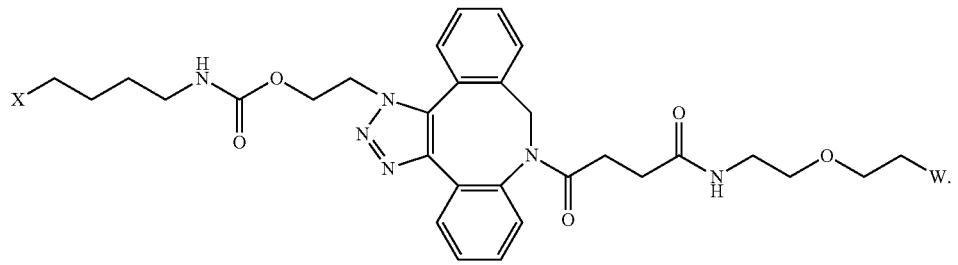

embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 37. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 38. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 39. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa.

In some embodiments, the [AzK_L1_PEG] has the structure of Formula (V)

PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 36. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 37. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 38. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid

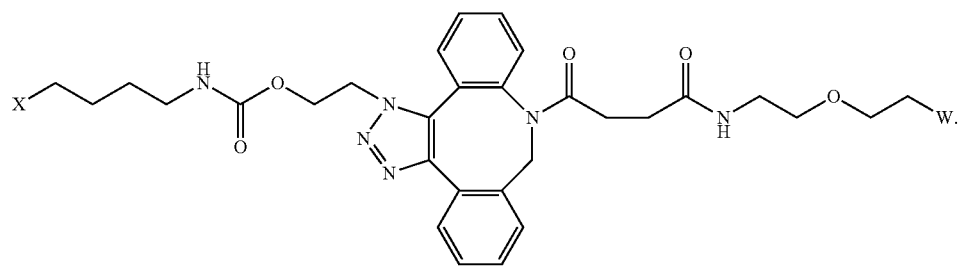

Formula (V)

Here and throughout, the structure of Formula (V) encompasses pharmaceutically acceptable salts, solvates, or hydrates thereof. In some embodiments, the IL-15 conjugate has the amino acid sequence of SEQ ID NO: 34. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 35. In some embodiments, W is a sequence of SEQ ID NO: 39. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa.

Described herein are IL-15 conjugates comprising the amino acid sequence of any one of SEQ ID NOS: 34-39, wherein [Azk_L1_PEG] is a mixture of the structures of Formula (IV) and Formula (V):

Formula (IV)

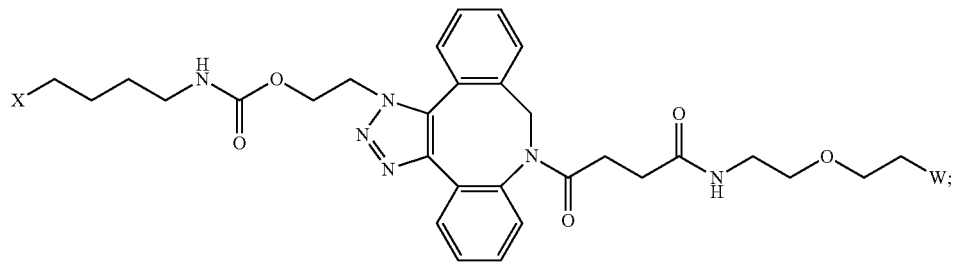

Formula (V)

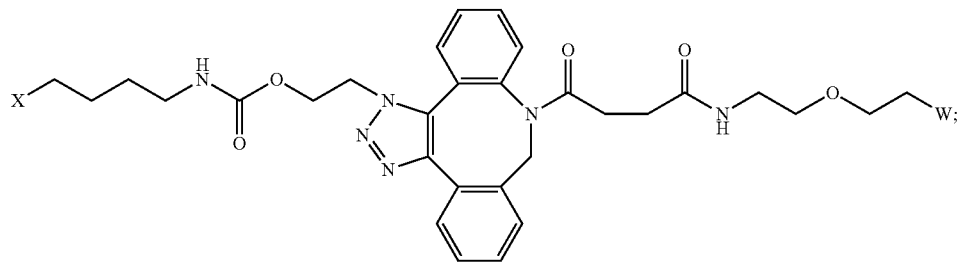

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

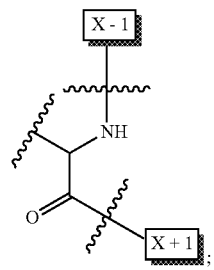

X−1 indicates the point of attachment to the preceding amino acid residue; and

X+1 indicates the point of attachment to the following amino acid residue.

In some embodiments, the IL-15 conjugate is a pharmaceutically acceptable salt, solvate, or hydrate. In some embodiments, the ratio of the amount of the structure of Formula (IV) to the amount of the structure of Formula (V) comprising the total amount of [AzK_L1_PEG] in the IL-15 conjugate is about 1:1. In some embodiments, the ratio of the amount of the structure of Formula (IV) to the amount of the structure of Formula (V) comprising the total amount of [AzK_L1_PEG] in the IL-15 conjugate is greater than 1:1. In some embodiments, the ratio of the amount of the structure of Formula (IV) to the amount of the structure of Formula (V) comprising the total amount of [AzK_L1_PEG] in the IL-15 conjugate is less than 1:1. In some embodiments, W is a linear or branched PEG group. In some embodiments, W is a linear PEG group. In some embodiments, W is a branched PEG group. In some embodiments, W is a methoxy PEG group. In some embodiments, the methoxy PEG group is linear or branched. In some embodiments, the methoxy PEG group is linear. In some embodiments, the methoxy PEG group is branched.

Described herein are IL-15 conjugates comprising the amino acid sequence of any one of SEQ ID NOS: 40-45, wherein [AzK_L1_PEG30] has the structure of Formula (IV) or Formula (V), or a mixture of Formula (IV) and Formula (V):

Formula (IV)

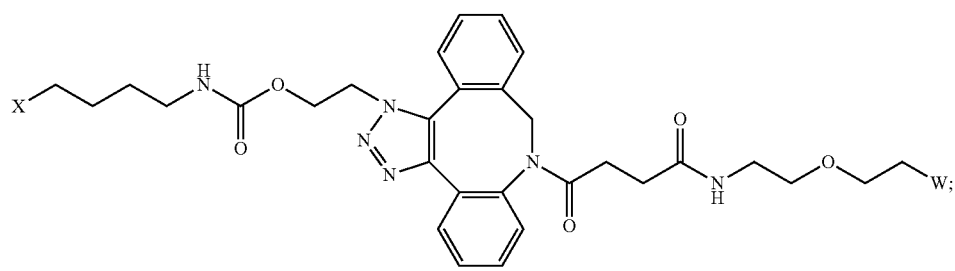

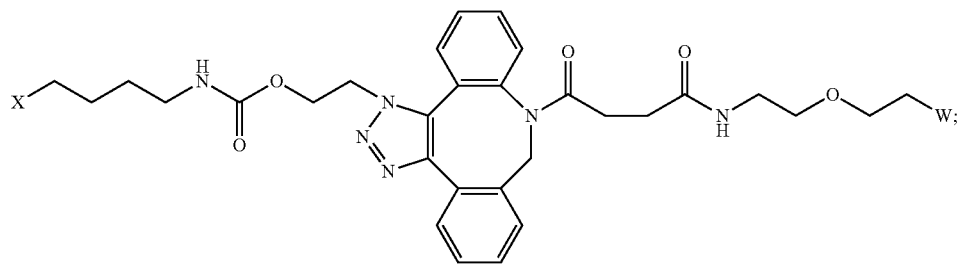

Formula (V)

wherein:
W is a PEG group having an average molecular weight of 30 kDa; and
X has the structure:

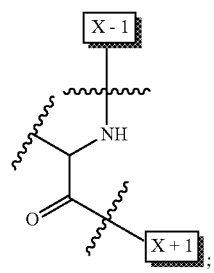

X−1 indicates the point of attachment to the preceding amino acid residue; and
X+1 indicates the point of attachment to the following amino acid residue.

In some embodiments, the IL-15 conjugate is a pharmaceutically acceptable salt, solvate, or hydrate. In some embodiments, the IL-15 conjugate has the amino acid sequence of SEQ ID NO: 40. In some embodiments, the IL-15 conjugate has the amino acid sequence of SEQ ID NO: 41. In some embodiments, the IL-15 conjugate has the amino acid sequence of SEQ ID NO: 42. In some embodiments, the IL-15 conjugate has the amino acid sequence of SEQ ID NO: 43. In some embodiments, the IL-15 conjugate has the amino acid sequence of SEQ ID NO: 44. In some embodiments, the IL-15 conjugate has the amino acid sequence of SEQ ID NO: 45. In some embodiments, the [AzK_L1_PEG30] has the structure of Formula (IV)

Formula (IV)

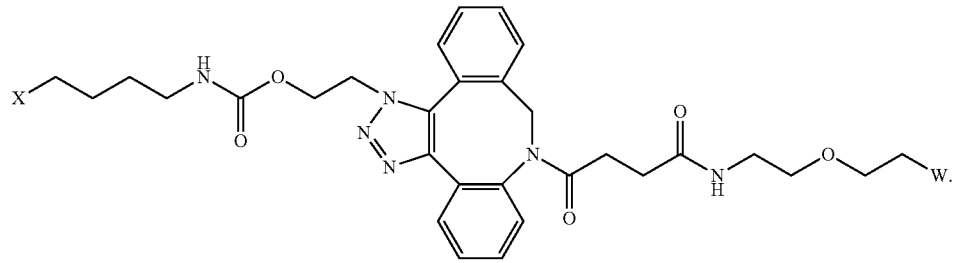

In some embodiments, the IL-15 conjugate has the amino acid sequence of SEQ ID NO: 40. In some embodiments, the IL-15 conjugate has the amino acid sequence of SEQ ID NO: 41. In some embodiments, the IL-15 conjugate has the amino acid sequence of SEQ ID NO: 42. In some embodiments, the IL-15 conjugate has the amino acid sequence of SEQ ID NO: 43. In some embodiments, the IL-15 conjugate has the amino acid sequence of SEQ ID NO: 44. In some embodiments, the IL-15 conjugate has the amino acid sequence of SEQ ID NO: 45. In some embodiments, the [AzK_L1_PEG30] has the structure of Formula (V)

Formula (V)

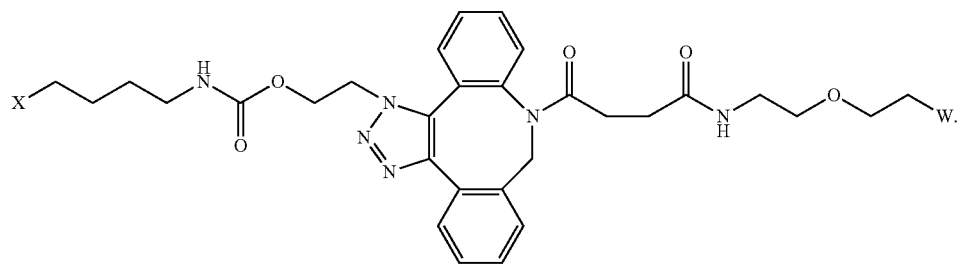

In some embodiments, the IL-15 conjugate has the amino acid sequence of SEQ ID NO: 40. In some embodiments, the IL-15 conjugate has the amino acid sequence of SEQ ID NO: 41. In some embodiments, the IL-15 conjugate has the amino acid sequence of SEQ ID NO: 42. In some embodiments, the IL-15 conjugate has the amino acid sequence of SEQ ID NO: 43. In some embodiments, the IL-15 conjugate has the amino acid sequence of SEQ ID NO: 44. In some embodiments, the IL-15 conjugate has the amino acid sequence of SEQ ID NO: 45.

Described herein are IL-15 conjugates comprising the amino acid sequence of any one of SEQ ID NOS: 40 to 45, wherein [AzK_L1_PEG30] is a mixture of the structures of Formula (IV) and Formula (V):

X−1 indicates the point of attachment to the preceding amino acid residue; and

X+1 indicates the point of attachment to the following amino acid residue.

In some embodiments, the IL-15 conjugate is a pharmaceutically acceptable salt, solvate, or hydrate. In some embodiments, the ratio of the amount of the structure of Formula (IV) to the amount of the structure of Formula (V) comprising the total amount of [AzK_L1_PEG30] in the IL-15 conjugate is about 1:1. In some embodiments, the ratio of the amount of the structure of Formula (IV) to the amount of the structure of Formula (V) comprising the total amount of [AzK_L1_PEG30] in the IL-15 conjugate is greater than 1:1. In some embodiments, the ratio of the amount of the Formula (IV)

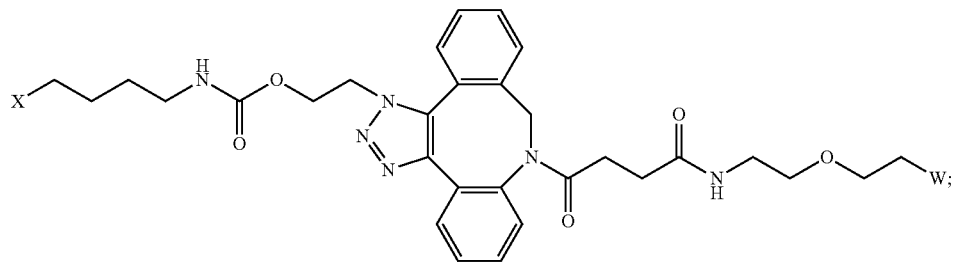

Formula (V)

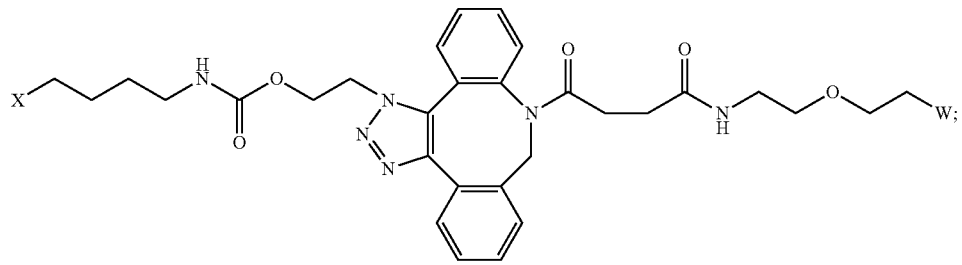

wherein:

W is a PEG group having an average molecular weight of 30 kDa; and

X has the structure:

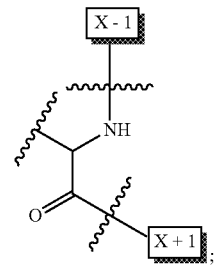

structure of Formula (IV) to the amount of the structure of Formula (V) comprising the total amount of [AzK_L1_PEG30] in the IL-15 conjugate is less than 1:1. In some embodiments, W is a linear or branched PEG group. In some embodiments, W is a linear PEG group. In some embodiments, W is a branched PEG group. In some embodiments, W is a methoxy PEG group. In some embodiments, the methoxy PEG group is linear or branched. In some embodiments, the methoxy PEG group is linear. In some embodiments, the methoxy PEG group is branched.

Described herein are IL-15 conjugates comprising the amino acid sequence of any one of SEQ ID NOS: 46-51, wherein [AzK_L1_PEG40] has the structure of Formula (IV) or Formula (V), or is a mixture of the structures of Formula (IV) and Formula (V):

Formula (IV)

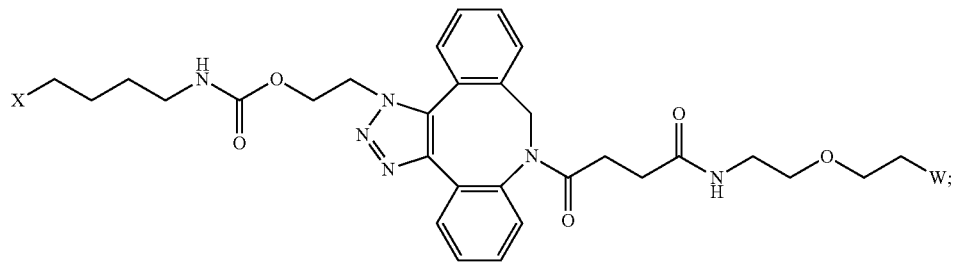

Formula (V)

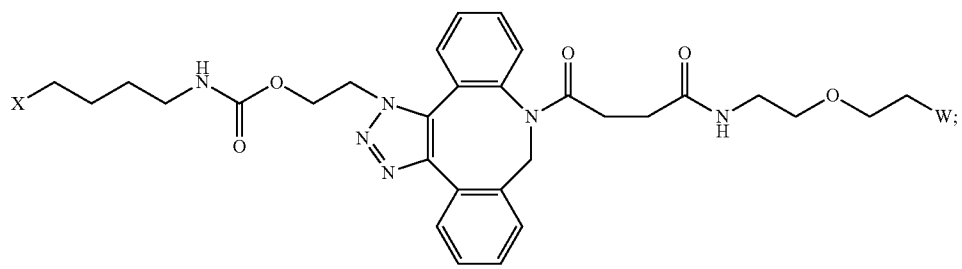

wherein:
W is a PEG group having an average molecular weight of 40 kDa; and
X has the structure:

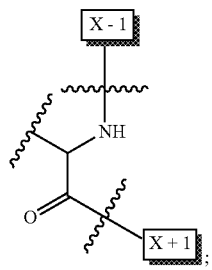

X−1 indicates the point of attachment to the preceding amino acid residue; and
X+1 indicates the point of attachment to the following amino acid residue.

In some embodiments, the IL-15 conjugate is a pharmaceutically acceptable salt, solvate, or hydrate. In some embodiments, the IL-15 conjugate has the amino acid sequence of SEQ ID NO: 46. In some embodiments, the IL-15 conjugate has the amino acid sequence of SEQ ID NO: 47. In some embodiments, the IL-15 conjugate has the amino acid sequence of SEQ ID NO: 48. In some embodiments, the IL-15 conjugate has the amino acid sequence of SEQ ID NO: 49. In some embodiments, the IL-15 conjugate has the amino acid sequence of SEQ ID NO: 50. In some embodiments, the IL-15 conjugate has the amino acid sequence of SEQ ID NO: 51.

In some embodiments, the [AzK_L1_PEG40] has the structure of Formula (IV):

Formula (IV)

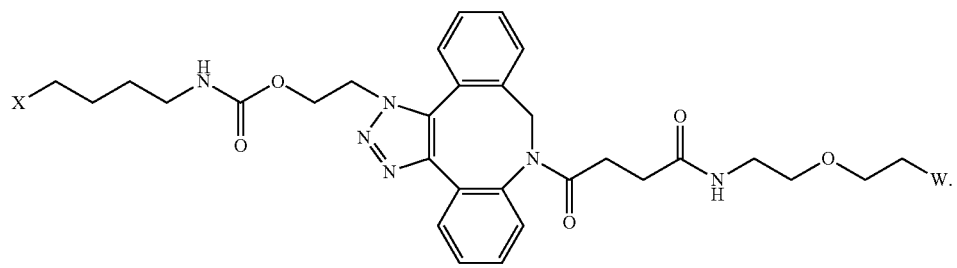

In some embodiments, the IL-15 conjugate has the amino acid sequence of SEQ ID NO: 46. In some embodiments, the IL-15 conjugate has the amino acid sequence of SEQ ID NO: 47. In some embodiments, the IL-15 conjugate has the amino acid sequence of SEQ ID NO: 48. In some embodiments, the IL-15 conjugate has the amino acid sequence of SEQ ID NO: 49. In some embodiments, the IL-15 conjugate has the amino acid sequence of SEQ ID NO: 50. In some embodiments, the IL-15 conjugate has the amino acid sequence of SEQ ID NO: 51.

In some embodiments, the [AzK_L1_PEG40] has the structure of Formula (V)

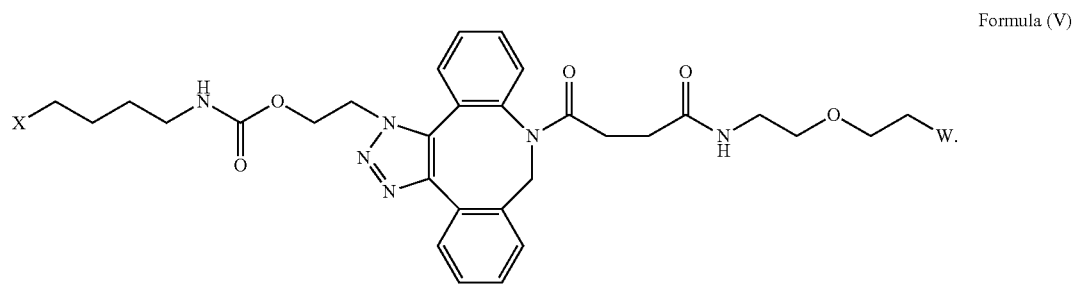

Formula (V)

In some embodiments, the IL-15 conjugate has the amino acid sequence of SEQ ID NO: 47. In some embodiments, the IL-15 conjugate has the amino acid sequence of SEQ ID NO: 48. In some embodiments, the IL-15 conjugate has the amino acid sequence of SEQ ID NO: 49. In some embodiments, the IL-15 conjugate has the amino acid sequence of SEQ ID NO: 50. In some embodiments, the IL-15 conjugate has the amino acid sequence of SEQ ID NO: 51.

Described herein are IL-15 conjugates comprising the amino acid sequence of any one of SEQ ID NOS: 46-51, wherein [AzK_L1_PEG40] is a mixture of the structures of Formula (IV) and Formula (V):

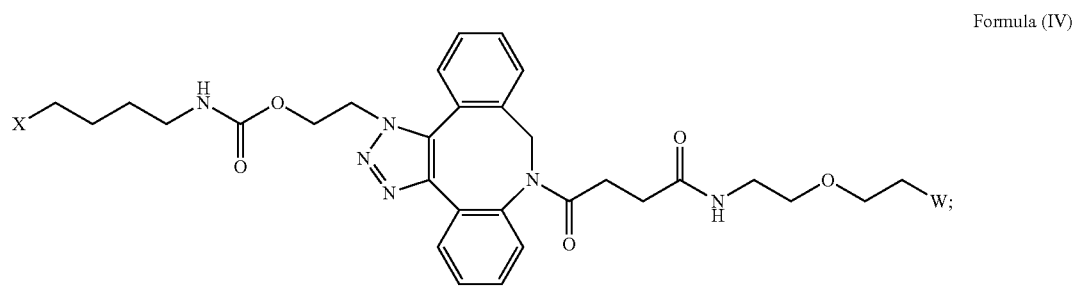

Formula (IV)

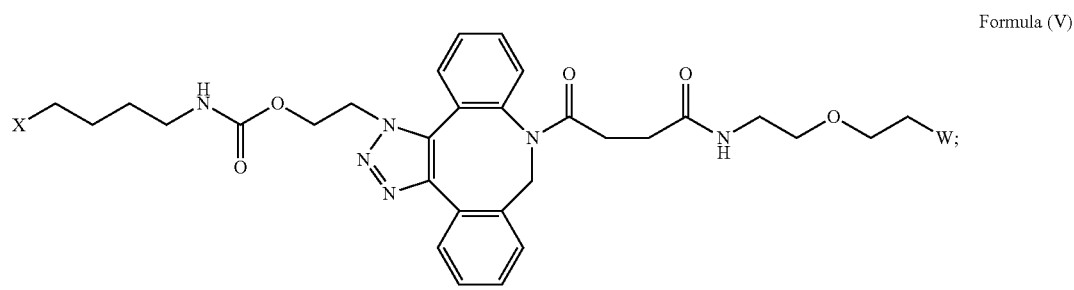

Formula (V)

wherein:
W is a PEG group having an average molecular weight of 40 kDa; and
X has the structure:

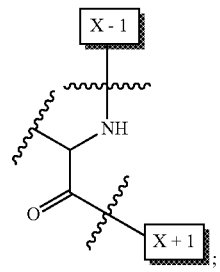

X−1 indicates the point of attachment to the preceding amino acid residue; and
X+1 indicates the point of attachment to the following amino acid residue.

In some embodiments, the IL-15 conjugate is a pharmaceutically acceptable salt, solvate, or hydrate. In some embodiments, the ratio of the amount of the structure of Formula (IV) to the amount of the structure of Formula (V) comprising the total amount of [AzK_L1_PEG40] in the IL-15 conjugate is about 1:1. In some embodiments, the ratio of the amount of the structure of Formula (IV) to the amount of the structure of Formula (V) comprising the total amount of [AzK_L1_PEG40] in the IL-15 conjugate is greater than 1:1. In some embodiments, the ratio of the amount of the structure of Formula (IV) to the amount of the structure of Formula (V) comprising the total amount of [AzK_L1_PEG40] in the IL-15 conjugate is less than 1:1. In some embodiments, W is a linear or branched PEG group. In some embodiments, W is a linear PEG group. In some embodiments, W is a branched PEG group. In some embodiments, W is a methoxy PEG group. In some embodiments, the methoxy PEG group is linear or branched. In some embodiments, the methoxy PEG group is linear. In some embodiments, the methoxy PEG group is branched.

Described herein are IL-15 conjugates comprising the amino acid sequence of any one of SEQ ID NOS: 64-69, wherein [AzK_PEG] has the structure of Formula (II) or Formula (III), or a mixture of Formula (II) and Formula (III):

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

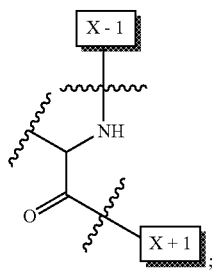

X−1 indicates the point of attachment to the preceding amino acid residue; and
X+1 indicates the point of attachment to the following amino acid residue.

In some embodiments, the IL-15 conjugate is a pharmaceutically acceptable salt, solvate, or hydrate. In some embodiments, the [AzK_PEG] is a mixture of Formula (II) and Formula (III).

In some embodiments, the [AzK_PEG] has the structure of Formula (II):

Formula (II)

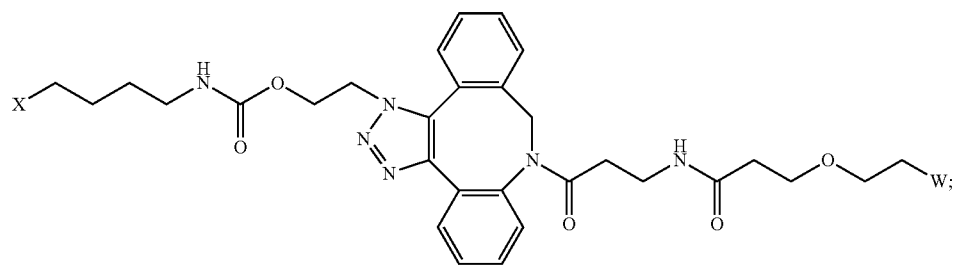

Formula (III)

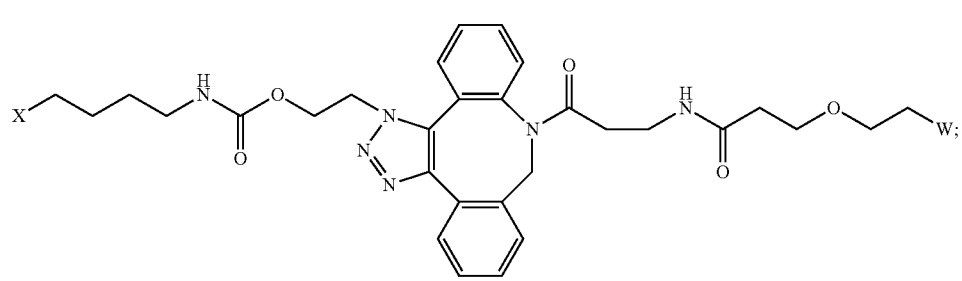

Formula (II)

In some embodiments, the IL-15 conjugate has the amino acid sequence of SEQ ID NO: 64. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 65. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 66. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 67. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 68. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 69. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa.

In some embodiments, the [AzK_PEG] has the structure of Formula (III)

Formula (III)

In some embodiments, the IL-15 conjugate has the amino acid sequence of SEQ ID NO: 64. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 65. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 66. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 67. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 68. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 69. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa.

Described herein are IL-15 conjugates comprising the amino acid sequence of any one of SEQ ID NOS: 64-69, wherein [AzK_PEG] is a mixture of the structures of Formula (II) and Formula (III):

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

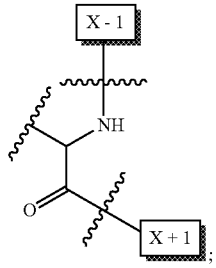

X−1 indicates the point of attachment to the preceding amino acid residue; and
X+1 indicates the point of attachment to the following amino acid residue.

In some embodiments, the IL-15 conjugate is a pharmaceutically acceptable salt, solvate, or hydrate. In some embodiments, the ratio of the amount of the structure of Formula (II) to the amount of the structure of Formula (III) comprising the total amount of [AzK_PEG] in the IL-15 conjugate is about 1:1. In some embodiments, the ratio of the amount of the structure of Formula (II) to the amount of the structure of Formula (III) comprising the total amount of [AzK_PEG] in the IL-15 conjugate is greater than 1:1. In some embodiments, the ratio of the amount of the structure of Formula (IV) to the amount of the structure of Formula (V) comprising the total amount of [AzK_PEG] in the IL-15 conjugate is less than 1:1. In some embodiments, W is a linear or branched PEG group. In some embodiments, W is a linear PEG group. In some embodiments, W is a branched PEG group. In some embodiments, W is a methoxy PEG group. In some embodiments, the methoxy PEG group is linear or branched. In some embodiments, the methoxy PEG group is linear. In some embodiments, the methoxy PEG group is branched.

Described herein are IL-15 conjugates comprising the amino acid sequence of any one of SEQ ID NOS: 70-75, wherein [AzK_PEG30] has the structure of Formula (II) or Formula (III), or a mixture of Formula (II) and Formula (III):

Formula (II)

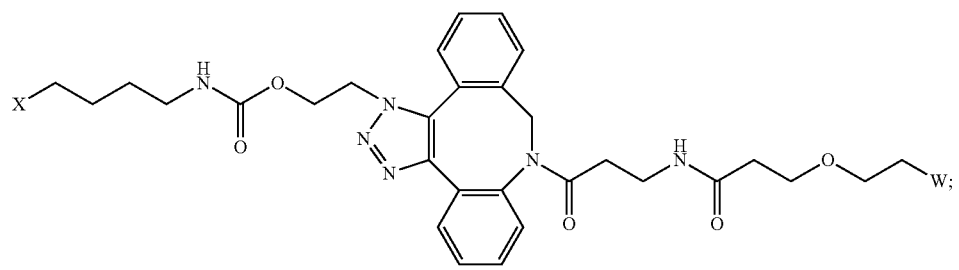

Formula (III)

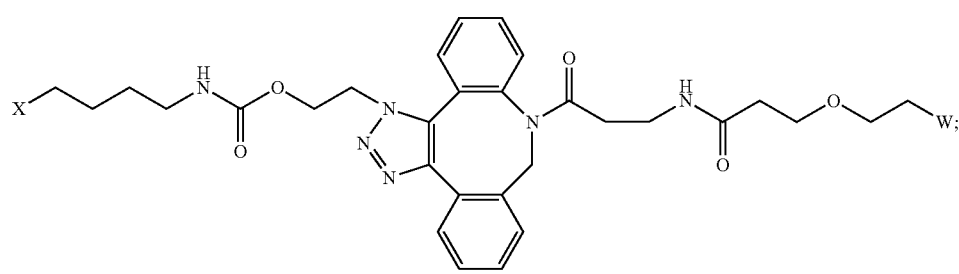

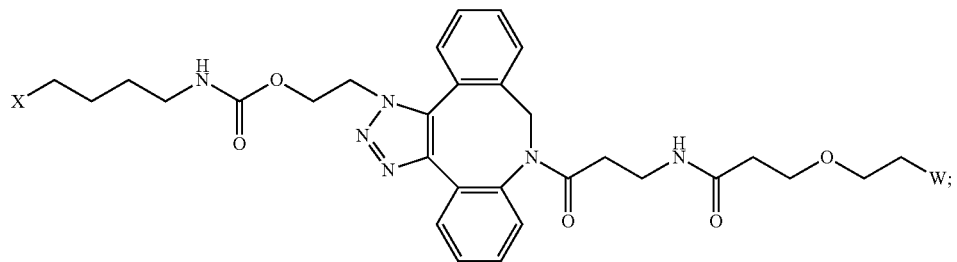

Formula (II)

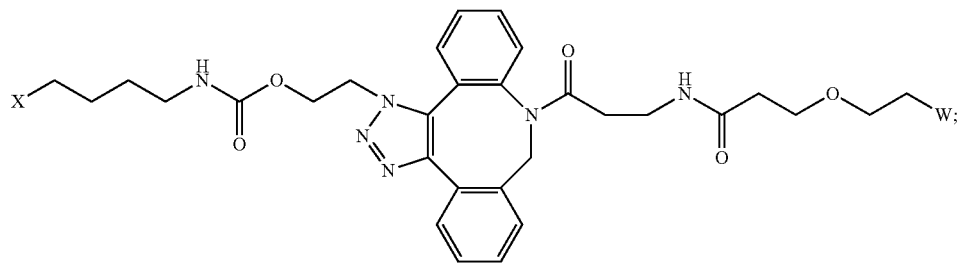

Formula (III)

wherein:
W is a PEG group having an average molecular weight of 30 kDa; and
X has the structure:

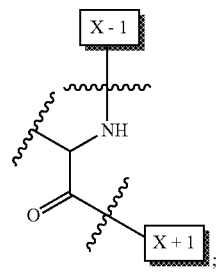

X−1 indicates the point of attachment to the preceding amino acid residue; and
X+1 indicates the point of attachment to the following amino acid residue.

In some embodiments, the IL-15 conjugate is a pharmaceutically acceptable salt, solvate, or hydrate. In some embodiments, the IL-15 conjugate has the amino acid sequence of SEQ ID NO: 70. In some embodiments, the IL-15 conjugate has the amino acid sequence of SEQ ID NO: 71. In some embodiments, the IL-15 conjugate has the amino acid sequence of SEQ ID NO: 72. In some embodiments, the IL-15 conjugate has the amino acid sequence of SEQ ID NO: 73. In some embodiments, the IL-15 conjugate has the amino acid sequence of SEQ ID NO: 74. In some embodiments, the IL-15 conjugate has the amino acid sequence of SEQ ID NO: 75.

In some embodiments, the [AzK_PEG30] has the structure of Formula (II)

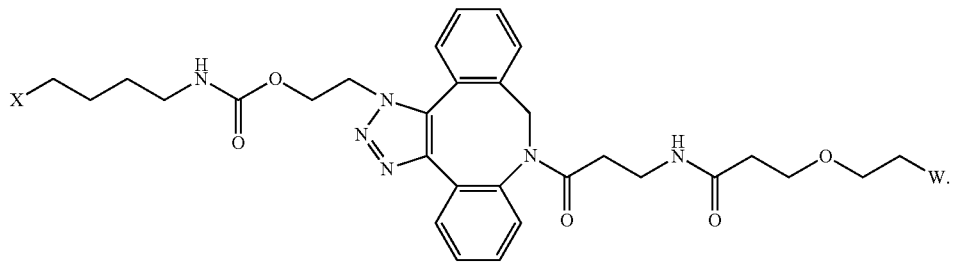

Formula (II)

In some embodiments, the IL-15 conjugate has the amino acid sequence of SEQ ID NO: 70. In some embodiments, the IL-15 conjugate has the amino acid sequence of SEQ ID NO: 71. In some embodiments, the IL-15 conjugate has the amino acid sequence of SEQ ID NO: 72. In some embodiments, the IL-15 conjugate has the amino acid sequence of SEQ ID NO: 73. In some embodiments, the IL-15 conjugate has the amino acid sequence of SEQ ID NO: 74. In some embodiments, the IL-15 conjugate has the amino acid sequence of SEQ ID NO: 75.

In some embodiments, the [AzK_PEG30] has the structure of Formula (III)

wherein:

W is a PEG group having an average molecular weight of 30 kDa; and

X has the structure:

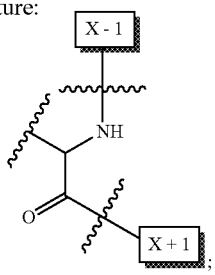

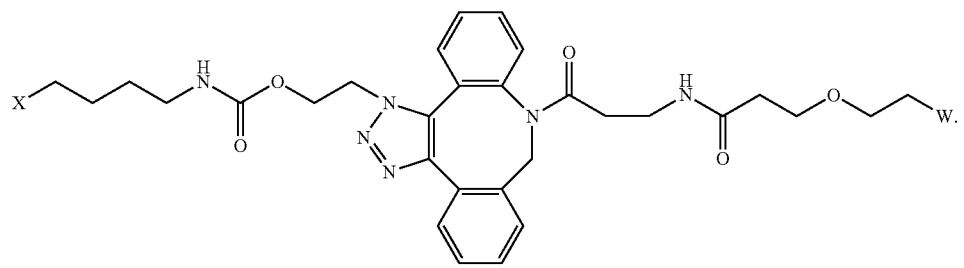

Formula (III)

In some embodiments, the IL-15 conjugate has the amino acid sequence of SEQ ID NO: 70. In some embodiments, the IL-15 conjugate has the amino acid sequence of SEQ ID NO: 71. In some embodiments, the IL-15 conjugate has the amino acid sequence of SEQ ID NO: 72. In some embodiments, the IL-15 conjugate has the amino acid sequence of SEQ ID NO: 73. In some embodiments, the IL-15 conjugate has the amino acid sequence of SEQ ID NO: 74. In some embodiments, the IL-15 conjugate has the amino acid sequence of SEQ ID NO: 75.

Described herein are IL-15 conjugates comprising the amino acid sequence of any one of SEQ ID NOS: 70-75, wherein [AzK_PEG30] is a mixture of the structures of Formula (II) and Formula (III):

X−1 indicates the point of attachment to the preceding amino acid residue; and

X+1 indicates the point of attachment to the following amino acid residue.

In some embodiments, the IL-15 conjugate is a pharmaceutically acceptable salt, solvate, or hydrate. In some embodiments, the ratio of the amount of the structure of Formula (II) to the amount of the structure of Formula (III) comprising the total amount of [AzK_PEG30] in the IL-15 conjugate is about 1:1. In some embodiments, the ratio of the amount of the structure of Formula (II) to the amount of the structure of Formula (III) comprising the total amount of [AzK_PEG30] in the IL-15 conjugate is greater than 1:1. In some embodiments, the ratio of the amount of the structure Formula (II)

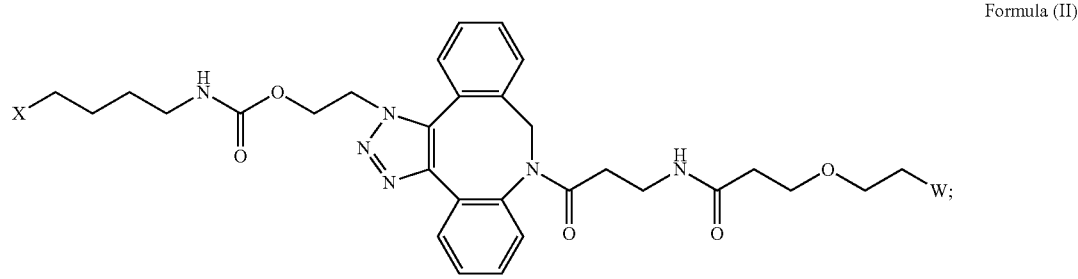

Formula (III)

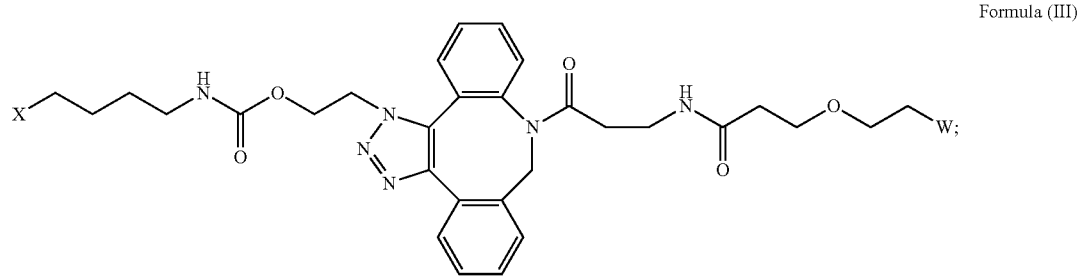

of Formula (II) to the amount of the structure of Formula (III) comprising the total amount of [AzK_PEG30] in the IL-15 conjugate is less than 1:1. In some embodiments, W is a linear or branched PEG group. In some embodiments, W is a linear PEG group. In some embodiments, W is a branched PEG group. In some embodiments, W is a methoxy PEG group. In some embodiments, the methoxy PEG group is linear or branched. In some embodiments, the methoxy PEG group is linear. In some embodiments, the methoxy PEG group is branched.

Described herein are IL-15 conjugates comprising the amino acid sequence of any one of SEQ ID NOS: 76-81, wherein [AzK_PEG40] has the structure of Formula (II) or Formula (III), or is a mixture of the structures of Formula (II) and Formula (III):

Formula (II)

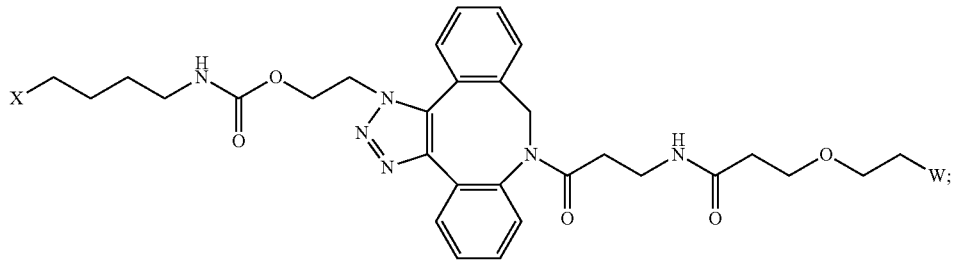

Formula (III)

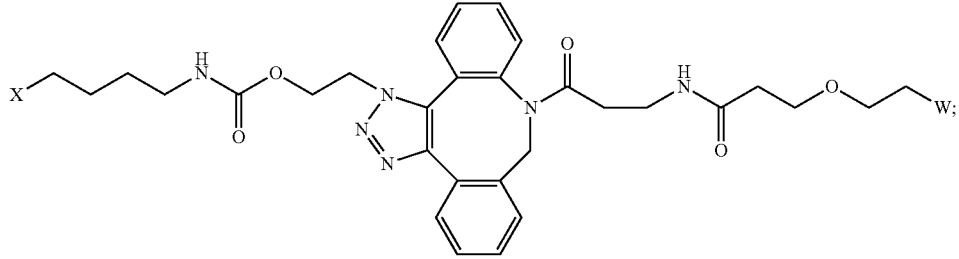

wherein:
W is a PEG group having an average molecular weight of 40 kDa; and
X has the structure:

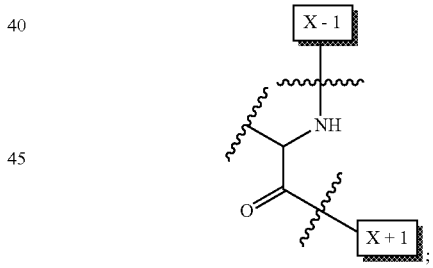

X−1 indicates the point of attachment to the preceding amino acid residue; and
X+1 indicates the point of attachment to the following amino acid residue.

In some embodiments, the IL-15 conjugate is a pharmaceutically acceptable salt, solvate, or hydrate. In some embodiments, the IL-15 conjugate has the amino acid sequence of SEQ ID NO: 76. In some embodiments, the IL-15 conjugate has the amino acid sequence of SEQ ID NO: 77. In some embodiments, the IL-15 conjugate has the amino acid sequence of SEQ ID NO: 78. In some embodiments, the IL-15 conjugate has the amino acid sequence of SEQ ID NO: 79. In some embodiments, the IL-15 conjugate has the amino acid sequence of SEQ ID NO: 80. In some embodiments, the IL-15 conjugate has the amino acid sequence of SEQ ID NO: 81.

In some embodiments, the [AzK_PEG40] has the structure of Formula (II):

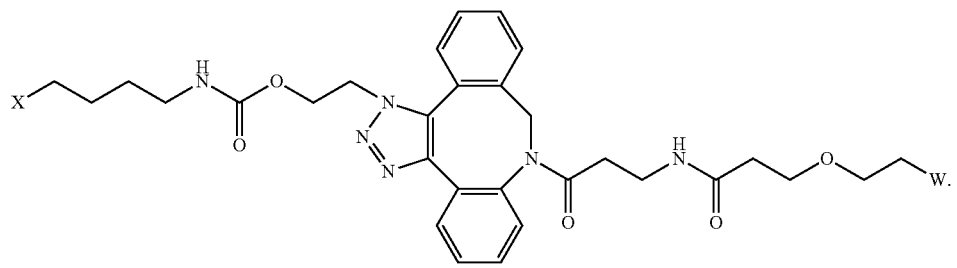

Formula (II)

In some embodiments, the IL-15 conjugate has the amino acid sequence of SEQ ID NO: 76. In some embodiments, the IL-15 conjugate has the amino acid sequence of SEQ ID NO: 77. In some embodiments, the IL-15 conjugate has the amino acid sequence of SEQ ID NO: 78. In some embodiments, the IL-15 conjugate has the amino acid sequence of SEQ ID NO: 79. In some embodiments, the IL-15 conjugate has the amino acid sequence of SEQ ID NO: 80. In some embodiments, the IL-15 conjugate has the amino acid sequence of SEQ ID NO: 81.

In some embodiments, the [AzK_PEG40] has the structure of Formula (III)

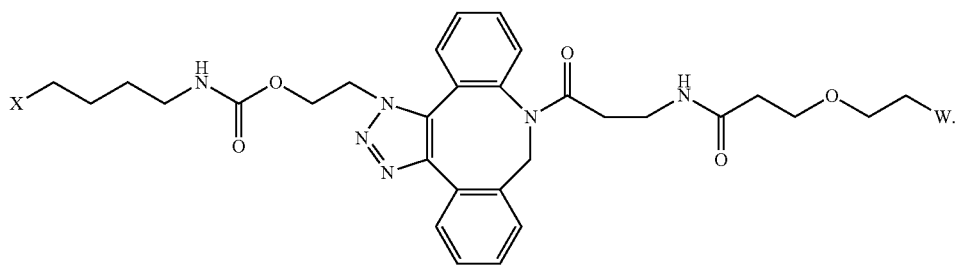

Formula (III)

In some embodiments, the IL-15 conjugate has the amino acid sequence of SEQ ID NO: 76. In some embodiments, the IL-15 conjugate has the amino acid sequence of SEQ ID NO: 77. In some embodiments, the IL-15 conjugate has the amino acid sequence of SEQ ID NO: 78. In some embodiments, the IL-15 conjugate has the amino acid sequence of SEQ ID NO: 79. In some embodiments, the IL-15 conjugate has the amino acid sequence of SEQ ID NO: 80. In some embodiments, the IL-15 conjugate has the amino acid sequence of SEQ ID NO: 81.

Described herein are IL-15 conjugates comprising the amino acid sequence of any one of SEQ ID NOS: 76-81, wherein [AzK_PEG40] is a mixture of the structures of Formula (II) and Formula (III):

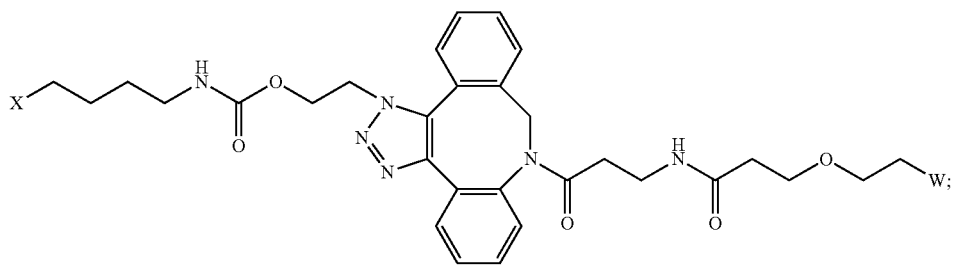

Formula (II)

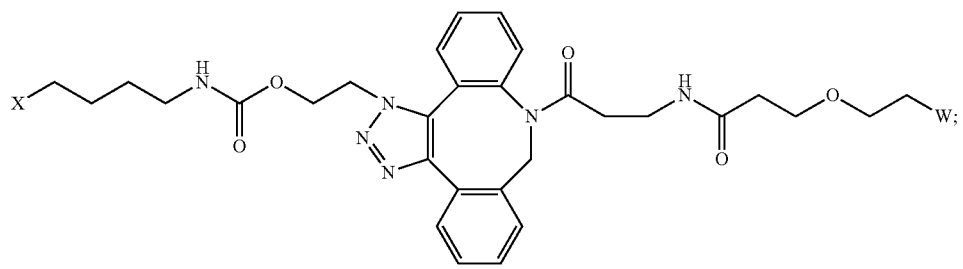

Formula (III)

wherein:
W is a PEG group having an average molecular weight of 40 kDa; and
X has the structure:

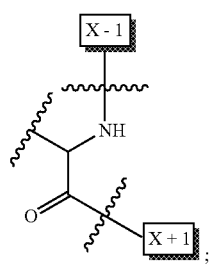

X−1 indicates the point of attachment to the preceding amino acid residue; and
X+1 indicates the point of attachment to the following amino acid residue.

In some embodiments, the IL-15 conjugate is a pharmaceutically acceptable salt, solvate, or hydrate.

In some embodiments, the ratio of the amount of the structure of Formula (II) to the amount of the structure of Formula (III) comprising the total amount of [AzK_PEG40] in the IL-15 conjugate is about 1:1. In some embodiments, the ratio of the amount of the structure of Formula (II) to the amount of the structure of Formula (III) comprising the total amount of [AzK_PEG40] in the IL-15 conjugate is greater than 1:1. In some embodiments, the ratio of the amount of the structure of Formula (II) to the amount of the structure of Formula (III) comprising the total amount of [AzK_PEG40] in the IL-15 conjugate is less than 1:1. In some embodiments, W is a linear or branched PEG group. In some embodiments, W is a linear PEG group. In some embodiments, W is a branched PEG group. In some embodiments, W is a methoxy PEG group. In some embodiments, the methoxy PEG group is linear or branched. In some embodiments, the methoxy PEG group is linear. In some embodiments, the methoxy PEG group is branched.

Described herein are IL-15 conjugates comprising the amino acid sequence of any one of SEQ ID NOS: 82-87, wherein [AzK_L1_PEG] has the structure of Formula (IV) or Formula (V), or a mixture of Formula (IV) and Formula (V):

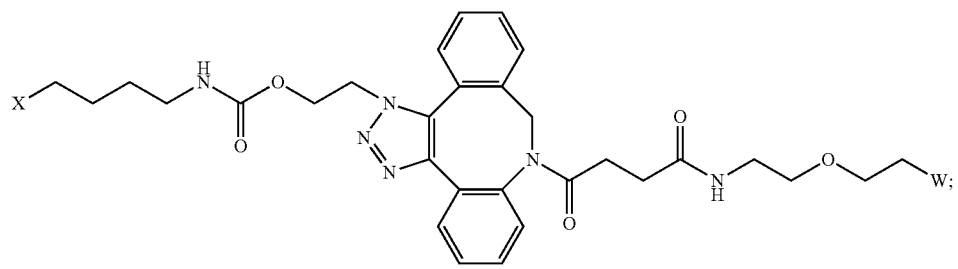

Formula (IV)

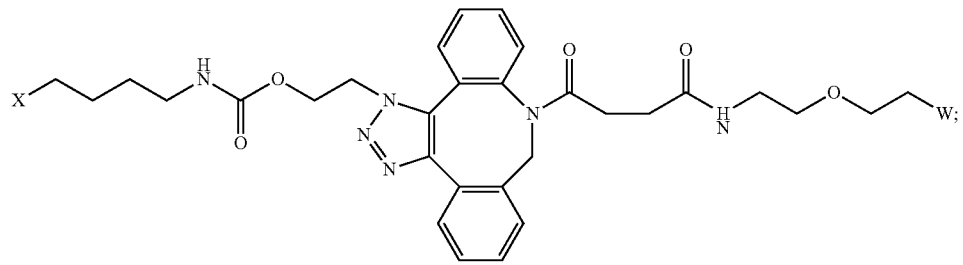

Formula (V)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

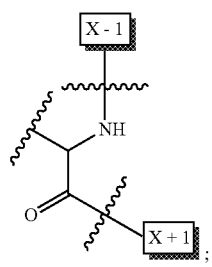

X−1 indicates the point of attachment to the preceding amino acid residue; and
X+1 indicates the point of attachment to the following amino acid residue.

In some embodiments, the IL-15 conjugate is a pharmaceutically acceptable salt, solvate, or hydrate. In some embodiments, the [AzK_L1_PEG] is a mixture of Formula (IV) and Formula (V).

In some embodiments, the [AzK_L1_PEG] has the structure of Formula (IV):

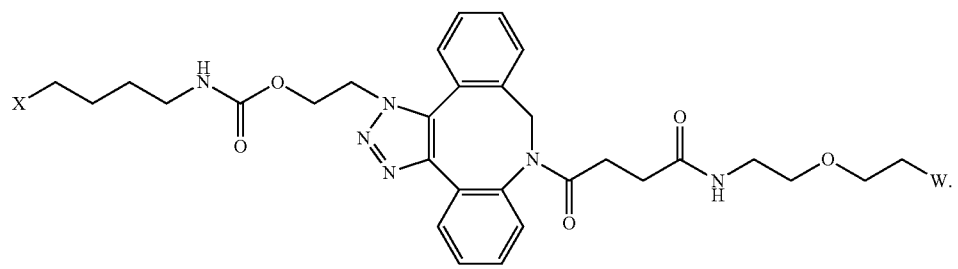

Formula (IV)

Here and throughout, the structure of Formula (IV) encompasses pharmaceutically acceptable salts, solvates, or hydrates thereof. In some embodiments, the IL-15 conjugate has the amino acid sequence of SEQ ID NO: 82. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 83. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 84. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 85. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 86. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 87. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa.

In some embodiments, the [AzK_L1_PEG] has the structure of Formula (V)

Formula (V)

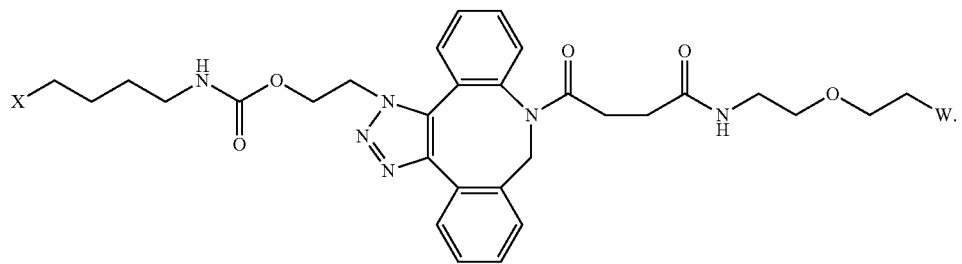

Here and throughout, the structure of Formula (V) encompasses pharmaceutically acceptable salts, solvates, or hydrates thereof. In some embodiments, the IL-15 conjugate has the amino acid sequence of SEQ ID NO: 82. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 83. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 84. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 85. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 86. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa. In some embodiments, the IL-15 conjugate has the amino acid sequence of SEQ ID NO: 87. In some embodiments, W is a PEG group having an average molecular weight selected from 5 kDa, 10 kDa, 15 kDa, 20 kDa, 25 kDa, 30 kDa, 35 kDa, 40 kDa, and 45 kDa. In some embodiments, W is a PEG group having an average molecular weight selected from 30 kDa and 40 kDa. In some embodiments, W is a PEG group having an average molecular weight of 30 kDa. In some embodiments, W is a PEG group having an average molecular weight of 40 kDa.

Described herein are IL-15 conjugates comprising the amino acid sequence of any one of SEQ ID NOS: 82-87, wherein [Azk_L1_PEG] is a mixture of the structures of Formula (IV) and Formula (V):

Formula (IV)

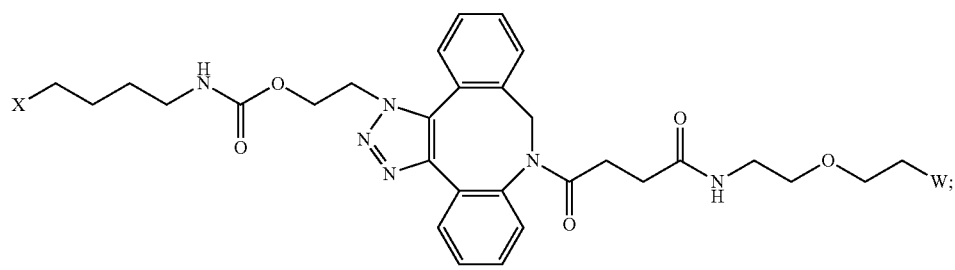

-continued

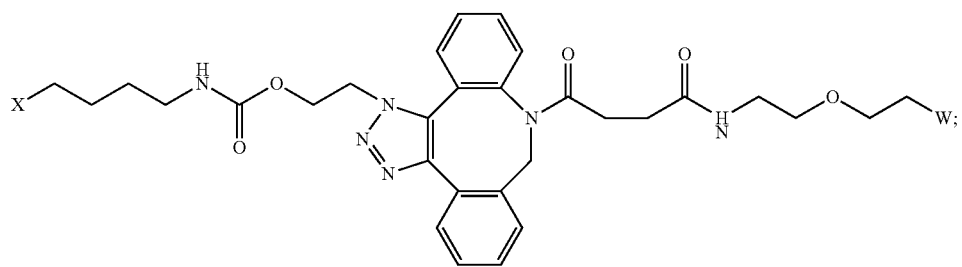

Formula (V)

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

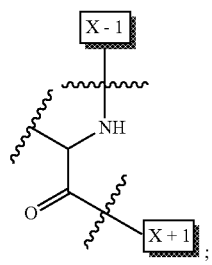

X−1 indicates the point of attachment to the preceding amino acid residue; and

X+1 indicates the point of attachment to the following amino acid residue.

In some embodiments, the IL-15 conjugate is a pharmaceutically acceptable salt, solvate, or hydrate. In some embodiments, the ratio of the amount of the structure of Formula (IV) to the amount of the structure of Formula (V) comprising the total amount of [AzK_L1_PEG] in the IL-15 conjugate is about 1:1. In some embodiments, the ratio of the amount of the structure of Formula (IV) to the amount of the structure of Formula (V) comprising the total amount of [AzK_L1_PEG] in the IL-15 conjugate is greater than 1:1. In some embodiments, the ratio of the amount of the structure of Formula (IV) to the amount of the structure of Formula (V) comprising the total amount of [AzK_L1_PEG] in the IL-15 conjugate is less than 1:1. In some embodiments, W is a linear or branched PEG group. In some embodiments, W is a linear PEG group. In some embodiments, W is a branched PEG group. In some embodiments, W is a methoxy PEG group. In some embodiments, the methoxy PEG group is linear or branched. In some embodiments, the methoxy PEG group is linear. In some embodiments, the methoxy PEG group is branched.

Described herein are IL-15 conjugates comprising the amino acid sequence of any one of SEQ ID NOS: 88-93, wherein [AzK_L1_PEG30] has the structure of Formula (IV) or Formula (V), or a mixture of Formula (IV) and Formula (V):

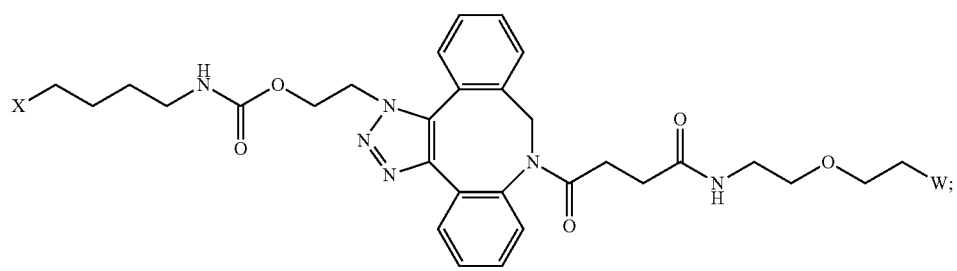

Formula (IV)

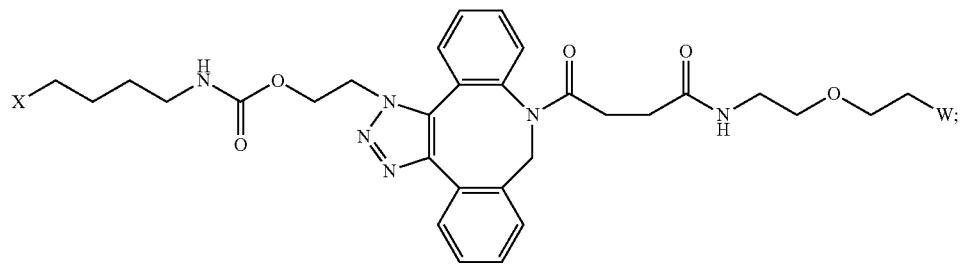

Formula (V)

wherein:

W is a PEG group having an average molecular weight of 30 kDa; and

X has the structure:

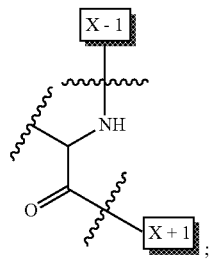

X-1 indicates the point of attachment to the preceding amino acid residue; and

X+1 indicates the point of attachment to the following amino acid residue.

In some embodiments, the IL-15 conjugate is a pharmaceutically acceptable salt, solvate, or hydrate. In some embodiments, the IL-15 conjugate has the amino acid sequence of SEQ ID NO: 88. In some embodiments, the IL-15 conjugate has the amino acid sequence of SEQ ID NO: 89. In some embodiments, the IL-15 conjugate has the amino acid sequence of SEQ ID NO: 90. In some embodiments, the IL-15 conjugate has the amino acid sequence of SEQ ID NO: 91. In some embodiments, the IL-15 conjugate has the amino acid sequence of SEQ ID NO: 92. In some embodiments, the IL-15 conjugate has the amino acid sequence of SEQ ID NO: 93.

In some embodiments, the [AzK_L1_PEG30] has the structure of Formula (IV)

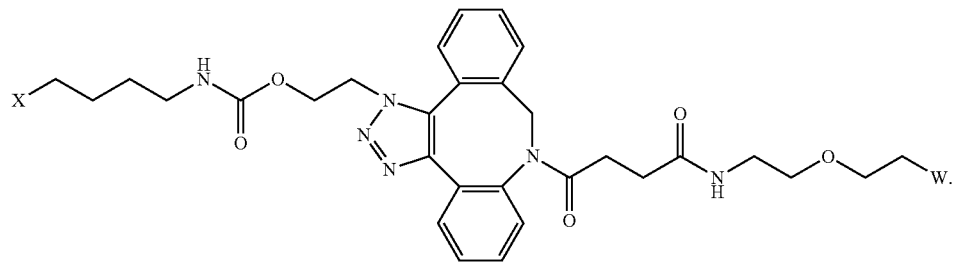

Formula (IV)

In some embodiments, the IL-15 conjugate has the amino acid sequence of SEQ ID NO: 88. In some embodiments, the IL-15 conjugate has the amino acid sequence of SEQ ID NO: 89. In some embodiments, the IL-15 conjugate has the amino acid sequence of SEQ ID NO: 90. In some embodiments, the IL-15 conjugate has the amino acid sequence of SEQ ID NO: 91. In some embodiments, the IL-15 conjugate has the amino acid sequence of SEQ ID NO: 92. In some embodiments, the IL-15 conjugate has the amino acid sequence of SEQ ID NO: 93.

In some embodiments, the [AzK_L1_PEG30] has the structure of Formula (V)

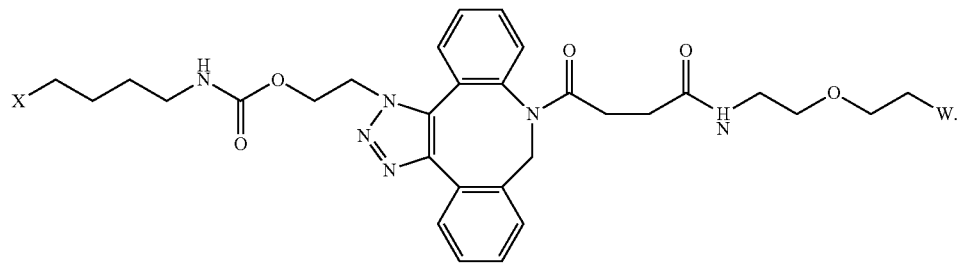

Formula (V)

In some embodiments, the IL-15 conjugate has the amino acid sequence of SEQ ID NO: 88. In some embodiments, the IL-15 conjugate has the amino acid sequence of SEQ ID NO: 89. In some embodiments, the IL-15 conjugate has the amino acid sequence of SEQ ID NO: 90. In some embodiments, the IL-15 conjugate has the amino acid sequence of SEQ ID NO: 91. In some embodiments, the IL-15 conjugate has the amino acid sequence of SEQ ID NO: 92. In some embodiments, the IL-15 conjugate has the amino acid sequence of SEQ ID NO: 93.

Described herein are IL-15 conjugates comprising the amino acid sequence of any one of SEQ ID NOS: 88-93, wherein [AzK_L1_PEG30] is a mixture of the structures of Formula (IV) and Formula (V):

X−1 indicates the point of attachment to the preceding amino acid residue; and

X+1 indicates the point of attachment to the following amino acid residue.

In some embodiments, the IL-15 conjugate is a pharmaceutically acceptable salt, solvate, or hydrate. In some embodiments, the ratio of the amount of the structure of Formula (IV) to the amount of the structure of Formula (V) comprising the total amount of [AzK_L1_PEG30] in the IL-15 conjugate is about 1:1. In some embodiments, the ratio of the amount of the structure of Formula (IV) to the amount of the structure of Formula (V) comprising the total amount of [AzK_L1_PEG30] in the IL-15 conjugate is greater than 1:1. In some embodiments, the ratio of the amount of the Formula (IV)

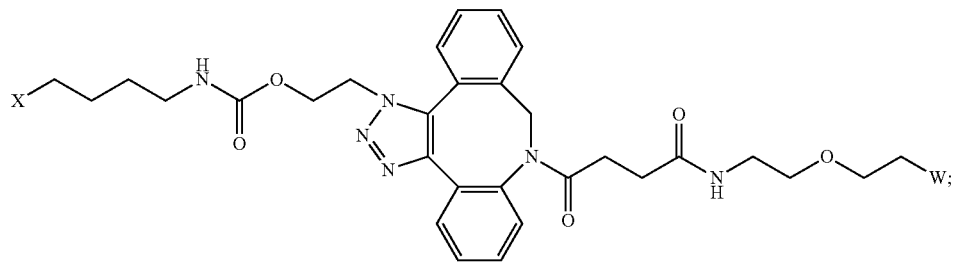

Formula (V)

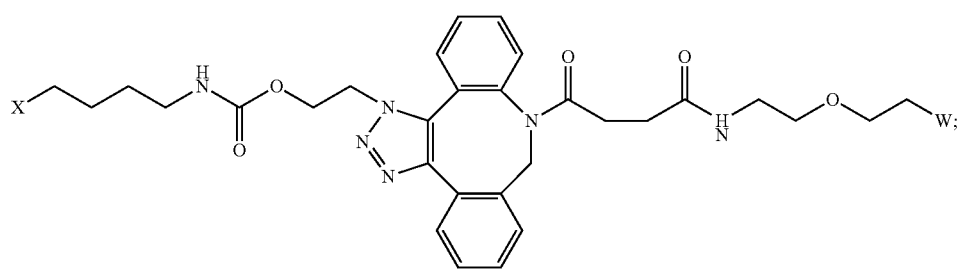

wherein:

W is a PEG group having an average molecular weight of 30 kDa; and

X has the structure:

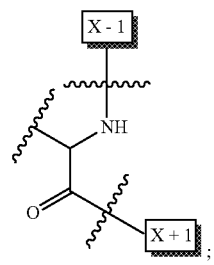

structure of Formula (IV) to the amount of the structure of Formula (V) comprising the total amount of [AzK_L1_PEG30] in the IL-15 conjugate is less than 1:1. In some embodiments, W is a linear or branched PEG group. In some embodiments, W is a linear PEG group. In some embodiments, W is a branched PEG group. In some embodiments, W is a methoxy PEG group. In some embodiments, the methoxy PEG group is linear or branched. In some embodiments, the methoxy PEG group is linear. In some embodiments, the methoxy PEG group is branched.

Described herein are IL-15 conjugates comprising the amino acid sequence of any one of SEQ ID NOS: 94-99, wherein [AzK_L1_PEG40] has the structure of Formula (IV) or Formula (V), or is a mixture of the structures of Formula (IV) and Formula (V):

Formula (IV)

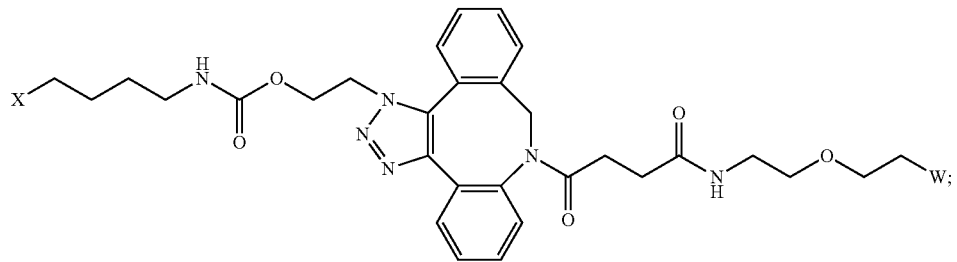

Formula (V)

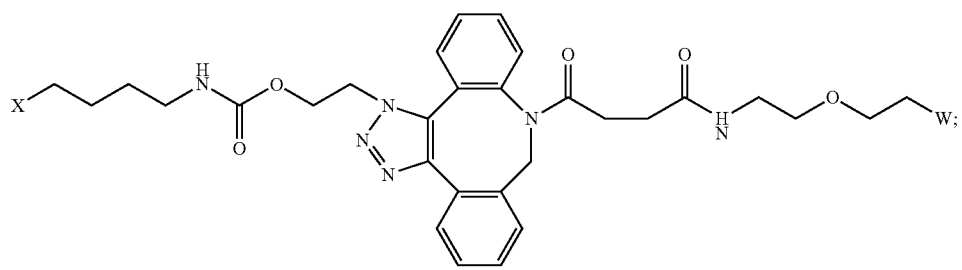

wherein:

W is a PEG group having an average molecular weight of 40 kDa; and

X has the structure:

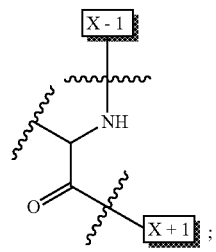

X−1 indicates the point of attachment to the preceding amino acid residue; and

X+1 indicates the point of attachment to the following amino acid residue.

In some embodiments, the IL-15 conjugate is a pharmaceutically acceptable salt, solvate, or hydrate. In some embodiments, the IL-15 conjugate has the amino acid sequence of SEQ ID NO: 94. In some embodiments, the IL-15 conjugate has the amino acid sequence of SEQ ID NO: 95. In some embodiments, the IL-15 conjugate has the amino acid sequence of SEQ ID NO: 96. In some embodiments, the IL-15 conjugate has the amino acid sequence of SEQ ID NO: 97. In some embodiments, the IL-15 conjugate has the amino acid sequence of SEQ ID NO: 98. In some embodiments, the IL-15 conjugate has the amino acid sequence of SEQ ID NO: 99.

In some embodiments, the [AzK_L1_PEG40] has the structure of Formula (IV):

Formula (IV)

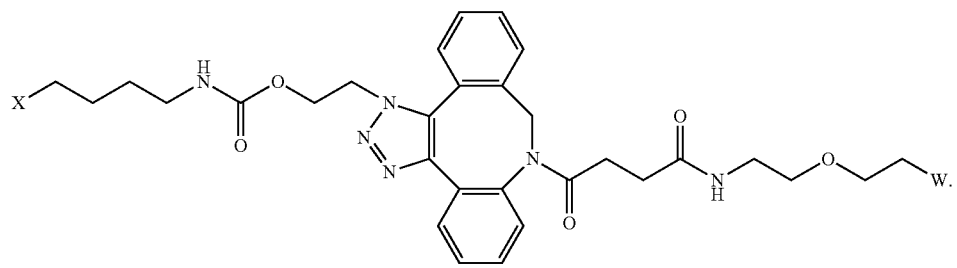

In some embodiments, the IL-15 conjugate has the amino acid sequence of SEQ ID NO: 94. In some embodiments, the IL-15 conjugate has the amino acid sequence of SEQ ID NO: 95. In some embodiments, the IL-15 conjugate has the amino acid sequence of SEQ ID NO: 96. In some embodiments, the IL-15 conjugate has the amino acid sequence of SEQ ID NO: 97. In some embodiments, the IL-15 conjugate has the amino acid sequence of SEQ ID NO: 98. In some embodiments, the IL-15 conjugate has the amino acid sequence of SEQ ID NO: 99.

In some embodiments, the [AzK_L1_PEG40] has the structure of Formula (V)

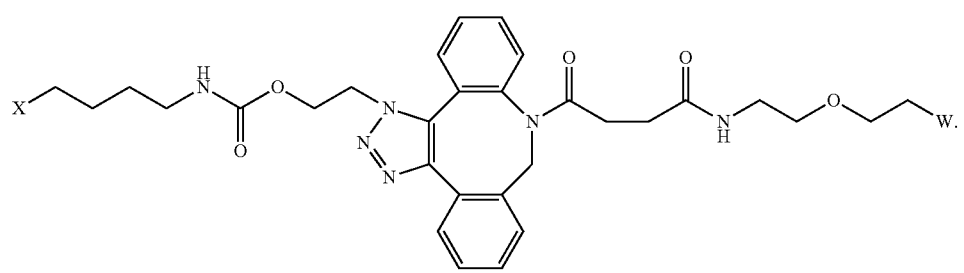

Formula (V)

In some embodiments, the IL-15 conjugate has the amino acid sequence of SEQ ID NO: 94. In some embodiments, the IL-15 conjugate has the amino acid sequence of SEQ ID NO: 95. In some embodiments, the IL-15 conjugate has the amino acid sequence of SEQ ID NO: 96. In some embodiments, the IL-15 conjugate has the amino acid sequence of SEQ ID NO: 97. In some embodiments, the IL-15 conjugate has the amino acid sequence of SEQ ID NO: 98. In some embodiments, the IL-15 conjugate has the amino acid sequence of SEQ ID NO: 99.

Described herein are IL-15 conjugates comprising the amino acid sequence of any one of SEQ ID NOS: 94-99, wherein [AzK_L1_PEG40] is a mixture of the structures of Formula (IV) and Formula (V):

wherein:

W is a PEG group having an average molecular weight of 40 kDa; and

X has the structure:

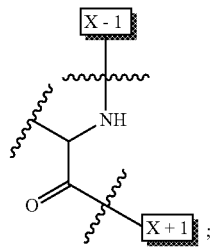

X−1 indicates the point of attachment to the preceding amino acid residue; and

X+1 indicates the point of attachment to the following amino acid residue.

In some embodiments, the IL-15 conjugate is a pharmaceutically acceptable salt, solvate, or hydrate.

In some embodiments, the ratio of the amount of the structure of Formula (IV) to the amount of the structure of Formula (V) comprising the total amount of [AzK_L1_PEG40] in the IL-15 conjugate is about 1:1. In some embodiments, the ratio of the amount of the structure of Formula (IV) to the amount of the structure of Formula (V) comprising the total amount of [AzK_L1_PEG40] in the IL-15 conjugate is greater than 1:1. In some embodiments, Formula (IV)

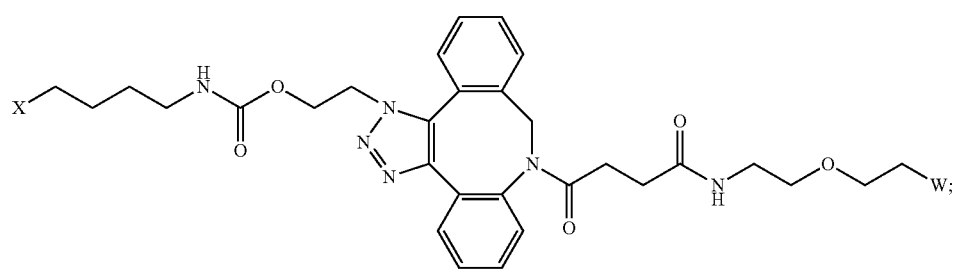

Formula (V)

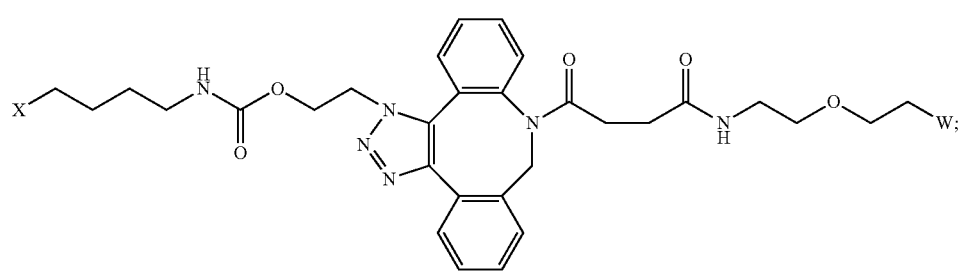

the ratio of the amount of the structure of Formula (IV) to the amount of the structure of Formula (V) comprising the total amount of [AzK_L1_PEG40] in the IL-15 conjugate is less than 1:1. In some embodiments, W is a linear or branched PEG group. In some embodiments, W is a linear PEG group. In some embodiments, W is a branched PEG group. In some embodiments, W is a methoxy PEG group. In some embodiments, the methoxy PEG group is linear or branched. In some embodiments, the methoxy PEG group is linear. In some embodiments, the methoxy PEG group is branched.

Described herein are IL-15 conjugates comprising the amino acid sequence of SEQ ID NO: 1 in which at least one amino acid residue in the IL-15 conjugate is replaced by the structure of Formula (VI) or (VII), or a mixture of (VI) and (VII):

of the IL-15 conjugate comprising SEQ ID NO: 1 is selected from S18, L25, E46, E53, N77, and S83. In some embodiments, the position of the structure of Formula (VI) or (VII), or a mixture of (VI) and (VII), in the amino acid sequence of the IL-15 conjugate comprising SEQ ID NO: 1 is selected from L25, E53, and N77. In some embodiments, the position of the structure of Formula (VI) or (VII), or a mixture of (VI) and (VII), in the amino acid sequence of the IL-15 conjugate comprising SEQ ID NO: 1 is S18. In some embodiments, the position of the structure of Formula (VI) or (VII), or a mixture of (VI) and (VII), in the amino acid sequence of the IL-15 conjugate comprising SEQ ID NO: 1 is L25. In some embodiments, the position of the structure of Formula (VI) or (VII), or a mixture of (VI) and (VII), in the amino acid sequence of the IL-15 conjugate is comprising SEQ ID NO: 1 E46. In some embodiments, the position of the structure of

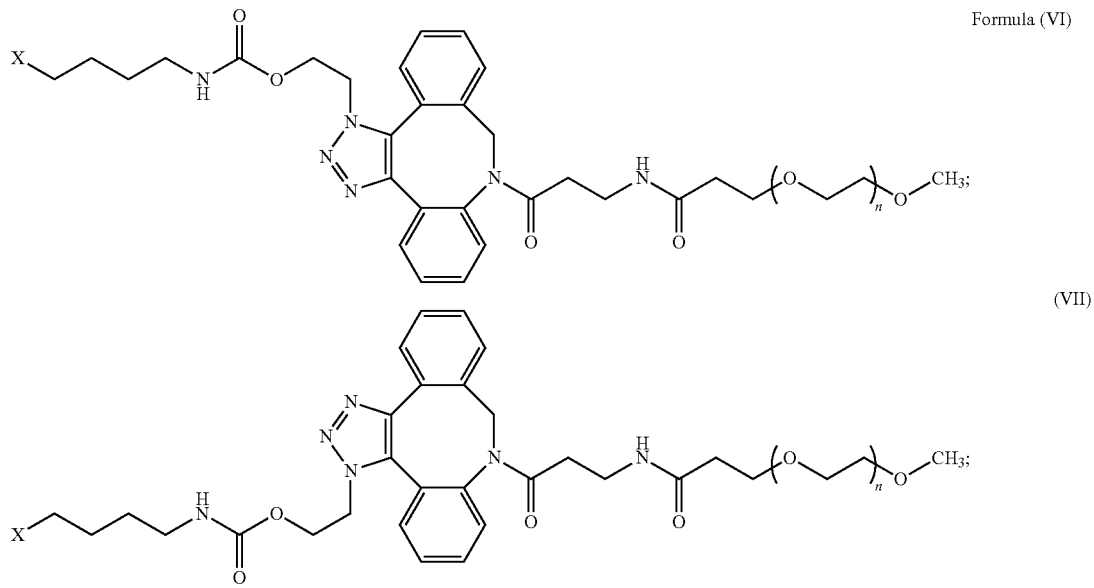

wherein:
n is an integer in the range from about 2 to about 5000; and
X has the structure:

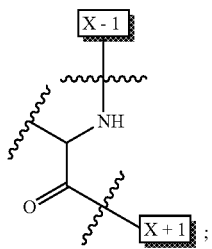

X−1 indicates the point of attachment to the preceding amino acid residue; and
X+1 indicates the point of attachment to the following amino acid residue.

In some embodiments, the IL-15 conjugate is a pharmaceutically acceptable salt, solvate, or hydrate. In some embodiments, the position of the structure of Formula (VI) or (VII), or a mixture of (VI) and (VII), in the amino acid sequence Formula (VI) or (VII), or a mixture of (VI) and (VII), in the amino acid sequence of the IL-15 conjugate is comprising SEQ ID NO: 1 E53. In some embodiments, the position of the structure of Formula (VI) or (VII), or a mixture of (VI) and (VII), in the amino acid sequence of the IL-15 conjugate is comprising SEQ ID NO: 1 N77. In some embodiments, the position of the structure of Formula (VI) or (VII), or a mixture of (VI) and (VII), in the amino acid sequence of the IL-15 conjugate comprising SEQ ID NO: 1 is S83. In some embodiments, n is about 75 to about 1000. In some embodiments, n is about 100 to about 1000. In some embodiments, n is about 200 to about 5000. In some embodiments, n is about 500 to about 1000. In some embodiments, n is about 400 to about 800. In some embodiments described herein, n is an integer from about 450 to about 800, or from about 454 to about 796, or from about 454 to about 682, or from about 568 to about 909. In some embodiments, n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 681. In some embodiments, n is about 795. In some embodiments, n is about 909. In some embodiments, n is about 1022. In some embodiments, n is about 1136.

Described herein are IL-15 conjugates comprising the amino acid sequence of SEQ ID NO: 3 in which at least one amino acid residue in the IL-15 conjugate is replaced by the structure of Formula (VI) or (VII), or a mixture of (VI) and (VII):

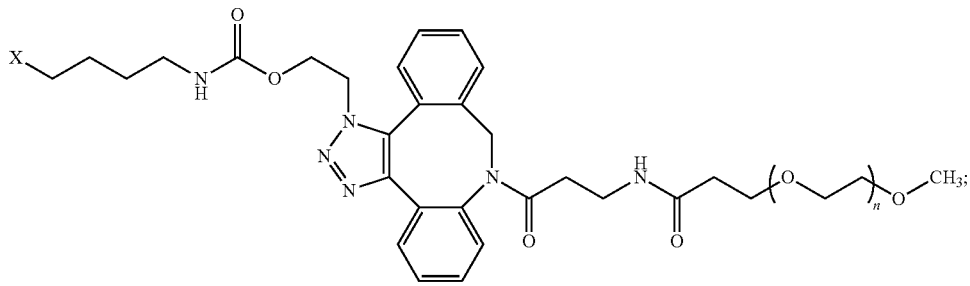

Formula (VI)

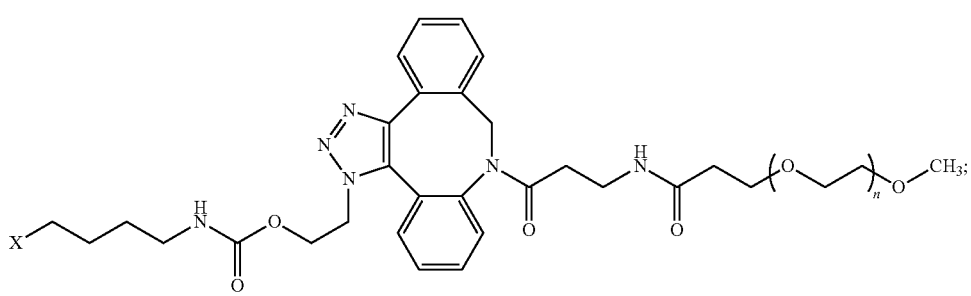

(VII)

wherein:
n is an integer in the range from about 2 to about 5000; and
X has the structure

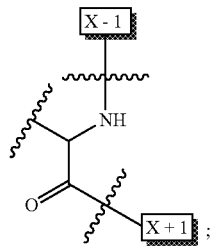

X−1 indicates the point of attachment to the preceding amino acid residue; and
X+1 indicates the point of attachment to the following amino acid residue.

In some embodiments, the IL-15 conjugate is a pharmaceutically acceptable salt, solvate, or hydrate. In some embodiments, the position of the structure of Formula (VI) or (VII), or a mixture of (VI) and (VII) in the amino acid sequence of the IL-15 conjugate comprising SEQ ID NO: 3 is selected from S19, L26, E47, E54, N78, and S84. In some embodiments, the position of the structure of Formula (VI) or (VII), or a mixture of (VI) and (VII) in the amino acid sequence of the IL-15 conjugate comprising SEQ ID NO: 3 is selected from L26, E54, and N78. In some embodiments, the position of the structure of Formula (VI) or (VII), or a mixture of (VI) and (VII) in the amino acid sequence of the IL-15 conjugate comprising SEQ ID NO: 3 is S19. In some embodiments, the position of the structure of Formula (VI) or (VII), or a mixture of (VI) and (VII) in the amino acid sequence of the IL-15 conjugate comprising SEQ ID NO: 3 is L26. In some embodiments, the position of the structure of Formula (VI) or (VII), or a mixture of (VI) and (VII) in the amino acid sequence of the IL-15 conjugate comprising SEQ ID NO: 3 is E47. In some embodiments, the position of the structure of Formula (VI) or (VII), or a mixture of (VI) and (VII) in the amino acid sequence of the IL-15 conjugate comprising SEQ ID NO: 3 is E54. In some embodiments, the position of the structure of Formula (VI) or (VII), or a mixture of (VI) and (VII) in the amino acid sequence of the IL-15 conjugate comprising SEQ ID NO: 3 is N78. In some embodiments, the position of the structure of Formula (VI) or (VII), or a mixture of (VI) and (VII) in the amino acid sequence of the IL-15 conjugate comprising SEQ ID NO: 3 is S84. In some embodiments, n is about 75 to about 1000. In some embodiments, n is about 100 to about 1000. In some embodiments, n is about 200 to about 5000. In some embodiments, n is about 500 to about 1000. In some embodiments, n is about 400 to about 800. In some embodiments described herein, n is an integer from about 450 to about 800, or from about 454 to about 796, or from about 454 to about 682, or from about 568 to about 909. In some embodiments, n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 795. In some embodiments, n is about 909. In some embodiments, n is about 1022. In some embodiments, n is about 1136.

Described herein are IL-15 conjugates comprising the amino acid sequence of SEQ ID NO: 1 in which at least one amino acid residue in the IL-15 conjugate is replaced by the structure of Formula (VIII) or (IX), or a mixture of (VIII) and (IX):

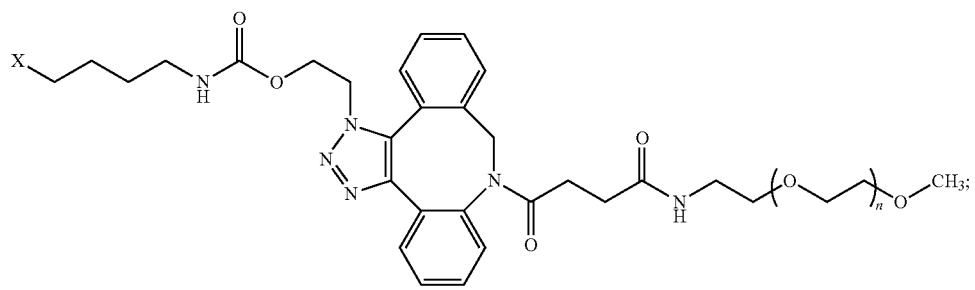

Formula (VIII)

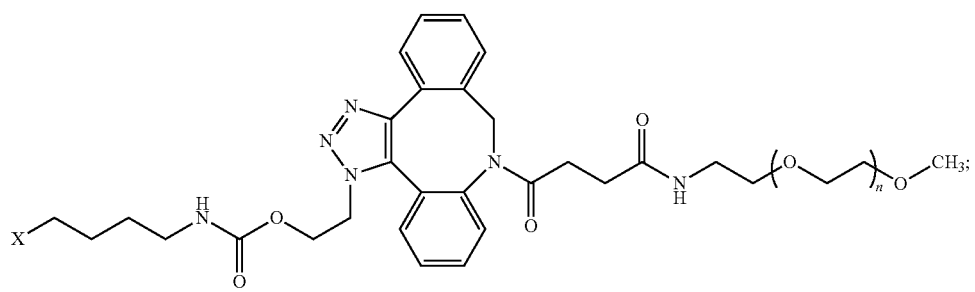

Formula (IX)

wherein:

n is an integer in the range from about 2 to about 5000, and X has the structure:

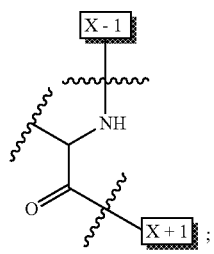

X−1 indicates the point of attachment to the preceding amino acid residue; and

X+1 indicates the point of attachment to the following amino acid residue.

In some embodiments, the IL-15 conjugate is a pharmaceutically acceptable salt, solvate, or hydrate. In some embodiments, the position of the structure of Formula (VIII) or (IX), or a mixture of (VIII) and (IX), in the amino acid sequence of the IL-15 conjugate comprising SEQ ID NO: 1 is selected from S18, L25, E46, E53, N77, and S83. In some embodiments, the position of the structure of Formula (VIII) or (IX), or a mixture of (VIII) and (IX), in the amino acid sequence of the IL-15 conjugate comprising SEQ ID NO: 1 is selected from L25, E53, and N77. In some embodiments, the position of the structure of Formula (VIII) or (IX), or a mixture of (VIII) and (IX), in the amino acid sequence of the IL-15 conjugate comprising SEQ ID NO: 1 is S18. In some embodiments, the position of the structure of Formula (VIII) or (IX), or a mixture of (VIII) and (IX), in the amino acid sequence of the IL-15 conjugate comprising SEQ ID NO: 1 is L25. In some embodiments, the position of the structure of Formula (VIII) or (IX), or a mixture of (VIII) and (IX), in the amino acid sequence of the IL-15 conjugate comprising SEQ ID NO: 1 is E46. In some embodiments, the position of the structure of Formula (VIII) or (IX), or a mixture of (VIII) and (IX), in the amino acid sequence of the IL-15 conjugate comprising SEQ ID NO: 1 is E53. In some embodiments, the position of the structure of Formula (VIII) or (IX), or a mixture of (VIII) and (IX), in the amino acid sequence of the IL-15 conjugate comprising SEQ ID NO: 1 is N77. In some embodiments, the position of the structure of Formula (VIII) or (IX), or a mixture of (VIII) and (IX), in the amino acid sequence of the IL-15 conjugate comprising SEQ ID NO: 1 is S83. In some embodiments, n is about 75 to about 1000. In some embodiments, n is about 100 to about 1000. In some embodiments, n is about 200 to about 5000. In some embodiments, n is about 500 to about 1000. In some embodiments, n is about 400 to about 800. In some embodiments described herein, n is an integer from about 450 to about 800, or from about 454 to about 796, or from about 454 to about 682, or from about 568 to about 909. In some embodiments, n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 795. In some embodiments, n is about 909. In some embodiments, n is about 1022. In some embodiments, n is about 1136.

Described herein are IL-15 conjugates comprising the amino acid sequence of SEQ ID NO: 3 in which at least one amino acid residue in the IL-15 conjugate is replaced by the structure of Formula (VIII) or (IX), or a mixture of (VIII) and (IX):

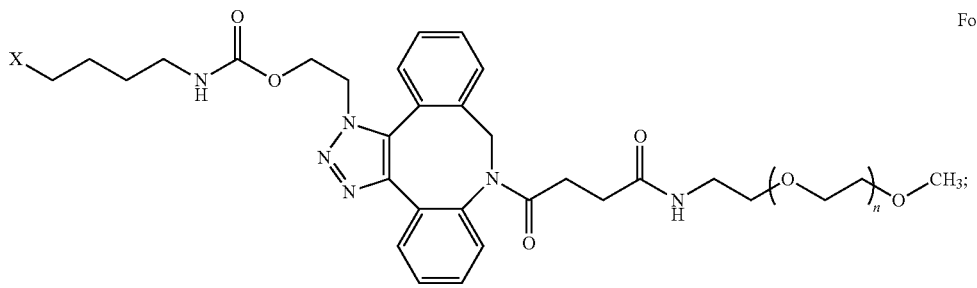

Formula (VIII)

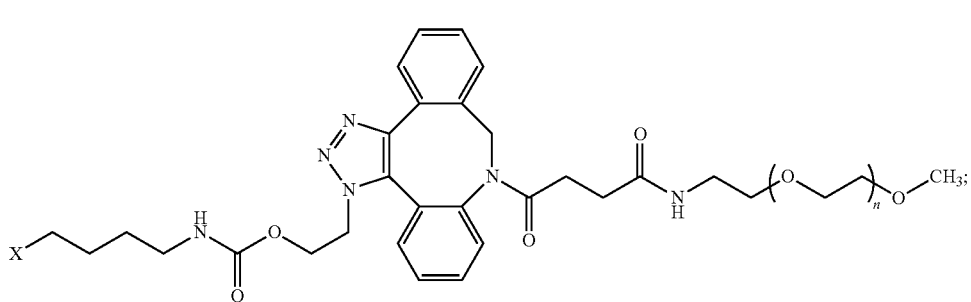

Formula (IX)

wherein:

n is an integer in the range from about 2 to about 5000; and

X has the structure:

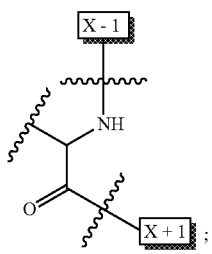

X−1 indicates the point of attachment to the preceding amino acid residue; and

X+1 indicates the point of attachment to the following amino acid residue.

In some embodiments, the IL-15 conjugate is a pharmaceutically acceptable salt, solvate, or hydrate. In some embodiments, the position of the structure of Formula (VIII) or (IX), or a mixture of (VIII) and (IX), in the amino acid sequence of the IL-15 conjugate comprising SEQ ID NO: 3 is selected from S19, L26, E47, E54, N78, and S84. In some embodiments, the position of the structure of Formula (VIII) or (IX), or a mixture of (VIII) and (IX), in the amino acid sequence of the IL-15 conjugate comprising SEQ ID NO: 3 is selected from L26, E54, and N78. In some embodiments, the position of the structure of Formula (VIII) or (IX), or a mixture of (VIII) and (IX), in the amino acid sequence of the IL-15 conjugate comprising SEQ ID NO: 3 is S19. In some embodiments, the position of the structure of Formula (VIII) or (IX), or a mixture of (VIII) and (IX), in the amino acid sequence of the IL-15 conjugate comprising SEQ ID NO: 3 is L26. In some embodiments, the position of the structure of Formula (VIII) or (IX), or a mixture of (VIII) and (IX) in the amino acid sequence of the IL-15 conjugate comprising SEQ ID NO: 3 is E47. In some embodiments, the position of the structure of Formula (VIII) or (IX), or a mixture of (VIII) and (IX), in the amino acid sequence of the IL-15 conjugate comprising SEQ ID NO: 3 is E54. In some embodiments, the position of the structure of Formula (VIII) or (IX), or a mixture of (VIII) and (IX), in the amino acid sequence of the IL-15 conjugate comprising SEQ ID NO: 3 is N78. In some embodiments, the position of the structure of Formula (VIII) or (IX), or a mixture of (VIII) and (IX), in the amino acid sequence of the IL-15 conjugate comprising SEQ ID NO: 3 is S84. In some embodiments, n is about 75 to about 1000. In some embodiments, n is about 100 to about 1000. In some embodiments, n is about 200 to about 5000. In some embodiments, n is about 500 to about 1000. In some embodiments, n is about 400 to about 800. In some embodiments described herein, n is an integer from about 450 to about 800, or from about 454 to about 796, or from about 454 to about 682, or from about 568 to about 909. In some embodiments, n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 795. In some embodiments, n is about 909. In some embodiments, n is about 1022. In some embodiments, n is about 1136.

Described herein are IL-15 conjugates comprising the amino acid sequence of SEQ ID NO: 1 or SEQ ID NO: 3 in which at least one amino acid residue in the IL-15 conjugate is replaced by the structure of Formula (X) or (XI), or a mixture of (X) and (XI):

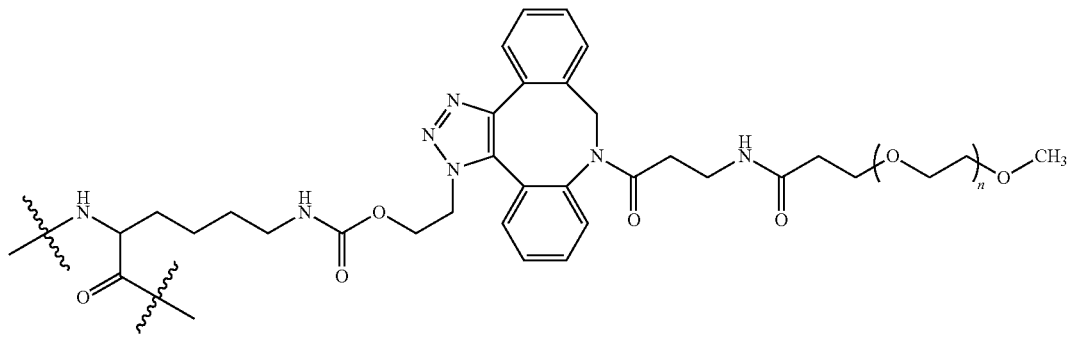

Formula (X)

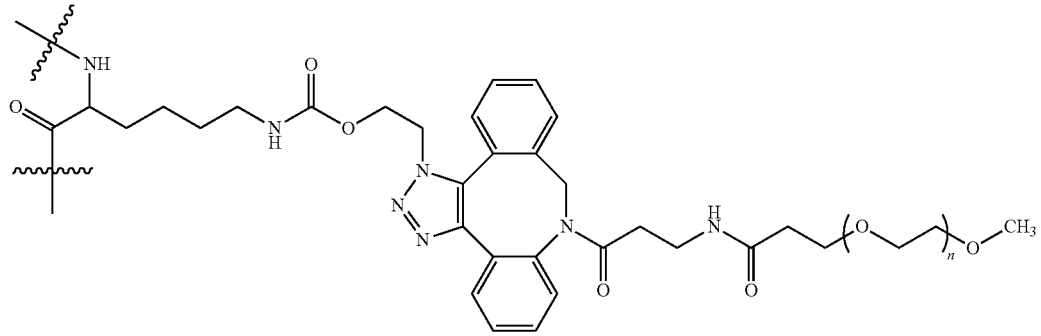

Formula (XI)

wherein:

n is an integer in the range from about 2 to about 5000; and the wavy lines indicate covalent bonds to amino acid residues within SEQ ID NO: 1 or SEQ ID NO: 3 that are not replaced. In some embodiments, the IL-15 conjugate is a pharmaceutically acceptable salt, solvate, or hydrate.

In some embodiments, the stereochemistry of the chiral center within Formula (X) and Formula (XI) is racemic, is enriched in (R), is enriched in (S), is substantially (R), is substantially (S), is (R) or is (S). In some embodiments, the stereochemistry of the chiral center within Formula (X) and Formula (XI) is racemic. In some embodiments, the stereochemistry of the chiral center within Formula (X) and Formula (XI) is enriched in (R). In some embodiments, the stereochemistry of the chiral center within Formula (X) and Formula (XI) is enriched in (S). In some embodiments, the stereochemistry of the chiral center within Formula (X) and Formula (XI) is substantially (R). In some embodiments, the stereochemistry of the chiral center within Formula (X) and Formula (XI) is substantially (S). In some embodiments, the stereochemistry of the chiral center within Formula (X) and Formula (XI) is (R). In some embodiments, the stereochemistry of the chiral center within Formula (X) and Formula (XI) is (S).

In some embodiments, the position of the structure of Formula (X) or (XI), or a mixture of (X) and (XI), in the amino acid sequence of the IL-15 conjugate comprising SEQ ID NO: 1 is selected from S18, L25, E46, E53, N77, and S83. In some embodiments, the position of the structure of Formula (X) or (XI), or a mixture of (X) and (XI), in the amino acid sequence of the IL-15 conjugate comprising SEQ ID NO: 1 is selected from L25, E53, and N77. In some embodiments, the position of the structure of Formula (X) or (XI), or a mixture of (X) and (XI), in the amino acid sequence of the IL-15 conjugate comprising SEQ ID NO: 1 is S18. In some embodiments, the position of the structure of Formula (X) or (XI), or a mixture of (X) and (XI), in the amino acid sequence of the IL-15 conjugate comprising SEQ ID NO: 1 is L25. In some embodiments, the position of the structure of Formula (X) or (XI), or a mixture of (X) and (XI), in the amino acid sequence of the IL-15 conjugate comprising SEQ ID NO: 1 is E46. In some embodiments, the position of the structure of Formula (X) or (XI), or a mixture of (X) and (XI), in the amino acid sequence of the IL-15 conjugate comprising SEQ ID NO: 1 is E53. In some embodiments, the position of the structure of Formula (X) or (XI), or a mixture of (X) and (XI), in the amino acid sequence of the IL-15 conjugate comprising SEQ ID NO: 1 is N77. In some embodiments, the position of the structure of Formula (X) or (XI), or a mixture of (X) and (XI), in the amino acid sequence of the IL-15 conjugate comprising SEQ ID NO: 1 is S83. In some embodiments, n is about 75 to about 1000. In some embodiments, n is about 100 to about 1000. In some embodiments, n is about 200 to about 5000. In some embodiments, n is about 500 to about 1000. In some embodiments, n is about 400 to about 800. In some embodiments described herein, n is an integer from about 450 to about 800, or from about 454 to about 796, or from about 454 to about 682, or from about 568 to about 909. In some embodiments, n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 795. In some embodiments, n is about 909. In some embodiments, n is about 1022. In some embodiments, n is about 1136.

In some embodiments, the position of the structure of Formula (X) or (XI), or a mixture of (X) and (XI), in the amino acid sequence of the IL-15 conjugate comprising SEQ ID NO: 3 is selected from S19, L26, E47, E54, N78, and S84. In some embodiments, the position of the structure of Formula (X) or (XI), or a mixture of (X) and (XI), in the amino acid sequence of the IL-15 conjugate comprising SEQ ID NO: 3 is selected from L26, E54, and N78. In some embodiments, the position of the structure of Formula (X) or (XI), or a mixture of (X) and (XI), in the amino acid sequence of the IL-15 conjugate comprising SEQ ID NO: 3 is S19. In some embodiments, the position of the structure of Formula (X) or (XI), or a mixture of (X) and (XI), in the amino acid sequence of the IL-15 conjugate comprising SEQ ID NO: 3 is L26. In some embodiments, the position of the structure of Formula (X) or (XI), or a mixture of (X) and (XI), in the amino acid sequence of the IL-15 conjugate comprising SEQ ID NO: 3 is E47. In some embodiments, the position of the structure of Formula (X) or (XI), or a mixture of (X) and (XI), in the amino acid sequence of the IL-15 conjugate comprising SEQ ID NO: 3 is E54. In some embodiments, the position of the structure of Formula (X) or (XI), or a mixture of (X) and (XI), in the amino acid sequence of the IL-15 conjugate comprising SEQ ID NO: 3 is N78. In some embodiments, the position of the structure of Formula (X) or (XI), or a mixture of (X) and (XI), in the amino acid sequence of the IL-15 conjugate comprising SEQ ID NO: 3 is S84. In some embodiments, n is about 75 to about 1000. In some embodiments, n is about 100 to about 1000. In some embodiments, n is about 200 to about 5000. In some embodiments, n is about 500 to about 1000. In some embodiments, n is about 400 to about 800. In some embodiments described herein, n is an integer from about 450 to about 800, or from about 454 to about 796, or from about 454 to about 682, or from about 568 to about 909. In some embodiments, n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 795. In some embodiments, n is about 909. In some embodiments, n is about 1022. In some embodiments, n is about 1136.

Described herein are IL-15 conjugates comprising the amino acid sequence of SEQ ID NO: 1 or SEQ ID NO: 3 in which at least one amino acid residue in the IL-15 conjugate is replaced by the structure of Formula (XII) or (XIII), or a mixture of (XII) and (XIII):

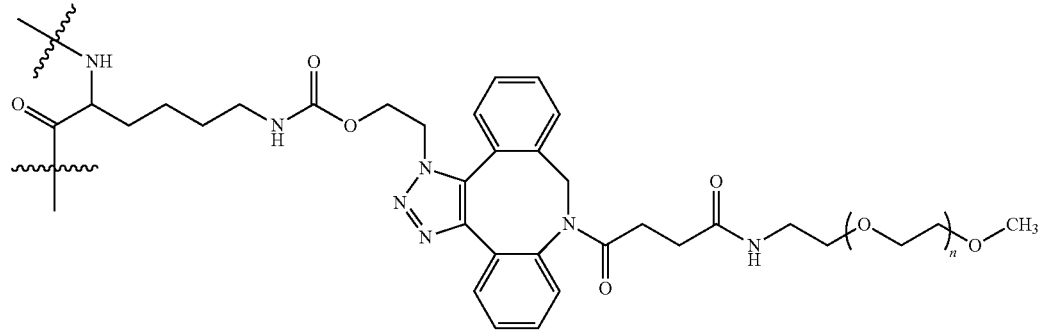

Formula (XII)

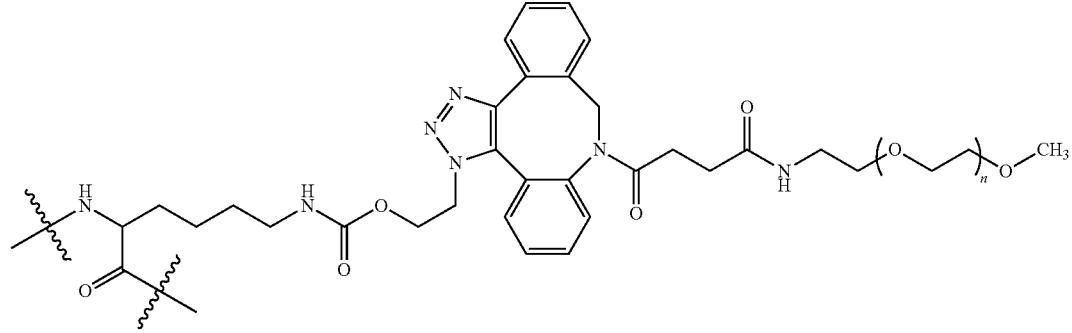

Formula (XIII)

wherein:
n is an integer in the range from about 2 to about 5000; and
the wavy lines indicate covalent bonds to amino acid residues within SEQ ID NO: 1 or SEQ ID NO: 3 that are not replaced. In some embodiments, the IL-15 conjugate is a pharmaceutically acceptable salt, solvate, or hydrate.

In some embodiments, the stereochemistry of the chiral center within Formula (XII) and Formula (XIII) is racemic, is enriched in (R), is enriched in (S), is substantially (R), is substantially (S), is (R) or is (S). In some embodiments, the stereochemistry of the chiral center within Formula (XII) and Formula (XIII) is racemic. In some embodiments, the stereochemistry of the chiral center within Formula (XII) and Formula (XIII) is enriched in (R). In some embodiments, the stereochemistry of the chiral center within Formula (XII) and Formula (XIII) is enriched in (S). In some embodiments, the stereochemistry of the chiral center within Formula (XII) and Formula (XIII) is substantially (R). In some embodiments, the stereochemistry of the chiral center within Formula (XII) and Formula (XIII) is substantially (S). In some embodiments, the stereochemistry of the chiral center within Formula (XII) and Formula (XIII) is (R). In some embodiments, the stereochemistry of the chiral center within Formula (XII) and Formula (XIII) is (S).

In some embodiments, the position of the structure of Formula (XII) or (XIII), or a mixture of (XII) and (XIII), in the amino acid sequence of the IL-15 conjugate comprising SEQ ID NO: 1 is selected from S18, L25, E46, E53, N77, and S83. In some embodiments, the position of the structure of Formula (XII) or (XIII), or a mixture of (XII) and (XIII), in the amino acid sequence of the IL-15 conjugate comprising SEQ ID NO: 1 is selected from L25, E53, and N77. In some embodiments, the position of the structure of Formula (XII) or (XIII), or a mixture of (XII) and (XIII), in the amino acid sequence of the IL-15 conjugate comprising SEQ ID NO: 1 is S18. In some embodiments, the position of the structure of Formula (XII) or (XIII), or a mixture of (XII) and (XIII), in the amino acid sequence of the IL-15 conjugate comprising SEQ ID NO: 1 is L25. In some embodiments, the position of the structure of Formula (XII) or (XIII), or a mixture of (XII) and (XIII), in the amino acid sequence of the IL-15 conjugate comprising SEQ ID NO: 1 is E46. In some embodiments, the position of the structure of Formula (XII) or (XIII), or a mixture of (XII) and (XIII), in the amino acid sequence of the IL-15 conjugate comprising SEQ ID NO: 1 is E53. In some embodiments, the position of the structure of Formula (XII) or (XIII), or a mixture of (XII) and (XIII), in the amino acid sequence of the IL-15 conjugate comprising SEQ ID NO: 1 is N77. In some embodiments, the position of the structure of Formula (XII) or (XIII), or a mixture of (XII) and (XIII), in the amino acid sequence of the IL-15 conjugate comprising SEQ ID NO: 1 is S83. In some embodiments, n is about 75 to about 1000. In some embodiments, n is about 100 to about 1000. In some embodiments, n is about 200 to about 5000. In some embodiments, n is about 500 to about 1000. In some embodiments, n is about 400 to about 800. In some embodiments described herein, n is an integer from about 450 to about 800, or from about 454 to about 796, or from about 454 to about 682, or from about 568 to about 909. In some embodiments, n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 795. In some embodiments, n is about 909. In some embodiments, n is about 1022. In some embodiments, n is about 1136.

In some embodiments, the position of the structure of Formula (XII) or (XIII), or a mixture of (XII) and (XIII), in the amino acid sequence of the IL-15 conjugate comprising SEQ ID NO: 3 is selected from S19, L26, E47, E54, N78, and S84. In some embodiments, the position of the structure of Formula (XII) or (XIII), or a mixture of (XII) and (XIII), in the amino acid sequence of the IL-15 conjugate comprising SEQ ID NO: 3 is selected from L26, E54, and N78. In some embodiments, the position of the structure of Formula (XII) or (XIII), or a mixture of (XII) and (XIII), in the amino acid sequence of the IL-15 conjugate comprising SEQ ID NO: 3 is S19. In some embodiments, the position of the structure of Formula (XII) or (XIII), or a mixture of (XII) and (XIII), in the amino acid sequence of the IL-15 conjugate comprising SEQ ID NO: 3 is L26. In some embodiments, the position of the structure of Formula (XII) or (XIII), or a mixture of (XII) and (XIII), in the amino acid sequence of the IL-15 conjugate comprising SEQ ID NO: 3 is E47. In some embodiments, the position of the structure of Formula (XII) or (XIII), or a mixture of (XII) and (XIII), in the amino acid sequence of the IL-15 conjugate comprising SEQ ID NO: 3 is E54. In some embodiments, the position of the structure of Formula (XII) or (XIII), or a mixture of (XII) and (XIII), in the amino acid sequence of the IL-15 conjugate comprising SEQ ID NO: 3 is N78. In some embodiments, the position of the structure of Formula (XII) or (XIII), or a mixture of (XII) and (XIII), in the amino acid sequence of the IL-15 conjugate comprising SEQ ID NO: 3 is S84. In some embodiments, n is about 75 to about 1000. In some embodiments, n is about 100 to about 1000. In some embodiments, n is about 200 to about 5000. In some embodiments, n is about 500 to about 1000. In some embodiments, n is about 400 to about 800. In some embodiments described herein, n is an integer from about 450 to about 800, or from about 454 to about 796, or from about 454 to about 682, or from about 568 to about 909. In some embodiments, n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 795. In some embodiments, n is about 909. In some embodiments, n is about 1022. In some embodiments, n is about 1136.

Described herein are IL-15 conjugates comprising the amino acid sequence of SEQ ID NO: 1 or SEQ ID NO: 3 in which at least one amino acid residue in the IL-15 conjugate is replaced by the structure of Formula (XIV) or (XV), or a mixture of (XIV) and (XV):

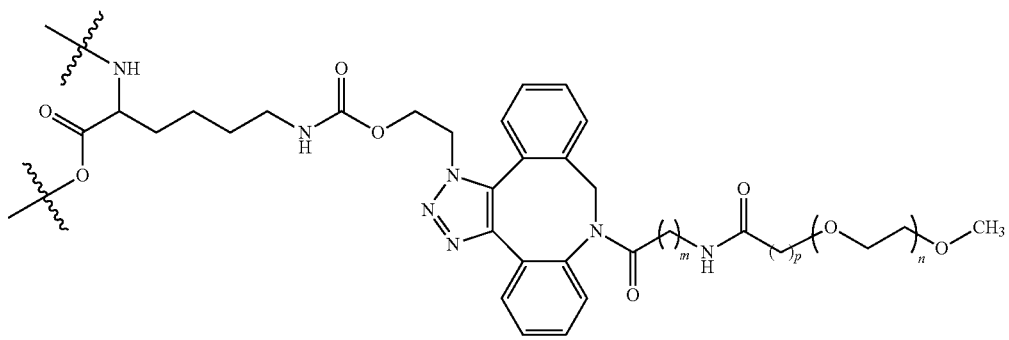

Formula (XIV)

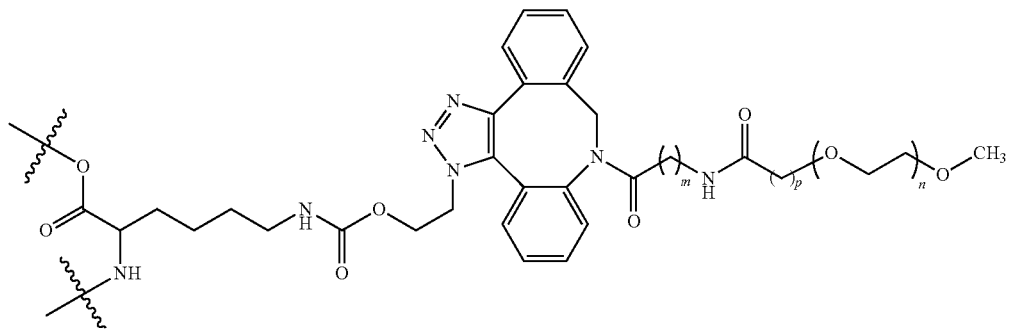

Formula (XV)

wherein:
m is an integer from 0 to 20;
p is an integer from 0 to 20;
n is an integer in the range from about 2 to about 5000; and
the wavy lines indicate covalent bonds to amino acid residues within SEQ ID NO: 1 or SEQ ID NO: 3 that are not replaced. In some embodiments, the IL-15 conjugate is a pharmaceutically acceptable salt, solvate, or hydrate. In some embodiments described herein are IL-15 conjugates comprising the amino acid sequence of SEQ ID NO: 1 in which at least one amino acid residue in the IL-15 conjugate is replaced by the structure of Formula (XIV) or (XV), or a mixture of (XIV) and (XV), wherein m, p, n, and the meaning of the wavy line are as described above. In some embodiments described herein are IL-15 conjugates comprising the amino acid sequence of SEQ ID NO: 3 in which at least one amino acid residue in the IL-15 conjugate is replaced by the structure of Formula (XIV) or (XV), or a mixture of (XIV) and (XV), wherein m, p, n, and the meaning of the wavy line are as described above.

In some embodiments, the stereochemistry of the chiral center within Formula (XIV) and Formula (XV) is racemic, is enriched in (R), is enriched in (S), is substantially (R), is substantially (S), is (R) or is (S). In some embodiments, the stereochemistry of the chiral center within Formula (XIV) and Formula (XV) is racemic. In some embodiments, the stereochemistry of the chiral center within Formula (XIV) and Formula (XV) is enriched in (R). In some embodiments, the stereochemistry of the chiral center within Formula (XIV) and Formula (XV) is enriched in (S). In some embodiments, the stereochemistry of the chiral center within Formula (XIV) and Formula (XV) is substantially (R). In some embodiments, the stereochemistry of the chiral center within Formula (XIV) and Formula (XV) is substantially (S). In some embodiments, the stereochemistry of the chiral center within Formula (XIV) and Formula (XV) is (R). In some embodiments, the stereochemistry of the chiral center within Formula (XIV) and Formula (XV) is (S).

In some embodiments of an IL-15 conjugate described herein, m in the compounds of Formula (XIV) and (XV) is from 0 to 20, or from 1 to 18, or from 1 to 16, or from 1 to 14, or from 1 to 12, or from 1 to 10, or from 1 to 9, or from 1 to 8, or from 1 to 7, or from 1 to 6, or from 1 to 5, or from 1 to 4, or from 1 to 3, or from 1 to 2. In some embodiments of an IL-15 conjugate described herein, m in the compounds of Formula (XIV) and (XV) is 1. In some embodiments of an IL-15 conjugate described herein, m in the compounds of Formula (XIV) and (XV) is 2. In some embodiments of an IL-15 conjugate described herein, m in the compounds of Formula (XIV) and (XV) is 3. In some embodiments of an IL-15 conjugate described herein, m in the compounds of Formula (XIV) and (XV) is 4. In some embodiments of an IL-15 conjugate described herein, m in the compounds of Formula (XIV) and (XV) is 5. In some embodiments of an IL-15 conjugate described herein, m in the compounds of Formula (XIV) and (XV) is 6. In some embodiments of an IL-15 conjugate described herein, m in the compounds of Formula (XIV) and (XV) is 7. In some embodiments of an IL-15 conjugate described herein, m in the compounds of Formula (XIV) and (XV) is 8. In some embodiments of an IL-15 conjugate described herein, m in the compounds of Formula (XIV) and (XV) is 9. In some embodiments of an IL-15 conjugate described herein, m in the compounds of Formula (XIV) and (XV) is 10. In some embodiments of an IL-15 conjugate described herein, m in the compounds of Formula (XIV) and (XV) is 11. In some embodiments of an IL-15 conjugate described herein, min the compounds of Formula (XIV) and (XV) is 12. In some embodiments of an IL-15 conjugate described herein, m in the compounds of Formula (XIV) and (XV) is 13. In some embodiments of an IL-15 conjugate described herein, m in the compounds of Formula (XIV) and (XV) is 14. In some embodiments of an IL-15 conjugate described herein, m in the compounds of Formula (XIV) and (XV) is 15. In some embodiments of an IL-15 conjugate described herein, m in the compounds of Formula (XIV) and (XV) is 16. In some embodiments of an IL-15 conjugate described herein, m in the compounds of Formula (XIV) and (XV) is 17. In some embodiments of an IL-15 conjugate described herein, m in the compounds of Formula (XIV) and (XV) is 18. In some embodiments of an IL-15 conjugate described herein, m in the compounds of Formula (XIV) and (XV) is 19. In some embodiments of an IL-15 conjugate described herein, m in the compounds of Formula (XIV) and (XV) is 20.

In some embodiments of an IL-15 conjugate described herein, pin the compounds of Formula (XIV) and (XV) is from 1 to 20, or from 1 to 18, or from 1 to 16, or from 1 to 14, or from 1 to 12, or from 1 to 10, or from 1 to 9, or from 1 to 8, or from 1 to 7, or from 1 to 6, or from 1 to 5, or from 1 to 4, or from 1 to 3, or from 1 to 2. In some embodiments of an IL-15 conjugate described herein, p in the compounds of Formula (XIV) and (XV) is 1. In some embodiments of an IL-15 conjugate described herein, p in the compounds of Formula (XIV) and (XV) is 2. In some embodiments of an IL-15 conjugate described herein, p in the compounds of Formula (XIV) and (XV) is 3. In some embodiments of an IL-15 conjugate described herein, p in the compounds of Formula (XIV) and (XV) is 4. In some embodiments of an IL-15 conjugate described herein, p in the compounds of Formula (XIV) and (XV) is 5. In some embodiments of an IL-15 conjugate described herein, p in the compounds of Formula (XIV) and (XV) is 6. In some embodiments of an IL-15 conjugate described herein, p in the compounds of Formula (XIV) and (XV) is 7. In some embodiments of an IL-15 conjugate described herein, p in the compounds of Formula (XIV) and (XV) is 8. In some embodiments of an IL-15 conjugate described herein, p in the compounds of Formula (XIV) and (XV) is 9. In some embodiments of an IL-15 conjugate described herein, p in the compounds of Formula (XIV) and (XV) is 10. In some embodiments of an IL-15 conjugate described herein, p in the compounds of Formula (XIV) and (XV) is 11. In some embodiments of an IL-15 conjugate described herein, p in the compounds of Formula (XIV) and (XV) is 12. In some embodiments of an IL-15 conjugate described herein, p in the compounds of Formula (XIV) and (XV) is 13. In some embodiments of an IL-15 conjugate described herein, p in the compounds of Formula (XIV) and (XV) is 14. In some embodiments of an IL-15 conjugate described herein, p in the compounds of Formula (XIV) and (XV) is 15. In some embodiments of an IL-15 conjugate described herein, m in the compounds of Formula (XIV) and (XV) is 16. In some embodiments of an IL-15 conjugate described herein, p in the compounds of Formula (XIV) and (XV) is 17. In some embodiments of an IL-15 conjugate described herein, p in the compounds of Formula (XIV) and (XV) is 18. In some embodiments of an IL-15 conjugate described herein, p in the compounds of Formula (XIV) and (XV) is 19. In some embodiments of an IL-15 conjugate described herein, p in the compounds of Formula (XIV) and (XV) is 20.

In some embodiments of an IL-15 conjugate described herein, n in the compounds of Formula (XIV) and (XV) is in the range from about 5 to about 4600, or from about 10 to about 4000, or from about 20 to about 3000, or from about 100 to about 3000, or from about 100 to about 2900, or from about 150 to about 2900, or from about 125 to about 2900, or from about 100 to about 2500, or from about 100 to about 2000, or from about 100 to about 1900, or from about 100 to about 1850, or from about 100 to about 1750, or from about 100 to about 1650, or from about 100 to about 1500, or from about 100 to about 1400, or from about 100 to about 1300, or from about 100 to about 1250, or from about 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575.

In some embodiments of an IL-15 conjugate described herein in the compounds of Formula (XIV) and (XV), m is an integer from 1 to 6, p is an integer from 1 to 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XIV) and (XV), m is an integer from 2 to 6, p is an integer from 2 to 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XIV) and (XV), m is an integer from 2 to 4, p is an integer from 2 to 4, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XIV) and (XV), m is 1, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XIV) and (XV), m is 2, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XIV) and (XV), m is 3, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XIV) and (XV), m is 4, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XIV) and (XV), m is 5, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XIV) and (XV), m is 6, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XIV) and (XV), m is 7, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XIV) and (XV), m is 8, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XIV) and (XV), m is 9, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XIV) and (XV), m is 10, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XIV) and (XV), m is 11, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XIV) and (XV), m is 11, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XIV) and (XV), m is 2, p is 2, and n is an integer selected from 680, 681, 682, 794, 795, 796, 908, 909, 910, 1021, 1022, 1023, 1135, 1136, and 1137.

In some embodiments of an IL-15 conjugate described herein, n in the compounds of Formula (XIV) and (XV) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

In some embodiments of an IL-15 conjugate described herein, when the IL-15 conjugate comprises SEQ ID NO: 1, the position of the structure of Formula (XIV) and (XV) or a mixture of Formula (XIV) and (XV) in the amino acid sequence of the IL-15 conjugate is selected from S18, L25, E46, E53, N77, and S83. Further described herein are IL-15 conjugates wherein the position of the structure of Formula (XIV) or (XV), or a mixture of (XIV) and (XV), in the amino acid sequence of the IL-15 conjugate is selected from S18, L25, and E46. Further described herein are IL-15 conjugates wherein the position of the structure of Formula (XIV) or (XV), or a mixture of (XIV) and (XV), in the amino acid sequence of the IL-15 conjugate is selected from E53, N77, and S83. Further described herein are IL-15 conjugates wherein the position of the structure of Formula (XIV) or (XV), or a mixture of (XIV) and (XV), in the amino acid sequence of the IL-15 conjugate is S18. Further described herein are IL-15 conjugates wherein the position of the structure of Formula (XIV) or (XV), or a mixture of (XIV) and (XV), in the amino acid sequence of the IL-15 conjugate is L25. Further described herein are IL-15 conjugates wherein the position of the structure of Formula (XIV) or (XV), or a mixture of (XIV) and (XV), in the amino acid sequence of the IL-15 conjugate is E46. Further described herein are IL-15 conjugates wherein the position of the structure of Formula (XIV) or (XV), or a mixture of (XIV) and (XV), in the amino acid sequence of the IL-15 conjugate is E53. Further described herein are IL-15 conjugates wherein the position of the structure of Formula (XIV) or (XV), or a mixture of (XIV) and (XV), in the amino acid sequence of the IL-15 conjugate is N77. Further described herein are IL-15 conjugates wherein the position of the structure of Formula (XIV) or (XV), or a mixture of (XIV) and (XV), in the amino acid sequence of the IL-15 conjugate is S83. In some embodiments of an IL-15 conjugate described herein, the ratio of the amount of the structure of Formula (XIV) to the amount of the structure of Formula (XV) comprising the total amount of the IL-15 conjugate is about 1:1. In some embodiments of an IL-15 conjugate described herein, the ratio of the amount of the structure of Formula (XIV) to the amount of the structure of Formula (XV) comprising the total amount of the IL-15 conjugate is greater than 1:1. In some embodiments of an IL-15 conjugate described herein, the ratio of the amount of the structure of Formula (XIV) to the amount of the structure of Formula (XV) comprising the total amount of the IL-15 conjugate is less than 1:1.

In some embodiments of an IL-15 conjugate described herein, when the IL-15 conjugate comprises SEQ ID NO: 3, the position of the structure of Formula (XIV) and (XV) or a mixture of Formula (XIV) and (XV) in the amino acid sequence of the IL-15 conjugate is selected from S19, L26, E47, E54, N78, and S84. Further described herein are IL-15 conjugates wherein the position of the structure of Formula (XIV) or (XV), or a mixture of (XIV) and (XV), in the amino acid sequence of the IL-15 conjugate is selected from S19, L26, E47. Further described herein are IL-15 conjugates wherein the position of the structure of Formula (XIV) or (XV), or a mixture of (XIV) and (XV), in the amino acid sequence of the IL-15 conjugate is selected from E54, N78, and S84. Further described herein are IL-15 conjugates wherein the position of the structure of Formula (XIV) or (XV), or a mixture of (XIV) and (XV), in the amino acid sequence of the IL-15 conjugate is 19. Further described herein are IL-15 conjugates wherein the position of the structure of Formula (XIV) or (XV), or a mixture of (XIV) and (XV), in the amino acid sequence of the IL-15 conjugate is L26. Further described herein are IL-15 conjugates wherein the position of the structure of Formula (XIV) or (XV), or a mixture of (XIV) and (XV), in the amino acid sequence of the IL-15 conjugate is E47. Further described herein are IL-15 conjugates wherein the position of the structure of Formula (XIV) or (XV), or a mixture of (XIV) and (XV), in the amino acid sequence of the IL-15 conjugate is E54. Further described herein are IL-15 conjugates wherein the position of the structure of Formula (XIV) or (XV), or a mixture of (XIV) and (XV), in the amino acid sequence of the IL-15 conjugate is N78. Further described herein are IL-15 conjugates wherein the position of the structure of Formula (XIV) or (XV), or a mixture of (XIV) and (XV), in the amino acid sequence of the IL-15 conjugate is S84. In some embodiments of an IL-15 conjugate described herein, the ratio of the amount of the structure of Formula (XIV) to the amount of the structure of Formula (XV) comprising the total amount of the IL-15 conjugate is about 1:1. In some embodiments of an IL-15 conjugate described herein, the ratio of the amount of the structure of Formula (XIV) to the amount of the structure of Formula (XV) comprising the total amount of the IL-15 conjugate is greater than 1:1. In some embodiments of an IL-15 conjugate described herein, the ratio of the amount of the structure of Formula (XIV) to the amount of the structure of Formula (XV) comprising the total amount of the IL-15 conjugate is less than 1:1.

In some embodiments described herein are IL-15 conjugates comprising the amino acid sequence of SEQ ID NO: 1 in which at least one amino acid residue in the IL-15 conjugate is replaced by the structure of Formula (XIV) or (XV), or a mixture of (XIV) and (XV), wherein the amino acid residue in in SEQ ID NO: 1 that is replaced is selected from S18, L25, E46, E53, N77, and S83 wherein n is an integer from 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments of an IL-15 conjugate described herein, n in the compounds of formula (XIV) and (XV) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

In some embodiments described herein are IL-15 conjugates comprising the amino acid sequence of SEQ ID NO: 3 in which at least one amino acid residue in the IL-15 conjugate is replaced by the structure of Formula (XIV) or (XV), or a mixture of (XIV) and (XV), wherein the amino acid residue in in SEQ ID NO: 3 that is replaced is selected from S19, L26, E47, E54, N78, and S84, and wherein n is an integer from 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments of an IL-15 conjugate described herein, n in the compounds of formula (XIV) and (XV) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

Described herein are IL-15 conjugates comprising the amino acid sequence of SEQ ID NO: 1 or SEQ ID NO: 3 in which at least one amino acid residue in the IL-15 conjugate is replaced by the structure of Formula (XIV) or (XV), or a mixture of (XIV) and (XV), wherein n is an integer such that the molecular weight of the PEG moiety is in the range from about 1,000 Daltons about 200,000 Daltons, or from about 2,000 Daltons to about 150,000 Daltons, or from about 3,000 Daltons to about 125,000 Daltons, or from about 4,000 Daltons to about 100,000 Daltons, or from about 5,000 Daltons to about 100,000 Daltons, or from about 6,000 Daltons to about 90,000 Daltons, or from about 7,000 Daltons to about 80,000 Daltons, or from about 8,000 Daltons to about 70,000 Daltons, or from about 5,000 Daltons to about 70,000 Daltons, or from about 5,000 Daltons to about 65,000 Daltons, or from about 5,000 Daltons to about 60,000 Daltons, or from about 5,000 Daltons to about 50,000 Daltons, or from about 6,000 Daltons to about 50,000 Daltons, or from about 7,000 Daltons to about 50,000 Daltons, or from about 7,000 Daltons to about 45,000 Daltons, or from about 7,000 Daltons to about 40,000 Daltons, or from about 8,000 Daltons to about 40,000 Daltons, or from about 8,500 Daltons to about 40,000 Daltons, or from about 8,500 Daltons to about 35,000 Daltons, or from about 9,000 Daltons to about 50,000 Daltons, or from about 9,000 Daltons to about 45,000 Daltons, or from about 9,000 Daltons to about 40,000 Daltons, or from about 9,000 Daltons to about 35,000 Daltons, or from about 9,000 Daltons to about 30,000 Daltons, or from about 9,500 Daltons to about 35,000 Daltons, or from about 9,500 Daltons to about 30,000 Daltons, or from about 10,000 Daltons to about 50,000 Daltons, or from about 10,000 Daltons to about 45,000 Daltons, or from about 10,000 Daltons to about 40,000 Daltons, or from about 10,000 Daltons to about 35,000 Daltons, or from about 10,000 Daltons to about 30,000 Daltons, or from about 15,000 Daltons to about 50,000 Daltons, or from about 15,000 Daltons to about 45,000 Daltons, or from about 15,000 Daltons to about 40,000 Daltons, or from about 15,000 Daltons to about 35,000 Daltons, or from about 15,000 Daltons to about 30,000 Daltons, or from about 20,000 Daltons to about 50,000 Daltons, or from about 20,000 Daltons to about 45,000 Daltons, or from about 20,000 Daltons to about 40,000 Daltons, or from about 20,000 Daltons to about 35,000 Daltons, or from about 20,000 Daltons to about 30,000 Daltons. Described herein are IL-15 conjugates comprising the amino acid sequence of SEQ ID NO: 1 or SEQ ID NO: 3 in which at least one amino acid residue in the IL-15 conjugate is replaced by the structure of Formula (XIV) or (XV), or a mixture of (XIV) and (XV), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, about 50,000 Daltons, about 60,000 Daltons, about 70,000 Daltons, about 80,000 Daltons, about 90,000 Daltons, about 100,000 Daltons, about 125,000 Daltons, about 150,000 Daltons, about 175,000 Daltons or about 200,000 Daltons. Described herein are IL-15 conjugates comprising the amino acid sequence of SEQ ID NO: 1 or SEQ ID NO: 3 in which at least one amino acid residue in the IL-15 conjugate is replaced by the structure of Formula (XIV) or (XV), or a mixture of (XIV) and (XV), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, or about 50,000 Daltons.

In some embodiments described herein are IL-15 conjugates comprising the amino acid sequence of SEQ ID NO: 1 in which at least one amino acid residue in the IL-15 conjugate is replaced by the structure of Formula (XIV) or (XV), or a mixture of (XIV) and (XV), wherein the amino acid residue in SEQ ID NO: 1 that is replaced is L25, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XIV) and (XV), m is 2, p is 2, and n is an integer selected from 454, 455, 568, 569, 680, 681, 682, 794, 795, 796, 908, 909, and 910.

In some embodiments described herein are IL-15 conjugates comprising the amino acid sequence of SEQ ID NO: 1 in which at least one amino acid residue in the IL-15 conjugate is replaced by the structure of Formula (XIV) or (XV), or a mixture of (XIV) and (XV), wherein the amino acid residue in SEQ ID NO: 1 that is replaced is L25, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XIV) and (XV), m is 2, p is 2, and n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 909.

In some embodiments described herein are IL-15 conjugates comprising the amino acid sequence of SEQ ID NO: 1 in which at least one amino acid residue in the IL-15 conjugate is replaced by the structure of Formula (XIV) or (XV), or a mixture of (XIV) and (XV), wherein the amino acid residue in SEQ ID NO: 1 that is replaced is L25, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XIV) and (XV), m is 2, p is 2, and n is an integer selected from 454, 455, 568, 569, 680, 681, 682, 794, 795, 796, 908, 909, and 910.

In some embodiments described herein are IL-15 conjugates comprising the amino acid sequence of SEQ ID NO: 1 in which at least one amino acid residue in the IL-15 conjugate is replaced by the structure of Formula (XIV) or (XV), or a mixture of (XIV) and (XV), wherein the amino acid residue in SEQ ID NO: 1 that is replaced is E53, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XIV) and (XV), m is 2, p is 2, and n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 909.

In some embodiments described herein are IL-15 conjugates comprising the amino acid sequence of SEQ ID NO: 1 in which at least one amino acid residue in the IL-15 conjugate is replaced by the structure of Formula (XIV) or (XV), or a mixture of (XIV) and (XV), wherein the amino acid residue in SEQ ID NO: 1 that is replaced is E53, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XIV) and (XV), m is 2, p is 2, and n is an integer selected from 454, 455, 568, 569, 680, 681, 682, 794, 795, 796, 908, 909, and 910.

In some embodiments described herein are IL-15 conjugates comprising the amino acid sequence of SEQ ID NO: 1 in which at least one amino acid residue in the IL-15 conjugate is replaced by the structure of Formula (XIV) or (XV), or a mixture of (XIV) and (XV), wherein the amino acid residue in SEQ ID NO: 1 that is replaced is N77, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XIV) and (XV), m is 2, p is 2, and n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 909.

In some embodiments described herein are IL-15 conjugates comprising the amino acid sequence of SEQ ID NO: 1 in which at least one amino acid residue in the IL-15 conjugate is replaced by the structure of Formula (XIV) or (XV), or a mixture of (XIV) and (XV), wherein the amino acid residue in SEQ ID NO: 1 that is replaced is N77, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XIV) and (XV), m is 2, p is 2, and n is an integer selected from 454, 455, 568, 569, 680, 681, 682, 794, 795, 796, 908, 909, and 910.

In some embodiments described herein are IL-15 conjugates comprising the amino acid sequence of SEQ ID NO: 3 in which at least one amino acid residue in the IL-15 conjugate is replaced by the structure of Formula (XIV) or (XV), or a mixture of (XIV) and (XV), wherein the amino acid residue in SEQ ID NO: 3 that is replaced is L26, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XIV) and (XV), m is 2, p is 2, and n is an integer selected from 454, 455, 568, 569, 680, 681, 682, 794, 795, 796, 908, 909, and 910.

In some embodiments described herein are IL-15 conjugates comprising the amino acid sequence of SEQ ID NO: 3 in which at least one amino acid residue in the IL-15 conjugate is replaced by the structure of Formula (XIV) or (XV), or a mixture of (XIV) and (XV), wherein the amino acid residue in SEQ ID NO: 3 that is replaced is L26, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XIV) and (XV), m is 2, p is 2, and n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 909.

In some embodiments described herein are IL-15 conjugates comprising the amino acid sequence of SEQ ID NO: 3 in which at least one amino acid residue in the IL-15 conjugate is replaced by the structure of Formula (XIV) or (XV), or a mixture of (XIV) and (XV), wherein the amino acid residue in SEQ ID NO: 3 that is replaced is E54, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XIV) and (XV), m is 2, p is 2, and n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 909.

In some embodiments described herein are IL-15 conjugates comprising the amino acid sequence of SEQ ID NO: 3 in which at least one amino acid residue in the IL-15 conjugate is replaced by the structure of Formula (XIV) or (XV), or a mixture of (XIV) and (XV), wherein the amino acid residue in SEQ ID NO: 3 that is replaced is E54, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XIV) and (XV), m is 2, p is 2, and n is an integer selected from 454, 455, 568, 569, 680, 681, 682, 794, 795, 796, 908, 909, and 910.

In some embodiments described herein are IL-15 conjugates comprising the amino acid sequence of SEQ ID NO: 3 in which at least one amino acid residue in the IL-15 conjugate is replaced by the structure of Formula (XIV) or (XV), or a mixture of (XIV) and (XV), wherein the amino acid residue in SEQ ID NO: 3 that is replaced is N78, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XIV) and (XV), m is 2, p is 2, and n is an integer selected from 454, 455, 568, 569, 680, 681, 682, 794, 795, 796, 908, 909, and 910.

In some embodiments described herein are IL-15 conjugates comprising the amino acid sequence of SEQ ID NO: 3 in which at least one amino acid residue in the IL-15 conjugate is replaced by the structure of Formula (XIV) or (XV), or a mixture of (XIV) and (XV), wherein the amino acid residue in SEQ ID NO: 3 that is replaced is N78, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XIV) and (XV), m is 2, p is 2, and n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 909.

Described herein are IL-15 conjugates comprising the amino acid sequence of SEQ ID NO: 1 or SEQ ID NO: 3 in which at least one amino acid residue in the IL-15 conjugate is replaced by the structure of Formula (XVI) or (XVII), or a mixture of (XVI) and (XVII):

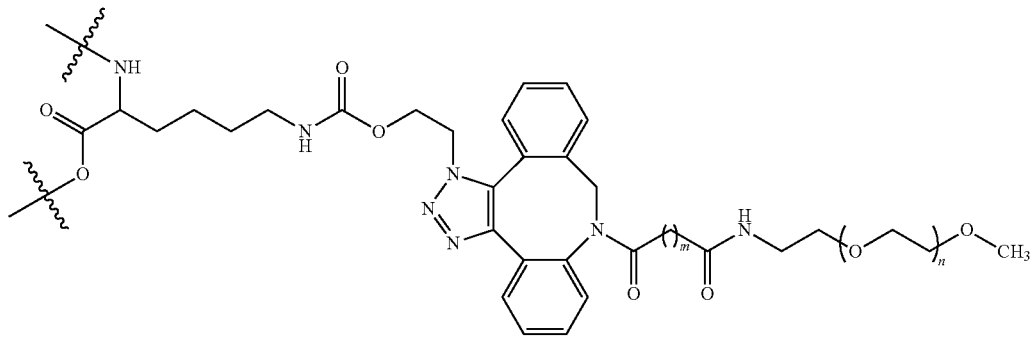

Formula (XVI)

Formula (XVII)

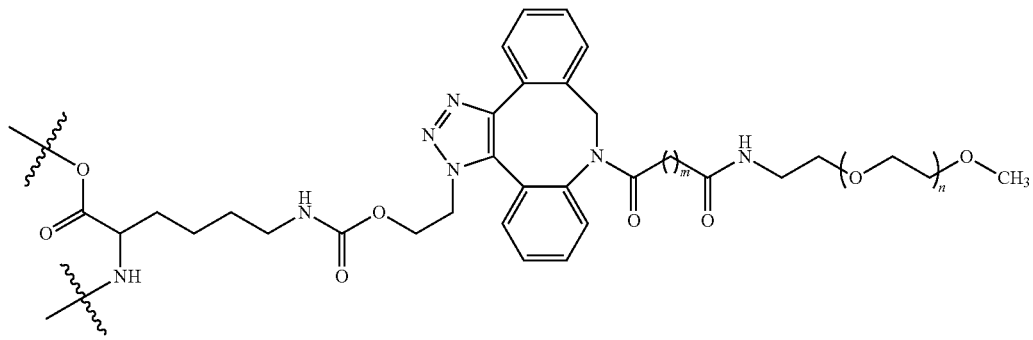

wherein:

m is an integer from 0 to 20;

n is an integer in the range from about 2 to about 5000; and the wavy lines indicate covalent bonds to amino acid residues within SEQ ID NO: 1 or SEQ ID NO: 3 that are not replaced. In some embodiments, the IL-15 conjugate is a pharmaceutically acceptable salt, solvate, or hydrate. In some embodiments described herein are IL-15 conjugates comprising the amino acid sequence of SEQ ID NO: 1 in which at least one amino acid residue in the IL-15 conjugate is replaced by the structure of Formula (XVI) or (XVII), or a mixture of (XVI) and (XVII), wherein m, p, n, and the meaning of the wavy line areas described above. In some embodiments described herein are IL-15 conjugates comprising the amino acid sequence of SEQ ID NO: 3 in which at least one amino acid residue in the IL-15 conjugate is replaced by the structure of Formula (XVI) or (XVII), or a mixture of (XVI) and (XVII), wherein m, p, n, and the meaning of the wavy line are as described above.

In some embodiments, the stereochemistry of the chiral center within Formula (XVI) and Formula (XVII) is racemic, is enriched in (R), is enriched in (S), is substantially (R), is substantially (S), is (R) or is (S). In some embodiments, the stereochemistry of the chiral center within Formula (XVI) and Formula (XVII) is racemic. In some embodiments, the stereochemistry of the chiral center within Formula (XVI) and Formula (XVII) is enriched in (R). In some embodiments, the stereochemistry of the chiral center within Formula (XVI) and Formula (XVII) is enriched in (S). In some embodiments, the stereochemistry of the chiral center within Formula (XVI) and Formula (XVII) is substantially (R). In some embodiments, the stereochemistry of the chiral center within Formula (XVI) and Formula (XVII) is substantially (S). In some embodiments, the stereochemistry of the chiral center within Formula (XVI) and Formula (XVII) is (R). In some embodiments, the stereochemistry of the chiral center within Formula (XVI) and Formula (XVII) is (S).

In some embodiments of an IL-15 conjugate described herein, min the compounds of Formula (XVI) and (XVII) is from 1 to 20, or from 1 to 18, or from 1 to 16, or from 1 to 14, or from 1 to 12, or from 1 to 10, or from 1 to 9, or from 1 to 8, or from 1 to 7, or from 1 to 6, or from 1 to 5, or from 1 to 4, or from 1 to 3, or from 1 to 2. In some embodiments of an IL-15 conjugate described herein, m in the compounds of Formula (XVI) and (XVII) is 1. In some embodiments of an IL-15 conjugate described herein, m in the compounds of Formula (XVI) and (XVII) is 2. In some embodiments of an IL-15 conjugate described herein, m in the compounds of Formula (XVI) and (XVII) is 3. In some embodiments of an IL-15 conjugate described herein, m in the compounds of Formula (XVI) and (XVII) is 4. In some embodiments of an IL-15 conjugate described herein, m in the compounds of Formula (XVI) and (XVII) is 5. In some embodiments of an IL-15 conjugate described herein, m in the compounds of Formula (XVI) and (XVII) is 6. In some embodiments of an IL-15 conjugate described herein, m in the compounds of Formula (XVI) and (XVII) is 7. In some embodiments of an IL-15 conjugate described herein, m in the compounds of Formula (XVI) and (XVII) is 8. In some embodiments of an IL-15 conjugate described herein, m in the compounds of Formula (XVI) and (XVII) is 9. In some embodiments of an IL-15 conjugate described herein, m in the compounds of Formula (XVI) and (XVII) is 10. In some embodiments of an IL-15 conjugate described herein, m in the compounds of Formula (XVI) and (XVII) is 11. In some embodiments of an IL-15 conjugate described herein, m in the compounds of Formula (XVI) and (XVII) is 12. In some embodiments of an IL-15 conjugate described herein, m in the compounds of Formula (XVI) and (XVII) is 13. In some embodiments of an IL-15 conjugate described herein, m in the compounds of Formula (XVI) and (XVII) is 14. In some embodiments of an IL-15 conjugate described herein, m in the compounds of Formula (XVI) and (XVII) is 15. In some embodiments of an IL-15 conjugate described herein, m in the compounds of Formula (XVI) and (XVII) is 16. In some embodiments of an IL-15 conjugate described herein, m in the compounds of Formula (XVI) and (XVII) is 17. In some embodiments of an IL-15 conjugate described herein, min the compounds of Formula (XVI) and (XVII) is 18. In some embodiments of an IL-15 conjugate described herein, m in the compounds of Formula (XVI) and (XVII) is 19. In some embodiments of an IL-15 conjugate described herein, m in the compounds of Formula (XVI) and (XVII) is 20.

In some embodiments of an IL-15 conjugate described herein, n in the compounds of Formula (XVI) and (XVII) is in the range from about 5 to about 4600, or from about 10 to about 4000, or from about 20 to about 3000, or from about 100 to about 3000, or from about 100 to about 2900, or from about 150 to about 2900, or from about 125 to about 2900, or from about 100 to about 2500, or from about 100 to about 2000, or from about 100 to about 1900, or from about 100 to about 1850, or from about 100 to about 1750, or from about 100 to about 1650, or from about 100 to about 1500, or from about 100 to about 1400, or from about 100 to about 1300, or from about 100 to about 1250, or from about 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575.

In some embodiments of an IL-15 conjugate described herein in the compounds of Formula (XVI) and (XVII), m is an integer from 1 to 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XVI) and (XVII), m is an integer from 2 to 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XVI) and (XVII), m is an integer from 2 to 4, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XVI) and (XVII), m is 1, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XVI) and (XVII), m is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XVI) and (XVII), m is 3, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XVI) and (XVII), m is 4, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XVI) and (XVII), m is 5, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XVI) and (XVII), m is 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XVI) and (XVII), m is 7, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XVI) and (XVII), m is 8, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XVI) and (XVII), m is 9, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XVI) and (XVII), m is 10, and n is an integer selected from 113, 114, 227, 228, 340,341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XVI) and (XVII), m is 11, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XVI) and (XVII), m is 12, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-15 conjugate described herein in the compounds of Formula (XVI) and (XVII), m is 2, and n is an integer selected from 680, 681, 682, 794, 795, 796, 908, 909, 910, 1021, 1022, 1023, 1135, 1136, and 1137.

In some embodiments of an IL-15 conjugate described herein, n in the compounds of Formula (XVI) and (XVII) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

In some embodiments of an IL-15 conjugate described herein, the position of the structure of Formula (XVI) and (XVII) or a mixture of Formula (XVI) and (XVII) in the amino acid sequence of the IL-15 conjugate comprising SEQ ID NO: 1 is selected from S18, L25, E46, E53, N77, and S83. In some embodiments of an IL-15 conjugate described herein, the position of the structure of Formula (XVI) and (XVII) or a mixture of Formula (XVI) and (XVII) in the amino acid sequence of the IL-15 conjugate of SEQ ID NO: 1 is selected from S18, L25, and E46. Further described herein are IL-15 conjugates wherein the position of the structure of Formula (XVI) or (XVII), or a mixture of (XVI) and (XVII), in the amino acid sequence of the IL-15 conjugate is selected from E53, N77, and S83. Further described herein are IL-15 conjugates wherein the position of the structure of Formula (XVI) or (XVII), or a mixture of (XVI) and (XVII), in the amino acid sequence of the IL-15 conjugate is S18. Further described herein are IL-15 conjugates wherein the position of the structure of Formula (XVI) or (XVII), or a mixture of (XVI) and (XVII), in the amino acid sequence of the IL-15 conjugate is L25. Further described herein are IL-15 conjugates wherein the position of the structure of Formula (XVI) or (XVII), or a mixture of (XVI) and (XVII), in the amino acid sequence of the IL-15 conjugate is E46. Further described herein are IL-15 conjugates wherein the position of the structure of Formula (XVI) or (XVII), or a mixture of (XVI) and (XVII), in the amino acid sequence of the IL-15 conjugate is E53. Further described herein are IL-15 conjugates wherein the position of the structure of Formula (XVI) or (XVII), or a mixture of (XVI) and (XVII), in the amino acid sequence of the IL-15 conjugate is N77. Further described herein are IL-15 conjugates wherein the position of the structure of Formula (XVI) or (XVII), or a mixture of (XVI) and (XVII), in the amino acid sequence of the IL-15 conjugate is S83. In some embodiments of an IL-15 conjugate described herein, the ratio of the amount of the structure of Formula (XVI) to the amount of the structure of Formula (XVII) comprising the total amount of the IL-15 conjugate is about 1:1. In some embodiments of an IL-15 conjugate described herein, the ratio of the amount of the structure of Formula (XVI) to the amount of the structure of Formula (XVII) comprising the total amount of the IL-15 conjugate is greater than 1:1. In some embodiments of an IL-15 conjugate described herein, the ratio of the amount of the structure of Formula (XVI) to the amount of the structure of Formula (XVII) comprising the total amount of the IL-15 conjugate is less than 1:1.

In some embodiments described herein are IL-15 conjugates comprising the amino acid sequence of SEQ ID NO: 1 in which at least one amino acid residue in the IL-15 conjugate is replaced by the structure of Formula (XVI) or (XVII), or a mixture of (XVI) and (XVII), wherein the amino acid residue in in SEQ ID NO: 1 that is replaced is selected from S18, L25, E46, E53, N77, and S83, and wherein n is an integer from 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments of an IL-15 conjugate described herein, n in the compounds of formula (XVI) and (XVII) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

In some embodiments described herein are IL-15 conjugates comprising the amino acid sequence of SEQ ID NO: 1 in which at least one amino acid residue in the IL-15 conjugate is replaced by the structure of Formula (XVI) or (XVII), or a mixture of (XVI) and (XVII), wherein the amino acid residue in in SEQ ID NO: 1 that is replaced is selected from L25, and wherein n is an integer from about 450 to about 800, or from about 454 to about 796, or from about 454 to about 682, or from about 568 to about 909. In some embodiments of an IL-15 conjugate described herein, n in the compounds of formula (XVI) and (XVII) is an integer selected from 454, 455, 568, 569, 680, 681, 682, 794, 795, 796, 908, 909, 910, 1021, 1022, 1023, 1135, 1136, 1137, and 1249.

In some embodiments described herein are IL-15 conjugates comprising the amino acid sequence of SEQ ID NO: 1 in which at least one amino acid residue in the IL-15 conjugate is replaced by the structure of Formula (XVI) or (XVII), or a mixture of (XVI) and (XVII), wherein the amino acid residue in SEQ ID NO: 1 that is replaced is selected from L25, and wherein n is an integer from about 450 to about 800, or from about 454 to about 796, or from about 454 to about 682, or from about 568 to about 909. In some embodiments of an IL-15 conjugate described herein, n in the compounds of formula (XVI) and (XVII) is an integer selected from 454, 455, 568, 569, 680, 681, 682, 794, 795, 796, 908, 909, and 910.

In some embodiments described herein are IL-15 conjugates comprising the amino acid sequence of SEQ ID NO: 1 in which at least one amino acid residue in the IL-15 conjugate is replaced by the structure of Formula (XVI) or (XVII), or a mixture of (XVI) and (XVII), wherein the amino acid residue in SEQ ID NO: 1 that is replaced is L25, and wherein n is an integer from about 450 to about 800, or from about 454 to about 796, or from about 454 to about 682, or from about 568 to about 909. In some embodiments of an IL-15 conjugate described herein, n in the compounds of formula (XVI) and (XVII) is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 909.

In some embodiments of an IL-15 conjugate described herein, the position of the structure of Formula (XVI) and (XVII) or a mixture of Formula (XVI) and (XVII) in the amino acid sequence of the IL-15 conjugate comprising SEQ ID NO: 3 is selected from S19, L26, E47, E54, N78, and S84. Further described herein are IL-15 conjugates wherein the position of the structure of Formula (XVI) or (XVII), or a mixture of (XVI) and (XVII), in the amino acid sequence of the IL-15 conjugate is selected from K95, L26, E47. Further described herein are IL-15 conjugates wherein the position of the structure of Formula (XVI) or (XVII), or a mixture of (XVI) and (XVII), in the amino acid sequence of the IL-15 conjugate is selected from E54, N78, S84. Further described herein are IL-15 conjugates wherein the position of the structure of Formula (XVI) or (XVII), or a mixture of (XVI) and (XVII), in the amino acid sequence of the IL-15 conjugate is K95. Further described herein are IL-15 conjugates wherein the position of the structure of Formula (XVI) or (XVII), or a mixture of (XVI) and (XVII), in the amino acid sequence of the IL-15 conjugate is L26. Further described herein are IL-15 conjugates wherein the position of the structure of Formula (XVI) or (XVII), or a mixture of (XVI) and (XVII), in the amino acid sequence of the IL-15 conjugate is E47. Further described herein are IL-15 conjugates wherein the position of the structure of Formula (XVI) or (XVII), or a mixture of (XVI) and (XVII), in the amino acid sequence of the IL-15 conjugate is E54. Further described herein are IL-15 conjugates wherein the position of the structure of Formula (XVI) or (XVII), or a mixture of (XVI) and (XVII), in the amino acid sequence of the IL-15 conjugate is N78. Further described herein are IL-15 conjugates wherein the position of the structure of Formula (XVI) or (XVII), or a mixture of (XVI) and (XVII), in the amino acid sequence of the IL-15 conjugate is S84.

Described herein are IL-15 conjugates comprising the amino acid sequence of SEQ ID NO: 1 or SEQ ID NO: 3 in which at least one amino acid residue in the IL-15 conjugate is replaced by the structure of Formula (XVI) or (XVII), or a mixture of (XVI) and (XVII), wherein n is an integer such that the molecular weight of the PEG moiety is in the range from about 1,000 Daltons about 200,000 Daltons, or from about 2,000 Daltons to about 150,000 Daltons, or from about 3,000 Daltons to about 125,000 Daltons, or from about 4,000 Daltons to about 100,000 Daltons, or from about 5,000 Daltons to about 100,000 Daltons, or from about 6,000 Daltons to about 90,000 Daltons, or from about 7,000 Daltons to about 80,000 Daltons, or from about 8,000 Daltons to about 70,000 Daltons, or from about 5,000 Daltons to about 70,000 Daltons, or from about 5,000 Daltons to about 65,000 Daltons, or from about 5,000 Daltons to about 60,000 Daltons, or from about 5,000 Daltons to about 50,000 Daltons, or from about 6,000 Daltons to about 50,000 Daltons, or from about 7,000 Daltons to about 50,000 Daltons, or from about 7,000 Daltons to about 45,000 Daltons, or from about 7,000 Daltons to about 40,000 Daltons, or from about 8,000 Daltons to about 40,000 Daltons, or from about 8,500 Daltons to about 40,000 Daltons, or from about 8,500 Daltons to about 35,000 Daltons, or from about 9,000 Daltons to about 50,000 Daltons, or from about 9,000 Daltons to about 45,000 Daltons, or from about 9,000 Daltons to about 40,000 Daltons, or from about 9,000 Daltons to about 35,000 Daltons, or from about 9,000 Daltons to about 30,000 Daltons, or from about 9,500 Daltons to about 35,000 Daltons, or from about 9,500 Daltons to about 30,000 Daltons, or from about 10,000 Daltons to about 50,000 Daltons, or from about 10,000 Daltons to about 45,000 Daltons, or from about 10,000 Daltons to about 40,000 Daltons, or from about 10,000 Daltons to about 35,000 Daltons, or from about 10,000 Daltons to about 30,000 Daltons, or from about 15,000 Daltons to about 50,000 Daltons, or from about 15,000 Daltons to about 45,000 Daltons, or from about 15,000 Daltons to about 40,000 Daltons, or from about 15,000 Daltons to about 35,000 Daltons, or from about 15,000 Daltons to about 30,000 Daltons, or from about 20,000 Daltons to about 50,000 Daltons, or from about 20,000 Daltons to about 45,000 Daltons, or from about 20,000 Daltons to about 40,000 Daltons, or from about 20,000 Daltons to about 35,000 Daltons, or from about 20,000 Daltons to about 30,000 Daltons. Described herein are IL-15 conjugates comprising the amino acid sequence of SEQ ID NO: 1 or SEQ ID NO: 3 in which at least one amino acid residue in the IL-15 conjugate is replaced by the structure of Formula (XVI) or (XVII), or a mixture of (XVI) and (XVII), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, about 50,000 Daltons, about 60,000 Daltons, about 70,000 Daltons, about 80,000 Daltons, about 90,000 Daltons, about 100,000 Daltons, about 125,000 Daltons, about 150,000 Daltons, about 175,000 Daltons or about 200,000 Daltons. Described herein are IL-15 conjugates comprising the amino acid sequence of SEQ ID NO: 1 or SEQ ID NO: 3 in which at least one amino acid residue in the IL-15 conjugate is replaced by the structure of Formula (XVI) or (XVII), or a mixture of (XVI) and (XVII), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, or about 50,000 Daltons.

In some embodiments described herein are IL-15 conjugates comprising the amino acid sequence of SEQ ID NO: 3 in which at least one amino acid residue in the IL-15 conjugate is replaced by the structure of Formula (XVI) or (XVII), or a mixture of (XVI) and (XVII), wherein the amino acid residue in in SEQ ID NO: 3 that is L26, m is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XVI) and (XVII), m is 2, and n is an integer selected from 454, 455, 568, 569, 680, 681, 682, 794, 795, 796, 908, 909, 910, 1021, 1022, 1023, 1135, 1136, 1137, and 1249.

In some embodiments described herein are IL-15 conjugates comprising the amino acid sequence of SEQ ID NO: 3 in which at least one amino acid residue in the IL-15 conjugate is replaced by the structure of Formula (XVI) or (XVII), or a mixture of (XVI) and (XVII), wherein the amino acid residue in SEQ ID NO: 3 that is replaced is L26, and wherein m is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XVI) and (XVII), m is 2, and n is an integer selected from 454, 455, 568, 569, 680, 681, 682, 794, 795, 796, 908, 909, and 910.

In some embodiments described herein are IL-15 conjugates comprising the amino acid sequence of SEQ ID NO: 3 in which at least one amino acid residue in the IL-15 conjugate is replaced by the structure of Formula (XVI) or (XVII), or a mixture of (XVI) and (XVII), wherein the amino acid residue in SEQ ID NO: 3 that is replaced is L26, and wherein m is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XVI) and (XVII), m is 2, and n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 909.

In some embodiments described herein are IL-15 conjugates comprising the amino acid sequence of SEQ ID NO: 3 in which at least one amino acid residue in the IL-15 conjugate is replaced by the structure of Formula (XVI) or (XVII), or a mixture of (XVI) and (XVII), wherein the amino acid residue in in SEQ ID NO: 3 that is E54, m is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XVI) and (XVII), m is 2, and n is an integer selected from 454, 455, 568, 569, 680, 681, 682, 794, 795, 796, 908, 909, 910, 1021, 1022, 1023, 1135, 1136, 1137, and 1249.

In some embodiments described herein are IL-15 conjugates comprising the amino acid sequence of SEQ ID NO: 3 in which at least one amino acid residue in the IL-15 conjugate is replaced by the structure of Formula (XVI) or (XVII), or a mixture of (XVI) and (XVII), wherein the amino acid residue in SEQ ID NO: 3 that is replaced is E54, and wherein m is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XVI) and (XVII), m is 2, and n is an integer selected from 454, 455, 568, 569, 680, 681, 682, 794, 795, 796, 908, 909, and 910.

In some embodiments described herein are IL-15 conjugates comprising the amino acid sequence of SEQ ID NO: 3 in which at least one amino acid residue in the IL-15 conjugate is replaced by the structure of Formula (XVI) or (XVII), or a mixture of (XVI) and (XVII), wherein the amino acid residue in SEQ ID NO: 3 that is replaced is E54, and wherein m is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XVI) and (XVII), m is 2, and n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 909.

In some embodiments described herein are IL-15 conjugates comprising the amino acid sequence of SEQ ID NO: 3 in which at least one amino acid residue in the IL-15 conjugate is replaced by the structure of Formula (XVI) or (XVII), or a mixture of (XVI) and (XVII), wherein the amino acid residue in in SEQ ID NO: 3 that is N78, m is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XVI) and (XVII), m is 2, and n is an integer selected from 454, 455, 568, 569, 680, 681, 682, 794, 795, 796, 908, 909, 910, 1021, 1022, 1023, 1135, 1136, 1137, and 1249.

In some embodiments described herein are IL-15 conjugates comprising the amino acid sequence of SEQ ID NO: 3 in which at least one amino acid residue in the IL-15 conjugate is replaced by the structure of Formula (XVI) or (XVII), or a mixture of (XVI) and (XVII), wherein the amino acid residue in SEQ ID NO: 3 that is replaced is N78, and wherein m is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XVI) and (XVII), m is 2, and n is an integer selected from 454, 455, 568, 569, 680, 681, 682, 794, 795, 796, 908, 909, and 910.

In some embodiments described herein are IL-15 conjugates comprising the amino acid sequence of SEQ ID NO: 3 in which at least one amino acid residue in the IL-15 conjugate is replaced by the structure of Formula (XVI) or (XVII), or a mixture of (XVI) and (XVII), wherein the amino acid residue in SEQ ID NO: 3 that is replaced is N78, and wherein m is an integer from 1 to 6, and n is an integer from about 450 to about 800, or from about 454 to about 796, or from about 454 to about 682, or from about 568 to about 909. In some embodiments of an IL-15 conjugate described herein in the compounds of formula (XVI) and (XVII), m is 2, and n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681. In some embodiments, n is about 909.

Described herein are methods of treating cancer in a subject, comprising administering to a subject in need thereof an effective amount of an IL-15 conjugate described herein. In some embodiments, the cancer is a solid tumor cancer. In some embodiments, the solid tumor cancer is bladder cancer, bone cancer, brain cancer, breast cancer, colorectal cancer, esophageal cancer, eye cancer, head and neck cancer, kidney cancer, lung cancer, melanoma, ovarian cancer, pancreatic cancer, or prostate cancer. In some embodiments, the cancer is a hematologic malignancy. In some embodiments, the hematologic malignancy is chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the cancer in the subject is selected from renal cell carcinoma (RCC), non-small cell lung cancer (NSCLC), head and neck squamous cell cancer (HNSCC), classical Hodgkin lymphoma (cHL), primary mediastinal large B-cell lymphoma (PMBCL), urothelial carcinoma, microsatellite unstable cancer, microsatellite stable cancer, gastric cancer, cervical cancer, hepatocellular carcinoma (HCC), Merkel cell carcinoma (MCC), melanoma, small cell lung cancer (SCLC), esophageal, glioblastoma, mesothelioma, breast cancer, triple-negative breast cancer, prostate cancer, bladder cancer, ovarian cancer, tumors of moderate to low mutational burden, cutaneous squamous cell carcinoma (CSCC), squamous cell skin cancer (SCSC), tumors of low- to non-expressing PD-L1, tumors disseminated systemically to the liver and CNS beyond their primary anatomic originating site, and diffuse large B-cell lymphoma. In some embodiments, the cancer in the subject is selected from renal cell carcinoma (RCC), non-small cell lung cancer (NSCLC), urothelial carcinoma, and melanoma. In some embodiments, the cancer in the subject is non-Hodgkin lymphoma (NHL). In some embodiments the cancer in the subject is multiple myeloma.

In some embodiments, the IL-15 conjugate is administered to the subject in need thereof once every week, every two weeks, once every three weeks, once every 4 weeks, once every 5 weeks, once every 6 weeks, once every 7 weeks, or once every 8 weeks. In some embodiments, the IL-15 conjugate is administered to the subject in need thereof once per week, once every two weeks, once every three weeks, or once every four weeks. In some embodiments, the IL-15 conjugate is administered to the subject in need thereof once per week. In some embodiments, the IL-15 conjugate is administered to the subject in need thereof once every two weeks. In some embodiments, the IL-15 conjugate is administered to the subject in need thereof once every three weeks. In some embodiments, the IL-15 conjugate is administered to the subject in need thereof once every four weeks.

In some embodiments, the amount of a given agent that corresponds to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

In some embodiments, the methods include the dosing of an IL-15 conjugate to a subject in need thereof at a dose in the range from 1 µg of the IL-15 conjugate per kg of the subject's body weight to about 200 µg of the IL-15 conjugate per kg of the subject's body weight, or from about 2 µg of the IL-15 conjugate per kg of the subject's body weight to about 200 µg of the IL-15 conjugate per kg of the subject's body weight, or from about 4 µg of the IL-15 conjugate per kg of the subject's body weight to about 200 µg of the IL-15 conjugate per kg of the subject's body weight, or from about 6 µg of the IL-15 conjugate per kg of the subject's body weight to about 200 µg of the IL-15 conjugate per kg of the subject's body weight, or from about 8 µg of the IL-15 conjugate per kg of the subject's body weight to about 200 µg of the IL-15 conjugate per kg of the subject's body weight, or from about 10 µg of the IL-15 conjugate per kg of the subject's body weight to about 200 µg of the IL-15 conjugate per kg of the subject's body weight, or from about 12 µg of the IL-15 conjugate per kg of the subject's body weight to about 200 µg of the IL-15 conjugate per kg of the subject's body weight, or from about 14 µg of the IL-15 conjugate per kg of the subject's body weight to about 200 µg of the IL-15 conjugate per kg of the subject's body weight, or from about 16 µg of the IL-15 conjugate per kg of the subject's body weight to about 200 µg of the IL-15 conjugate per kg of the subject's body weight, or from about 18 µg of the IL-15 conjugate per kg of the subject's body weight to about 200 µg of the IL-15 conjugate per kg of the subject's body weight, or from about 20 µg of the IL-15 conjugate per kg of the subject's body weight to about 200 µg of the IL-15 conjugate per kg of the subject's body weight, or from about 22 µg of the IL-15 conjugate per kg of the subject's body weight to about 200 µg of the IL-15 conjugate per kg of the subject's body weight, or from about 24 µg of the IL-15 conjugate per kg of the subject's body weight to about 200 µg of the IL-15 conjugate per kg of the subject's body weight, or from about 26 µg of the IL-15 conjugate per kg of the subject's body weight to about 200 µg of the IL-15 conjugate per kg of the subject's body weight, or from about 28 µg of the IL-15 conjugate per kg of the subject's body weight to about 200 µg of the IL-15 conjugate per kg of the subject's body weight, or from about 32 µg of the IL-15 conjugate per kg of the subject's body weight to about 200 µg of the IL-15 conjugate per kg of the subject's body weight, or from about 34 µg of the IL-15 conjugate per kg of the subject's body weight to about 200 µg of the IL-15 conjugate per kg of the subject's body weight, or from about 36 µg of the IL-15 conjugate per kg of the subject's body weight to about 200 µg of the IL-15 conjugate per kg of the subject's body weight, or from about 40 µg of the IL-15 conjugate per kg of the subject's body weight to about 200 µg of the IL-15 conjugate per kg of the subject's body weight, or from about 45 µg of the IL-15 conjugate per kg of the subject's body weight to about 200 µg of the IL-15 conjugate per kg of the subject's body weight, or from about 50 µg of the IL-15 conjugate per kg of the subject's body weight to about 200 µg of the IL-15 conjugate per kg of the subject's body weight, or from about 55 µg of the IL-15 conjugate per kg of the subject's body weight to about 200 µg of the IL-15 conjugate per kg of the subject's body weight, or from about 60 µg of the IL-15 conjugate per kg of the subject's body weight to about 200 µg of the IL-15 conjugate per kg of the subject's body weight, or from about 65 µg of the IL-15 conjugate per kg of the subject's body weight to about 200 µg of the IL-15 conjugate per kg of the subject's body weight, or from about 70 µg of the IL-15 conjugate per kg of the subject's body weight to about 200 µg of the IL-15 conjugate per kg of the subject's body weight, or from about 75 µg of the IL-15 conjugate per kg of the subject's body weight to about 200 µg of the IL-15 conjugate per kg of the subject's body weight, or from about 80 µg of the IL-15 conjugate per kg of the subject's body weight to about 200 µg of the IL-15 conjugate per kg of the subject's body weight, or from about 85 µg of the IL-15 conjugate per kg of the subject's body weight to about 200 µg of the IL-15 conjugate per kg of the subject's body weight, or from about 90 µg of the IL-15 conjugate per kg of the subject's body weight to about 200 µg of the IL-15 conjugate per kg of the subject's body weight, or from about 95 µg of the IL-15 conjugate per kg of the subject's body weight to about 200 µg of the IL-15 conjugate per kg of the subject's body weight, or from about 100 µg of the IL-15 conjugate per kg of the subject's body weight to about 200 µg of the IL-15 conjugate per kg of the subject's body weight, or from about 110 µg of the IL-15 conjugate per kg of the subject's body weight to about 200 µg of the IL-15 conjugate per kg of the subject's body weight, or from about 120 µg of the IL-15 conjugate per kg of the subject's body weight to about 200 µg of the IL-15 conjugate per kg of the subject's body weight, or from about 130 µg of the IL-15 conjugate per kg of the subject's body weight to about 200 µg of the IL-15 conjugate per kg of the subject's body weight, or from about 140 µg of the IL-15 conjugate per kg of the subject's body weight to about 200 µg of the IL-15 conjugate per kg of the subject's body weight, or from about 150 µg of the IL-15 conjugate per kg of the subject's body weight to about 200 µg of the IL-15 conjugate per kg of the subject's body weight, or from about 160 µg of the IL-15 conjugate per kg of the subject's body weight to about 200 µg of the IL-15 conjugate per kg of the subject's body weight, or from about 170 µg of the IL-15 conjugate per kg of the subject's body weight to about 200 µg of the IL-15 conjugate per kg of the subject's body weight, or from about 180 µg of the IL-15 conjugate per kg of the subject's body weight to about 200 µg of the IL-15 conjugate per kg of the subject's body weight, or from about 190 µg of the IL-15 conjugate per kg of the subject's body weight to about 200 µg of the IL-15 conjugate per kg of the subject's body weight. The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner. In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

In some embodiments, the methods include the dosing of an IL-15 conjugate to a subject in need thereof at a dose of about 1 μg of the IL-15 conjugate per kg of the subject's body weight, or about 2 μg of the IL-15 conjugate per kg of the subject's body weight, about 4 μg of the IL-15 conjugate per kg of the subject's body weight, about 6 μg of the IL-15 conjugate per kg of the subject's body weight, about 8 μg of the IL-15 conjugate per kg of the subject's body weight, about 10 μg of the IL-15 conjugate per kg of the subject's body weight, about 12 μg of the IL-15 conjugate per kg of the subject's body weight, about 14 μg of the IL-15 conjugate per kg of the subject's body weight, about 16 μg of the IL-15 conjugate per kg of the subject's body weight, about 18 μg of the IL-15 conjugate per kg of the subject's body weight, about 20 μg of the IL-15 conjugate per kg of the subject's body weight, about 22 μg of the IL-15 conjugate per kg of the subject's body weight, about 24 μg of the IL-15 conjugate per kg of the subject's body weight, about 26 μg of the IL-15 conjugate per kg of the subject's body weight, about 28 μg of the IL-15 conjugate per kg of the subject's body weight, about 30 μg of the IL-15 conjugate per kg of the subject's body weight, about 32 μg of the IL-15 conjugate per kg of the subject's body weight, about 34 μg of the IL-15 conjugate per kg of the subject's body weight, about 36 μg of the IL-15 conjugate per kg of the subject's body weight, about 38 μg of the IL-15 conjugate per kg of the subject's body weight, about 40 μg of the IL-15 conjugate per kg of the subject's body weight, about 42 μg of the IL-15 conjugate per kg of the subject's body weight, about 44 μg of the IL-15 conjugate per kg of the subject's body weight, about 46 μg of the IL-15 conjugate per kg of the subject's body weight, about 48 μg of the IL-15 conjugate per kg of the subject's body weight, about 50 μg of the IL-15 conjugate per kg of the subject's body weight, about 55 μg of the IL-15 conjugate per kg of the subject's body weight, about 60 μg of the IL-15 conjugate per kg of the subject's body weight, about 65 μg of the IL-15 conjugate per kg of the subject's body weight, about 70 μg of the IL-15 conjugate per kg of the subject's body weight, about 75 μg of the IL-15 conjugate per kg of the subject's body weight, about 80 μg of the IL-15 conjugate per kg of the subject's body weight, about 85 μg of the IL-15 conjugate per kg of the subject's body weight, about 90 μg of the IL-15 conjugate per kg of the subject's body weight, about 95 μg of the IL-15 conjugate per kg of the subject's body weight, about 100 μg of the IL-15 conjugate per kg of the subject's body weight, about 110 μg of the IL-15 conjugate per kg of the subject's body weight, about 120 μg of the IL-15 conjugate per kg of the subject's body weight, about 130 μg of the IL-15 conjugate per kg of the subject's body weight, about 140 μg of the IL-15 conjugate per kg of the subject's body weight, about 150 μg of the IL-15 conjugate per kg of the subject's body weight, about 160 μg of the IL-15 conjugate per kg of the subject's body weight, about 170 μg of the IL-15 conjugate per kg of the subject's body weight, about 180 μg of the IL-15 conjugate per kg of the subject's body weight, about 190 μg of the IL-15 conjugate per kg of the subject's body weight, or about 200 μg of the IL-15 conjugate per kg of the subject's body weight. The foregoing amounts are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner. In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

Described herein are methods of expanding effector T (Teff) cell, memory T (Tmem) cell, and Natural Killer (NK) cell populations, comprising: (a) contacting a cell with an IL-15 conjugate described herein; and (b) interacting the IL-15 with IL-15Rβ and IL-15Rγ subunits to form an IL-15/IL-15Rβγ complex, wherein the IL-15 conjugate has a decreased affinity to IL-15Rα subunit, and wherein the IL-15/IL-15Rβγ complex stimulates the expansion of Teff, Tmem, and NK cells. In some embodiments, the cell is a eukaryotic cell. In some embodiments, the cell is a mammalian cell. In some embodiments, the cell is a human cell.

Described herein are pharmaceutical compositions comprising an effective amount of an IL-15 conjugate described herein and one or more pharmaceutically acceptable excipients.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A shows the dose response in CD8+ T cells. FIG. 1B shows the dose response in NK cells. (native IL-15=closed triangles; IL-15_N78[AzK_PEG30]=closed circles; IL-15_L26[AzK_PEG30]=closed diamonds; IL-15_E54 [AzK_PEG30]=closed squares.)

FIGS. 12A-12B show flow cytometry plots showing memory CD8+T population (gated out of CD3+ T cells) at 5 days post-dose of vehicle (FIG. 12A) and 1 mg/kg of test compound IL-15_N77[AzK_L1_PEG30] in C57BL/6 mice (FIG. 12B) according to Example 3.

DETAILED DESCRIPTION OF THE DISCLOSURE

Figure 1A:
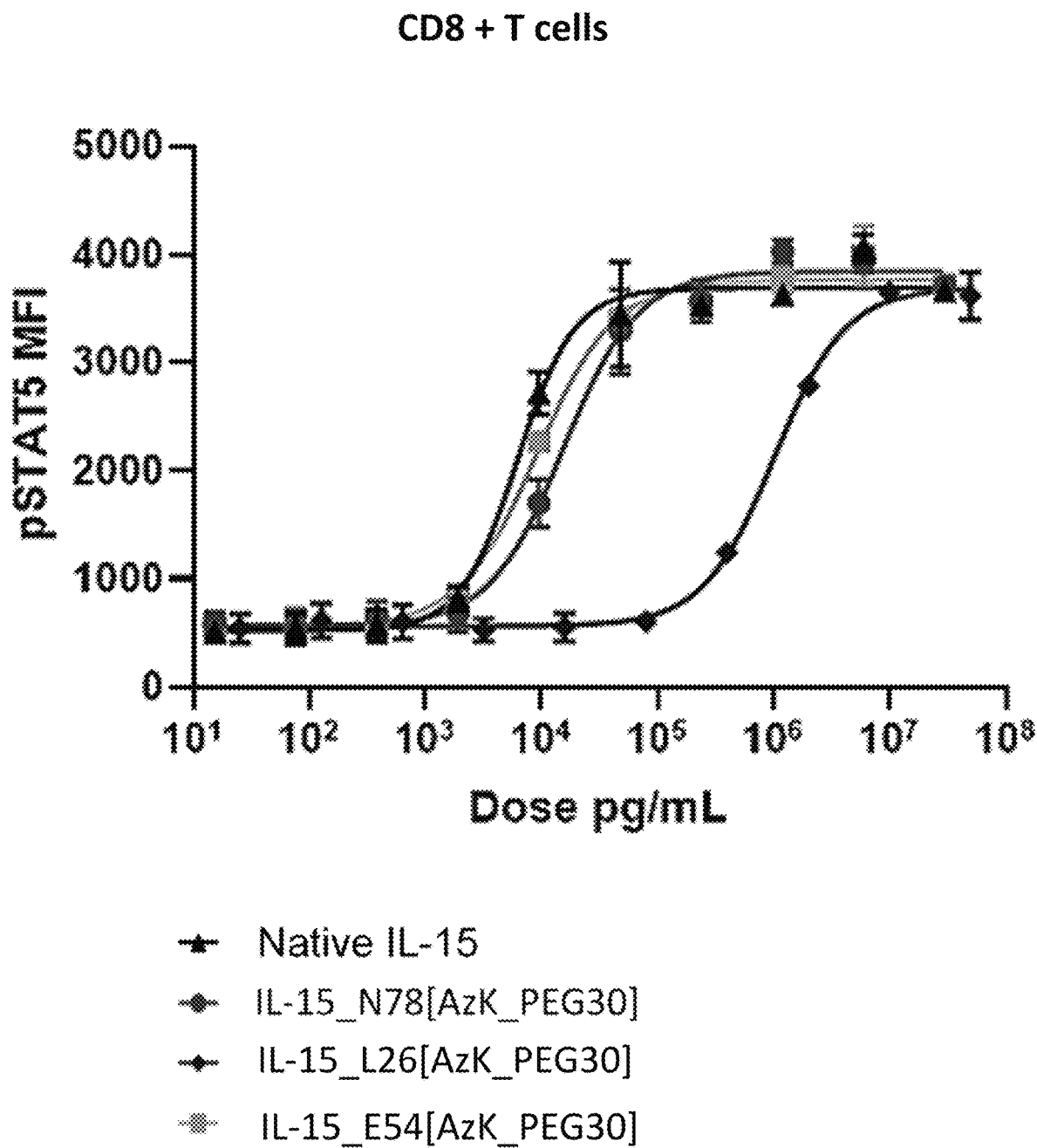
FIGS. 1A and 1B show the dose response for STAT5 signaling (EC50) in cynomolgus monkey whole blood treated with native IL-15 or the IL-15 conjugates from Example 2.

Cancer is a complex group of diseases involving abnormal cell growth with the potential to invade or spread to other parts of the body. Cancer therapies such as radiation and chemotherapy that target cancer drivers and pathways can be successful. In some instances, cancer cells are able to adapt to these therapies, limiting the efficacy of such therapies. Immunotherapy, unlike surgery, chemotherapy, or radiation, stimulates the immune system to recognize and kill tumor cells.

Several cytokines are used in immunotherapy for their ability to trigger an immune response. However, current immunotherapies utilizing cytokines result in several adverse effects including toxicity and uncontrolled cellular proliferation. Provided herein are modified cytokines or cytokine conjugates for use in treatment of cancer with ability to stimulate or expand specific T cell and NK populations resulting in improved treatment and reduced adverse events.

Cytokines comprise a family of cell signaling proteins such as chemokines, interferons, interleukins, lymphokines, and tumor necrosis factors. Cytokines are produced by immune cells such as macrophages, B lymphocytes, T lymphocytes and mast cells, endothelial cells, fibroblasts, and different stromal cells. In some instances, cytokines modulate the balance between humoral and cell-based immune responses.

Interleukins are signaling proteins which modulate the development and differentiation of T and B lymphocytes and hematopoietic cells. Interleukins are produced by helper CD4 T lymphocytes, monocytes, macrophages, and endothelial cells. In some cases, there are about 15 interleukins, interleukins 1-13, interleukin 15, and interleukin 17.

Interleukin-15 (IL-15) is a pleiotropic cytokine whose structure is a 14-15 kDa glycoprotein. IL-15 transcription, translation and secretion are regulated through multiple complex mechanisms. IL-15 and IL-15 receptor α (IL-15R α, CD215) proteins are co-expressed predominantly by activated monocytes and dendritic cells (DCs). The transcription of the heterodimer IL-15/IL-15Rα occurs following the interaction of monocytes/DCs with type 1 or type 2 interferons (IFN) or CD40 ligation or agents that act through Toll-like receptors (TLR) that activate NF-kB. Further, IL-15/IL-15Rα protein expression is predominantly controlled at the levels of translation and secretion. IL-15 signals through a heterotrimeric receptor comprising a unique a chain (IL-15R α), a shared β subunit (IL-15R β, CD132) with IL-2 (CD122) and a common γ subunit (CD132; IL-15R γ) shared with several cytokines. IL-15Rα has high affinity for IL-15 with a $K_d$ about $10^{-11}$ M.

In some embodiments, IL-15 signaling is utilized to modulate T cell responses and subsequently for treatment of cancer. In some embodiments, IL-15 signaling is utilized to simulate proliferation of activated $CD4^-CD8^-$, $CD4^+CD8^+$, $CD4^+$, and $CD8^+$ T cells and their differentiation in defined effector T-cell subsets. In some embodiments, IL-15 signaling is utilized to simulate the generation and proliferation of natural killer (NK) cells. In some embodiments, IL-15 signaling is utilized to promote maintenance and survival of memory CD8 T cells, naïve CD8 T cells, and NK cells. In some embodiments, IL-15 signaling is utilized to induce formation of memory CD8 T cells. In some embodiments, IL-15 signaling is utilized for priming NK cell target-specific activation. In some embodiments, IL-15 signaling does not result in Treg expansion.

Described herein, in some embodiments, are modified IL-15 polypeptides or IL-15 conjugates for modulating T cell responses and subsequently for treating cancer. In some embodiments, the modified IL-15 polypeptide comprises decrease binding with interleukin 15 receptor α (IL-15Rα). In some embodiments, the decrease in binding affinity is relative to binding affinity between a wild-type IL-15 polypeptide and the IL-15Rα. In some embodiments, the modified IL-15 polypeptide has little or no effect on interaction of the modified IL-15 polypeptide with interleukin 2/interleukin 15 receptor βγ (IL-2/IL-15R βγ). In some embodiments, the modified IL-15 polypeptide comprises one or more modifications that have little or no effect on the binding affinity of the modified IL-15 polypeptide with the IL-15R α and IL-15R γ. In some embodiments, the modified IL-15 polypeptide comprises decrease binding with IL-2/IL-15R γ and IL-15R α interaction is unaffected.

Described herein are modified IL-15 polypeptides or IL-15 conjugates with improved ability to stimulate an anti-tumor response. In some embodiments, the modified IL-15 polypeptides or IL-15 conjugates have improved safety profile. In some embodiments, the modified IL-15 polypeptides or IL-15 conjugates comprise a site-specific pegylation for increasing half-life. In some embodiments, the site-specific pegylation increases half-life and has little or no effect on biological activity. In some embodiments, signaling of the modified IL-15 polypeptides or IL-15 conjugates is biased to IL-15R βγ. In some embodiments, the modified IL-15 polypeptides or IL-15 conjugates comprise a site-specific pegylation for increasing half-life and reducing toxicity. In some embodiments, the site-specific pegylation results in less dosing of the modified IL-15 polypeptides or IL-15 conjugates. In some embodiments, toxicity is reduced by the modified IL-15 polypeptides or IL-15 conjugates blocking IL-15R α interaction. In some embodiments, activity of the modified IL-15 polypeptides or IL-15 conjugates is limited to a tumor site. In some embodiments, the modified IL-15 polypeptides or IL-15 conjugates comprise a site-specific pegylation such that trans-presentation of IL-15 is not required for natural killer (NK) and effector cell proliferation and function. In some embodiments, the modified IL-15 polypeptides or IL-15 conjugates comprise a site-specific pegylation such that clearance is inhibited or prohibited.

Modified IL-15 Polypeptides and IL-15 Conjugates

Described herein, in some embodiments, are modified IL-15 polypeptides. In some instances, the modification is to a natural amino acid. In some instances, the modification is to an unnatural amino acid. In some instances, described herein is an isolated and modified IL-15 polypeptide that comprises at least one unnatural amino acid. In some instances, the IL-15 polypeptide is an isolated and purified mammalian IL-15, for example, a human IL-15 protein. In some cases, the IL-15 polypeptide is a human IL-15 protein. In some cases, the IL-15 polypeptide comprises about 80%, 85%, 90%, 95%, 96%, 97%, 98%, or 99% sequence identity to SEQ ID NO: 1, 2, or 3. In some cases, the IL-15 polypeptide comprises or consists of the sequence of SEQ ID NO: 1 or 2. In some cases, the IL-15 polypeptide comprises or consists of the sequence of SEQ ID NO: 2 or 3.

In some instances, the modified IL-15 polypeptide is a truncated variant. In some instances, the truncation is an N-terminal deletion. In other instances, the truncation is a C-terminal deletion. In additional instances, the truncation comprises both N-terminal and C-terminal deletions. For example, the truncation can be a deletion of at least or about 1, 2, 3, 4, 5, 6, 7, 8, 9, 10, 11, 12, 13, 14, 15, 20, or more residues from either the N-terminus or the C-terminus, or both termini. In some cases, the modified IL-15 polypeptide comprises an N-terminal deletion of at least or about 1, 2, 3, 4, 5, 6, 7, 8, 9, 10, 11, 12, 13, 14, 15, 20, or more residues. In some cases, the modified IL-15 polypeptide comprises an N-terminal deletion of at least or about 1, 2, 3, 4, 5, 6, 7, 8, 9, or 10 residues. In some cases, the modified IL-15 polypeptide comprises an N-terminal deletion of at least or about 2 residues. In some cases, the modified IL-15 polypeptide comprises an N-terminal deletion of at least or about 3 residues. In some cases, the modified IL-15 polypeptide comprises an N-terminal deletion of at least or about 4 residues. In some cases, the modified IL-15 polypeptide comprises an N-terminal deletion of at least or about 5 residues. In some cases, the modified IL-15 polypeptide comprises an N-terminal deletion of at least or about 6 residues. In some cases, the modified IL-15 polypeptide comprises an N-terminal deletion of at least or about 7 residues. In some cases, the modified IL-15 polypeptide comprises an N-terminal deletion of at least or about 8 residues. In some cases, the modified IL-15 polypeptide comprises an N-terminal deletion of at least or about 9 residues. In some cases, the modified IL-15 polypeptide comprises an N-terminal deletion of at least or about 10 residues.

In some embodiments, the modified IL-15 polypeptide is a functionally active fragment. In some cases, the functionally active fragment comprises IL-15 region 5-114, 10-114, 15-114, 20-114, 1-110, 5-110, 10-110, 15-110, 20-110, 1-105, 5-105, 10-105, 15-105, 20-105, 1-100, 5-100, 10-100, 15-100, or 20-100, wherein the residue positions are in reference to the positions in SEQ ID NO: 1. In some instances, the functionally active fragment comprises IL-15 region 5-114, 10-114, 15-114, or 20-114, wherein the residue positions are in reference to the positions in SEQ ID NO: 1. In some instances, the functionally active fragment comprises IL-15 region 1-110, 5-110, 10-110, 15-110, or 20-110, wherein the residue positions are in reference to the positions in SEQ ID NO: 1. In some instances, the functionally active fragment comprises IL-15 region 1-105, 5-105, 10-105, 15-105, or 20-105, wherein the residue positions are in reference to the positions in SEQ ID NO: 1. In some instances, the functionally active fragment comprises IL-15 region 1-100, 5-100, 10-100, 15-100, or 20-100, wherein the residue positions are in reference to the positions in SEQ ID NO: 1.

In some embodiments, the functionally active IL-15 fragment comprises an internal deletion. In some cases, the internal deletion comprises a loop region. In some cases, the internal deletion comprises a deletion of 2, 3, 4, 5, 6, 7, 8, 9, 10, 11, 12, 13, 14, 15, or more residues.

In some embodiments, an IL-15 polypeptide described herein comprises at least one unnatural amino acid. In some instances, the residue position of the at least one unnatural amino acid is selected from N1, W2, V3, N4, I6, S7, D8, K10, K11, E13, D14, L15, Q17, S18, M19, H20, I21, D22, A23, T24, L25, Y26, T27, E28, S29, D30, V31, H32, P33, S34, C35, K36, V37, T38, A39, K41, L44, L45, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S114, wherein the residue positions correspond to the positions as set forth in SEQ ID NO: 1. In some embodiments, the residue position of the at least one unnatural amino acid is selected from N1, W2, V3, N4, I6, S7, D8, K10, K11, E13, D14, L15, Q17, S18, M19, H20, I21, D22, A23, T24, L25, Y26, E28, S29, D30, V31, H32, P33, S34, C35, K36, V37, T38, K41, L44, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S14, wherein the residue positions correspond to the positions as set forth in SEQ ID NO: 1. In some embodiments, the residue position of the at least one unnatural amino acid is selected from E13, D14, L15, Q17, S18, M19, H20, I21, S34, C35, K36, V37, T38, K41, L44, S51, L52, S54, G55, D56, A57, S58, H60, V63, I67, N71, S73, L74, S75, S76, N77, G78, N79, V80, T81, E82, S83, G84, C85, K86, E87, C88, L91, E92, K94, N95, I96, K97, E98, L100, Q101, and F110. In some embodiments, the residue position of the at least one unnatural amino acid is selected from D14, Q17, S18, K41, S51, L52, G55, D56, A57, S58, S75, S76, N77, N79, V80, T81, S83, G84, E92, K94, N95, K97, and E98. In some embodiments, the residue position of the at least one unnatural amino acid is selected from N1, N4, S7, D8, K11, D61, T62, E64, N65, I68, L69, and N72. In some embodiments, the residue position of the at least one unnatural amino acid is selected from V3, I6, K10, E28, S29, D30, V31, H32, P33, S102, V104, H105, Q108, M109, I111, N112, T113, and S114. In some embodiments, the residue position of the at least one unnatural amino acid is selected from D22, A23, T24, L25, Y26, L44, E46, Q48, V49, E53, E89, E90, and E93. In some embodiments, the residue position of the at least one unnatural amino acid is selected from Y26, E46, V49, E53, and L25. In some embodiments, the residue position of the at least one unnatural amino acid is selected from V3, K10, S29, D30, H32, H105, Q108, M109, I111, N112, T113, and S14. In some embodiments, the residue position of the at least one unnatural amino acid is selected from N4, S7, K11, and D61. In some embodiments, the residue position of the at least one unnatural amino acid is selected from L25, E53, N77, and S83. In some embodiments, the residue position of the at least one unnatural amino acid is selected from L25 and E53. In some embodiments, the residue position of the at least one unnatural amino acid is selected from E46, Y26, V49, E53, T24, N4, K11, N65, L69, S18, H20, and S83. In some embodiments, the residue position of the at least one unnatural amino acid is selected from E46, Y26, V49, E53, and T24. In some embodiments, the residue position of the at least one unnatural amino acid is selected from E46, V49, E53, and T24. In some embodiments, the residue position of the at least one unnatural amino acid is selected from Y26, V49, E53, and T24. In some embodiments, the residue position of the at least one unnatural amino acid is selected from V49, E53, and T24. In some embodiments, the residue position of the at least one unnatural amino acid is selected from E46 and Y26. In some embodiments, the residue position of the at least one unnatural amino acid is E46. In some embodiments, the residue position of the at least one unnatural amino acid is L25. In some embodiments, the residue position of the at least one unnatural amino acid is Y26. In some embodiments, the residue position of the at least one unnatural amino acid is V49. In some embodiments, the residue position of the at least one unnatural amino acid is E53. In some embodiments, the residue position of the at least one unnatural amino acid is T24. In some embodiments, the residue position of the at least one unnatural amino acid is N77. In some embodiments, the residue position of the at least one unnatural amino acid is selected from N4, K11, N65, L69, S18, H20, and S583. An exemplary amino acids sequence for IL-15 is illustrated in Table 1 below.

TABLE 1

| NAME | SEQUENCE | SEQ ID NO. |
|---|---|---|
| IL-15 (mature form) | NWVNVISDLKKIEDLIQSMHIDATLYTESDVH PSCKVTAMKCFLLELQVISLESGDASIHDTVE NLIILANNSLSSNGNVTESGCKECEELEEKNIK EFLQSFVHIVQMFINTS | 1 |
| IL15 GenBank: CAA71044.1 (precursor) | MDFQVQIFSFLLISASVIMSRANWVNVISDLK KIEDLIQSMHIDATLYTESDVHPSCKVTAMKC FLLELQVISLESGDASIHDTVENLIILANNSLSS NGNVTESGCKECEELEEKNIKEFLQSFVHIVQ MFINTS | 2 |
| Met-IL-15 (mature form with N-terminal methionine) | MNWVNVISDLKKIEDLIQSMHIDATLYTESDV HPSCKVTAMKCFLLELQVISLESGDASIHDTV ENLIILANNSLSSNGNVTESGCKECEELEEKNI KEFLQSFVHIVQMFINTS | 3 |

TABLE 1-continued

| NAME | SEQUENCE | SEQ ID NO. |
|---|---|---|
| IL-15_S18X | NWVNVISDLKKIEDLIQXMHIDATLYTESDVH PSCKVTAMKCFLLELQVISLESGDASIHDTVE NLIILANNSLSSNGNVTESGCKECEELEEKNIK EFLQSFVHIVQMFINTS | 4 |
| IL-15_L25X | NWVNVISDLKKIEDLIQSMHIDATXYTESDVH PSCKVTAMKCFLLELQVISLESGDASIHDTVE NLIILANNSLSSNGNVTESGCKECEELEEKNIK EFLQSFVHIVQMFINTS | 5 |
| IL-15_E46X | NWVNVISDLKKIEDLIQSMHIDATLYTESDVH PSCKVTAMKCFLLXLQVISLESGDASIHDTVE NLIILANNSLSSNGNVTESGCKECEELEEKNIK EFLQSFVHIVQMFINTS | 6 |
| IL-15_E53X | NWVNVISDLKKIEDLIQSMHIDATLYTESDVH PSCKVTAMKCFLLELQVISLXSGDASIHDTVE NLIILANNSLSSNGNVTESGCKECEELEEKNIK EFLQSFVHIVQMFINTS | 7 |
| IL-15_N77X | NWVNVISDLKKIEDLIQSMHIDATLYTESDVH PSCKVTAMKCFLLELQVISLESGDASIHDTVE NLIILANNSLSSXGNVTESGCKECEELEEKNIK EFLQSFVHIVQMFINTS | 8 |
| IL-15_S83X | NWVNVISDLKKIEDLIQSMHIDATLYTESPVH PSCKVTAMKCFLLELQVISLESGDASIHDTVE NLIILANNSLSSNGNVTEXGCKECEELEEKNIK EFLQSFVHIVQMFINTS | 9 |
| IL-15_S18[AzK] | NWVNVISDLKKIEDLIQ[AzK]MHIDATLYTES DVHPSCKVTAMKCFLLELQVISLESGDASIHD TVENLIILANNSLSSNGNVTESGCKECEELEEK NIKEFLQSFVHIVQMFINTS | 10 |
| IL-15_L25[AzK] | NWVNVISDLKKIEDLIQSMHIDAT[AzK]YTES DVHPSCKVTAMKCFLLELQVISLESGDASIHD TVENLIILANNSLSSNGNVTESGCKECEELEEK NIKEFLQSFVHIVQMFINTS | 11 |
| IL-15_E46[AzK] | NWVNVISDLKKIEDLIQSMHIDATLYTESDVH PSCKVTAMKCFLL[AzK]LQVISLESGDASIHD TVENLIILANNSLSSNGNVTESGCKECEELEEK NIKEFLQSFVHIVQMFINTS | 12 |
| IL-15_E53[AzK] | NWVNVISDLKKIEDLIQSMHIDATLYTESDVH PSCKVTAMKCFLLELQVISL[AzK]SGDASIHP TVENLIILANNSLSSNGNVTESGCKECEELEEK NIKEFLQSFVHIVQMFINTS | 13 |
| IL-15_N77[AzK] | NWVNVISDLKKIEDLIQSMHIDATLYTESDVH PSCKVTAMKCFLLELQVISLESGDASIHDTVE NLIILANNSLSS[AzK]GNVTESGCKECEELEEK NIKEFLQSFVHIVQMFINTS | 14 |
| IL-15_S83[AzK] | NWVNVISDLKKIEDLIQSMHIDATLYTESDVH PSCKVTAMKCFLLELQVISLESGDASIHDTVE NLIILANNSLSSNGNVTE[AzK]GCKECEELEE KNIKEFLQSFVHIVQMFINTS | 15 |
| IL-15_S18 [AzK_PEG] | NWVNVISDLKKIEDLIQ[AzK_PEG]MHIDATL YTESDVHPSCKVTAMKCFLLELQVISLESGDA SIHDTVENLIILANNSLSSNGNVTESGCKECEE LEEKNIKEFLQSFVHIVQMFINTS | 16 |
| IL-15_L25 [AzK_PEG] | NWVNVISDLKKIEDLIQSMHIDAT[AzK_PEG] YTESDVMPSCKVTAMKCFLLELQVISLESGDA SIHDTVENLIILANNSLSSNGNVTESGCKECEE LEEKNIKEFLQSFVHIVQMFINTS | 17 |
| IL-15_E46 [AzK_PEG] | NWVNVISDLKKIEDLIQSMHIDATLYTESDVH PSCKVTAMKCFLL[AzK_PEG]LQVISLESGDA SIHDTVENLIILANNSLSSNGNVTESGCKECEE LEEKNIKEFLQSFVHIVQMFINTS | 18 |

TABLE 1-continued

| NAME | SEQUENCE | SEQ ID NO. |
|---|---|---|
| IL-15_E53 [AzK_PEG] | NWVNVISDLKKIEDLIQSMHIDATLYTESDVH PSCKVTAMKCFLLELQVISL[AzK_PEG]SGDA SIHDTVENLIILANNSLSSNGNVTESGCKECEE LEEKNIKEFLQSFVHIVQMFINTS | 19 |
| IL-15_N77 [AzK_PEG] | NWVNVISDLKKIEDLIQSMHIDATLYTESDVH PSCKVTAMKCFLLELQVISLESGDASIHDTVE NLIILANNSLSS[AzK_PEG]GNVTESGCKECEE LEEKNIKEFLQSFVHIVQMFINTS | 20 |
| IL-15_S83 [AzK_PEG] | NWVNVISDLKKIEDLIQSMHIDATLYTESDVH PSCKVTAMKCFLLELQVISLESGDASIHDTVE NLIILANNSLSSNGNVTE[AzK_PEG]GCKECE ELEEKNIKEFLQSFVHIVQMFINTS | 21 |
| IL-15_S18 [AzK_PEG30] | NWVNVISDLKKIEDLIQ[AzK_PEG30]MHIDA TLYTESDVHPSCKVTAMKCFLLELQVISLESG DASIHDTVENLIILANNSLSSNGNVTESGCKEC EELEEKNIKEFLQSFVHIVQMFINTS | 22 |
| IL-15_L25 [AzK_PEG30] | NWVNVISDLKKIEDLIQSMHIDAT[AzK_PEG30] YTESDVHPSCKVTAMKCFLLELQVISLESGD ASIHDTVENLIILANNSLSSNGNVTESGCKECE ELEEKNIKEFLQSFVHIVQMFINTS | 23 |
| IL-15_E46 [AzK_PEG30] | NWVNVISDLKKIEDLIQSMHIDATLYTESDVH PSCKVTAMKCFLL[AzK_PEG30]LQVISLESG DASIHDTVENLIILANNSLSSNGNVTESGCKEC EELEEKNIKEFLQSFVHIVQMFINTS | 24 |
| IL-15_E53 [AzK_PEG30] | NWVNVISDLKKIEDLIQSMHIDATLYTESDVH PSCKVTAMKCFLLELQVISL[AzK_PEG30]SG DASIHDTVENLIILANNSLSSNGNVTESGCKEC EELEEKNIKEFLQSFVHIVQMFINTS | 25 |
| IL-15_N77 [AzK_PEG30] | NWVNVISDLKKIEDLIQSMHIDATLYTESDVH PSCKVTAMKCFLLELQVISLESGDASIHDTVE NLIILANNSLSS[AzK_PEG30]GNVTESGCKEC EELEEKNIKEFLQSFVHIVQMFINTS | 26 |
| IL-15_S83 [AzK_PEG30] | NWVNVISDLKKIEDLIQSMHIDATLYTESDVH PSCKVTAMKCFLLELQVISLESGDASIHDTVE NLIILANNSLSSNGNVTE[AzK_PEG30]GCKEC EELEEKNEKEFLQSFVHIVQMFINTS | 27 |
| IL-15_S18 [AzK_PEG40] | NWVNVISDLKKIEDLIQ[AzK_PEG40]MHIDA TLYTESDVHPSCKVTAMKCFLLELQVISLESG DASIHDTVENLIILANNSLSSNGNVTESGCKEC EELEEKNIKEFLQSFVHIVQMFINTS | 28 |
| IL-15_L25 [AzK_PEG40] | NWVNVISDLKKIEDLIQSMHIDAT[AzK_PEG40] YTESDVHPSCKVTAMKCFLLELQVISLESGD ASIHDTVENLIILANNSLSSNGNVTESGCKECE ELEEKNIKEFLQSFVHIVQMFINTS | 29 |
| IL-15_E46 [AzK_PEG40] | NWVNVISDLKKIEDLIQSMHIDATLYTESDVH PSCKVTAMKGFLL[AzK_PEG40]LQVISLESG DASIHDTVENLIILANNSLSSNGNVTESGCKEC EELEEKNIKEFLQSFVHIVQMFINTS | 30 |
| IL-15_E53 [AzK_PEG40] | NWVNVISDLKKIEDLIQSMHIDATLYTESDVH PSCKVTAMKCFLLELQVISL[AzK_PEG40]SG DASIHDTVENLIILANNSLSSNGNVTESGCKEC EELEEKNIKEFLQSFVHIVQMFINTS | 31 |
| IL-15_N77 [AzK_PEG40] | NWVNVISDLKKIEDLIQSMHIDATLYTESDVH PSCKVTAMKCFLLELQVISLESGDASIHDTVE NLIILANNSLSS[AzK_PEG40]GNVTESGCKEC EELEEKNIKEFLQSFVHIVQMFINTS | 32 |
| IL-15_S83 [AzK_PEG40] | NWVNVISDLKKIEDLIQSMHIDATLYTESDVH PSCKVTAMKCFLLELQVISLESGDASIHDTVE NLIILANNSLSSNGNVTE[AzK_PEG40]GCKEC EELEEKNIKEFLQSFVHIVQMFINTS | 33 |
| IL-15_S18 [AzK_L1_PEG] | NWVNVISDLKKIEPLIQ[AzK_L1_PEG]MHID ATLYTESDVHPSCKVTAMKCFLLELQVISLES | 34 |

TABLE 1-continued

| NAME | SEQUENCE | SEQ ID NO. |
|---|---|---|
| | GDASIHDTVENLIILANNSLSSNGNVTESGCKE CEELEEKNIKEFLQSFVHIVQMFINTS | |
| IL-15_L25 [AzK_L1_PEG] | NWVNVISDLKKIEDLIQSMHIDAT[AzK L1 PEG] YTESDVHPSCKVTAMKCFLLELQVISLES GDASIHDTVENLIILANNSLSSNGNVTESGCKE CEELEEKNIKEFLQSFVHIVQMFINTS | 35 |
| IL-15_E46 [AzK_L1_PEG] | NWVNVISDLKKIEDLIQSMHIDATLYTESDVH PSCKVTAMKCFLL[AzK L1 PEG]LQVISLESG DASIHDFVENLIILANNSLSSNGNVTESGCKEC EELEEKNIKEFLQSFVHIVQMFINTS | 36 |
| IL-15_E53 [AzK_L1_PEG] | NWVNVISDLKKIEDLIQSMHIDATLYTESDVH PSCKVTAMKCFLLELQVISL[AzK L1 PEG]SG DASIHDTVENLIILANNSLSSNGNVTESGCKEC EELEEKNIKEFLQSFVHIVQMFINTS | 37 |
| IL-15_N77 [AzK_L1_PEG] | NWVNVISDLKKIEDLIQSMHIDATLYTESDVH PSCKVTAMKCFLLELQVISLESGDASIHDTVE NLIILANNSLSS[AzK L1 PEG]GNVTESGCKE CEELEEKNIKEFLQSFVHIVQMFINTS | 38 |
| IL-15_S83 [AzK_L1_PEG] | NWVNVISDLKKIEDLIQSMHIDATLYTESDVH PSCKVTAMKCFLLELQVISLESGDASIHDTVE NLIILANNSLSSNGNVTE[AzK L1 PEG]GCKE CEELEEKNIKEFLQSFVHIVQMFINTS | 39 |
| IL-15_S18 [AzK_L1_PEG30] | NWVNVISDLKKIEDLIQ[AzK L1 PEG30]MHI DATLYTESDVHPSCKVTAMKCFLLELQVISLE SGDASIHDTVENLIILANNSLSSNGNVTESGCK ECEELEEKNTKEFLQSFVHIVQMFINTS | 40 |
| IL-15_L25 [AzK_L1_PEG30] | NWVNVISDLKKIEDLIQSMHIDAT[AzK L1 PEG30] YTESDVHPSCKVTAMKCFLLELQVISLE SGDASIHDTVENLIILANNSLSSNGNVTESGCK ECEELEEKMKEFLQSFVHIVQMFINTS | 41 |
| IL-15_E46 [AzK_L1_PEG30] | NWVNVISDLKKIEDLIQSMHIDATLYTESDVH PSCKVTAMKCFLL[AzK L1 PEG30]LQVISLE SGDASIHDTVENLIILANNSLSSNGNVTESGCK ECEELEEKNIKEFLQSFVHIVQMFINTS | 42 |
| IL-15_E53 [AzK_L1_PEG30] | NWVNVISDLKKIEDLIQSMHIDATLYTESDVH PSCKVTAMKCFLLELQVISL[AzK L1 PEG30] SGDASIHDTVENLIILANNSESSNGNVTESGCK ECEELEEKNIKEFLQSFVHIVQMFINTS | 43 |
| IL-15_N77 [AzK_L1_PEG30] | NWVNVISDLKKIEDLIQSMHIDATLYTESDVH PSCKVTAMKCFLLELQVISLESGDASIHDTVE NLIILANNSLSS[AzK L1 PEG30]GNVTESGC KECEELEEKNIKEFLQSFVHIVQMFINTS | 44 |
| IL-15_S83 [AzK_L1_PEG30] | NWVNVISDLKKIEDLIQSMHIDATLYTESDVH PSCKVTAMKCFLLELQVISLESGDASIHDTVE NLIILANNSLSSNGNVTE[AzK L1 PEG30]GC KECEELEEKNIKEFLQSFVHIVQMFINTS | 45 |
| IL-15_S18 [AzK_L1_PEG40] | NWVNVISDLKKIEDLIQ[AzK L1 PEG40]MHI DATLYTESDVHPSCKVTAMKCFLLELQVISLE SGDASIHDTVENLIILANNSLSSNGNVTESGCK ECEELEEKNIKEFLQSFVHIVQMFINTS | 46 |
| IL-15_L25 [AzK_L1_PEG40] | NWVNVISDLKKIEDLIQSMHIDAT[AzK L1 PEG40] YTESDVHPSCKVTAMKCFLLELQVISLE SGDASIHDTVENLIILANNSLSSNGNVTESGCK ECEELEEKNIKEFLQSFVHIVQMFINTS | 47 |
| IL-15_E46 [AzK_L1_PEG40] | NWVNVISDLKKIEDLIQSMHIDATLYTESDVH PSCKVTAMKCFLL[AzK L1 PEG40]LQVISLE SGDASIHDTVENLIILANNSLSSNGNVTESGCK ECEELEEKNIKEFLQSFVHIVQMFINTS | 48 |
| IL-15_E53 [AzK_L1_PEG40] | NWVNVISDLKKIEDLIQSMHIDATLYTESDVH PSCKVTAMKCFLLELQVISL[AzK L1 PEG40] SGDASIHDTVENLIILANNSLSSNGNVTESGCK ECEELEEKNIKEFLQSFVHIVQMFINITS | 49 |

TABLE 1-continued

| NAME | SEQUENCE | SEQ ID NO. |
|---|---|---|
| IL-15_N77 [AzK_L1_PEG40] | NWWVISDLKKIEDLIQSMHIDATLYTESDVH PSCKVTAMKCFLLELQVISLESGDASFHDTVE NLIILANNSLSS[AzK_L1_PEG40]GNVTESGC KECEELEEKNIKEFLQSFVHIVQMFINTS | 50 |
| IL-15_S83 [AzK_L1_PEG40] | NWYWISDLKKIEDLIQSMHIDATLYTESDVH PSCKVTAMKCFLLELQVISLESGDASIHDTVE NLIILANNSLSSNGNVTE[AzK_L1_PEG40]GC KECEELEEKNIKEFLQSFVHIVQMFINTS | 51 |
| IL-15_S19X | MNWVNVISDLKKIEDLIQXMHIDATLYTESD VHPSCKVTAMKCFLLELQVISLESGDASIHDT VENLIILANNSLSSNGNVTESGCKECEELEEK NIKEFLQSFVHIVQMFINTS | 52 |
| IL-15_L26X | MNWVNVISDLKKIEDLIQSMHIDATXYTESD VHPSCKVTAMKCFLLELQVISLESGDASIHDT VENLIILANNSLSSNGNVTESGCKECEELEEK NIKEFLQSFVHIVQMFINTS | 53 |
| IL-15_E47X | MNWVNVISDLKKIEDLIQSMHIDATLYTESDV HPSCKVTAMKCFLLXLQVISLESGDASIHDTV ENLIILANNSLSSNGNVTESGCKECEELEEKNI KEFLQSFVHIVQMFINTS | 54 |
| IL-15_E54X | MNWVNVISDLKKIEDLIQSMHIDATLYTESDV HPSCKVTAMKCFLLELQVISLXSGDASIHDTV ENLIILANNSLSSNGNVTESGCKECEELEEKNI KEFLQSFVHIVQMFINTS | 55 |
| IL-15_N78X | MNWVNVISDLKKIEDLIQSMHIDATLYTESDV HPSCKVTAMKCFLLELQVISLESGDASIHDTV ENLIILANNSLSSXGNVTESGCKECEELEEKNI KEFLQSFVHIVQMFINTS | 56 |
| IL-15_S84X | MNWVNVISDLKKIEDLIQSMHIDATLYTESDV HPSCKVTAMKCFLLELQVISLESGDASIHDTV ENLIILANNSLSSNGNVTEXGCKECEELEEKNI KEFLQSFVHIVQMFINTS | 57 |
| IL-15_S19 [AzK] | MNWVNVISDLKKIEDLIQ[AzK]MHIDATLYTE SDVHPSCKVTAMKCFLLELQVISLESGDASIH DTVENLIILANNSLSSNGNVTESGCKECEELEE KNIKEFLQSFVHIVQMFINTS | 58 |
| IL-15_L26 [AzK] | MNWVNVISDLKKIEDLIQSMHIDAT[AzK]YTE SDVHPSCKVTAMKCFLLELQVISLESGDASIH DTVENLIILANNSLSSNGNVTESGCKECEELEE KNIKEFLQSFVHIVQMFINTS | 59 |
| IL-15_E47 [AzK] | MNWVNVISDLKKIEDLIQSMHIDATLYTESDV HPSCKVTAMKCFLL[AzK]LQVISLESGDASIH DTVENLIILANNSLSSNGNVTESGCKECEELEE KNIKEFLQSFVHIVQMFINTS | 60 |
| IL-15_E54 [AzK] | MNWVNVISDLKKIEDLIQSMHIDATLYTESDV HPSCKVTAMKCFLLELQVISL[AzK]SGDASIH DTVENLIILANNSLSSNGNVTESGCKECEELEE KNIKEFLQSFVHIVQMFINTS | 61 |
| IL-15_N78 [AzK] | MNWVNVISDLKKIEDLIQSMHIDATLYTESDV HPSCKVTAMKCFLLELQVISLESGDASIHDTV ENLIILANNSLSS[AzK]GNVTESGCKECEELEE KNIKEFLQSFVHIVQMFINTS | 62 |
| IL-15_S84 [AzK] | MNWVNVISDLKKIEDLIQSMHIDATLYTESDV HPSCKVTAMKCFLLELQYTSLESGDASIHDTV ENLIILANNSLSSNGNVTE[AzK]GCKECEELEE KNIKEFLQSFVHIVQMFINTS | 63 |
| IL-15_S19 [AzK_PEG] | MNWVNVISDLKKIEDLIQ[AzK_PEG]MHIDAT LYTESDVHPSCKVTAMKCFLLELQVISLESGD ASIHDTVENLIILANNSLSSNGNVTESGCKECE ELEEKNIKEFLQSFVHIVQMFINTS | 64 |

TABLE 1-continued

| NAME | SEQUENCE | SEQ ID NO. |
|---|---|---|
| IL-15_L26 [AzK_PEG] | MNWVNVISDLKKIEDLIQSMHIDAT[AzK_PEG]YTESDVHPSCKVTAMKCFLLELQVISLESGDASIHDTVENLIILANNSLSSNGNVTESGCKECEELEEKNIKEFLQSFVHIVQMFINTS | 65 |
| IL-15_E47 [AzK_PEG] | MNWVNVISDLKKIEDLIQSMHIDATLYTESDVHPSCKVTAMKCFLL[AzK_PEG]LQVISLESGDASIHDTVENLIILANNSLSSNGNVTESGCKECEELEEKNIKEFLQSFVHIVQMFINTS | 66 |
| IL-15_E54 [AzK_PEG] | MNWVNVISDLKKIEDLIQSMHIDATLYTESDVHPSCKVTAMKCFLLELQVISL[AzK_PEG]SGDASIHDTVENLIILANNSLSSNGNVTESGCKECEELEEKNIKEFLQSFVHIVQMFINTS | 67 |
| IL-15_N78 [AzK_PEG] | MNWVNVISDLKKIEDLIQSMHIDATLYTESDVHPSCKVTAMKCFLLELQVISLESGDASIHDTVENLFILANNSLSS[AzK_PEG]GNVTESGCKECEELEEKNIKEFLQSFVHIVQMFINTS | 68 |
| IL-15_S84 [AzK_PEG] | MNWVNVISDLKKIEDLIQSMHIDATLYTESDVHPSCKVTAMKCFLLELQVISLESGDASIHDTVENLIILANNSLSSNGNVTE[AzK_PEG]GCKECEELEEKNIKEFLQSFVHIVQMFINTS | 69 |
| IL-15_S19 [AzK_PEG30] | MNWVNVISDLKKIEDLIQ[AzK_PEG30]MHIDATLYTESDVHPSCKVTAMKCFLLELQVISLESGDASIHDTVENLIILANNSLSSNGNVTESGCKECEELEEKNIKEFLQSFVHIVQMFINTS | 70 |
| IL-15_L26 [AzK_PEG30] | MNWVNVISDLKKIEDLIQSMHIDAT[AzK_PEG30]YTESDVHPSCKVTAMKCFLLELQVISLESGDASIHDTVENLIILANNSLSSNGNVTESGCKECEELEEKNIKEFLQSFVHIVQMFINTS | 71 |
| IL-15_E47 [AzK_PEG30] | MNWVNVISDLKKIEDLIQSMHIDATLYTESDVHPSCKVTAMKCFLL[AzK_PEG30]LQVISLESGDASIHDTVENLIILANNSLSSNGNVTESGCKECEELEEKNIKEFLQSFVHIVQMFINTS | 72 |
| IL-15_E54 [AzK_PEG30] | MNWVNVISDLKKIEDLIQSMHIDATLYTESDVHPSCKVTAMKCFLLELQVISL[AzK_PEG30]SGDASIHDTVENLIILANNSLSSNGNVTESGCKECEELEEKNIKEFLQSFVHIVQMFINTS | 73 |
| IL-15_N78 [AzK_PEG30] | MNWVNVISDLKKIEDLIQSMHIDATLYTESDVHPSCKVTAMKCFLLELQVISLESGDASIHDTVENLIILANNSLSS[AzK_PEG30]GNVTESGCKECEELEEKNIKEFLQSFVHIVQMFINTS | 74 |
| IL-15_S84 [AzK_PEG30] | MNWVNVISDLKKIEDLIQSMHIDATLYTESDVHPSCKVTAMKCFLLELQVISLESGDASIHDTVENLIILANNSLSSNGNVTE[AzK_PEG30]GCKECEELEEKNIKEFLQSFVHIVQMFINTS | 75 |
| IL-15_S19 [AzK_PEG40] | MNWVNVISDLKKIEDLIQ[AzK_PEG40]MHIDATLYTESDVHPSCKVTAMKCFLLELQVISLESGDASIHDTVENLIILANNSLSSNGNVTESGCKECEELEEKNIKEFLQSFVHIVQMFINTS | 76 |
| IL-15_L26 [AzK_PEG40] | MNWVNVISDLKKIEDLIQSMHIDAT[AzK_PEG40]YTESDVHPSCKVTAMKCFLLELQVISLESGDASIHDTVENLHLANNSLSSNGNVTESGCKECEELEEKNIKEFLQSFVHIVQMFINTS | 77 |
| IL-15_E47 [AzK_PEG40] | MNWVNVISDLKKIEDLIQSMHIDATLYTESDVHPSCKVTAMKCFLL[AzK_PEG40]LQVISLESGDASIHDTVENLIILANNSLSSNGNVTESGCKECEELEEKNIKEFLQSFVHIVQMFINTS | 78 |
| IL-15_E54 [AzK_PEG40] | MNWVNVISDLKKIEDLIQSMHIDATLYTESDVHPSCKVTAMKCFLLELQVISL[AzK_PEG40]SGDASIHDTVENLIILANNSLSSNGNVTESGCKECEELEEKNIKEFLQSFVHIVQMFINTS | 79 |
| IL-15_N78 [AzK_PEG40] | MNWVNVISDLKKIEDLIQSMHIDATLYTESDVHPSCKVTAMKCFLLELQVISLESGDASIHDTV | 80 |

TABLE 1-continued

| NAME | SEQUENCE | SEQ ID NO. |
|---|---|---|
| | ENLIILANNSLSS[AzK_PEG40]GNVTESGCKE CEELEEKNIKEFLQSFVHIVQMFINTS | |
| IL-15_S84 [AzK_PEG40] | MNWVNVISDLKKIEDLIQSMHIDATLYTESDV HPSCKVTAMKCFLLELQVISLESGDASIHDTV ENLIILANNSLSSNGNVTE[AzK_PEG40]GCKE CEELEEKNIKEFLQSFVHIVQMFINTS | 81 |
| IL-15_S19 [AzK_L1_PEG] | MNWVNVISDLKKIEDLIQ[AzK_L1_PEG]MHI DATLYTESDVHPSCKVTAMKCFLLELQVISLE SGDASIHDTVENLIILANNSLSSNGNVTESGCK ECEELEEKNIKEFLQSFVHIVQMFINTS | 82 |
| IL-15_L26 [AzK_L1_PEG] | MNWVNVISDLKKIEDLIQSMHIDAT[AzK_L1_PEG] YTESDVHPSCKVTAMKCFLLELQVISLE SGDASIHDTVENLIILANNSLSSNGNVTESGCK ECEELEEKNIKEFLQSFVHIVQMFINTS | 83 |
| IL-15_E47 [AzK_L1_PEG] | MNWVNVISDLKKIEDLIQSMHIDATLYTESDV HPSCKVTAMKCFLL[AzK_L1_PEG]LQVISLES GDASIHDTVENLIILANNSLSSNGNVTESGCKE CEELEEKNIKEFLQSFVHIVQMFINTS | 84 |
| IL-15_E54 [AzK_L1_PEG] | MNWVNVISDLKKIEDLIQSMHIDATLYTESDV HPSCKVTAMKCFLLELQVISL[AzK_L1_PEG]S GDASIHDTVENLIILANNSLSSNGNVTESGCKE CEELEEKNIKEFLQSFVHIVQMEINTS | 85 |
| IL-15_N78 [AzK_L1_PEG] | MNWVNVISDLKKIEDLIQSMHIDATLYTESDV HPSCKVTAMKCFLLELQVISLESGDASIHDTV ENLIILANNSLSS[AzK_L1_PEG]GNVTESGCK ECEELEEKNIKEFLQSFVHIVQMFINTS | 86 |
| IL-15_S84 [AzK_L1_PEG] | MNWVNVISDLKKIEDLIQSMHIDATLYTESDV HPSCKVTAMKCFLLELQVISLESGDASIHDTV ENLIILANNSLSSNGNVTE[AzK_L1_PEG]GCK ECEELEEKNIKEFLQSFVHIVQMFINTS | 87 |
| IL-15_S19 [AzK_L1_PEG30] | MNWVNVISDLKKIEDLIQ[AzK_L1_PEG30]M HIDATLYTESDVHPSCKVTAMKCFLLELQVIS LESGDASIHDTVENLIILANNSLSSNGNVTESG CKECEELEEKNIKEFLQSFVHIVQMFINTS | 88 |
| IL-15_L26 [AzK_L1_PEG30] | MNWVNVISDLKKIEDLIQSMHIDAT[AzK_L1_PEG30] YTESDVHPSCKVTAMKCFLLELQVISL ESGDASIHDTVENLIILANNSLSSNGNVTESGC KECEELEEKNIKEFLQSFVHIVQMFINTS | 89 |
| IL-15_E47 [AzK_L1_PEG30] | MNWVNVISDLKKIEDLIQSMHIDATLYTESDV HPSCKVTAMKCFLL[AzK_L1_PEG30]LQVISL ESGDASIHDTVENLIILANNSLSSNGNVTESGC KECEELEEKNIKEFLQSFVHIVQMFINTS | 90 |
| IL-15_E54 [AzK_L1_PEG30] | MNWVNVISDLKKIEDLIQSMHIDATLYTESDV HPSCKVTAMKCFLLELQVISL[AzK_L1_PEG30] SGDASIHDTVENLIILANNSLSSNGNVTESG CKECEELEEKNIKEFLQSFVHIVQVIFINTS | 91 |
| IL-15_N78 [AzK_L1_PEG30] | MNWVNVISDLKKIEDLIQSMHIDATLYTESDV HPSCKVTAMKCFLLELQVISLESGDASIHDTV ENLIILANNSLSS[AzK_L1_PEG30]GNVTESGC KECEELEEKNIKEFLQSFVHIVQMFINTS | 92 |
| IL-15_S84 [AzK_L1_PEG30] | MNWVNVISDLKKIEDLIQSMHIDATLYTESDV HPSCKVTAMKCFLLELQVISLESGDASIHDTV ENLIILANNSLSSNGNVTE[AzK_L1_PEG30]G CKECEELEEKNIKEFLQSFVHIVQMFINTS | 93 |
| IL-15_S19 [AzK_L1_PEG40] | MNWVNVISDLKKIEDLIQ[AzK_L1_PEG40]M HIDATLYTESDVHPSCKVTAMKCFLLELQVIS LESGDASIHDTVENLIILANNSLSSNGNVTESG CKECEELEEKNIKEFLQSFVHIVQMFINTS | 94 |
| IL-15_L26 [AzK_L1_PEG40] | MNWVNVISDLKKIEDLIQSMHIDAT[AzK_L1_PEG40] YTESDVHPSCKVTAMKCFLLELQVISL ESGDASIHDTVENLIILANNSLSSNGNVTESGC KECEELEEKNIKEFLQSFVHIVQMFINTS | 95 |

TABLE 1-continued

| NAME | SEQUENCE | SEQ ID NO. |
|---|---|---|
| IL-15_E47 [AzK_L1_PEG40] | MNWVNVISDLKKIEDLIQSMHIDATLYTESDV HPSCKVTAMKCFLL[AzK L1 PEG40]LQVISL ESGDASIHDTVENLIILANNSLSSNGNVTESGC KECEELEEKNIKEFLQSFVHIVQMFINTS | 96 |
| IL-15_E54 [AzK_L1_PEG40] | MNWVNVISDLKKIEDLIQSMHIDATLYTESDV HPSCKVTAMKCFLLELQVISL[AzK L1 PEG40] SGDASIHDTVENLIILANNSLSSNGNVTESG CKECEELEEKNIKEFLQSFVHIVQMFINTS | 97 |
| IL-15_N78 [AzK_L1_PEG40] | MNWVNVISDLKKIEDLIQSMHIDATLYTESDV HPSCKVTAMKCFLLELQVISLESGDASIHDTV ENLIILANNSLSS[AzK L1 PEG40]GNVTESGC KECEELEEKNIKEFLQSFVHIVQMFINTS | 98 |
| IL-15_S84 [AzK_L1_PEG40] | MNWVNVISDLKKIEDLIQSMHIDATLYTESDV HPSCKVTAMKCFLLELQVISLESGDASIHDTV ENLIILANNSLSSNGNVTE[AzK L1 PEG40]G CKECEELEEKNIKEFLQSFVHIVQMFINTS | 99 |

X=site comprising an unnatural amino acid.
[AzK]=N6-((2-azidoethoxy)-carbonyl)-L-lysine. The compound has Chemical Abstracts Registry No. 1167421-25-1.
[AzK_PEG]=N6-((2-azidoethoxy)-carbonyl)-L-lysine stably-conjugated to PEG via DBCO-mediated click chemistry, to form a compound comprising a structure of Formula (II) or Formula (III). For example, if specified, PEG30 indicates a linear polyethylene glycol chain with an average molecular weight of 30 kiloDaltons, capped with a methoxy group. For example, if specified, PEG40 indicates a branched polyethylene glycol chain with an average molecular weight of 40 kiloDaltons, capped with a methoxy group. The ratio of regioisomers generated from the click reaction is about 1:1 or greater than 1:1. The term "DBCO" means a chemical moiety comprising a dibenzocyclooctyne group, such as comprising the mPEG-DBCO compound illustrated in Scheme 1 of Example 1. An exemplary structure of a methoxy PEG group is illustrated in the mPEG-DBCO structure in Scheme 1 and 2 of Example 1.
[AzK_L1_PEG]=N6-((2-azidoethoxy)-carbonyl)-L-lysine stably-conjugated to PEG via DBCO-mediated click chemistry to form a compound comprising a structure of Formula (IV) or Formula (V). For example, if specified, PEG30 indicates a linear polyethylene glycol chain with an average molecular weight of 30 kiloDaltons, capped with a methoxy group. The ratio of regioisomers generated from the click reaction is about 1:1 or greater than 1:1. The term "DBCO" means a chemical moiety comprising a dibenzocyclooctyne group, such as comprising the mPEG-DBCO compound illustrated in Scheme 1 or 2 of Example 1. In some instances, sequences in Table 1 comprise an N-terminal methionine (Met). In some instances, sequences in Table 1 comprise an N-terminal methionine, wherein the N-terminal methionine is an N-formyl methionine (fMet). In some instances, an IL-15 conjugate described herein comprises a mixture of peptides, wherein the mixture comprises both sequences with and without N-terminal methionine residues. In some instances, an IL-15 conjugate described herein comprises a mixture of peptides, wherein the mixture comprises both sequences with N-terminal methionine residues and N-formylmethionine residues. In some instances, an IL-15 conjugate described herein comprises a mixture of peptides, wherein the mixture comprises both sequences with and without N-terminal, N-formylmethionine residues.

In some instances, the at least one unnatural amino acid is located proximal to the N-terminus. As used herein, proximal refers to a residue located at least 1 residue away from the N-terminal residue and up to about 50 residues away from the N-terminal residue. In some cases, the at least one unnatural amino acid is located within the first 10, 20, 30, 40, or 50 residues from the N-terminal residue. In some cases, the at least one unnatural amino acid is located within the first 10 residues from the N-terminal residue. In some cases, the at least one unnatural amino acid is located within the first 20 residues from the N-terminal residue. In some cases, the at least one unnatural amino acid is located within the first 30 residues from the N-terminal residue. In some cases, the at least one unnatural amino acid is located within the first 40 residues from the N-terminal residue. In some cases, the at least one unnatural amino acid is located within the first 50 residues from the N-terminal residue.

In some instances, the at least one unnatural amino acid is the N-terminal residue.

In some instances, the at least one unnatural amino acid is located proximal to the C-terminus. As used herein, proximal refers to a residue located at least 1 residue away from the C-terminal residue and up to about 50 residues away from the C-terminal residue. In some cases, the at least one unnatural amino acid is located within the first 10, 20, 30, 40, or 50 residues from the C-terminal residue. In some cases, the at least one unnatural amino acid is located within the first 10 residues from the C-terminal residue. In some cases, the at least one unnatural amino acid is located within the first 20 residues from the C-terminal residue. In some cases, the at least one unnatural amino acid is located within the first 30 residues from the C-terminal residue. In some cases, the at least one unnatural amino acid is located within the first 40 residues from the C-terminal residue. In some cases, the at least one unnatural amino acid is located within the first 50 residues from the C-terminal residue.

In some instances, the at least one unnatural amino acid is the C-terminal residue.

In some embodiments, described herein is a method of treating a proliferative disease or condition in a subject in need thereof, which comprises administering to the subject a therapeutically effective amount of a cytokine conjugate (e.g., an IL-15 conjugate) described herein.

Described herein are pharmaceutical compositions comprising an effective amount of an IL-15 conjugate described herein and one or more pharmaceutically acceptable excipients.

In some embodiments, described herein is a method of treating a proliferative disease or condition in a subject in need thereof, which comprises administering to the subject a therapeutically effective amount of a cytokine conjugate (e.g., an IL-15 conjugate) described Table 1. In some embodiments, the IL-15 conjugate comprises SEQ ID NOs.: 1-99. In some embodiments, the IL-15 conjugate comprises SEQ ID NOs.: 4-99. In some embodiments, the IL-15 conjugate comprises SEQ ID NOs.: 4-9. In some embodiments, the IL-15 conjugate comprises SEQ ID NOs.: 10-15. In some embodiments, the IL-15 conjugate comprises SEQ ID NOs.: 16-21. In some embodiments, the IL-15 conjugate comprises SEQ ID NOs.: 22-27. In some embodiments, the IL-15 conjugate comprises SEQ ID NOs.: 28-33. In some embodiments, the IL-15 conjugate comprises a structure of Formula (I). In some embodiments, the IL-15 conjugate comprises a structure of Formula (II). In some embodiments, the IL-15 conjugate comprises a structure of Formula (III). In some embodiments, the IL-15 conjugate comprises a structure of Formula (IV). In some embodiments, the IL-15 conjugate comprises a structure of Formula (V). In some embodiments, the IL-15 conjugate comprises a structure of Formula (VI). In some embodiments, the IL-15 conjugate comprises a structure of Formula (VII). In some embodiments, the IL-15 conjugate comprises a structure of Formula (VIII). In some embodiments, the IL-15 conjugate comprises a structure of Formula (IX). In some embodiments, the IL-15 conjugate comprises a structure of Formula (X). In some embodiments, the IL-15 conjugate comprises a structure of Formula (XI). In some embodiments, the IL-15 conjugate comprises a structure of Formula (XII). In some embodiments, the IL-15 conjugate comprises a structure of Formula (XIII). In some embodiments, the IL-15 conjugate comprises SEQ ID NO: 1. In some embodiments, the IL-15 conjugate comprises SEQ ID NO: 2. In some embodiments, the IL-15 conjugate comprises SEQ ID NO: 3. In some embodiments, the IL-15 conjugate comprises SEQ ID NO: 4. In some embodiments, the IL-15 conjugate comprises SEQ ID NO: 5. In some embodiments, the IL-15 conjugate comprises SEQ ID NO: 6. In some embodiments, the IL-15 conjugate comprises SEQ ID NO: 7. In some embodiments, the IL-15 conjugate comprises SEQ ID NO: 8. In some embodiments, the IL-15 conjugate comprises SEQ ID NO: 9. In some embodiments, the IL-15 conjugate comprises SEQ ID NO: 10. In some embodiments, the IL-15 conjugate comprises SEQ ID NO: 11. In some embodiments, the IL-15 conjugate comprises SEQ ID NO: 12. In some embodiments, the IL-15 conjugate comprises SEQ ID NO: 13. In some embodiments, the IL-15 conjugate comprises SEQ ID NO: 14. In some embodiments, the IL-15 conjugate comprises SEQ ID NO: 15. In some embodiments, the IL-15 conjugate comprises SEQ ID NO: 16. In some embodiments, the IL-15 conjugate comprises SEQ ID NO: 17. In some embodiments, the IL-15 conjugate comprises SEQ ID NO: 18. In some embodiments, the IL-15 conjugate comprises SEQ ID NO: 19. In some embodiments, the IL-15 conjugate comprises SEQ ID NO: 20. In some embodiments, the IL-15 conjugate comprises SEQ ID NO: 21. In some embodiments, the IL-15 conjugate comprises SEQ ID NO: 22. In some embodiments, the IL-15 conjugate comprises SEQ ID NO: 23. In some embodiments, the IL-15 conjugate comprises SEQ ID NO: 24. In some embodiments, the IL-15 conjugate comprises SEQ ID NO: 25. In some embodiments, the IL-15 conjugate comprises SEQ ID NO: 26. In some embodiments, the IL-15 conjugate comprises SEQ ID NO: 27. In some embodiments, the IL-15 conjugate comprises SEQ ID NO: 28. In some embodiments, the IL-15 conjugate comprises SEQ ID NO: 24. In some embodiments, the IL-15 conjugate comprises SEQ ID NO: 25. In some embodiments, the IL-15 conjugate comprises SEQ ID NO: 26. In some embodiments, the IL-15 conjugate comprises SEQ ID NO: 27. In some embodiments, the IL-15 conjugate comprises SEQ ID NO: 28. In some embodiments, the IL-15 conjugate comprises SEQ ID NO: 29. In some embodiments, the IL-15 conjugate comprises SEQ ID NO: 30. In some embodiments, the IL-15 conjugate comprises SEQ ID NO: 31. In some embodiments, the IL-15 conjugate comprises SEQ ID NO: 32. In some embodiments, the IL-15 conjugate comprises SEQ ID NO: 33. In some embodiments, the IL-15 conjugate comprises SEQ ID NO: 34. In some embodiments, the IL-15 conjugate comprises SEQ ID NO: 35. In some embodiments, the IL-15 conjugate comprises SEQ ID NO: 36. In some embodiments, the IL-15 conjugate comprises SEQ ID NO: 37. In some embodiments, the IL-15 conjugate comprises SEQ ID NO: 38. In some embodiments, the IL-15 conjugate comprises SEQ ID NO: 39. In some embodiments, the IL-15 conjugate comprises SEQ ID NO: 40. In some embodiments, the IL-15 conjugate comprises SEQ ID NO: 41. In some embodiments, the IL-15 conjugate comprises SEQ ID NO: 42. In some embodiments, the IL-15 conjugate comprises SEQ ID NO: 43. In some embodiments, the IL-15 conjugate comprises SEQ ID NO: 44. In some embodiments, the IL-15 conjugate comprises SEQ ID NO: 45. In some embodiments, the IL-15 conjugate comprises SEQ ID NO: 46. In some embodiments, the IL-15 conjugate comprises SEQ ID NO: 47. In some embodiments, the IL-15 conjugate comprises SEQ ID NO: 48. In some embodiments, the IL-15 conjugate comprises SEQ ID NO: 49. In some embodiments, the IL-15 conjugate comprises SEQ ID NO: 50. In some embodiments, the IL-15 conjugate comprises SEQ ID NO: 51. In some embodiments, the IL-15 conjugate comprises SEQ ID NO: 52. In some embodiments, the IL-15 conjugate comprises SEQ ID NO: 53. In some embodiments, the IL-15 conjugate comprises SEQ ID NO: 54. In some embodiments, the IL-15 conjugate comprises SEQ ID NO: 55. In some embodiments, the IL-15 conjugate comprises SEQ ID NO: 56. In some embodiments, the IL-15 conjugate comprises SEQ ID NO: 57. In some embodiments, the IL-15 conjugate comprises SEQ ID NO: 58. In some embodiments, the IL-15 conjugate comprises SEQ ID NO: 59. In some embodiments, the IL-15 conjugate comprises SEQ ID NO: 60. In some embodiments, the IL-15 conjugate comprises SEQ ID NO: 61. In some embodiments, the IL-15 conjugate comprises SEQ ID NO: 62. In some embodiments, the IL-15 conjugate comprises SEQ ID NO: 63. In some embodiments, the IL-15 conjugate comprises SEQ ID NO: 64. In some embodiments, the IL-15 conjugate comprises SEQ ID NO: 65. In some embodiments, the IL-15 conjugate comprises SEQ ID NO: 66. In some embodiments, the IL-15 conjugate comprises SEQ ID NO: 67. In some embodiments, the IL-15 conjugate comprises SEQ ID NO: 68. In some embodiments, the IL-15 conjugate comprises SEQ ID NO: 69. In some embodiments, the IL-15 conjugate comprises SEQ ID NO: 70. In some embodiments, the IL-15 conjugate comprises SEQ ID NO: 71. In some embodiments, the IL-15 conjugate comprises SEQ ID NO: 72. In some embodiments, the IL-15 conjugate comprises SEQ ID NO: 73. In some embodiments, the IL-15 conjugate comprises SEQ ID NO: 74. In some embodiments, the IL-15 conjugate comprises SEQ ID NO: 75. In some embodiments, the IL-15 conjugate comprises SEQ ID NO: 76. In some embodiments, the IL-15 conjugate comprises SEQ ID NO: 77. In some embodiments, the IL-15 conjugate comprises SEQ ID NO: 78. In some embodiments, the IL-15 conjugate comprises SEQ ID NO: 79. In some embodiments, the IL-15 conjugate comprises SEQ ID NO: 80. In some embodiments, the IL-15 conjugate comprises SEQ ID NO: 81. In some embodiments, the IL-15 conjugate comprises SEQ ID NO: 82. In some embodiments, the IL-15 conjugate comprises SEQ ID NO: 83. In some embodiments, the IL-15 conjugate comprises SEQ ID NO: 84. In some embodiments, the IL-15 conjugate comprises SEQ ID NO: 85. In some embodiments, the IL-15 conjugate comprises SEQ ID NO: 86. In some embodiments, the IL-15 conjugate comprises SEQ ID NO: 87. In some embodiments, the IL-15 conjugate comprises SEQ ID NO: 88. In some embodiments, the IL-15 conjugate comprises SEQ ID NO: 89. In some embodiments, the IL-15 conjugate comprises SEQ ID NO: 90. In some embodiments, the IL-15 conjugate comprises SEQ ID NO: 91. In some embodiments, the IL-15 conjugate comprises SEQ ID NO: 92. In some embodiments, the IL-15 conjugate comprises SEQ ID NO: 93. In some embodiments, the IL-15 conjugate comprises SEQ ID NO: 94. In some embodiments, the IL-15 conjugate comprises SEQ ID NO: 95. In some embodiments, the IL-15 conjugate comprises SEQ ID NO: 96. In some embodiments, the IL-15 conjugate comprises SEQ ID NO: 97. In some embodiments, the IL-15 conjugate comprises SEQ ID NO: 98. In some embodiments, the IL-15 conjugate comprises SEQ ID NO: 99.

In some embodiments, described herein are IL-15 conjugates modified at an amino acid position. In some instances, the modification is to a natural amino acid. In some instances, the modification is to an unnatural amino acid. In some instances, described herein is an isolated and modified IL-15 polypeptide that comprises at least one unnatural amino acid. In some cases, the IL-15 polypeptide comprises about 80%, 85%, 90%, 95%, 96%, 97%, 98%, or 990% sequence identity to any one of SEQ ID NOS: 4 to 99.

In some cases, the PEG group is not limited to a particular structure. In some cases, the PEG is linear (e.g., an end capped, e.g., alkoxy PEG or a bifunctional PEG), branched or multi-armed (e.g., forked PEG or PEG attached to a polyol core), a dendritic (or star) architecture, each with or without one or more degradable linkages. Moreover, the internal structure of the water-soluble polymer can be organized in any number of different repeat patterns and can be selected from the group consisting of homopolymer, alternating copolymer, random copolymer, block copolymer, alternating tripolymer, random tripolymer, and block tripolymer.

PEGs will typically comprise a number of ($OCH_2CH_2$) monomers [or ($CH_2CH_2O$) monomers, depending on how the PEG is defined]. As used herein, the number of repeating units is identified by the subscript "n" in "($OCH_2CH_2$)$_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

In some instances, the PEG is an end-capped polymer, that is, a polymer having at least one terminus capped with a relatively inert group, such as a lower $C_{1-6}$ alkoxy group, or a hydroxyl group. When the polymer is PEG, for example, a methoxy-PEG (commonly referred to as mPEG) may be used, which is a linear form of PEG wherein one terminus of the polymer is a methoxy (—$OCH_3$) group, while the other terminus is a hydroxyl or other functional group that can be optionally chemically modified.

In some embodiments, the PEG group comprising the IL-15 conjugates disclosed herein is a linear or branched PEG group. In some embodiments, the PEG group is a linear PEG group. In some embodiments, the PEG group is a branched PEG group. In some embodiments, the PEG group is a methoxy PEG group. In some embodiments, the PEG group is a linear or branched methoxy PEG group. In some embodiments, the PEG group is a linear methoxy PEG group. In some embodiments, the PEG group is a branched methoxy PEG group. In some embodiments, the PEG group is a linear or branched PEG group having an average molecular weight of from about 100 Daltons to about 150,000 Daltons. Exemplary ranges include, for example, weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons. Exemplary weight-average molecular weights for the PEG group include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, about 75,000 Daltons, about 80,000 Daltons, about 90,000 Daltons, about 95,000 Daltons, and about 100,000 Daltons. In some embodiments, the PEG group is a linear PEG group having an average molecular weight as disclosed above. In some embodiments, the PEG group is a branched PEG group having an average molecular weight as disclosed above. In some embodiments, the PEG group comprising the IL-15 conjugates disclosed herein is a linear or branched PEG group having a defined molecular weight 10%, or 15% or 20% or 25%. For example, included within the scope of the present disclosure are IL-15 conjugates comprising a PEG group having a molecular weight of 30,000 Da±3000 Da, or 30,000 Da±4,500 Da, or 30,000 Da±6,000 Da.

In some embodiments, the PEG group comprising the IL-15 conjugates disclosed herein is a linear or branched PEG group having an average molecular weight of from about 5,000 Daltons to about 60,000 Daltons. In some embodiments, the PEG group is a linear or branched PEG group having an average molecular weight of about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, about 75,000 Daltons, about 80,000 Daltons, about 90,000 Daltons, about 95,000 Daltons, and about 100,000 Daltons. In some embodiments, the PEG group is a linear or branched PEG group having an average molecular weight of about 5,000 Daltons, about 10,000 Daltons, about 20,000 Daltons, about 30,000 Daltons, about 50,000 Daltons, or about 60,000 Daltons. In some embodiments, the PEG group is a linear or branched PEG group having an average molecular weight of about 5,000 Daltons, about 30,000 Daltons, about 50,000 Daltons, or about 60,000 Daltons. In some embodiments, the PEG group is a linear PEG group having an average molecular of about 5,000 Daltons, about 10,000 Daltons, about 20,000 Daltons, about 30,000 Daltons, about 50,000 Daltons, or about 60,000 Daltons. In some embodiments, the PEG group is a branched PEG group having an average molecular weight of about 5,000 Daltons, about 10,000 Daltons, about 20,000 Daltons, about 30,000 Daltons, about 50,000 Daltons, or about 60,000 Daltons.

In some embodiments, the PEG group comprising the IL-15 conjugates disclosed herein is a linear methoxy PEG group having an average molecular weight of from about 5,000 Daltons to about 60,000 Daltons. In some embodiments, the PEG group is a linear methoxy PEG group having an average molecular weight of about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, about 75,000 Daltons, about 80,000 Daltons, about 90,000 Daltons, about 95,000 Daltons, and about 100,000 Daltons. In some embodiments, the PEG group is a linear methoxy PEG group having an average molecular weight of about 5,000 Daltons, about 10,000 Daltons, about 20,000 Daltons, about 30,000 Daltons, about 50,000 Daltons, or about 60,000 Daltons. In some embodiments, the PEG group is a linear methoxy PEG group having an average molecular weight of about 5,000 Daltons, about 30,000 Daltons, about 50,000 Daltons, or about 60,000 Daltons. In some embodiments, the PEG group is a linear methoxy PEG group having an average molecular of about 5,000 Daltons, about 10,000 Daltons, about 20,000 Daltons, about 30,000 Daltons, about 50,000 Daltons, or about 60,000 Daltons. In some embodiments, the PEG group is a linear methoxy PEG group having an average molecular of about 5,000 Daltons. In some embodiments, the PEG group is a linear methoxy PEG group having an average molecular of about 10,000 Daltons. In some embodiments, the PEG group is a linear methoxy PEG group having an average molecular of about 20,000 Daltons. In some embodiments, the PEG group is a linear methoxy PEG group having an average molecular of about 30,000 Daltons. In some embodiments, the PEG group is a linear methoxy PEG group having an average molecular of about 50,000 Daltons. In some embodiments, the PEG group is a linear methoxy PEG group having an average molecular of about 60,000 Daltons. In some embodiments, the PEG group comprising the IL-15 conjugates disclosed herein is a linear methoxy PEG group having a defined molecular weight 10%, or 15% or 20% or 25%. For example, included within the scope of the present disclosure are IL-15 conjugates comprising a linear methoxy PEG group having a molecular weight of 30,000 Da±3000 Da, or 30,000 Da±4,500 Da, or 30,000 Da±6,000 Da.

In some embodiments, are IL-15 conjugates in which n, when present, is an integer from 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments, are IL-15 conjugates in which n, when present, is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

In some embodiments, the PEG group comprising the IL-15 conjugates disclosed herein is a branched methoxy PEG group having an average molecular weight of from about 5,000 Daltons to about 60,000 Daltons. In some embodiments, the PEG group is a branched methoxy PEG group having an average molecular weight of about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, about 75,000 Daltons, about 80,000 Daltons, about 90,000 Daltons, about 95,000 Daltons, and about 100,000 Daltons. In some embodiments, the PEG group is a branched methoxy PEG group having an average molecular weight of about 5,000 Daltons, about 10,000 Daltons, about 20,000 Daltons, about 30,000 Daltons, about 50,000 Daltons, or about 60,000 Daltons. In some embodiments, the PEG group is a branched methoxy PEG group having an average molecular weight of about 5,000 Daltons, about 30,000 Daltons, about 50,000 Daltons, or about 60,000 Daltons. In some embodiments, the PEG group is a branched methoxy PEG group having an average molecular of about 5,000 Daltons, about 10,000 Daltons, about 20,000 Daltons, about 30,000 Daltons, about 50,000 Daltons, or about 60,000 Daltons. In some embodiments, the PEG group is a branched methoxy PEG group having an average molecular of about 5,000 Daltons, about 10,000 Daltons, about 20,000 Daltons, about 30,000 Daltons, about 50,000 Daltons, or about 60,000 Daltons. In some embodiments, the PEG group is a branched methoxy PEG group having an average molecular of about 5,000 Daltons. In some embodiments, the PEG group is a branched methoxy PEG group having an average molecular of about 10,000 Daltons. In some embodiments, the PEG group is a branched methoxy PEG group having an average molecular of about 20,000 Daltons. In some embodiments, the PEG group is a branched methoxy PEG group having an average molecular of about 30,000 Daltons. In some embodiments, the PEG group is a branched methoxy PEG group having an average molecular of about 50,000 Daltons. In some embodiments, the PEG group is a branched methoxy PEG group having an average molecular of about 60,000 Daltons. In some embodiments, the PEG group comprising the IL-15 conjugates disclosed herein is a branched methoxy PEG group having a defined molecular weight±10%, or 15% or 20% or 25%. For example, included within the scope of the present disclosure are IL-15 conjugates comprising a branched methoxy PEG group having a molecular weight of 30,000 Da±3000 Da, or 30,000 Da±4,500 Da, or 30,000 Da±6,000 Da.

In some embodiments, exemplary PEG groups include, but are not limited to, linear or branched discrete PEG (dPEG) from Quanta Biodesign, Ltd; linear, branched, or forked PEGs from Nektar Therapeutics; and Y-shaped PEG derivatives from JenKem Technology.

In some embodiments, the modified IL-15 polypeptides comprising at least one unnatural amino acid, wherein a residue position of the at least one unnatural amino acid is at a residue position that selectively decreases the binding affinity of the IL-15 polypeptide with the interleukin 15 receptor α (IL-15R α). In some embodiments, the decrease in binding affinity is relative to binding affinity between a wild-type IL-15 polypeptide and the IL-15Rα. In some embodiments, the binding of the modified IL-15 polypeptide to IL-15R α does not affect the interaction of the modified IL-15 polypeptide with interleukin 2/interleukin 15 receptor βγ (IL-2/IL-15R βγ) or improves the interaction of the modified IL-15 polypeptide with IL-2/IL-15R βγ. In some instances, the residue position of the at least one unnatural amino acid is selected from D22, A23, T24, L25, Y26, L44, E46, Q48, V49, E53, E89, E90, and E93, wherein the residue positions correspond to the positions as set forth in SEQ ID NO: 1. In some embodiments, the residue position of the at least one unnatural amino acid is selected from Y26, E46, V49, E53, and L25, wherein the residue positions correspond to the positions as set forth in SEQ ID NO: 1. In some embodiments, the residue position of the at least one unnatural amino acid is selected from A23, T24, E89, and E93, wherein the residue positions correspond to the positions as set forth in SEQ ID NO: 1. In some embodiments, the residue position of the at least one unnatural amino acid is selected from D22, L44, Q48, and E90, wherein the residue positions correspond to the positions as set forth in SEQ ID NO: 1. In some instances, the residue position of the at least one unnatural amino acid is Y26. In some instances, the residue position of the at least one unnatural amino acid is E46. In some instances, the residue position of the at least one unnatural amino acid is V49. In some instances, the residue position of the at least one unnatural amino acid is E53. In some instances, the residue position of the at least one unnatural amino acid is L25. In some embodiments, the modified IL-15 polypeptide further comprises a PEG. In some cases, the PEG is conjugated at a residue position selected from D22, A23, T24, L25, Y26, L44, E46, Q48, V49, E53, E89, E90, and E93. In some embodiments, the modified IL-15 polypeptide further comprises a PEG for increased half-life. In some cases, the PEG is conjugated at a residue position selected from E13, D14, L15, Q17, S18, M19, H20, I21, S34, C35, K36, V37, T38, K41, L44, S51, L52, S54, G55, D56, A57, S58, H60, V63, I67, N71, S73, L74, S75, S76, N77, G78, N79, V80, T81, E82, S83, G84, C85, K86, E87, C88, L91, E92, K94, N95, I96, K97, E98, L100, Q101, and F110, for increased half-life. In some cases, the PEG is conjugated at a residue position selected from N71, N72, and N77. In some cases, the residue conjugated to the PEG is mutated to a natural amino acid. In other cases, the residue conjugated to the PEG is mutated to an unnatural amino acid. In additional cases, the mutation at N71, N72, or N77 further improves a CMC condition (e.g., yield, purity, stability, decreased aggregation, and/or improving protein folding), potency, or a combination thereof.

In some instances, the modified IL-15 polypeptides comprising at least one unnatural amino acid, wherein the at least one unnatural amino acid is at a residue position that selectively decreases the binding affinity of the modified IL-15 polypeptide with IL-2/IL-15R β, IL-15Rγ, or a combination thereof. In some embodiments, the modified IL-15 has little or no effect on interaction with IL-15R α. In some embodiments, the residue position of the at least one unnatural amino acid is selected from N1, V3, N4, I6, S7, D8, K10, K11, E28, S29, D30, V31, H32, P33, D61, T62, E64, N65, I68, L69, N72, S102, V104, H105, Q108, M109, I111, N112, T113, and S14, wherein the residue positions correspond to the positions as set forth in SEQ ID NO: 1. In some embodiments, the at least one unnatural amino acid is at a residue position that selectively decreases the binding affinity of the modified IL-15 polypeptide with IL-2/IL-15R β. In some instances, the residue position of the at least one unnatural amino acid is selected from N1, N4, S7, D8, K11, D61, T62, E64, N65, I68, L69, and N72, wherein the residue positions correspond to the positions as set forth in SEQ ID NO: 1. In some instances, the residue position of the at least one unnatural amino acid is selected from N4, S7, K11, and D61. In some instances, the residue position of the at least one unnatural amino acid is selected from D8, E64, N65, I68, and N72. In some instances, the residue position of the at least one unnatural amino acid is selected from N1, T62, and L69. In some instances, the residue position of the at least one unnatural amino acid is N4. In some instances, the residue position of the at least one unnatural amino acid is S7. In some instances, the residue position of the at least one unnatural amino acid is K11. In some instances, the residue position of the at least one unnatural amino acid is D61. In some embodiments, the at least one unnatural amino acid is at a residue position that selectively decreases the binding affinity of the modified IL-15 polypeptide with IL-2/IL-15Rγ. In some instances, the residue position of the at least one unnatural amino acid is selected from V3, I6, K10, E28, S29, D30, V31, H32, P33, S102, V104, H105, Q108, M109, I111, N112, T113, and S114, wherein the residue positions correspond to the positions as set forth in SEQ ID NO: 1. In some instances, the residue position of the at least one unnatural amino acid is selected from V3, K10, S29, D30, H32, H105, Q108, M109, I11, N112, T113, and S14. In some instances, the residue position of the at least one unnatural amino acid is selected from E28, P33, S102, and V104. In some instances, the residue position of the at least one unnatural amino acid is selected from I6 and V31. In some instances, the residue position of the at least one unnatural amino acid is V3. In some instances, the residue position of the at least one unnatural amino acid is K10. In some instances, the residue position of the at least one unnatural amino acid is S29. In some instances, the residue position of the at least one unnatural amino acid is D30. In some instances, the residue position of the at least one unnatural amino acid is H32. In some instances, the residue position of the at least one unnatural amino acid is H105. In some instances, the residue position of the at least one unnatural amino acid is Q108. In some instances, the residue position of the at least one unnatural amino acid is M109. In some instances, the residue position of the at least one unnatural amino acid is I111. In some instances, the residue position of the at least one unnatural amino acid is N112. In some instances, the residue position of the at least one unnatural amino acid is T113. In some instances, the residue position of the at least one unnatural amino acid is S114. In some embodiments, the modified IL-15 polypeptide further comprises a PEG. In some cases, the PEG is conjugated at a residue position selected from N1, V3, N4, I6, S7, D8, K10, K11, E28, S29, D30, V31, H32, P33, D61, T62, E64, N65, I68, L69, N72, S102, V104, H105, Q108, M109, I111, N112, T113, and S114. In some embodiments, the modified IL-15 polypeptide further comprises a PEG for increased half-life. In some cases, the PEG is conjugated at a residue position selected from E13, D14, L15, Q17, S18, M19, H20, I21, S34, C35, K36, V37, T38, K41, L44, S51, L52, S54, G55, D56, A57, S58, H60, V63, I67, N71, S73, L74, S75, S76, N77, G78, N79, V80, T81, E82, S83, G84, C85, K86, E87, C88, L91, E92, K94, N95, I96, K97, E98, L100, Q101, and F110 for increased half-life. In some cases, the PEG is conjugated at a residue position selected from N71, N72, and N77. In some cases, the residue conjugated to the PEG is mutated to a natural amino acid. In other cases, the residue conjugated to the PEG is mutated to an unnatural amino acid. In additional cases, the mutation at N71, N72, or N77 further improves a CMC condition (e.g., yield, purity, stability, decreased aggregation, and/or improving protein folding), potency, or a combination thereof.

In some cases, the modified IL-15 polypeptides comprising at least one unnatural amino acid, wherein the at least one unnatural amino acid is at a residue position that does not affect the binding affinity of the modified IL-15 polypeptide with the IL-15R α and IL-15R βγ. In some embodiments, the modified IL-15 polypeptide further comprises a PEG for increased half-life. In some embodiments, the modified IL-15 comprises a PEG with no change in biological activity. In some embodiments, the residue is modified for half-life extension. In some cases, the residue position of the at least one unnatural amino acid is selected from E13, D14, L15, Q17, S18, M19, H20, I21, S34, C35, K36, V37, T38, K41, L44, S51, L52, S54, G55, D56, A57, S58, H60, V63, I67, N71, S73, L74, S75, S76, N77, G78, N79, V80, T81, E82, S83, G84, C85, K86, E87, C88, L91, E92, K94, N95, I96, K97, E98, L100, Q101, and F110, wherein the residue positions correspond to the positions as set forth in SEQ ID NO: 1. In some embodiments, the residue position of the at least one unnatural amino acid is selected from D14, Q17, S18, K41, S51, L52, G55, D56, A57, S58, S75, S76, N77, N79, V80, T81, S83, G84, E92, K94, N95, K97, and E98, wherein the residue positions correspond to the positions as set forth in SEQ ID NO: 1. In some embodiments, the residue position of the at least one unnatural amino acid is selected from E13, L15, M19, H20, K36, V37, T38, S54, H60, I67, N71, G78, K86, E87, and Q101, wherein the residue positions correspond to the positions as set forth in SEQ ID NO: 1. In some embodiments, the residue position of the at least one unnatural amino acid is selected from I21, S34, C35, L44, V63, S73, L74, E82, C85, C88, L91, I96, L100, and F110, wherein the residue positions correspond to the positions as set forth in SEQ ID NO: 1. In some embodiments, the residue position of the at least one unnatural amino acid is selected from N71, N72, and N77, wherein the residue positions correspond to the positions as set forth in SEQ ID NO: 1. In some embodiments, the residue position of the at least one unnatural amino acid is selected from N77 and S83. In some embodiments, the residue position of the at least one unnatural amino acid is D14. In some embodiments, the residue position of the at least one unnatural amino acid is Q17. In some embodiments, the residue position of the at least one unnatural amino acid is S18. In some embodiments, the residue position of the at least one unnatural amino acid is K41. In some embodiments, the residue position of the at least one unnatural amino acid is S51. In some embodiments, the residue position of the at least one unnatural amino acid is L52. In some embodiments, the residue position of the at least one unnatural amino acid is G55. In some embodiments, the residue position of the at least one unnatural amino acid is D56. In some embodiments, the residue position of the at least one unnatural amino acid is A57. In some embodiments, the residue position of the at least one unnatural amino acid is S58. In some embodiments, the residue position of the at least one unnatural amino acid is S75. In some embodiments, the residue position of the at least one unnatural amino acid is S76. In some embodiments, the residue position of the at least one unnatural amino acid is N77. In some embodiments, the residue position of the at least one unnatural amino acid is N79. In some embodiments, the residue position of the at least one unnatural amino acid is V80. In some embodiments, the residue position of the at least one unnatural amino acid is T81. In some embodiments, the residue position of the at least one unnatural amino acid is S83. In some embodiments, the residue position of the at least one unnatural amino acid is G84. In some embodiments, the residue position of the at least one unnatural amino acid is E92. In some embodiments, the residue position of the at least one unnatural amino acid is K94. In some embodiments, the residue position of the at least one unnatural amino acid is N95. In some embodiments, the residue position of the at least one unnatural amino acid is K97. In some embodiments, the residue position of the at least one unnatural amino acid is E98. In some cases, the mutation at N71, N72, or N77 comprises a mutation to a natural amino acid. In some cases, the mutation at N71, N72, or N77 further improves a CMC condition (e.g., yield, purity, stability, decreased aggregation, and/or improving protein folding), potency, or a combination thereof.

In some embodiments, the IL-15 polypeptide comprising at least one unnatural amino acid is further conjugated to a conjugating moiety to generate an IL-15 conjugate. In some cases, the amino acid position of the at least one unnatural amino acid is at N1, W2, V3, N4, I6, S7, D8, K10, K11, E13, D14, L15, Q17, S18, M19, H20, I21, D22, A23, T24, L25, Y26, T27, E28, S29, D30, V31, H32, P33, S34, C35, K36, V37, T38, A39, K41, L44, L45, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, or S114, wherein the residue positions correspond to the positions as set forth in SEQ ID NO: 1. In some cases, the amino acid position of the at least one unnatural amino acid is at N1, W2, V3, N4, I6, S7, D8, K10, K11, E13, D14, L15, Q17, S18, M19, H20, I21, D22, A23, T24, L25, Y26, E28, S29, D30, V31, H32, P33, S34, C35, K36, V37, T38, K41, L44, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, or S14. In some cases, the conjugating moiety is bound to the at least one unnatural amino acid. In some cases, the conjugating moiety is bound to the N-terminal or the C-terminal amino acid residue. In some instances, the conjugating moiety is directly bound to the at least one unnatural amino acid or a terminal residue. In other instances, the conjugating moiety is indirectly bound to the at least one unnatural amino acid or a terminal residue via a linker described infra.

In some embodiments, the decreased affinity of the IL-15 polypeptide or IL-15 conjugate to an IL-15 receptor α (IL-15Rα) subunit relative to a wild-type IL-15 polypeptide is about 10%, 20%, 30%, 40%, 50%, 60%, 70%, 80%, 90%, 95%, or 99%. In some embodiments, the decreased affinity is about 10%. In some embodiments, the decreased affinity is about 20%. In some embodiments, the decreased affinity is about 40%. In some embodiments, the decreased affinity is about 50%. In some embodiments, the decreased affinity is about 60%. In some embodiments, the decreased affinity is about 80%. In some embodiments, the decreased affinity is about 90%. In some embodiments, the decreased affinity is about 95%. In some embodiments, the decreased affinity is 100%.

In some embodiments, the decreased affinity of the IL-15 polypeptide or IL-15 conjugate to an IL-15 receptor α (IL-15Rα) subunit relative to a wild-type IL-15 polypeptide is about 1-fold, 2-fold, 3-fold, 4-fold, 5-fold, 6-fold, 7-fold, 8-fold, 9-fold, 10-fold, or more. In some embodiments, the decreased affinity is about 1-fold. In some embodiments, the decreased affinity is about 2-fold. In some embodiments, the decreased affinity is about 4-fold. In some embodiments, the decreased affinity is about 5-fold. In some embodiments, the decreased affinity is about 6-fold. In some embodiments, the decreased affinity is about 8-fold. In some embodiments, the decreased affinity is about 10-fold.

In some embodiments, the IL-15 polypeptide or IL-15 conjugate does not interact with IL-15Rα.

In some embodiments, the decreased affinity of the IL-15 polypeptide or IL-15 conjugate to an IL-2 receptor (IL-2R) subunit relative to a wild-type IL-15 polypeptide is about 10%, 20%, 30%, 40%, 50%, 60%, 70%, 80%, 90%, 95%, or 99%. In some embodiments, the IL-2R subunit is IL-2R βγ. In some embodiments, the decreased affinity is about 10%. In some embodiments, the decreased affinity is about 20%. In some embodiments, the decreased affinity is about 40%. In some embodiments, the decreased affinity is about 50%. In some embodiments, the decreased affinity is about 60%. In some embodiments, the decreased affinity is about 80%. In some embodiments, the decreased affinity is about 90%. In some embodiments, the decreased affinity is about 95%. In some embodiments, the decreased affinity is 100%.

In some embodiments, the decreased affinity of the IL-15 polypeptide or IL-15 conjugate to an IL-2 receptor (IL-2R) subunit relative to a wild-type IL-15 polypeptide is about 1-fold, 2-fold, 3-fold, 4-fold, 5-fold, 6-fold, 7-fold, 8-fold, 9-fold, 10-fold, or more. In some embodiments, the IL-2R subunit is IL-2R βγ. In some embodiments, the decreased affinity is about 1-fold. In some embodiments, the decreased affinity is about 2-fold. In some embodiments, the decreased affinity is about 4-fold. In some embodiments, the decreased affinity is about 5-fold. In some embodiments, the decreased affinity is about 6-fold. In some embodiments, the decreased affinity is about 8-fold. In some embodiments, the decreased affinity is about 10-fold.

In some embodiments, the IL-15 polypeptide or IL-15 conjugate does not interact with IL-2Rα.

In some embodiments, the IL-15 polypeptide or IL-15 conjugate has an enhanced half-life. In some instances, the enhanced half-life is compared to a half-life of a wild-type IL-15 protein or wild-type IL-15 conjugate.

In some cases, the enhanced half-life of the IL-15 polypeptide or IL-15 conjugate is at least 90 minutes, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, 3 days, 4 days, 5 days, 6 days, 7 days, 10 days, 12 days, 14 days, 21 days, 28 days, 30 days, or longer than the half-life of the wild-type IL-15 protein or wild-type IL-15 conjugate. In some cases, the enhanced half-life of the IL-15 polypeptide or IL-15 conjugate is at least 90 minutes or longer than the half-life of the wild-type IL-15 protein or wild-type IL-15 conjugate. In some cases, the enhanced half-life of the IL-15 polypeptide or IL-15 conjugate is at least 2 hours or longer than the half-life of the wild-type IL-15 protein or wild-type IL-15 conjugate. In some cases, the enhance half-life of the IL-15 polypeptide or IL-15 conjugate is at least 3 hours or longer than the half-life of the wild-type IL-15 protein or wild-type IL-15 conjugate. In some cases, the enhanced half-life of the IL-15 polypeptide or IL-15 conjugate is at least 4 hours or longer than the half-life of the wild-type IL-15 protein or wild-type IL-15 conjugate. In some cases, the enhanced half-life of the IL-15 polypeptide or IL-15 conjugate is at least 5 hours or longer than the half-life of the wild-type IL-15 protein or wild-type IL-15 conjugate. In some cases, the enhanced half-life of the IL-15 polypeptide or IL-15 conjugate is at least 6 hours or longer than the half-life of the wild-type IL-15 protein or wild-type IL-15 conjugate. In some cases, the enhanced half-life of the IL-15 polypeptide or IL-15 conjugate is at least 10 hours or longer than the half-life of the wild-type IL-15 protein or wild-type IL-15 conjugate. In some cases, the enhanced half-life of the IL-15 polypeptide or IL-15 conjugate is at least 12 hours or longer than the half-life of the wild-type IL-15 protein or wild-type IL-15 conjugate. In some cases, the enhanced half-life of the IL-15 polypeptide or IL-15 conjugate is at least 18 hours or longer than the half-life of the wild-type IL-15 protein or wild-type IL-15 conjugate. In some cases, the enhanced half-life of the IL-15 polypeptide or IL-15 conjugate is at least 24 hours or longer than the half-life of the wild-type IL-15 protein or wild-type IL-15 conjugate. In some cases, the enhanced half-life of the IL-15 polypeptide or IL-15 conjugate is at least 36 hours or longer than the half-life of the wild-type IL-15 protein or wild-type IL-15 conjugate. In some cases, the enhanced half-life of the IL-15 polypeptide or IL-15 conjugate is at least 48 hours or longer than the half-life of the wild-type IL-15 protein or wild-type IL-15 conjugate. In some cases, the enhanced half-life of the IL-15 polypeptide or IL-15 conjugate is at least 3 days or longer than the half-life of the wild-type IL-15 protein or wild-type IL-15 conjugate. In some cases, the enhanced half-life of the IL-15 polypeptide or IL-15 conjugate is at least 4 days or longer than the half-life of the wild-type IL-15 protein or wild-type IL-15 conjugate. In some cases, the enhanced half-life of the IL-15 polypeptide or IL-15 conjugate is at least 5 days or longer than the half-life of the wild-type IL-15 protein or wild-type IL-15 conjugate. In some cases, the enhanced half-life of the IL-15 polypeptide or IL-15 conjugate is at least 6 days or longer than the half-life of the wild-type IL-15 protein or wild-type IL-15 conjugate. In some cases, the enhanced half-life of the IL-15 polypeptide or IL-15 conjugate is at least 7 days or longer than the half-life of the wild-type IL-15 protein or wild-type IL-15 conjugate. In some cases, the enhanced half-life of the IL-15 polypeptide or IL-15 conjugate is at least 10 days or longer than thali-life of the wild-type IL-15 protein or wild-type IL-15 conjugate. In some cases, the enhanced half-life of the IL-15 polypeptide or IL-15 conjugate is at least 12 days or longer than the half-life of the wild-type IL-15 protein or wild-type IL-15 conjugate. In some cases, the enhanced half-life of the IL-15 polypeptide or IL-15 conjugate is at least 14 days or longer than the half-life of the wild-type IL-15 protein or wild-type IL-15 conjugate. In some cases, the enhanced half-life of the IL-15 polypeptide or IL-15 conjugate is at least 21 days or longer than the half-life of the wild-type IL-15 protein or wild-type IL-15 conjugate. In some cases, the enhanced half-life of the IL-15 polypeptide or IL-15 conjugate is at least 28 days or longer than the half-life of the wild-type IL-15 protein or wild-type IL-15 conjugate. In some cases, the enhanced half-life of the IL-15 polypeptide or IL-15 conjugate is at least 30 days or longer than the half-life of the wild-type IL-15 protein or wild-type IL-15 conjugate.

In some cases, the enhanced half-life of the IL-15 polypeptide or IL-15 conjugate is about 4 hours, 5 hours, 6 hours, 7 hours, 8 hours, 9 hours, 10 hours, 11 hours, 12 hours, 18 hours, 24 hours, 36 hours, 48 hours, 3 days, 4 days, 5 days, 6 days, 7 days, 10 days, 12 days, 14 days, 21 days, 28 days, or 30 days compared to the half-life of the wild-type IL-15 protein or wild-type IL-15 conjugate. In some cases, the biologically active IL-15 polypeptide or IL-15 conjugate has an enhanced half-life of about 90 minutes. In some cases, the biologically active IL-15 polypeptide or IL-15 conjugate has an enhanced half-life of about 2 hours. In some cases, the biologically active IL-15 polypeptide or IL-15 conjugate has an enhanced half-life of about 3 hours. In some cases, the biologically active IL-15 polypeptide or IL-15 conjugate has an enhanced half-life of about 4 hours. In some cases, the biologically active IL-15 polypeptide or IL-15 conjugate has an enhanced half-life of about 5 hours. In some cases, the biologically active IL-15 polypeptide or IL-15 conjugate has an enhanced half-life of about 6 hours. In some cases, the biologically active IL-15 polypeptide or IL-15 conjugate has an enhanced half-life of about 7 hours. In some cases, the biologically active IL-15 polypeptide or IL-15 conjugate has an enhanced half-life of about 8 hours. In some cases, the biologically active IL-15 polypeptide or IL-15 conjugate has an enhanced half-life of about 9 hours. In some cases, the biologically active IL-15 polypeptide or IL-15 conjugate has an enhanced half-life of about 10 hours. In some cases, the biologically active IL-15 polypeptide or IL-15 conjugate has an enhanced half-life of about 11 hours. In some cases, the biologically active IL-15 polypeptide or IL-15 conjugate has an enhanced half-life of about 12 hours. In some cases, the biologically active IL-15 polypeptide or IL-15 conjugate has an enhanced half-life of about 18 hours. In some cases, the biologically active IL-15 polypeptide or IL-15 conjugate has an enhanced half-life of about 24 hours. In some cases, the biologically active IL-15 polypeptide or IL-15 conjugate has an enhanced half-life of about 36 hours. In some cases, the biologically active IL-15 polypeptide or IL-15 conjugate has an enhanced half-life of about 48 hours. In some cases, the biologically active IL-15 polypeptide or IL-15 conjugate has an enhanced half-life of about 3 days. In some cases, the biologically active IL-15 polypeptide or IL-15 conjugate has an enhanced half-life of about 4 days. In some cases, the biologically active IL-15 polypeptide or IL-15 conjugate has an enhanced half-life of about 5 days. In some cases, the biologically active IL-15 polypeptide or IL-15 conjugate has an enhanced half-life of about 6 days. In some cases, the biologically active IL-15 polypeptide or IL-15 conjugate has an enhanced half-life of about 7 days. In some cases, the biologically active IL-15 polypeptide or IL-15 conjugate has an enhanced half-life of about 10 days. In some cases, the biologically active IL-15 polypeptide or IL-15 conjugate has an enhanced half-life of about 12 days. In some cases, the biologically active IL-15 polypeptide or IL-15 conjugate has an enhanced half-life of about 14 days. In some cases, the biologically active IL-15 polypeptide or IL-15 conjugate has an enhanced half-life of about 21 days. In some cases, the biologically active IL-15 polypeptide or IL-15 conjugate has an enhanced half-life of about 28 days. In some cases, the biologically active IL-15 polypeptide or IL-15 conjugate has an enhanced half-life of about 30 days.

In some embodiments, the modified IL-15 polypeptide retains significant signaling potency with interleukin 15 receptor βγ (IL-15Rβγ) signaling complex. In some cases, the signaling potency is compared to a signaling potency between a wild-type IL-15 polypeptide and IL-15Rβγ. In some cases, a difference in receptor signaling potency between the modified IL-15/IL-15Rβγ complex and the wild-type IL-15/IL-15Rβγ complex is less than 1000-fold, less than 500-fold, less than 200-fold, less than 100-fold, less than 50-fold, less than 10-fold, less than 5-fold, less than 4-fold, less than 3-fold, less than 2-fold, or less than 1-fold. In some cases, a difference in receptor signaling potency between the modified IL-15/IL-15Rβγ complex and the wild-type IL-15/EL-15Rβγ complex is greater than 10-fold, greater than 20-fold, greater than 30-fold, greater than 40-fold, greater than 50-fold, greater than 100-fold, greater than 200-fold, greater than 300-fold, greater than 400-fold, or greater than 500-fold. In some instances, the modified IL-15 polypeptide is a partial agonist, e.g., an agonist that activates a receptor (e.g., an IL-15βγ signaling complex) but has only a partial efficacy at the receptor relative to a full agonist. In some instances, the modified IL-15 polypeptide is a full agonist, e.g., an agonist that activates a receptor (e.g., an IL-15βγ signaling complex) at a maximum response.

In some instances, the receptor signaling potency is measured by an EC50 value. In some instances, the modified IL-15 polypeptide provides an EC50 value that is less than 1000-fold, less than 500-fold, less than 200-fold, less than 100-fold, less than 50-fold, less than 10-fold, less than 5-fold, less than 4-fold, less than 3-fold, less than 2-fold, or less than 1-fold different than an EC50 value of the wild-type IL-15/IL-15Rβγ complex. In some instances, the modified IL-15 polypeptide provides an EC50 value that is greater than 10-fold, greater than 20-fold, greater than 30-fold, greater than 40-fold, greater than 50-fold, greater than 100-fold, greater than 200-fold, greater than 300-fold, greater than 400-fold, or greater than 500-fold different than an EC50 value of the wild-type IL-15/IL-15Rβγ complex.

In some instances, the receptor signaling potency is measured by an ED50 value. In some instances, the modified IL-15 polypeptide provides an ED50 value that is less than 1000-fold, less than 500-fold, less than 200-fold, less than 100-fold, less than 50-fold, less than 10-fold, less than 5-fold, less than 4-fold, less than 3-fold, less than 2-fold, or less than 1-fold different than an EC50 value of the wild-type IL-15/IL-15Rβγ complex. In some instances, the modified IL-15 polypeptide provides an ED50 value that is greater than 10-fold, greater than 20-fold, greater than 30-fold, greater than 40-fold, greater than 50-fold, greater than 100-fold, greater than 200-fold, greater than 300-fold, greater than 400-fold, or greater than 500-fold different than an EC50 value of the wild-type IL-15/IL-15Rβγ complex.

In some embodiments, an IL-15 polypeptide is modified (e.g., pegylated) to extend half-life, improve stability, improve purification yield, improve purity, decrease aggregation, improve protein folding, or a combination thereof, during the Chemistry, Manufacturing and Controls (CMC) stage. In some cases, the IL-15 polypeptide is modified at an amino acid position: N71, N72, or N77, wherein the residue positions correspond to the positions as set forth in SEQ ID NO: 1. In some cases, the IL-15 polypeptide is modified at residue N77, e.g., via pegylation, to extend half-life, improve stability, improve purification yield, improve purity, decrease aggregation, improve protein folding, or a combination thereof, during the CMC stage. In some cases, the IL-15 polypeptide is further modified at position N1, W2, V3, N4, I6, S7, D8, K10, K11, E13, D14, L15, Q17, S18, M19, H20, I21, D22, A23, T24, L25, Y26, E28, S29, D30, V31, H32, P33, S34, C35, K36, V37, T38, K41, L44, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, or S114. In some cases, the IL-15 polypeptide is further modified at a position D22, A23, T24, L25, Y26, L44, E46, Q48, V49, E53, E89, E90, or E93, wherein the modification impairs interaction with IL-15Rα. In some cases, the IL-15 polypeptide is further modified at a position N1, N4, S7, D8, K11, D61, T62, E64, N65, I68, L69, or N72, wherein the modification impairs interaction with IL-15R. In some cases, the IL-15 polypeptide is further modified at a position V3, I6, K10, E28, S29, D30, V31, H32, P33, S102, V104, H105, Q108, M109, I111, N112, T113, or S114, wherein the modification impairs interaction with IL-15R. In some cases, the IL-15 polypeptide is further modified at a position E13, D14, L15, Q17, S18, M19, H20, I21, S34, C35, K36, V37, T38, K41, L44, S51, L52, S54, G55, D56, A57, S58, H60, V63, I67, N71, S73, L74, S75, S76, N77, G78, N79, V80, T81, E82, S83, G84, C85, K86, E87, C88, L91, E92, K94, N95, I96, K97, E98, L100, Q101, or F110, wherein the modification improves half-life extension.

In some cases, the IL-15 polypeptide is further modified at one or more of the above positions for impairs interaction with IL-15Rα, impairs interaction with IL-15Rβ, impairs interaction with IL-15Rγ, improves half-life extension, or a combination thereof.

IL-15 Conjugate Precursors

Disclosed herein are IL-15 conjugate precursors, comprising a modified IL-15 polypeptide, wherein one or more amino acids have been mutated from the wild type amino acid. Such precursors are often used with the methods disclosed herein for the treatment of diseases or conditions. In some embodiments, an IL-15 precursor is not conjugated. Such mutations variously comprise additions, deletions, or substitutions. In some cases, the addition comprises inclusion of 1, 2, 3, 4, 5, 6, 7, 8, 9, 10, or more residues at the N-terminus, the C-terminus, or an internal region of the IL-15 polypeptide. In additional cases, the deletion comprises removal of 1, 2, 3, 4, 5, 6, 7, 8, 9, 10, or more residues from the N-terminus, the C-terminus, or within an internal region of the IL-15 polypeptide.

Natural and Unnatural Amino Acids

In some embodiments, an amino acid residue disclosed herein (e.g., within an IL-15 polypeptide) is mutated to lysine, cysteine, histidine, arginine, aspartic acid, glutamic acid, serine, threonine, or tyrosine prior to binding to (or reacting with) a conjugating moiety. For example, the side chain of lysine, cysteine, histidine, arginine, aspartic acid, glutamic acid, serine, threonine, or tyrosine may bind to a conjugating moiety disclosed herein. In some instances, the amino acid residue is mutated to cysteine, lysine, or histidine. In some cases, the amino acid residue is mutated to cysteine. In some cases, the amino acid residue is mutated to lysine. In some cases, the amino acid residue is mutated to histidine. In some cases, the amino acid residue is mutated to tyrosine. In some cases, the amino acid residue is mutated to tryptophan. In some instances, the amino acid residue is located proximal to the N- or C-terminus, at the N- or C-terminus, or at an internal residue position. In some instances, the amino acid residue is the N- or C-terminal residue and the mutation is to cysteine or lysine. In some instances, the amino acid residue is located proximal to the N- or C-terminal residue (e.g., within 50, 40, 30, 20, or 10 residues from the N- or C-terminal residue) and the mutation is to cysteine or lysine.

In some instances, an amino acid residue is added to the N- or C-terminal residue, i.e., the IL-15 polypeptide comprises an additional amino acid residue at either the N- or C-terminus and the additional amino acid residue is cysteine or lysine. In some cases, the additional amino acid residue is cysteine. In some cases, the additional amino acid is conjugated to a conjugating moiety.

In some embodiments, an amino acid residue described herein (e.g., within an IL-15 polypeptide) is mutated to an unnatural amino acid. In some embodiments, an unnatural amino acid is not conjugated with a conjugating moiety. In some embodiments, an IL-15 polypeptide disclosed herein comprises an unnatural amino acid, wherein the IL-15 is conjugated to the protein, wherein the point of attachment is not the unnatural amino acid.

In some embodiments, an amino acid residue disclosed herein (e.g., within an IL-15 polypeptide) is mutated to an unnatural amino acid prior to binding to a conjugating moiety. In some cases, the mutation to an unnatural amino acid prevents or minimizes a self-antigen response of the immune system. As used herein, the term "unnatural amino acid" refers to an amino acid other than the 20 amino acids that occur naturally in protein. Non-limiting examples of unnatural amino acids include: p-acetyl-L-phenylalanine, p-iodo-L-phenylalanine, p-methoxyphenylalanine, O-methyl-L-tyrosine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, p-Boronophenylalanine, O-propargyltyrosine, L-phosphoserine, phosphonoserine, phosphonotyrosine, p-bromophenylalanine, selenocysteine, p-amino-L-phenylalanine, isopropyl-L-phenylalanine, N6-[(2-azidoethoxy)carbonyl]-L-lysine (AzK), an unnatural analogue of a tyrosine amino acid; an unnatural analogue of a glutamine amino acid; an unnatural analogue of a phenylalanine amino acid; an unnatural analogue of a seine amino acid; an unnatural analogue of a threonine amino acid; an alkyl, aryl, acyl, azido, cyano, halo, hydrazine, hydrazide, hydroxyl, alkenyl, alkynyl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an a-hydroxy containing acid; an amino thio acid; an α, α disubstituted amino acid; a β-amino acid; a cyclic amino acid other than proline or histidine, and an aromatic amino acid other than phenylalanine, tyrosine or tryptophan.

In some embodiments, the unnatural amino acid comprises a selective reactive group, or a reactive group for site-selective labeling of a target polypeptide. In some instances, the chemistry is a biorthogonal reaction (e.g., biocompatible and selective reactions). In some cases, the chemistry is a Cu(I)-catalyzed or "copper-free" alkyne-azide triazole-forming reaction, the Staudinger ligation, inverse-electron-demand Diels-Alder (IEDDA) reaction, "photo-click" chemistry, or a metal-mediated process such as olefin metathesis and Suzuki-Miyaura or Sonogashira cross-coupling.

In some embodiments, the unnatural amino acid comprises a photoreactive group, which crosslinks, upon irradiation with, e.g., UV.

In some embodiments, the unnatural amino acid comprises a photo-caged amino acid.

In some instances, the unnatural amino acid is a para-substituted, meta-substituted, or an ortho-substituted amino acid derivative.

In some instances, the unnatural amino acid comprises p-acetyl-L-phenylalanine, p-azidomethyl-L-phenylalanine (pAMF), p-iodo-L-phenylalanine, O-methyl-L-tyrosine, p-methoxyphenylalanine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-bromophenylalanine, p-amino-L-phenylalanine, or isopropyl-L-phenylalanine.

In some cases, the unnatural amino acid is 3-aminotyrosine, 3-nitrotyrosine, 3,4-dihydroxy-phenylalanine, or 3-iodotyrosine.

In some cases, the unnatural amino acid is phenylselenocysteine.

In some instances, the unnatural amino acid is a benzophenone, ketone, iodide, methoxy, acetyl, benzoyl, or azide containing phenylalanine derivative.

In some instances, the unnatural amino acid is a benzophenone, ketone, iodide, methoxy, acetyl, benzoyl, or azide containing lysine derivative.

In some instances, the unnatural amino acid comprises an aromatic side chain.

In some instances, the unnatural amino acid does not comprise an aromatic side chain.

In some instances, the unnatural amino acid comprises an azido group.

In some instances, the unnatural amino acid comprises a Michael-acceptor group. In some instances, Michael-acceptor groups comprise an unsaturated moiety capable of forming a covalent bond through a 1,2-addition reaction. In some instances, Michael-acceptor groups comprise electron-deficient alkenes or alkynes. In some instances, Michael-acceptor groups include but are not limited to alpha,beta unsaturated: ketones, aldehydes, sulfoxides, sulfones, nitriles, imines, or aromatics.

In some instances, the unnatural amino acid is dehydroalanine.

In some instances, the unnatural amino acid comprises an aldehyde or ketone group.

In some instances, the unnatural amino acid is a lysine derivative comprising an aldehyde or ketone group.

In some instances, the unnatural amino acid is a lysine derivative comprising one or more O, N, Se, or S atoms at the beta, gamma, or delta position. In some instances, the unnatural amino acid is a lysine derivative comprising O, N, Se, or S atoms at the gamma position.

In some instances, the unnatural amino acid is a lysine derivative wherein the epsilon N atom is replaced with an oxygen atom.

In some instances, the unnatural amino acid is a lysine derivative that is not naturally-occurring post-translationally modified lysine.

In some instances, the unnatural amino acid is an amino acid comprising a side chain, wherein the sixth atom from the alpha position comprises a carbonyl group. In some instances, the unnatural amino acid is an amino acid comprising a side chain, wherein the sixth atom from the alpha position comprises a carbonyl group, and the fifth atom from the alpha position is a nitrogen. In some instances, the unnatural amino acid is an amino acid comprising a side chain, wherein the seventh atom from the alpha position is an oxygen atom.

In some instances, the unnatural amino acid is a serine derivative comprising selenium. In some instances, the unnatural amino acid is selenoserine (2-amino-3-hydroselenopropanoic acid). In some instances, the unnatural amino acid is 2-amino-3-((2-((3-(benzyloxy)-3-oxopropyl)amino)ethyl)selanyl)propanoic acid. In some instances, the unnatural amino acid is 2-amino-3-(phenylselanyl)propanoic acid. In some instances, the unnatural amino acid comprises selenium, wherein oxidation of the selenium results in the formation of an unnatural amino acid comprising an alkene.

In some instances, the unnatural amino acid comprises a cyclooctynyl group.

In some instances, the unnatural amino acid comprises a transcycloctenyl group.

In some instances, the unnatural amino acid comprises a norbornenyl group.

In some instances, the unnatural amino acid comprises a cyclopropenyl group.

In some instances, the unnatural amino acid comprises a diazirine group.

In some instances, the unnatural amino acid comprises a tetrazine group.

In some instances, the unnatural amino acid is a lysine derivative, wherein the side-chain nitrogen is carbamylated. In some instances, the unnatural amino acid is a lysine derivative, wherein the side-chain nitrogen is acylated. In some instances, the unnatural amino acid is 2-amino-6-{[(tert-butoxy)carbonyl]amino}hexanoic acid. In some instances, the unnatural amino acid is 2-amino-6-([(tert-butoxy)carbonyl]amino)hexanoic acid. In some instances, the unnatural amino acid is N6-Boc-N6-methyllysine. In some instances, the unnatural amino acid is N6-acetyllysine. In some instances, the unnatural amino acid is pyrrolysine. In some instances, the unnatural amino acid is N6-trifluoroacetyllysine. In some instances, the unnatural amino acid is 2-amino-6-([(benzyloxy)carbonyl]amino)hexanoic acid. In some instances, the unnatural amino acid is 2-amino-6-([(p-iodobenzyloxy)carbonyl]amino)hexanoic acid. In some instances, the unnatural amino acid is 2-amino-6-([(p-nitrobenzyloxy)carbonyl]amino)hexanoic acid. In some instances, the unnatural amino acid is N6-prolyllysine. In some instances, the unnatural amino acid is 2-amino-6-{[(cyclopentyloxy)carbonyl]amino}hexanoic acid. In some instances, the unnatural amino acid is N6-(cyclopentanecarbonyl)lysine. In some instances, the unnatural amino acid is N6-(tetrahydrofuran-2-carbonyl)lysine. In some instances, the unnatural amino acid is N6-(3-ethynyltetrahydrofuran-2-carbonyl)lysine. In some instances, the unnatural amino acid is N6-((prop-2-yn-1-yloxy)carbonyl)lysine. In some instances, the unnatural amino acid is 2-amino-6-{[(2-azidocyclopentyloxy)carbonyl]amino}hexanoic acid. In some instances, the unnatural amino acid is N6-[(2-azidoethoxy)carbonyl]lysine. In some instances, the unnatural amino acid is 2-amino-6-([(2-nitrobenzyloxy)carbonyl]amino)hexanoic acid. In some instances, the unnatural amino acid is 2-amino-6-([(2-cyclooctynyloxy)carbonyl]amino)hexanoic acid. In some instances, the unnatural amino acid is N6-(2-aminobut-3-ynoyl)lysine. In some instances, the unnatural amino acid is 2-amino-6-((2-aminobut-3-ynoyl)oxy)hexanoic acid. In some instances, the unnatural amino acid is N6-(allyloxycarbonyl)lysine. In some instances, the unnatural amino acid is N6-(butenyl-4-oxycarbonyl)lysine. In some instances, the unnatural amino acid is N6-(pentenyl-5-oxycarbonyl)lysine. In some instances, the unnatural amino acid is N6-((but-3-yn-1-yloxy)carbonyl)-lysine. In some instances, the unnatural amino acid is N6-((pent-4-yn-1-yloxy)carbonyl)-lysine. In some instances, the unnatural amino acid is N6-(thiazolidine-4-carbonyl)lysine. In some instances, the unnatural amino acid is 2-amino-8-oxononanoic acid. In some instances, the unnatural amino acid is 2-amino-8-oxooctanoic acid. In some instances, the unnatural amino acid is N6-(2-oxoacetyl)lysine.

In some instances, the unnatural amino acid is N6-propionyllysine. In some instances, the unnatural amino acid is N6-butyryllysine. In some instances, the unnatural amino acid is N6-(but-2-enoyl)lysine. In some instances, the unnatural amino acid is N6-((bicyclo[2.2.1]hept-5-en-2-yloxy)carbonyl)lysine. In some instances, the unnatural amino acid is N6-((spiro[2.3]hex-1-en-5-ylmethoxy)carbonyl)lysine. In some instances, the unnatural amino acid is N6-(((4-(1-(trifluoromethyl)cycloprop-2-en-1-yl)benzyl)oxy)carbonyl)lysine. In some instances, the unnatural amino acid is N6-((bicyclo[2.2.1]hept-5-en-2-ylmethoxy)carbonyl)lysine. In some instances, the unnatural amino acid is cysteinyllysine. In some instances, the unnatural amino acid is N6-((1-(6-nitrobenzo[d][1,3]dioxol-5-yl)ethoxy)carbonyl)lysine. In some instances, the unnatural amino acid is N6-((2-(3-methyl-3H-diazirin-3-yl)ethoxy)carbonyl)lysine. In some instances, the unnatural amino acid is N6-((3-(3-methyl-3H-diazirin-3-yl)propoxy)carbonyl)lysine. In some instances, the unnatural amino acid is N6-((meta nitrobenyloxy)N6-methylcarbonyl)lysine. In some instances, the unnatural amino acid is N6-((bicyclo[6.1.0]non-4-yn-9-ylmethoxy)carbonyl)-lysine. In some instances, the unnatural amino acid is N6-((cyclohept-3-en-1-yloxy)carbonyl)-L-lysine.

In some instances, the unnatural amino acid is 2-amino-3-(((((benzyloxy)carbonyl)amino)methyl)selanyl)propanoic acid.

In some embodiments, the unnatural amino acid is incorporated into the IL-15 polypeptide by a repurposed amber, opal, or ochre stop codon.

In some embodiments, the unnatural amino acid is incorporated into the IL-15 polypeptide by a 4-base codon.

In some embodiments, the unnatural amino acid is incorporated into the IL-15 polypeptide by a repurposed rare sense codon or a repurposed common sense codon.

In some embodiments, the unnatural amino acid is incorporated into the IL-15 polypeptide by a synthetic codon comprising an unnatural nucleic acid.

In some instances, the unnatural amino acid is incorporated into the IL-15 by an orthogonal, modified synthetase/tRNA pair. Such orthogonal pairs comprise an unnatural synthetase that is capable of charging the unnatural tRNA with the unnatural amino acid, while minimizing charging of a) other endogenous amino acids onto the unnatural tRNA and b) unnatural amino acids onto other endogenous tRNAs. Such orthogonal pairs comprise tRNAs that are capable of being charged by the unnatural synthetase, while avoiding being charged with other endogenous amino acids by endogenous synthetases. In some embodiments, such pairs are identified from various organisms, such as bacteria, yeast, *Archaea*, or human sources. In some embodiments, an orthogonal synthetase/tRNA pair comprises components from a single organism. In some embodiments, an orthogonal synthetase/tRNA pair comprises components from two different organisms. In some embodiments, an orthogonal synthetase/tRNA pair comprising components that prior to modification, promote translation of two different amino acids. In some embodiments, an orthogonal synthetase is a modified alanine synthetase. In some embodiments, an orthogonal synthetase is a modified arginine synthetase. In some embodiments, an orthogonal synthetase is a modified asparagine synthetase. In some embodiments, an orthogonal synthetase is a modified aspartic acid synthetase. In some embodiments, an orthogonal synthetase is a modified cysteine synthetase. In some embodiments, an orthogonal synthetase is a modified glutamine synthetase. In some embodiments, an orthogonal synthetase is a modified glutamic acid synthetase. In some embodiments, an orthogonal synthetase is a modified alanine glycine. In some embodiments, an orthogonal synthetase is a modified histidine synthetase. In some embodiments, an orthogonal synthetase is a modified leucine synthetase. In some embodiments, an orthogonal synthetase is a modified isoleucine synthetase. In some embodiments, an orthogonal synthetase is a modified lysine synthetase. In some embodiments, an orthogonal synthetase is a modified methionine synthetase. In some embodiments, an orthogonal synthetase is a modified phenylalanine synthetase. In some embodiments, an orthogonal synthetase is a modified proline synthetase. In some embodiments, an orthogonal synthetase is a modified serine synthetase. In some embodiments, an orthogonal synthetase is a modified threonine synthetase. In some embodiments, an orthogonal synthetase is a modified tryptophan synthetase. In some embodiments, an orthogonal synthetase is a modified tyrosine synthetase. In some embodiments, an orthogonal synthetase is a modified valine synthetase. In some embodiments, an orthogonal synthetase is a modified phosphoserine synthetase. In some embodiments, an orthogonal tRNA is a modified alanine tRNA. In some embodiments, an orthogonal tRNA is a modified arginine tRNA. In some embodiments, an orthogonal tRNA is a modified asparagine tRNA. In some embodiments, an orthogonal tRNA is a modified aspartic acid tRNA. In some embodiments, an orthogonal tRNA is a modified cysteine tRNA. In some embodiments, an orthogonal tRNA is a modified glutamine tRNA. In some embodiments, an orthogonal tRNA is a modified glutamic acid tRNA. In some embodiments, an orthogonal tRNA is a modified alanine glycine. In some embodiments, an orthogonal tRNA is a modified histidine tRNA. In some embodiments, an orthogonal tRNA is a modified leucine tRNA. In some embodiments, an orthogonal tRNA is a modified isoleucine tRNA. In some embodiments, an orthogonal tRNA is a modified lysine tRNA. In some embodiments, an orthogonal tRNA is a modified methionine tRNA. In some embodiments, an orthogonal tRNA is a modified phenylalanine tRNA. In some embodiments, an orthogonal tRNA is a modified proline tRNA. In some embodiments, an orthogonal tRNA is a modified serine tRNA. In some embodiments, an orthogonal tRNA is a modified threonine tRNA. In some embodiments, an orthogonal tRNA is a modified tryptophan tRNA. In some embodiments, an orthogonal tRNA is a modified tyrosine tRNA. In some embodiments, an orthogonal tRNA is a modified valine tRNA. In some embodiments, an orthogonal tRNA is a modified phosphoserine tRNA.

In some embodiments, the unnatural amino acid is incorporated into the IL-15 polypeptide by an aminoacyl (aaRS or RS)-tRNA synthetase-tRNA pair. Exemplary aaRS-tRNA pairs include, but are not limited to, *Methanococcus janaschii* (Mj-Tyr) aaRS/tRNA pairs, *E. coli* TyrRS (Ec-Tyr)/*B. stearothermophilus* tRNA$_{CUA}$ pairs, *E. coli* LeuRS (Ec-Leu)/*B. stearothermophilus* tRNA$_{CUA}$ pairs, and pyrrolysyl-tRNA pairs. In some instances, the unnatural amino acid is incorporated into the cytokine (e.g., the IL polypeptide) by a Mj-TyrRS/tRNA pair. Exemplary UAAs that can be incorporated by a Mj-TyrRS/tRNA pair include, but are not limited to, para-substituted phenylalanine derivatives such asp-aminophenylalanine and p-methoxyphenylalanine; meta-substituted tyrosine derivatives such as 3-aminotyrosine, 3-nitrotyrosine, 3,4-dihydroxyphenylalanine, and 3-iodotyrosine; phenylselenocysteine; p-boronophenylalanine; and o-nitrobenzyltyrosine.

In some instances, the unnatural amino acid is incorporated into the IL-15 polypeptide by a Ec-Tyr/tRNA$_{CUA}$ or a Ec-Leu/tRNA$_{CUA}$ pair. Exemplary UAAs that can be incorporated by a Ec-Tyr/tRNA$_{CUA}$ or a Ec-Leu/tRNA$_{CUA}$ pair include, but are not limited to, phenylalanine derivatives containing benzophenone, ketone, iodide, or azide substituents; O-propargyltyrosine; α-aminocaprylic acid, O-methyl tyrosine, O-nitrobenzyl cysteine; and 3-(naphthalene-2-ylamino)-2-amino-propanoic acid.

In some instances, the unnatural amino acid is incorporated into the IL-15 polypeptide by a pyrrolysyl-tRNA pair. In some cases, the PylRS is obtained from an archaebacterial, e.g., from a methanogenic archaebacterial. In some cases, the PylRS is obtained from *Methanosarcina barkeri*, *Methanosarcina mazei*, or *Methanosarcina acetivorans*. Exemplary UAAs that can be incorporated by a pyrrolysyl-tRNA pair include, but are not limited to, amide and carbamate substituted lysines such as 2-amino-6-((R)-tetrahydrofuran-2-carboxamido)hexanoic acid, N-ε-D-prolyl-L-lysine, and N-ε-cyclopentyloxycarbonyl-L-lysine; N-ε-Acryloyl-L-lysine; N-ε-[(1-(6-nitrobenzo[d][1,3]dioxol-5-yl)ethoxy)carbonyl]-L-lysine; and N-ε-(1-methylcyclopro-2-enecarboxamido)lysine.

In some instances, an unnatural amino acid is incorporated into an IL-15 polypeptide by a synthetase disclosed in U.S. Pat. Nos. 9,988,619 and 9,938,516. Exemplary UAAs that can be incorporated by such synthetases include para-methylazido-L-phenylalanine, aralkyl, heterocyclyl, heteroaralkyl unnatural amino acids, and others. In some embodiments, such UAAs comprise pyridyl, pyrazinyl, pyrazolyl, triazolyl, oxazolyl, thiazolyl, thiophenyl, or other heterocycle. Such amino acids in some embodiments comprise azides, tetrazines, or other chemical group capable of conjugation to a coupling partner, such as a water soluble moiety. In some embodiments, such synthetases are expressed and used to incorporate UAAs into cytokines in-vivo. In some embodiments, such synthetases are used to incorporate UAAs into cytokines using a cell-free translation system.

In some instances, an unnatural amino acid is incorporated into an IL-15 polypeptide by a naturally occurring synthetase. In some embodiments, an unnatural amino acid is incorporated into a cytokine by an organism that is auxotrophic for one or more amino acids. In some embodiments, synthetases corresponding to the auxotrophic amino acid are capable of charging the corresponding tRNA with an unnatural amino acid. In some embodiments, the unnatural amino acid is selenocysteine, or a derivative thereof. In some embodiments, the unnatural amino acid is selenomethionine, or a derivative thereof. In some embodiments, the unnatural amino acid is an aromatic amino acid, wherein the aromatic amino acid comprises an aryl halide, such as an iodide. In embodiments, the unnatural amino acid is structurally similar to the auxotrophic amino acid.

In some instances, the unnatural amino acid comprises a lysine or phenylalanine derivative or analogue. In some instances, the unnatural amino acid comprises a lysine derivative or a lysine analogue. In some instances, the unnatural amino acid comprises a pyrrolysine (Pyl). In some instances, the unnatural amino acid comprises a phenylalanine derivative or a phenylalanine analogue. In some instances, the unnatural amino acid is an unnatural amino acid described in Wan, et al., "Pyrrolysyl-tRNA synthetase: an ordinary enzyme but an outstanding genetic code expansion tool," Biochim Biophys Acta 1844(6): 1059-4070 (2014).

In some embodiments, an unnatural amino acid incorporated into an IL-15 polypeptide is disclosed in U.S. Pat. Nos. 9,840,493; 9,682,934; US 2017/0260137; U.S. Pat. No. 9,938,516; or US 2018/0086734. Exemplary UAAs that can be incorporated by such synthetases include para-methylazido-L-phenylalanine, aralkyl, heterocyclyl, and heteroaralkyl, and lysine derivative unnatural amino acids. In some embodiments, such UAAs comprise pyridyl, pyrazinyl, pyrazolyl, triazolyl, oxazolyl, thiazolyl, thiophenyl, or other heterocycle. Such amino acids in some embodiments comprise azides, tetrazines, or other chemical group capable of conjugation to a coupling partner, such as a water soluble moiety. In some embodiments, a UAA comprises an azide attached to an aromatic moiety via an alkyl linker. In some embodiments, an alkyl linker is a $C_1$-$C_{10}$ linker. In some embodiments, a UAA comprises a tetrazine attached to an aromatic moiety via an alkyl linker. In some embodiments, a UAA comprises a tetrazine attached to an aromatic moiety via an amino group. In some embodiments, a UAA comprises a tetrazine attached to an aromatic moiety via an alkylamino group. In some embodiments, a UAA comprises an azide attached to the terminal nitrogen (e.g., N6 of a lysine derivative, or N5, N4, or N3 of a derivative comprising a shorter alkyl side chain) of an amino acid side chain via an alkyl chain. In some embodiments, a UAA comprises a tetrazine attached to the terminal nitrogen of an amino acid side chain via an alkyl chain. In some embodiments, a UAA comprises an azide or tetrazine attached to an amide via an alkyl linker. In some embodiments, the UAA is an azide or tetrazine-containing carbamate or amide of 3-aminoalanine, serine, lysine, or derivative thereof. In some embodiments, such UAAs are incorporated into cytokines in-vivo. In some embodiments, such UAAs are incorporated into cytokines in a cell-free system.

Conjugating Moieties

In certain embodiments, disclosed herein are conjugating moieties that are bound to one or more modified IL-15 polypeptide described supra. In some embodiments, the conjugating moiety is a molecule that perturbs the interaction of IL-15 with its receptor. In some embodiments, the conjugating moiety is any molecule that when bond to IL-15, enables IL-15 conjugate to modulate an immune response. In some embodiments, the conjugating moiety is bound to the IL-15 through a covalent bond. In some instances, an IL-15 described herein is attached to a conjugating moiety with a triazole group. In some instances, an IL-15 described herein is attached to a conjugating moiety with a dihydropyridazine or pyridazine group. In some instances, the conjugating moiety comprises a water-soluble polymer. In other instances, the conjugating moiety comprises a protein or a binding fragment thereof. In additional instances, the conjugating moiety comprises a peptide. In additional instances, the conjugating moiety comprises a nucleic acid. In additional instances, the conjugating moiety comprises a small molecule. In additional instances, the conjugating moiety comprises a bioconjugate (e.g., a TLR agonist such as a TLR1, TLR2, TLR3, TLR4, TLR5, TLR6, TLR7, TLR8, or TLR9 agonist; or a synthetic ligand such as Pam3Cys, CFA, MALP2, Pam2Cys, FSL-1, Hib-OMPC, Poly I:C, poly A:U, AGP, MPL A, RC-529, MDF2β, CFA, or Flagellin). In some cases, the conjugating moiety increases serum half-life, and/or improves stability. In some cases, the conjugating moiety reduces cytokine interaction with one or more cytokine receptor domains or subunits. In additional cases, the conjugating moiety blocks IL-15 interaction with one or more IL-15 domains or subunits with its cognate receptor(s). In some embodiments, IL-15 conjugates described herein comprise multiple conjugating moieties. In some embodiments, a conjugating moiety is attached to an unnatural or natural amino acid in the IL-15 polypeptide. In some embodiments, an IL-15 conjugate comprises a conjugating moiety attached to a natural amino acid. In some embodiments, an IL-15 conjugate is attached to an unnatural amino acid in the cytokine peptide. In some embodiments, a conjugating moiety is attached to the N or C terminal amino acid of the IL-15 polypeptide. Various combinations sites are disclosed herein, for example, a first conjugating moiety is attached to an unnatural or natural amino acid in the IL-15 polypeptide, and a second conjugating moiety is attached to the N or C terminal amino acid of the IL-15 polypeptide. In some embodiments, a single conjugating moiety is attached to multiple residues of the IL-15 polypeptide (e.g. a staple). In some embodiments, a conjugating moiety is attached to both the N and C terminal amino acids of the IL-15 polypeptide.

Methods of Use

Proliferative Diseases or Conditions

In some embodiments, described herein is a method of treating a proliferative disease or condition in a subject in need thereof, which comprises administering to the subject a therapeutically effective amount of an IL-15 conjugate described herein. In some embodiments, the IL-15 conjugate comprises an isolated and purified IL-15 polypeptide and a conjugating moiety, wherein the IL-15 conjugate has a decreased affinity to an IL-15 receptor α (IL-15Rα) subunit relative to a wild-type IL-15 polypeptide. In some embodiments, the IL-15 conjugate comprises an isolated and purified IL-15 polypeptide; and a conjugating moiety that binds to the isolated and purified IL-15 polypeptide at an amino acid position selected from N, W2, V3, N4, I6, S7, D8, K10, K11, E13, D14, L15, Q17, S18, M19, H20, I21, D22, A23, T24, L25, Y26, T27, E28, S29, D30, V31, H32, P33, S34, C35, K36, V37, T38, A39, K41, L44, L45, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S14, wherein the numbering of the amino acid residues corresponds to SEQ ID NO: 1. In some embodiments, the IL-15 conjugate comprises an isolated and purified IL-15 polypeptide; and a conjugating moiety that binds to the isolated and purified IL-15 polypeptide at an amino acid position selected from N1, W2, V3, N4, I6, S7, D8, K10, K11, E13, D14, L15, Q17, S18, M19, H20, I21, D22, A23, T24, L25, Y26, E28, S29, D30, V31, H32, P33, S34, C35, K36, V37, T38, K41, L44, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S114.

In some embodiments, the IL-15 conjugate preferentially interact with the IL-15Rβ and IL-15Rβγ subunits to form an IL-15/IL-15Rβγ complex. In some embodiments, the IL-15/IL-15Rβγ complex stimulates and/or enhances expansion of Teff cells (e.g., CD8+ Teff cells) and/or NK cells. In additional cases, the expansion of Teff cells skews the Teff:Treg ratio toward the Teff population.

In some embodiments, the proliferative disease or condition is a cancer. In some embodiments, the cancer is a solid tumor. In some embodiments, an IL-15 conjugate described herein is administered to a subject in need thereof, for treating a solid tumor. In such cases, the subject has a bladder cancer, a bone cancer, a brain cancer, a breast cancer, a colorectal cancer, an esophageal cancer, an eye cancer, a head and neck cancer, a kidney cancer, a lung cancer, a melanoma, an ovarian cancer, a pancreatic cancer, or a prostate cancer. In some embodiments, the IL-15 conjugate is administered to a subject for the treatment of a bladder cancer. In some embodiments, the IL-15 conjugate is administered to a subject for the treatment of a breast cancer. In some embodiments, the IL-15 conjugate is administered to a subject for the treatment of a colorectal cancer. In some embodiments, the IL-15 conjugate is administered to a subject for the treatment of an esophageal cancer. In some embodiments, the IL-15 conjugate is administered to a subject for the treatment of a head and neck cancer. In some embodiments, the IL-15 conjugate is administered to a subject for the treatment of a kidney cancer. In some embodiments, the IL-15 conjugate is administered to a subject for the treatment of a lung cancer. In some embodiments, the IL-15 conjugate is administered to a subject for the treatment of a melanoma. In some embodiments, the IL-15 conjugate is administered to a subject for the treatment of an ovarian cancer. In some embodiments, the IL-15 conjugate is administered to a subject for the treatment of a pancreatic cancer. In some embodiments, the IL-15 conjugate is administered to a subject for the treatment of a prostate cancer. In some embodiments, the IL-15 conjugate is administered to a subject for the treatment of a metastatic cancer. In additional cases, the IL-15 conjugate is administered to a subject for the treatment of a relapsed or refractory cancer.

In some embodiments, the cancer is a hematologic malignancy. In some embodiments, an IL-15 conjugate described herein is administered to a subject in need thereof, for treating a hematologic malignancy. In some embodiments, the subject has chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the IL-15 conjugate is administered to a subject for the treatment of CLL. In some embodiments, the IL-15 conjugate is administered to a subject for the treatment of SLL. In some embodiments, the IL-15 conjugate is administered to a subject for the treatment of FL. In some embodiments, the IL-15 conjugate is administered to a subject for the treatment of DLBCL. In some embodiments, the IL-15 conjugate is administered to a subject for the treatment of MCL. In some embodiments, the IL-15 conjugate is administered to a subject for the treatment of Waldenstrom's macroglobulinemia. In some embodiments, the IL-15 conjugate is administered to a subject for the treatment of multiple myeloma. In some embodiments, the IL-15 conjugate is administered to a subject for the treatment of Burkitt's lymphoma. In some embodiments, the IL-15 conjugate is administered to a subject for the treatment of a metastatic hematologic malignancy. In additional cases, the IL-15 conjugate is administered to a subject for the treatment of a relapsed or refractory hematologic malignancy.

In some embodiments, an additional therapeutic agent is further administered to the subject. In some embodiments, the additional therapeutic agent is administered simultaneously with an IL-15 conjugate. In other cases, the additional therapeutic agent and the IL-15 conjugate are administered sequentially, e.g., the IL-15 conjugate is administered prior to the additional therapeutic agent or that the IL-15 conjugate is administered after administration of the additional therapeutic agent.

In some embodiments, the additional therapeutic agent comprises a chemotherapeutic agent, an immunotherapeutic agent, a targeted therapy, radiation therapy, or a combination thereof. Illustrative additional therapeutic agents include, but are not limited to, alkylating agents such as altretamine, busulfan, carboplatin, carmustine, chlorambucil, cisplatin, cyclophosphamide, dacarbazine, lomustine, melphalan, oxalaplatin, temozolomide, or thiotepa; antimetabolites such as 5-fluorouracil (5-FU), 6-mercaptopurine (6-MP), capecitabine, cytarabine, floxuridine, fludarabine, gemcitabine, hydroxyurea, methotrexate, or pemetrexed; anthracyclines such as daunorubicin, doxorubicin, epirubicin, or idarubicin; topoisomerase I inhibitors such as topotecan or irinotecan (CPT-11); topoisomerase II inhibitors such as etoposide (VP-16), teniposide, or mitoxantrone; mitotic inhibitors such as docetaxel, estramustine, ixabepilone, paclitaxel, vinblastine, vincristine, or vinorelbine; or corticosteroids such as prednisone, methylprednisolone, or dexamethasone.

In some cases, the additional therapeutic agent comprises a first-line therapy. As used herein, "first-line therapy" comprises a primary treatment for a subject with a cancer. In some instances, the cancer is a primary or local cancer. In other instances, the cancer is a metastatic or recurrent cancer. In some cases, the first-line therapy comprises chemotherapy. In other cases, the first-line treatment comprises immunotherapy, targeted therapy, or radiation therapy. A skilled artisan would readily understand that different first-line treatments may be applicable to different type of cancers.

In some embodiments, an IL-15 conjugate is administered with an additional therapeutic agent selected from an alkylating agent such as altretamine, busulfan, carboplatin, carmustine, chlorambucil, cisplatin, cyclophosphamide, dacarbazine, lomustine, melphalan, oxalaplatin, temozolomide, or thiotepa; an antimetabolite such as 5-fluorouracil (5-FU), 6-mercaptopurine (6-MP), capecitabine, cytarabine, floxuridine, fludarabine, gemcitabine, hydroxyurea, methotrexate, or pemetrexed; an anthracycline such as daunorubicin, doxorubicin, epirubicin, or idarubicin; a topoisomerase I inhibitor such as topotecan or irinotecan (CPT-11); a topoisomerase II inhibitor such as etoposide (VP-16), teniposide, or mitoxantrone; a mitotic inhibitor such as docetaxel, estramustine, ixabepilone, paclitaxel, vinblastine, vincristine, or vinorelbine; or a corticosteroid such as prednisone, methylprednisolone, or dexamethasone.

In some instances, an IL-15 conjugate described herein is administered with an inhibitor of the enzyme poly ADP ribose polymerase (PARP). Exemplary PARP inhibitors include, but are not limited to, olaparib (AZD-2281, Lynparza®, from Astra Zeneca), rucaparib (PF-01367338, Rubraca®, from Clovis Oncology), niraparib (MK-4827, Zejula®, from Tesaro), talazoparib (BMN-673, from BioMarin Pharmaceutical Inc.), veliparib (ABT-888, from AbbVie), CK-102 (formerly CEP 9722, from Teva Pharmaceutical Industries Ltd.), E7016 (from Eisai), iniparib (BSI 201, from Sanofi), and pamiparib (BGB-290, from BeiGene). In some cases, the IL-15 conjugate is administered in combination with a PARP inhibitor such as olaparib, rucaparib, niraparib, talazoparib, veliparib, CK-102, E7016, iniparib, or pamiparib.

In some embodiments, an IL-15 conjugate described herein is administered with a tyrosine kinase inhibitor (TKI). Exemplary TKIs include, but are not limited to, afatinib, alectinib, axitinib, bosutinib, cabozantinib, ceritinib, cobimetinib, crizotinib, dabrafenib, dasatinib, erlotinib, gefitinib, ibrutinib, imatinib, lapatinib, lenvatinib, nilotinib, nintedanib, osimertinib, pazopanib, ponatinib, regorafenib, ruxolitinib, sorafenib, sunitinib, tofacitinib, and vandetanib.

In some instances, an IL-15 conjugate described herein is administered with an immune checkpoint modulator. Exemplary checkpoint modulators include:

PD-L1 modulators such as Genentech's MPDL3280A (RG7446), Avelumab (Bavencio) from Merck/Pfizer, durvalumab (Imfinzi) from AstraZeneca, Anti-mouse PD-L1 antibody Clone 10F.9G2 (Cat #BE0101) from BioXcell, anti-PD-L1 monoclonal antibody MDX-1105 (BMS-936559), BMS-935559 and BMS-986192 from Bristol-Meyer's Squibb, MSB0010718C, mouse anti-PD-L1 Clone 29E.2A3, CX-072 from XytomX Therapeutics, FAZ053 from Novartis Pharmaceuticals, KN035 from 3D Medicine, LY3300054 from Eli Lilly, and AstraZeneca's MEDI4736;

PD-L2 modulators such as GlaxoSmithKline's AMP-224 (Amplimmune), and rHIgM12B7;

PD-1 modulators such as anti-mouse PD-1 antibody Clone J43 (Cat #BE0033-2) from BioXcell, anti-mouse PD-1 antibody Clone RMP1-14 (Cat #BE0146) from BioXcell, mouse anti-PD-1 antibody Clone EH12, Merck's MK-3475 anti-mouse PD-1 antibody (Keytruda, pembrolizumab, lambrolizumab), Anaptys-Bio's anti-PD-1 antibody known as ANB011, antibody MDX-1 106 (ONO-4538), Bristol-Myers Squibb's human IgG4 monoclonal antibody nivolumab (Opdivo®, BMS-936558, MDX1106), AstraZeneca's AMP-514 and AMP-224, sintilimab (IBI-308) from Eli Lilly/Innovent Biologics, AGEN 2034 from Agenus, BGB-A317 from BeiGene, B1-754091 from Boehringer-Ingelheim Pharmaceuticals, CBT-501 (genolimzumab) from CBT Pharmaceuticals, INCSHR1210 from Incyte, JNJ-63723283 from Janssen Research & Development, MEDI0680 from MedImmune, PDR001 from Novartis Pharmaceuticals, PF-06801591 from Pfizer, REGN2810 from Regeneron Pharmaceuticals, Pidilizumab (CT-011) from CureTech Ltd; and cemiplimab.

CTLA-4 modulators such as Bristol Meyers Squibb's anti-CTLA-4 antibody ipilimumab (also known as Yervoy®, MDX-010, BMS-734016 and MDX-101), anti-CTLA4 antibody clone 9H10 from Millipore, Pfizer's tremelimumab (CP-675,206, ticilimumab), AGEN 1884 from Agenus, and anti-CTLA4 antibody clone BNI3 from Abcam; LAG3 modulators such as anti-Lag-3 antibody clone eBioC9B7W (C9B7W) from eBioscience, anti-Lag3 antibody LS-B2237 from LifeSpan Biosciences, IMP701 and LAG525 from Novartis Pharmaceuticals, IMP321 (ImmuFact) from Immutep, anti-Lag3 antibody BMS-986016, BMS-986016 from Bristol-Myers Squibb, REGN3767 from Regeneron Pharmaceuticals, and the LAG-3 chimeric antibody A9H12;

B7-H3 modulators such as MGA271;

KIR modulators such as Lirilumab (IPH2101) from Bristol-Myers Squibb;

CD137 modulators such as urelumab (BMS-663513, Bristol-Myers Squibb), PF-05082566 (anti-4-1BB, PF-2566, Pfizer), or XmAb-5592 (Xencor);

PS modulators such as Bavituximab;

OX40 modulators such as BMS-986178 from Bristol-Myers Squibb, GSK3174998 from GlaxoSmithKline, INCAGN1949 from Agenus, MEDI0562 from MedImmune, PF-04518600 from Pfizer, or RG7888 from Genentech;

GITR modulators such as GWN323 from Novartis Pharmaceuticals, INCAGN1876 from Agenus, or TRX518 from Leap Therapeutics;

TIM3 modulators such as MBG453 from Novartis Pharmaceuticals, or TSR-042 from TESARO;

and modulators such as an antibody or fragments (e.g., a monoclonal antibody, a human, humanized, or chimeric antibody) thereof, RNAi molecules, or small molecules to CD52, CD30, CD20, CD33, CD27, ICOS, BTLA (CD272), CD160, 2B4, LAIR1, TIGHT, LIGHT, DR3, CD226, CD2, or SLAM.

In some instances, the IL-15 conjugate is administered in combination with pembrolizumab, nivolumab, tremelimumab, or ipilimumab.

In some instances, an IL-15 conjugate described herein is administered with an antibody such as alemtuzumab, trastuzumab, ibritumomab tiuxetan, brentuximab vedotin, ado-trastuzumab emtansine, or blinatumomab.

In some instances, an IL-15 conjugate is administered with an additional therapeutic agent selected from an anti-VEGFR antibody. Exemplary anti-VEGFR antibodies include, but are not limited to, bevacizumab or ramucirumab. In some instances, the IL-15 conjugate enhances the ADCC effect of the additional therapeutic agent.

In some instances, an IL-15 conjugate is administered with an additional therapeutic agent selected from cetuximab, imgatuzumab, matuzumab (EMD 72000), tomuzotuximab, or panitumumab. In some instances, the IL-15 conjugate enhances the ADCC effect of the additional therapeutic agent.

In some instances, an IL-15 conjugate is administered with an additional therapeutic agent selected from an additional cytokine (e.g., either a native cytokine or an engineered cytokine such as a PEGylated and/or fusion cytokine). In some instances, the additional cytokine enhances and/or synergizes T effector cell expansion and/or proliferation. In some cases, the additional cytokine comprises IL-1β, IL-2, IL-6, IL-7, IL-10, IL-12, IL-18, IL-21, or TNFα. In some cases, the additional cytokine is IL-2. In some cases, the additional cytokine is IL-21. In some cases, the additional cytokine is IL-10. In some cases, the additional cytokine is TNFα. In some embodiments, the IL-2 cytokine is selected from aldesleukin, NKTR-214, or THOR-707. In some embodiments, the IL-2 cytokine is aldesleukin. In some embodiments, the IL-2 cytokine is NKTR-214. In some embodiments, the IL-2 cytokine is THOR-707.

In some instances, an IL-15 conjugate is administered with an additional therapeutic agent selected from a receptor agonist. In some instances, the receptor agonist comprises a Toll-like receptor (TLR) ligand. In some cases, the TLR ligand comprises TLR1, TLR2, TLR3, TLR4, TLR5, TLR6, TLR7, TLR8, or TLR9. In some cases, the TLR ligand comprises a synthetic ligand such as, for example, Pam3Cys, CFA, MALP2, Pam2Cys, FSL-1, Hib-OMPC, Poly I:C, poly A:U, AGP, MPL A, RC-529, MDF2β, CFA, or Flagellin. In some cases, the IL-21 conjugate is administered with one or more TLR agonists selected from TLR1, TLR2, TLR3, TLR4, TLR5, TLR6, TLR7, TLR8, and TLR9. In some cases, the IL-15 conjugate is administered with one or more TLR agonists selected from Pam3Cys, CFA, MALP2, Pam2Cys, FSL-1, Hib-OMPC, Poly I:C, poly A:U, AGP, MPL A, RC-529, MDF2β, CFA, and Flagellin.

In some embodiments, an IL-15 conjugate described herein is used in conjunction with an adoptive T cell transfer (ACT) therapy. In one embodiment, ACT involves identification of autologous T lymphocytes in a subject with, e.g., anti-tumor activity, expansion of the autologous T lymphocytes in vitro, and subsequent reinfusion of the expanded T lymphocytes into the subject. In another embodiment, ACT comprises use of allogeneic T lymphocytes with, e.g., anti-tumor activity, expansion of the T lymphocytes in vitro, and subsequent infusion of the expanded allogeneic T lymphocytes into a subject in need thereof. In some embodiments, an IL-15 conjugate described herein is used in conjunction with an autologous T lymphocytes as part of an ACT therapy. In other instances, an IL-15 conjugate described herein is used in conjunction with an allogeneic T lymphocytes as part of an ACT therapy. In some embodiments, the IL-15 conjugate is administered simultaneously with the ACT therapy to a subject in need thereof. In other cases, the IL-15 conjugate is administered sequentially with the ACT therapy to a subject in need thereof.

In some embodiments, an IL-15 conjugate described herein is used for an ex vivo activation and/or expansion of an autologous and/or allogenic T cell transfer. In such cases, the IL-15 conjugate is used to activate and/or expand a sample comprising autologous and/or allogenic T cells and the IL-15 conjugate is optionally removed from the sample prior to administering the sample to a subject in need thereof.

In some embodiments, an IL-15 conjugate described herein is administered with a vaccine. In some instances, an IL-21 conjugate is utilized in combination with an oncolytic virus. In such cases, the IL-21 conjugate acts as a stimulatory agent to modulate the immune response. In some instances, the IL-21 conjugate is used with an oncolytic virus as part of an adjuvant therapy. Exemplary oncolytic viruses include T-Vec (Amgen), G47Δ (Todo et al.), JX-594 (Sillajen), CG0070 (Cold Genesys), and Reolysin (Oncolytics Biotech). In some cases, the IL-21 conjugate is used in combination with an oncolytic virus such as T-Vec, G47A, JX-594, CG0070, or Reolysin.

In some embodiments, an IL-15 conjugate is administered in combination with a radiation therapy.

In some embodiments, an IL-15 conjugate is administered in combination with anti-CD38 monoclonal antibodies. In some embodiments, the anti-CD38 antibody is daratumumab (Darzalex).

In some embodiments, an IL-15 conjugate is administered in combination with anti-CD20 antibodies. In some embodiments, the anti-CD20 antibody is rituximab.

Methods of Cell Population Expansion

In some embodiments, additionally described herein are methods of expanding lymphocyte populations, e.g., effector T (Teff) cell, memory T (Tmem) cell, and/or Natural Killer (NK) cell populations. In some embodiments, the method comprises contacting a cell with a cytokine conjugate described herein, and interacting the cytokine with a cytokine receptor to form a complex, wherein the complex stimulates expansion of a distinct lymphocyte population.

In some embodiments, the method of expanding effector T (Teff) cell, memory T (Tmem) cell, and/or Natural Killer (NK) cell populations, comprising: (a) contacting a cell with a modified IL-15 polypeptide or an IL-15 conjugate; and interacting the IL-15 with IL-15Rβ and IL-15Rγ subunits to form an IL-15/IL-15Rβγ complex; wherein the IL-15 conjugate has a decreased affinity to IL-15Rα subunit, and wherein the IL-15/IL-15Rβγ complex stimulates the expansion of Teff, Tmem, and NK cells. As described herein, in some embodiments, the modified IL-15 polypeptide comprise at least one post-translationally modified unnatural amino acid at a residue position selected from N1, W2, V3, N4, I6, S7, D8, K10, K11, E13, D14, L15, Q17, S18, M19, H20, I21, D22, A23, T24, L25, Y26, T27, E28, S29, D30, V31, H32, P33, S34, C35, K36, V37, T38, A39, K41, L44, L45, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S14, wherein the residue positions correspond to the positions as set forth in SEQ ID NO: 1. In some embodiments, the residue position is selected from N1, W2, V3, N4, I6, S7, D8, K10, K11, E13, D14, L15, Q17, S18, M19, H20, I21, D22, A23, T24, L25, Y26, E28, S29, D30, V31, H32, P33, S34, C35, K36, V37, T38, K41, L44, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S114. In some embodiments, the residue position is selected from E13, D14, L15, Q17, S18, M19, H20, I21, S34, C35, K36, V37, T38, K41, L44, S51, L52, S54, G55, D56, A57, S58, H60, V63, I67, N71, S73, L74, S75, S76, N77, G78, N79, V80, T81, E82, S83, G84, C85, K86, E87, C88, L91, E92, K94, N95, I96, K97, E98, L100, Q101, and F110. In some embodiments, the residue position is selected from D14, Q17, S18, K41, S51, L52, G55, D56, A57, S58, S75, S76, N77, N79, V80, T81, S83, G84, E92, K94, N95, K97, and E98. In some embodiments, the residue position is selected from N, N4, S7, D8, Ki1, D61, T62, E64, N65, I168, L69, and N72. In some embodiments, the residue position is selected from V3, I6, K10, E28, S29, D30, V31, H32, P33, S102, V104, H105, Q108, M109, I111, N112, T113, and S114. In some embodiments, the residue position is selected from D22, A23, T24, L25, Y26, L44, E46, Q48, V49, E53, E89, E90, and E93. In some embodiments, the residue position is selected from Y26, E46, V49, E53, and L25. In some embodiments, the residue position is selected from V3, K10, S29, D30, H32, H105, Q108, M109, I111, N112, T113, and S114. In some embodiments, the residue position is selected from N4, S7, K11, and D61. In some embodiments, the residue position is selected from L25, E53, N77, and S83. In some embodiments, the residue position is selected from L25 and E53. In some embodiments, the residue position is selected from E46, Y26, V49, E53, T24, N4, K11, N65, L69, S18, H20, and S83. In some embodiments, the residue position is selected from E46, Y26, V49, E53, and T24. In some embodiments, the residue position is selected from E46, V49, E53, and T24. In some embodiments, the residue position is selected from Y26, V49, E53, and T24. In some embodiments, the residue position is selected from V49, E53, and T24. In some embodiments, the residue position is selected from E46 and Y26. In some embodiments, the residue position is E46. In some embodiments, the residue position is L25. In some embodiments, the residue position is Y26. In some embodiments, the residue position is V49. In some embodiments, the residue position is E53. In some embodiments, the residue position is T24. In some embodiments, the residue position is N77. In some embodiments, the residue position is S83.

Methods of expanding effector T (Teff) cell, memory T (Tmem) cells, and/or Natural Killer (NK) cell populations as described herein, in some embodiments, comprise contacting a cell with an IL-15 conjugate. As described herein, in some embodiments, the interleukin 15 (IL-15) conjugates comprise: an isolated and purified IL-15 polypeptide; and a conjugating moiety that binds to the isolated and purified IL-15 polypeptide at an amino acid position selected from N1, W2, V3, N4, I6, S7, D8, K10, K11, E13, D14, L15, Q17, S18, M19, H20, I21, D22, A23, T24, L25, Y26, T27, E28, S29, D30, V31, H32, P33, S34, C35, K36, V37, T38, A39, K41, L44, L45, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T113, and S114, wherein the residue positions correspond to the positions as set forth in SEQ ID NO: 1. In some embodiments, the residue position is selected from N1, W2, V3, N4, I6, S7, D8, K10, K11, E13, D14, L15, Q17, S18, M19, H20, I21, D22, A23, T24, L25, Y26, E28, S29, D30, V31, H32, P33, S34, C35, K36, V37, T38, K41, L44, E46, Q48, V49, S51, L52, E53, S54, G55, D56, A57, S58, H60, D61, T62, V63, E64, N65, I67, I68, L69, N71, N72, S73, L74, S75, S76, N77, G78, N79, V80, T81, E82, S83, G84, C85, K86, E87, C88, E89, E90, L91, E92, E93, K94, N95, I96, K97, E98, L100, Q101, S102, V104, H105, Q108, M109, F110, I111, N112, T13, and S114. In some embodiments, the residue position is selected from E13, D14, L15, Q17, S18, M19, H20, I21, S34, C35, K36, V37, T38, K41, L44, S51, L52, S54, G55, D56, A57, S58, H60, V63, I67, N71, S73, L74, S75, S76, N77, G78, N79, V80, T81, E82, S83, G84, C85, K86, E87, C88, L91, E92, K94, N95, I96, K97, E98, L100, Q101, and F110. In some embodiments, the residue position is selected from D14, Q17, S18, K41, S51, L52, G55, D56, A57, S58, S75, S76, N77, N79, V80, T81, S83, G84, E92, K94, N95, K97, and E98. In some embodiments, the residue position is selected from N1, N4, S7, D8, K11, D61, T62, E64, N65, I68, L69, and N72. In some embodiments, the residue position is selected from V3, I6, K10, E28, S29, D30, V31, H32, P33, S102, V104, H105, Q108, M109, I111, N112, T113, and S14. In some embodiments, the residue position is selected from D22, A23, T24, L25, Y26, L44, E46, Q48, V49, E53, E89, E90, and E93. In some embodiments, the residue position is selected from Y26, E46, V49, E53, and L25. In some embodiments, the residue position is selected from V3, K10, S29, D30, H32, H105, Q108, M109, I111, N112, T113, and S114. In some embodiments, the residue position is selected from N4, S7, K11, and D61. In some embodiments, the residue position is selected from L25, E53, N77, and S83. In some embodiments, the residue position is selected from L25 and E53. In some embodiments, the residue position is selected from E46, Y26, V49, E53, T24, N4, K11, N65, L69, S18, H20, and S83. In some embodiments, the residue position is selected from E46, Y26, V49, E53, and T24. In some embodiments, the residue position is selected from E46, V49, E53, and T24. In some embodiments, the residue position is selected from Y26, V49, E53, and T24. In some embodiments, the residue position is selected from V49, E53, and T24. In some embodiments, the residue position is selected from E46 and Y26. In some embodiments, the residue position is E46. In some embodiments, the residue position is L25. In some embodiments, the residue position is Y26. In some embodiments, the residue position is V49. In some embodiments, the residue position is E53. In some embodiments, the residue position is T24. In some embodiments, the residue position is N77. In some embodiments, the residue position is S83.

Conjugation Chemistry

Various conjugation reactions are used to conjugate linkers, conjugation moieties, and unnatural amino acids incorporated into cytokine peptides described herein. Such conjugation reactions are often compatible with aqueous conditions, such as "bioorthogonal" reactions. In some embodiments, conjugation reactions are mediated by chemical reagents such as catalysts, light, or reactive chemical groups found on linkers, conjugation moieties, or unnatural amino acids. In some embodiments, conjugation reactions are mediated by enzymes. In some embodiments, a conjugation reaction used herein is described in Gong, Y., Pan, L. Tett. Lett. 2015, 56, 2123. In some embodiments, a conjugation reaction used herein is described in Chen, X.; Wu. Y-W. Org. Biomol. Chem. 2016, 14, 5417.

In some embodiments described herein, a conjugation reaction described herein comprises a 1,3-dipolar cycloaddition reaction. In some embodiments, the 1,3-dipolar cycloaddition reaction comprises reaction of an azide and a phosphine ("Click" reaction). In some embodiments, the conjugation reaction is catalyzed by copper. In some embodiments, a conjugation reaction described herein results in cytokine peptide comprising a linker or conjugation moiety attached via a triazole. In some embodiments, a conjugation reaction described herein comprises reaction of an azide with a strained olefin. In some embodiments, a conjugation reaction described herein comprises reaction of an azide with a strained alkyne. In some embodiments, a conjugation reaction described herein comprises reaction of an azide with a cycloalkyne, for example DBCO.

In some embodiments described herein, a conjugation reaction described herein comprises:

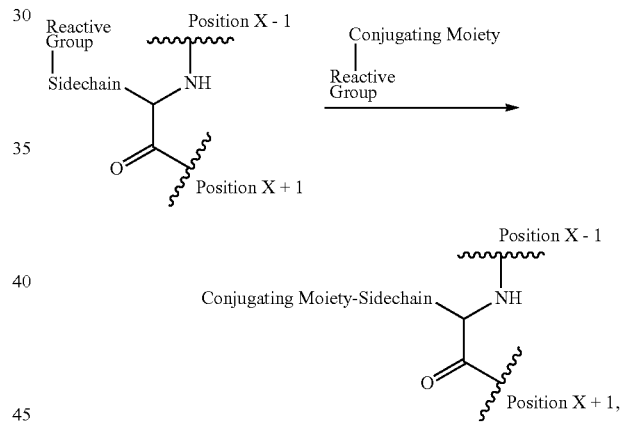

wherein X is the position in the IL-15 conjugate comprising an unnatural amino acid, such as in any one of SEQ ID NOS: 4 to 9 and 52 to 57. In some embodiments, the conjugating moiety comprises water soluble polymer. In some embodiments, a reactive group comprises an alkyne or azide. In some embodiments described herein, a conjugation reaction described herein comprises:

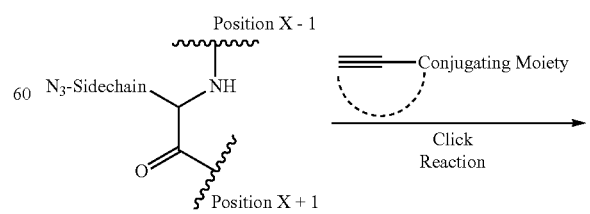

157
-continued

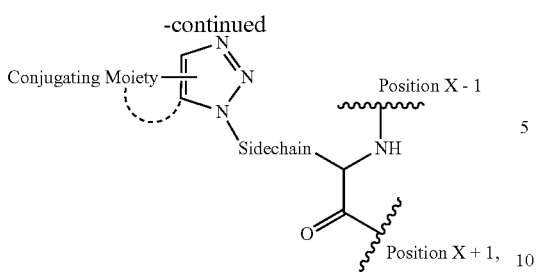

158
-continued

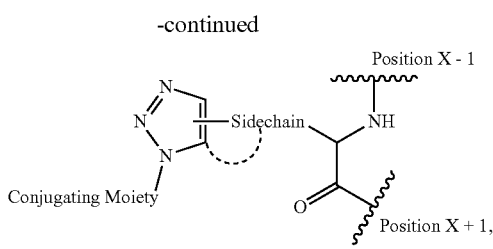

wherein X is the position in the IL-15 conjugate comprising an unnatural amino acid, such as in any one of SEQ ID NOS: 4 to 9 and 52 to 57. In some embodiments described herein, a conjugation reaction described herein comprises:

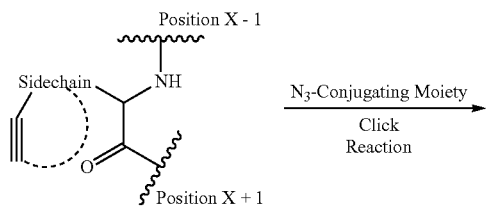

wherein X is the position in the IL-15 conjugate comprising an unnatural amino acid, such as in any one of SEQ ID NOS: 4 to 9 and 52 to 57. In some embodiments described herein, a conjugation reaction described herein comprises:

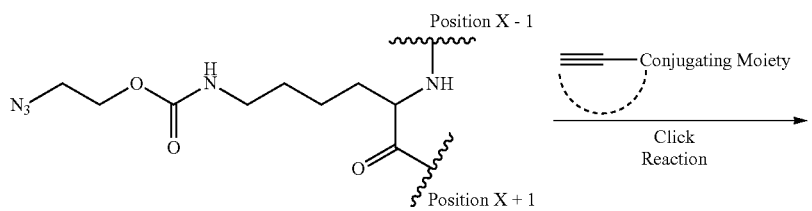

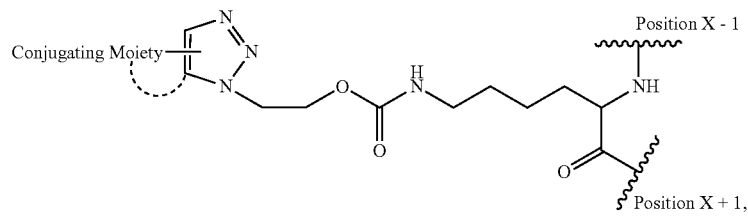

wherein X is the position in the IL-15 conjugate comprising an unnatural amino acid, such as in any one of SEQ ID NOS: 4 to 9 and 52 to 57.

In some embodiments described herein, a conjugation reaction described herein comprises are cycloaddition reaction between an azide moiety, such as that contained in a protein containing an amino acid residue derived from N6-((2-azidoethoxy)-carbonyl)-L-lysine (AzK), and a strained cycloalkyne, such as that derived from DBCO, which is a chemical moiety comprising a dibenzocyclooctyne group. PEG groups comprising a DBCO moiety are commercially available or may be prepared by methods know to those of ordinary skill in the art.

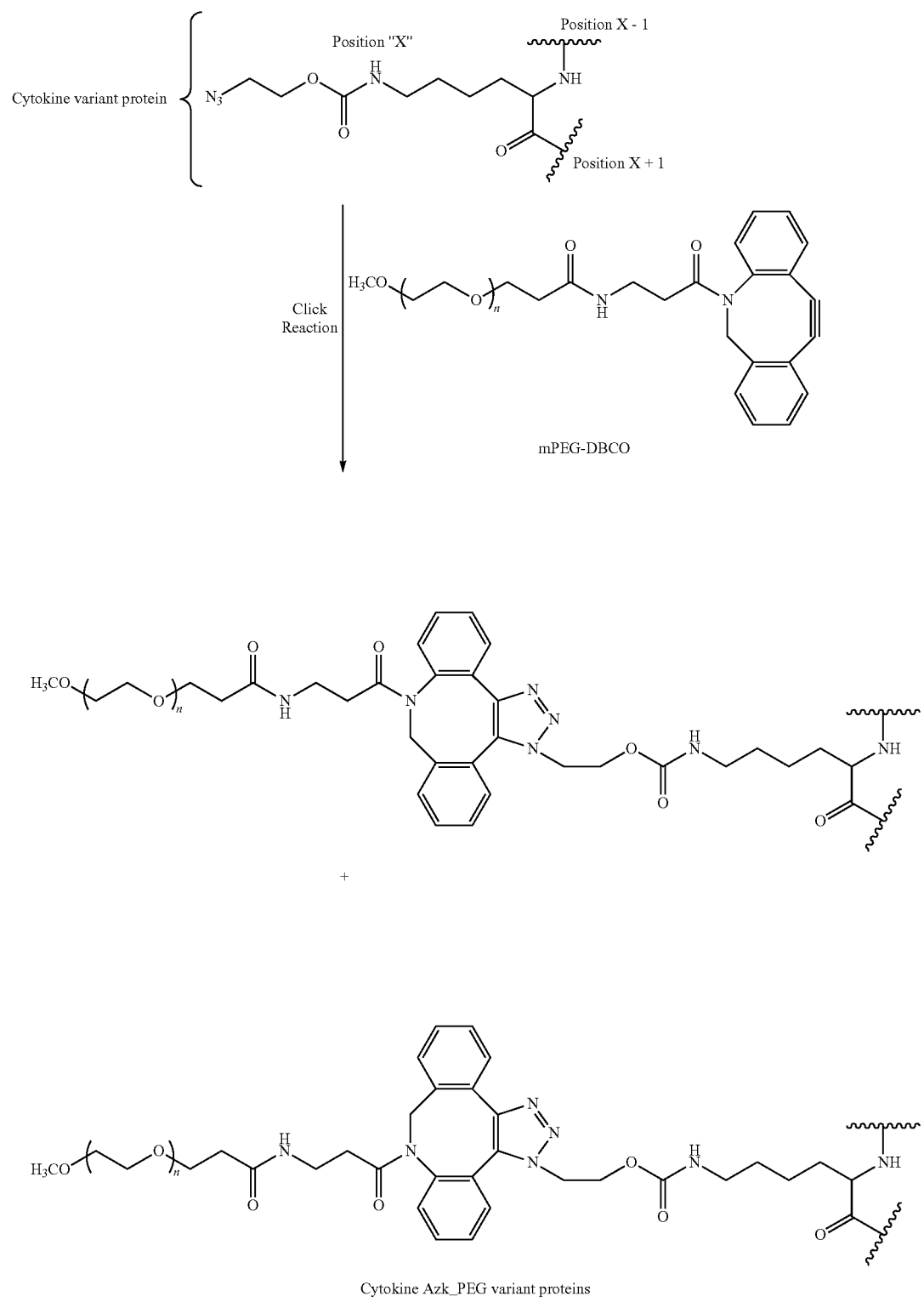

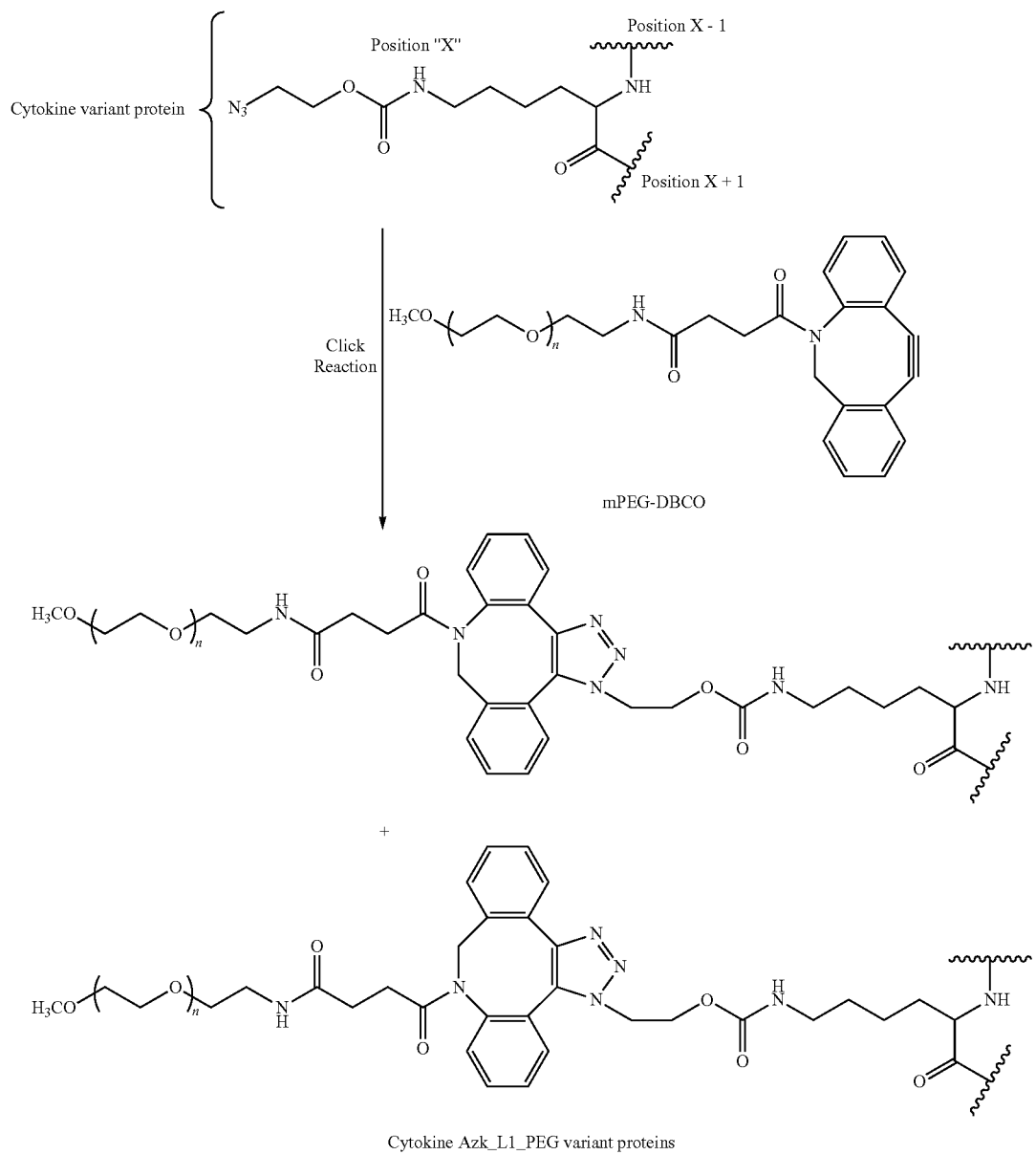

Conjugation reactions such as a click reaction described herein may generate a single regioisomer, or a mixture of regioisomers. In some instances the ratio of regioisomers is about 1:1. In some instances the ratio of regioisomers is about 2:1. In some instances the ratio of regioisomers is about 1.5:1. In some instances the ratio of regioisomers is about 1.2:1. In some instances the ratio of regioisomers is about 1.1:1. In some instances the ratio of regioisomers is greater than 1:1.

Cytokine Polypeptide Production

In some instances, the IL-15 conjugates described herein, either containing a natural amino acid mutation or an unnatural amino acid mutation, are generated recombinantly or are synthesized chemically. In some instances, IL-15 conjugates described herein are generated recombinantly, for example, either by a host cell system, or in a cell-free system.

In some instances, IL-15 conjugates are generated recombinantly through a host cell system. In some cases, the host cell is a eukaryotic cell (e.g., mammalian cell, insect cells, yeast cells or plant cell) or a prokaryotic cell (e.g., gram-positive bacterium or a gram-negative bacterium). In some cases, a eukaryotic host cell is a mammalian host cell. In some cases, a mammalian host cell is a stable cell line, or a cell line that has incorporated a genetic material of interest into its own genome and has the capability to express the product of the genetic material after many generations of cell division. In other cases, a mammalian host cell is a transient cell line, or a cell line that has not incorporated a genetic material of interest into its own genome and does not have the capability to express the product of the genetic material after many generations of cell division.

Exemplary mammalian host cells include 293T cell line, 293A cell line, 293FT cell line, 293F cells, 293 H cells, A549 cells, MDCK cells, CHO DG44 cells, CHO-S cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line.

In some embodiments, an eukaryotic host cell is an insect host cell. Exemplary insect host cell include *Drosophila* S2 cells, Sf9 cells, Sf21 cells, High Five™ cells, and expresSF+® cells.

In some embodiments, a eukaryotic host cell is a yeast host cell. Exemplary yeast host cells include *Pichia pastoris* yeast strains such as GS115, KM71H, SMD1168, SMD1168H, and X-33, and *Saccharomyces cerevisiae* yeast strain such as INVSc1.

In some embodiments, an eukaryotic host cell is a plant host cell. In some instances, the plant cells comprise a cell from algae. Exemplary plant cell lines include strains from *Chlamydomonas reinhardtii* 137c, or *Synechococcus elongatus* PPC 7942.

In some embodiments, a host cell is a prokaryotic host cell. Exemplary prokaryotic host cells include BL21, Mach1™, DH10B™, TOP10, DH5α, DH10Bac™, Omni-Max™, MegaX™, DH12S™, INV110, TOP10F', INVαF, TOP10/P3, ccdB Survival, PIR1, PIR2, Stbl2™, Stbl3™ or Stbl4™.

In some instances, suitable polynucleic acid molecules or vectors for the production of an IL-2 polypeptide described herein include any suitable vectors derived from either a eukaryotic or prokaryotic source. Exemplary polynucleic acid molecules or vectors include vectors from bacteria (e.g., *E. coli*), insects, yeast (e.g., *Pichia pastoris*), algae, or mammalian source. Bacterial vectors include, for example, pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Insect vectors include, for example, pFastBac1, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

Yeast vectors include, for example, Gateway® pDEST™ 14 vector, Gateway® pDEST™ 15 vector, Gateway® pDEST™ 17 vector, Gateway pDEST™ 24 vector, Gateway® pYES-DEST52 vector, pBAD-DEST49 Gateway® destination vector, pAO815 *Pichia* vector, pFLD1 *Pichi pastoris* vector, pGAPZA, B, & C *Pichia pastoris* vector, pPIC3.5K *Pichia* vector, pPIC6 A, B, & C *Pichia* vector, pPIC9K *Pichia* vector, pTEFI/Zeo, pYES2 yeast vector, pYES2/CT yeast vector, pYES2/NT A, B, & C yeast vector, or pYES3/CT yeast vector.

Algae vectors include, for example, pChlamy-4 vector or MCS vector.

Mammalian vectors include, for example, transient expression vectors or stable expression vectors. Exemplary mammalian transient expression vectors include p3×FLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3×FLAG-CMV 7.1, pFLAG-CMV 20, p3×FLAG-Myc-CMV 24, pCMV-FLAG-MAT1, pCMV-FLAG-MAT2, pBICEP-CMV 3, or pBICEP-CMV 4. Exemplary mammalian stable expression vectors include pFLAG-CMV 3, p3×FLAG-CMV 9, p3×FLAG-CMV 13, pFLAG-Myc-CMV 21, p3×FLAG-Myc-CMV 25, pFLAG-CMV 4, p3×FLAG-CMV 10, p3×FLAG-CMV 14, pFLAG-Myc-CMV 22, p3×FLAG-Myc-CMV 26, pBICEP-CMV 1, or pBICEP-CMV 2.

In some instances, a cell-free system is used for the production of a cytokine (e.g., IL-15) polypeptide described herein. In some cases, a cell-free system comprises a mixture of cytoplasmic and/or nuclear components from a cell and is suitable for in vitro nucleic acid synthesis. In some instances, a cell-free system utilizes prokaryotic cell components. In other instances, a cell-free system utilizes eukaryotic cell components. Nucleic acid synthesis obtained in a cell-free system based on, for example, *Drosophila* cell, *Xenopus* egg, *Archaea*, or HeLa cells. Exemplary cell-free systems include *E. coli* S30 Extract system, *E. coli* T7 S30 system, or PURExpress®, XpressCF, and XpressCF+.

Production of Cytokine Polypeptide Comprising an Unnatural Amino Acid

An orthogonal or expanded genetic code can be used in the present disclosure, in which one or more specific codons present in the nucleic acid sequence of a cytokine (e.g., IL-15) polypeptide are allocated to encode the unnatural amino acid so that it can be genetically incorporated into the cytokine (e.g., IL-15) by using an orthogonal tRNA synthetase/tRNA pair. The orthogonal tRNA synthetase/tRNA pair is capable of charging a tRNA with an unnatural amino acid and is capable of incorporating that unnatural amino acid into the polypeptide chain in response to the codon.

In some instances, the codon is the codon amber, ochre, opal or a quadruplet codon. In some cases, the codon corresponds to the orthogonal tRNA which will be used to carry the unnatural amino acid. In some cases, the codon is amber. In other cases, the codon is an orthogonal codon.

In some instances, the codon is a quadruplet codon, which can be decoded by an orthogonal ribosome ribo-Q. In some cases, the quadruplet codon is as illustrated in Neumann, et al., "Encoding multiple unnatural amino acids via evolution of a quadruplet-decoding ribosome," Nature, 464(7287): 441-444 (2010).

In some instances, a codon used in the present disclosure is a recoded codon, e.g., a synonymous codon or a rare codon that is replaced with alternative codon. In some cases, the recoded codon is as described in Napolitano, et al., "Emergent rules for codon choice elucidated by editing rare arginine codons in *Escherichia coli*," PNAS, 113(38): E5588-5597 (2016). In some cases, the recoded codon is as described in Ostrov et al., "Design, synthesis, and testing toward a 57-codon genome," Science 353(6301): 819-822 (2016).

In some instances, unnatural nucleic acids are utilized leading to incorporation of one or more unnatural amino acids into the cytokine (e.g., IL-15). Exemplary unnatural nucleic acids include, but are not limited to, uracil-5-yl, hypoxanthin-9-yl (I), 2-aminoadenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain unnatural nucleic acids, such as 5-substituted pyrimidines, 6-azapyrimidines and N-2 substituted purines, N-6 substituted purines, 0-6 substituted purines, 2-aminopropyladenine, 5-propynyluracil, 5-propynylcytosine, 5-methylcytosine, those that increase the stability of duplex formation, universal nucleic acids, hydrophobic nucleic acids, promiscuous nucleic acids, size-expanded nucleic acids, fluorinated nucleic acids, 5-substituted pyrimidines, 6-azapyrimidines and N-2, N-6 and 0-6 substituted purines, including 2-aminopropyladenine, 5-propynyluracil and 5-propynylcytosine. 5-methylcytosine (5-me-C), 5-hydroxymethyl cytosine, xanthine, hypoxanthine, 2-aminoadenine, 6-methyl, other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl (—C≡C—CH3) uracil, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyladenine, 2-F-adenine, 2-amino-adenine, 8-azaguanine, 8-azaadenine, 7-deazaguanine, 7-deazaadenine, 3-deazaguanine, 3-deazaadenine, tricyclic pyrimidines, phenoxazine cytidine ([5,4-b][1,4]benzoxazin-2(3H)-one), phenothiazine cytidine (1H-pyrimido[5,4-b][1,4]benzothiazin-2(3H)-one), G-clamps, phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one), those in which the purine or pyrimidine base is replaced with other heterocycles, 7-deaza-adenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 2-amino-adenine, 6-thio-guanine, 2-thio-thymine, 4-thio-thymine, 5-propynyl-uracil, 4-thiouracil, N4-ethylcytosine, 7-deazaguanine, 7-deaza-8-azaguanine, 5-hydroxycytosine, 2'-deoxyuridine, 2-amino-2'-deoxyadenosine, and those described in U.S. Pat. Nos. 3,687,808; 4,845,205; 4,910,300; 4,948,882; 5,093,232; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096; WO 99/62923; Kandimalla et al., (2001) Bioorg. Med. Chem. 9:807-813; The Concise Encyclopedia of Polymer Science and Engineering, Kroschwitz, J. I., Ed., John Wiley & Sons, 1990, 858-859; Englisch et al., Angewandte Chemie, International Edition, 1991, 30, 613; and Sanghvi, Chapter 15, Antisense Research and Applications, Crooke and Lebleu Eds., CRC Press, 1993, 273-288. Additional base modifications can be found, for example, in U.S. Pat. No. 3,687,808; Englisch et al., Angewandte Chemie, International Edition, 1991, 30, 613; and Sanghvi, Chapter 15, Antisense Research and Applications, pages 289-302, Crooke and Lebleu ed., CRC Press, 1993.

Unnatural nucleic acids comprising various heterocyclic bases and various sugar moieties (and sugar analogs) are available in the art, and the nucleic acids in some cases include one or several heterocyclic bases other than the principal five base components of naturally-occurring nucleic acids. For example, the heterocyclic base includes, in some cases, uracil-5-yl, cytosin-5-yl, adenin-7-yl, adenin-8-yl, guanin-7-yl, guanin-8-yl, 4-aminopyrrolo [2.3-d] pyrimidin-5-yl, 2-amino-4-oxopyrolo [2, 3-d] pyrimidin-5-yl, 2-amino-4-oxopyrrolo [2.3-d] pyrimidin-3-yl groups, where the purines are attached to the sugar moiety of the nucleic acid via the 9-position, the pyrimidines via the 1-position, the pyrrolopyrimidines via the 7-position and the pyrazolopyrimidines via the 1-position.

In some embodiments, nucleotide analogs are also modified at the phosphate moiety. Modified phosphate moieties include, but are not limited to, those with modification at the linkage between two nucleotides and contains, for example, a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides are through a 3'-5' linkage or a 2'-5' linkage, and the linkage contains inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

In some embodiments, unnatural nucleic acids include 2',3'-dideoxy-2',3'-didehydro-nucleosides (PCT/US2002/006460), 5'-substituted DNA and RNA derivatives (PCT/US2011/033961; Saha et al., J. Org Chem., 1995, 60, 788-789; Wang et al., Bioorganic & Medicinal Chemistry Letters, 1999, 9, 885-890; and Mikhailov et al., Nucleosides & Nucleotides, 1991, 10(1-3), 339-343; Leonid et al., 1995, 14(3-5), 901-905; and Eppacher et al., Helvetica Chimica Acta, 2004, 87, 3004-3020; PCT/JP2000/004720; PCT/JP2003/002342; PCT/JP2004/013216; PCT/JP2005/020435; PCT/JP2006/315479; PCT/JP2006/324484; PCT/JP2009/056718; PCT/JP2010/067560), or 5'-substituted monomers made as the monophosphate with modified bases (Wang et al., Nucleosides Nucleotides & Nucleic Acids, 2004, 23 (1 & 2), 317-337).

In some embodiments, unnatural nucleic acids include modifications at the 5'-position and the 2'-position of the sugar ring (PCT/US94/02993), such as 5'-CH$_2$-substituted 2'-O-protected nucleosides (Wu et al., Helvetica Chimica Acta, 2000, 83, 1127-1143 and Wu et al., Bioconjugate Chem. 1999, 10, 921-924). In some cases, unnatural nucleic acids include amide linked nucleoside dimers have been prepared for incorporation into oligonucleotides wherein the 3' linked nucleoside in the dimer (5' to 3') comprises a 2'-OCH$_3$ and a 5'-(S)—CH$_3$ (Mesmaeker et al., Synlett, 1997, 1287-1290). Unnatural nucleic acids can include 2'-substituted 5'-CH$_2$ (or O) modified nucleosides (PCT/US92/01020). Unnatural nucleic acids can include 5'-methylenephosphonate DNA and RNA monomers, and dimers (Bohringer et al., Tet. Lett., 1993, 34, 2723-2726; Collingwood et al., Synlett, 1995, 7, 703-705; and Hutter et al., Helvetica Chimica Acta, 2002, 85, 2777-2806). Unnatural nucleic acids can include 5'-phosphonate monomers having a 2'-substitution (US2006/0074035) and other modified 5'-phosphonate monomers (WO1997/35869). Unnatural nucleic acids can include 5'-modified methylenephosphonate monomers (EP614907 and EP629633). Unnatural nucleic acids can include analogs of 5' or 6'-phosphonate ribonucleosides comprising a hydroxyl group at the 5' and/or 6'-position (Chen et al., Phosphorus, Sulfur and Silicon, 2002, 777, 1783-1786; Jung et al., Bioorg. Med. Chem., 2000, 8, 2501-2509; Gallier et al., Eur. J. Org. Chem., 2007, 925-933; and Hampton et al., J. Med. Chem., 1976, 19(8), 1029-1033). Unnatural nucleic acids can include 5'-phosphonate deoxyribonucleoside monomers and dimers having a 5'-phosphate group (Nawrot et al., Oligonucleotides, 2006, 16(1), 68-82). Unnatural nucleic acids can include nucleosides having a 6'-phosphonate group wherein the 5' or/and 6'-position is unsubstituted or substituted with a thio-tert-butyl group ($SC(CH_3)_3$) (and analogs thereof); a methyleneamino group ($CH_2NH_2$) (and analogs thereof) or a cyano group (CN) (and analogs thereof) (Fairhurst et al., Synlett, 2001, 4, 467-472; Kappler et al., J. Med. Chem., 1986, 29, 1030-1038; Kappler et al., J. Med. Chem., 1982, 25, 1179-1184; Vrudhula et al., J. Med. Chem., 1987, 30, 888-894; Hampton et al., J. Med. Chem., 1976, 19, 1371-1377; Geze et al., J. Am. Chem. Soc, 1983, 105(26), 7638-7640; and Hampton et al., J. Am. Chem. Soc, 1973, 95(13), 4404-4414).

In some embodiments, unnatural nucleic acids also include modifications of the sugar moiety. In some cases, nucleic acids contain one or more nucleosides wherein the sugar group has been modified. Such sugar modified nucleosides may impart enhanced nuclease stability, increased binding affinity, or some other beneficial biological property. In certain embodiments, nucleic acids comprise a chemically modified ribofuranose ring moiety. Examples of chemically modified ribofuranose rings include, without limitation, addition of substituent groups (including 5' and/or 2' substituent groups; bridging of two ring atoms to form bicyclic nucleic acids (BNA); replacement of the ribosyl ring oxygen atom with S, N(R), or C(R1)(R2) (R=H, C1-C12 alkyl or a protecting group); and combinations thereof. Examples of chemically modified sugars can be found in WO2008/101157, US2005/0130923, and WO2007/134181.

In some instances, a modified nucleic acid comprises modified sugars or sugar analogs. Thus, in addition to ribose and deoxyribose, the sugar moiety can be pentose, deoxypentose, hexose, deoxyhexose, glucose, arabinose, xylose, lyxose, or a sugar "analog" cyclopentyl group. The sugar can be in a pyranosyl or furanosyl form. The sugar moiety may be the furanoside of ribose, deoxyribose, arabinose or 2'-O-alkylribose, and the sugar can be attached to the respective heterocyclic bases either in [alpha] or [beta] anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification may include 2'-O-methyl-uridine or 2'-O-methyl-cytidine. Sugar modifications include 2'-O-alkyl-substituted deoxyribonucleosides and 2'-O-ethyleneglycol like ribonucleosides. The preparation of these sugars or sugar analogs and the respective "nucleosides" wherein such sugars or analogs are attached to a heterocyclic base (nucleic acid base) is known. Sugar modifications may also be made and combined with other modifications.

Modifications to the sugar moiety include natural modifications of the ribose and deoxy ribose as well as unnatural modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' sugar modifications also include but are not limited to —O[$(CH_2)_n$O]$_m$CH$_3$, —O($CH_2)_n$OCH$_3$, —O($CH_2)_n$NH$_2$, —O($CH_2)_n$CH$_3$, —O($CH_2)_n$ONH$_2$, and —O($CH_2)_n$ON[($CH_2)_n$CH$_3$)]$_2$, where n and m are from 1 to about 10.

Other modifications at the 2' position include but are not limited to: C1 to C10 lower alkyl, substituted lower alkyl, alkaryl, aralkyl, O-alkaryl, O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of the 5' terminal nucleotide. Modified sugars also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures and which detail and describe a range of base modifications, such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,700,920, each of which is herein incorporated by reference in its entirety.

Examples of nucleic acids having modified sugar moieties include, without limitation, nucleic acids comprising 5'-vinyl, 5'-methyl (R or S), 4'-S, 2'-F, 2'-OCH$_3$, and 2'-O(CH$_2$)$_2$OCH$_3$ substituent groups. The substituent at the 2' position can also be selected from allyl, amino, azido, thio, O-allyl, O—(C$_1$-C$_{10}$ alkyl), OCF$_3$, O(CH$_2$)$_2$SCH$_3$, O(CH$_2$)$_2$—O—N(R$_m$)(R$_n$), and O—CH$_2$—C(=O)—N(R$_m$)(R$_n$), where each R$_m$ and R$_n$ is, independently, H or substituted or unsubstituted C$_1$-C$_{10}$ alkyl.

In certain embodiments, nucleic acids described herein include one or more bicyclic nucleic acids. In certain such embodiments, the bicyclic nucleic acid comprises a bridge between the 4' and the 2' ribosyl ring atoms. In certain embodiments, nucleic acids provided herein include one or more bicyclic nucleic acids wherein the bridge comprises a 4' to 2' bicyclic nucleic acid. Examples of such 4' to 2' bicyclic nucleic acids include, but are not limited to, one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2', and analogs thereof (see, U.S. Pat. No. 7,399,845); 4'-C(CH$_3$)(CH$_3$)—O-2' and analogs thereof, (see WO2009/006478, WO2008/150729, US2004/0171570, U.S. Pat. No. 7,427,672, Chattopadhyaya et al., J. Org. Chem., 209, 74, 118-134, and WO2008/154401). Also see, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129(26) 8362-8379; Elayadi et al., Curr. Opinion Invens. Drugs, 2001, 2, 558-561; Braasch et al., Chem. Biol, 2001, 8, 1-7; Oram et al., Curr. Opinion Mol. Ther., 2001, 3, 239-243; U.S. Pat. Nos. 4,849,513; 5,015,733; 5,118,800; 5,118,802; 7,053,207; 6,268,490; 6,770,748; 6,794,499; 7,034,133; 6,525,191; 6,670,461; and 7,399,845; International Publication Nos. WO2004/106356, WO1994/14226, WO2005/021570, WO2007/090071, and WO2007/134181; U.S. Patent Publication Nos. US2004/0171570, US2007/0287831, and US2008/0039618; U.S. Provisional Application Nos. 60/989,574, 61/026,995, 61/026,998, 61/056,564, 61/086,231, 61/097,787, and 61/099,844; and International Applications Nos. PCT/US2008/064591, PCT US2008/066154, PCT US2008/068922, and PCT/DK98/00393.

In certain embodiments, nucleic acids comprise linked nucleic acids. Nucleic acids can be linked together using any inter nucleic acid linkage. The two main classes of inter nucleic acid linking groups are defined by the presence or absence of a phosphorus atom. Representative phosphorus containing inter nucleic acid linkages include, but are not limited to, phosphodiesters, phosphotriesters, methylphosphonates, phosphoramidate, and phosphorothioates (P=S). Representative non-phosphorus containing inter nucleic acid linking groups include, but are not limited to, methylenemethylimino (—$CH_2$—N($CH_3$)—O—$CH_2$—), thiodiester (—O—C(O)—S—), thionocarbamate (—O—C(O)(NH)—S—); siloxane (—O—Si(H)$_2$—O—); and N,N*-dimethylhydrazine (—$CH_2$—N($CH_3$)—N($CH_3$)). In certain embodiments, inter nucleic acids linkages having a chiral atom can be prepared as a racemic mixture, as separate enantiomers, e.g., alkylphosphonates and phosphorothioates. Unnatural nucleic acids can contain a single modification. Unnatural nucleic acids can contain multiple modifications within one of the moieties or between different moieties.

Backbone phosphate modifications to nucleic acid include, but are not limited to, methyl phosphonate, phosphorothioate, phosphoramidate (bridging or non-bridging), phosphotriester, phosphorodithioate, phosphodithioate, and boranophosphate, and may be used in any combination. Other non-phosphate linkages may also be used.

In some embodiments, backbone modifications (e.g., methylphosphonate, phosphorothioate, phosphoroamidate and phosphorodithioate internucleotide linkages) can confer immunomodulatory activity on the modified nucleic acid and/or enhance their stability in vivo.

In some instances, a phosphorous derivative (or modified phosphate group) is attached to the sugar or sugar analog moiety in and can be a monophosphate, diphosphate, triphosphate, alkylphosphonate, phosphorothioate, phosphorodithioate, phosphoramidate or the like. Exemplary polynucleotides containing modified phosphate linkages or non-phosphate linkages can be found in Peyrottes et al., 1996, Nucleic Acids Res. 24: 1841-1848; Chaturvedi et al., 1996, Nucleic Acids Res. 24:2318-2323; and Schultz et al., (1996) Nucleic Acids Res. 24:2966-2973; Matteucci, 1997, "Oligonucleotide Analogs: an Overview" in Oligonucleotides as Therapeutic Agents, (Chadwick and Cardew, ed.) John Wiley and Sons, New York, NY; Zon, 1993, "Oligonucleoside Phosphorothioates" in Protocols for Oligonucleotides and Analogs, Synthesis and Properties, Humana Press, pp. 165-190; Miller et al., 1971, JACS 93:6657-6665; Jager et al., 1988, Biochem. 27:7247-7246; Nelson et al., 1997, JOC 62:7278-7287; U.S. Pat. No. 5,453,496; and Micklefield, 2001, Curr. Med. Chem. 8: 1157-1179.

In some cases, backbone modification comprises replacing the phosphodiester linkage with an alternative moiety such as an anionic, neutral or cationic group. Examples of such modifications include: anionic internucleoside linkage; N3' to P5' phosphoramidate modification; boranophosphate DNA; prooligonucleotides; neutral internucleoside linkages such as methylphosphonates; amide linked DNA; methylene (methylimino) linkages; formacetal and thioformacetal linkages; backbones containing sulfonyl groups; morpholino oligos; peptide nucleic acids (PNA); and positively charged deoxyribonucleic guanidine (DNG) oligos (Micklefield, 2001, Current Medicinal Chemistry 8: 1157-1179). A modified nucleic acid may comprise a chimeric or mixed backbone comprising one or more modifications, e.g. a combination of phosphate linkages such as a combination of phosphodiester and phosphorothioate linkages.

Substitutes for the phosphate include, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439. It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. See also Nielsen et al., Science, 1991, 254, 1497-1500. It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. KY. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EM5OJ, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1-di-O-hexadecyl-rac-glycero-S—H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochem. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937). Numerous United States patents teach the preparation of such conjugates and include, but are not limited to U.S. Pat. Nos. 4,828,979; 4,948,882; 5,218,105, 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some cases, the unnatural nucleic acids further form unnatural base pairs. Exemplary unnatural nucleotides capable of forming an unnatural DNA or RNA base pair (UBP) under conditions in vivo includes, but is not limited to, TPT3, dTPT3, 5SICS, d5SICS, NaM, dNaM, CNMO, dCNMO, and combinations thereof. Other examples of unnatural nucleotides capable of forming unnatural UBPs that may be used to prepare the IL-15 conjugates disclosed herein may be found in Dien et al., J Am Chem Soc., 2018, 140:16115-16123; Feldman et al., J Am Chem Soc, 2017, 139:11427-11433; Ledbetter et al., J Am Chem Soc., 2018, 140:758-765; Dhami et al., Nucleic Acids Res. 2014, 42:10235-10244; Malyshev et al., Nature, 2014, 509:385-388; Betz et al., J Am Chem Soc., 2013, 135:18637-18643; Lavergne et al., J Am Chem Soc. 2013, 135:5408-5419; and Malyshev et al. Proc Natl Acad Sci USA, 2012, 109:12005-12010. In some embodiments, unnatural nucleotides include:

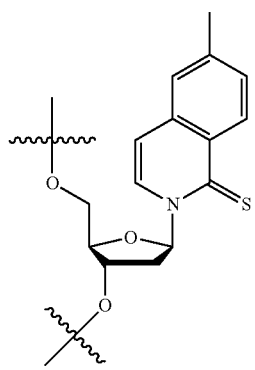

d5SICS

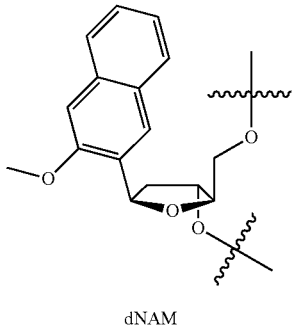

dNAM

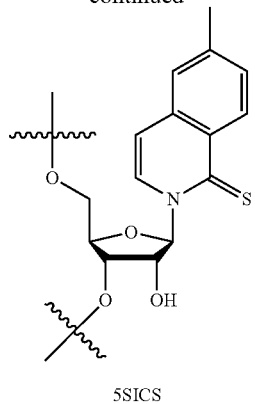

5SICS

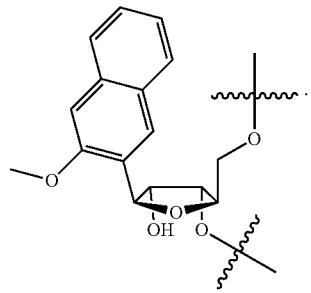

NAM

In some embodiments, the unnatural nucleotides that may be used to prepare the IL-15 conjugates disclosed herein may be derived from a compound of the formula

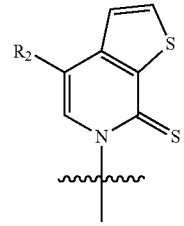

wherein $R_2$ is selected from the group consisting of hydrogen, alkyl, alkenyl, alkynyl, methoxy, methanethiol, methaneseleno, halogen, cyano, and azido; and the wavy line indicates a bond to a ribosyl or 2'-deoxyribosyl, wherein the 5'-hydroxy group of the ribosyl or 2'-deoxyribosyl moiety is in free form, or is optionally bonded to a monophosphate, a diphosphate, or a triphosphate group.

In some embodiments, the unnatural nucleotides that may be used to prepare the IL-15 conjugates disclosed herein may be derived from

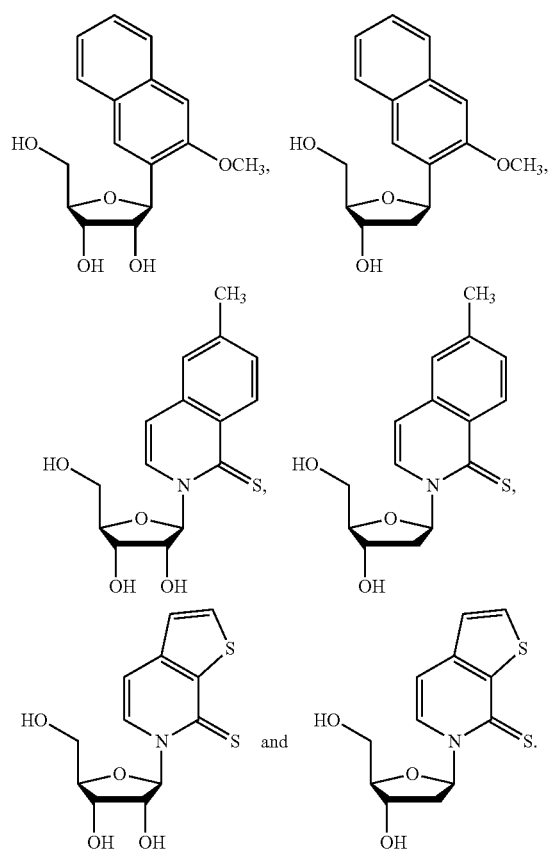

In some embodiments, the unnatural nucleotides that may be used to prepare the IL-15 conjugates disclosed herein include

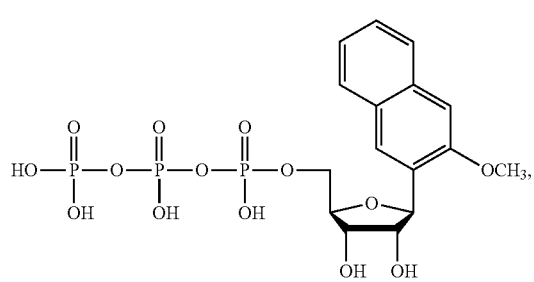

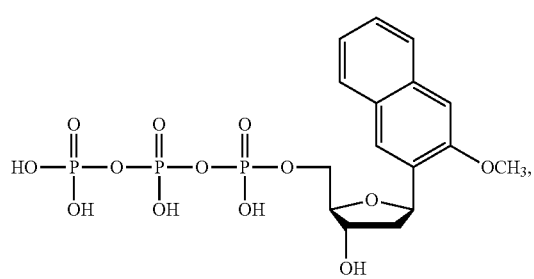

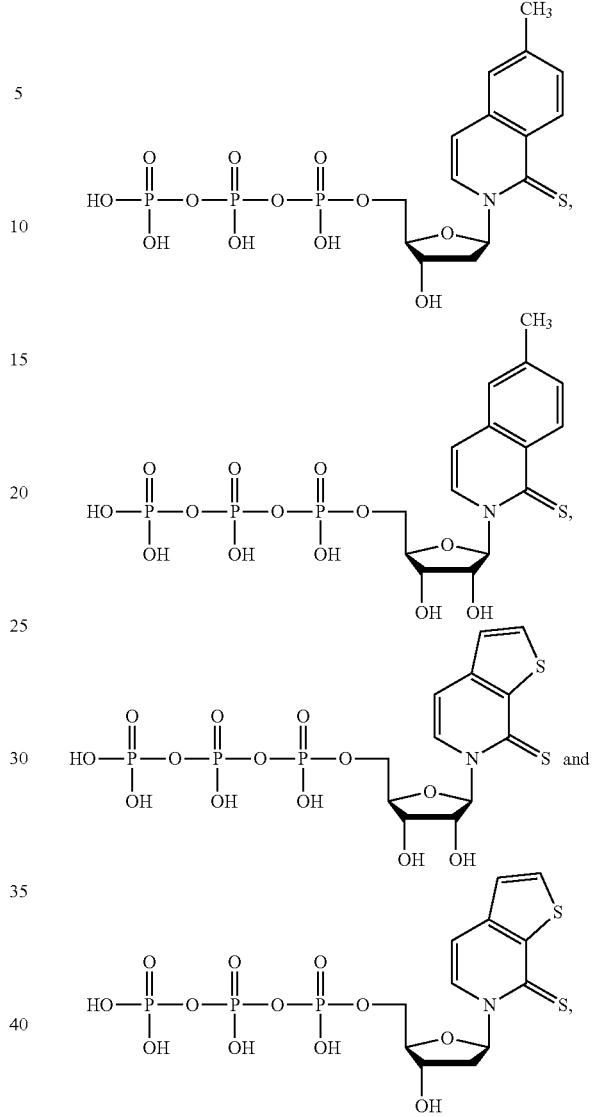

or salts thereof.

In some embodiments, an unnatural base pair generate an unnatural amino acid described in Dumas et al., "Designing logical codon reassignment—Expanding the chemistry in biology," *Chemical Science*, 6: 50-69 (2015).

In some embodiments, the unnatural amino acid is incorporated into the cytokine (e.g., the IL polypeptide) by a synthetic codon comprising an unnatural nucleic acid. In some instances, the unnatural amino acid is incorporated into the cytokine by an orthogonal, modified synthetase/tRNA pair. Such orthogonal pairs comprise an unnatural synthetase that is capable of charging the unnatural tRNA with the unnatural amino acid, while minimizing charging of a) other endogenous amino acids onto the unnatural tRNA and b) unnatural amino acids onto other endogenous tRNAs. Such orthogonal pairs comprise tRNAs that are capable of being charged by the unnatural synthetase, while avoiding being charged with a) other endogenous amino acids by endogenous synthetases. In some embodiments, such pairs are identified from various organisms, such as bacteria, yeast, *Archaea*, or human sources. In some embodiments, an orthogonal synthetase/tRNA pair comprises components from a single organism. In some embodiments, an orthogonal synthetase/tRNA pair comprises components from two different organisms. In some embodiments, an orthogonal synthetase/tRNA pair comprising components that prior to modification, promote translation of two different amino acids. In some embodiments, an orthogonal synthetase is a modified alanine synthetase. In some embodiments, an orthogonal synthetase is a modified arginine synthetase. In some embodiments, an orthogonal synthetase is a modified asparagine synthetase. In some embodiments, an orthogonal synthetase is a modified aspartic acid synthetase. In some embodiments, an orthogonal synthetase is a modified cysteine synthetase. In some embodiments, an orthogonal synthetase is a modified glutamine synthetase. In some embodiments, an orthogonal synthetase is a modified glutamic acid synthetase. In some embodiments, an orthogonal synthetase is a modified alanine glycine. In some embodiments, an orthogonal synthetase is a modified histidine synthetase. In some embodiments, an orthogonal synthetase is a modified leucine synthetase. In some embodiments, an orthogonal synthetase is a modified isoleucine synthetase. In some embodiments, an orthogonal synthetase is a modified lysine synthetase. In some embodiments, an orthogonal synthetase is a modified methionine synthetase. In some embodiments, an orthogonal synthetase is a modified phenylalanine synthetase. In some embodiments, an orthogonal synthetase is a modified proline synthetase. In some embodiments, an orthogonal synthetase is a modified serine synthetase. In some embodiments, an orthogonal synthetase is a modified threonine synthetase. In some embodiments, an orthogonal synthetase is a modified tryptophan synthetase. In some embodiments, an orthogonal synthetase is a modified tyrosine synthetase. In some embodiments, an orthogonal synthetase is a modified valine synthetase. In some embodiments, an orthogonal synthetase is a modified phosphoserine synthetase. In some embodiments, an orthogonal tRNA is a modified alanine tRNA. In some embodiments, an orthogonal tRNA is a modified arginine tRNA. In some embodiments, an orthogonal tRNA is a modified asparagine tRNA. In some embodiments, an orthogonal tRNA is a modified aspartic acid tRNA. In some embodiments, an orthogonal tRNA is a modified cysteine tRNA. In some embodiments, an orthogonal tRNA is a modified glutamine tRNA. In some embodiments, an orthogonal tRNA is a modified glutamic acid tRNA. In some embodiments, an orthogonal tRNA is a modified alanine glycine. In some embodiments, an orthogonal tRNA is a modified histidine tRNA. In some embodiments, an orthogonal tRNA is a modified leucine tRNA. In some embodiments, an orthogonal tRNA is a modified isoleucine tRNA. In some embodiments, an orthogonal tRNA is a modified lysine tRNA. In some embodiments, an orthogonal tRNA is a modified methionine tRNA. In some embodiments, an orthogonal tRNA is a modified phenylalanine tRNA. In some embodiments, an orthogonal tRNA is a modified proline tRNA. In some embodiments, an orthogonal tRNA is a modified serine tRNA. In some embodiments, an orthogonal tRNA is a modified threonine tRNA. In some embodiments, an orthogonal tRNA is a modified tryptophan tRNA. In some embodiments, an orthogonal tRNA is a modified tyrosine tRNA. In some embodiments, an orthogonal tRNA is a modified valine tRNA. In some embodiments, an orthogonal tRNA is a modified phosphoserine tRNA.

In some embodiments, the unnatural amino acid is incorporated into the cytokine (e.g., the Il polypeptide) by an aminoacyl (aaRS or RS)-tRNA synthetase-tRNA pair. Exemplary aaRS-tRNA pairs include, but are not limited to, *Methanococcus jannaschii* (Mj-Tyr) aaRS/tRNA pairs, *E. coli* TyrRS (Ec-Tyr)/*B. stearothermophilus* tRNA$_{CUA}$ pairs, *E. coli* LeuRS (Ec-Leu)/*B. searothermophilus* tRNA$_{CUA}$ pairs, and pyrrolysyl-tRNA pairs. In some instances, the unnatural amino acid is incorporated into the cytokine (e.g., the IL polypeptide) by a Mj-TyrRS/tRNA pair. Exemplary UAAs that can be incorporated by a Mj-TyrRS/tRNA pair include, but are not limited to, para-substituted phenylalanine derivatives such as p-aminophenylalanine and p-methoyphenylalanine; meta-substituted tyrosine derivatives such as 3-aminotyrosine, 3-nitrotyrosine, 3,4-dihydroxyphenylalanine, and 3-iodotyrosine; phenylselenocysteine; p-boronophenylalanine; and o-nitrobenzyltyrosine.

In some instances, the unnatural amino acid is incorporated into the cytokine (e.g., the IL polypeptide) by a Ec-Tyr/tRNA$_{CUA}$ or a Ec-Leu/tRNA$_{CUA}$ pair. Exemplary UAAs that can be incorporated by a Ec-Tyr/tRNA$_{CUA}$ or a Ec-Leu/tRNA$_{CUA}$ pair include, but are not limited to, phenylalanine derivatives containing benzophenone, ketone, iodide, or azide substituents; O-propargyltyrosine; α-aminocaprylic acid, O-methyl tyrosine, O-nitrobenzyl cysteine; and 3-(naphthalene-2-ylamino)-2-amino-propanoic acid.

In some instances, the unnatural amino acid is incorporated into the cytokine (e.g., the IL polypeptide) by a pyrrolysyl-tRNA pair. In some cases, the PylRS is obtained from an archaebacterial, e.g., from a methanogenic archaebacterial. In some cases, the PylRS is obtained from *Methanosarcina barkeri*, *Methanosarcina mazei*, or *Methanosarcina acetivorans*. Exemplary UAAs that can be incorporated by a pyrrolysyl-tRNA pair include, but are not limited to, amide and carbamate substituted lysines such as 2-amino-6-((R)-tetrahydrofuran-2-carboxamido)hexanoic acid, N-ε-D-prolyl-L-lysine, and N-ε-cyclopentyloxycarbonyl-L-lysine; N-ε-Acryloyl-L-lysine; N-ε-[(1-(6-nitrobenzo[d][1,3]dioxol-5-yl)ethoxy)carbonyl]-L-lysine; and N-ε-(1-methylcyclopro-2-enecarboxamido)lysine. In some embodiments, the IL-15 conjugates disclosed herein may be prepared by use of *M. mazei* tRNA which is selectively charged with a non-natural amino acid such as N6-((2-azidoethoxy)-carbonyl)-L-lysine (AzK) by the *M. barkeri* pyrrolysyl-tRNA synthetase (Mb PylRS). Other methods are known to those of ordinary skill in the art, such as those disclosed in Zhang et al., Nature 2017, 551(7682): 644-647.

In some instances, an unnatural amino acid is incorporated into a cytokine described herein (e.g., the IL polypeptide) by a synthetase disclosed in U.S. Pat. Nos. 9,988,619 and 9,938,516.

The host cell into which the constructs or vectors disclosed herein are introduced is cultured or maintained in a suitable medium such that the tRNA, the tRNA synthetase and the protein of interest are produced. The medium also comprises the unnatural amino acid(s) such that the protein of interest incorporates the unnatural amino acid(s). In some embodiments, a nucleoside triphosphate transporter (NTT) from bacteria, plant, or algae is also present in the host cell. In some embodiments, the IL-15 conjugates disclosed herein are prepared by use of a host cell that expresses a NTT. In some embodiments, the nucleotide nucleoside triphosphate transporter used in the host cell may be selected from TpNTT1, TpNTT2, TpNTT3, TpNTT4, TpNTT5, TpNTT6, TpNTT7, TpNTT8 (*T. pseudonana*), PtNTT1, PtNTT2, PtNTT3, PtNTT4, PtNTT5, PtNTT6 (*P. tricornulum*), GsNTT (*Galdieria sulphuraria*), AtNTT1, AtNTT2 (*Arabidopsis thaliana*), CtNTT1, CtNTT2 (*Chlamydia trachomatis*), PamNTT1, PamNTT2 (*Protochlamydia amoebophila*), CcNTT (*Caedibacter caryophilus*), RpNTT1 (*Rickettsia prowazekii*). In some embodiments, the NTT is selected from PtNTT1, PtNTT2, PtNTT3, PtNTT4, PtNTT5, and PtNTT6. In some embodiments, the NTT is PtNTT1. In some embodiments, the NTT is PtNTT2. In some embodiments, the NTT is PtNTT3. In some embodiments, the NTT is PtNTT4. In some embodiments, the NTT is PtNTT5. In some embodiments, the NTT is PtNTT6. Other NTTs that may be used are disclosed in Zhang et al., Nature 2017, 551(7682): 644-647; Malyshev et al. Nature 2014 (509 (7500), 385-388; and Zhang et al. Proc Nat Acad Sci USA, 2017, 114:1317-1322.

The orthogonal tRNA synthetase/tRNA pair charges a tRNA with an unnatural amino acid and incorporates the unnatural amino acid into the polypeptide chain in response to the codon. Exemplary aaRS-tRNA pairs include, but are not limited to, *Methanococcus jannaschii* (Mj-Tyr) aaRS/tRNA pairs, *E. coli* TyrRS (Ec-Tyr)/*B. stearothermophilus* tRNA$_{CUA}$ pairs, *E. coli* LeuRS (Ec-Leu)/*B. stearothermophilus* tRNA$_{CUA}$ pairs, and pyrrolysyl-tRNA pairs. Other aaRS-tRNA pairs that may be used according to the present disclosure include those derived from *M. mazei* those described in Feldman et al., J Am Chem Soc., 2018 140: 1447-1454; and Zhang et al. Proc Natl Acad Sci USA, 2017, 114:1317-1322.

In some embodiments are provided methods of preparing the IL-15 conjugates disclosed herein in a cellular system that expresses a NTT and a tRNA synthetase. In some embodiments described herein, the NTT is selected from PtNTT1, PtNTT2, PtNTT3, PtNTT4, PtNTT5, and PtNTT6, and the tRNA synthetase is selected from *Methanococcus jannaschii, E. coli* TyrRS (Ec-Tyr)/*B. stearothermophilus*, and *M. mazei*. In some embodiments, the NTT is PtNTT1 and the tRNA synthetase is derived from *Methanococcus jannaschii, E. coli* TyrRS (Ec-Tyr)/*B. stearothermophilus*, or *M. mazei*. In some embodiments, the NTT is PtNTT2 and the tRNA synthetase is derived from *Methanococcus jannaschii, E. coli* TyrRS (Ec-Tyr)/*B. stearothermophilus*, or *M. mazei*. In some embodiments, the NTT is PtNTT3 and the tRNA synthetase is derived from *Methanococcus jannaschii, E. coli* TyrRS (Ec-Tyr)/*B. stearothermophilus*, or *M. mazei*. In some embodiments, the NTT is PtNTT3 and the tRNA synthetase is derived from *Methanococcus jannaschii, E. coli* TyrRS (Ec-Tyr)/*B. stearothermophilus*, or *M. mazei*. In some embodiments, the NTT is PtNTT4 and the tRNA synthetase is derived from *Methanococcus jannaschii, E. coli* TyrRS (Ec-Tyr)/*B. stearothermophilus*, or *M. mazei*. In some embodiments, the NTT is PtNTT5 and the tRNA synthetase is derived from *Methanococcus jannaschii, E. coli* TyrRS (Ec-Tyr)/*B. stearothermophilus*, or *M. mazei*. In some embodiments, the NTT is PtNTT6 and the tRNA synthetase is derived from *Methanococcus jannaschii, E. coli* TyrRS (Ec-Tyr)/*B. stearothermophilus*, or *M. mazei*.

In some embodiments, the IL-15 conjugates disclosed herein may be prepared in a cell, such as *E. coli*, comprising (a) nucleotide triphosphate transporter PtNTT2 (including a truncated variant in which the first 65 amino acid residues of the full-length protein are deleted), (b) a plasmid comprising a double-stranded oligonucleotide that encodes an IL-15 variant having a desired amino acid sequence and that contains a unnatural base pair comprising a first unnatural nucleotide and a second unnatural nucleotide to provide a codon at the desired position at which an unnatural amino acid, such as N6-((2-azidoethoxy)-carbonyl)-L-lysine (AzK), will be incorporated, (c) a plasmid encoding a tRNA derived from *M. mazei* and which comprises an unnatural nucleotide to provide a recognized anticodon (to the codon of the IL-15 variant) in place of its native sequence, and (d) a plasmid encoding a *M. barkeri* derived pyrrolysyl-tRNA synthetase (Mb PylRS), which may be the same plasmid that encodes the tRNA or a different plasmid. In some embodiments, the cell is further supplemented with deoxyribo triphosphates comprising one or more unnatural bases. In some embodiments, the cell is further supplemented with ribo triphosphates comprising one or more unnatural bases. In some embodiments, the cells is further supplemented with one or more unnatural amino acids, such as N6-((2-azidoethoxy)-carbonyl)-L-lysine (AzK). In some embodiments, the double-stranded oligonucleotide that encodes the amino acid sequence of the desired IL-15 variant contains a codon AXC at, for example, position 18, 25, 46, 53, 77, or 83 of the sequence that encodes the protein having SEQ ID NO: 1 or at position 19, 26, 47, 54, 78, or 84 of the sequence that encodes the protein having SEQ ID NO: 3, wherein X is an unnatural nucleotide. In some embodiments, the cell further comprises a plasmid, which may be the protein expression plasmid or another plasmid, that encodes an orthogonal tRNA gene from *M. mazei* that comprises an AXC-matching anticodon GYT in place of its native sequence, wherein Y is an unnatural nucleotide that is complementary and may be the same or different as the unnatural nucleotide in the codon. In some embodiments, the unnatural nucleotide in the codon is different than and complimentary to the unnatural nucleotide in the anti-codon. In some embodiments, the unnatural nucleotide in the codon is the same as the unnatural nucleotide in the anti-codon. In some embodiments, the first and second unnatural nucleotides comprising the unnatural base pair in the double-stranded oligonucleotide may be derived from

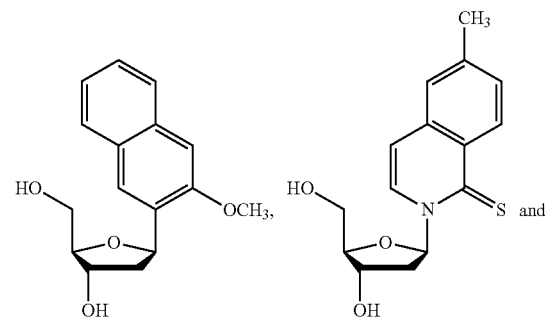

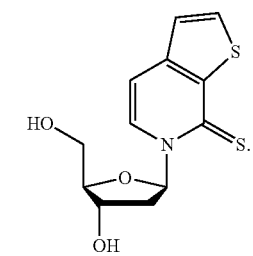

In some embodiments, the first and second unnatural nucleotides comprising the unnatural base pair in the double-stranded oligonucleotide may be derived from

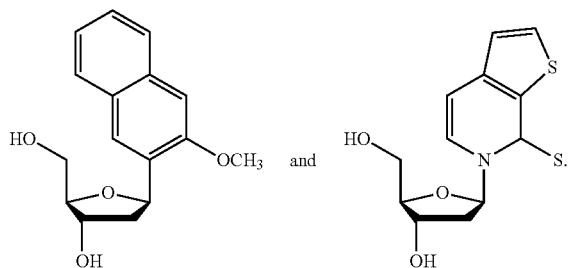 and 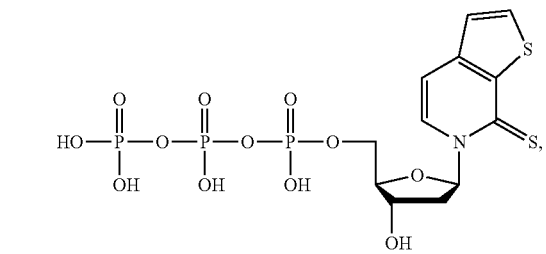

In some embodiments, the triphosphates of the first and second unnatural nucleotides include,

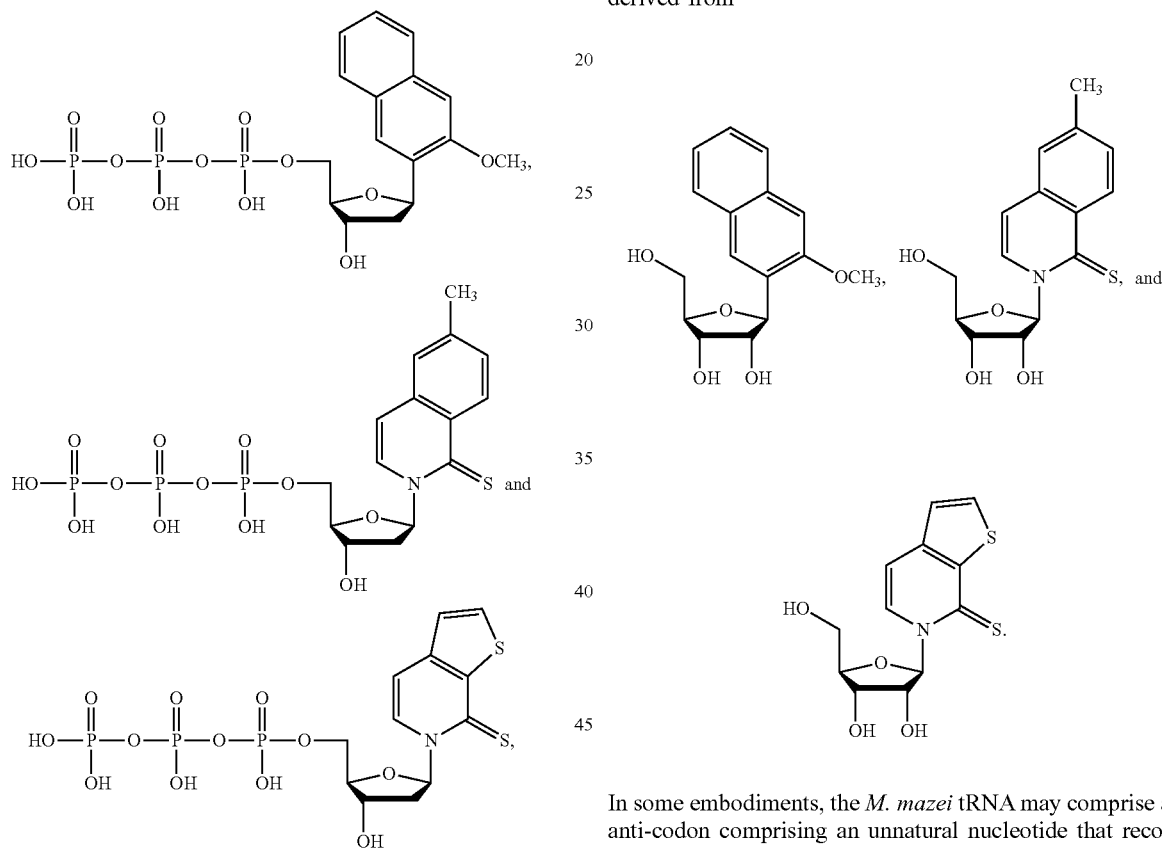

or salts thereof. In some embodiments, the triphosphates of the first and second unnatural nucleotides include, or salts thereof. In some embodiments, the mRNA derived the double-stranded oligonucleotide comprising a first unnatural nucleotide and a second unnatural nucleotide may comprise a codon comprising an unnatural nucleotide derived from

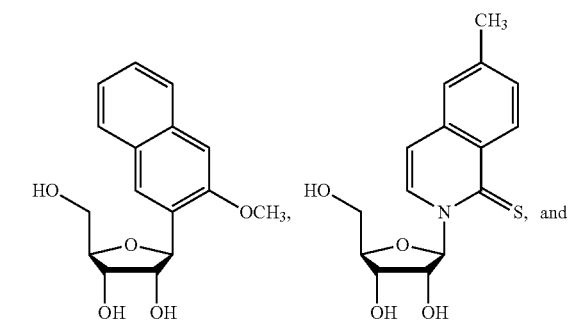

In some embodiments, the *M. mazei* tRNA may comprise an anti-codon comprising an unnatural nucleotide that recognizes the codon comprising the unnatural nucleotide of the mRNA. The anti-codon in the *M. mazei* tRNA may comprise an unnatural nucleotide derived from

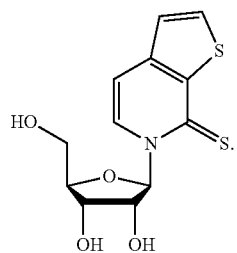

In some embodiments, the mRNA comprises an unnatural nucleotide derived from

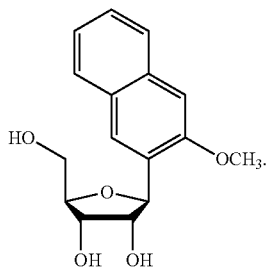

In some embodiments, the mRNA comprises an unnatural nucleotide derived from

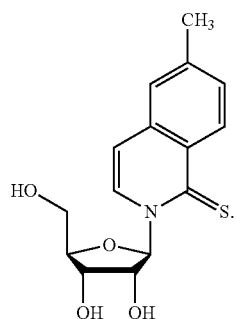

In some embodiments, the tRNA comprises an unnatural nucleotide derived from

In some embodiments, the tRNA comprises an unnatural nucleotide derived from

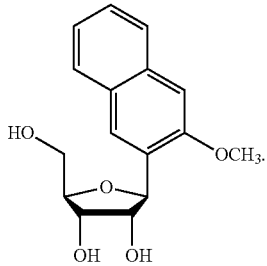

In some embodiments, the tRNA comprises an unnatural nucleotide derived from

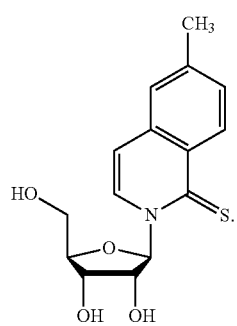

In some embodiments, the tRNA comprises an unnatural nucleotide derived from

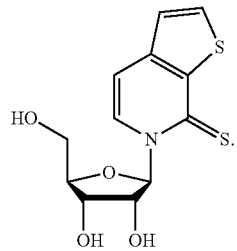

In some embodiments, the mRNA comprises an unnatural nucleotide derived from

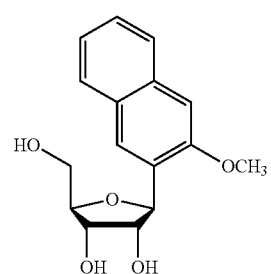

and the tRNA comprises an unnatural nucleotide derived from

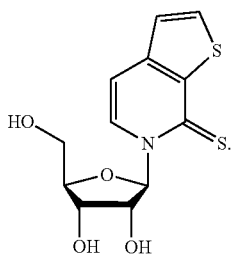

In some embodiments, the mRNA comprises an unnatural nucleotide derived from

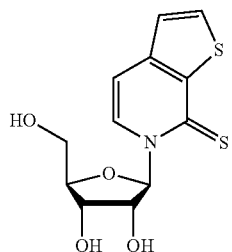

and the tRNA comprises an unnatural nucleotide derived from

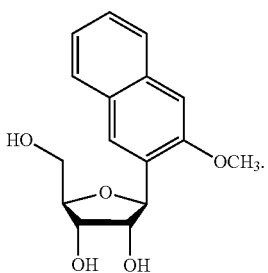

The host cell is cultured in a medium containing appropriate nutrients, and is supplemented with (a) the triphosphates of the deoxyribonucleosides comprising one or more unnatural bases that are necessary for replication of the plasmid(s) encoding the cytokine gene harboring the codon, (b) the triphosphates of the ribonucleosides comprising one or more unnatural bases necessary for transcription of (i) the mRNA corresponding to the coding sequence of the cytokine and containing the codon comprising one or more unnatural bases, and (ii) the tRNA containing the anticodon comprising one or more unnatural bases, and (c) the unnatural amino acid(s) to be incorporated in to the polypeptide sequence of the cytokine of interest. The host cells are then maintained under conditions which permit expression of the protein of interest.

The resulting protein comprising the one or more unnatural amino acids, AzK for example, that is expressed may be purified by methods known to those of ordinary skill in the art and may then be allowed to react with an alkyne, such as DBCO comprising a PEG chain having a desired average molecular weight as disclosed herein, under conditions known to those of ordinary skill in the art, to afford the IL-15 conjugates disclosed herein. Other methods are known to those of ordinary skill in the art, such as those disclosed in Zhang et al., Nature 2017, 551(7682): 644-647; WO 2015157555; WO 2015021432; WO 2016115168; WO 2017106767; WO 2017223528; WO 2019014262; WO 2019014267; WO 2019028419; and W2019/028425.

Alternatively, a cytokine (e.g., IL-15) polypeptide comprising an unnatural amino acid(s) are prepared by introducing the nucleic acid constructs described herein comprising the tRNA and aminoacyl tRNA synthetase and comprising a nucleic acid sequence of interest with one or more in-frame orthogonal (stop) codons into a host cell. The host cell is cultured in a medium containing appropriate nutrients, is supplemented with (a) the triphosphates of the deoxyribonucleosides comprising one or more unnatural bases required for replication of the plasmid(s) encoding the cytokine gene harboring the new codon and anticodon, (b) the triphosphates of the ribonucleosides required for transcription of the mRNA corresponding to (i) the cytokine sequence containing the codon, and (ii) the orthogonal tRNA containing the anticodon, and (c) the unnatural amino acid(s). The host cells are then maintained under conditions which permit expression of the protein of interest. The unnatural amino acid(s) is incorporated into the polypeptide chain in response to the unnatural codon. For example, one or more unnatural amino acids are incorporated into the cytokine (e.g., IL-15) polypeptide. Alternatively, two or more unnatural amino acids may be incorporated into the cytokine (e.g., IL-15) polypeptide at two or more sites in the protein.

Once the cytokine (e.g., IL-15) polypeptide incorporating the unnatural amino acid(s) has been produced in the host cell it can be extracted therefrom by a variety of techniques known in the art, including enzymatic, chemical and/or osmotic lysis and physical disruption. The cytokine (e.g., IL-15) polypeptide can be purified by standard techniques known in the art such as preparative ion exchange chromatography, hydrophobic chromatography, affinity chromatography, or any other suitable technique known to those of ordinary skill in the art.

Suitable host cells may include bacterial cells (e.g., E. coli, BL21(DE3)), but most suitably host cells are eukaryotic cells, for example insect cells (e.g. Drosophila such as Drosophila melanogaster), yeast cells, nematodes (e.g., C. elegans), mice (e.g., Mus musculus), or mammalian cells (such as Chinese hamster ovary cells (CHO) or COS cells, human 293T cells, HeLa cells, NIH 3T3 cells, and mouse erythroleukemia (MEL) cells) or human cells or other eukaryotic cells. Other suitable host cells are known to those skilled in the art. Suitably, the host cell is a mammalian cell—such as a human cell or an insect cell. In some embodiments, the suitable host cells comprise E. coli.

Other suitable host cells which may be used generally in the embodiments of the invention are those mentioned in the examples section. Vector DNA can be introduced into host cells via conventional transformation or transfection techniques. As used herein, the terms "transformation" and "transfection" are intended to refer to a variety of well-recognized techniques for introducing a foreign nucleic acid molecule (e.g., DNA) into a host cell, including calcium phosphate or calcium chloride co-precipitation, DEAE-dextran-mediated transfection, lipofection, or electroporation. Suitable methods for transforming or transfecting host cells are well known in the art.

When creating cell lines, it is generally preferred that stable cell lines are prepared. For stable transfection of mammalian cells for example, it is known that, depending upon the expression vector and transfection technique used, only a small fraction of cells may integrate the foreign DNA into their genome. In order to identify and select these integrants, a gene that encodes a selectable marker (for example, for resistance to antibiotics) is generally introduced into the host cells along with the gene of interest. Preferred selectable markers include those that confer resistance to drugs, such as G418, hygromycin, or methotrexate. Nucleic acid molecules encoding a selectable marker can be introduced into a host cell on the same vector or can be introduced on a separate vector. Cells stably transfected with the introduced nucleic acid molecule can be identified by drug selection (for example, cells that have incorporated the selectable marker gene will survive, while the other cells die).

In one embodiment, the constructs described herein are integrated into the genome of the host cell. An advantage of stable integration is that the uniformity between individual cells or clones is achieved. Another advantage is that selection of the best producers may be carried out. Accordingly, it is desirable to create stable cell lines. In another embodiment, the constructs described herein are transfected into a host cell. An advantage of transfecting the constructs into the host cell is that protein yields may be maximized. In one aspect, there is described a cell comprising the nucleic acid construct or the vector described herein.

Pharmaceutical Compositions and Formulations

In some embodiments, the pharmaceutical composition and formulations described herein are administered to a subject by multiple administration routes, including but not limited to, parenteral, oral, or transdermal administration routes. In some cases, parenteral administration comprises intravenous, subcutaneous, intramuscular, intracerebral, intranasal, intra-arterial, intra-articular, intradermal, intravitreal, intraosseous infusion, intraperitoneal, or intrathecal administration. In some instances, the pharmaceutical composition is formulated for local administration. In other instances, the pharmaceutical composition is formulated for systemic administration.

In some embodiments, the pharmaceutical formulations include, but are not limited to, aqueous liquid dispersions, self-emulsifying dispersions, liposomal dispersions, aerosols, immediate release formulations, controlled release formulations, delayed release formulations, extended release formulations, pulsatile release formulations, and mixed immediate and controlled release formulations.

In some embodiments, the pharmaceutical formulations include a carrier or carrier materials selected on the basis of compatibility with the composition disclosed herein, and the release profile properties of the desired dosage form. Exemplary carrier materials include, e.g., binders, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphatidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995), Hoover, John E., *Remington's Pharmaceutical Sciences*, Mack Publishing Co., Easton, Pennsylvania 1975, Liberman, H. A. and Lachman, L., Eds., *Pharmaceutical Dosage Forms*, Marcel Decker, New York, N.Y., 1980, and *Pharmaceutical Dosage Forms and Drug Delivery Systems*, Seventh Ed. (Lippincott Williams & Wilkins 1999).

In some cases, the pharmaceutical composition is formulated as an immunoliposome, which comprises a plurality of IL-15 conjugates bound either directly or indirectly to lipid bilayer of liposomes. Exemplary lipids include, but are not limited to, fatty acids; phospholipids; sterols such as cholesterols; sphingolipids such as sphingomyelin; glycosphingolipids such as gangliosides, globosides, and cerebrosides; surfactant amines such as stearyl, oleyl, and linoleyl amines. In some instances, the lipid comprises a cationic lipid. In some instances, the lipid comprises a phospholipid. Exemplary phospholipids include, but are not limited to, phosphatidic acid ("PA"), phosphatidylcholine ("PC"), phosphatidylglycerol ("PG"), phophatidylethanolamine ("PE"), phophatidylinositol ("PI"), and phosphatidylserine ("PS"), sphingomyelin (including brain sphingomyelin), lecithin, lysolecithin, lysophosphatidylethanolamine, cerebrosides, diarachidoylphosphatidylcholine ("DAPC"), didecanoyl-L-alpha-phosphatidylcholine ("DDPC"), dielaidoylphosphatidylcholine ("DEPC"), dilauroylphosphatidylcholine ("DLPC"), dilinoleoylphosphatidylcholine, dimyristoylphosphatidylcholine ("DMPC"), dioleoylphosphatidylcholine ("DOPC"), dipalmitoylphosphatidylcholine ("DPPC"), distearoylphosphatidylcholine ("DSPC"), 1-palmitoyl-2-oleoyl-phosphatidylcholine ("POPC"), diarachidoylphosphatidylglycerol ("DAPG"), didecanoyl-L-alpha-phosphatidylglycerol ("DDPG"), dielaidoylphosphatidylglycerol ("DEPG"), dilauroylphosphatidylglycerol ("DLPG"), dilinoleoylphosphatidylglycerol, dimyristoylphosphatidylglycerol ("DMPG"), dioleoylphosphatidylglycerol ("DOPG"), dipalmitoylphosphatidylglycerol ("DPPG"), distearoylphosphatidylglycerol ("DSPG"), 1-palmitoyl-2-oleoyl-phosphatidylglycerol ("POPG"), diarachidoylphosphatidylethanolamine ("DAPE"), didecanoyl-L-alpha-phosphatidylethanolamine ("DDPE"), dielaidoylphosphatidylethanolamine ("DEPE"), dilauroylphosphatidylethanolamine ("DLPE"), dilinoleoylphosphatidylethanolamine, dimyristoylphosphatidylethanolamine ("DMPE"), dioleoylphosphatidylethanolamine ("DOPE"), dipalmitoylphosphatidylethanolamine ("DPPE"), distearoylphosphatidylethanolamine ("DSPE"), 1-palmitoyl-2-oleoyl-phosphatidylethanolamine ("POPE"), diarachidoylphosphatidylinositol ("DAPI"), didecanoyl-L-alpha-phosphatidylinositol ("DDPI"), dielaidoylphosphatidylinositol ("DEPI"), dilauroylphosphatidylinositol ("DLPI"), dilinoleoylphosphatidylinositol, dimyristoylphosphatidylinositol ("DMPI"), dioleoylphosphatidylinositol ("DOPI"), dipalmitoylphosphatidylinositol ("DPPI"), distearoylphosphatidylinositol ("DSPI"), 1-palmitoyl-2-oleoyl-phosphatidylinositol ("POPI"), diarachidoylphosphatidylserine ("DAPS"), didecanoyl-L-alpha-phosphatidylserine ("DDPS"), dielaidoylphosphatidylserine ("DEPS"), dilauroylphosphatidylserine ("DLPS"), dilinoleoylphosphatidylserine, dimyristoylphosphatidylserine ("DMPS"), dioleoylphosphatidylserine ("DOPS"), dipalmitoylphosphatidylserine ("DPPS"), distearoylphosphatidylserine ("DSPS"), 1-palmitoyl-2-oleoyl-phosphatidylserine ("POPS"), diarachidoyl sphingomyelin, didecanoyl sphingomyelin, dielaidoyl sphingomyelin, dilauroyl sphingomyelin, dilinoleoyl sphingomyelin, dimyristoyl sphingomyelin, sphingomyelin, dioleoyl sphingomyelin, dipalmitoyl sphingomyelin, distearoyl sphingomyelin, and 1-palmitoyl-2-oleoyl-sphingomyelin.

In some embodiments, the pharmaceutical formulations further include pH adjusting agents or buffering agents which include acids such as acetic, boric, citric, lactic, phosphoric and hydrochloric acids, bases such as sodium hydroxide, sodium phosphate, sodium borate, sodium citrate, sodium acetate, sodium lactate and tris-hydroxymethylaminomethane, and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions, suitable salts include sodium chloride, potassium chloride, sodium thiosulfate, sodium bisulfite and ammonium sulfate.

In some embodiments, the pharmaceutical formulations include, but are not limited to, sugars like trehalose, sucrose, mannitol, sorbitol, maltose, glucose, or salts like potassium phosphate, sodium citrate, ammonium sulfate and/or other agents such as heparin to increase the solubility and in vivo stability of polypeptides.

In some instances, the pharmaceutical formulations further include diluent which are used to stabilize compounds because they can provide a more stable environment. Salts dissolved in buffered solutions (which also can provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds can include e.g., lactose, starch, mannitol, sorbitol, dextrose, microcrystalline cellulose such as Avicel®, dibasic calcium phosphate, dicalcium phosphate dihydrate, tricalcium phosphate, calcium phosphate, anhydrous lactose, spray-dried lactose, pregelatinized starch, compressible sugar, such as Di-Pac® (Amstar), mannitol, hydroxypropylmethylcellulose, hydroxypropylmethylcellulose acetate stearate, sucrose-based diluents, confectioner's sugar, monobasic calcium sulfate monohydrate, calcium sulfate dihydrate, calcium lactate trihydrate, dextrates, hydrolyzed cereal solids, amylose, powdered cellulose, calcium carbonate, glycine, kaolin, mannitol, sodium chloride, inositol, bentonite, and the like. In some embodiments, the IL-15 conjugates disclosed herein may be used in pharmaceutical formulations comprising histidine, sorbitol, and polysorbate 80, or any combination that affords a stable formulation and can be administered to subjects in need thereof. In one embodiment, the IL-15 conjugates disclosed herein may be presented as a finished drug product in a suitable container, such as a vial, as follows: IL-15 conjugate (about 2 mg to about 10 mg); L-histidine (about 0.5 mg to about 2 mg); L-histidine hydrochloride (about 1 mg to about 2 mg); sorbitol (about 20 mg to about 80 mg); and polysorbate 80 (about 0.1 mg to about 0.2 mg); with a sufficient quantity of water for injection to provide a liquid formulation suitable for use in the disclosed methods.

In some cases, the pharmaceutical formulations include disintegration agents or disintegrants to facilitate the breakup or disintegration of a substance. The term "disintegrate" includes both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulations include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumarate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers can also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like. Exemplary stabilizers include L-arginine hydrochloride, tromethamine, albumin (human), citric acid, benzyl alcohol, phenol, disodium biphosphate dehydrate, propylene glycol, metacresol or m-cresol, zinc acetate, polysorbate-20 or Tween® 20, or trometamol.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

In some embodiments, the pharmaceutical formulations further include diluent which are used to stabilize compounds because they can provide a more stable environment. Salts dissolved in buffered solutions (which also can provide pH control or maintenance) are utilized as diluents in the art, including, but not limited to a phosphate buffered saline solution.

Stabilizers include compounds such as any antioxidation agents, buffers, acids, preservatives and the like. Exemplary stabilizers include L-arginine hydrochloride, tromethamine, albumin (human), citric acid, benzyl alcohol, phenol, disodium biphosphate dehydrate, propylene glycol, metacresol or m-cresol, zinc acetate, polysorbate-20 or Tween® 20, or trometamol.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxamers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil, and polyoxyethylene alkylethers and alkylphenyl ethers, e.g., octoxynol 10, octoxynol 40. Sometimes, surfactants is included to enhance physical stability or for other purposes.

Therapeutic Regimens

In some embodiments, the pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In the case wherein the patient's status does improve, upon the doctor's discretion the administration of the composition is given continuously, alternatively, the dose of the composition being administered is temporarily reduced or temporarily suspended for a certain length of time (i.e., a "drug holiday"). In some embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, byway of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some embodiments, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages is altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or more methods and compositions described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include one or more of the IL-15 polypeptides or IL-15 conjugates disclosed herein, and optionally one or more pharmaceutical excipients described herein to facilitate the delivery of IL-15 polypeptides or IL-15 conjugates. Such kits further optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself, a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack.

In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for drugs, or the approved product insert. In one embodiment, compositions containing a compound provided herein formulated in a compatible pharmaceutical carrier are also prepared, placed in an appropriate container, and labeled for treatment of an indicated condition.

Certain Terminology

Unless defined otherwise, all technical and scientific terms used herein have the same meaning as is commonly understood by one of skill in the art to which the claimed subject matter belongs. It is to be understood that the detailed description are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described. To the extent any material incorporated by reference may be inconsistent with the express content of this disclosure, the express content controls. "Or" is used in the inclusive sense, i.e., equivalent to "and/or", unless the context clearly dictates otherwise.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

As used herein, the terms "significant" and "significantly" in reference to receptor binding means a change sufficient to impact binding of the IL-15 polypeptide to a target receptor. In some instances, the term refers to a change of at least 10%, 20%, 30%, 40%, 50%, 60%, 70%, 80%, 90%, 95%, or more. In some instances, the term means a change of at least 2-fold, 3-fold, 4-fold, 5-fold, 6-fold, 7-fold, 8-fold, 9-fold, 10-fold, 50-fold, 100-fold, 500-fold, 1000-fold, or more.

In some instances, the term "significantly" in reference to activation of one or more cell populations via a cytokine signaling complex means a change sufficient to activate the cell population. In some cases, the change to activate the cell population is measured as a receptor signaling potency. In such cases, an EC50 value may be provided. In other cases, an ED50 value may be provided. In additional cases, a concentration or dosage of the cytokine may be provided.

As used herein, the term "potency" refers to the amount of a cytokine (e.g., IL-15 polypeptide) required to produce a target effect. In some instances, the term "potency" refers to the amount of cytokine (e.g., IL-15 polypeptide) required to activate a target cytokine receptor (e.g., IL-15 receptor). In other instances, the term "potency" refers to the amount of cytokine (e.g., IL-15 polypeptide) required to activate a target cell population. In some cases, potency is measured as ED50 (Effective Dose 50), or the dose required to produce 50% of a maximal effect. In other cases, potency is measured as EC50 (Effective Concentration 50), or the dose required to produce the target effect in 50% of the population.

As used herein, the term "tumor infiltrating immune cell(s)" refers to immune cells that have infiltrated into a region comprising tumor cells (e.g., in a tumor microenvironment). In some instances, the tumor infiltrating immune cells are associated with tumor cell destruction, a decrease in tumor cell proliferation, a reduction in tumor burden, or combinations thereof. In some instances, the tumor infiltrating immune cells comprise tumor infiltration lymphocytes (TILs). In some instances, the tumor infiltrating immune cells comprise T cells, B cells, natural killer cells, macrophages, neutrophils, dendritic cells, mast cells, eosinophils or basophils. In some instances, the tumor infiltrating immune cells comprise CD4+ or CD8+ T cells.

As used herein, an "IL-15 conjugate" is an IL-15 polypeptide attached (such as through a linker) to a conjugating moiety, e.g., comprising a PEG group; the IL-15 conjugate may be but is not necessarily in the form of a pharmaceutically acceptable salt, solvate, or hydrate. As described in detail elsewhere herein, the IL-15 polypeptide may comprise an unnatural amino acid, which can serve as the site of attachment to the conjugating moiety.

Numbered Embodiments. The present disclosure includes the following non-limiting numbered embodiments:

Embodiment 1. An IL-15 conjugate comprising the amino acid sequence of SEQ ID NO: 1 in which at least one amino acid residue in the IL-15 conjugate is replaced by the structure of Formula (I):

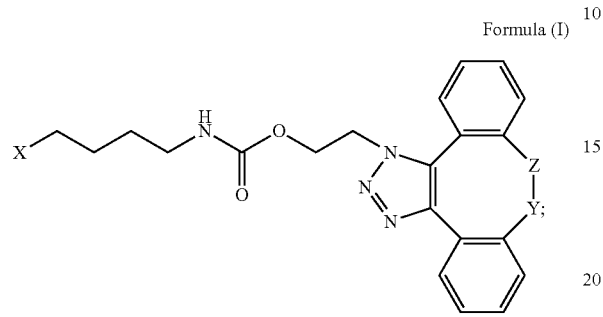

Formula (I)

wherein:
Z is CH$_2$ and Y is

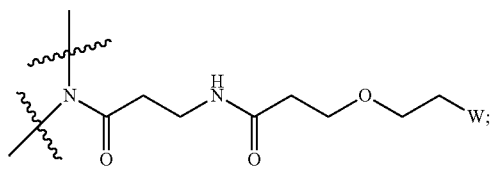

Y is CH$_2$ and Z is

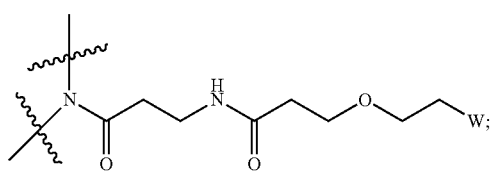

Z is CH$_2$ and Y is

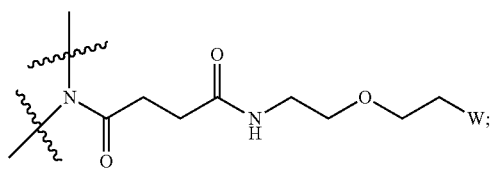

or
Y is CH$_2$ and Z is

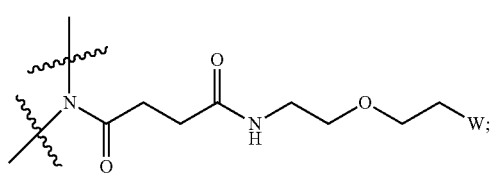

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

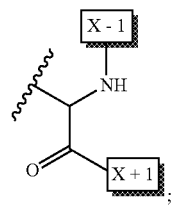

or a pharmaceutically acceptable salt, solvate, or hydrate thereof.

Embodiment 1.1. An IL-15 conjugate comprising the amino acid sequence of SEQ ID NO: 1 in which at least one amino acid residue in the IL-15 conjugate is replaced by the structure of Formula (I):

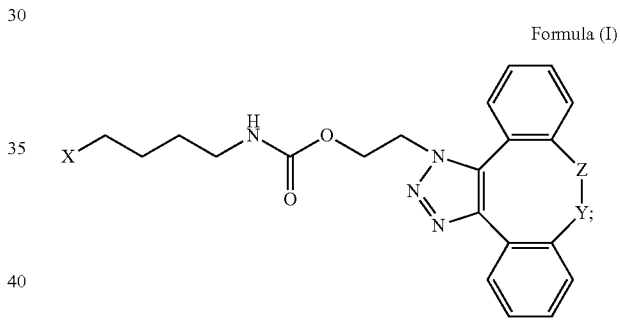

Formula (I)

wherein:
Z is CH$_2$ and Y is

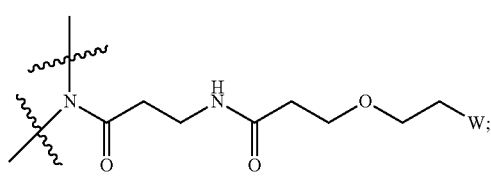

Y is CH$_2$ and Z is

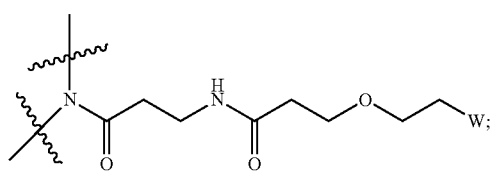

Z is CH$_2$ and a Y is

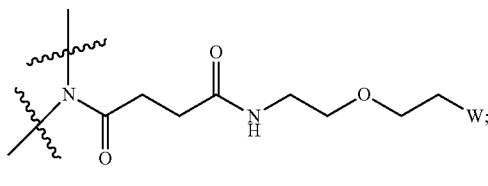

or

Y is CH$_2$ and Z is

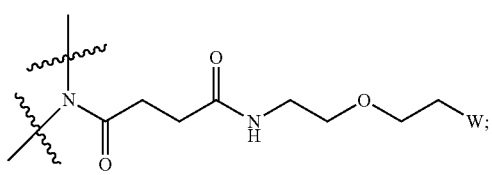

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

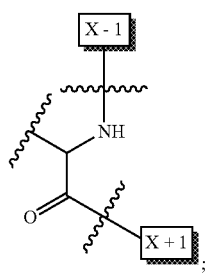

X−1 indicates the point of attachment to the preceding amino acid residue; and

X+1 indicates the point of attachment to the following amino acid residue.

Embodiment 2. An IL-15 conjugate comprising the amino acid sequence of SEQ ID NO: 3 in which at least one amino acid residue in the IL-15 conjugate is replaced by the structure of Formula (I):

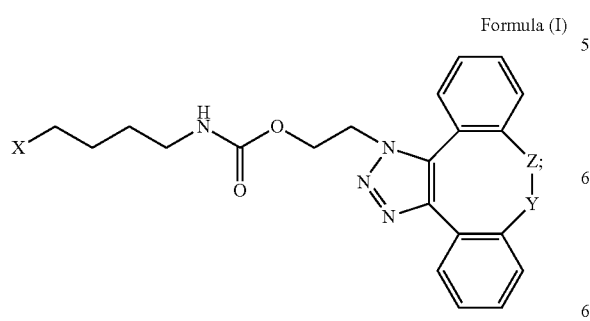

Formula (I)

wherein:

Z is CH$_2$ and Y is

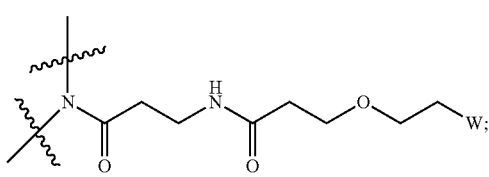

Y is CH$_2$ and Z is

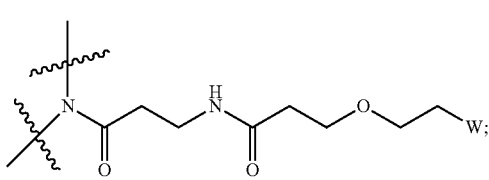

Z is CH$_2$ and Y is

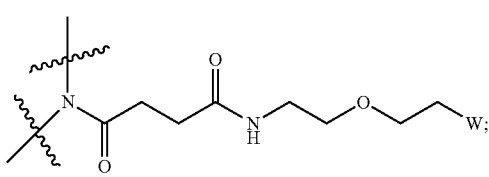

or

Y is CH$_2$ and Z is

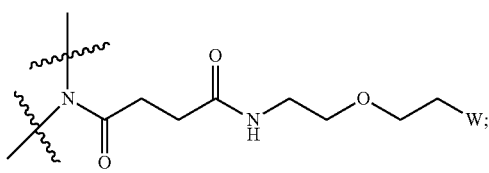

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

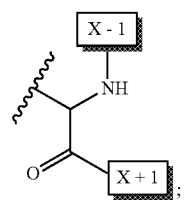

or a pharmaceutically acceptable salt, solvate, or hydrate thereof.

Embodiment 2.1. An IL-15 conjugate comprising the amino acid sequence of SEQ ID NO: 3 in which at least one amino acid residue in the IL-15 conjugate is replaced by the structure of Formula (I):

Formula (I)

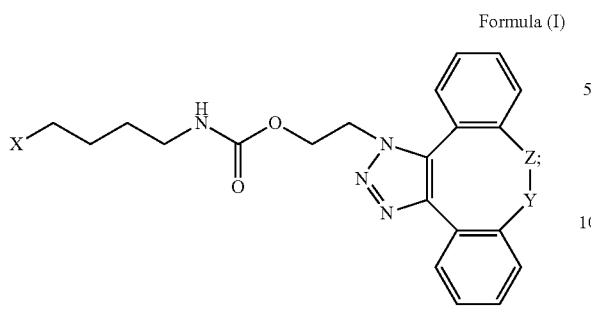

wherein:
Z is CH$_2$ and Y is

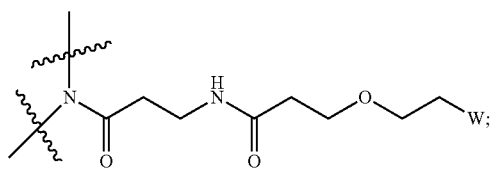

Y is CH$_2$ and Z is

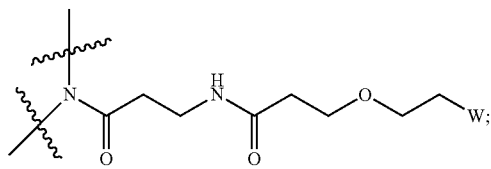

Z is CH$_2$ and Y is

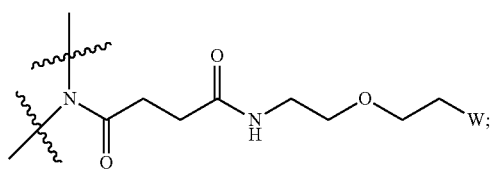

or
Y is CH$_2$ and Z is

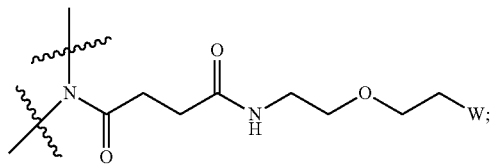

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

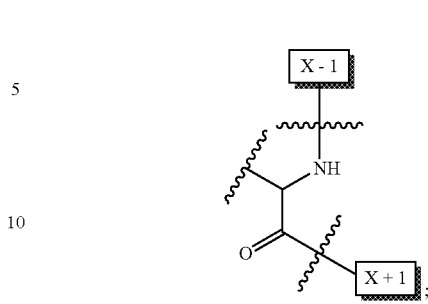

X-1 indicates the point of attachment to the preceding amino acid residue; and
X+1 indicates the point of attachment to the following amino acid residue.

Embodiment 3. The IL-15 conjugate of any one of embodiments 1-2.1 wherein Z is CH$_2$ and Y is

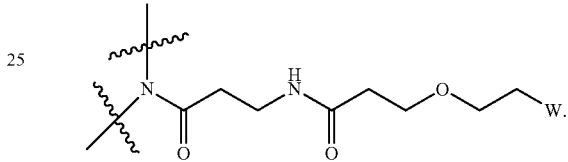

Embodiment 4. The IL-15 conjugate of any one of embodiments 1-2.1 wherein Y is CH$_2$ and Z is

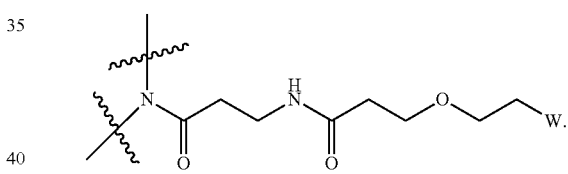

Embodiment 5. The IL-15 conjugate of any one of embodiments 1-2.1 wherein Z is CH$_2$ and Y is

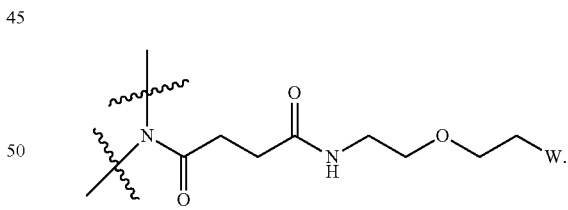

Embodiment 6. The IL-15 conjugate of any one of embodiments 1-2.1 wherein Z is CH$_2$ and Y is

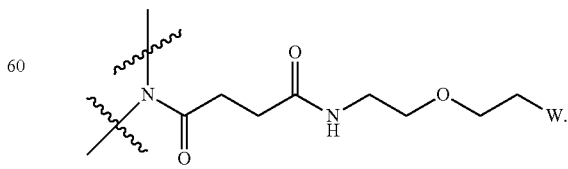

Embodiment 7. The IL-15 conjugate of any one of embodiments 1-2.1 wherein Y is CH$_2$ and Z is

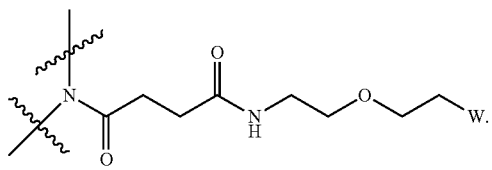

Embodiment 8. The IL-15 conjugate of any one of embodiments 1 to 7 wherein the PEG group has an average molecular weight selected from 5 kDa, 10 kDa, 15 kDa, 20 kDa, 25 kDa, 30 kDa, 35 kDa, 40 kDa, and 45 kDa.

Embodiment 9. The IL-15 conjugate of embodiment 8 wherein the PEG group has an average molecular weight of 5 kDa.

Embodiment 10. The IL-15 conjugate of embodiment 8 wherein the PEG group has an average molecular weight of 30 kDa.

Embodiment 11. The IL-15 conjugate of embodiment 1 or 1.1 wherein the position of the structure of Formula (I) in the amino acid sequence of the IL-15 conjugate is selected from S18, L25, E46, E53, N77, and S83.

Embodiment 12. The IL-15 conjugate of embodiment 11 wherein the position of the structure of Formula (I) in the amino acid sequence of the IL-15 conjugate is selected from L25, E53, and N77.

Embodiment 13. The IL-15 conjugate of embodiment 11 wherein the position of the structure of Formula (I) in the amino acid sequence of the IL-15 conjugate is S18.

Embodiment 14. The IL-15 conjugate of embodiment 11 wherein the position of the structure of Formula (I) in the amino acid sequence of the IL-15 conjugate is L25.

Embodiment 15. The IL-15 conjugate of embodiment 11 wherein the position of the structure of Formula (I) in the amino acid sequence of the IL-15 conjugate is E46.

Embodiment 16. The IL-15 conjugate of embodiment 11 wherein the position of the structure of Formula (I) in the amino acid sequence of the IL-15 conjugate is E53.

Embodiment 17. The IL-15 conjugate of embodiment 11 wherein the position of the structure of Formula (I) in the amino acid sequence of the IL-15 conjugate is N77.

Embodiment 18. The IL-15 conjugate of embodiment 11 wherein the position of the structure of Formula (I) in the amino acid sequence of the IL-15 conjugate is S83.

Embodiment 19. The IL-15 conjugate of embodiment 2 or 2.1 wherein the position of the structure of Formula (I) in the amino acid sequence of the IL-15 conjugate is selected from S19, L26, E47, E54, N78, and S84.

Embodiment 20. The IL-15 conjugate of embodiment 19 wherein the position of the structure of Formula (I) in the amino acid sequence of the IL-15 conjugate is selected from L26, E54, and N78.

Embodiment 21. The IL-15 conjugate of embodiment 20 wherein the position of the structure of Formula (I) in the amino acid sequence of the IL-15 conjugate is S19.

Embodiment 22. The IL-15 conjugate of embodiment 19 wherein the position of the structure of Formula (I) in the amino acid sequence of the IL-15 conjugate is L26.

Embodiment 23. The IL-15 conjugate of embodiment 19 wherein the position of the structure of Formula (I) in the amino acid sequence of the IL-15 conjugate is E47.

Embodiment 24. The IL-15 conjugate of embodiment 19 wherein the position of the structure of Formula (I) in the amino acid sequence of the IL-15 conjugate is E54.

Embodiment 25. The IL-15 conjugate of embodiment 19 wherein the position of the structure of Formula (I) in the amino acid sequence of the IL-15 conjugate is N78.

Embodiment 26. The IL-15 conjugate of embodiment 19 wherein the position of the structure of Formula (I) in the amino acid sequence of the IL-15 conjugate is S84.

Embodiment 27. An IL-15 conjugate comprising the amino acid sequence of any one of SEQ ID NOS: 16-21, wherein [AzK_PEG] has the structure of Formula (II) or Formula (III), or a mixture of Formula (II) and Formula (III):

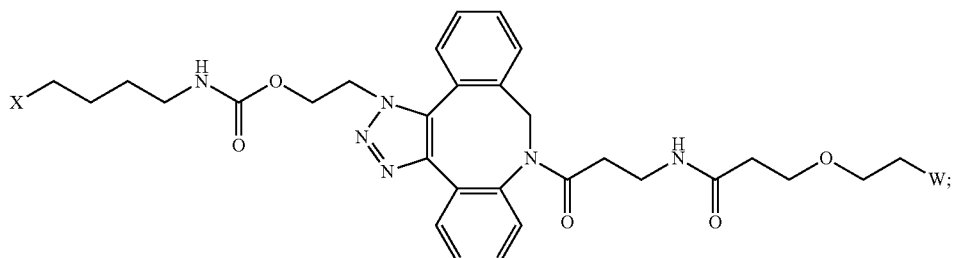

Formula (II)

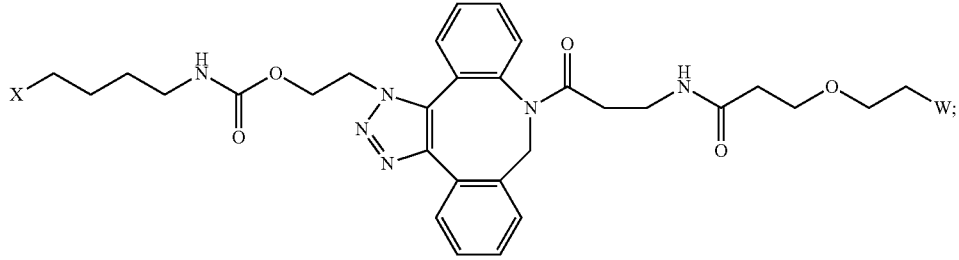

Formula (III)

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

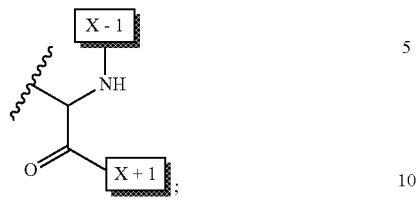

or a pharmaceutically acceptable salt, solvate, or hydrate thereof.

Embodiment 27.1. An IL-15 conjugate comprising the amino acid sequence of any one of SEQ ID NOS: 16-21, wherein [AzK_PEG] has the structure of Formula (II) or Formula (III), or a mixture of Formula (II) and Formula (III):

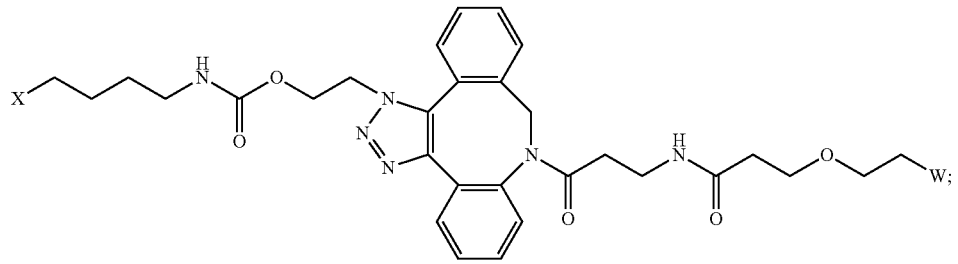

Formula (II)

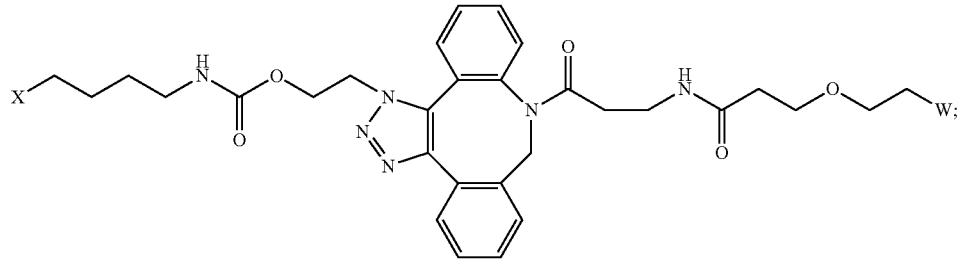

Formula (III)

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

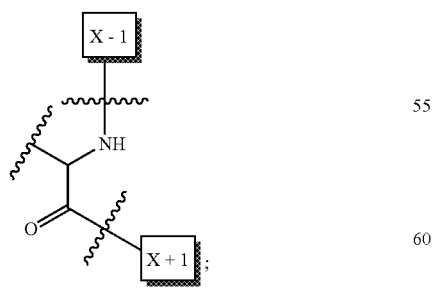

X−1 indicates the point of attachment to the preceding amino acid residue; and

X+1 indicates the point of attachment to the following amino acid residue.

Embodiment 28. The IL-15 conjugate of embodiment 27 or 27.1, wherein the [AzK_PEG] is a mixture of Formula (II) and Formula (III).

Embodiment 29. The IL-15 conjugate of embodiment 27 or 27.1, wherein the [AzK_PEG] has the structure of Formula (II):

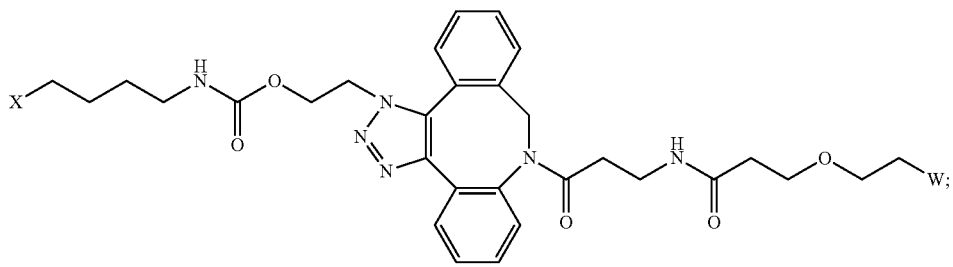

Formula (II)

or a pharmaceutically acceptable salt, solvate, or hydrate thereof.

Embodiment 30. The IL-15 conjugate of embodiment 29, wherein the IL-15 conjugate has the amino acid sequence of SEQ ID NO: 16.

Embodiment 31. The IL-15 conjugate of embodiment 30, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 32. The IL-15 conjugate of embodiment 31, wherein W is a PEG group having an average molecular weight selected from 30 kDa and 40 kDa.

Embodiment 33. The IL-15 conjugate of embodiment 32, wherein W is a PEG group having an average molecular weight of 30 kDa.

Embodiment 34. The IL-15 conjugate of embodiment 32, wherein W is a PEG group having an average molecular weight of 40 kDa.

Embodiment 35. The IL-15 conjugate of embodiment 29, wherein the IL-15 conjugate has the amino acid sequence of SEQ ID NO: 17.

Embodiment 36. The IL-15 conjugate of embodiment 35, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 37. The IL-15 conjugate of embodiment 36, wherein W is a PEG group having an average molecular weight selected from 30 kDa and 40 kDa.

Embodiment 38. The IL-15 conjugate of embodiment 37, wherein W is a PEG group having an average molecular weight of 30 kDa.

Embodiment 39. The IL-15 conjugate of embodiment 37, wherein W is a PEG group having an average molecular weight of 40 kDa.

Embodiment 40. The IL-15 conjugate of embodiment 29, wherein the IL-15 conjugate has the amino acid sequence of SEQ ID NO: 18.

Embodiment 41. The IL-15 conjugate of embodiment 40, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 42. The IL-15 conjugate of embodiment 41, wherein W is a PEG group having an average molecular weight selected from 30 kDa and 40 kDa.

Embodiment 43. The IL-15 conjugate of embodiment 42, wherein W is a PEG group having an average molecular weight of 30 kDa.

Embodiment 44. The IL-15 conjugate of embodiment 42, wherein W is a PEG group having an average molecular weight of 40 kDa.

Embodiment 45. The IL-15 conjugate of embodiment 29, wherein the IL-15 conjugate has the amino acid sequence of SEQ ID NO: 19.

Embodiment 46. The IL-15 conjugate of embodiment 45, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 47. The IL-15 conjugate of embodiment 46, wherein W is a PEG group having an average molecular weight selected from 30 kDa and 40 kDa.

Embodiment 48. The IL-15 conjugate of embodiment 47, wherein W is a PEG group having an average molecular weight of 30 kDa.

Embodiment 49. The IL-15 conjugate of embodiment 47, wherein W is a PEG group having an average molecular weight of 40 kDa.

Embodiment 50. The IL-15 conjugate of embodiment 29, wherein the IL-15 conjugate has the amino acid sequence of SEQ ID NO: 20.

Embodiment 51. The IL-15 conjugate of embodiment 50, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 52. The IL-15 conjugate of embodiment 51, wherein W is a PEG group having an average molecular weight selected from 30 kDa and 40 kDa.

Embodiment 53. The IL-15 conjugate of embodiment 52, wherein W is a PEG group having an average molecular weight of 30 kDa.

Embodiment 54. The IL-15 conjugate of embodiment 52, wherein W is a PEG group having an average molecular weight of 40 kDa.

Embodiment 55. The IL-15 conjugate of embodiment 29, wherein the IL-15 conjugate has the amino acid sequence of SEQ ID NO: 21.

Embodiment 56. The IL-15 conjugate of embodiment 55, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 57. The IL-15 conjugate of embodiment 56, wherein W is a PEG group having an average molecular weight selected from 30 kDa and 40 kDa.

Embodiment 58. The IL-15 conjugate of embodiment 57, wherein W is a PEG group having an average molecular weight of 30 kDa.

Embodiment 59. The IL-15 conjugate of embodiment 57, wherein W is a PEG group having an average molecular weight of 40 kDa.

Embodiment 60. The IL-15 conjugate of embodiment 27 or 27.1, wherein the [AzK_PEG] has the structure of Formula (III)

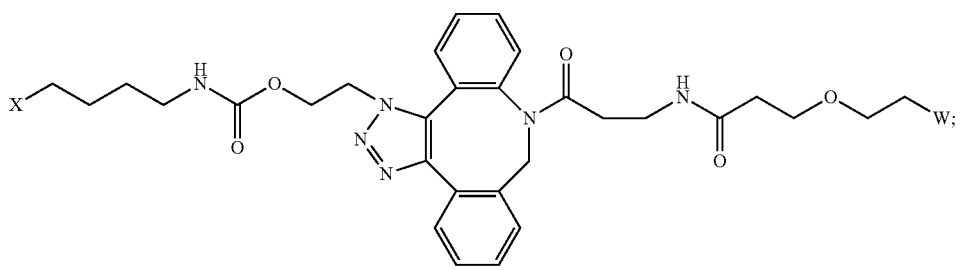

Formula (III)

or a pharmaceutically acceptable salt, solvate, or hydrate thereof.

Embodiment 61. The IL-15 conjugate of embodiment 60, wherein the IL-15 conjugate has the amino acid sequence of SEQ ID NO: 16.

Embodiment 62. The IL-15 conjugate of embodiment 61, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 63. The IL-15 conjugate of embodiment 62, wherein W is a PEG group having an average molecular weight selected from 30 kDa and 40 kDa.

Embodiment 64. The IL-15 conjugate of embodiment 63, wherein W is a PEG group having an average molecular weight of 30 kDa.

Embodiment 65. The IL-15 conjugate of embodiment 63, wherein W is a PEG group having an average molecular weight of 40 kDa.

Embodiment 66. The IL-15 conjugate of embodiment 60, wherein the IL-15 conjugate has the amino acid sequence of SEQ ID NO: 17.

Embodiment 67. The IL-15 conjugate of embodiment 66, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 68. The IL-15 conjugate of embodiment 67, wherein W is a PEG group having an average molecular weight selected from 30 kDa and 40 kDa.

Embodiment 69. The IL-15 conjugate of embodiment 68, wherein W is a PEG group having an average molecular weight of 30 kDa.

Embodiment 70. The IL-15 conjugate of embodiment 68, wherein W is a PEG group having an average molecular weight of 40 kDa.

Embodiment 71. The IL-15 conjugate of embodiment 60, wherein the IL-15 conjugate has the amino acid sequence of SEQ ID NO: 18.

Embodiment 72. The IL-15 conjugate of embodiment 71, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 73. The IL-15 conjugate of embodiment 72, wherein W is a PEG group having an average molecular weight selected from 30 kDa and 40 kDa.

Embodiment 74. The IL-15 conjugate of embodiment 73, wherein W is a PEG group having an average molecular weight of 30 kDa.

Embodiment 75. The IL-15 conjugate of embodiment 73, wherein W is a PEG group having an average molecular weight of 40 kDa.

Embodiment 76. The IL-15 conjugate of embodiment 60, wherein the IL-15 conjugate has the amino acid sequence of SEQ ID NO: 19.

Embodiment 77. The IL-15 conjugate of embodiment 76, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 78. The IL-15 conjugate of embodiment 77, wherein W is a PEG group having an average molecular weight selected from 30 kDa and 40 kDa.

Embodiment 79. The IL-15 conjugate of embodiment 78, wherein W is a PEG group having an average molecular weight of 30 kDa.

Embodiment 80. The IL-15 conjugate of embodiment 78, wherein W is a PEG group having an average molecular weight of 40 kDa.

Embodiment 81. The IL-15 conjugate of embodiment 60, wherein the IL-15 conjugate has the amino acid sequence of SEQ ID NO: 20.

Embodiment 82. The IL-15 conjugate of embodiment 81, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 83. The IL-15 conjugate of embodiment 82, wherein W is a PEG group having an average molecular weight selected from 30 kDa and 40 kDa.

Embodiment 84. The IL-15 conjugate of embodiment 83, wherein W is a PEG group having an average molecular weight of 30 kDa.

Embodiment 85. The IL-15 conjugate of embodiment 83, wherein W is a PEG group having an average molecular weight of 40 kDa.

Embodiment 86. The IL-15 conjugate of embodiment 60, wherein the IL-15 conjugate has the amino acid sequence of SEQ ID NO: 21.

Embodiment 87. The IL-15 conjugate of embodiment 86, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 88. The IL-15 conjugate of embodiment 87, wherein W is a PEG group having an average molecular weight selected from 30 kDa and 40 kDa.

Embodiment 89. The IL-15 conjugate of embodiment 88, wherein W is a PEG group having an average molecular weight of 30 kDa.

Embodiment 90. The IL-15 conjugate of embodiment 88, wherein W is a PEG group having an average molecular weight of 40 kDa.

Embodiment 91. An IL-15 conjugate comprising the amino acid sequence of any one of SEQ ID NOS: 16-21, wherein [AzK_PEG] is a mixture of the structures of Formula (II) and Formula (III):

Formula (II)

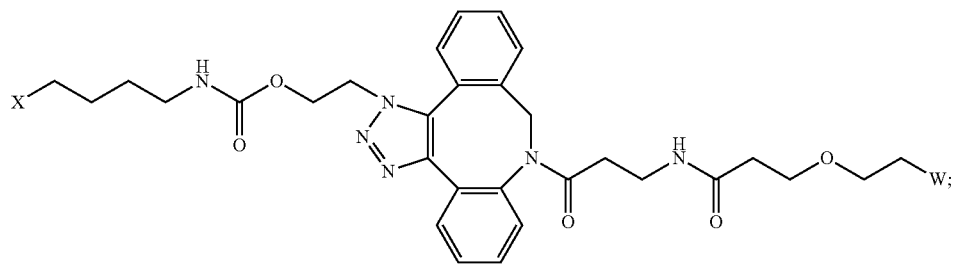

Formula (III)

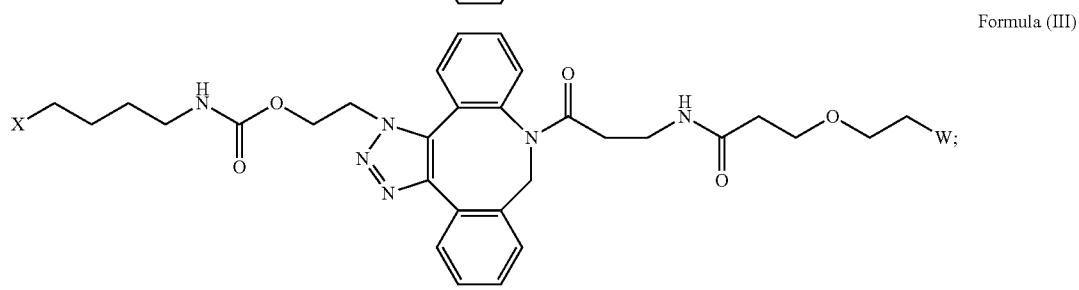

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

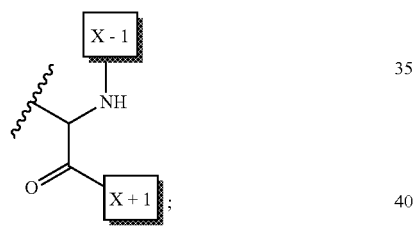

or a pharmaceutically acceptable salt, solvate, or hydrate thereof.

Embodiment 91.1. An IL-15 conjugate comprising the amino acid sequence of any one of SEQ ID NOS: 16-21, wherein [AzK_PEG] is a mixture of the structures of Formula (II) and Formula (III):

Formula (II)

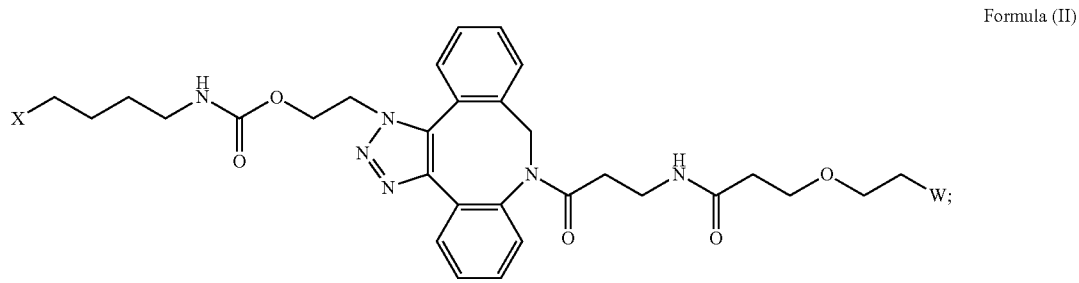

-continued

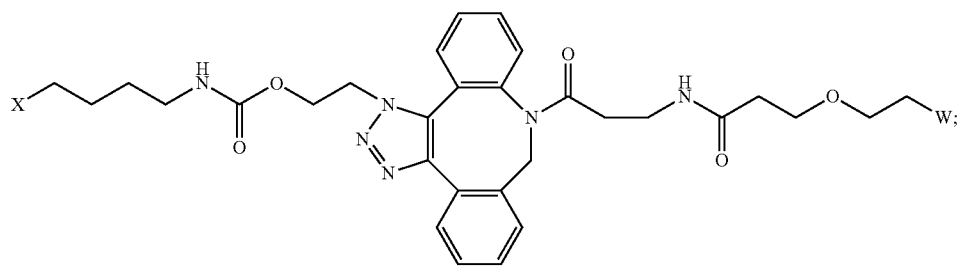

Formula (III)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

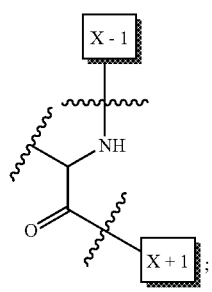

X−1 indicates the point of attachment to the preceding amino acid residue; and
X+1 indicates the point of attachment to the following amino acid residue.

Embodiment 92. The IL-15 conjugate according to embodiment 91 or 91.1, wherein the ratio of the amount of the structure of Formula (II) to the amount of the structure of Formula (III) comprising the total amount of [AzK_PEG] in the IL-15 conjugate is about 1:1.

Embodiment 93. The IL-15 conjugate according to embodiment 91 or 91.1, wherein the ratio of the amount of the structure of Formula (II) to the amount of the structure of Formula (III) comprising the total amount of [AzK_PEG] in the IL-15 conjugate is greater than 1:1.

Embodiment 94. The IL-15 conjugate according to embodiment 91 or 91.1, wherein the ratio of the amount of the structure of Formula (II) to the amount of the structure of Formula (III) comprising the total amount of [AzK_PEG] in the IL-15 conjugate is less than 1:1.

Embodiment 95. The IL-15 conjugate according to any one of embodiments 1 to 94, wherein W is a linear or branched PEG group.

Embodiment 96. The IL-15 conjugate according to any one of embodiments 1 to 94, wherein W is a linear PEG group.

Embodiment 97. The IL-15 conjugate according to any one of embodiments 1 to 94, wherein W is a branched PEG group.

Embodiment 98. The IL-15 conjugate according to any one of embodiments 1 to 94, wherein W is a methoxy PEG group.

Embodiment 99. The IL-15 conjugate according to embodiment 98, wherein the methoxy PEG group is linear or branched.

Embodiment 100. The IL-15 conjugate according to embodiment 98, wherein the methoxy PEG group is linear.

Embodiment 101. The IL-15 conjugate according to embodiment 98, wherein the methoxy PEG group is branched.

Embodiment 102. An IL-15 conjugate comprising the amino acid sequence of any one of SEQ ID NOS: 22-27, wherein [AzK_PEG30] has the structure of Formula (II) or Formula (III), or a mixture of Formula (II) and Formula (III):

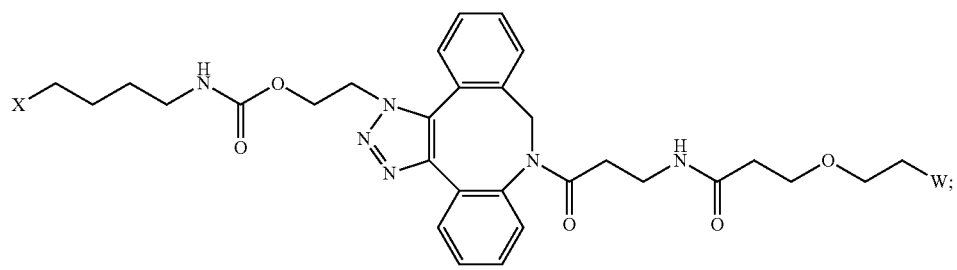

Formula (II)

-continued

Formula (III)

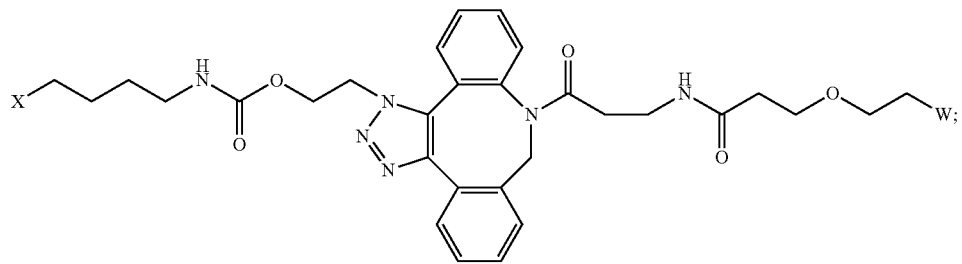

wherein:
W is a PEG group having an average molecular weight of 30 kDa; and
X has the structure:

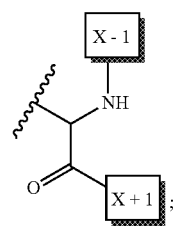

or a pharmaceutically acceptable salt, solvate, or hydrate thereof.

Embodiment 102.1. An IL-15 conjugate comprising the amino acid sequence of any one of SEQ ID NOS: 22-27, wherein [AzK_PEG30] has the structure of Formula (II) or Formula (III), or a mixture of Formula (II) and Formula (III):

X has the structure:

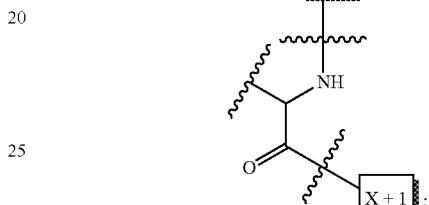

X−1 indicates the point of attachment to the preceding amino acid residue; and
X+1 indicates the point of attachment to the following amino acid residue.

Embodiment 103. The IL-15 conjugate of embodiment 102 or 102.1, wherein the IL-15 conjugate has the amino acid sequence of SEQ ID NO: 22.

Formula (II)

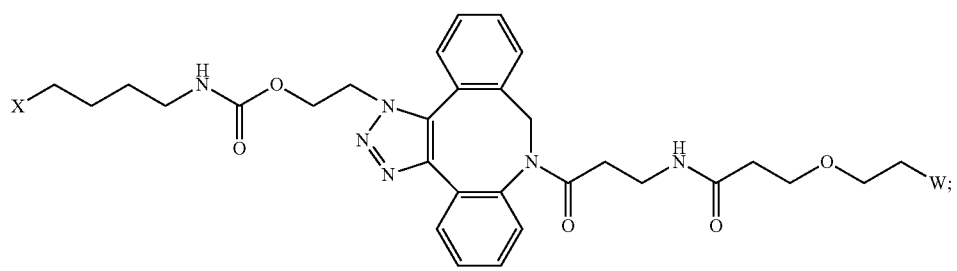

Formula (III)

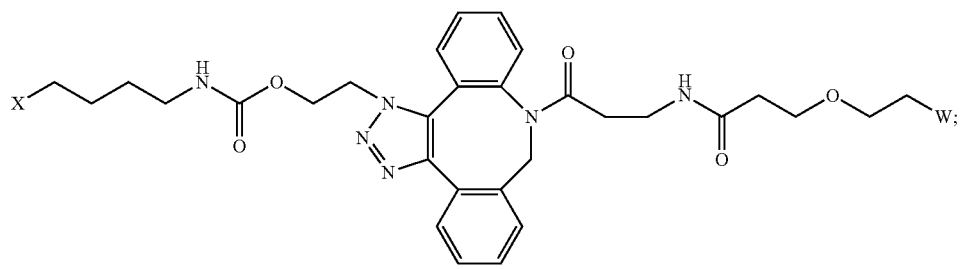

wherein:
W is a PEG group having an average molecular weight of 30 kDa; and

Embodiment 104. The IL-15 conjugate of embodiment 102 or 102.1, wherein the IL-15 conjugate has the amino acid sequence of SEQ ID NO: 23.

Embodiment 105. The IL-15 conjugate of embodiment 102 or 102.1, wherein the IL-15 conjugate has the amino acid sequence of SEQ ID NO: 24.

Embodiment 106. The IL-15 conjugate of embodiment 102 or 102.1, wherein the IL-15 conjugate has the amino acid sequence of SEQ ID NO: 25.

Embodiment 107. The IL-15 conjugate of embodiment 102 or 102.1, wherein the IL-15 conjugate has the amino acid sequence of SEQ ID NO: 26.

Embodiment 108. The IL-15 conjugate of embodiment 102 or 102.1, wherein the IL-15 conjugate has the amino acid sequence of SEQ ID NO: 27.

Embodiment 109. The IL-15 conjugate of embodiment 102 or 102.1, wherein the [AzK_PEG30] has the structure of Formula (II)

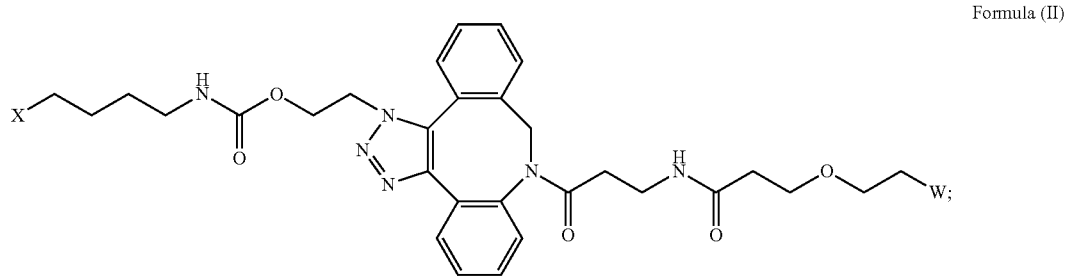

Formula (II)

or a pharmaceutically acceptable salt, solvate, or hydrate thereof.

Embodiment 110. The IL-15 conjugate of embodiment 109, wherein the IL-15 conjugate has the amino acid sequence of SEQ ID NO: 22.

Embodiment 111. The IL-15 conjugate of embodiment 109, wherein the IL-15 conjugate has the amino acid sequence of SEQ ID NO: 23.

Embodiment 112. The IL-15 conjugate of embodiment 109, wherein the IL-15 conjugate has the amino acid sequence of SEQ ID NO: 24.

Embodiment 113. The IL-15 conjugate of embodiment 109, wherein the IL-15 conjugate has the amino acid sequence of SEQ ID NO: 25.

Embodiment 114. The IL-15 conjugate of embodiment 109, wherein the IL-15 conjugate has the amino acid sequence of SEQ ID NO: 26.

Embodiment 115. The IL-15 conjugate of embodiment 109, wherein the IL-15 conjugate has the amino acid sequence of SEQ ID NO: 27.

Embodiment 116. The IL-15 conjugate of embodiment 102 or 102.1, wherein the [AzK_PEG30] has the structure of Formula (III)

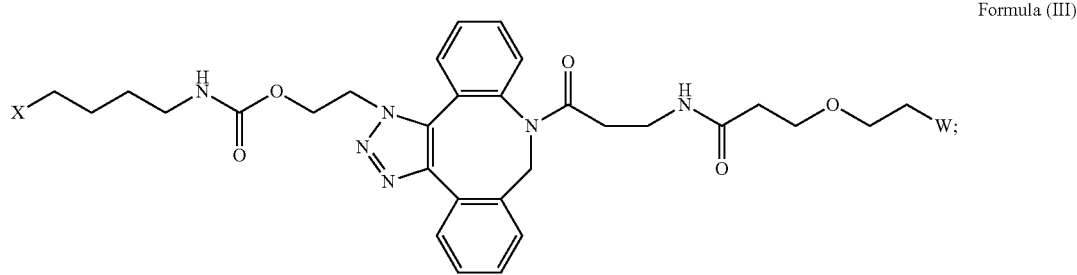

Formula (III)

or a pharmaceutically acceptable salt, solvate, or hydrate thereof.

Embodiment 117. The IL-15 conjugate of embodiment 116, wherein the IL-15 conjugate has the amino acid sequence of SEQ ID NO: 22.

Embodiment 118. The IL-15 conjugate of embodiment 116, wherein the IL-15 conjugate has the amino acid sequence of SEQ ID NO: 23.

Embodiment 119. The IL-15 conjugate of embodiment 116, wherein the IL-15 conjugate has the amino acid sequence of SEQ ID NO: 24.

Embodiment 120. The IL-15 conjugate of embodiment 116, wherein the IL-15 conjugate has the amino acid sequence of SEQ ID NO: 25.

Embodiment 121. The IL-15 conjugate of embodiment 116, wherein the IL-15 conjugate has the amino acid sequence of SEQ ID NO: 26.

Embodiment 122. The IL-15 conjugate of embodiment 116, wherein the IL-15 conjugate has the amino acid sequence of SEQ ID NO: 27.

Embodiment 123. An IL-15 conjugate comprising the amino acid sequence of any one of SEQ ID NOS: 22 to 27, wherein [AzK_PEG30] is a mixture of the structures of Formula (II) and Formula (III):

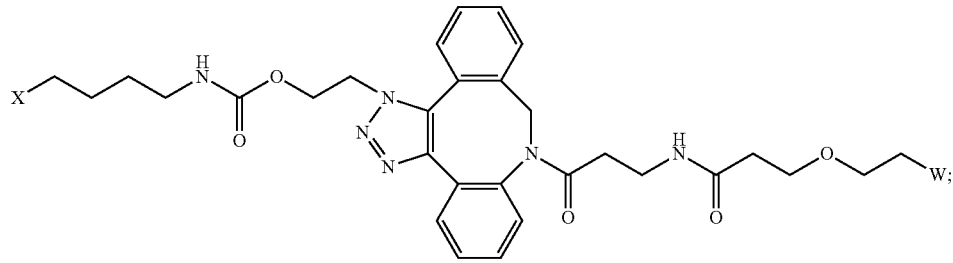

Formula (II)

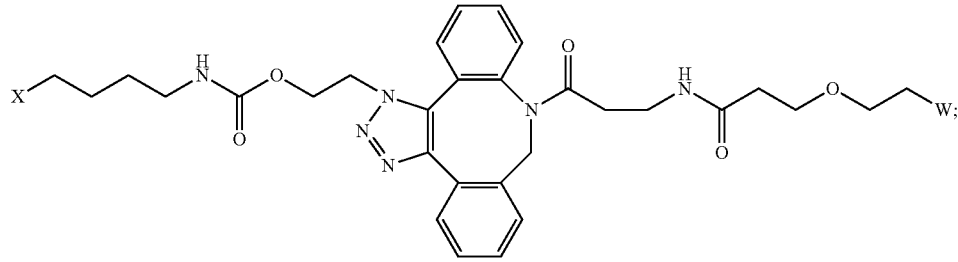

Formula (III)

wherein:

W is a PEG group having an average molecular weight of 30 kDa; and

X has the structure:

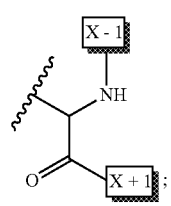

or a pharmaceutically acceptable salt, solvate, or hydrate thereof.

Embodiment 123.1. An IL-15 conjugate comprising the amino acid sequence of anyone of SEQ ID NOS: 22 to 27, wherein [AzK_PEG30] is a mixture of the structures of Formula (II) and Formula (III):

Formula (II)

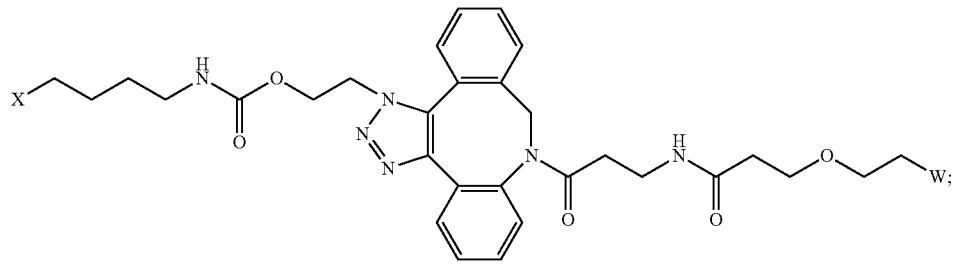

Formula (III)

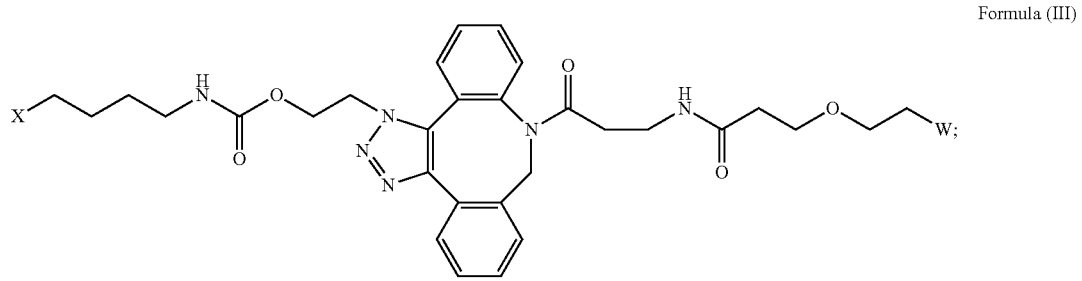

wherein:
W is a PEG group having an average molecular weight of 30 kDa; and
X has the structure:

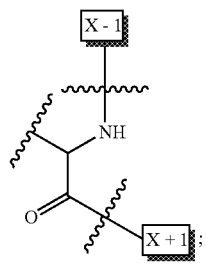

X−1 indicates the point of attachment to the preceding amino acid residue; and
X+1 indicates the point of attachment to the following amino acid residue.

Embodiment 124. The IL-15 conjugate according to embodiment 123 or 123.1, wherein the ratio of the amount of the structure of Formula (II) to the amount of the structure of Formula (III) comprising the total amount of [AzK_PEG30] in the IL-15 conjugate is about 1:1.

Embodiment 125. The IL-15 conjugate according to embodiment 123 or 123.1, wherein the ratio of the amount of the structure of Formula (II) to the amount of the structure of Formula (III) comprising the total amount of [AzK_PEG30] in the IL-15 conjugate is greater than 1:1.

Embodiment 126. The IL-15 conjugate according to embodiment 123 or 123.1, wherein the ratio of the amount of the structure of Formula (II) to the amount of the structure of Formula (III) comprising the total amount of [AzK_PEG30] in the IL-15 conjugate is less than 1:1.

Embodiment 127. The IL-15 conjugate according to any one of embodiments 102 to 126, wherein W is a linear or branched PEG group.

Embodiment 128. The IL-15 conjugate according to any one of embodiments 102 to 126, wherein W is a linear PEG group.

Embodiment 129. The IL-15 conjugate according to any one of embodiments 102 to 126, wherein W is a branched PEG group.

Embodiment 130. The IL-15 conjugate according to any one of embodiments 102 to 126, wherein W is a methoxy PEG group.

Embodiment 131. The IL-15 conjugate according to embodiment 130, wherein the methoxy PEG group is linear or branched.

Embodiment 132. The IL-15 conjugate according to embodiment 131, wherein the methoxy PEG group is linear.

Embodiment 133. The IL-15 conjugate according to embodiment 131, wherein the methoxy PEG group is branched.

Embodiment 134. An IL-15 conjugate comprising the amino acid sequence of any one of SEQ ID NOS: 28-33, wherein [AzK_PEG40] has the structure of Formula (II) or Formula (III), or is a mixture of the structures of Formula (II) and Formula (III):

Formula (II)

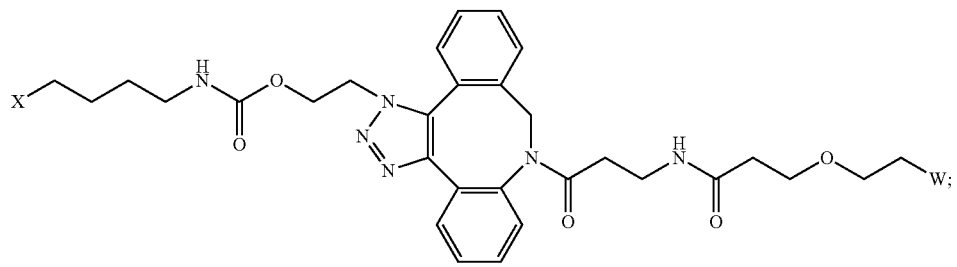

Formula (III)

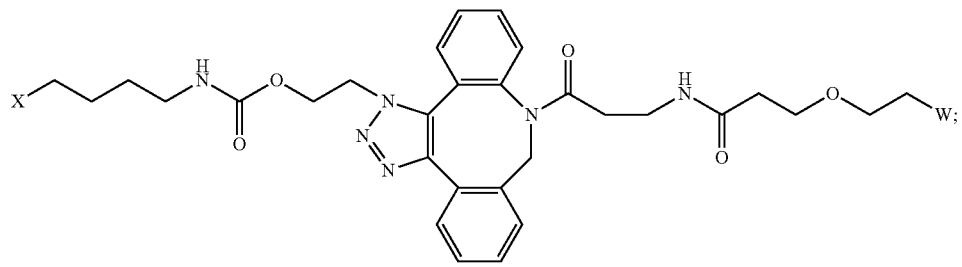

wherein:
W is a PEG group having an average molecular weight of 40 kDa; and
X has the structure:

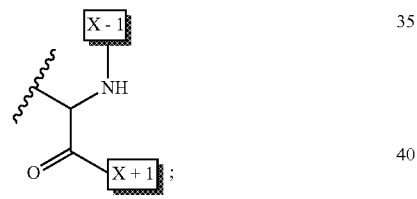

or a pharmaceutically acceptable salt, solvate, or hydrate thereof.

Embodiment 134.1. An IL-15 conjugate comprising the amino acid sequence of anyone of SEQ ID NOS: 28-33, wherein [AzK_PEG40] has the structure of Formula (II) or Formula (III), or is a mixture of the structures of Formula (II) and Formula (III):

Formula (II)

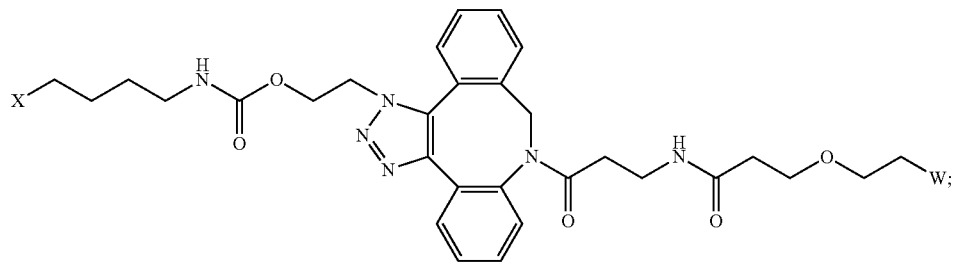

Formula (III)

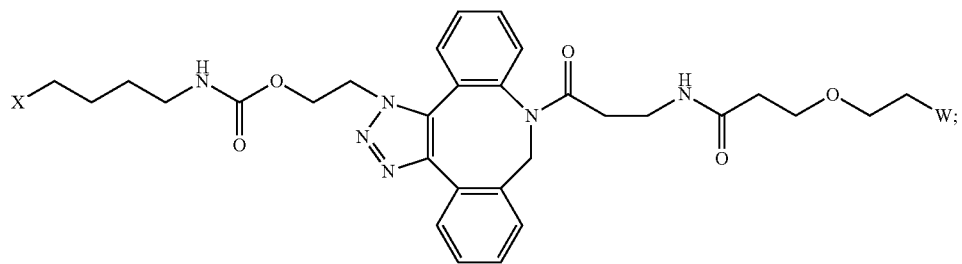

wherein:
W is a PEG group having an average molecular weight of 40 kDa; and
X has the structure:

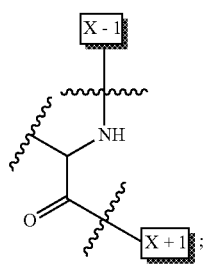

X−1 indicates the point of attachment to the preceding amino acid residue; and
X+1 indicates the point of attachment to the following amino acid residue.

Embodiment 135. The IL-15 conjugate of embodiment 134 or 134.1, wherein the IL-15 conjugate has the amino acid sequence of SEQ ID NO: 28.
Embodiment 136. The IL-15 conjugate of embodiment 134 or 134.1, wherein the IL-15 conjugate has the amino acid sequence of SEQ ID NO: 29.
Embodiment 137. The IL-15 conjugate of embodiment 134 or 134.1, wherein the IL-15 conjugate has the amino acid sequence of SEQ ID NO: 30.
Embodiment 138. The IL-15 conjugate of embodiment 134 or 134.1, wherein the IL-15 conjugate has the amino acid sequence of SEQ ID NO: 31.
Embodiment 139. The IL-15 conjugate of embodiment 134 or 134.1, wherein the IL-15 conjugate has the amino acid sequence of SEQ ID NO: 32.
Embodiment 140. The IL-15 conjugate of embodiment 134 or 134.1, wherein the IL-15 conjugate has the amino acid sequence of SEQ ID NO: 33.
Embodiment 141. The IL-15 conjugate of embodiment 134 or 134.1, wherein the [AzK_PEG40] has the structure of Formula (II):

Formula (II)

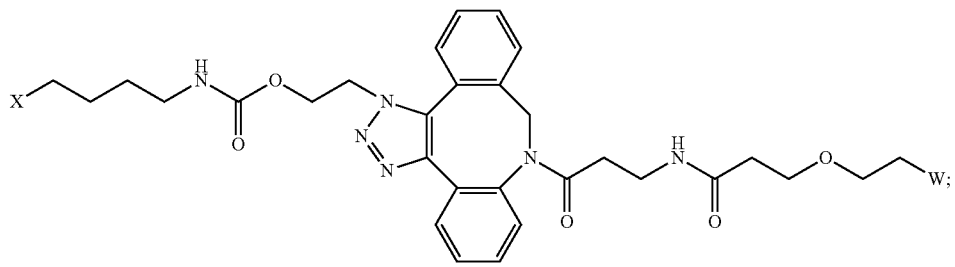

or a pharmaceutically acceptable salt, solvate, or hydrate thereof.
Embodiment 142. The IL-15 conjugate of embodiment 141, wherein the IL-15 conjugate has the amino acid sequence of SEQ ID NO: 28.
Embodiment 143. The IL-15 conjugate of embodiment 141, wherein the IL-15 conjugate has the amino acid sequence of SEQ ID NO: 29.
Embodiment 144. The IL-15 conjugate of embodiment 141, wherein the IL-15 conjugate has the amino acid sequence of SEQ ID NO: 30.
Embodiment 145. The IL-15 conjugate of embodiment 141, wherein the IL-15 conjugate has the amino acid sequence of SEQ ID NO: 31.
Embodiment 146. The IL-15 conjugate of embodiment 141, wherein the IL-15 conjugate has the amino acid sequence of SEQ ID NO: 32.

Embodiment 147. The IL-15 conjugate of embodiment 141, wherein the IL-15 conjugate has the amino acid sequence of SEQ ID NO: 33.

Embodiment 148. The IL-15 conjugate of embodiment 134, wherein the [AzK_PEG40] has the structure of Formula (III)

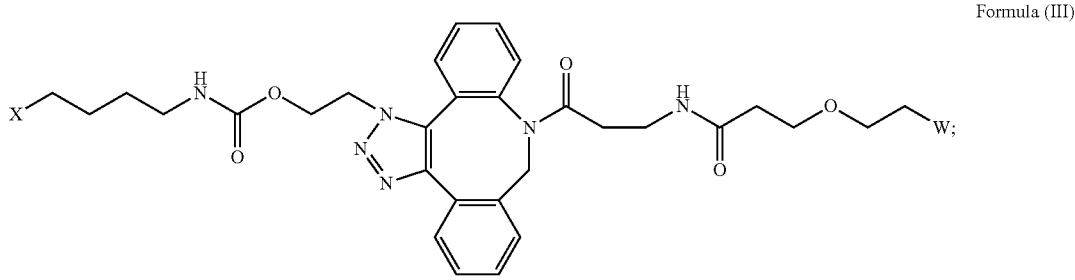

Formula (III)

or a pharmaceutically acceptable salt, solvate, or hydrate thereof.

Embodiment 149. The IL-15 conjugate of embodiment 148, wherein the IL-15 conjugate has the amino acid sequence of SEQ ID NO: 28.

Embodiment 150. The IL-15 conjugate of embodiment 148, wherein the IL-15 conjugate has the amino acid sequence of SEQ ID NO: 29.

Embodiment 151. The IL-15 conjugate of embodiment 148, wherein the IL-15 conjugate has the amino acid sequence of SEQ ID NO: 30.

Embodiment 152. The IL-15 conjugate of embodiment 148, wherein the IL-15 conjugate has the amino acid sequence of SEQ ID NO: 31.

Embodiment 153. The IL-15 conjugate of embodiment 148, wherein the IL-15 conjugate has the amino acid sequence of SEQ ID NO: 32.

Embodiment 154. The IL-15 conjugate of embodiment 148, wherein the IL-15 conjugate has the amino acid sequence of SEQ ID NO: 33.

Embodiment 155. An IL-15 conjugate comprising the amino acid sequence of any one of SEQ ID NOS: 28-33, wherein [AzK_PEG40] is a mixture of the structures of Formula (II) and Formula (III):

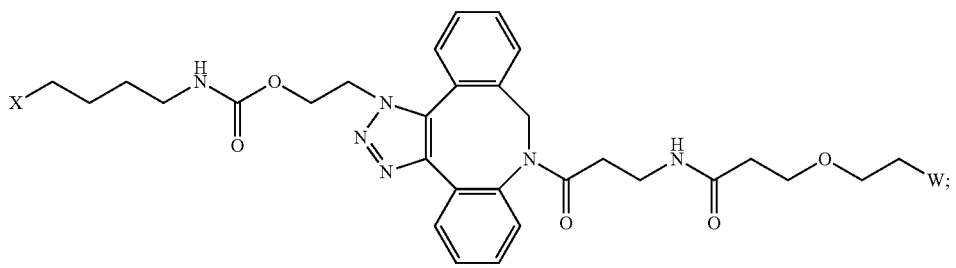

Formula (II)

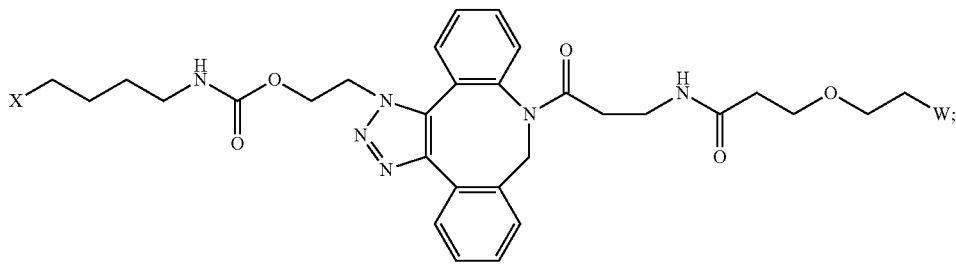

Formula (III)

wherein:
W is a PEG group having an average molecular weight of 40 kDa; and
X has the structure:

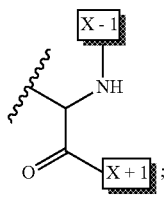

or a pharmaceutically acceptable salt, solvate, or hydrate thereof.

Embodiment 155.1. An IL-15 conjugate comprising the amino acid sequence of anyone of SEQ ID NOS: 28-33, wherein [AzK_PEG40] is a mixture of the structures of Formula (II) and Formula (III):

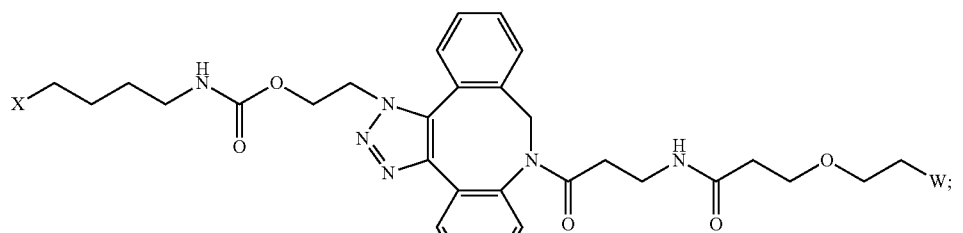

Formula (II)

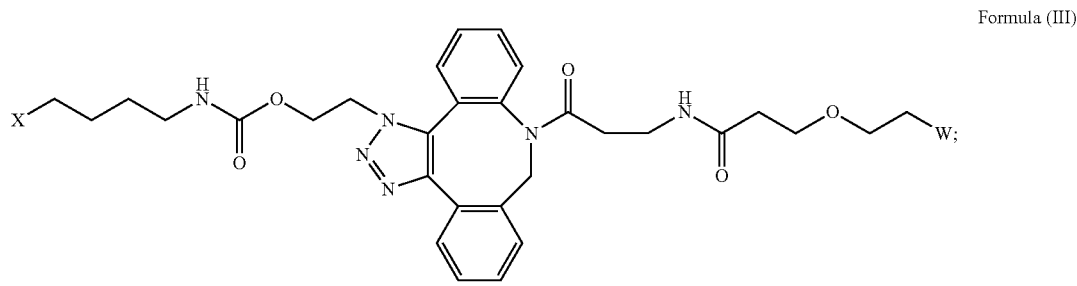

Formula (III)

wherein:
W is a PEG group having an average molecular weight of 40 kDa; and
X has the structure:

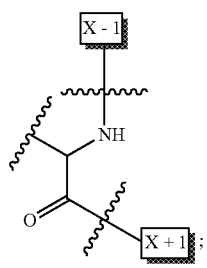

X−1 indicates the point of attachment to the preceding amino acid residue; and
X+1 indicates the point of attachment to the following amino acid residue.

Embodiment 156. The IL-15 conjugate according to embodiment 155 or 155.1, wherein the ratio of the amount of the structure of Formula (II) to the amount of the structure of Formula (III) comprising the total amount of [AzK_PEG40] in the IL-15 conjugate is about 1:1.

Embodiment 157. The IL-15 conjugate according to embodiment 155 or 155.1, wherein the ratio of the amount of the structure of Formula (II) to the amount of the structure of Formula (III) comprising the total amount of [AzK_PEG40] in the IL-15 conjugate is greater than 1:1.

Embodiment 158. The IL-15 conjugate according to embodiment 155 or 155.1, wherein the ratio of the amount of the structure of Formula (II) to the amount of the structure of Formula (III) comprising the total amount of [AzK_PEG40] in the IL-15 conjugate is less than 1:1.

Embodiment 159. The IL-15 conjugate according to any one of embodiments 134 to 158, wherein W is a linear or branched PEG group.

Embodiment 160. The IL-15 conjugate according to any one of embodiments 134 to 158, wherein W is a linear PEG group.

Embodiment 161. The IL-15 conjugate according to any one of embodiments 134 to 158, wherein W is a branched PEG group.

Embodiment 162. The IL-15 conjugate according to any one of embodiments 134 to 158, wherein W is a methoxy PEG group.

Embodiment 163. The IL-15 conjugate according to embodiment 162, wherein the methoxy PEG group is linear or branched.

Embodiment 164. The IL-15 conjugate according to embodiment 163, wherein the methoxy PEG group is linear.

Embodiment 165. The IL-15 conjugate according to embodiment 163, wherein the methoxy PEG group is branched.

Embodiment 166. An IL-15 conjugate comprising the amino acid sequence of any one of SEQ ID NOS: 34-39, wherein [AzK_L1_PEG] has the structure of Formula (IV) or Formula (V), or a mixture of Formula (IV) and Formula (V):

Formula (IV)

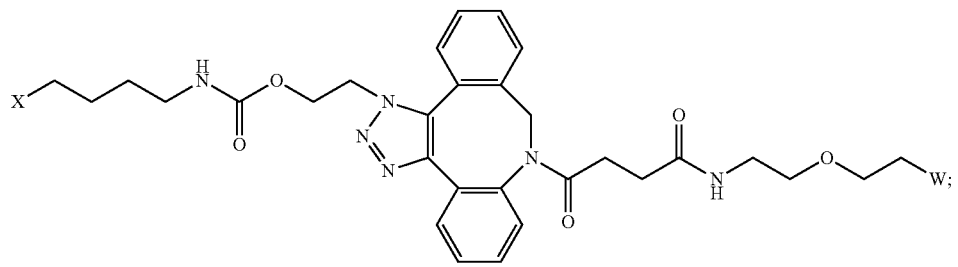

Formula (V)

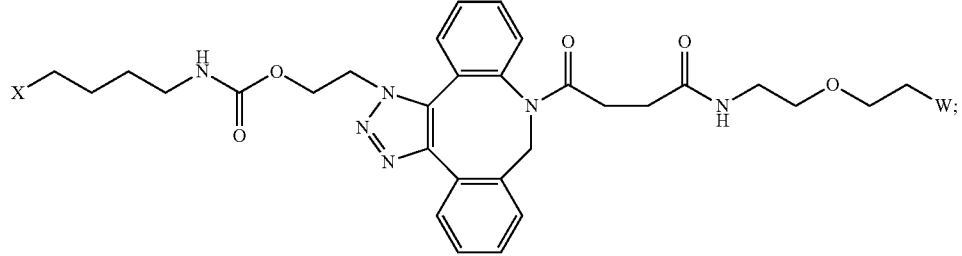

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

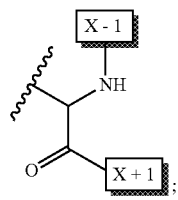

or a pharmaceutically acceptable salt, solvate, or hydrate thereof.

Embodiment 166.1. An IL-15 conjugate comprising the amino acid sequence of anyone of SEQ ID NOS: 34-39, wherein [AzK_L1_PEG] has the structure of Formula (IV) or Formula (V), or a mixture of Formula (IV) and Formula (V):

Formula (IV)

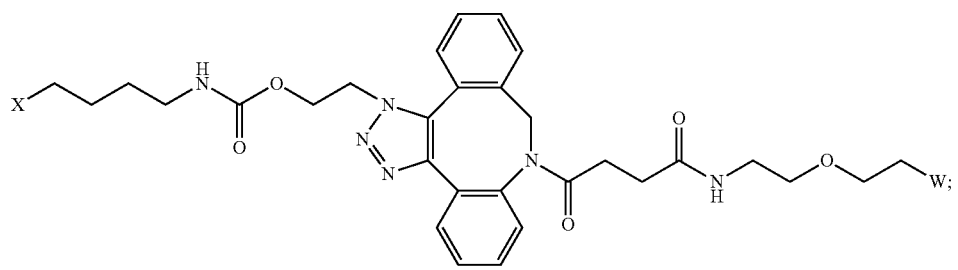

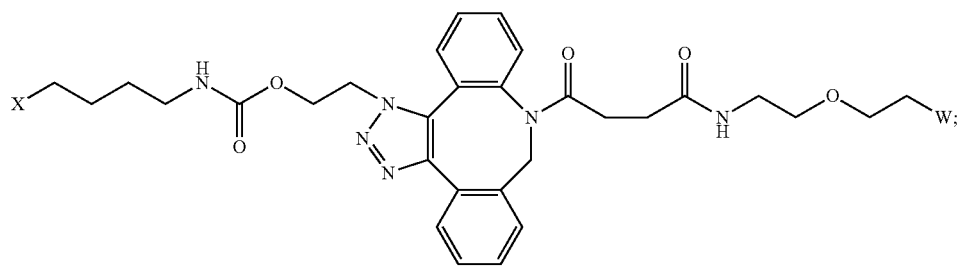

Formula (V)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

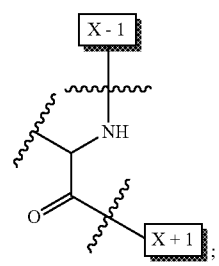

X−1 indicates the point of attachment to the preceding amino acid residue; and
X+1 indicates the point of attachment to the following amino acid residue.

Embodiment 167. The IL-15 conjugate of embodiment 166 or 166.1, wherein the [AzK_L1_PEG] is a mixture of Formula (IV) and Formula (V).
Embodiment 168. The IL-15 conjugate of embodiment 166 or 166.1, wherein the [AzK_L1_PEG] has the structure of Formula (IV):

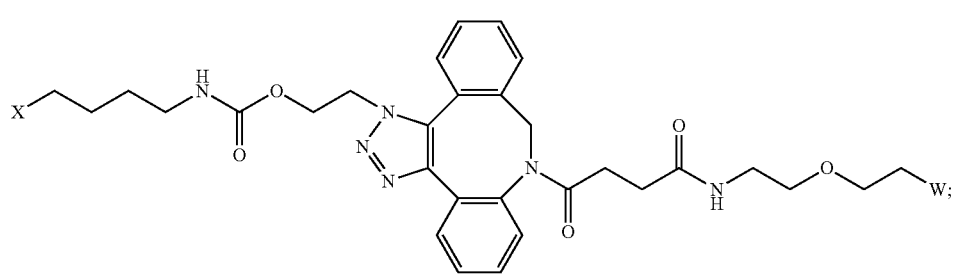

Formula (IV)

or a pharmaceutically acceptable salt, solvate, or hydrate thereof.
Embodiment 169. The IL-15 conjugate of embodiment 168, wherein the IL-15 conjugate has the amino acid sequence of SEQ ID NO: 34.
Embodiment 170. The IL-15 conjugate of embodiment 169, wherein W is a PEG group having an average molecular weight selected from 5 kDa, 10 kDa, 15 kDa, 20 kDa, 25 kDa, 30 kDa, 35 kDa, 40 kDa, and 45 kDa.
Embodiment 171. The IL-15 conjugate of embodiment 170, wherein W is a PEG group having an average molecular weight selected from 30 kDa and 40 kDa.
Embodiment 172. The IL-15 conjugate of embodiment 171, wherein W is a PEG group having an average molecular weight of 30 kDa.
Embodiment 173. The IL-15 conjugate of embodiment 171, wherein W is a PEG group having an average molecular weight of 40 kDa.
Embodiment 174. The IL-15 conjugate of embodiment 168, wherein the IL-15 conjugate has the amino acid sequence of SEQ ID NO: 35.
Embodiment 175. The IL-15 conjugate of embodiment 174, wherein W is a PEG group having an average molecular weight selected from 5 kDa, 10 kDa, 15 kDa, 20 kDa, 25 kDa, 30 kDa, 35 kDa, 40 kDa, and 45 kDa.
Embodiment 176. The IL-15 conjugate of embodiment 175, wherein W is a PEG group having an average molecular weight selected from 30 kDa and 40 kDa.
Embodiment 177. The IL-15 conjugate of embodiment 176, wherein W is a PEG group having an average molecular weight of 30 kDa.
Embodiment 178. The IL-15 conjugate of embodiment 176, wherein W is a PEG group having an average molecular weight of 40 kDa.
Embodiment 179. The IL-15 conjugate of embodiment 168, wherein the IL-15 conjugate has the amino acid sequence of SEQ ID NO: 36.
Embodiment 180. The IL-15 conjugate of embodiment 179, wherein W is a PEG group having an average molecular weight selected from 5 kDa, 10 kDa, 15 kDa, 20 kDa, 25 kDa, 30 kDa, 35 kDa, 40 kDa, and 45 kDa.
Embodiment 181. The IL-15 conjugate of embodiment 180, wherein W is a PEG group having an average molecular weight selected from 30 kDa and 40 kDa.
Embodiment 182. The IL-15 conjugate of embodiment 181, wherein W is a PEG group having an average molecular weight of 30 kDa.

Embodiment 183. The IL-15 conjugate of embodiment 181, wherein W is a PEG group having an average molecular weight of 40 kDa.

Embodiment 199. The IL-15 conjugate of embodiment 166, wherein the [AzK_L1_PEG] has the structure of Formula (V)

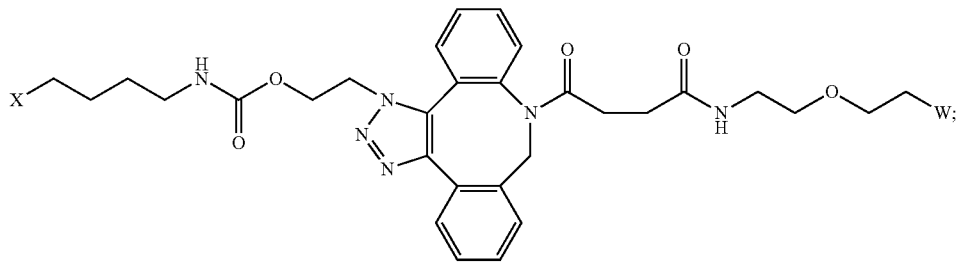

Formula (V)

or a pharmaceutically acceptable salt, solvate, or hydrate thereof.

Embodiment 184. The IL-15 conjugate of embodiment 168, wherein the IL-15 conjugate has the amino acid sequence of SEQ ID NO: 37.

Embodiment 185. The IL-15 conjugate of embodiment 184, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 186. The IL-15 conjugate of embodiment 185, wherein W is a PEG group having an average molecular weight selected from 30 kDa and 40 kDa.

Embodiment 187. The IL-15 conjugate of embodiment 186, wherein W is a PEG group having an average molecular weight of 30 kDa.

Embodiment 188. The IL-15 conjugate of embodiment 186, wherein W is a PEG group having an average molecular weight of 40 kDa.

Embodiment 189. The IL-15 conjugate of embodiment 168, wherein the IL-15 conjugate has the amino acid sequence of SEQ ID NO: 38.

Embodiment 190. The IL-15 conjugate of embodiment 189, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 191. The IL-15 conjugate of embodiment 190, wherein W is a PEG group having an average molecular weight selected from 30 kDa and 40 kDa.

Embodiment 192. The IL-15 conjugate of embodiment 191, wherein W is a PEG group having an average molecular weight of 30 kDa.

Embodiment 193. The IL-15 conjugate of embodiment 191, wherein W is a PEG group having an average molecular weight of 40 kDa.

Embodiment 194. The IL-15 conjugate of embodiment 168, wherein the IL-15 conjugate has the amino acid sequence of SEQ ID NO: 39.

Embodiment 195. The IL-15 conjugate of embodiment 194, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 196. The IL-15 conjugate of embodiment 195, wherein W is a PEG group having an average molecular weight selected from 30 kDa and 40 kDa.

Embodiment 197. The IL-15 conjugate of embodiment 196, wherein W is a PEG group having an average molecular weight of 30 kDa.

Embodiment 198. The IL-15 conjugate of embodiment 196, wherein W is a PEG group having an average molecular weight of 40 kDa.

Embodiment 200. The IL-15 conjugate of embodiment 199, wherein the IL-15 conjugate has the amino acid sequence of SEQ ID NO: 34.

Embodiment 201. The IL-15 conjugate of embodiment 200, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 202. The IL-15 conjugate of embodiment 201, wherein W is a PEG group having an average molecular weight selected from 30 kDa and 40 kDa.

Embodiment 203. The IL-15 conjugate of embodiment 202, wherein W is a PEG group having an average molecular weight of 30 kDa.

Embodiment 204. The IL-15 conjugate of embodiment 202, wherein W is a PEG group having an average molecular weight of 40 kDa.

Embodiment 205. The IL-15 conjugate of embodiment 199, wherein the IL-15 conjugate has the amino acid sequence of SEQ ID NO: 35.

Embodiment 206. The IL-15 conjugate of embodiment 205, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 207. The IL-15 conjugate of embodiment 206, wherein W is a PEG group having an average molecular weight selected from 30 kDa and 40 kDa.

Embodiment 208. The IL-15 conjugate of embodiment 207, wherein W is a PEG group having an average molecular weight of 30 kDa.

Embodiment 209. The IL-15 conjugate of embodiment 207, wherein W is a PEG group having an average molecular weight of 40 kDa.

Embodiment 210. The IL-15 conjugate of embodiment 199, wherein the IL-15 conjugate has the amino acid sequence of SEQ ID NO: 36.

Embodiment 211. The IL-15 conjugate of embodiment 210, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 212. The IL-15 conjugate of embodiment 211, wherein W is a PEG group having an average molecular weight selected from 30 kDa and 40 kDa.

Embodiment 213. The IL-15 conjugate of embodiment 212, wherein W is a PEG group having an average molecular weight of 30 kDa.

Embodiment 214. The IL-15 conjugate of embodiment 212, wherein W is a PEG group having an average molecular weight of 40 kDa.

Embodiment 215. The IL-15 conjugate of embodiment 199, wherein the IL-15 conjugate has the amino acid sequence of SEQ ID NO: 37.

Embodiment 216. The IL-15 conjugate of embodiment 215, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 217. The IL-15 conjugate of embodiment 216, wherein W is a PEG group having an average molecular weight selected from 30 kDa and 40 kDa.

Embodiment 218. The IL-15 conjugate of embodiment 217, wherein W is a PEG group having an average molecular weight of 30 kDa.

Embodiment 219. The IL-15 conjugate of embodiment 217, wherein W is a PEG group having an average molecular weight of 40 kDa.

Embodiment 220. The IL-15 conjugate of embodiment 199, wherein the IL-15 conjugate has the amino acid sequence of SEQ ID NO: 38.

Embodiment 221. The IL-15 conjugate of embodiment 220, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 222. The IL-15 conjugate of embodiment 221, wherein W is a PEG group having an average molecular weight selected from 30 kDa and 40 kDa.

Embodiment 223. The IL-15 conjugate of embodiment 222, wherein W is a PEG group having an average molecular weight of 30 kDa.

Embodiment 224. The IL-15 conjugate of embodiment 222, wherein W is a PEG group having an average molecular weight of 40 kDa.

Embodiment 225. The IL-15 conjugate of embodiment 199, wherein the IL-15 conjugate has the amino acid sequence of SEQ ID NO: 39.

Embodiment 226. The IL-15 conjugate of embodiment 225, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 227. The IL-15 conjugate of embodiment 226, wherein W is a PEG group having an average molecular weight selected from 30 kDa and 40 kDa.

Embodiment 228. The IL-15 conjugate of embodiment 227, wherein W is a PEG group having an average molecular weight of 30 kDa.

Embodiment 229. The IL-15 conjugate of embodiment 227, wherein W is a PEG group having an average molecular weight of 40 kDa.

Embodiment 230. An IL-15 conjugate comprising the amino acid sequence of any one of SEQ ID NOS: 34-39, wherein [Azk_L1_PEG] is a mixture of the structures of Formula (IV) and Formula (V):

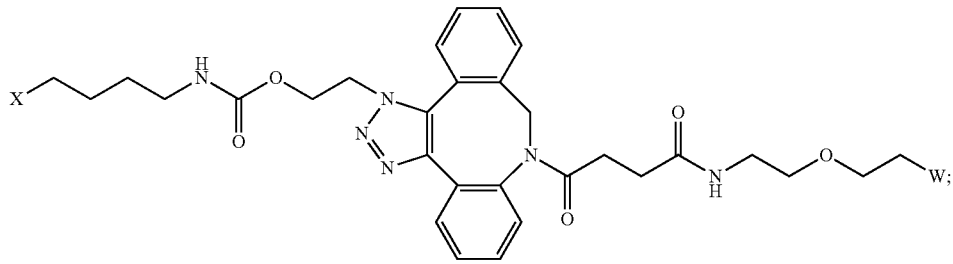

Formula (IV)

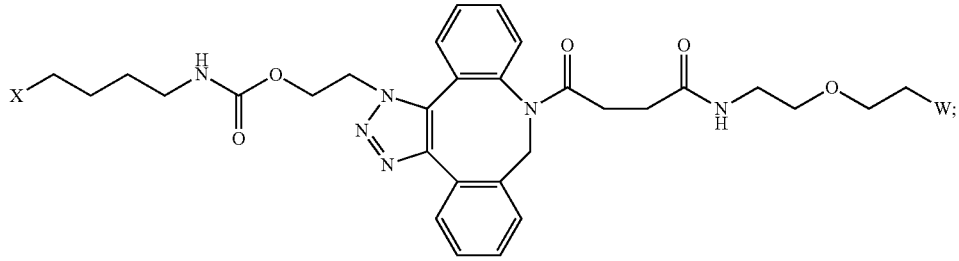

Formula (V)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

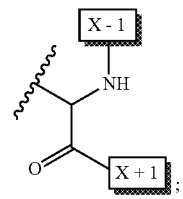

or a pharmaceutically acceptable salt, solvate, or hydrate thereof.

Embodiment 230.1. An IL-15 conjugate comprising the amino acid sequence of anyone of SEQ ID NOS: 34-39, wherein [Azk_L1_PEG] is a mixture of the structures of Formula (IV) and Formula (V):

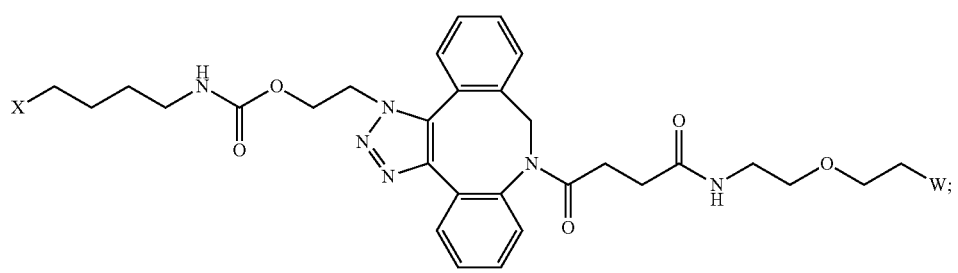

Formula (IV)

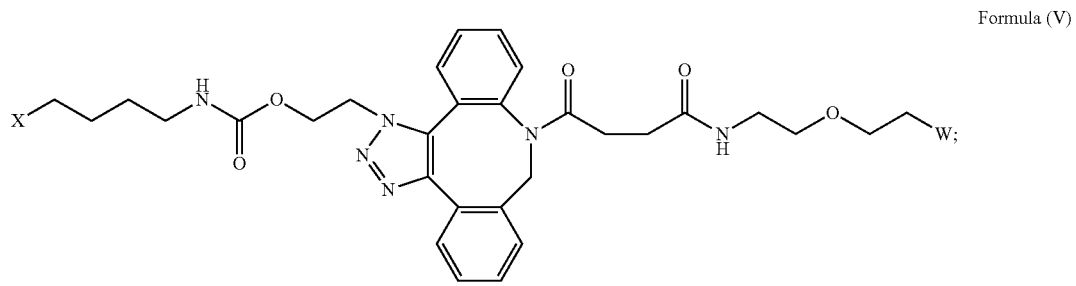

Formula (V)

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

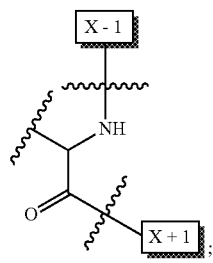

X−1 indicates the point of attachment to the preceding amino acid residue; and

X+1 indicates the point of attachment to the following amino acid residue.

Embodiment 231. The IL-15 conjugate according to embodiment 230 or 230.1, wherein the ratio of the amount of the structure of Formula (IV) to the amount of the structure of Formula (V) comprising the total amount of [AzK_L1_PEG] in the IL-15 conjugate is about 1:1.

Embodiment 232. The IL-15 conjugate according to embodiment 230 or 230.1, wherein the ratio of the amount of the structure of Formula (IV) to the amount of the structure of Formula (V) comprising the total amount of [AzK_L1_PEG] in the IL-15 conjugate is greater than 1:1.

Embodiment 233. The IL-15 conjugate according to embodiment 230 or 230.1, wherein the ratio of the amount of the structure of Formula (IV) to the amount of the structure of Formula (V) comprising the total amount of [AzK_L1_PEG] in the IL-15 conjugate is less than 1:1.

Embodiment 234. The IL-15 conjugate according to any one of embodiments 166 to 233, wherein W is a linear or branched PEG group.

Embodiment 235. The IL-15 conjugate according to any one of embodiments 166 to 233, wherein W is a linear PEG group.

Embodiment 236. The IL-15 conjugate according to any one of embodiments 166 to 233, wherein W is a branched PEG group.

Embodiment 237. The IL-15 conjugate according to any one of embodiments 166 to 233, wherein W is a methoxy PEG group.

Embodiment 238. The IL-15 conjugate according to embodiment 237, wherein the methoxy PEG group is linear or branched.

Embodiment 239. The IL-15 conjugate according to embodiment 238, wherein the methoxy PEG group is linear.

Embodiment 240. The IL-15 conjugate according to embodiment 238, wherein the methoxy PEG group is branched.

Embodiment 241. An IL-15 conjugate comprising the amino acid sequence of any one of SEQ ID NOS: 40-45, wherein [AzK_L1_PEG30] has the structure of Formula (IV) or Formula (V), or a mixture of Formula (IV) and Formula (V):

Formula (IV)

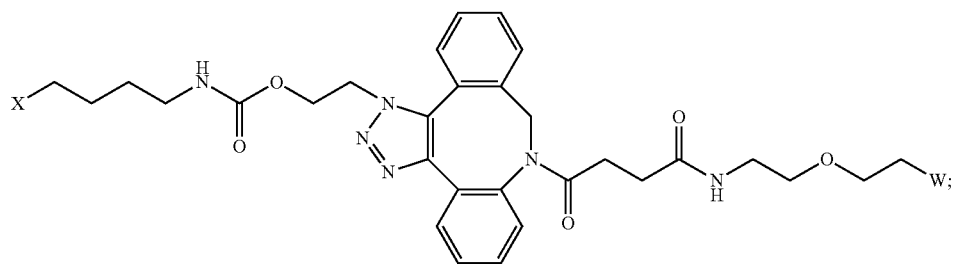

Formula (V)

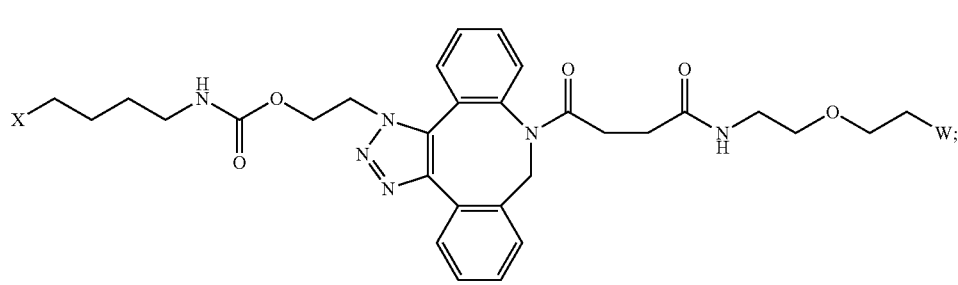

wherein:
W is a PEG group having an average molecular weight of 30 kDa; and
X has the structure:

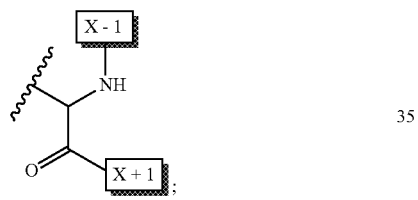

or a pharmaceutically acceptable salt, solvate, or hydrate thereof.

Embodiment 241.1. An IL-15 conjugate comprising the amino acid sequence of anyone of SEQ ID NOS: 40-45, wherein [AzK_L1_PEG30] has the structure of Formula (IV) or Formula (V), or a mixture of Formula (IV) and Formula (V):

Formula (IV)

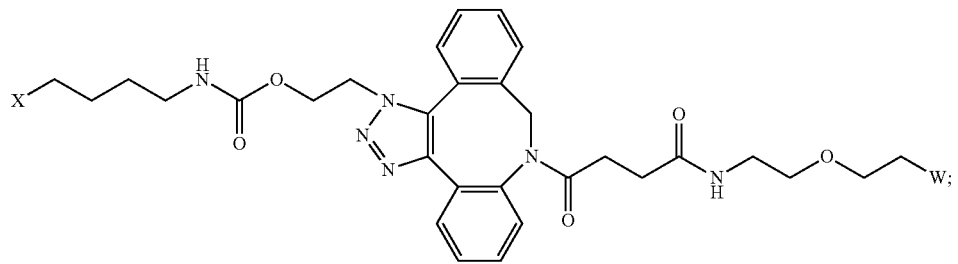

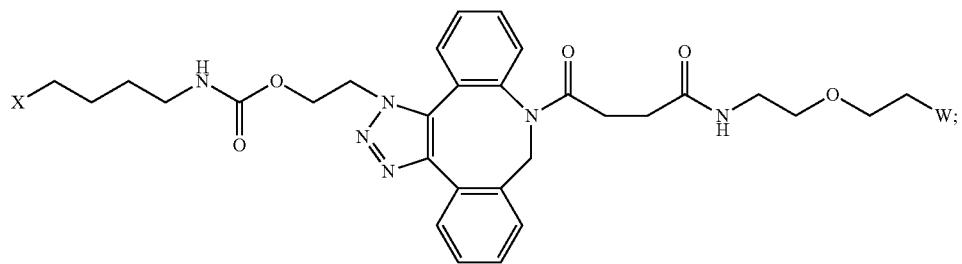

Formula (V)

wherein:
W is a PEG group having an average molecular weight of 30 kDa; and
X has the structure:

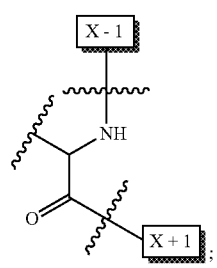

X−1 indicates the point of attachment to the preceding amino acid residue; and
X+1 indicates the point of attachment to the following amino acid residue.

Embodiment 242. The IL-15 conjugate of embodiment 241 or 241.1, wherein the IL-15 conjugate has the amino acid sequence of SEQ ID NO: 40.

Embodiment 243. The IL-15 conjugate of embodiment 241 or 241.1, wherein the IL-15 conjugate has the amino acid sequence of SEQ ID NO: 41.

Embodiment 244. The IL-15 conjugate of embodiment 241 or 241.1, wherein the IL-15 conjugate has the amino acid sequence of SEQ ID NO: 42.

Embodiment 245. The IL-15 conjugate of embodiment 241 or 241.1, wherein the IL-15 conjugate has the amino acid sequence of SEQ ID NO: 43.

Embodiment 246. The IL-15 conjugate of embodiment 241 or 241.1, wherein the IL-15 conjugate has the amino acid sequence of SEQ ID NO: 44.

Embodiment 247. The IL-15 conjugate of embodiment 241 or 241.1, wherein the IL-15 conjugate has the amino acid sequence of SEQ ID NO: 45.

Embodiment 248. The IL-15 conjugate of embodiment 241 or 241.1, wherein the [AzK_L1_PEG30] has the structure of Formula (IV)

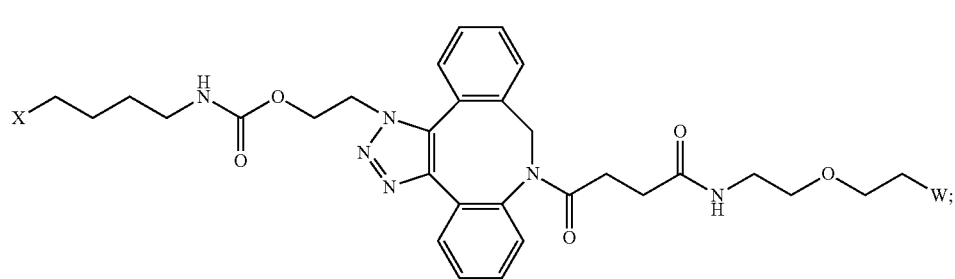

Formula (IV)

or a pharmaceutically acceptable salt, solvate, or hydrate thereof.

Embodiment 249. The IL-15 conjugate of embodiment 248, wherein the IL-15 conjugate has the amino acid sequence of SEQ ID NO: 40.

Embodiment 250. The IL-15 conjugate of embodiment 248, wherein the IL-15 conjugate has the amino acid sequence of SEQ ID NO: 41.

Embodiment 251. The IL-15 conjugate of embodiment 248, wherein the IL-15 conjugate has the amino acid sequence of SEQ ID NO: 42.

Embodiment 252. The IL-15 conjugate of embodiment 248, wherein the IL-15 conjugate has the amino acid sequence of SEQ ID NO: 43.

Embodiment 253. The IL-15 conjugate of embodiment 248, wherein the IL-15 conjugate has the amino acid sequence of SEQ ID NO: 44.

Embodiment 254. The IL-15 conjugate of embodiment 248, wherein the IL-15 conjugate has the amino acid sequence of SEQ ID NO: 45.

Embodiment 255. The IL-15 conjugate of embodiment 241 or 241.1, wherein the [AzK_L1_PEG30] has the structure of Formula (V)

Formula (V)

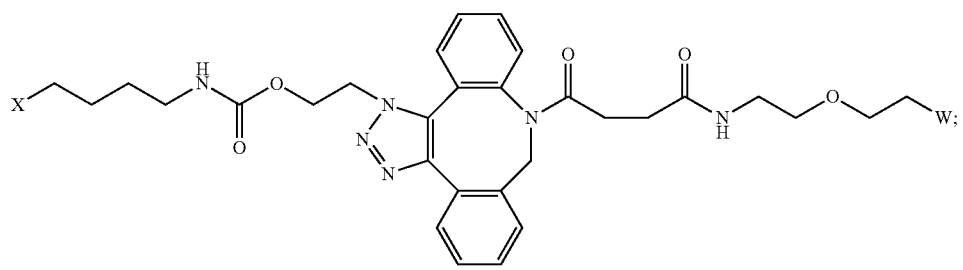

or a pharmaceutically acceptable salt, solvate, or hydrate thereof.

Embodiment 256. The IL-15 conjugate of embodiment 255, wherein the IL-15 conjugate has the amino acid sequence of SEQ ID NO: 40.

Embodiment 257. The IL-15 conjugate of embodiment 255, wherein the IL-15 conjugate has the amino acid sequence of SEQ ID NO: 41.

Embodiment 258. The IL-15 conjugate of embodiment 255, wherein the IL-15 conjugate has the amino acid sequence of SEQ ID NO: 42.

Embodiment 259. The IL-15 conjugate of embodiment 255, wherein the IL-15 conjugate has the amino acid sequence of SEQ ID NO: 43.

Embodiment 260. The IL-15 conjugate of embodiment 255, wherein the IL-15 conjugate has the amino acid sequence of SEQ ID NO: 44.

Embodiment 261. The IL-15 conjugate of embodiment 255, wherein the IL-15 conjugate has the amino acid sequence of SEQ ID NO: 45.

Embodiment 262. An IL-15 conjugate comprising the amino acid sequence of any one of SEQ ID NOS: 40 to 45, wherein [AzK_L1_PEG30] is a mixture of the structures of Formula (IV) and Formula (V):

Formula (IV)

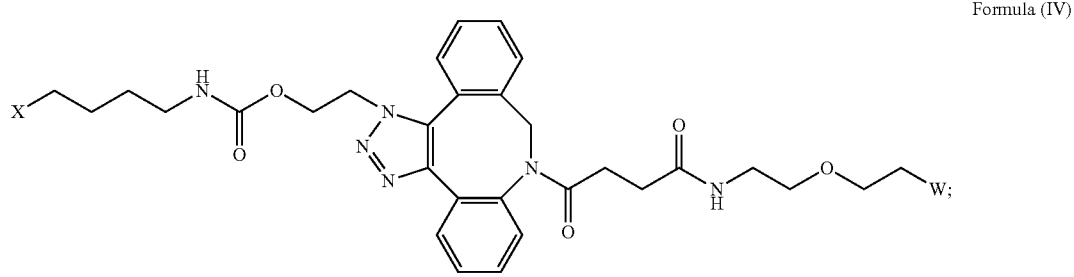

Formula (V)

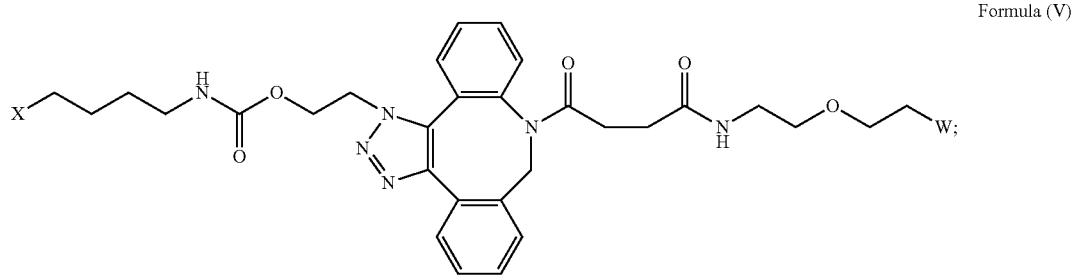

wherein:
W is a PEG group having an average molecular weight of 30 kDa; and
X has the structure:

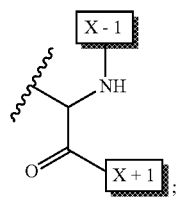

or a pharmaceutically acceptable salt, solvate, or hydrate thereof.

Embodiment 262.1. An IL-15 conjugate comprising the amino acid sequence of anyone of SEQ ID NOS: 40 to 45, wherein [AzK_L1_PEG30] is a mixture of the structures of Formula (IV) and Formula (V):

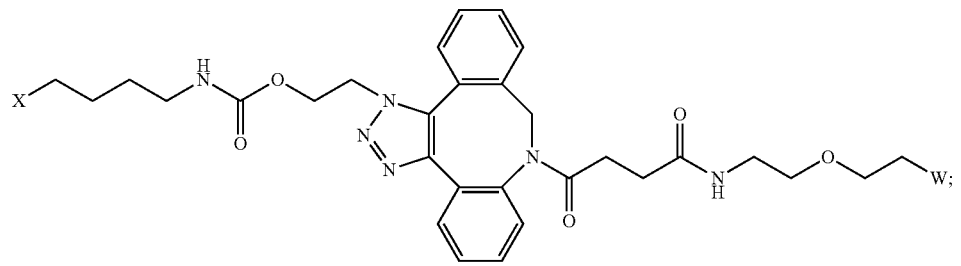

Formula (IV)

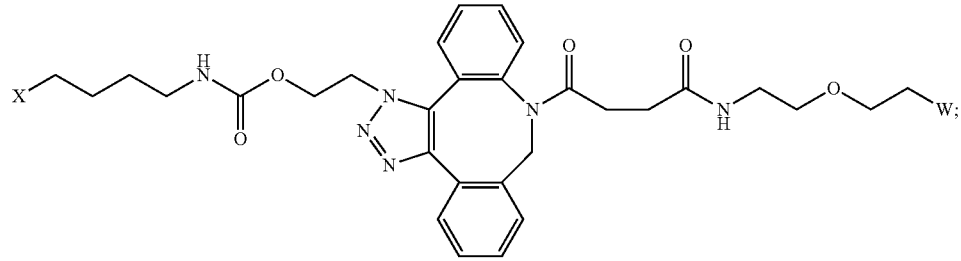

Formula (V)

wherein:
W is a PEG group having an average molecular weight of 30 kDa; and
X has the structure:

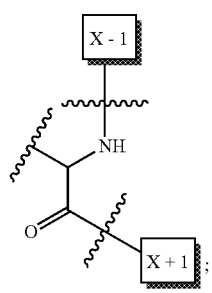

X−1 indicates the point of attachment to the preceding amino acid residue; and

X+1 indicates the point of attachment to the following amino acid residue.

Embodiment 263. The IL-15 conjugate according to embodiment 262 or 262.1, wherein the ratio of the amount of the structure of Formula (IV) to the amount of the structure of Formula (V) comprising the total amount of [AzK_L1_PEG30] in the IL-15 conjugate is about 1:1.

Embodiment 264. The IL-15 conjugate according to embodiment 262 or 262.1, wherein the ratio of the amount of the structure of Formula (IV) to the amount of the structure of Formula (V) comprising the total amount of [AzK_L1_PEG30] in the IL-15 conjugate is greater than 1:1.

Embodiment 265. The IL-15 conjugate according to embodiment 262 or 262.1, wherein the ratio of the amount of the structure of Formula (IV) to the amount of the structure of Formula (V) comprising the total amount of [AzK_L1_PEG30] in the IL-15 conjugate is less than 1:1.

Embodiment 266. The IL-15 conjugate according to any one of embodiments 241 to 265, wherein W is a linear or branched PEG group.

Embodiment 267. The IL-15 conjugate according to any one of embodiments 241 to 265, wherein W is a linear PEG group.

Embodiment 268. The IL-15 conjugate according to any one of embodiments 241 to 265, wherein W is a branched PEG group.

Embodiment 269. The IL-15 conjugate according to any one of embodiments 241 to 265, wherein W is a methoxy PEG group.

Embodiment 270. The IL-15 conjugate according to embodiment 269, wherein the methoxy PEG group is linear or branched.

Embodiment 271. The IL-15 conjugate according to embodiment 270, wherein the methoxy PEG group is linear.

Embodiment 272. The IL-15 conjugate according to embodiment 270, wherein the methoxy PEG group is branched.

Embodiment 273. An IL-15 conjugate comprising the amino acid sequence of any one of SEQ ID NOS: 46-51, wherein [AzK_L1_PEG40] has the structure of Formula (IV) or Formula (V), or is a mixture of the structures of Formula (IV) and Formula (V):

Formula (IV)

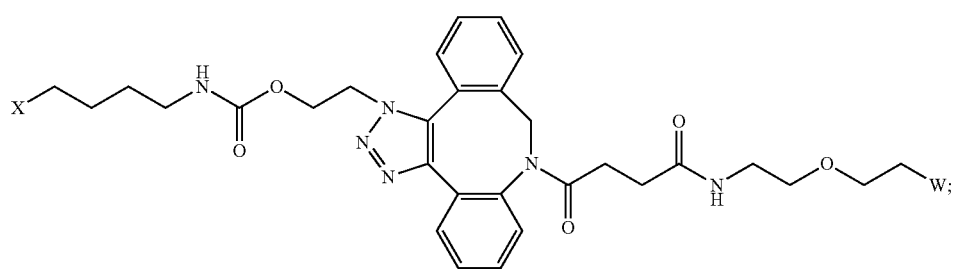

Formula (V)

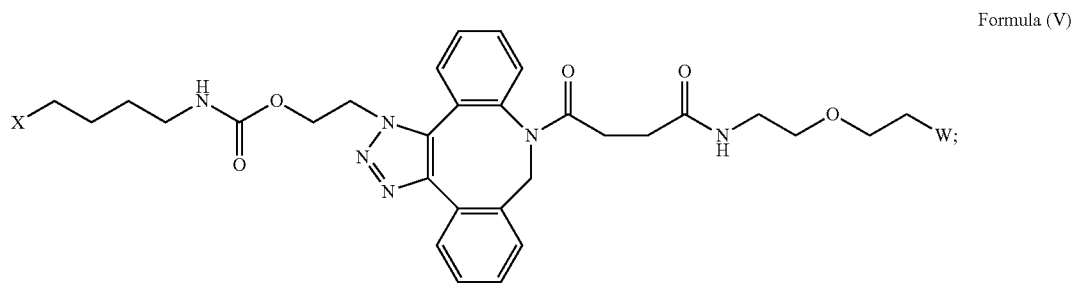

wherein:
W is a PEG group having an average molecular weight of 40 kDa; and
X has the structure:

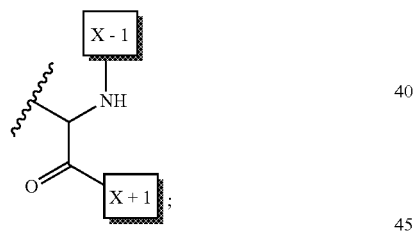

or a pharmaceutically acceptable salt, solvate, or hydrate thereof.

Embodiment 273.1. An IL-15 conjugate comprising the amino acid sequence of anyone of SEQ ID NOS: 46-51, wherein [AzK_L1_PEG40] has the structure of Formula (IV) or Formula (V), or is a mixture of the structures of Formula (IV) and Formula (V):

Formula (IV)

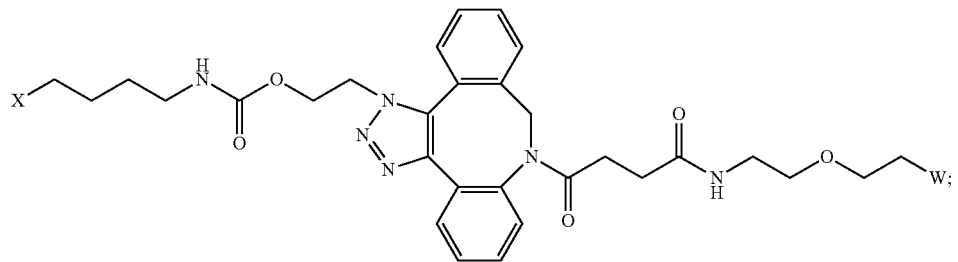

-continued

Formula (V)

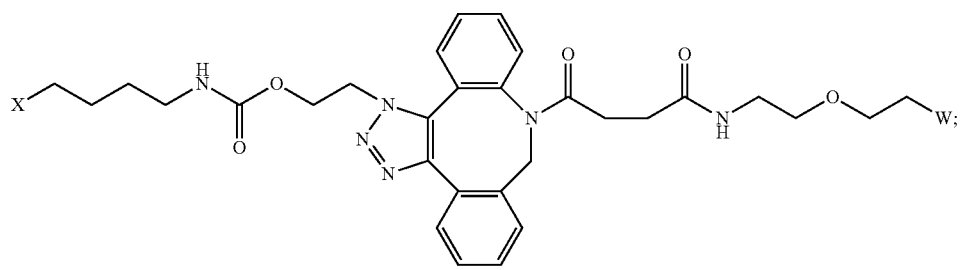

wherein:
W is a PEG group having an average molecular weight of 40 kDa; and
X has the structure:

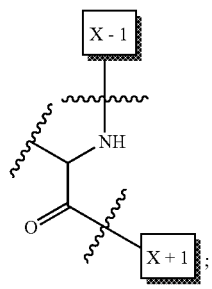

X−1 indicates the point of attachment to the preceding amino acid residue; and
X+1 indicates the point of attachment to the following amino acid residue.

Embodiment 274. The IL-15 conjugate of embodiment 273 or 273.1, wherein the IL-15 conjugate has the amino acid sequence of SEQ ID NO: 46.

Embodiment 275. The IL-15 conjugate of embodiment 273 or 273.1, wherein the IL-15 conjugate has the amino acid sequence of SEQ ID NO: 47.

Embodiment 276. The IL-15 conjugate of embodiment 273 or 273.1, wherein the IL-15 conjugate has the amino acid sequence of SEQ ID NO: 48.

Embodiment 277. The IL-15 conjugate of embodiment 273 or 273.1, wherein the IL-15 conjugate has the amino acid sequence of SEQ ID NO: 49.

Embodiment 278. The IL-15 conjugate of embodiment 273 or 273.1, wherein the IL-15 conjugate has the amino acid sequence of SEQ ID NO: 50.

Embodiment 279. The IL-15 conjugate of embodiment 273 or 273.1, wherein the IL-15 conjugate has the amino acid sequence of SEQ ID NO: 51.

Embodiment 280. The IL-15 conjugate of embodiment 273 or 273.1, wherein the [AzK_L1_PEG40] has the structure of Formula (IV):

Formula (IV)

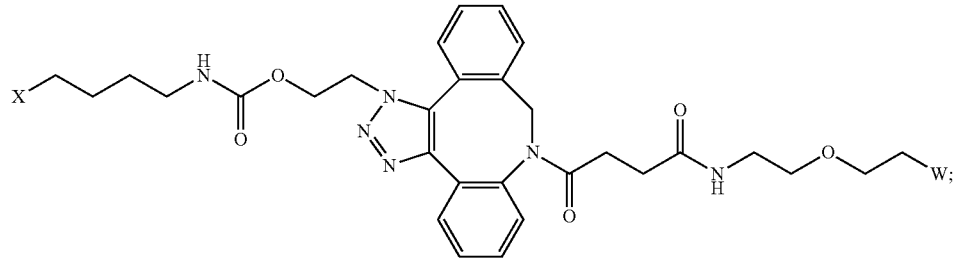

or a pharmaceutically acceptable salt, solvate, or hydrate thereof.

Embodiment 281. The IL-15 conjugate of embodiment 280, wherein the IL-15 conjugate has the amino acid sequence of SEQ ID NO: 46.

Embodiment 282. The IL-15 conjugate of embodiment 280, wherein the IL-15 conjugate has the amino acid sequence of SEQ ID NO: 47.

Embodiment 283. The IL-15 conjugate of embodiment 280, wherein the IL-15 conjugate has the amino acid sequence of SEQ ID NO: 48.

Embodiment 284. The IL-15 conjugate of embodiment 280, wherein the IL-15 conjugate has the amino acid sequence of SEQ ID NO: 49.

Embodiment 285. The IL-15 conjugate of embodiment 280, wherein the IL-15 conjugate has the amino acid sequence of SEQ ID NO: 50.

Embodiment 286. The IL-15 conjugate of embodiment 280, wherein the IL-15 conjugate has the amino acid sequence of SEQ ID NO: 51.

Embodiment 287. The IL-15 conjugate of embodiment 273 or 273.1, wherein the [AzK_L1_PEG40] has the structure of Formula (V)

Formula (V)

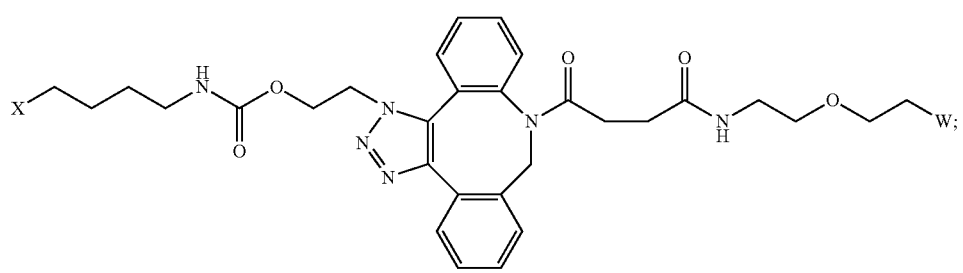

or a pharmaceutically acceptable salt, solvate, or hydrate thereof.

Embodiment 288. The IL-15 conjugate of embodiment 287, wherein the IL-15 conjugate has the amino acid sequence of SEQ ID NO: 46.

Embodiment 289. The IL-15 conjugate of embodiment 287, wherein the IL-15 conjugate has the amino acid sequence of SEQ ID NO: 47.

Embodiment 290. The IL-15 conjugate of embodiment 287, wherein the IL-15 conjugate has the amino acid sequence of SEQ ID NO: 48.

Embodiment 291. The IL-15 conjugate of embodiment 287, wherein the IL-15 conjugate has the amino acid sequence of SEQ ID NO: 49.

Embodiment 292. The IL-15 conjugate of embodiment 287, wherein the IL-15 conjugate has the amino acid sequence of SEQ ID NO: 50.

Embodiment 293. The IL-15 conjugate of embodiment 287, wherein the IL-15 conjugate has the amino acid sequence of SEQ ID NO: 51.

Embodiment 294. An IL-15 conjugate comprising the amino acid sequence of any one of SEQ ID NOS: 46-51, wherein [AzK_L1_PEG40] is a mixture of the structures of Formula (IV) and Formula (V):

wherein:
W is a PEG group having an average molecular weight of 40 kDa; and
X has the structure:

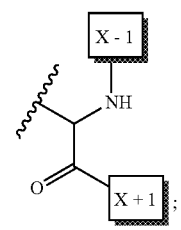

or a pharmaceutically acceptable salt, solvate, or hydrate thereof.

Embodiment 294.1. An IL-15 conjugate comprising the amino acid sequence of anyone of SEQ ID NOS: 46-51, wherein [AzK_L1_PEG40] is a mixture of the structures of Formula (IV) and Formula (V):

Formula (IV)

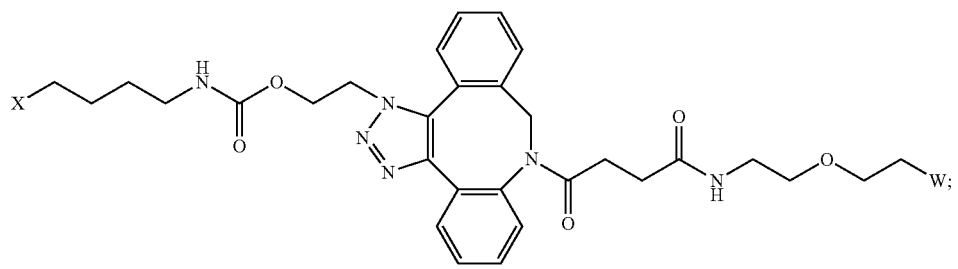

Formula (V)

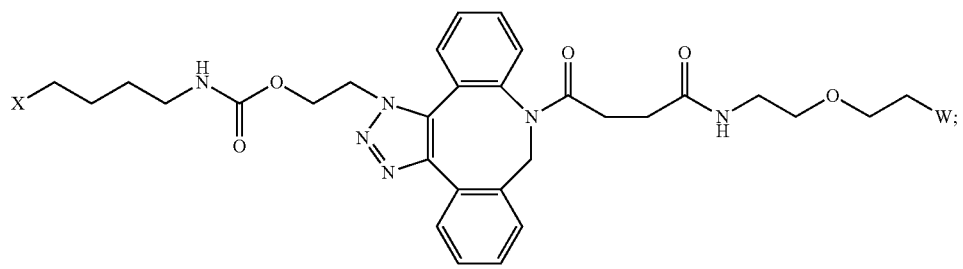

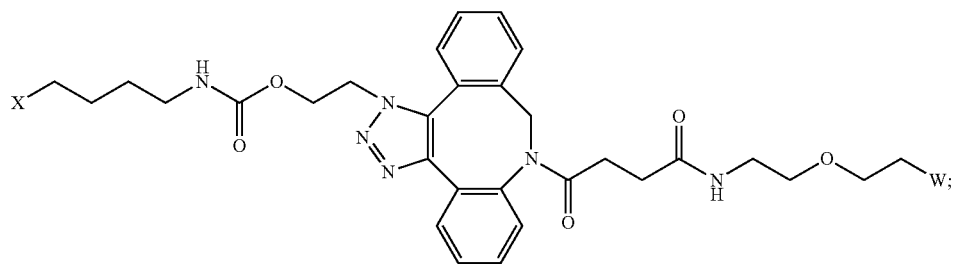

Formula (IV)

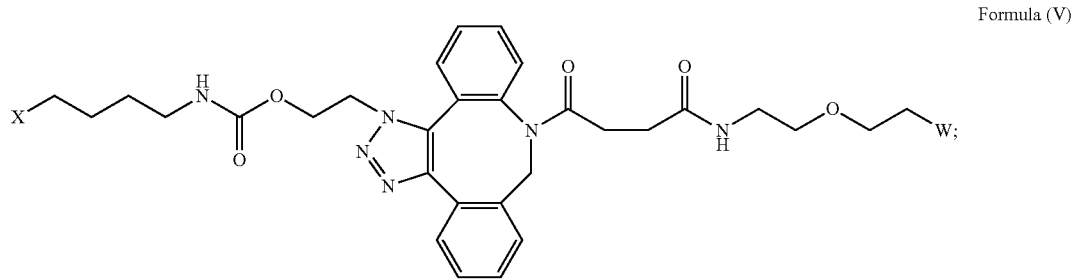

Formula (V)

wherein:
W is a PEG group having an average molecular weight of 40 kDa; and
X has the structure:

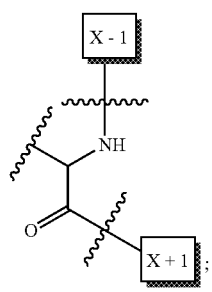

X−1 indicates the point of attachment to the preceding amino acid residue; and
X+1 indicates the point of attachment to the following amino acid residue.

Embodiment 295. The IL-15 conjugate according to embodiment 294 or 294.1, wherein the ratio of the amount of the structure of Formula (IV) to the amount of the structure of Formula (V) comprising the total amount of [AzK_L1_PEG40] in the IL-15 conjugate is about 1:1.

Embodiment 296. The IL-15 conjugate according to embodiment 294 or 294.1, wherein the ratio of the amount of the structure of Formula (IV) to the amount of the structure of Formula (V) comprising the total amount of [AzK_L1_PEG40] in the IL-15 conjugate is greater than 1:1.

Embodiment 297. The IL-15 conjugate according to embodiment 294 or 294.1, wherein the ratio of the amount of the structure of Formula (IV) to the amount of the structure of Formula (V) comprising the total amount of [AzK_L1_PEG40] in the IL-15 conjugate is less than 1:1.

Embodiment 298. The IL-15 conjugate according to any one of embodiments 273 to 297, wherein W is a linear or branched PEG group.

Embodiment 299. The IL-15 conjugate according to any one of embodiments 273 to 297, wherein W is a linear PEG group.

Embodiment 300. The IL-15 conjugate according to any one of embodiments 273 to 297, wherein W is a branched PEG group.

Embodiment 301. The IL-15 conjugate according to any one of embodiments 273 to 297, wherein W is a methoxy PEG group.

Embodiment 302. The IL-15 conjugate according to embodiment 301, wherein the methoxy PEG group is linear or branched.

Embodiment 303. The IL-15 conjugate according to embodiment 302, wherein the methoxy PEG group is linear.

Embodiment 304. The IL-15 conjugate according to embodiment 302, wherein the methoxy PEG group is branched.

Embodiment 305. An IL-15 conjugate comprising the amino acid sequence of any one of SEQ ID NOS: 64-69, wherein [AzK_PEG] has the structure of Formula (II) or Formula (III), or a mixture of Formula (II) and Formula (III):

Formula (II)

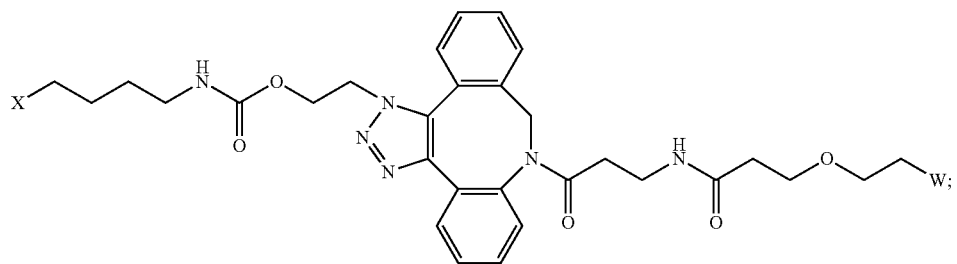

Formula (III)

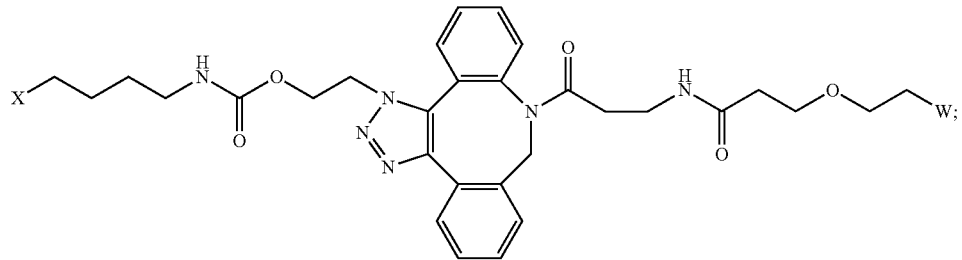

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

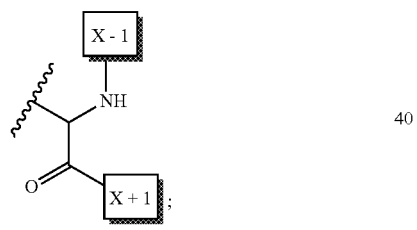

or a pharmaceutically acceptable salt, solvate, or hydrate thereof.

Embodiment 305.1. An IL-15 conjugate comprising the amino acid sequence of anyone of SEQ ID NOS: 64-69, wherein [AzK_PEG] has the structure of Formula (II) or Formula (III), or a mixture of Formula (II) and Formula (III):

Formula (II)

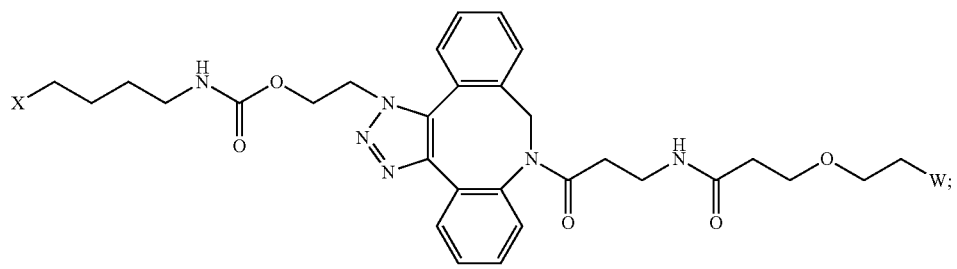

-continued

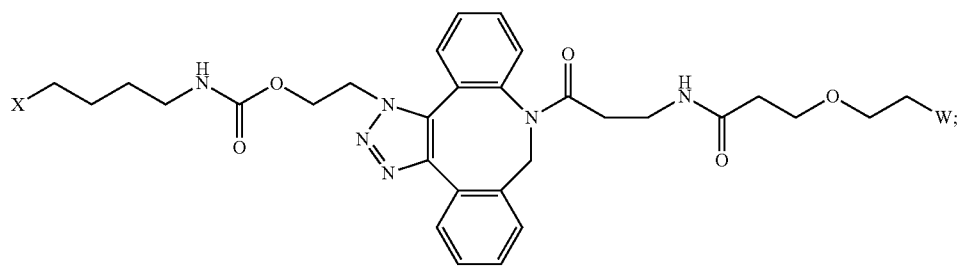

Formula (III)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

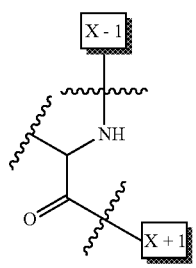

X−1 indicates the point of attachment to the preceding amino acid residue; and
X+1 indicates the point of attachment to the following amino acid residue.

Embodiment 306. The IL-15 conjugate of embodiment 305 or 305.1, wherein the [AzK_PEG] is a mixture of Formula (II) and Formula (III).

Embodiment 307. The IL-15 conjugate of embodiment 305 or 305.1, wherein the [AzK_PEG] has the structure of Formula (II):

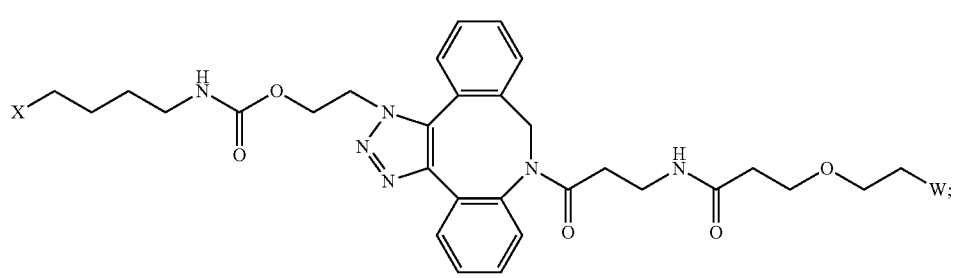

Formula (II)

or a pharmaceutically acceptable salt, solvate, or hydrate thereof.

Embodiment 308. The IL-15 conjugate of embodiment 307, wherein the IL-15 conjugate has the amino acid sequence of SEQ ID NO: 64.

Embodiment 309. The IL-15 conjugate of embodiment 308, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 310. The IL-15 conjugate of embodiment 309, wherein W is a PEG group having an average molecular weight selected from 30 kDa and 40 kDa.

Embodiment 311. The IL-15 conjugate of embodiment 310, wherein W is a PEG group having an average molecular weight of 30 kDa.

Embodiment 312. The IL-15 conjugate of embodiment 310, wherein W is a PEG group having an average molecular weight of 40 kDa.

Embodiment 313. The IL-15 conjugate of embodiment 307, wherein the IL-15 conjugate has the amino acid sequence of SEQ ID NO: 65.

Embodiment 314. The IL-15 conjugate of embodiment 313, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 315. The IL-15 conjugate of embodiment 314, wherein W is a PEG group having an average molecular weight selected from 30 kDa and 40 kDa.

Embodiment 316. The IL-15 conjugate of embodiment 315, wherein W is a PEG group having an average molecular weight of 30 kDa.

Embodiment 317. The IL-15 conjugate of embodiment 315, wherein W is a PEG group having an average molecular weight of 40 kDa.

Embodiment 318. The IL-15 conjugate of embodiment 307, wherein the IL-15 conjugate has the amino acid sequence of SEQ ID NO: 66.

Embodiment 319. The IL-15 conjugate of embodiment 318, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 320. The IL-15 conjugate of embodiment 319, wherein W is a PEG group having an average molecular weight selected from 30 kDa and 40 kDa.

Embodiment 321. The IL-15 conjugate of embodiment 320, wherein W is a PEG group having an average molecular weight of 30 kDa.

Embodiment 322. The IL-15 conjugate of embodiment 320, wherein W is a PEG group having an average molecular weight of 40 kDa.

Embodiment 323. The IL-15 conjugate of embodiment 307, wherein the IL-15 conjugate has the amino acid sequence of SEQ ID NO: 67.

Embodiment 324. The IL-15 conjugate of embodiment 323, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 325. The IL-15 conjugate of embodiment 324, wherein W is a PEG group having an average molecular weight selected from 30 kDa and 40 kDa.

Embodiment 326. The IL-15 conjugate of embodiment 325, wherein W is a PEG group having an average molecular weight of 30 kDa.

Embodiment 327. The IL-15 conjugate of embodiment 325, wherein W is a PEG group having an average molecular weight of 40 kDa.

Embodiment 328. The IL-15 conjugate of embodiment 307, wherein the IL-15 conjugate has the amino acid sequence of SEQ ID NO: 68.

Embodiment 329. The IL-15 conjugate of embodiment 328, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 330. The IL-15 conjugate of embodiment 329, wherein W is a PEG group having an average molecular weight selected from 30 kDa and 40 kDa.

Embodiment 331. The IL-15 conjugate of embodiment 330, wherein W is a PEG group having an average molecular weight of 30 kDa.

Embodiment 332. The IL-15 conjugate of embodiment 330, wherein W is a PEG group having an average molecular weight of 40 kDa.

Embodiment 333. The IL-15 conjugate of embodiment 307, wherein the IL-15 conjugate has the amino acid sequence of SEQ ID NO: 69.

Embodiment 334. The IL-15 conjugate of embodiment 333, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 335. The IL-15 conjugate of embodiment 334, wherein W is a PEG group having an average molecular weight selected from 30 kDa and 40 kDa.

Embodiment 336. The IL-15 conjugate of embodiment 335, wherein W is a PEG group having an average molecular weight of 30 kDa.

Embodiment 337. The IL-15 conjugate of embodiment 336, wherein W is a PEG group having an average molecular weight of 40 kDa.

Embodiment 338. The IL-15 conjugate of embodiment 305 or 305.1, wherein the [AzK_PEG] has the structure of Formula (III)

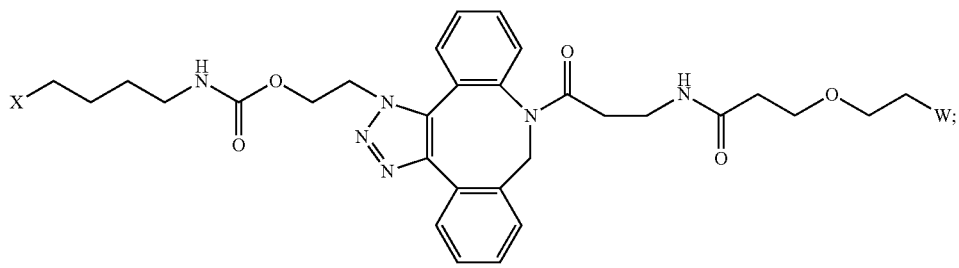

Formula (III)

or a pharmaceutically acceptable salt, solvate, or hydrate thereof.

Embodiment 339. The IL-15 conjugate of embodiment 338, wherein the IL-15 conjugate has the amino acid sequence of SEQ ID NO: 64.

Embodiment 340. The IL-15 conjugate of embodiment 339, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 341. The IL-15 conjugate of embodiment 340, wherein W is a PEG group having an average molecular weight selected from 30 kDa and 40 kDa.

Embodiment 342. The IL-15 conjugate of embodiment 341, wherein W is a PEG group having an average molecular weight of 30 kDa.

Embodiment 343. The IL-15 conjugate of embodiment 341, wherein W is a PEG group having an average molecular weight of 40 kDa.

Embodiment 344. The IL-15 conjugate of embodiment 338, wherein the IL-15 conjugate has the amino acid sequence of SEQ ID NO: 65.

Embodiment 345. The IL-15 conjugate of embodiment 344, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 346. The IL-15 conjugate of embodiment 345, wherein W is a PEG group having an average molecular weight selected from 30 kDa and 40 kDa.

Embodiment 347. The IL-15 conjugate of embodiment 346, wherein W is a PEG group having an average molecular weight of 30 kDa.

Embodiment 348. The IL-15 conjugate of embodiment 346, wherein W is a PEG group having an average molecular weight of 40 kDa.

Embodiment 349. The IL-15 conjugate of embodiment 338, wherein the IL-15 conjugate has the amino acid sequence of SEQ ID NO: 66.

Embodiment 350. The IL-15 conjugate of embodiment 349, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 351. The IL-15 conjugate of embodiment 350, wherein W is a PEG group having an average molecular weight selected from 30 kDa and 40 kDa.

Embodiment 352. The IL-15 conjugate of embodiment 351, wherein W is a PEG group having an average molecular weight of 30 kDa.
Embodiment 353. The IL-15 conjugate of embodiment 351, wherein W is a PEG group having an average molecular weight of 40 kDa.
Embodiment 354. The IL-15 conjugate of embodiment 338, wherein the IL-15 conjugate has the amino acid sequence of SEQ ID NO: 67.
Embodiment 355. The IL-15 conjugate of embodiment 354, wherein W is a PEG group having an average molecular weight selected from 5 kDa, 10 kDa, 15 kDa, 20 kDa, 25 kDa, 30 kDa, 35 kDa, 40 kDa, and 45 kDa.
Embodiment 356. The IL-15 conjugate of embodiment 355, wherein W is a PEG group having an average molecular weight selected from 30 kDa and 40 kDa.
Embodiment 357. The IL-15 conjugate of embodiment 356, wherein W is a PEG group having an average molecular weight of 30 kDa.
Embodiment 358. The IL-15 conjugate of embodiment 356, wherein W is a PEG group having an average molecular weight of 40 kDa.
Embodiment 359. The IL-15 conjugate of embodiment 338, wherein the IL-15 conjugate has the amino acid sequence of SEQ ID NO: 68.
Embodiment 360. The IL-15 conjugate of embodiment 359, wherein W is a PEG group having an average molecular weight selected from 5 kDa, 10 kDa, 15 kDa, 20 kDa, 25 kDa, 30 kDa, 35 kDa, 40 kDa, and 45 kDa.
Embodiment 361. The IL-15 conjugate of embodiment 360, wherein W is a PEG group having an average molecular weight selected from 30 kDa and 40 kDa.
Embodiment 362. The IL-15 conjugate of embodiment 361, wherein W is a PEG group having an average molecular weight of 30 kDa.
Embodiment 363. The IL-15 conjugate of embodiment 361, wherein W is a PEG group having an average molecular weight of 40 kDa.
Embodiment 364. The IL-15 conjugate of embodiment 338, wherein the IL-15 conjugate has the amino acid sequence of SEQ ID NO: 69.
Embodiment 365. The IL-15 conjugate of embodiment 364, wherein W is a PEG group having an average molecular weight selected from 5 kDa, 10 kDa, 15 kDa, 20 kDa, 25 kDa, 30 kDa, 35 kDa, 40 kDa, and 45 kDa.
Embodiment 366. The IL-15 conjugate of embodiment 365, wherein W is a PEG group having an average molecular weight selected from 30 kDa and 40 kDa.
Embodiment 367. The IL-15 conjugate of embodiment 366, wherein W is a PEG group having an average molecular weight of 30 kDa.
Embodiment 368. The IL-15 conjugate of embodiment 366, wherein W is a PEG group having an average molecular weight of 40 kDa.
Embodiment 369. An IL-15 conjugate comprising the amino acid sequence of any one of SEQ ID NOS: 64-69, wherein [AzK_PEG] is a mixture of the structures of Formula (II) and Formula (III):

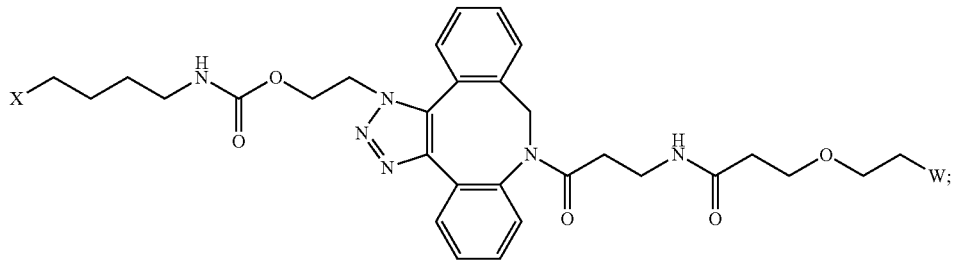

Formula (II)

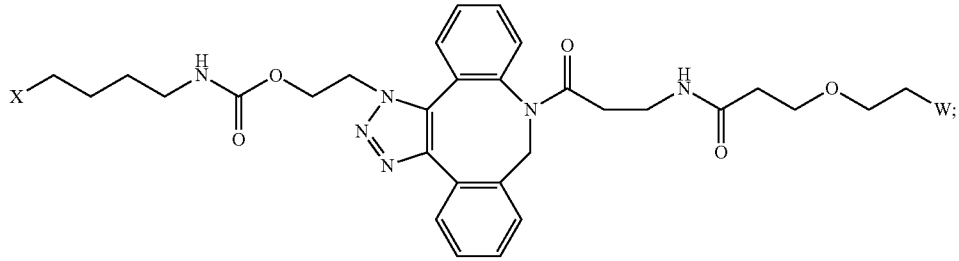

Formula (III)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

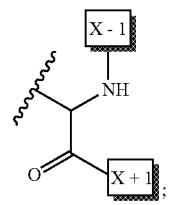

or a pharmaceutically acceptable salt, solvate, or hydrate thereof.

Embodiment 369.1. An IL-15 conjugate comprising the amino acid sequence of anyone of SEQ ID NOS: 64-69, wherein [AzK_PEG] is a mixture of the structures of Formula (II) and Formula (III):

Formula (II)

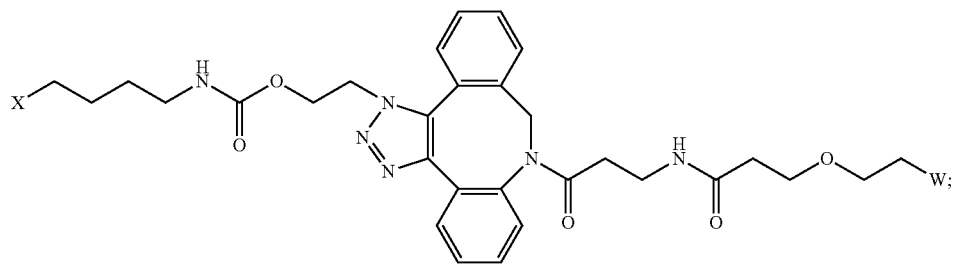

Formula (III)

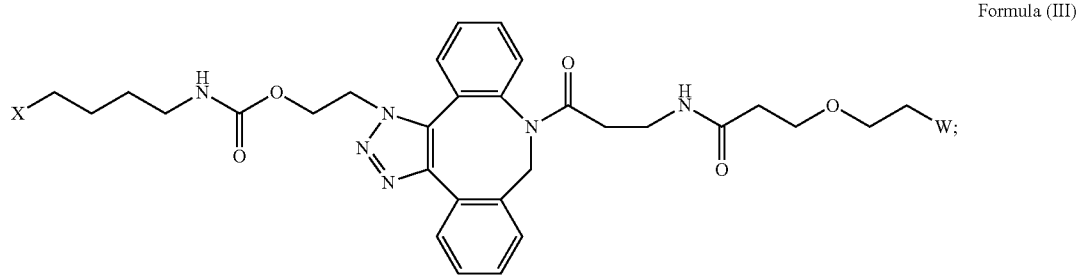

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

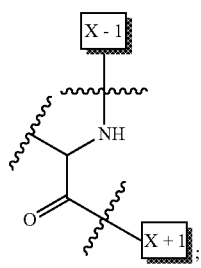

X−1 indicates the point of attachment to the preceding amino acid residue; and

X+1 indicates the point of attachment to the following amino acid residue.

Embodiment 370. The IL-15 conjugate according to embodiment 369 or 369.1, wherein the ratio of the amount of the structure of Formula (II) to the amount of the structure of Formula (III) comprising the total amount of [AzK_PEG] in the IL-15 conjugate is about 1:1.

Embodiment 371. The IL-15 conjugate according to embodiment 369 or 369.1, wherein the ratio of the amount of the structure of Formula (II) to the amount of the structure of Formula (III) comprising the total amount of [AzK_PEG] in the IL-15 conjugate is greater than 1:1.

Embodiment 372. The IL-15 conjugate according to embodiment 369 or 369.1, wherein the ratio of the amount of the structure of Formula (IV) to the amount of the structure of Formula (V) comprising the total amount of [AzK_PEG] in the IL-15 conjugate is less than 1:1.

Embodiment 373. The IL-15 conjugate according to any one of embodiments 305 to 372, wherein W is a linear or branched PEG group.

Embodiment 374. The IL-15 conjugate according to any one of embodiments 305 to 372, wherein W is a linear PEG group.

Embodiment 375. The IL-15 conjugate according to any one of embodiments 305 to 372, wherein W is a branched PEG group.

Embodiment 376. The IL-15 conjugate according to any one of embodiments 305 to 372, wherein W is a methoxy PEG group.

Embodiment 377. The IL-15 conjugate according to embodiment 376, wherein the methoxy PEG group is linear or branched.

Embodiment 378. The IL-15 conjugate according to embodiment 377, wherein the methoxy PEG group is linear.

Embodiment 379. The IL-15 conjugate according to embodiment 377, wherein the methoxy PEG group is branched.

Embodiment 380. An IL-15 conjugate comprising the amino acid sequence of any one of SEQ ID NOS: 70-75, wherein [AzK_PEG30] has the structure of Formula (II) or Formula (III), or a mixture of Formula (II) and Formula (III):

Formula (II)

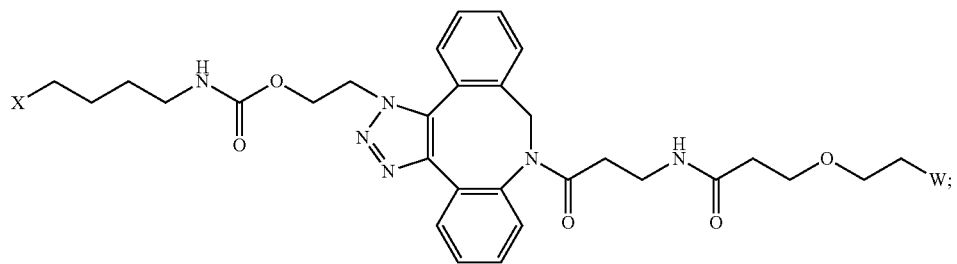

Formula (III)

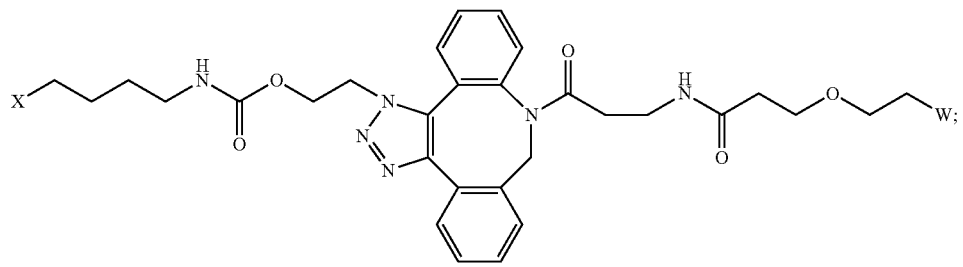

wherein:
W is a PEG group having an average molecular weight of 30 kDa; and
X has the structure:

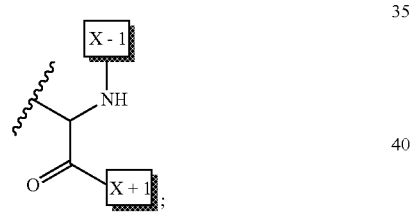

or a pharmaceutically acceptable salt, solvate, or hydrate thereof.

Embodiment 380.1. An IL-15 conjugate comprising the amino acid sequence of anyone of SEQ ID NOS: 70-75, wherein [AzK_PEG30] has the structure of Formula (II) or Formula (III), or a mixture of Formula (II) and Formula (III):

Formula (II)

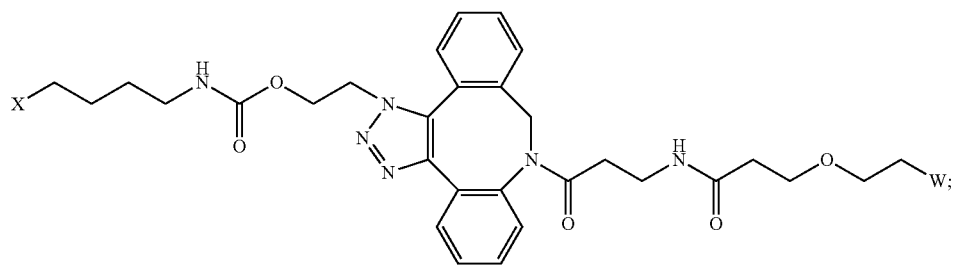

-continued

Formula (III)

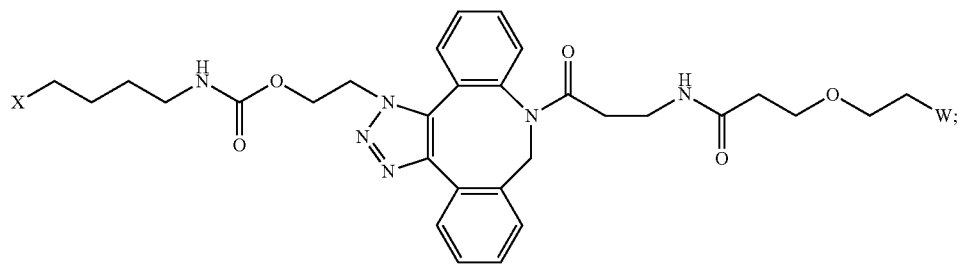

wherein:
W is a PEG group having an average molecular weight of 30 kDa; and
X has the structure:

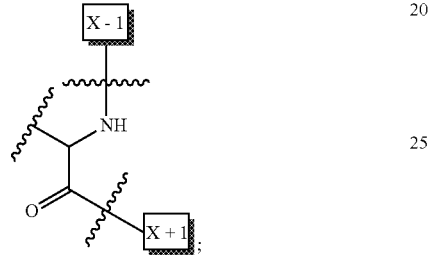

X−1 indicates the point of attachment to the preceding amino acid residue; and
X+1 indicates the point of attachment to the following amino acid residue.

Embodiment 381. The IL-15 conjugate of embodiment 380 or 380.1, wherein the IL-15 conjugate has the amino acid sequence of SEQ ID NO: 70.

Embodiment 382. The IL-15 conjugate of embodiment 380 or 380.1, wherein the IL-15 conjugate has the amino acid sequence of SEQ ID NO: 71.

Embodiment 383. The IL-15 conjugate of embodiment 380 or 380.1, wherein the IL-15 conjugate has the amino acid sequence of SEQ ID NO: 72.

Embodiment 384. The IL-15 conjugate of embodiment 380 or 380.1, wherein the IL-15 conjugate has the amino acid sequence of SEQ ID NO: 73.

Embodiment 385. The IL-15 conjugate of embodiment 380 or 380.1, wherein the IL-15 conjugate has the amino acid sequence of SEQ ID NO: 74.

Embodiment 386. The IL-15 conjugate of embodiment 380 or 380.1, wherein the IL-15 conjugate has the amino acid sequence of SEQ ID NO: 75.

Embodiment 387. The IL-15 conjugate of embodiment 380 or 380.1, wherein the [AzK_PEG30] has the structure of Formula (II)

Formula (II)

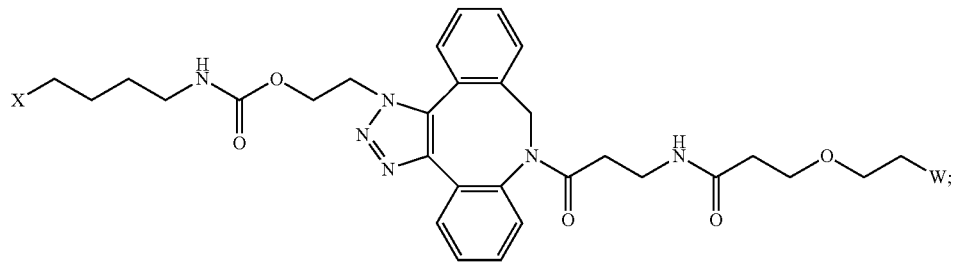

or a pharmaceutically acceptable salt, solvate, or hydrate thereof.

Embodiment 388. The IL-15 conjugate of embodiment 387, wherein the IL-15 conjugate has the amino acid sequence of SEQ ID NO: 70.

Embodiment 389. The IL-15 conjugate of embodiment 387, wherein the IL-15 conjugate has the amino acid sequence of SEQ ID NO: 71.

Embodiment 390. The IL-15 conjugate of embodiment 387, wherein the IL-15 conjugate has the amino acid sequence of SEQ ID NO: 72.

Embodiment 391. The IL-15 conjugate of embodiment 387, wherein the IL-15 conjugate has the amino acid sequence of SEQ ID NO: 73.

Embodiment 392. The IL-15 conjugate of embodiment 387, wherein the IL-15 conjugate has the amino acid sequence of SEQ ID NO: 74.

Embodiment 393. The IL-15 conjugate of embodiment 387, wherein the IL-15 conjugate has the amino acid sequence of SEQ ID NO: 75.

Embodiment 394. The IL-15 conjugate of embodiment 380 or 380.1, wherein the [AzK_PEG30] has the structure of Formula (III)

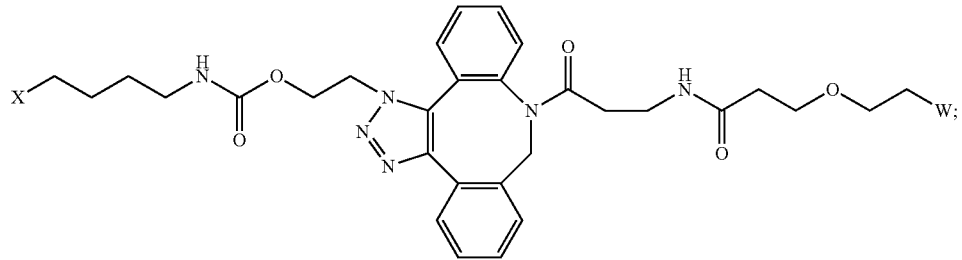

Formula (III)

or a pharmaceutically acceptable salt, solvate, or hydrate thereof.

Embodiment 395. The IL-15 conjugate of embodiment 394, wherein the IL-15 conjugate has the amino acid sequence of SEQ ID NO: 70.

Embodiment 396. The IL-15 conjugate of embodiment 394, wherein the IL-15 conjugate has the amino acid sequence of SEQ ID NO: 71.

Embodiment 397. The IL-15 conjugate of embodiment 394, wherein the IL-15 conjugate has the amino acid sequence of SEQ ID NO: 72.

Embodiment 398. The IL-15 conjugate of embodiment 394, wherein the IL-15 conjugate has the amino acid sequence of SEQ ID NO: 73.

Embodiment 399. The IL-15 conjugate of embodiment 394, wherein the IL-15 conjugate has the amino acid sequence of SEQ ID NO: 74.

Embodiment 400. The IL-15 conjugate of embodiment 394, wherein the IL-15 conjugate has the amino acid sequence of SEQ ID NO: 75.

Embodiment 401. An IL-15 conjugate comprising the amino acid sequence of any one of SEQ ID NOS: 70-75, wherein [AzK_PEG30] is a mixture of the structures of Formula (II) and Formula (III):

Formula (II)
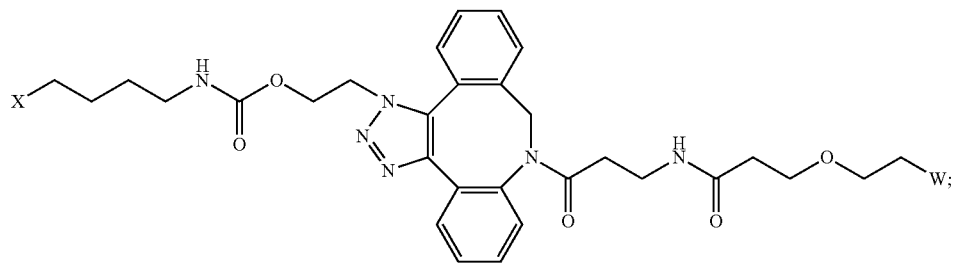
Formula (III)
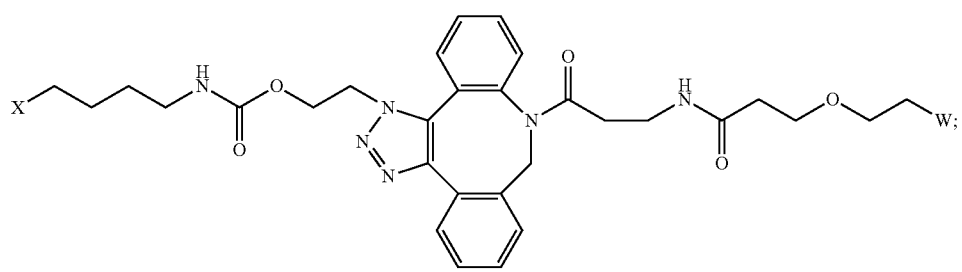
wherein:
W is a PEG group having an average molecular weight of 30 kDa; and
X has the structure:
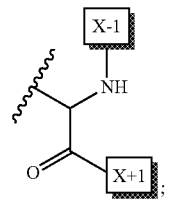
or a pharmaceutically acceptable salt, solvate, or hydrate thereof.
Embodiment 401.1. An IL-15 conjugate comprising the amino acid sequence of anyone of SEQ ID NOS: 70-75, wherein [AzK_PEG30] is a mixture of the structures of Formula (II) and Formula (III):
Formula (II)
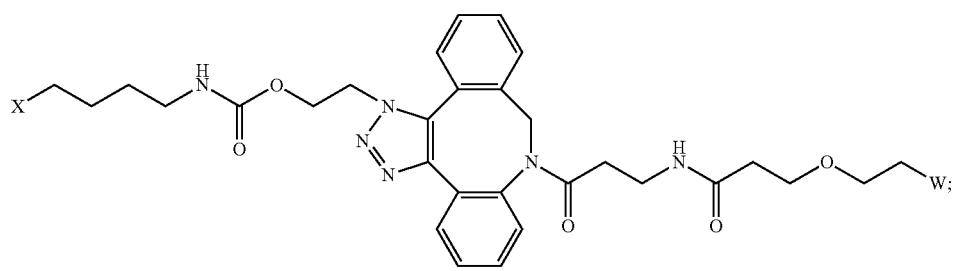

-continued

Formula (III)

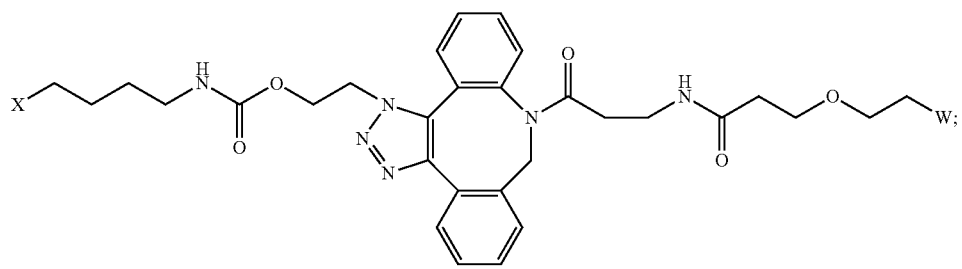

wherein:
W is a PEG group having an average molecular weight of 30 kDa; and
X has the structure:

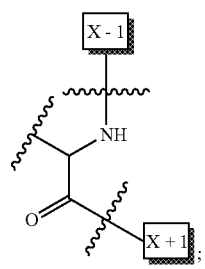

X−1 indicates the point of attachment to the preceding amino acid residue; and
X+1 indicates the point of attachment to the following amino acid residue.

Embodiment 402. The IL-15 conjugate according to embodiment 401 or 401.1, wherein the ratio of the amount of the structure of Formula (II) to the amount of the structure of Formula (III) comprising the total amount of [AzK_PEG30] in the IL-15 conjugate is about 1:1.

Embodiment 403. The IL-15 conjugate according to embodiment 401 or 401.1, wherein the ratio of the amount of the structure of Formula (II) to the amount of the structure of Formula (III) comprising the total amount of [AzK_PEG30] in the IL-15 conjugate is greater than 1:1.

Embodiment 404. The IL-15 conjugate according to embodiment 401 or 401.1, wherein the ratio of the amount of the structure of Formula (II) to the amount of the structure of Formula (III) comprising the total amount of [AzK_PEG30] in the IL-15 conjugate is less than 1:1.

Embodiment 405. The IL-15 conjugate according to any one of embodiments 380 to 404, wherein W is a linear or branched PEG group.

Embodiment 406. The IL-15 conjugate according to any one of embodiments 380 to 404, wherein W is a linear PEG group.

Embodiment 407. The IL-15 conjugate according to any one of embodiments 380 to 404, wherein W is a branched PEG group.

Embodiment 408. The IL-15 conjugate according to any one of embodiments 380 to 404, wherein W is a methoxy PEG group.

Embodiment 409. The IL-15 conjugate according to embodiment 408, wherein the methoxy PEG group is linear or branched.

Embodiment 410. The IL-15 conjugate according to embodiment 409, wherein the methoxy PEG group is linear.

Embodiment 411. The IL-15 conjugate according to embodiment 409, wherein the methoxy PEG group is branched.

Embodiment 412. An IL-15 conjugate comprising the amino acid sequence of any one of SEQ ID NOS: 76-81, wherein [AzK_PEG40] has the structure of Formula (II) or Formula (III), or is a mixture of the structures of Formula (II) and Formula (III):

Formula (II)

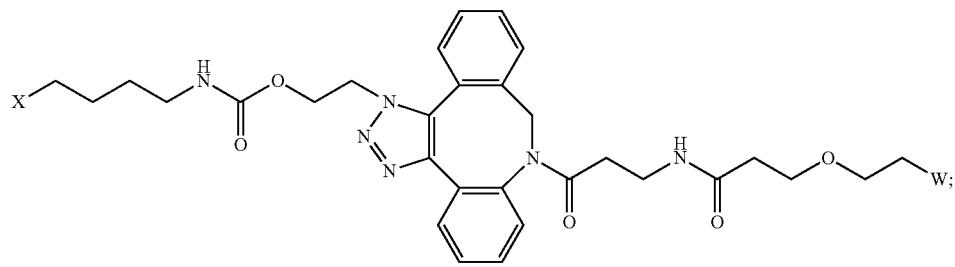

-continued

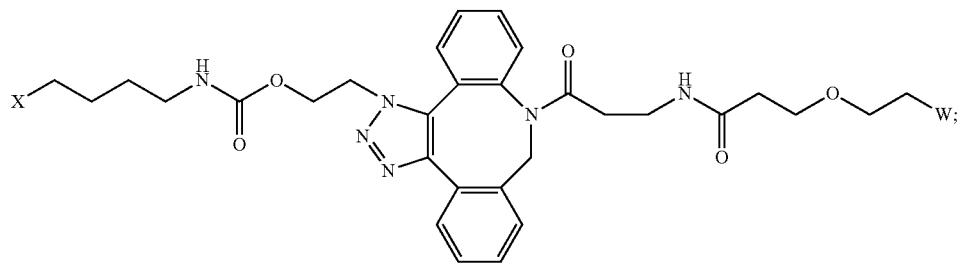

wherein:
W is a PEG group having an average molecular weight of 40 kDa; and
X has the structure:

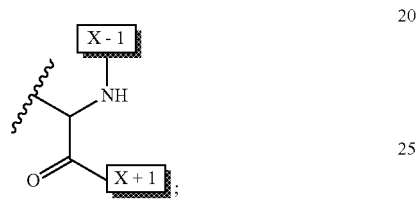

or a pharmaceutically acceptable salt, solvate, or hydrate thereof.

Embodiment 412.1. An IL-15 conjugate comprising the amino acid sequence of anyone of SEQ ID NOS: 76-81, wherein [AzK_PEG40] has the structure of Formula (II) or Formula (III), or is a mixture of the structures of Formula (II) and Formula (III):

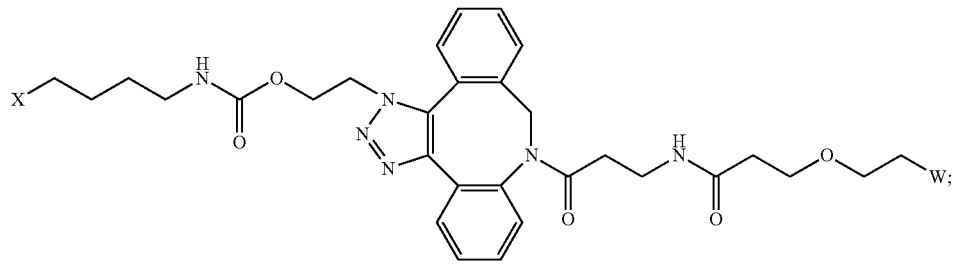

Formula (II)

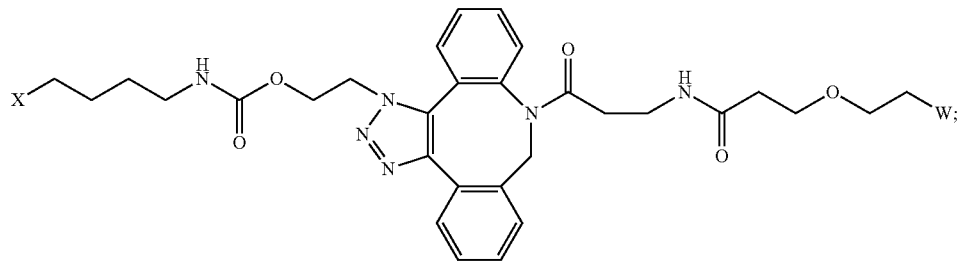

Formula (III)

wherein:
W is a PEG group having an average molecular weight of 40 kDa; and
X has the structure:

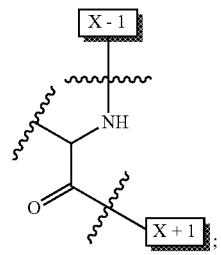

X−1 indicates the point of attachment to the preceding amino acid residue; and
X+1 indicates the point of attachment to the following amino acid residue.

Embodiment 413. The IL-15 conjugate of embodiment 412 or 412.1, wherein the IL-15 conjugate has the amino acid sequence of SEQ ID NO: 76.
Embodiment 414. The IL-15 conjugate of embodiment 412 or 412.1, wherein the IL-15 conjugate has the amino acid sequence of SEQ ID NO: 77.
Embodiment 415. The IL-15 conjugate of embodiment 412 or 412.1, wherein the IL-15 conjugate has the amino acid sequence of SEQ ID NO: 78.
Embodiment 416. The IL-15 conjugate of embodiment 412 or 412.1, wherein the IL-15 conjugate has the amino acid sequence of SEQ ID NO: 79.
Embodiment 417. The IL-15 conjugate of embodiment 412 or 412.1, wherein the IL-15 conjugate has the amino acid sequence of SEQ ID NO: 80.
Embodiment 418. The IL-15 conjugate of embodiment 412 or 412.1, wherein the IL-15 conjugate has the amino acid sequence of SEQ ID NO: 81.
Embodiment 419. The IL-15 conjugate of embodiment 412 or 412.1, wherein the [AzK_PEG40] has the structure of Formula (II):

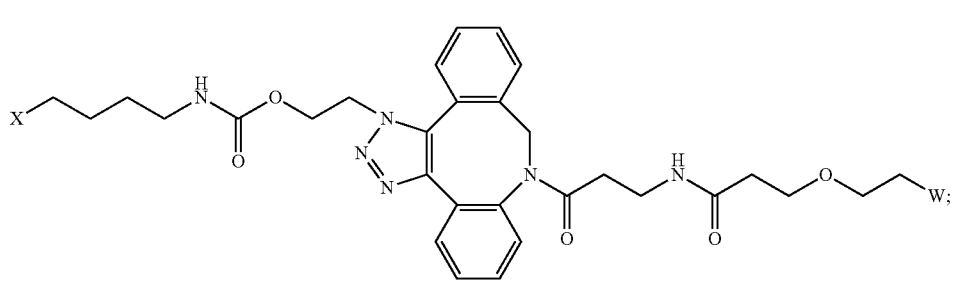

Formula (II)

or a pharmaceutically acceptable salt, solvate, or hydrate thereof.
Embodiment 420. The IL-15 conjugate of embodiment 419, wherein the IL-15 conjugate has the amino acid sequence of SEQ ID NO: 76.
Embodiment 421. The IL-15 conjugate of embodiment 419, wherein the IL-15 conjugate has the amino acid sequence of SEQ ID NO: 77.
Embodiment 422. The IL-15 conjugate of embodiment 419, wherein the IL-15 conjugate has the amino acid sequence of SEQ ID NO: 78.
Embodiment 423. The IL-15 conjugate of embodiment 419, wherein the IL-15 conjugate has the amino acid sequence of SEQ ID NO: 79.
Embodiment 424. The IL-15 conjugate of embodiment 419, wherein the IL-15 conjugate has the amino acid sequence of SEQ ID NO: 80.
Embodiment 425. The IL-15 conjugate of embodiment 419, wherein the IL-15 conjugate has the amino acid sequence of SEQ ID NO: 81.
Embodiment 426. The IL-15 conjugate of embodiment 412 or 412.1, wherein the [AzK_PEG40] has the structure of Formula (III)

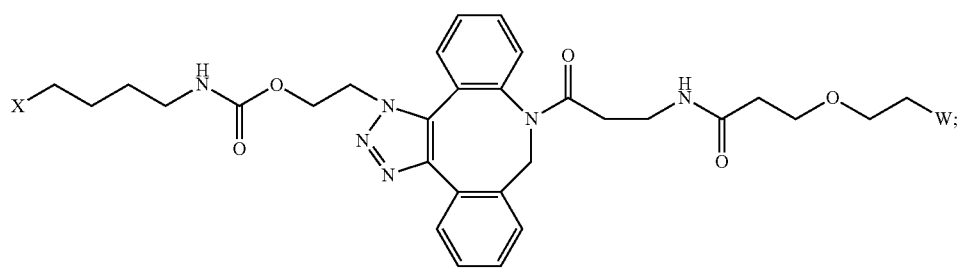

Formula (III)

or a pharmaceutically acceptable salt, solvate, or hydrate thereof.

Embodiment 427. The IL-15 conjugate of embodiment 426, wherein the IL-15 conjugate has the amino acid sequence of SEQ ID NO: 76.

Embodiment 428. The IL-15 conjugate of embodiment 426, wherein the IL-15 conjugate has the amino acid sequence of SEQ ID NO: 77.

Embodiment 429. The IL-15 conjugate of embodiment 426, wherein the IL-15 conjugate has the amino acid sequence of SEQ ID NO: 78.

Embodiment 430. The IL-15 conjugate of embodiment 426, wherein the IL-15 conjugate has the amino acid sequence of SEQ ID NO: 79.

Embodiment 431. The IL-15 conjugate of embodiment 426, wherein the IL-15 conjugate has the amino acid sequence of SEQ ID NO: 80.

Embodiment 432. The IL-15 conjugate of embodiment 426, wherein the IL-15 conjugate has the amino acid sequence of SEQ ID NO: 81.

Embodiment 433. An IL-15 conjugate comprising the amino acid sequence of any one of SEQ ID NOS: 76-81, wherein [AzK_PEG40] is a mixture of the structures of Formula (II) and Formula (III):

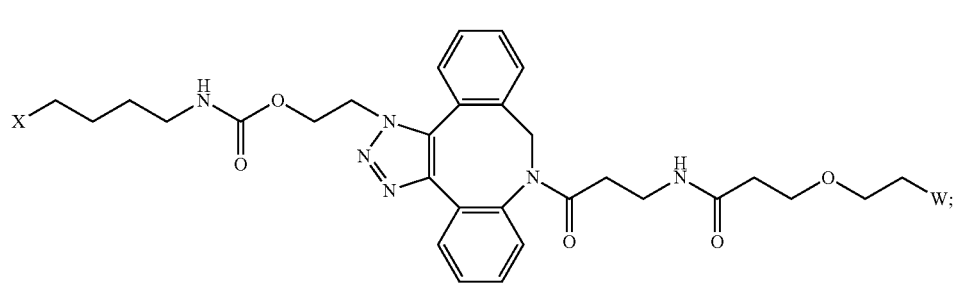

Formula (II)

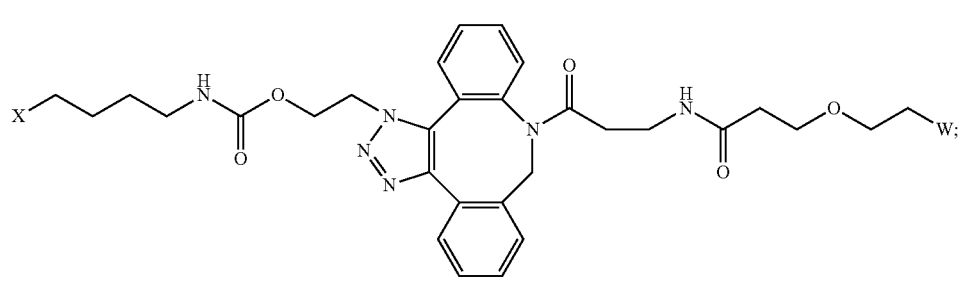

Formula (III)

wherein:
W is a PEG group having an average molecular weight of 40 kDa; and
X has the structure:

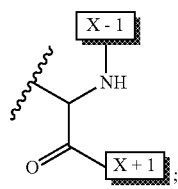

or a pharmaceutically acceptable salt, solvate, or hydrate thereof.

Embodiment 433.1. An IL-15 conjugate comprising the amino acid sequence of anyone of SEQ ID NOS: 76-81, wherein [AzK_PEG40] is a mixture of the structures of Formula (II) and Formula (III):

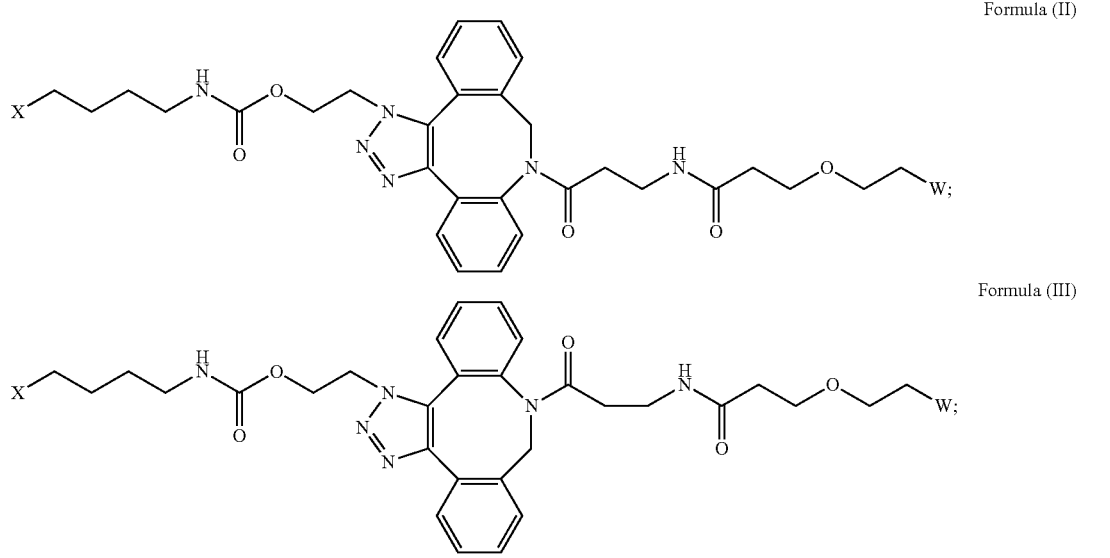

wherein:
W is a PEG group having an average molecular weight of 40 kDa; and
X has the structure:

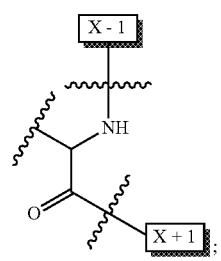

X−1 indicates the point of attachment to the preceding amino acid residue; and
X+1 indicates the point of attachment to the following amino acid residue.

Embodiment 434. The IL-15 conjugate according to embodiment 433 or 433.1, wherein the ratio of the amount of the structure of Formula (II) to the amount of the structure of Formula (III) comprising the total amount of [AzK_PEG40] in the IL-15 conjugate is about 1:1.

Embodiment 435. The IL-15 conjugate according to embodiment 433 or 433.1, wherein the ratio of the amount of the structure of Formula (II) to the amount of the structure of Formula (III) comprising the total amount of [AzK_PEG40] in the IL-15 conjugate is greater than 1:1.

Embodiment 436. The IL-15 conjugate according to embodiment 433 or 433.1, wherein the ratio of the amount of the structure of Formula (II) to the amount of the structure of Formula (III) comprising the total amount of [AzK_PEG40] in the IL-15 conjugate is less than 1:1.

Embodiment 437. The IL-15 conjugate according to any one of embodiments 412 to 436, wherein W is a linear or branched PEG group.

Embodiment 438. The IL-15 conjugate according to any one of embodiments 412 to 436, wherein W is a linear PEG group.

Embodiment 439. The IL-15 conjugate according to any one of embodiments 412 to 436, wherein W is a branched PEG group.

Embodiment 440. The IL-15 conjugate according to any one of embodiments 412 to 436, wherein W is a methoxy PEG group.

Embodiment 441. The IL-15 conjugate according to embodiment 440, wherein the methoxy PEG group is linear or branched.

Embodiment 442. The IL-15 conjugate according to embodiment 441, wherein the methoxy PEG group is linear.

Embodiment 443. The IL-15 conjugate according to embodiment 441, wherein the methoxy PEG group is branched.

Embodiment 444. An IL-15 conjugate comprising the amino acid sequence of any one of SEQ ID NOS: 82-87, wherein [AzK_L1_PEG] has the structure of Formula (IV) or Formula (V), or a mixture of Formula (IV) and Formula (V):

Formula (IV)
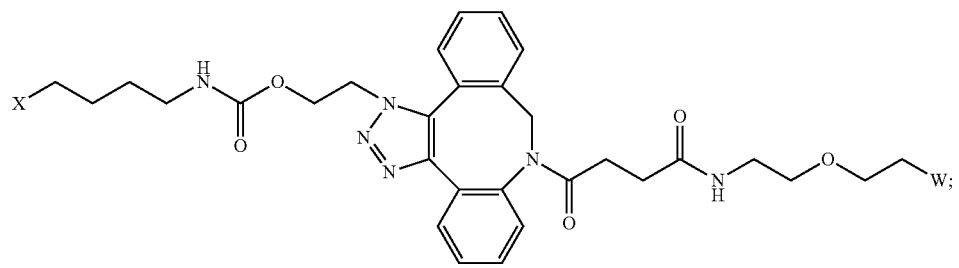
Formula (V)
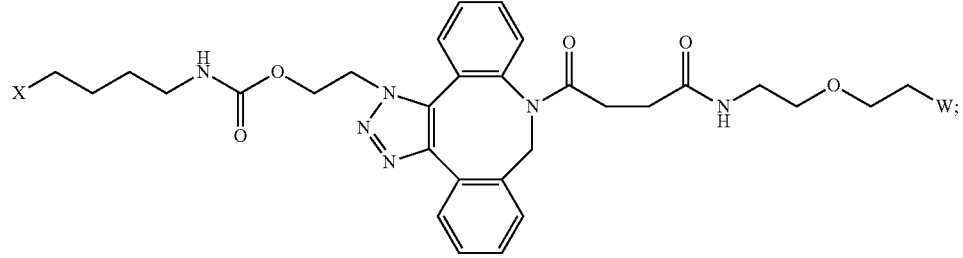
wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:
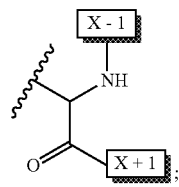
Formula (IV)
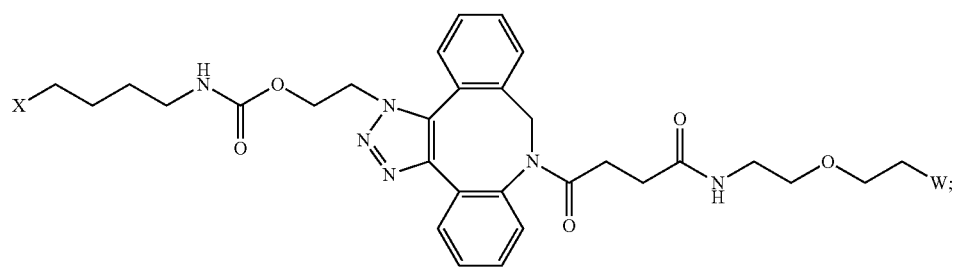
Formula (V)
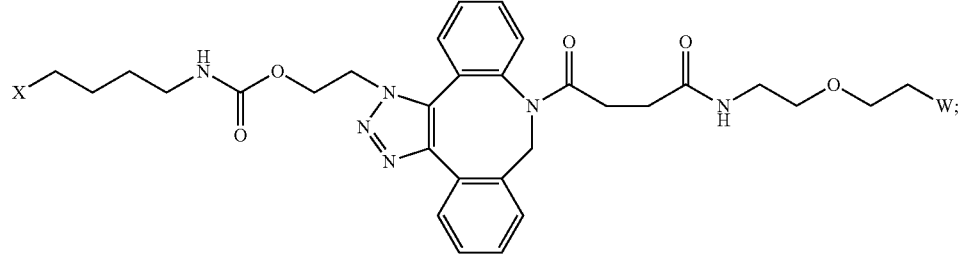

or a pharmaceutically acceptable salt, solvate, or hydrate thereof.

Embodiment 444.1. An IL-15 conjugate comprising the amino acid sequence of anyone of SEQ ID NOS: 82-87, wherein [AzK_L1_PEG] has the structure of Formula (IV) or Formula (V), or a mixture of Formula (IV) and Formula (V):
  wherein:
  W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
  X has the structure:

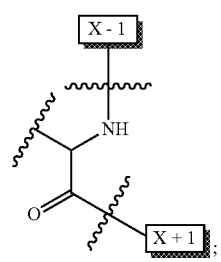

X−1 indicates the point of attachment to the preceding amino acid residue; and
  X+1 indicates the point of attachment to the following amino acid residue.

Embodiment 445. The IL-15 conjugate of embodiment 444 or 444.1, wherein the [AzK_L1_PEG] is a mixture of Formula (IV) and Formula (V).

Embodiment 446. The IL-15 conjugate of embodiment 444 or 444.1, wherein the [AzK_L1_PEG] has the structure of Formula (IV):

Embodiment 451. The IL-15 conjugate of embodiment 449, wherein W is a PEG group having an average molecular weight of 40 kDa.

Embodiment 452. The IL-15 conjugate of embodiment 446, wherein the IL-15 conjugate has the amino acid sequence of SEQ ID NO: 83.

Embodiment 453. The IL-15 conjugate of embodiment 452, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 454. The IL-15 conjugate of embodiment 453, wherein W is a PEG group having an average molecular weight selected from 30 kDa and 40 kDa.

Embodiment 455. The IL-15 conjugate of embodiment 454, wherein W is a PEG group having an average molecular weight of 30 kDa.

Embodiment 456. The IL-15 conjugate of embodiment 454, wherein W is a PEG group having an average molecular weight of 40 kDa.

Embodiment 457. The IL-15 conjugate of embodiment 446, wherein the IL-15 conjugate has the amino acid sequence of SEQ ID NO: 84.

Embodiment 458. The IL-15 conjugate of embodiment 457, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 459. The IL-15 conjugate of embodiment 458, wherein W is a PEG group having an average molecular weight selected from 30 kDa and 40 kDa.

Embodiment 460. The IL-15 conjugate of embodiment 459, wherein W is a PEG group having an average molecular weight of 30 kDa.

Embodiment 461. The IL-15 conjugate of embodiment 459, wherein W is a PEG group having an average molecular weight of 40 kDa.

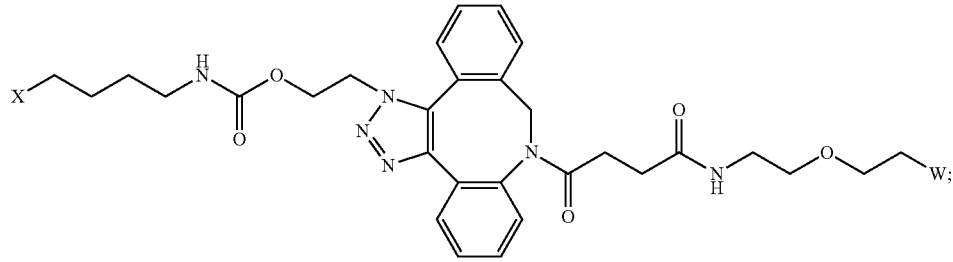

Formula (IV)

or a pharmaceutically acceptable salt, solvate, or hydrate thereof.

Embodiment 447. The IL-15 conjugate of embodiment 446, wherein the IL-15 conjugate has the amino acid sequence of SEQ ID NO: 82.

Embodiment 448. The IL-15 conjugate of embodiment 447, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 449. The IL-15 conjugate of embodiment 448, wherein W is a PEG group having an average molecular weight selected from 30 kDa and 40 kDa.

Embodiment 450. The IL-15 conjugate of embodiment 449, wherein W is a PEG group having an average molecular weight of 30 kDa.

Embodiment 462. The IL-15 conjugate of embodiment 446, wherein the IL-15 conjugate has the amino acid sequence of SEQ ID NO: 85.

Embodiment 463. The IL-15 conjugate of embodiment 462, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 464. The IL-15 conjugate of embodiment 463, wherein W is a PEG group having an average molecular weight selected from 30 kDa and 40 kDa.

Embodiment 465. The IL-15 conjugate of embodiment 464, wherein W is a PEG group having an average molecular weight of 30 kDa.

Embodiment 466. The IL-15 conjugate of embodiment 464, wherein W is a PEG group having an average molecular weight of 40 kDa.

Embodiment 467. The IL-15 conjugate of embodiment 446, wherein the IL-15 conjugate has the amino acid sequence of SEQ ID NO: 86.

Embodiment 468. The IL-15 conjugate of embodiment 467, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 469. The IL-15 conjugate of embodiment 468, wherein W is a PEG group having an average molecular weight selected from 30 kDa and 40 kDa.

Embodiment 470. The IL-15 conjugate of embodiment 469, wherein W is a PEG group having an average molecular weight of 30 kDa.

Embodiment 471. The IL-15 conjugate of embodiment 469, wherein W is a PEG group having an average molecular weight of 40 kDa.

Embodiment 472. The IL-15 conjugate of embodiment 446, wherein the IL-15 conjugate has the amino acid sequence of SEQ ID NO: 87.

Embodiment 473. The IL-15 conjugate of embodiment 472, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 474. The IL-15 conjugate of embodiment 473, wherein W is a PEG group having an average molecular weight selected from 30 kDa and 40 kDa.

Embodiment 475. The IL-15 conjugate of embodiment 474, wherein W is a PEG group having an average molecular weight of 30 kDa.

Embodiment 476. The IL-15 conjugate of embodiment 474, wherein W is a PEG group having an average molecular weight of 40 kDa.

Embodiment 477. The IL-15 conjugate of embodiment 444 or 444.1, wherein the [AzK_L1_PEG] has the structure of Formula (V)

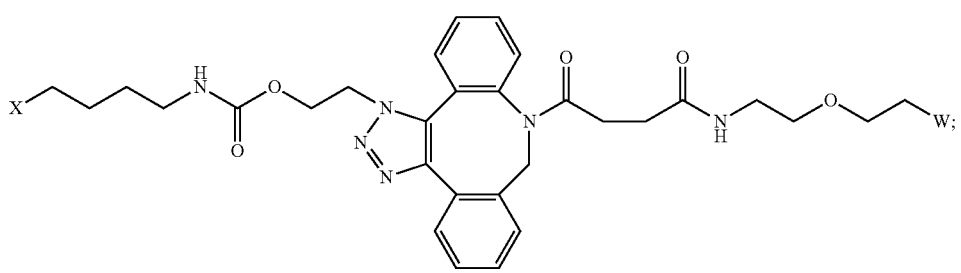

Formula (V)

or a pharmaceutically acceptable salt, solvate, or hydrate thereof.

Embodiment 478. The IL-15 conjugate of embodiment 477, wherein the IL-15 conjugate has the amino acid sequence of SEQ ID NO: 82.

Embodiment 479. The IL-15 conjugate of embodiment 478, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 480. The IL-15 conjugate of embodiment 479, wherein W is a PEG group having an average molecular weight selected from 30 kDa and 40 kDa.

Embodiment 481. The IL-15 conjugate of embodiment 480, wherein W is a PEG group having an average molecular weight of 30 kDa.

Embodiment 482. The IL-15 conjugate of embodiment 480, wherein W is a PEG group having an average molecular weight of 40 kDa.

Embodiment 483. The IL-15 conjugate of embodiment 477, wherein the IL-15 conjugate has the amino acid sequence of SEQ ID NO: 83.

Embodiment 484. The IL-15 conjugate of embodiment 483, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 485. The IL-15 conjugate of embodiment 484, wherein W is a PEG group having an average molecular weight selected from 30 kDa and 40 kDa.

Embodiment 486. The IL-15 conjugate of embodiment 485, wherein W is a PEG group having an average molecular weight of 30 kDa.

Embodiment 487. The IL-15 conjugate of embodiment 485, wherein W is a PEG group having an average molecular weight of 40 kDa.

Embodiment 488. The IL-15 conjugate of embodiment 477, wherein the IL-15 conjugate has the amino acid sequence of SEQ ID NO: 84.

Embodiment 489. The IL-15 conjugate of embodiment 488, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 490. The IL-15 conjugate of embodiment 489, wherein W is a PEG group having an average molecular weight selected from 30 kDa and 40 kDa.

Embodiment 491. The IL-15 conjugate of embodiment 490, wherein W is a PEG group having an average molecular weight of 30 kDa.

Embodiment 492. The IL-15 conjugate of embodiment 490, wherein W is a PEG group having an average molecular weight of 40 kDa.

Embodiment 493. The IL-15 conjugate of embodiment 477, wherein the IL-15 conjugate has the amino acid sequence of SEQ ID NO: 85.

Embodiment 494. The IL-15 conjugate of embodiment 493, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 495. The IL-15 conjugate of embodiment 494, wherein W is a PEG group having an average molecular weight selected from 30 kDa and 40 kDa.

Embodiment 496. The IL-15 conjugate of embodiment 495, wherein W is a PEG group having an average molecular weight of 30 kDa.

Embodiment 497. The IL-15 conjugate of embodiment 495, wherein W is a PEG group having an average molecular weight of 40 kDa.

Embodiment 498. The IL-15 conjugate of embodiment 477, wherein the IL-15 conjugate has the amino acid sequence of SEQ ID NO: 86.

Embodiment 499. The IL-15 conjugate of embodiment 498, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 500. The IL-15 conjugate of embodiment 499, wherein W is a PEG group having an average molecular weight selected from 30 kDa and 40 kDa.

Embodiment 501. The IL-15 conjugate of embodiment 500, wherein W is a PEG group having an average molecular weight of 30 kDa.

Embodiment 502. The IL-15 conjugate of embodiment 500, wherein W is a PEG group having an average molecular weight of 40 kDa.

Embodiment 503. The IL-15 conjugate of embodiment 477, wherein the IL-15 conjugate has the amino acid sequence of SEQ ID NO: 87.

Embodiment 504. The IL-15 conjugate of embodiment 503, wherein W is a PEG group having an average molecular weight selected from 5 kDa, 10 kDa, 15 kDa, 20 kDa, 25 kDa, 30 kDa, 35 kDa, 40 kDa, and 45 kDa.

Embodiment 505. The IL-15 conjugate of embodiment 504, wherein W is a PEG group having an average molecular weight selected from 30 kDa and 40 kDa.

Embodiment 506. The IL-15 conjugate of embodiment 505, wherein W is a PEG group having an average molecular weight of 30 kDa.

Embodiment 507. The IL-15 conjugate of embodiment 505, wherein W is a PEG group having an average molecular weight of 40 kDa.

Embodiment 508. An IL-15 conjugate comprising the amino acid sequence of any one of SEQ ID NOS: 82-87, wherein [Azk_L1_PEG] is a mixture of the structures of Formula (IV) and Formula (V):

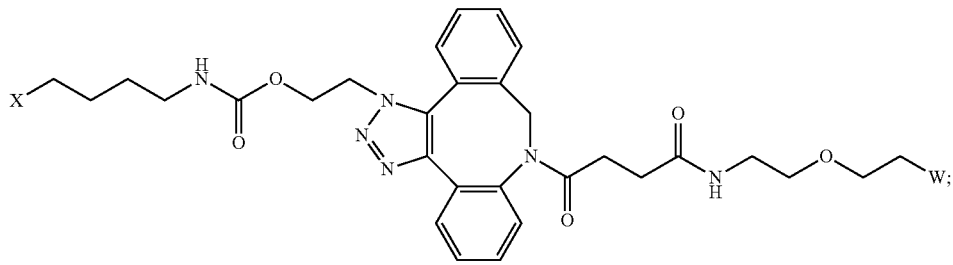

Formula (IV)

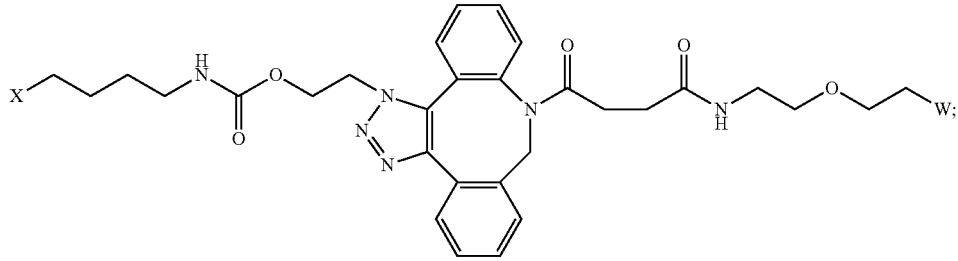

Formula (V)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

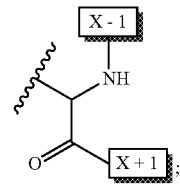

or a pharmaceutically acceptable salt, solvate, or hydrate thereof.

Embodiment 508.1. An IL-15 conjugate comprising the amino acid sequence of anyone of SEQ ID NOS: 82-87, wherein [Azk_L1_PEG] is a mixture of the structures of Formula (IV) and Formula (V):

Formula (IV)

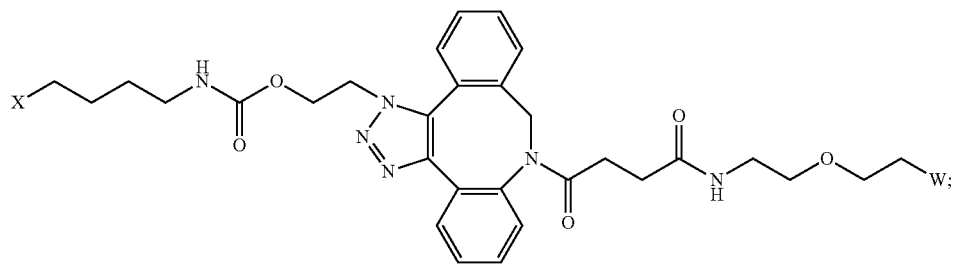

Formula (V)

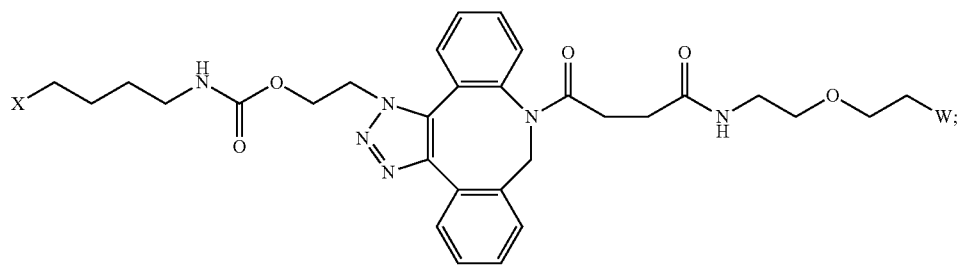

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

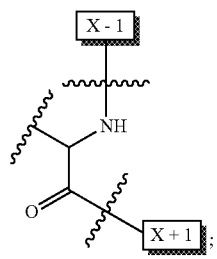

X−1 indicates the point of attachment to the preceding amino acid residue; and
X+1 indicates the point of attachment to the following amino acid residue.

Embodiment 509. The IL-15 conjugate according to embodiment 508 or 508.1, wherein the ratio of the amount of the structure of Formula (IV) to the amount of the structure of Formula (V) comprising the total amount of [AzK_L1_PEG] in the IL-15 conjugate is about 1:1.

Embodiment 510. The IL-15 conjugate according to embodiment 508 or 508.1, wherein the ratio of the amount of the structure of Formula (IV) to the amount of the structure of Formula (V) comprising the total amount of [AzK_L1_PEG] in the IL-15 conjugate is greater than 1:1.

Embodiment 511. The IL-15 conjugate according to embodiment 508 or 508.1, wherein the ratio of the amount of the structure of Formula (IV) to the amount of the structure of Formula (V) comprising the total amount of [AzK_L1_PEG] in the IL-15 conjugate is less than 1:1.

Embodiment 512. The IL-15 conjugate according to any one of embodiments 444 to 511, wherein W is a linear or branched PEG group.

Embodiment 513. The IL-15 conjugate according to any one of embodiments 444 to 511, wherein W is a linear PEG group.

Embodiment 514. The IL-15 conjugate according to any one of embodiments 444 to 511, wherein W is a branched PEG group.

Embodiment 515. The IL-15 conjugate according to any one of embodiments 444 to 511, wherein W is a methoxy PEG group.

Embodiment 516. The IL-15 conjugate according to embodiment 515, wherein the methoxy PEG group is linear or branched.

Embodiment 517. The IL-15 conjugate according to embodiment 516, wherein the methoxy PEG group is linear.

Embodiment 518. The IL-15 conjugate according to embodiment 516, wherein the methoxy PEG group is branched.

Embodiment 519. An IL-15 conjugate comprising the amino acid sequence of any one of SEQ ID NOS: 88-93, wherein [AzK_L1_PEG30] has the structure of Formula (IV) or Formula (V), or a mixture of Formula (IV) and Formula (V):

Formula (IV)

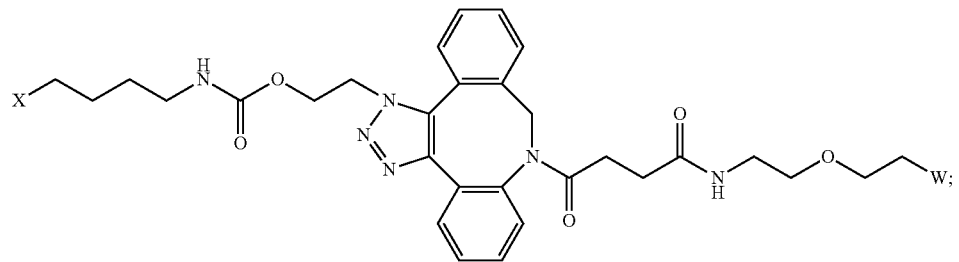

Formula (V)

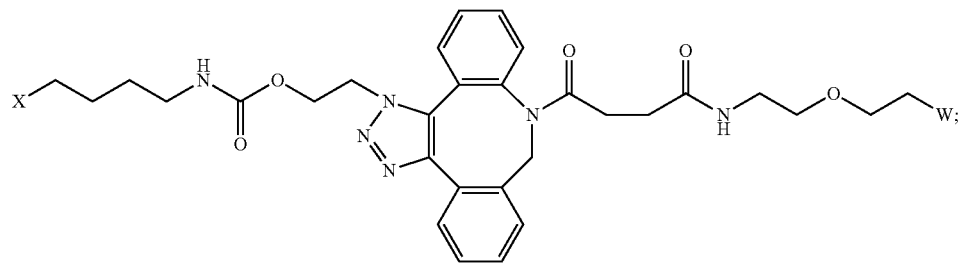

wherein:
W is a PEG group having an average molecular weight of 30 kDa; and
X has the structure:

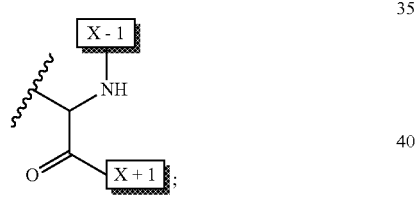

or a pharmaceutically acceptable salt, solvate, or hydrate thereof.

Embodiment 519.1. An IL-15 conjugate comprising the amino acid sequence of anyone of SEQ ID NOS: 88-93, wherein [AzK_L1_PEG30] has the structure of Formula (IV) or Formula (V), or a mixture of Formula (IV) and Formula (V):

Formula (IV)

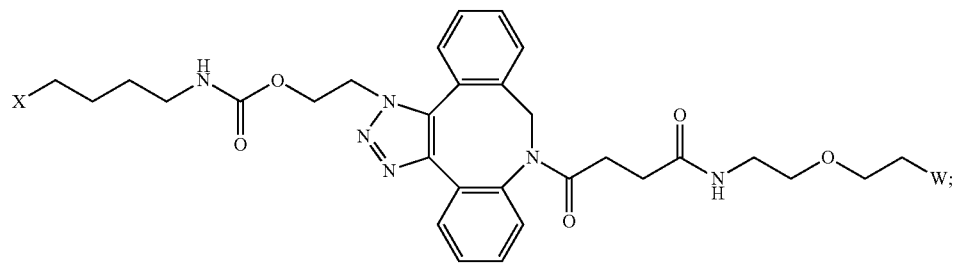

-continued

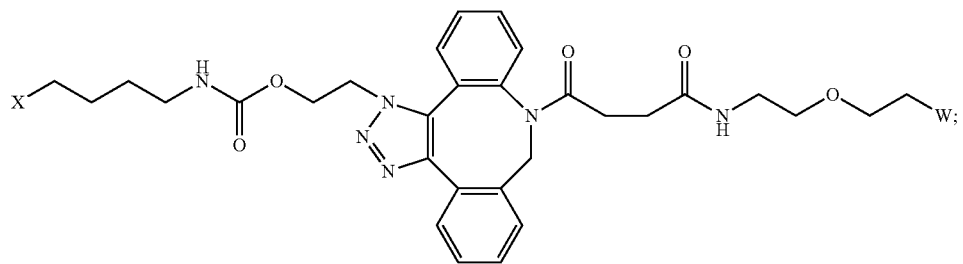

Formula (V)

wherein:
W is a PEG group having an average molecular weight of 30 kDa; and
X has the structure:

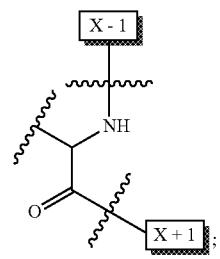

X−1 indicates the point of attachment to the preceding amino acid residue; and
X+1 indicates the point of attachment to the following amino acid residue.

Embodiment 520. The IL-15 conjugate of embodiment 519 or 519.1, wherein the IL-15 conjugate has the amino acid sequence of SEQ ID NO: 88.

Embodiment 521. The IL-15 conjugate of embodiment 519 or 519.1, wherein the IL-15 conjugate has the amino acid sequence of SEQ ID NO: 89.

Embodiment 522. The IL-15 conjugate of embodiment 519 or 519.1, wherein the IL-15 conjugate has the amino acid sequence of SEQ ID NO: 90.

Embodiment 523. The IL-15 conjugate of embodiment 519 or 519.1, wherein the IL-15 conjugate has the amino acid sequence of SEQ ID NO: 91.

Embodiment 524. The IL-15 conjugate of embodiment 519 or 519.1, wherein the IL-15 conjugate has the amino acid sequence of SEQ ID NO: 92.

Embodiment 525. The IL-15 conjugate of embodiment 519 or 519.1, wherein the IL-15 conjugate has the amino acid sequence of SEQ ID NO: 93.

Embodiment 526. The IL-15 conjugate of embodiment 519 or 519.1, wherein the [AzK_L1_PEG30] has the structure of Formula (IV)

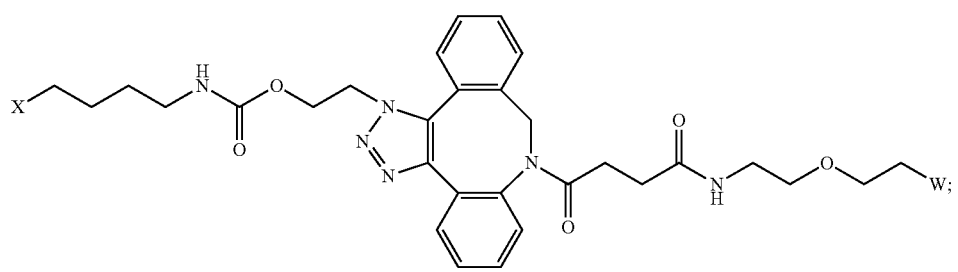

Formula (IV)

or a pharmaceutically acceptable salt, solvate, or hydrate thereof.

Embodiment 527. The IL-15 conjugate of embodiment 526, wherein the IL-15 conjugate has the amino acid sequence of SEQ ID NO: 88.

Embodiment 528. The IL-15 conjugate of embodiment 526, wherein the IL-15 conjugate has the amino acid sequence of SEQ ID NO: 89.

Embodiment 529. The IL-15 conjugate of embodiment 526, wherein the IL-15 conjugate has the amino acid sequence of SEQ ID NO: 90.

Embodiment 530. The IL-15 conjugate of embodiment 526, wherein the IL-15 conjugate has the amino acid sequence of SEQ ID NO: 91.

Embodiment 531. The IL-15 conjugate of embodiment 526, wherein the IL-15 conjugate has the amino acid sequence of SEQ ID NO: 92.
Embodiment 532. The IL-15 conjugate of embodiment 526, wherein the IL-15 conjugate has the amino acid sequence of SEQ ID NO: 93.
Embodiment 533. The IL-15 conjugate of embodiment 519 or 519.1, wherein the [AzK_L1_PEG30] has the structure of Formula (V)

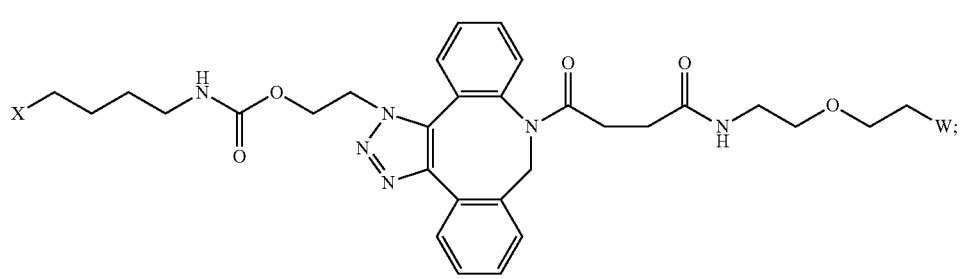

Formula (V)

or a pharmaceutically acceptable salt, solvate, or hydrate thereof.

Embodiment 534. The IL-15 conjugate of embodiment 533, wherein the IL-15 conjugate has the amino acid sequence of SEQ ID NO: 88.
Embodiment 535. The IL-15 conjugate of embodiment 533, wherein the IL-15 conjugate has the amino acid sequence of SEQ ID NO: 89.
Embodiment 536. The IL-15 conjugate of embodiment 533, wherein the IL-15 conjugate has the amino acid sequence of SEQ ID NO: 90.
Embodiment 537. The IL-15 conjugate of embodiment 533, wherein the IL-15 conjugate has the amino acid sequence of SEQ ID NO: 91.
Embodiment 538. The IL-15 conjugate of embodiment 533, wherein the IL-15 conjugate has the amino acid sequence of SEQ ID NO: 92.
Embodiment 539. The IL-15 conjugate of embodiment 533, wherein the IL-15 conjugate has the amino acid sequence of SEQ ID NO: 93.
Embodiment 540. An IL-15 conjugate comprising the amino acid sequence of any one of SEQ ID NOS: 88-93, wherein [AzK_L1_PEG30] is a mixture of the structures of Formula (IV) and Formula (V):

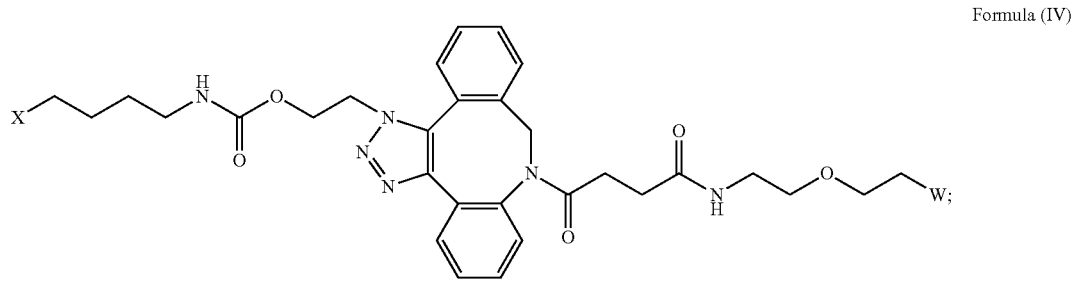

Formula (IV)

-continued
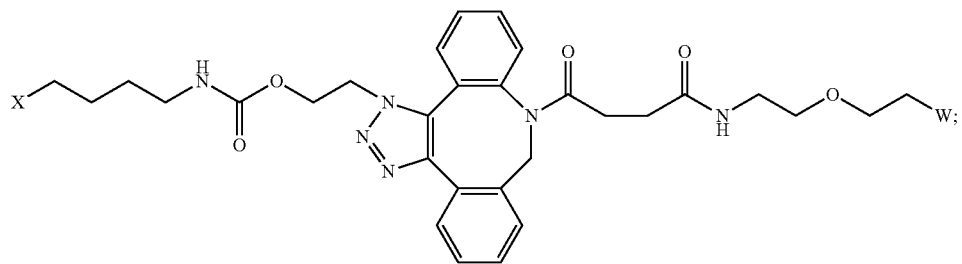
Formula (V)
wherein:
W is a PEG group having an average molecular weight of 30 kDa; and
X has the structure:
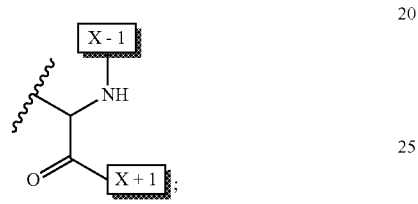
or a pharmaceutically acceptable salt, solvate, or hydrate thereof.
Embodiment 540.1. An IL-15 conjugate comprising the amino acid sequence of anyone of SEQ ID NOS: 88-93, wherein [AzK_L1_PEG30] is a mixture of the structures of Formula (IV) and Formula (V):
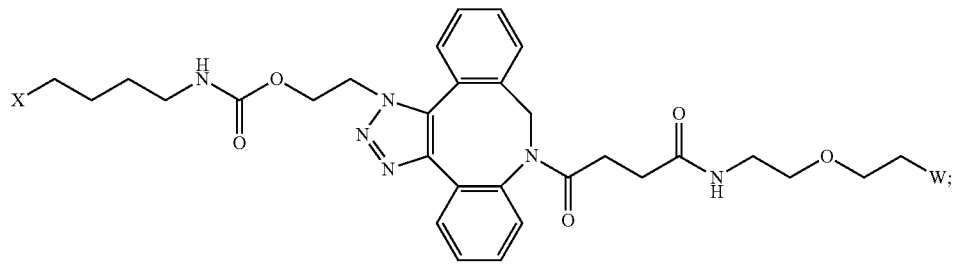
Formula (IV)
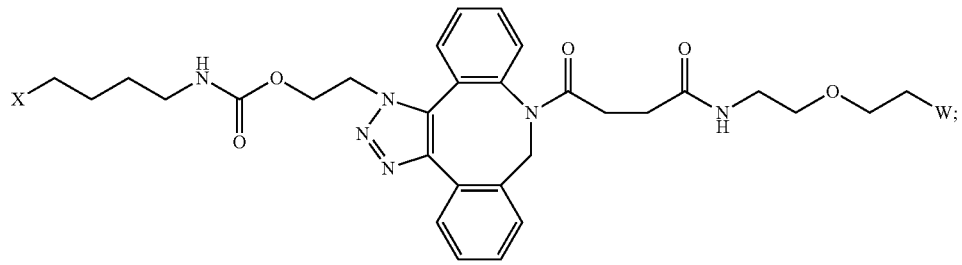
Formula (V)

wherein:
W is a PEG group having an average molecular weight of 30 kDa; and
X has the structure:

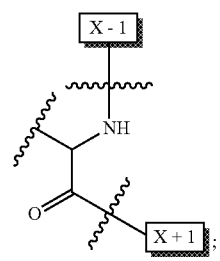

X−1 indicates the point of attachment to the preceding amino acid residue; and
X+1 indicates the point of attachment to the following amino acid residue.

Embodiment 541. The IL-15 conjugate according to embodiment 540 or 540.1, wherein the ratio of the amount of the structure of Formula (IV) to the amount of the structure of Formula (V) comprising the total amount of [AzK_L1_PEG30] in the IL-15 conjugate is about 1:1.

Embodiment 542. The IL-15 conjugate according to embodiment 540 or 540.1, wherein the ratio of the amount of the structure of Formula (IV) to the amount of the structure of Formula (V) comprising the total amount of [AzK_L1_PEG30] in the IL-15 conjugate is greater than 1:1.

Embodiment 543. The IL-15 conjugate according to embodiment 540 or 540.1, wherein the ratio of the amount of the structure of Formula (IV) to the amount of the structure of Formula (V) comprising the total amount of [AzK_L1_PEG30] in the IL-15 conjugate is less than 1:1.

Embodiment 544. The IL-15 conjugate according to any one of embodiments 519 to 543, wherein W is a linear or branched PEG group.

Embodiment 545. The IL-15 conjugate according to any one of embodiments 519 to 543, wherein W is a linear PEG group.

Embodiment 546. The IL-15 conjugate according to any one of embodiments 519 to 543, wherein W is a branched PEG group.

Embodiment 547. The IL-15 conjugate according to any one of embodiments 519 to 543, wherein W is a methoxy PEG group.

Embodiment 548. The IL-15 conjugate according to embodiment 547, wherein the methoxy PEG group is linear or branched.

Embodiment 549. The IL-15 conjugate according to embodiment 548, wherein the methoxy PEG group is linear.

Embodiment 550. The IL-15 conjugate according to embodiment 548, wherein the methoxy PEG group is branched.

Embodiment 551. An IL-15 conjugate comprising the amino acid sequence of any one of SEQ ID NOS: 94-99, wherein [AzK_L1_PEG40] has the structure of Formula (IV) or Formula (V), or is a mixture of the structures of Formula (IV) and Formula (V):

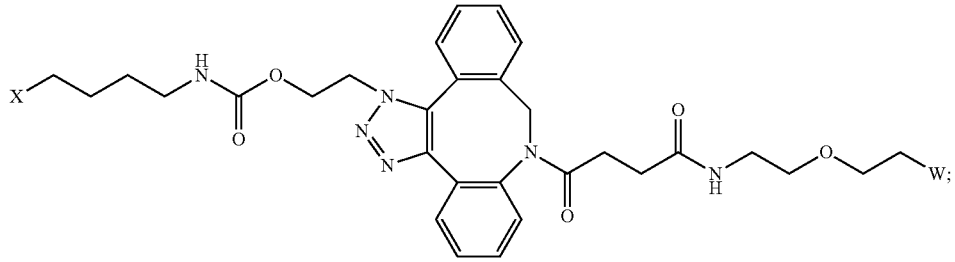

Formula (IV)

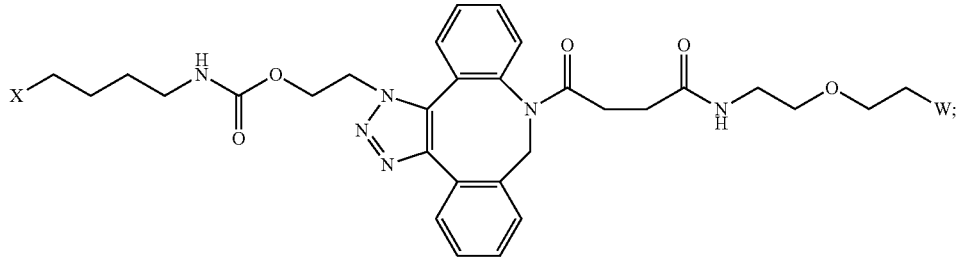

Formula (V)

wherein:
W is a PEG group having an average molecular weight of 40 kDa; and
X has the structure:

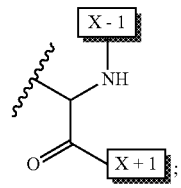

or a pharmaceutically acceptable salt, solvate, or hydrate thereof.

Embodiment 551.1. An IL-15 conjugate comprising the amino acid sequence of anyone of SEQ ID NOS: 94-99, wherein [AzK_L1_PEG40] has the structure of Formula (IV) or Formula (V), or is a mixture of the structures of Formula (IV) and Formula (V):

Formula (IV)

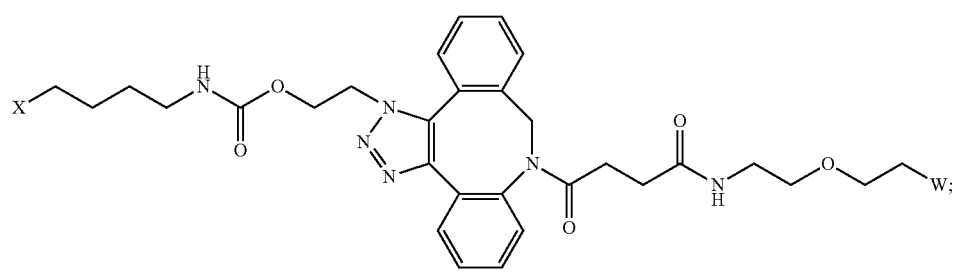

Formula (V)

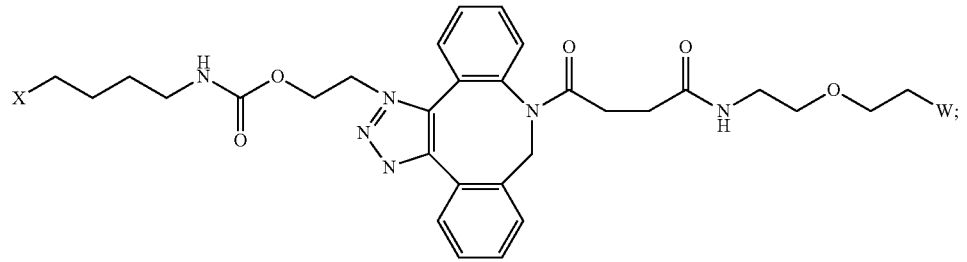

wherein:
W is a PEG group having an average molecular weight of 40 kDa; and
X has the structure:

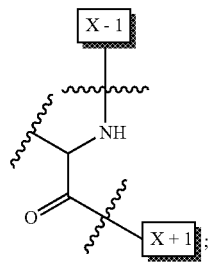

X-1 indicates the point of attachment to the preceding amino acid residue; and

X+1 indicates the point of attachment to the following amino acid residue.

Embodiment 552. The IL-15 conjugate of embodiment 551 or 551.1, wherein the IL-15 conjugate has the amino acid sequence of SEQ ID NO: 94.

Embodiment 553. The IL-15 conjugate of embodiment 551 or 551.1, wherein the IL-15 conjugate has the amino acid sequence of SEQ ID NO: 95.

Embodiment 554. The IL-15 conjugate of embodiment 551 or 551.1, wherein the IL-15 conjugate has the amino acid sequence of SEQ ID NO: 96.

Embodiment 555. The IL-15 conjugate of embodiment 551 or 551.1, wherein the IL-15 conjugate has the amino acid sequence of SEQ ID NO: 97.

Embodiment 556. The IL-15 conjugate of embodiment 551 or 551.1, wherein the IL-15 conjugate has the amino acid sequence of SEQ ID NO: 98.

Embodiment 557. The IL-15 conjugate of embodiment 551 or 551.1, wherein the IL-15 conjugate has the amino acid sequence of SEQ ID NO: 99.

Embodiment 558. The IL-15 conjugate of embodiment 551 or 551.1, wherein the [AzK_L1_PEG40] has the structure of Formula (IV):

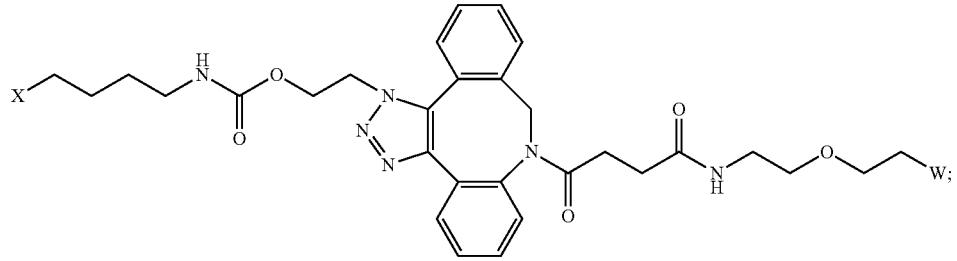

Formula (IV)

or a pharmaceutically acceptable salt, solvate, or hydrate thereof.

Embodiment 559. The IL-15 conjugate of embodiment 558, wherein the IL-15 conjugate has the amino acid sequence of SEQ ID NO: 94.

Embodiment 560. The IL-15 conjugate of embodiment 558, wherein the IL-15 conjugate has the amino acid sequence of SEQ ID NO: 95.

Embodiment 561. The IL-15 conjugate of embodiment 558, wherein the IL-15 conjugate has the amino acid sequence of SEQ ID NO: 96.

Embodiment 562. The IL-15 conjugate of embodiment 558, wherein the IL-15 conjugate has the amino acid sequence of SEQ ID NO: 97.

Embodiment 563. The IL-15 conjugate of embodiment 558, wherein the IL-15 conjugate has the amino acid sequence of SEQ ID NO: 98.

Embodiment 564. The IL-15 conjugate of embodiment 558, wherein the IL-15 conjugate has the amino acid sequence of SEQ ID NO: 99.

Embodiment 565. The IL-15 conjugate of embodiment 551 or 551.1, wherein the [AzK_L1_PEG40] has the structure of Formula (V)

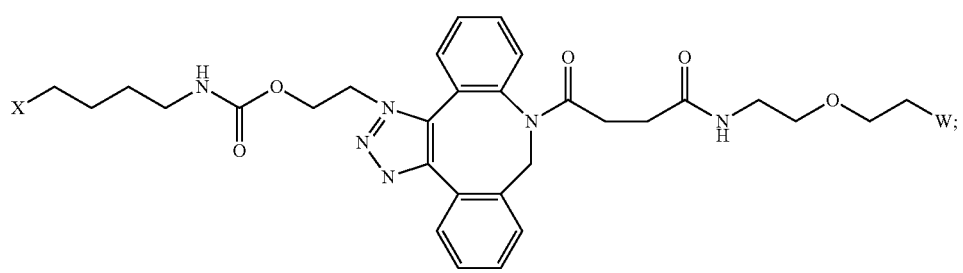

Formula (V)

or a pharmaceutically acceptable salt, solvate, or hydrate thereof.

Embodiment 566. The IL-15 conjugate of embodiment 565, wherein the IL-15 conjugate has the amino acid sequence of SEQ ID NO: 94.

Embodiment 567. The IL-15 conjugate of embodiment 565, wherein the IL-15 conjugate has the amino acid sequence of SEQ ID NO: 95.

Embodiment 568. The IL-15 conjugate of embodiment 565, wherein the IL-15 conjugate has the amino acid sequence of SEQ ID NO: 96.

Embodiment 569. The IL-15 conjugate of embodiment 565, wherein the IL-15 conjugate has the amino acid sequence of SEQ ID NO: 97.

Embodiment 570. The IL-15 conjugate of embodiment 565, wherein the IL-15 conjugate has the amino acid sequence of SEQ ID NO: 98.

Embodiment 571. The IL-15 conjugate of embodiment 565, wherein the IL-15 conjugate has the amino acid sequence of SEQ ID NO: 99.

Embodiment 572. An IL-15 conjugate comprising the amino acid sequence of any one of SEQ ID NOS: 94-99, wherein [AzK_L1_PEG40] is a mixture of the structures of Formula (IV) and Formula (V):

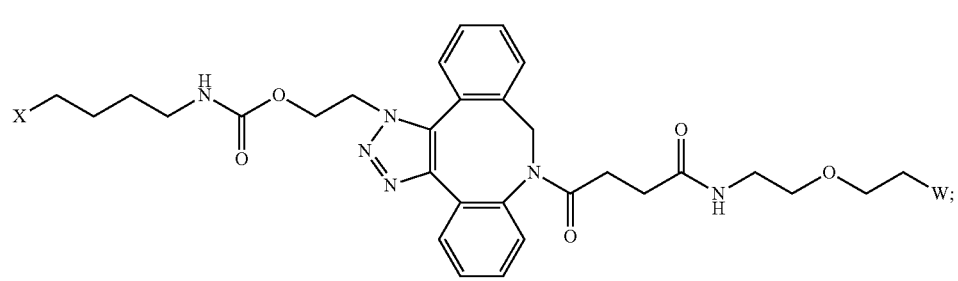

Formula (IV)

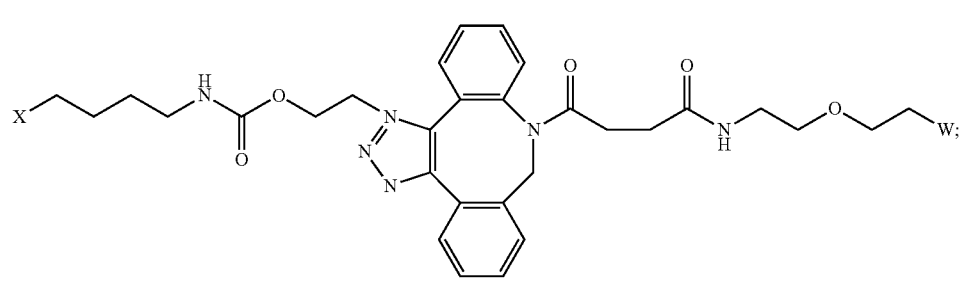

Formula (V)

wherein:
W is a PEG group having an average molecular weight of 40 kDa; and
X has the structure:

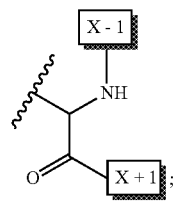

or a pharmaceutically acceptable salt, solvate, or hydrate thereof.

Embodiment 572.1. An IL-15 conjugate comprising the amino acid sequence of anyone of SEQ ID NOS: 94-99, wherein [AzK_L1_PEG40] is a mixture of the structures of Formula (IV) and Formula (V):

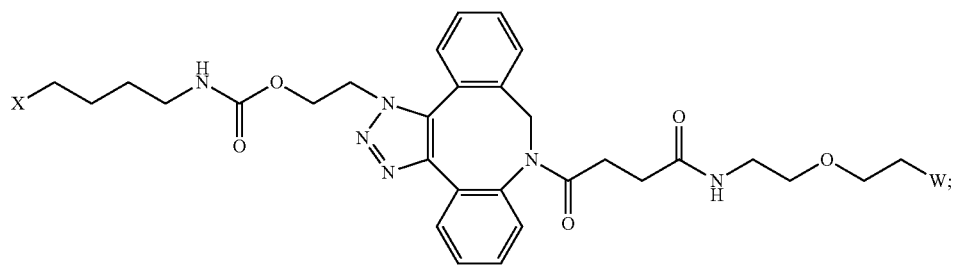

Formula (IV)

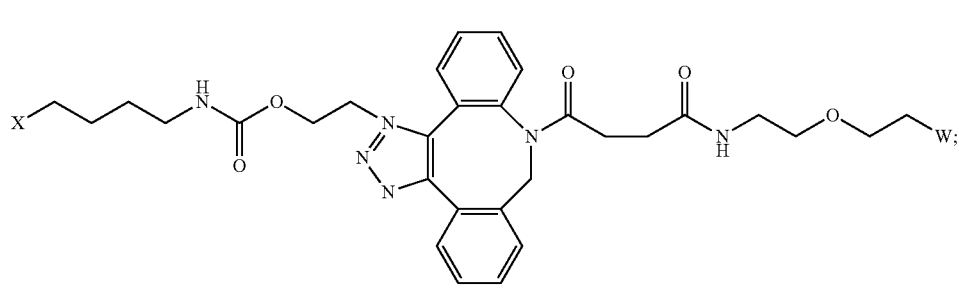

Formula (V)

wherein:
W is a PEG group having an average molecular weight of 40 kDa; and
X has the structure:

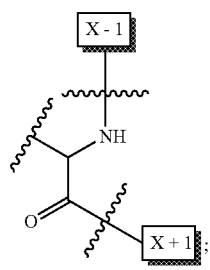

X−1 indicates the point of attachment to the preceding amino acid residue; and
X+1 indicates the point of attachment to the following amino acid residue.

Embodiment 573. The IL-15 conjugate according to embodiment 572 or 572.1, wherein the ratio of the amount of the structure of Formula (IV) to the amount of the structure of Formula (V) comprising the total amount of [AzK_L1_PEG40] in the IL-15 conjugate is about 1:1.

Embodiment 574. The IL-15 conjugate according to embodiment 572 or 572.1, wherein the ratio of the amount of the structure of Formula (IV) to the amount of the structure of Formula (V) comprising the total amount of [AzK_L1_PEG40] in the IL-15 conjugate is greater than 1:1.

Embodiment 575. The IL-15 conjugate according to embodiment 572 or 572.1, wherein the ratio of the amount of the structure of Formula (IV) to the amount of the structure of Formula (V) comprising the total amount of [AzK_L1_PEG40] in the IL-15 conjugate is less than 1:1.

Embodiment 576. The IL-15 conjugate according to any one of embodiments 551 to 575, wherein W is a linear or branched PEG group.

Embodiment 577. The IL-15 conjugate according to any one of embodiments 551 to 575, wherein W is a linear PEG group.

Embodiment 578. The IL-15 conjugate according to any one of embodiments 551 to 575, wherein W is a branched PEG group.

Embodiment 579. The IL-15 conjugate according to any one of embodiments 551 to 575, wherein W is a methoxy PEG group.

Embodiment 580. The IL-15 conjugate according to embodiment 579, wherein the methoxy PEG group is linear or branched.

Embodiment 581. The IL-15 conjugate according to embodiment 580, wherein the methoxy PEG group is linear.

Embodiment 582. The IL-15 conjugate according to embodiment 580, wherein the methoxy PEG group is branched.

Embodiment 583. An IL-15 conjugate comprising the amino acid sequence of SEQ ID NO: 1 in which at least one amino acid residue in the IL-15 conjugate is replaced by the structure of Formula (VI) or (VII), or a mixture of (VI) and (VII):

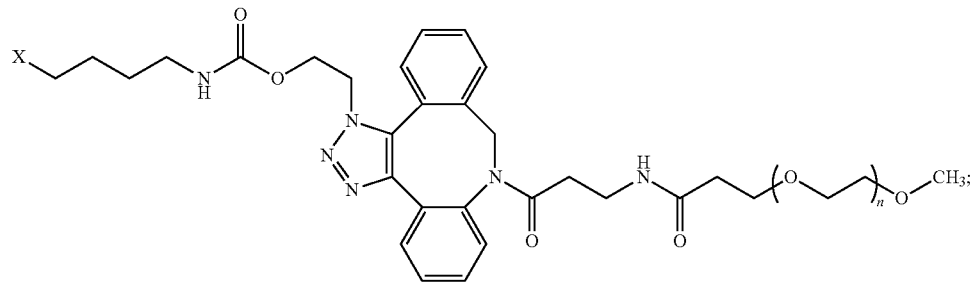
Formula (VI)
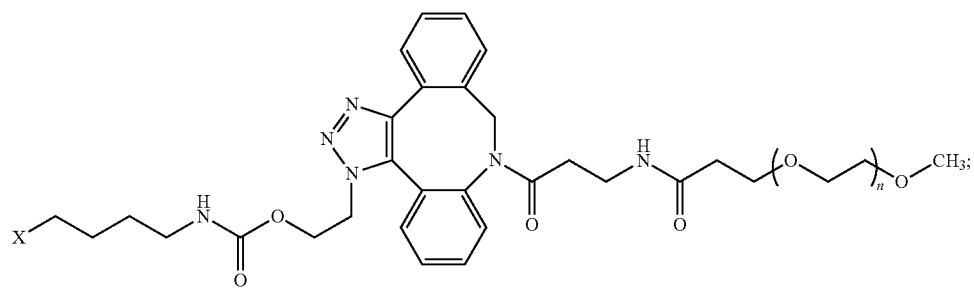
(VII)
wherein:
n is an integer in the range from about 2 to about 5000;
and
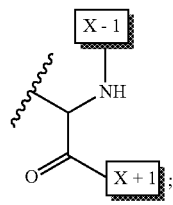
X has the structure:
Embodiment 583.1. An IL-15 conjugate comprising the amino acid sequence of SEQ ID NO: 1 in which at least one amino acid residue in the IL-15 conjugate is replaced by the structure of Formula (VI) or (VII), or a mixture of (VI) and (VII):
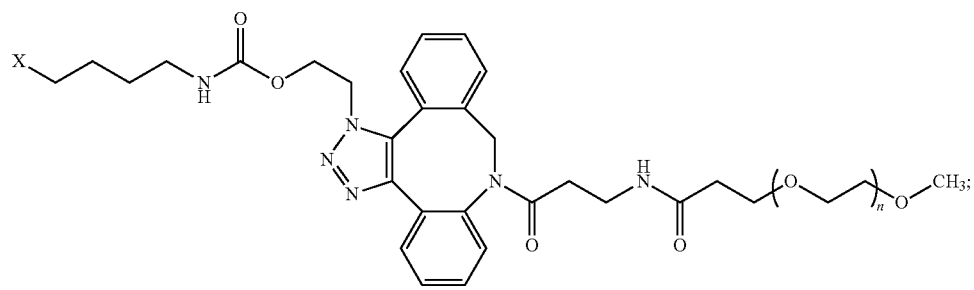
Formula (VI)

(VII)

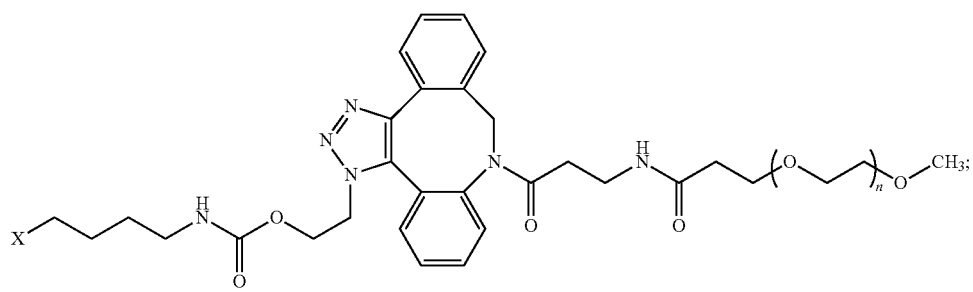

wherein:
n is an integer in the range from about 2 to about 5000; and

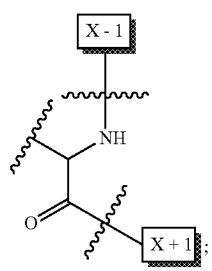

X−1 indicates the point of attachment to the preceding amino acid residue; and
X+1 indicates the point of attachment to the following amino acid residue.

Embodiment 584. The IL-15 conjugate of embodiment 583 or 583.1, wherein the position of the structure of Formula (VI) or (VII), or a mixture of (VI) and (VII), in the amino acid sequence of the IL-15 conjugate is selected from S18, L25, E46, E53, N77, and S83.

Embodiment 585. The IL-15 conjugate of embodiment 584 wherein the position of the structure of Formula (VI) or (VII), or a mixture of (VI) and (VII), in the amino acid sequence of the IL-15 conjugate is selected from L25, E53, and N77.

Embodiment 586. The IL-15 conjugate of embodiment 584, wherein the position of the structure of Formula (VI) or (VII), or a mixture of (VI) and (VII), in the amino acid sequence of the IL-15 conjugate is S18.

Embodiment 587. The IL-15 conjugate of embodiment 584, wherein the position of the structure of Formula (VI) or (VII), or a mixture of (VI) and (VII), in the amino acid sequence of the IL-15 conjugate is L25.

Embodiment 588. The IL-15 conjugate of embodiment 584, wherein the position of the structure of Formula (VI) or (VII), or a mixture of (VI) and (VII), in the amino acid sequence of the IL-15 conjugate is E46.

Embodiment 589. The IL-15 conjugate of embodiment 584, wherein the position of the structure of Formula (VI) or (VII), or a mixture of (VI) and (VII), in the amino acid sequence of the IL-15 conjugate is E53.

Embodiment 590. The IL-15 conjugate of embodiment 584, wherein the position of the structure of Formula (VI) or (VII), or a mixture of (VI) and (VII), in the amino acid sequence of the IL-15 conjugate is N77.

Embodiment 591. The IL-15 conjugate of embodiment 584, wherein the position of the structure of Formula (VI) or (VII), or a mixture of (VI) and (VII), in the amino acid sequence of the IL-15 conjugate is S83.

Embodiment 592. The IL-15 conjugate of any one of embodiments 583 to 591, wherein n is about 75 to about 1000.

Embodiment 593. The IL-15 conjugate of any one of embodiments 583 to 591, wherein n is about 100 to about 1000.

Embodiment 594. The IL-15 conjugate of any one of embodiments 583 to 591, wherein n is about 200 to about 5000.

Embodiment 595. The IL-15 conjugate of any one of embodiments 583 to 591, wherein n is about 500 to about 1000.

Embodiment 596. The IL-15 conjugate of any one of embodiments 583 to 591, wherein n is about 400 to about 800.

Embodiment 597. An IL-15 conjugate comprising the amino acid sequence of SEQ ID NO: 3 in which at least one amino acid residue in the IL-15 conjugate is replaced by the structure of Formula (VI) or (VII), or a mixture of (VI) and (VII):

Formula (VI)

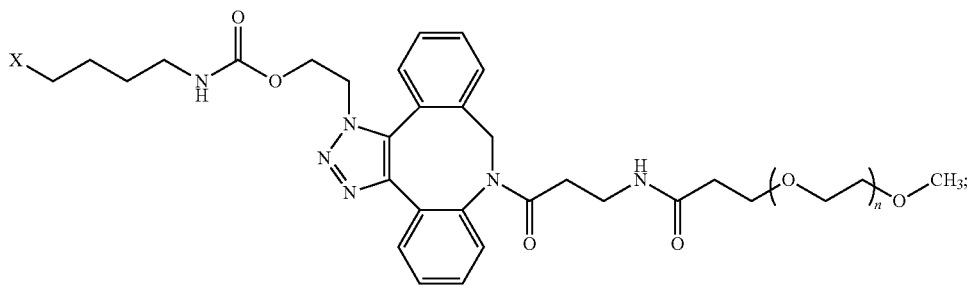

-continued
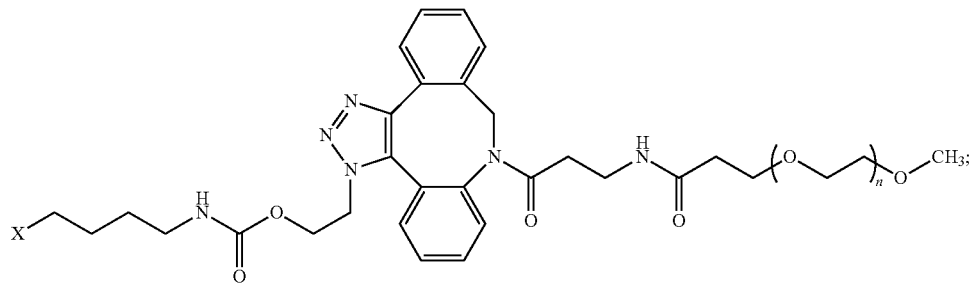
wherein:
n is an integer in the range from about 2 to about 5000; and
X has the structure:
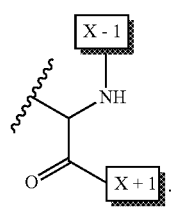
Embodiment 597.1. An IL-15 conjugate comprising the amino acid sequence of SEQ ID NO: 3 in which at least one amino acid residue in the IL-15 conjugate is replaced by the structure of Formula (VI) or (VII), or a mixture of (VI) and (VII):
Formula (VI)
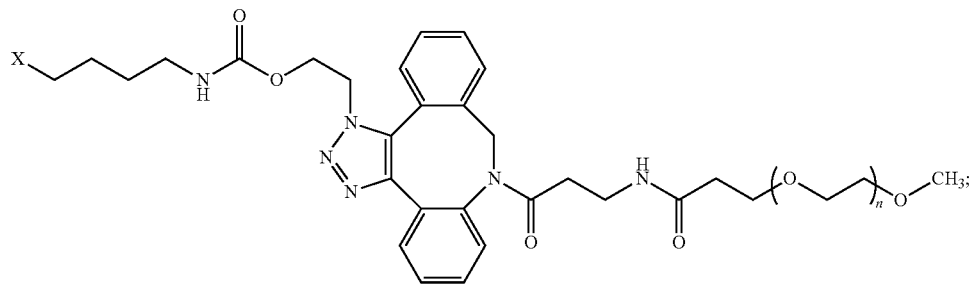
(VII)
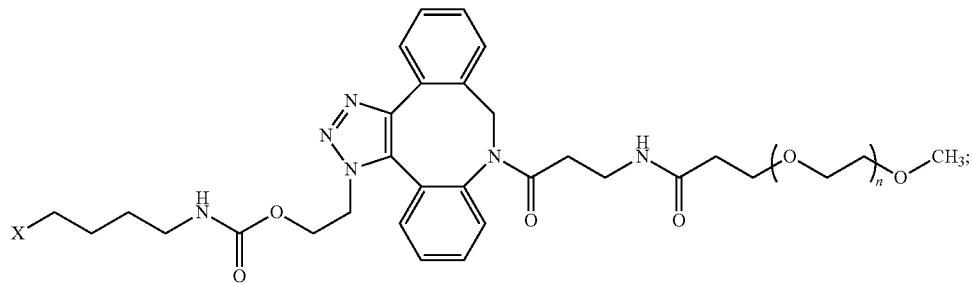

wherein:
n is an integer in the range from about 2 to about 5000; and

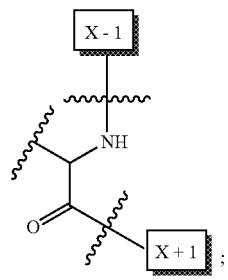

X−1 indicates the point of attachment to the preceding amino acid residue; and
X+1 indicates the point of attachment to the following amino acid residue.

Embodiment 598. The IL-15 conjugate of embodiment 597 or 597.1, wherein the position of the structure of Formula (VI) or (VII), or a mixture of (VI) and (VII) in the amino acid sequence of the IL-15 conjugate is selected from S19, L26, E47, E54, N78, and S84.

Embodiment 599. The IL-15 conjugate of embodiment 598, wherein the position of the structure of Formula (VI) or (VII), or a mixture of (VI) and (VII) in the amino acid sequence of the IL-15 conjugate is selected from L26, E54, and N78.

Embodiment 600. The IL-15 conjugate of embodiment 598, wherein the position of the structure of Formula (VI) or (VII), or a mixture of (VI) and (VII) in the amino acid sequence of the IL-15 conjugate is S19.

Embodiment 601. The IL-15 conjugate of embodiment 598, wherein the position of the structure of Formula (VI) or (VII), or a mixture of (VI) and (VII) in the amino acid sequence of the IL-15 conjugate is L26.

Embodiment 602. The IL-15 conjugate of embodiment 598, wherein the position of the structure of Formula (VI) or (VII), or a mixture of (VI) and (VII) in the amino acid sequence of the IL-15 conjugate is E47.

Embodiment 603. The IL-15 conjugate of embodiment 598, wherein the position of the structure of Formula (VI) or (VII), or a mixture of (VI) and (VII) in the amino acid sequence of the IL-15 conjugate is E54.

Embodiment 604. The IL-15 conjugate of embodiment 598, wherein the position of the structure of Formula (VI) or (VII), or a mixture of (VI) and (VII) in the amino acid sequence of the IL-15 conjugate is N78.

Embodiment 605. The IL-15 conjugate of embodiment 598, wherein the position of the structure of Formula (VI) or (VII), or a mixture of (VI) and (VII) in the amino acid sequence of the IL-15 conjugate is S84.

Embodiment 606. The IL-15 conjugate of any one of embodiments 597 to 605, wherein n is about 75 to about 1000.

Embodiment 607. The IL-15 conjugate of any one of embodiments 597 to 605, wherein n is about 100 to about 1000.

Embodiment 608. The IL-15 conjugate of any one of embodiments 597 to 605, wherein n is about 200 to about 5000.

Embodiment 609. The IL-15 conjugate of any one of embodiments 597 to 605, wherein n is about 500 to about 1000.

Embodiment 610. An IL-15 conjugate comprising the amino acid sequence of SEQ ID NO: 1 in which at least one amino acid residue in the IL-15 conjugate is replaced by the structure of Formula (VIII) or (IX), or a mixture of (VIII) and (IX):

Formula (VIII)
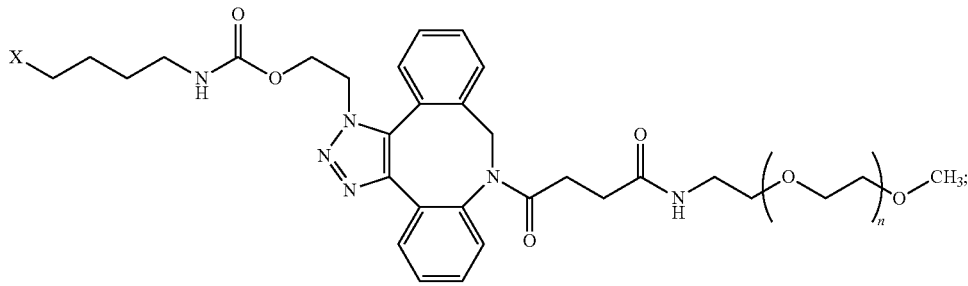

Formula (IX)
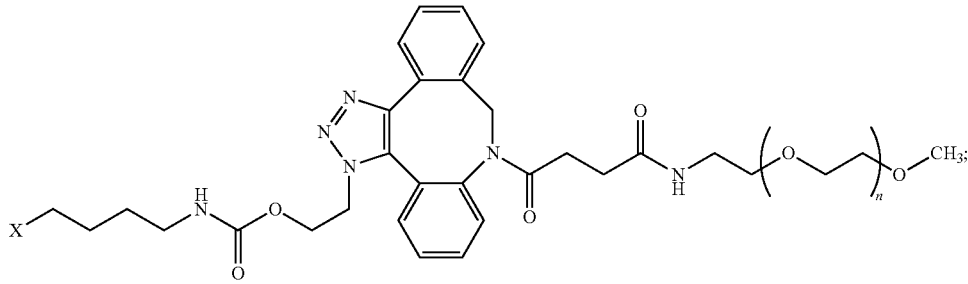

wherein:

n is an integer in the range from about 2 to about 5000; and

X has the structure:

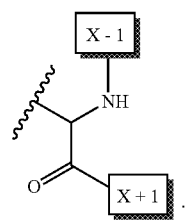

Embodiment 610.1. An IL-15 conjugate comprising the amino acid sequence of SEQ ID NO: 1 in which at least one amino acid residue in the IL-15 conjugate is replaced by the structure of Formula (VIII) or (IX), or a mixture of (VIII) and (IX):

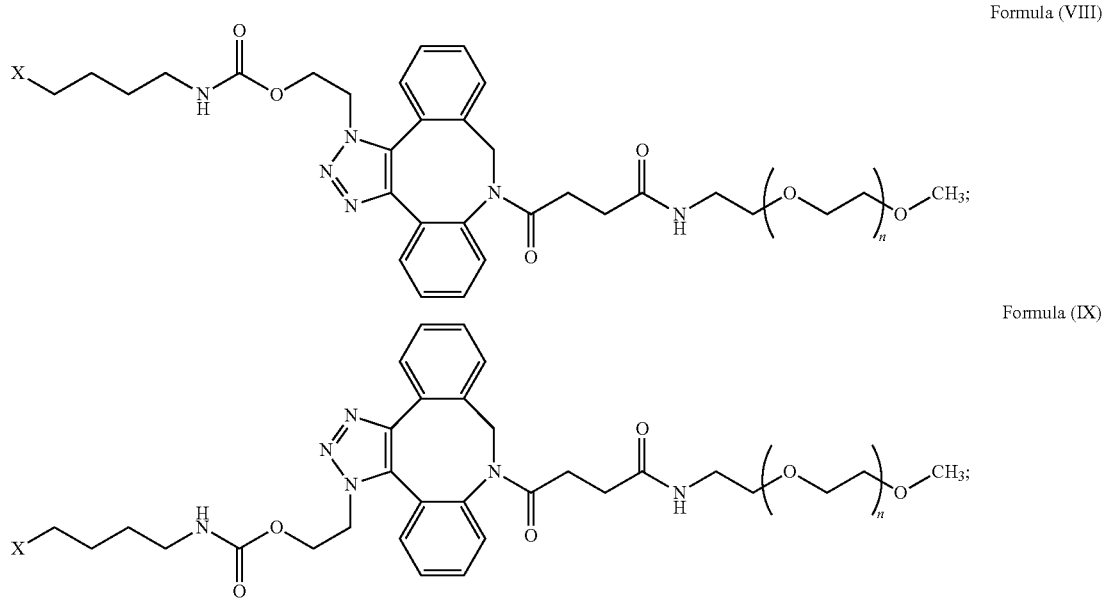

Formula (VIII)

Formula (IX)

wherein:

n is an integer in the range from about 2 to about 5000; and

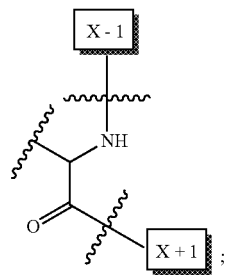

X−1 indicates the point of attachment to the preceding amino acid residue; and

X+1 indicates the point of attachment to the following amino acid residue.

Embodiment 611. The IL-15 conjugate of embodiment 610 or 610.1, wherein the position of the structure of Formula (VIII) or (IX), or a mixture of (VIII) and (IX), in the amino acid sequence of the IL-15 conjugate is selected from S18, L25, E46, E53, N77, and S83.

Embodiment 612. The IL-15 conjugate of embodiment 611 wherein the position of the structure of Formula (VIII) or (IX), or a mixture of (VIII) and (IX), in the amino acid sequence of the IL-15 conjugate is selected from L25, E53, and N77.

Embodiment 613. The IL-15 conjugate of embodiment 611 wherein the position of the structure of Formula (VIII) or (IX), or a mixture of (VIII) and (IX), in the amino acid sequence of the IL-15 conjugate is S18.

Embodiment 614. The IL-15 conjugate of embodiment 611 wherein the position of the structure of Formula (VIII) or (IX), or a mixture of (VIII) and (IX), in the amino acid sequence of the IL-15 conjugate is L25.

Embodiment 615. The IL-15 conjugate of embodiment 611, wherein the position of the structure of Formula (VIII) or (IX), or a mixture of (VIII) and (IX), in the amino acid sequence of the IL-15 conjugate is E46.

Embodiment 616. The IL-15 conjugate of embodiment 611, wherein the position of the structure of Formula (VIII) or (IX), or a mixture of (VIII) and (IX), in the amino acid sequence of the IL-15 conjugate is E53.

Embodiment 617. The IL-15 conjugate of embodiment 611, wherein the position of the structure of Formula (VIII) or (IX), or a mixture of (VIII) and (IX), in the amino acid sequence of the IL-15 conjugate is N77.

Embodiment 618. The IL-15 conjugate of embodiment 611, wherein the position of the structure of Formula (VIII) or (IX), or a mixture of (VIII) and (IX), in the amino acid sequence of the IL-15 conjugate is S83.

Embodiment 619. The IL-15 conjugate of any one of embodiments 610 to 618, wherein n is about 75 to about 1000.

Embodiment 620. The IL-15 conjugate of any one of embodiments 610 to 618, wherein n is about 100 to about 1000.

Embodiment 621. The IL-15 conjugate of any one of embodiments 610 to 618, wherein n is about 200 to about 5000.

Embodiment 622. The IL-15 conjugate of any one of embodiments 610 to 618, wherein n is about 500 to about 1000.

Embodiment 623. The IL-15 conjugate of any one of embodiments 610 to 618, wherein n is about 400 to about 800.

Embodiment 624. An IL-15 conjugate comprising the amino acid sequence of SEQ ID NO: 3 in which at least one amino acid residue in the IL-15 conjugate is replaced by the structure of Formula (VIII) or (IX), or a mixture of (VIII) and (IX):

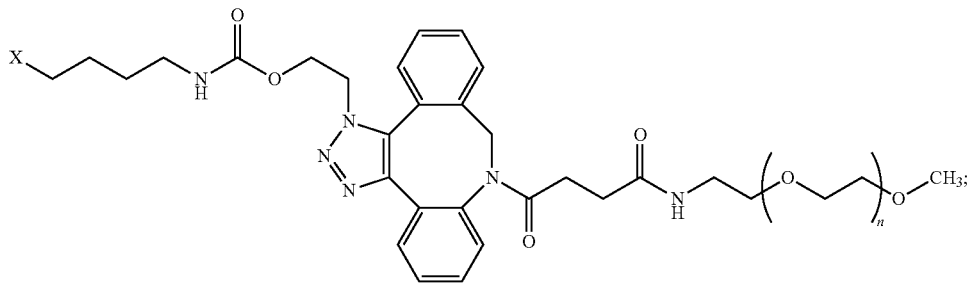

Formula (VIII)

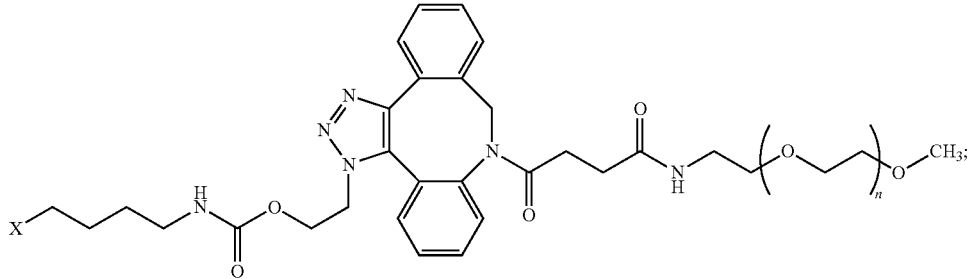

Formula (IX)

wherein:

n is an integer in the range from about 2 to about 5000; and

X has the structure:

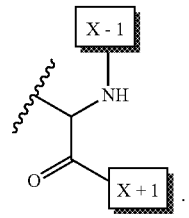

Embodiment 624.1. An IL-15 conjugate comprising the amino acid sequence of SEQ ID NO: 3 in which at least one amino acid residue in the IL-15 conjugate is replaced by the structure of Formula (VIII) or (IX), or a mixture of (VIII) and (IX):

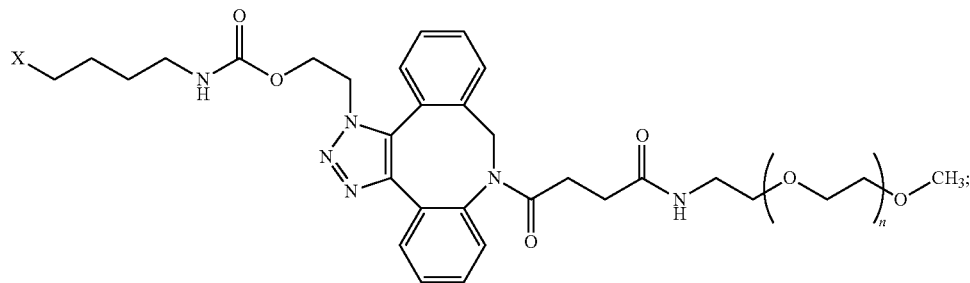

Formula (VIII)

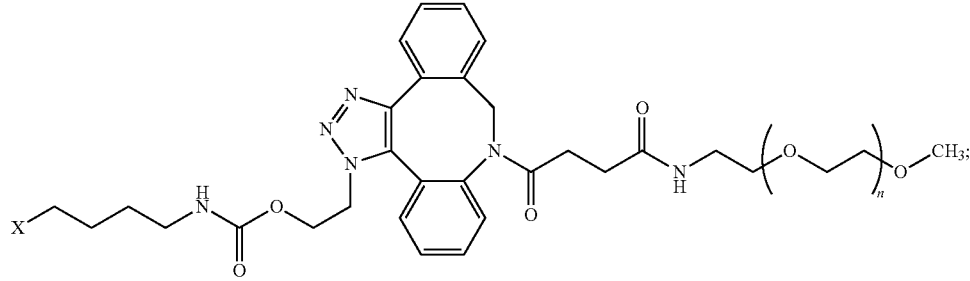

Formula (IX)

wherein:
n is an integer in the range from about 2 to about 5000; and

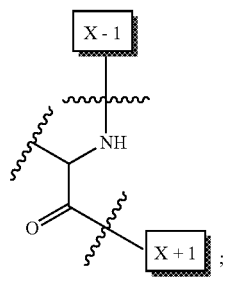

X−1 indicates the point of attachment to the preceding amino acid residue; and
X+1 indicates the point of attachment to the following amino acid residue.

Embodiment 625. The IL-15 conjugate of embodiment 624 or 624.1, wherein the position of the structure of Formula (VIII) or (IX), or a mixture of (VIII) and (IX), in the amino acid sequence of the IL-15 conjugate is selected from S19, L26, E47, E54, N78, and S84.

Embodiment 626. The IL-15 conjugate of embodiment 625, wherein the position of the structure of Formula (VIII) or (IX), or a mixture of (VIII) and (IX), in the amino acid sequence of the IL-15 conjugate is selected from L26, E54, and N78.

Embodiment 627. The IL-15 conjugate of embodiment 625, wherein the position of the structure of Formula (VIII) or (IX), or a mixture of (VIII) and (IX), in the amino acid sequence of the IL-15 conjugate is 19.

Embodiment 628. The IL-15 conjugate of embodiment 625, wherein the position of the structure of Formula (VIII) or (IX), or a mixture of (VIII) and (IX), in the amino acid sequence of the IL-15 conjugate is L26.

Embodiment 629. The IL-15 conjugate of embodiment 625, wherein the position of the structure of Formula (VIII) or (IX), or a mixture of (VIII) and (IX), in the amino acid sequence of the IL-15 conjugate is E47.

Embodiment 630. The IL-15 conjugate of embodiment 625, wherein the position of the structure of Formula (VIII) or (IX), or a mixture of (VIII) and (IX), in the amino acid sequence of the IL-15 conjugate is E54.

Embodiment 631. The IL-15 conjugate of embodiment 625, wherein the position of the structure of Formula (VIII) or (IX), or a mixture of (VIII) and (IX), in the amino acid sequence of the IL-15 conjugate is N78.

Embodiment 632. The IL-15 conjugate of embodiment 625, wherein the position of the structure of Formula (VIII) or (IX), or a mixture of (VIII) and (IX), in the amino acid sequence of the IL-15 conjugate is S84.

Embodiment 633. The IL-15 conjugate of any one of embodiments 624 to 632, wherein n is about 75 to about 1000.

Embodiment 634. The IL-15 conjugate of any one of embodiments 624 to 632, wherein n is about 100 to about 1000.

Embodiment 635. The IL-15 conjugate of any one of embodiments 624 to 632, wherein n is about 200 to about 5000.

Embodiment 636. The IL-15 conjugate of any one of embodiments 624 to 632, wherein n is about 500 to about 1000.

Embodiment 637. A method of treating cancer in a subject, comprising administering to a subject in need thereof an effective amount of an IL-15 conjugate according to any one of embodiments 1 to 636.

Embodiment 638. The method of embodiment 637, wherein the cancer is a solid tumor cancer.

Embodiment 639. The method of embodiment 638, wherein the solid tumor cancer is bladder cancer, bone cancer, brain cancer, breast cancer, colorectal cancer, esophageal cancer, eye cancer, head and neck cancer, kidney cancer, lung cancer, melanoma, ovarian cancer, pancreatic cancer, or prostate cancer.

Embodiment 640. The method of embodiment 637, wherein the cancer is a hematologic malignancy.

Embodiment 641. The method of embodiment 640, wherein the hematologic malignancy is chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

Embodiment 642. The method of embodiment 637, wherein the cancer in the subject is selected from renal cell carcinoma (RCC), non-small cell lung cancer (NSCLC), head and neck squamous cell cancer (HNSCC), classical Hodgkin lymphoma (cHL), primary mediastinal large B-cell lymphoma (PMBCL), urothelial carcinoma, microsatellite unstable cancer, microsatellite stable cancer, gastric cancer, cervical cancer, hepatocellular carcinoma (HCC), Merkel cell carcinoma (MCC), melanoma, small cell lung cancer (SCLC), esophageal, glioblastoma, mesothelioma, breast cancer, triple-negative breast cancer, prostate cancer, bladder cancer, ovarian cancer, tumors of moderate to low mutational burden, cutaneous squamous cell carcinoma (CSCC), squamous cell skin cancer (SCSC), tumors of low- to non-expressing PD-L1, tumors disseminated systemically to the liver and CNS beyond their primary anatomic originating site, and diffuse large B-cell lymphoma.

Embodiment 643. The method of embodiment 642, wherein the cancer in the subject is selected from renal cell carcinoma (RCC), non-small cell lung cancer (NSCLC), urothelial carcinoma, and melanoma.

Embodiment 644. The method of any one of embodiments 637 to 643, wherein the IL-15 conjugate is administered to the subject in need thereof once every week, every two weeks, once every three weeks, once every 4 weeks, once every 5 weeks, once every 6 weeks, once every 7 weeks, or once every 8 weeks.

Embodiment 645. The method of any one of embodiments 637 to 644, wherein the IL-15 conjugate is administered to the subject in need thereof once per week, once every two weeks, once every three weeks, or once every four weeks.

Embodiment 646. The method of embodiment 645, wherein the IL-15 conjugate is administered to the subject in need thereof once per week.

Embodiment 647. The method of embodiment 645, wherein the IL-15 conjugate is administered to the subject in need thereof once every two weeks.

Embodiment 648. The method of embodiment 645, wherein the IL-15 conjugate is administered to the subject in need thereof once every three weeks.

Embodiment 649. The method of embodiment 645, wherein the IL-15 conjugate is administered to the subject in need thereof once every four weeks.

Embodiment 650. A method of expanding effector T (Teff) cell, memory T (Tmem) cell, and Natural Killer (NK) cell populations, comprising:
(a) contacting a cell with an IL-15 conjugate of any one of embodiments 1 to 636; and
(b) interacting the IL-15 with IL-15Rβ and IL-15Rγ subunits to form an IL-15/IL-15Rβγ complex, wherein the IL-15 conjugate has a decreased affinity to IL-15Rα subunit, and wherein the IL-15/IL-15Rβγ complex stimulates the expansion of Teff, Tmem, and NK cells.

Embodiment 651. The method of embodiment 650, wherein the cell is a eukaryotic cell.

Embodiment 652. The method of embodiment 650, wherein the cell is a mammalian cell.

Embodiment 653. The method of embodiment 652, wherein the cell is a human cell.

Embodiment 654. A pharmaceutical composition comprising an effective amount of an IL-15 conjugate according to any one of embodiments 1 to 636 and one or more pharmaceutically acceptable excipients.

Embodiment 655. A method of making an IL-15 conjugate, comprising:
reacting an IL-15 polypeptide comprising an unnatural amino acid of formula

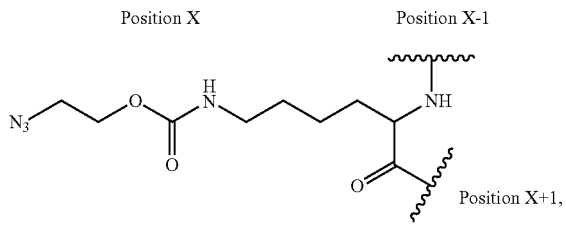 [SMILES: *NC(CCCCNC(=O)OCCN=[N+]=[N-])C(*)=O]

wherein the IL-15 polypeptide comprises the amino acid sequence of SEQ ID NO: 1 or 3 in which at least one amino acid residue in the IL-15 polypeptide is replaced by the unnatural amino acid, Position X−1 indicates the point of attachment to the preceding amino acid residue, Position X+1 indicates the point of attachment to the following amino acid residue, and Position X indicates the position of the amino acid for which the unnatural amino acid substitutes,
with an mPEG-DBCO of formula

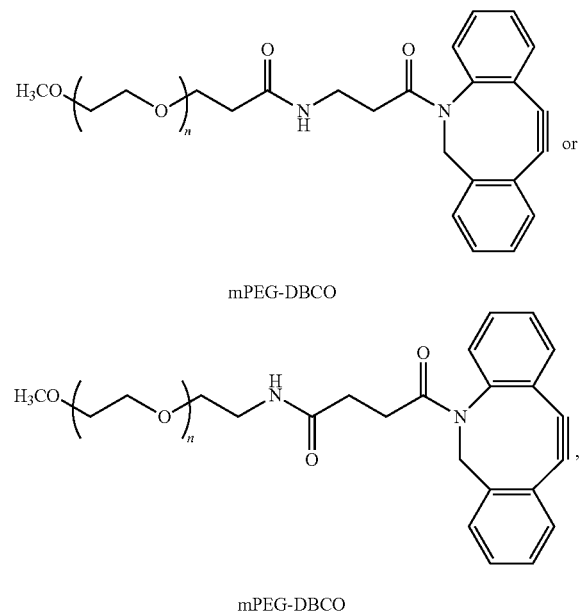

wherein n is such that the mPEG-DBCO comprises a PEG having a molecular weight of about 5 kDa, 10 kDa, 15 kDa, 20 kDa, 25 kDa, 30 kDa, 35 kDa, 40 kDa, 45 kDa, or 50 kDa, thereby producing the IL-15 conjugate.

Embodiment 656. The method of embodiment 655, wherein Position X is S18, L25, E46, E53, N77, or S83, in reference to the amino acid positions within SEQ ID NO: 1.

Embodiment 657. The method of embodiment 655 or 656, wherein the IL-15 polypeptide comprises the amino acid sequence of SEQ ID NO: 1 in which at least one amino acid residue in the IL-15 polypeptide is replaced by the unnatural amino acid.

Embodiment 658. The method of embodiment 655, wherein Position X is S19, L26, E47, E54, N78, or S84 in reference to the amino acid positions within SEQ ID NO: 3.

Embodiment 659. The method of embodiment 655 or 658, wherein the IL-15 polypeptide comprises the amino acid sequence of SEQ ID NO: 3 in which at least one amino acid residue in the IL-15 polypeptide is replaced by the unnatural amino acid.

Embodiment 660. The method of any one of embodiments 655-659, wherein the PEG has a molecular weight of about 30 kDa.

Embodiment 661. The method of any one of embodiments 655-659, wherein the PEG has a molecular weight of about 40 kDa.

Embodiment 662. The method of embodiment 655, wherein the IL-15 conjugate is the IL-15 conjugate of any one of embodiments 1-636.

EXAMPLES

These examples are provided for illustrative purposes only and not to limit the scope of the claims provided herein.

Example 1

Expression of Modified IL-15 Polypeptides

The IL-15 conjugates were expressed as inclusion bodies in *E. coli* using methods disclosed herein wherein expression plasmids encoding the protein with the desired amino acid sequence were prepared that contained (a) an unnatural base pair comprising a first unnatural nucleotide and a second unnatural nucleotide to provide a codon at the desired position at which an unnatural amino acid N6-((2-azidoethoxy)-carbonyl)-L-lysine (AzK) was incorporated and a matching anticodon in a tRNA, (b) a plasmid encoding a tRNA derived from *M. mazei* Pyl and which comprises an unnatural nucleotide to provide a matching anticodon in place of its native sequence, (c) a plasmid encoding a *M. barkeri* derived pyrrolysyl-tRNA synthetase (Mb PylRS), and (d) N6-((2-azidoethoxy)-carbonyl)-L-lysine (AzK). The double-stranded oligonucleotide that encodes the amino acid sequence of the desired IL-15 variant contained a codon AXC at, for example, position 18, 25, 46, 53, 77, or 83 of the sequence that encodes the protein having SEQ ID NO: 1, or at position 19, 26, 47, 54, 78, or 84 of the sequence that encodes the protein having SEQ ID NO: 3, wherein X is an unnatural nucleotide as disclosed herein. In some embodiments, the cell further comprises a plasmid, which may be the protein expression plasmid or another plasmid, that encodes an orthogonal tRNA gene from *M. mazei* that comprises an AXC-matching anticodon GYT in place of its native sequence, wherein Y is an unnatural nucleotide as disclosed herein and that may be the same or different as the unnatural nucleotide in the codon. X and Y were selected from unnatural nucleotides deoxyribo TPT3 (dTPT3), deoxyribo NaM (dNaM), deoxyribo CNMO (dCNMO), ribo TPT3 (TPT3), ribo NaM (NaM), ribo CNMO (CNMO), and the triphosphates of each (dTPT3TP, dNaMTP, dCNMOTP, TPT3TP, NaMTP, and CNMOTP) as disclosed herein (see also, for example, Feldman et al., *Acc. Chem. Res.* 2018, 51, pp. 394 to 403; Zhang et al., *Nature* 2017, 551 (7682), pp. 644 to 647); and Zhang et al., *PNAS* 2017, 114(6), pp. 1317 to 1322).

The modified IL-15 polypeptide was grown at 37° C., 250 rpm, and 5 hours induction. The media component was as illustrated in Table 2.

TABLE 2

| Name | Composition |
|---|---|
| Growth Media | 2xYT |
| For 1 L: 2x 2xYT pellets, | 30.8 mM Potassium phosphate dibasic |
| Potassium phosphate | 19.2 mM Potassium phosphate |
| monobasic, Potassium | monobasic |
| phosphate dibasic | 100 ug/mL Ampicillin |
| Autoclave on liquid cycle to | 5 ug/mL Chloramphenicol |
| sterilize | 50 ug/mL Zeocin |
|  | 37.5 uM dTPT3TP |
|  | 150 uM dNaMTP |

When expression culture reaches $OD_{600}$ 0.85-0.9, the culture was pre-loaded with NaM triphosphate (NaMTP) (at a final concentration of 250 uM), TPT3 triphosphate (TPT3TP) (at a final concentration of 25 uM), and Azido-lysine (at a final concentration of 15 mM). About 15-20 minutes after pre-loading with ribonucleotides and amino acid, IPTG was add and the protein was expressed for about 5 hours.

Inclusion Body

Upon cell pellet collection, the pellets were further processed for inclusion bodies. In brief, a 1 L cell pellet was resuspended in 10 mL lysis buffer (20 mM Tris-HCl, pH 8.0; 150 mM NaCl; 1 mM DTT; and Protease inhibitor (1 pellet/50 mL)). After resuspension, the volume of 1 L pellet was increased to 45 mL with lysis buffer and run through a microfluidizer for 2x. The sample was then transferred to a 50 mL centrifuge tube and centrifuge at 16 k rpm for 20 minutes at 4° C. Next, the pellet was resuspended pellet in 5 mL lysis buffer and the total volume was increased to 30 mL with lysis buffer. About 10% Triton X-100 was added to a final concentration of 0.5%. Then the solution was centrifuged at 16 k rpm for 20 minutes at 4° C., and the pellet was then collected and washed 3x with 30 mL lysis buffer. A 5 mL syringe with needles was used to fully resuspend with each wash. After a final spin, discard supernatant and the pellet was snap frozen to store at −80° C.

Solubilization and Refolding

About 5 mL solubilization buffer was added to the inclusion body pellet. After resuspension, the volume was increased to 30 mL in solubilization buffer. Next, the sample was incubated at 4° C. for 30-60 minutes. Then, the sample was transferred to 2x50 mL centrifuge tube (15 mL/tube) and 15 mL dilution buffer was added to each tube. The sample was then dialyzed subsequently in buffer A1 overnight at 4° C., followed by A2 dialysis buffer, A3 dialysis buffer, A4 dialysis buffer, and A5 dialysis buffer. After dialysis, the sample was centrifuged at 4000 rpm for 30 minutes at 4° C. and concentrated to about 5 mL.

Table 3 illustrates the solubilization buffers.

| Name | Composition |
|---|---|
| Solubilization Buffer | 6M Guanidine-HCL |
|  | 20 mM Tris-HCl, pH 8.0 |
|  | 1 mM DTT |
|  | 20 mM Imidazole |

-continued

| Name | Composition |
| --- | --- |
| Dilution Buffer | 3M Guanidine-HCL<br>20 mM Tris-HCl, pH 8.0<br>1 mM DTT<br>20 mM Imidazole |
| A1 Dialysis Buffer | 2M Guanidine-HCl<br>20 mM Tris-HCl, pH 8.5<br>150 mM NaCl<br>1 mM GSH (reduced glutathione)<br>0.1 mM GSSG (oxidized glutathione)<br>0.4M L-Arginine |
| A2 Dialysis Buffer | 0.75M Guanidine-HCl<br>20 mM Tris-HCl, pH 8.5<br>150 mM NaCl<br>1 mM GSH (reduced glutathione)<br>0.1 mM GSSG (oxidized glutathione)<br>0.4M L-Arginine |
| A3 Dialysis Buffer | 20 mM Tris-HCl, pH 8.5<br>150 mM NaCl<br>1 mM GSH (reduced glutathione)<br>0.1 mM GSSG (oxidized glutathione)<br>0.1M L-Arginine |
| A4 Dialysis Buffer | 20 mM Tris-HCl, pH 8.5<br>150 mM NaCl |
| A5 Dialysis Buffer | 20 mM Tris-HCl, pH 7.5<br>12.5 mM NaCl |

Purification

The sample was purified first on a GEH HiLoad 16/600 Superdex 200 µg gel filtration column with 1×PBS elution buffer, followed by a GE HiTrapQ anion exchange column to remove free PEG, and then a reverse phase chromatography with a gradient elution of 30%-70 elution buffer in 20 column volumes.

Table 4 illustrates the buffers used for the anion exchange chromatography. Table 5 illustrates the buffers used for the reverse phase chromatography.

TABLE 4

| Name | Composition |
| --- | --- |
| Running buffer | 20 mM Tris-HCl, pH 7.5 |
| Elution buffer | 20 mM Tris-HCl, pH 7.5<br>500 mM NaCl |

TABLE 5

| Name | Composition |
| --- | --- |
| Running buffer | 4.5% Acetonitrile<br>0.043% TFA |
| Elution buffer | 90% Acetonitrile<br>0.028% TFA |

Conjugation

After purification, the AzK-containing IL-15 product was site-specifically pegylated using DBCO-mediated copper-free click chemistry to attach stable, covalent mPEG moieties to the AzK (Scheme 1 and 2).

Schemes 1 and 2. Exemplary synthesis of AzK_PEG interleukin variants (wherein n indicates the number of repeating PEG units). The reaction of the AzK moiety with the DBCO alkynyl moiety may afford one regioisomeric product or a mixture of regioisomeric products.

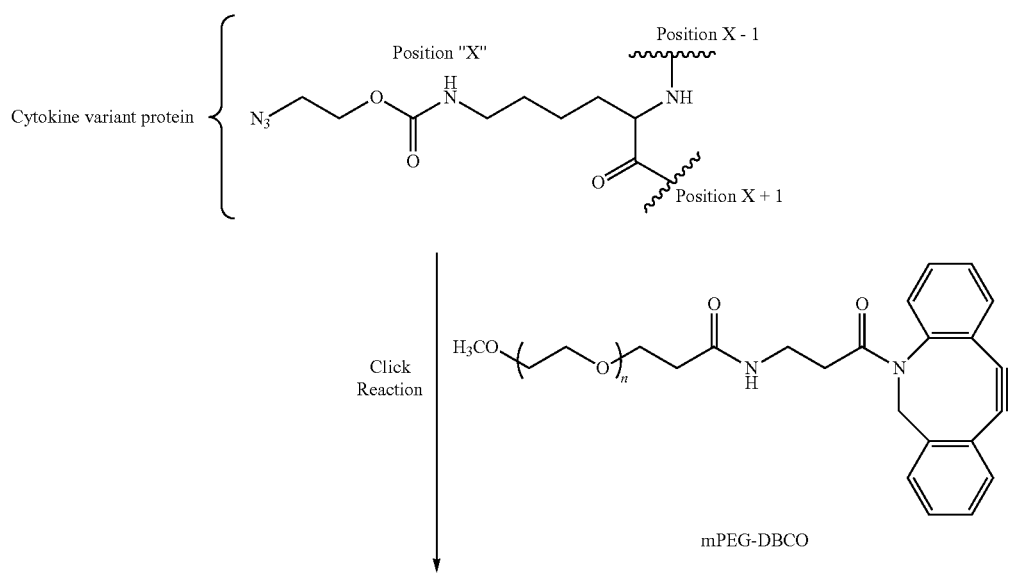

Scheme 1

-continued

Cytokine Azk_PEG variant proteins

Scheme 2 mPEG-DBCO

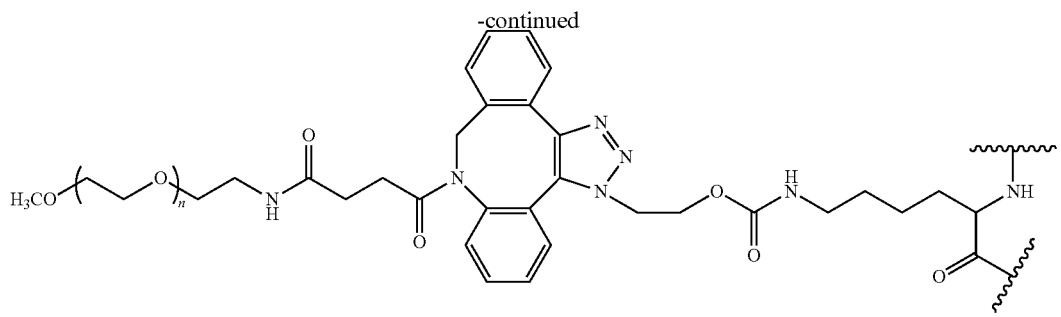

Cytokine Azk_L1_PEG variant proteins

Compounds IL-15_L26[AzK_PEG30], IL-15_E54[AzK_PEG30], and IL-15_N78[AzK_PEG30] were used in Examples 2 and 3, below.

Compound IL-15_L26[AzK_PEG30] is the compound having SEQ ID NO: 71 in which [AzK_PEG30] is the structure of Formula (II), Formula (III), or a mixture of Formula (II) and (III), wherein W is linear, methoxy PEG group having an average molecular weight of 30 kDa. The compound was prepared by first preparing a protein having SEQ ID NO: 3 in which the leucine residue at position 26 (L26) (wherein position 1 is the N-terminal methionine residue) was replaced by N6-((2-azidoethoxy)-carbonyl)-L-lysine (AzK) to provide a compound having SEQ ID NO: 59. The AzK-containing protein was then allowed to react under click chemistry conditions with DBCO comprising a methoxy, linear PEG group having an average molecular weight of 30 kDa to afford a product having SEQ ID NO: 71 comprising Formula (II), Formula (III), or a mixture of Formula (II) and (III), wherein W is a methoxy, linear PEG group having an average molecular weight of 30 kDa. The compound can also be defined as comprising the amino acid sequence of SEQ ID NO: 3 in which the leucine residue at position 26 (L26) is replaced by the structure of Formula (VI) or (VII), or a mixture of (VI) and (VII), and wherein n is an integer such that the PEG group has a molecular weight of about 30 kDa. The compound can also be defined as comprising the amino acid sequence of SEQ ID NO: 3 in which the leucine residue at position 26 (L26) is replaced by the structure of Formula (X) or (XI), or a mixture of (X) and (XI), and wherein n is an integer such that the PEG group has a molecular weight of about 30 kDa.

Compound IL-15_E54[AzK_PEG30] is the compound having SEQ ID NO: 73 in which [AzK_PEG30] is the structure of Formula (II), Formula (III), or a mixture of Formula (II) and (III), wherein W is linear, methoxy PEG group having an average molecular weight of 30 kDa. The compound was prepared by first preparing a protein having SEQ ID NO: 3 in which the glutamic acid residue at position 54 (E54) (wherein position 1 is the N-terminal methionine residue) was replaced by N6-((2-azidoethoxy)-carbonyl)-L-lysine (AzK) to provide a compound having SEQ ID NO: 61. The AzK-containing protein was then allowed to react under click chemistry conditions with DBCO comprising a methoxy, linear PEG group having an average molecular weight of 30 kDa to afford a product having SEQ ID NO: 73 comprising Formula (II), Formula (III), or a mixture of Formula (II) and (III), wherein W is a methoxy, linear PEG group having an average molecular weight of 30 kDa. The compound can also be defined as comprising the amino acid sequence of SEQ ID NO: 3 in which the glutamic acid residue at position 54 (E54) is replaced by the structure of Formula (VI) or (VII), or a mixture of (VI) and (VII), and wherein n is an integer such that the PEG group has a molecular weight of about 30 kDa. The compound can also be defined as comprising the amino acid sequence of SEQ ID NO: 3 in which the glutamic acid at position 54 (E54) is replaced by the structure of Formula (X) or (XI), or a mixture of (X) and (XI), and wherein n is an integer such that the PEG group has a molecular weight of about 30 kDa.

Compound IL-15_N78[AzK_PEG30] is the compound having SEQ ID NO: 74 in which [AzK_PEG30] is the structure of Formula (II), Formula (III), or a mixture of Formula (II) and (III), wherein W is linear, methoxy PEG group having an average molecular weight of 30 kDa. The compound was prepared by first preparing a protein having SEQ ID NO: 3 in which the asparagine residue at position 78 (N78) (wherein position 1 is the N-terminal methionine residue) was replaced by N6-((2-azidoethoxy)-carbonyl)-L-lysine (AzK) to provide a compound having SEQ ID NO: 62. The AzK-containing protein was then allowed to react under click chemistry conditions with DBCO comprising a methoxy, linear PEG group having an average molecular weight of 30 kDa to afford a product having SEQ ID NO: 74 comprising Formula (II), Formula (III), or a mixture of Formula (II) and (III), wherein W is a methoxy, linear PEG group having an average molecular weight of 30 kDa. The compound can also be defined as comprising the amino acid sequence of SEQ ID NO: 3 in which the asparagine residue at position 78 (N78) is replaced by the structure of Formula (VI) or (VII), or a mixture of (VI) and (VII), and wherein n is an integer such that the PEG group has a molecular weight of about 30 kDa. The compound can also be defined as comprising the amino acid sequence of SEQ ID NO: 3 in which the asparagine residue at position 78 (N78) is replaced by the structure of Formula (X) or (XI), or a mixture of (X) and (XI), and wherein n is an integer such that the PEG group has a molecular weight of about 30 kDa.

Example 2

Ex-Vivo Immune Response Profiling of IL-15 Conjugates in Non-Human Primate (NHP) Whole Blood Concentration-response profiling of STAT5 phosphorylation in cynomolgus monkey whole blood with compounds IL-15_L26[AzK_PEG30], IL-15_E54[AzK_PEG30], and IL-15_N78[AzK_PEG30] were performed using multicolor flow cytometry (PrimityBio LLC, Fremont, CA) to determine differences in activation of primary immune cell subpopulations upon stimulation with each of the conjugates. Fresh monkey whole blood from 2 donors was treated with native IL-15, IL-15_L26[AzK_PEG30], IL-15_E54[AzK_PEG30], or IL-15_N78[AzK_PEG30] in 5-fold dilution series. The top concentration of IL-15_L26 [AzK_PEG30] was 100 µg/mL, while the top concentrations of IL-15_E54[AzK_PEG30] and IL-15_N78[AzK_PEG30] were each 30 µg/mL. Treated cell populations were incubated at 37° C. for 45 minutes before addition of BD Lyse/Fix Buffer and staining with the fluorescent antibody panel shown in Table 6. Multi-color flow cytometry was used to detect and quantify pSTAT5 activation in different CD8+T and NK cell subsets.

TABLE 6

Staining panel for flow cytometry study of cynomolgus monkey whole blood

| Cell population | Marker |
| --- | --- |
| Pan-T | CD3 |
| CD4 | CD4 |
| CD8 | CD8 |
| Treg | FoxP3 |
| Treg (activation) | CD25 |
| Memory/naive | CD45RA |
| NK | CD7 |
| NK | CD16 |
| Signaling | pSTAT5 |

Figure 1B:
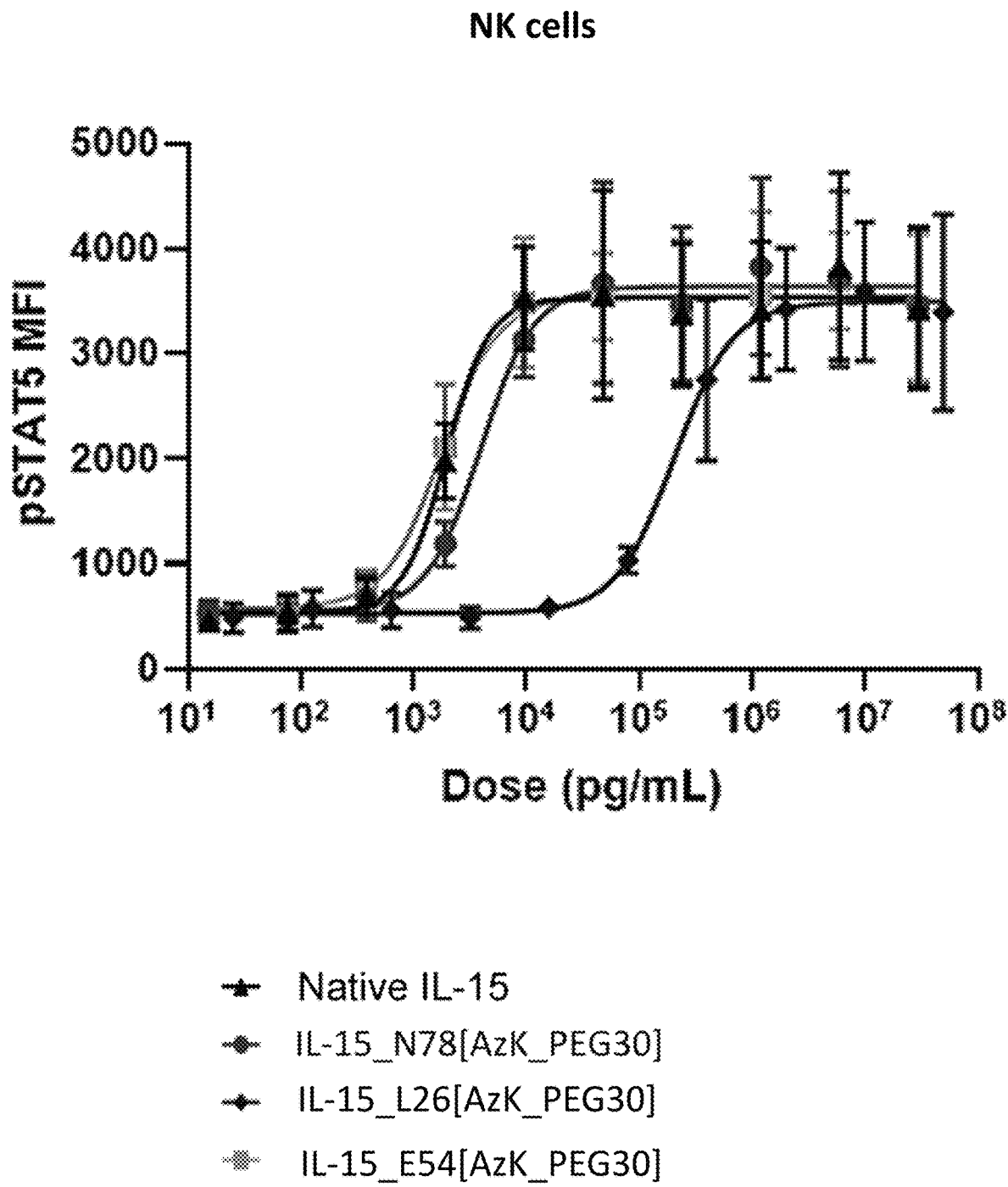

In NK and effector T cell (CD3+CD8+) populations, IL-15_N78[AzK_PEG30] and IL-15_E54[AzK_PEG30] retained potency relative to native IL-15, with $EC_{50}$ values for pSTAT5 production within 2 to 3-fold of the native cytokine. In contrast, the $EC_{50}$ values for pSTAT5 induction for IL-15_L26[AzK_PEG30] in CD8+T and NK cell populations was reduced by ~164 and ~115-fold, respectively, compared to native IL-15. The substantial increase in $EC_{50}$ for IL-15_L26[AzK_PEG30] indicates that pegylation at this position reduces agonism of IL-15 receptors. $EC_{50}$ data for the compounds is shown in Table 7 and the plots are shown in FIGS. 1A and 1B.

TABLE 7

Dose response for STAT5 signaling ($EC_{50}$) in cynomolgus monkey whole blood treated with native IL-15 or IL-15 conjugates

| Compounds | CD8+ T cells $EC_{50}$ (ng/ml) | NK cells $EC_{50}$ (ng/ml) |
| --- | --- | --- |
| Native IL-15 | 6.3 | 1.9 |
| IL-15_N78[AzK_PEG30] | 15.7 | 3.9 |
| IL-15_E54[AzK_PEG30] | 9.2 | 1.8 |
| IL-15_L26[AzK_PEG30] | 1,036.7 | 218.6 |

Ex-Vivo Immune Response Profiling of IL-15 PEG Conjugates in Mouse Splenocytes

Concentration-response profiling of STAT5 phosphorylation in C57BL6 mouse splenocytes was performed using multi-color flow cytometry to determine differences in $EC_{50}$ upon stimulation with compounds IL-15_L26 [AzK_PEG30], IL-15_E54[AzK_PEG30], and IL-15_N78 [AzK_PEG30]. Mouse splenocytes were processed following a standard method. Briefly, spleens from C57BL6 mice were sliced into small pieces and pressed through strainer and cells were washed through the strainer with PBS. After centrifugation, cells were recovered in the pellet. Red blood cells (RBC) were lysed using RBC lysis buffer (Biolegend 420301) and remaining cells were recovered after passing through a strainer. Following centrifugation, cells were washed once and resuspended in complete splenocyte RPMI medium (RPMI (Gibco Cat3 22-400-089), 10% FBS, 1% P/S). Freshly prepared splenocytes were treated for 45 min at 37° C. with native IL-15, IL-15_L26[AzK_PEG30], IL-15_E54[AzK_PEG30], or IL-15_N78[AzK_PEG30] in 5-fold dilution series. The top starting concentration for the IL-15_L26[AzK_PEG30] compound was 200 µg/mL. The top starting concentration of the IL-15_E54[AzK_PEG30] and IL-5_N78[AzK_PEG30] compounds were each 20 µg/mL. Cells were then fixed with Cytofix (BD 554655) and stained with the fluorescent antibody panel shown in Table 8.

TABLE 8

Staining panel for flow cytometry study of mouse splenocytes

| Cell population | Marker |
| --- | --- |
| Pan-T | CD3 |
| CD4 T cell | CD4 |
| CD8 T cell | CD8 |
| Treg | FoxP3 |
| Treg (activation) | CD25 |
| Naïve T cell | CD62L |
| Effector/memory cell | CD44 |
| NK | CD49b |
| NK | NKp46 |
| Signaling | pSTAT5 |

In CD8+ T cell populations, native IL-15 and the IL-15_N78[AzK_PEG30] compound showed a biphasic dose-response relationship consistent with heterogeneous levels of IL-15Rα expression in unstimulated cells (Ring A M et al. *Nature Immunol* 2012). The same profile was observed with this compound for naïve and effector/memory CD8+ T cells. The IL-15_L26[AzK_PEG30] and IL-15_E54 [AzK_PEG30] compounds are not-alpha variants that have been demonstrated to possess reduced in vitro binding to IL15Rα in surface plasmon resonance studies. The compounds demonstrated monophasic dose-response curves consistent with a lack of engagement of IL-15Rα. Unstimulated NK cells are known to possess very low levels of IL-15Rα, and so the dose-response curves for the compounds reflect different engagement of IL-15Rβ/IL-2Rβ.

Example 3

In Vivo Study of Exemplary IL-15 Conjugate

Compound IL-15_N77[AzK_L1_PEG30](SEQ ID NO: 44) was prepared and tested in an in vivo study in C57BL/6 mice. It was understood the sample of the compound tested may have also comprised the compound comprising an N-terminal methionine residue ((IL-15_N78 [AzK_L1_PEG30] (SEQ ID NO: 92)), which was not expected to affect the results of the study. The mice were divided into 5 groups as shown in Table 9: (a) Group 1 was administered vehicle; (b) Group 2 was administered a single intravenous (IV) dose of IL-15_N77[AzK_L1_PEG30] at a dose of 0.1 mg/kg; (c) Group 3 was administered a single IV dose of IL-15_N77[AzK_L1_PEG30] at a dose of 0.3 mg/kg; (d) Group 4 was administered a single IV dose of IL-15_N77[AzK_L1_PEG30] at a dose of 1 mg/kg; and (e) Group 5 received neither vehicle nor IL-5_N77 [AzK_L1_PEG30].

TABLE 9

| Group | Treatment | Dose level (mg/kg) |
| --- | --- | --- |
| 1 | Vehicle | 0 |
| 2 | IL-15_N77[AzK_L1_PEG30] | 0.1 |

TABLE 9-continued

| Group | Treatment | Dose level (mg/kg) |
|---|---|---|
| 3 | IL-15_N77[AzK_L1_PEG30] | 0.3 |
| 4 | IL-15_N77[AzK_L1_PEG30] | 1.0 |
| 5 | Pre-dose | Not applicable |

Mice whole blood was drawn at the following time points post-dosing: 8 min, 15 min, 30 min, 1 hour, 2 hours, 4 hours, 8 hours, 24 hours, 48 hours, 72 hours, 120 hours, 168 hours, 240 hours, and 288 hours. The blood samples were placed into a K3-EDTA tube, and about 100 µL was placed into a microfuge tube, placed on ice, and processed for plasma within 1 hour. Concentrations of the test compound in the samples derived from plasma were determined using an ELISA assay. Remaining blood was inverted several times and lysed and fixed for staining of pharmacodynamic (PD) biomarkers. PD readouts included intracellular pSTAT5 monitoring, and phenotyping of NK, CD8+T and Treg cells for all time points.

Figure 2:
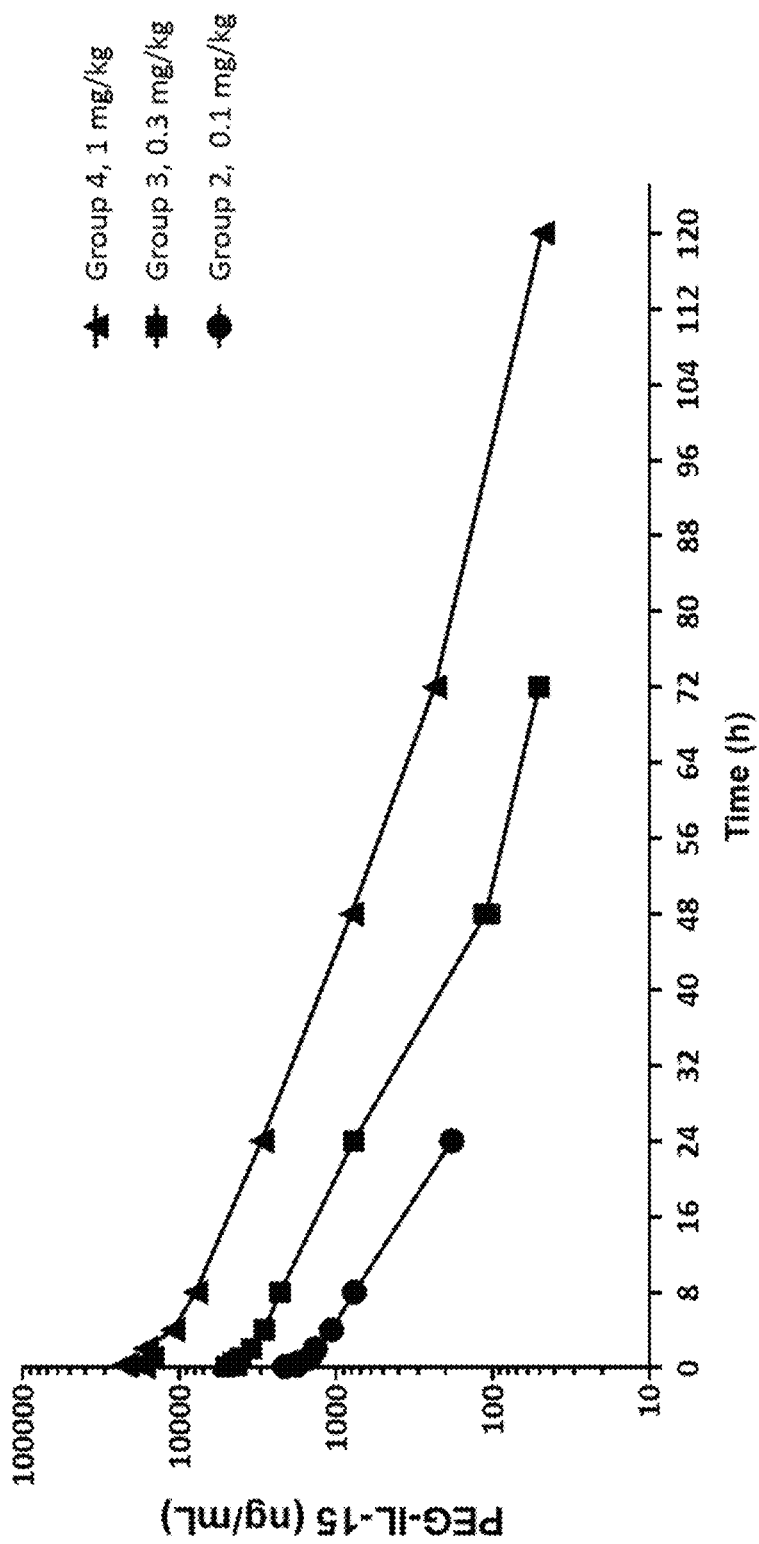
FIG. 2 illustrates the plasma concentration versus time curves for the mice in Groups 2, 3 and 4 administered test compound IL-15_N77[AzK_L1_PEG30] in Example 3 (Group 4 (1 mg/kg dose)=closed triangles; Group 3 (0.3 mg/kg dose)=closed squares; Group 2 (0.1 mg/kg dose) =closed circles).

The group plasma concentration of test compound versus time data were analyzed with noncompartmental methods using an IV bolus administration model. The reported half-life ($t_{1/2}$) in the literature for native (wild-type) IL-15 has been reported as about 0.64 h in mice (Cytokine. 2011 December; 56(3): 804-810. doi: 10.1016j.cyto.2011.09.028). The estimated half-life for test compound IL-15_N77[AzK_L1_PEG30] was between 7.71 hours to 14.6 hours depending on the dose administered to the mice in the respective groups. The clearance (C1_obs) of for test compound IL-15_N77[AzK_L1_PEG30] ranged from 5.34 mL/hour/kg to 3.97 mL/hour/kg and the volume of distribution (Vz_obs) ranged 58.8 mL/kg to 84.2 mL/kg. The plasma concentration versus time curves for the mice in Groups 2, 3 and 4 are shown in FIG. 2 (Group 4 (1 mg/kg dose)=closed triangles; Group 3 (0.3 mg/kg dose)=closed squares; and Group 2 (0.1 mg/kg dose)=closed circles). The mean pharmacokinetic (PK) parameters for the mice in Groups 2, 3, and 4 as shown in Table 10.

TABLE 10

| Parameter | Unit | Group 2 | Group 3 Mean Value | Group 4 |
|---|---|---|---|---|
| AUC last | h*ng/mL | 16955 | 62024 | 251431 |
| AUC last_D | h*ng/mL/mg | 169548 | 206745 | 251431 |
| Cl_obs | mL/h/kg | 5.34 | 4.79 | 3.97 |
| Cmax | ng/mL | 2173 | 5188 | 23100 |
| Cmax_D | kg*ng/mL/mg | 21727 | 17292 | 23100 |
| Dose | mg/kg | 0.1 | 0.3 | 1.0 |
| Half-life ($t_{1/2}$) | h | 7.71 | 10.9 | 14.6 |
| Tmax | h | 0.16 | 0.35 | 0.31 |
| Vz_obs | mL/kg | 58.8 | 75.7 | 84.2 |

STAT5 phosphorylation and induction of cell proliferation were measured in each of Groups 2, 3 and 4. The results demonstrated that a single IV dose of test compound IL-15_N77[AzK_L1_PEG30] in C57BL/6 mice induces STAT5 phosphorylation in NK, CD8+ and Treg cells, but upregulation of Ki67 is limited to NK and CD8+ T cells (single IV dose 0.1, 0.3 and 1 mg/kg).

Figure 3:
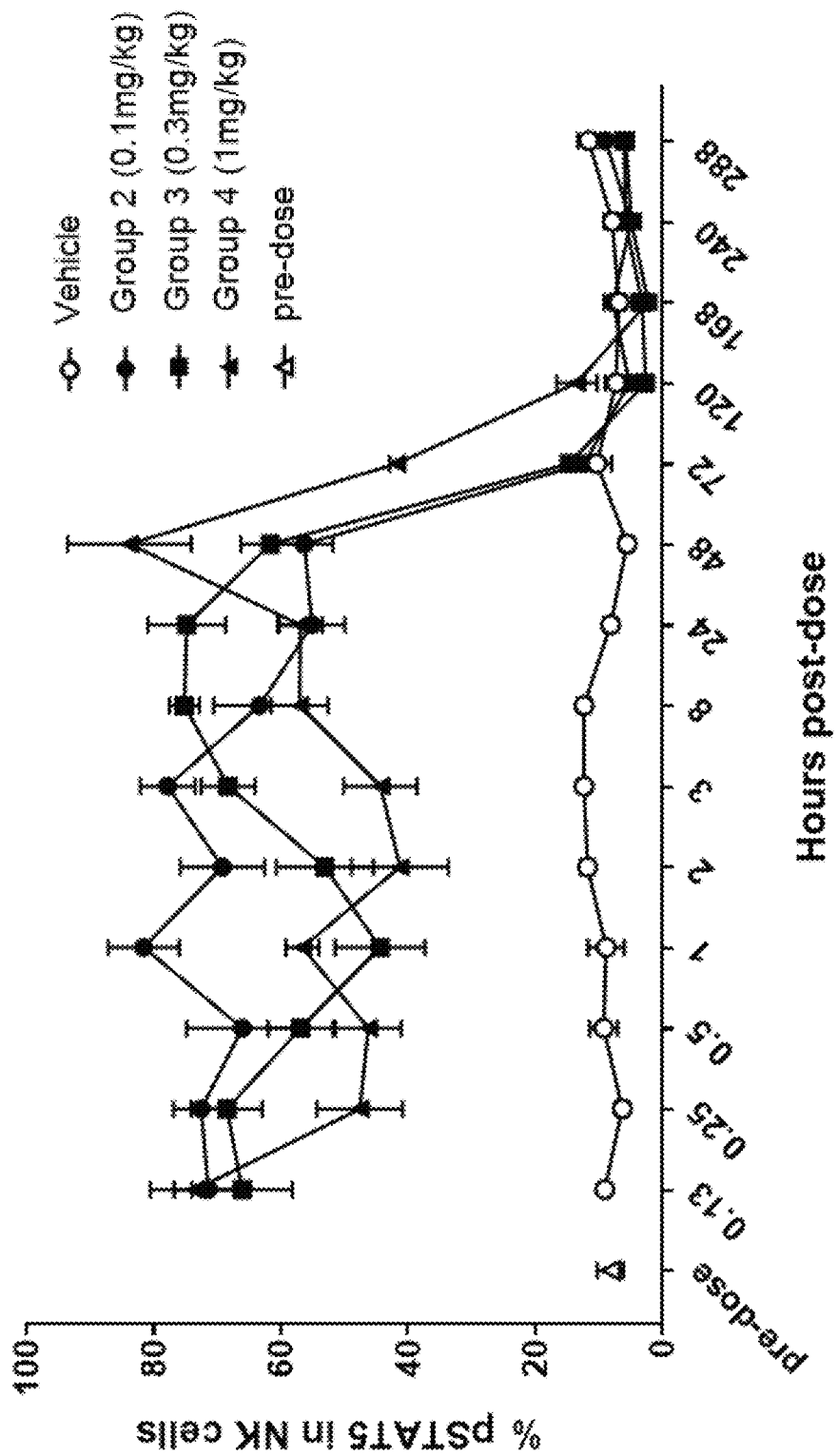
FIG. 3 illustrates % pSTAT5 in the NK cell population in mice after administration of test compound IL-15_N77 [AzK_L1_PEG30] according to Example 3 (Group 1 (vehicle=open circles); Group 4 (1 mg/kg dose)=closed triangles; Group 3 (0.3 mg/kg dose)=closed squares; Group 2 (0.1 mg/kg dose)=closed circles).
Figure 4:
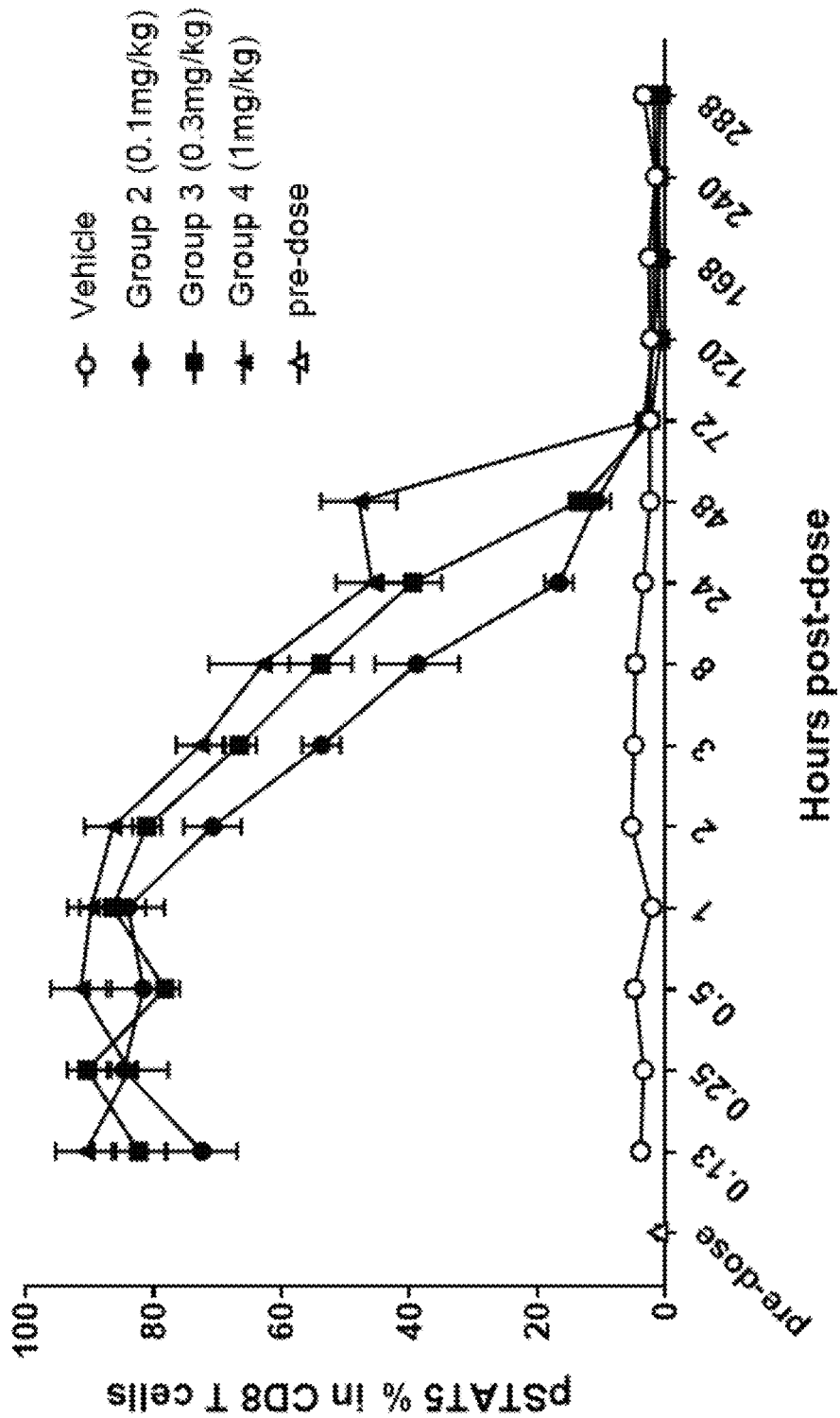
FIG. 4 illustrates % pSTAT5 in the CD8 T-cell population in mice after administration of test compound IL-15_N77 [AzK_L1_PEG30] according to Example 3 (Group 1 (vehicle)=open circles); Group 4 (1 mg/kg dose)=closed triangles; Group 3 (0.3 mg/kg dose)=closed squares; Group 2 (0.1 mg/kg dose)=closed circles).
Figure 5:
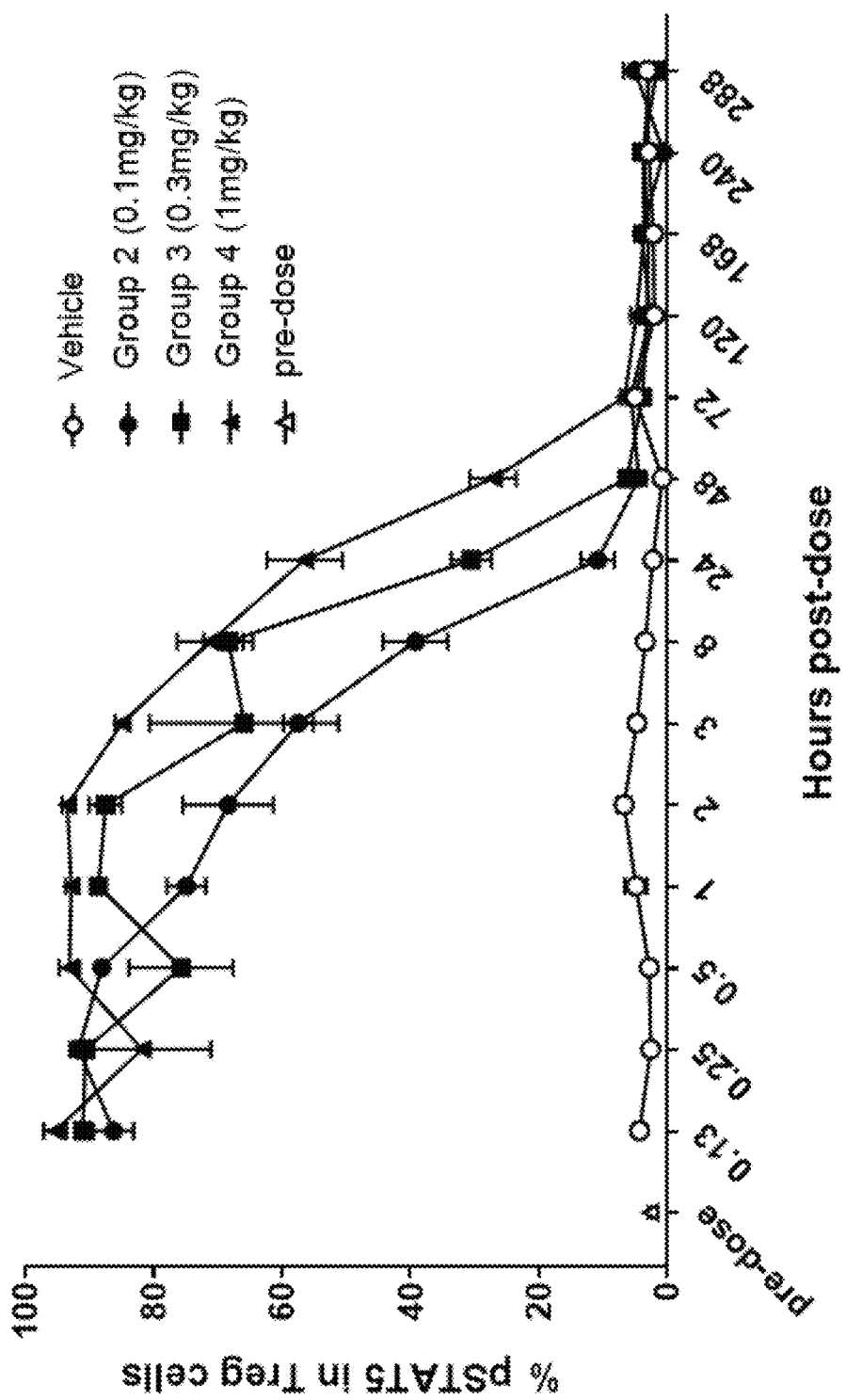
FIG. 5 illustrates % pSTAT5 in Treg cell populations in mice after administration of test compound IL-15_N77 [AzK_L1_PEG30] according to Example 3 (Group 1 (vehicle)=open circles; Group 4 (1 mg/kg dose)=closed triangles; Group 3 (0.3 mg/kg dose)=closed squares; Group 2 (0.1 mg/kg dose)=closed circles).

FIGS. 3 to 5 illustrate % pSTAT5 in different peripheral blood cell populations: vehicle=open circles; Group 2 (0.1 mg/kg dose)=closed circles; Group 3 (0.3 mg/kg dose)=closed squares; Group 4 (1 mg/kg) dose=closed triangles; and pre-dose=open triangles. FIG. 3 shows % pSTAT5 in the NK cell population. FIG. 4 shows % pSTAT5 in the CD8 T-cell population. FIG. 5 shows % pSTAT5 in Treg cell populations.

Figure 6:
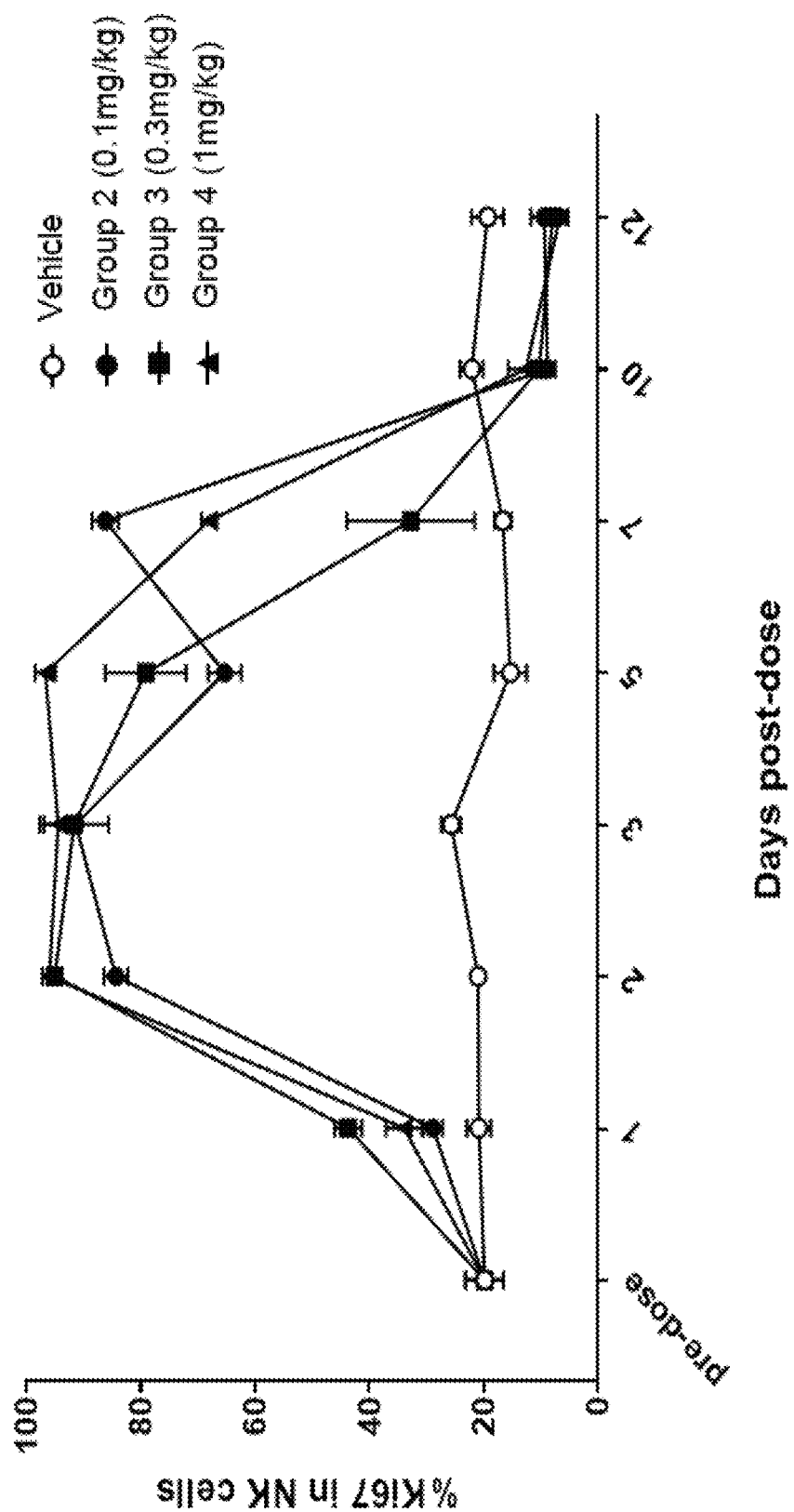
FIG. 6 illustrates % Ki67 in NK cell population in mice after administration of test compound IL-15_N77 [AzK_L1_PEG30] according to Example 3 (Group 1 (vehicle)=open circles; Group 4 (1 mg/kg dose)=closed triangles; Group 3 (0.3 mg/kg dose)=closed squares; Group 2 (0.1 mg/kg dose)=closed circles).
Figure 7:
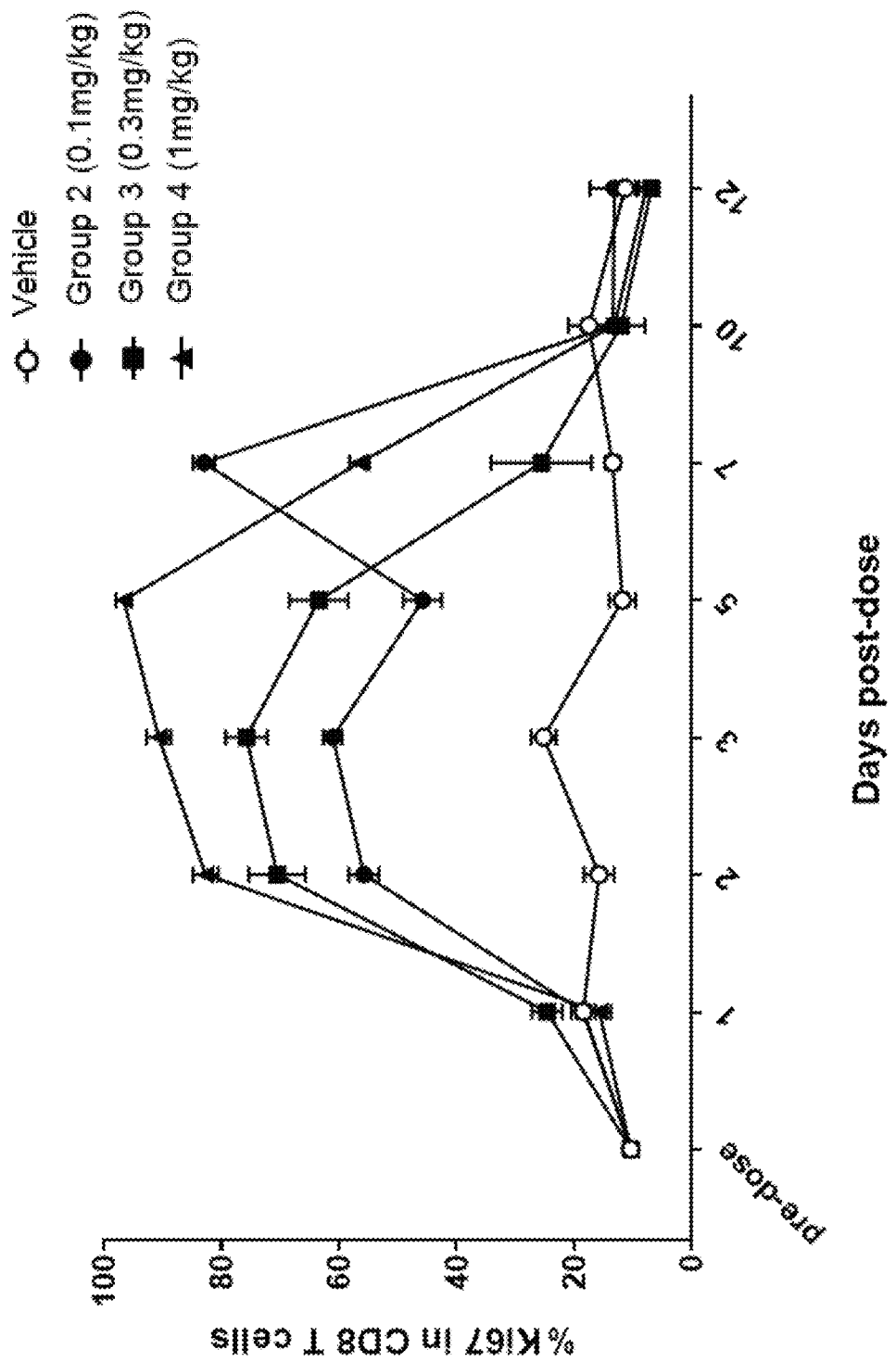
FIG. 7 illustrates % Ki67 in CD8 T cell population in mice after administration of test compound IL-15_N77 [AzK_L1_PEG30] according to Example 3 (Group 1 (vehicle)=open circles; Group 4 (1 mg/kg dose)=closed triangles; Group 3 (0.3 mg/kg dose)=closed squares; Group 2 (0.1 mg/kg dose)=closed circles).
Figure 8:
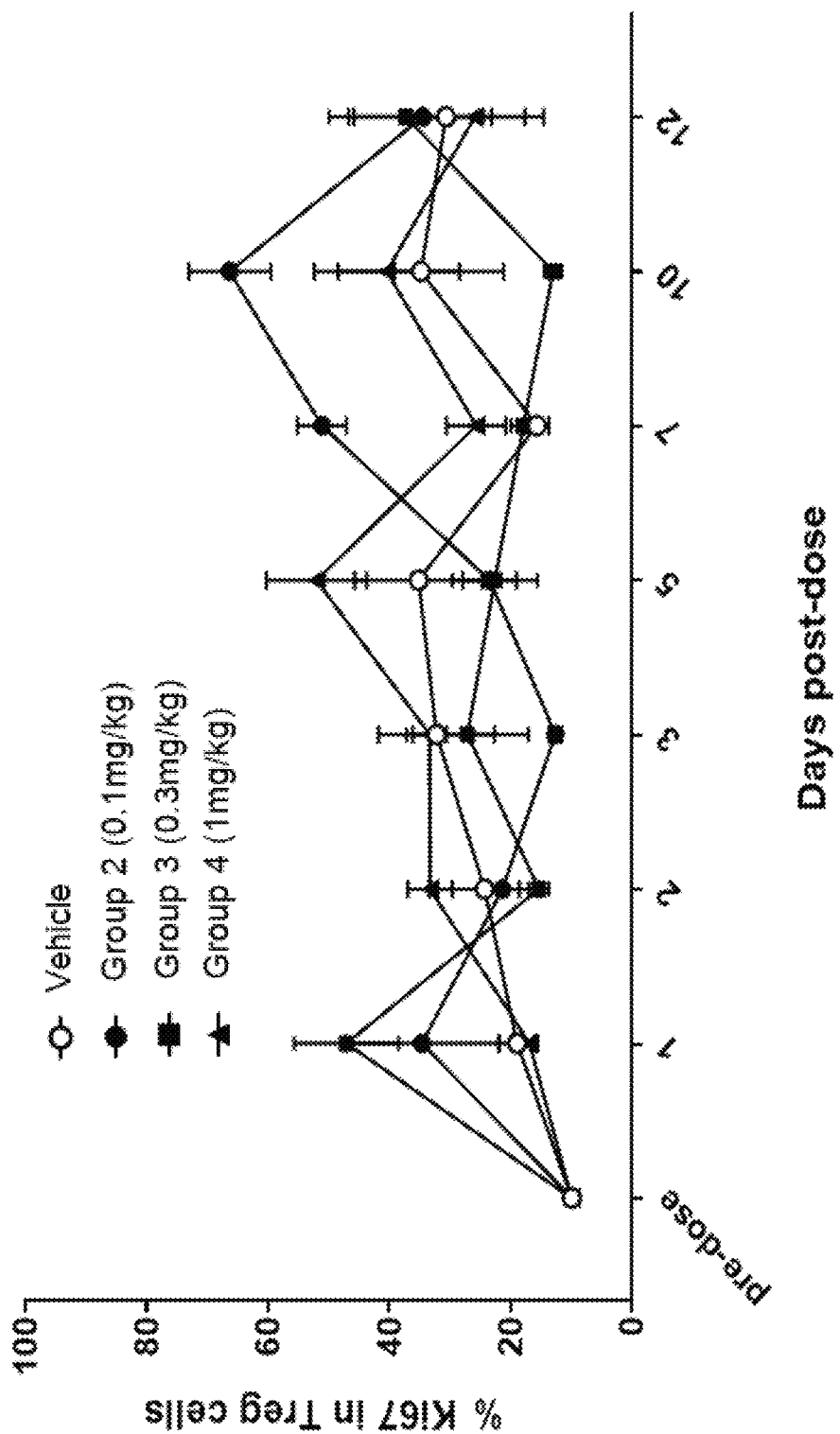
FIG. 8 illustrates % Ki67 in Treg cell population in mice after administration of test compound IL-15_N77 [AzK_L1_PEG30] according to Example 3 (Group 1 (vehicle)=open circles; Group 4 (1 mg/kg dose)=closed triangles; Group 3 (0.3 mg/kg dose)=closed squares; Group 2 (0.1 mg/kg dose)=closed circles).

Ki67 was measured in different peripheral blood cell populations in each of Groups 1, 2, 3, and 4 and are illustrated in FIGS. 6 to 8 (vehicle=open circles; Group 2 (0.1 mg/kg dose)=closed circles; Group 3 (0.3 mg/kg dose)=closed squares; and Group 4 (1 mg/kg dose)=closed triangles). FIG. 6 illustrates % Ki67 in NK cell population. FIG. 7 illustrates % K67 in CD8 T cells. FIG. 8 illustrates % K67 in Treg cell population. The results showed increased expression of the early proliferation molecular marker Ki67 in CD8+T, and NK cells but not Treg cells.

Figure 9:
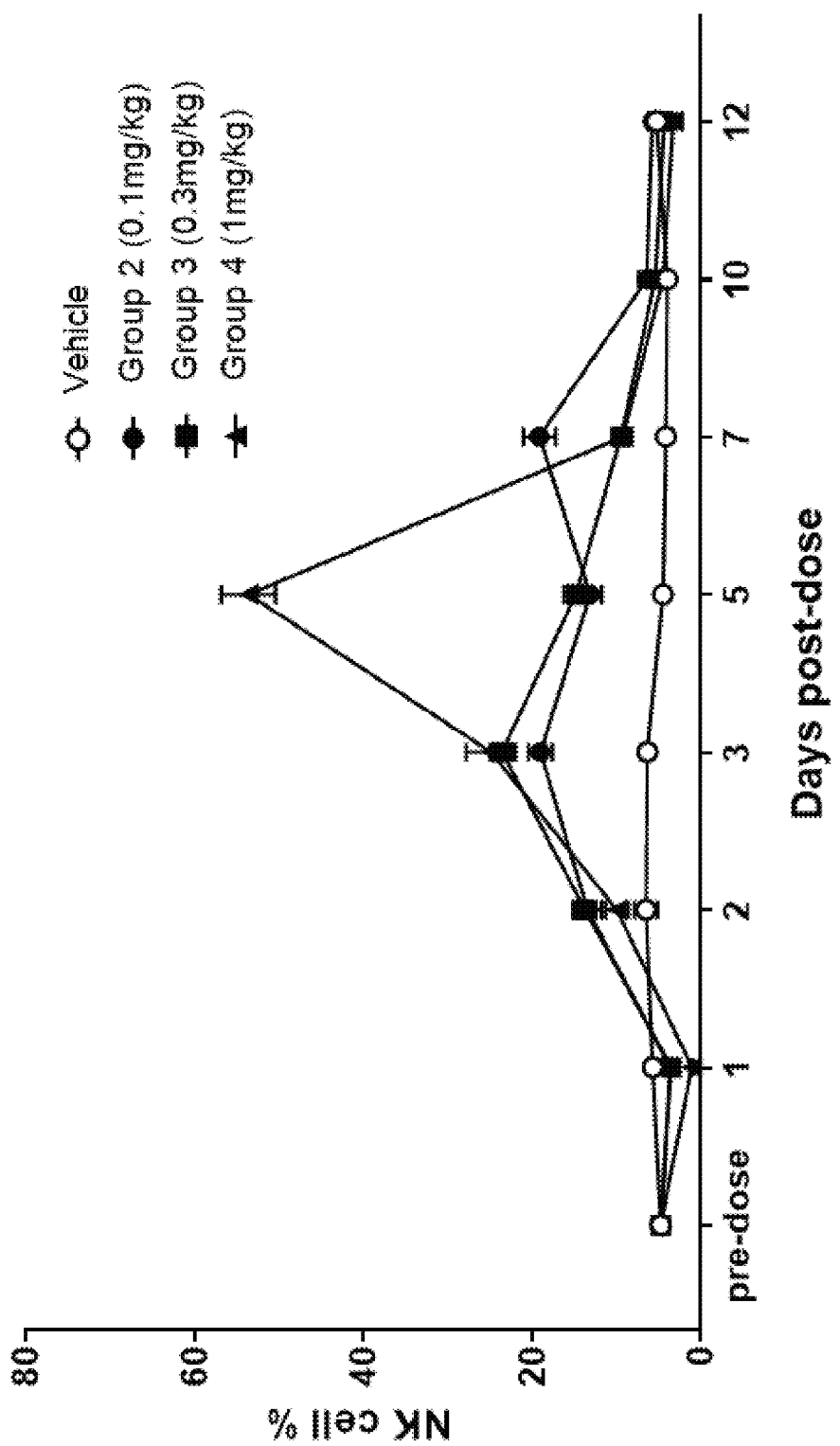
FIG. 9 illustrates % NK cell expansion versus days post-dose in mice after administration of test compound IL-15_N77[AzK_L1_PEG30] according to Example 3 (Group 1 (vehicle)=open circles; Group 4 (1 mg/kg dose)=closed triangles; Group 3 (0.3 mg/kg dose)=closed squares; Group 2 (0.1 mg/kg dose)=closed circles).
Figure 10:
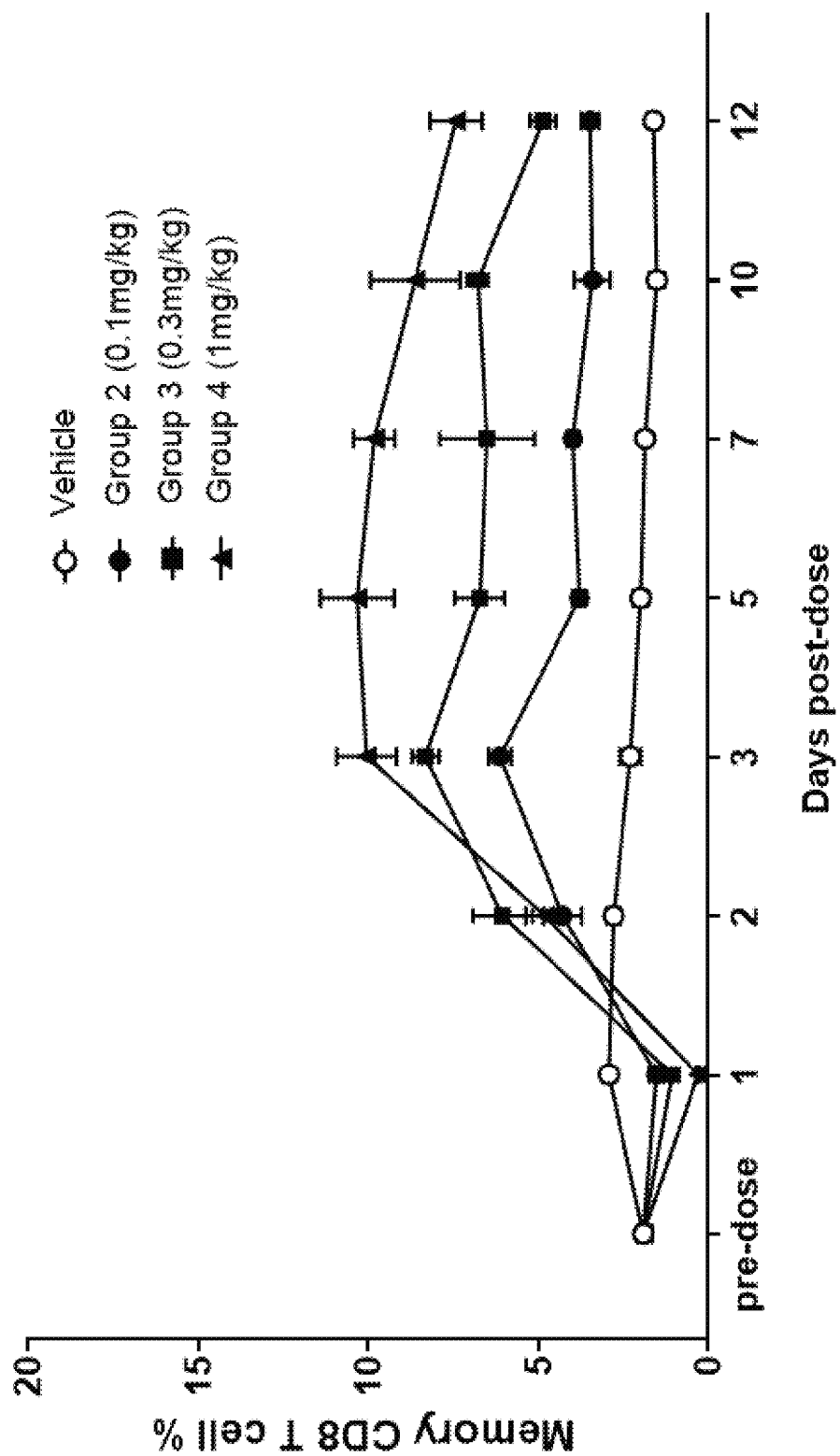
FIG. 10 illustrates % memory CD8 T-cell expansion versus days post-dose in mice after administration of test compound IL-15_N77[AzK_L1_PEG30] according to Example 3 (Group 1 (vehicle)=open circles; Group 4 (1 mg/kg dose)=closed triangles; Group 3 (0.3 mg/kg dose)=closed squares; Group 2 (0.1 mg/kg dose)=closed circles).

The expansion of NK and memory CD8 T-cell populations were measured in each of Groups 1, 2, 3, and 4 and are illustrated in FIGS. 9 and 10, respectively (vehicle=open circles; Group 2 (0.1 mg/kg dose)=closed circles; Group 3 (0.3 mg/kg dose)=closed squares; and Group 4 (1 mg/kg dose)=closed triangles). FIG. 9 illustrates % NK cell expansion versus days post-dose. FIG. 10 illustrates % memory CD8 T-cell expansion versus days post-dose.

Figure 11B:
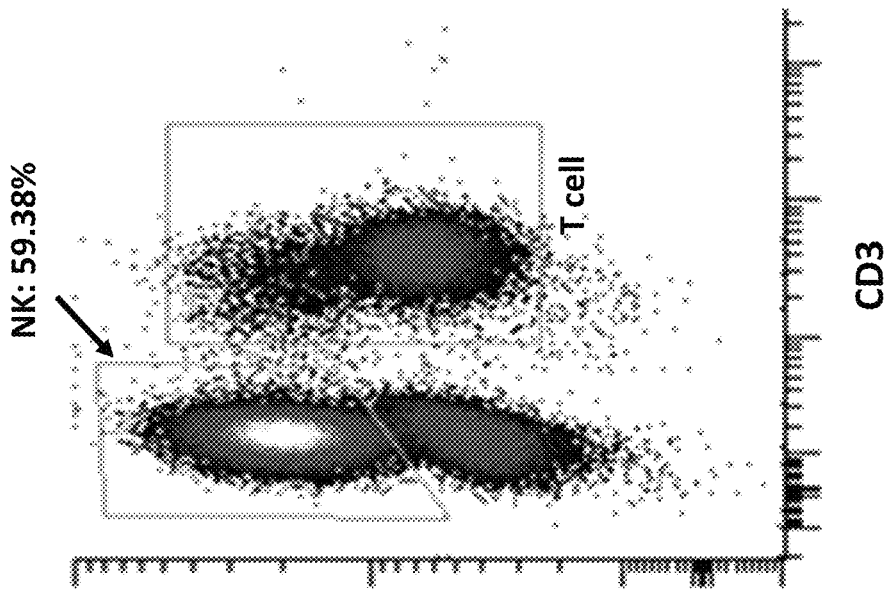
FIGS. 11A-11B show flow cytometry plots showing the NK cell population (gated out of all the peripheral cells) at 5 days post-dose of vehicle (FIG. 11A) and 1 mg/kg of test compound IL-15_N77[AzK_L1_PEG30] in C57BL/6 mice (FIG. 11B) according to Example 3.
Figure 11A:
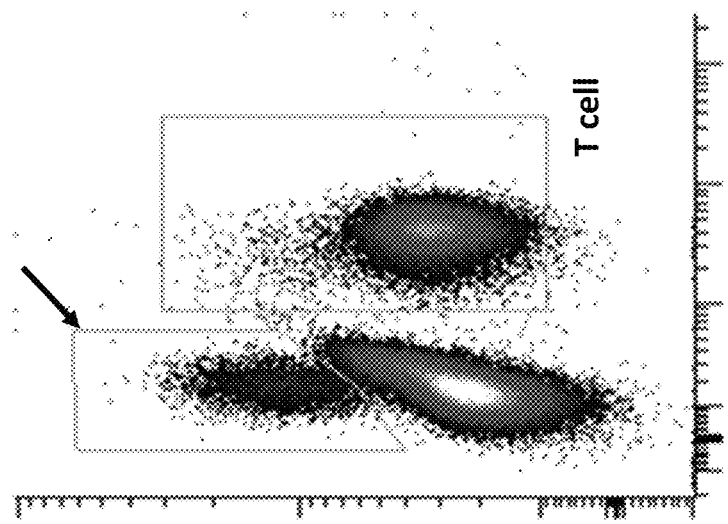

FIGS. 1A-11B show flow cytometry plots showing the NK cell population (gated out of all the peripheral cells) at 5 days post-dose of vehicle (FIG. 11A) and 1 mg/kg of test compound IL-15_N77[AzK_L1_PEG30] in C57BL/6 mice (FIG. 11B). FIGS. 12A-12B show flow cytometry plots showing memory CD8+T population (gated out of CD3+ T cells) at 5 days post-dose of vehicle (FIG. 12A) and 1 mg/kg of test compound IL-15_N77[AzK_L1_PEG30] in C57BL/6 mice (FIG. 12B).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. An interleukin-15 (IL-15) conjugate comprising an IL-15 polypeptide comprising an amino acid sequence that is at least 95% identical to the amino acid sequence of SEQ ID NO: 1 or 3 in which at least one amino acid residue in the IL-15 polypeptide is replaced by the structure of Formula (I):

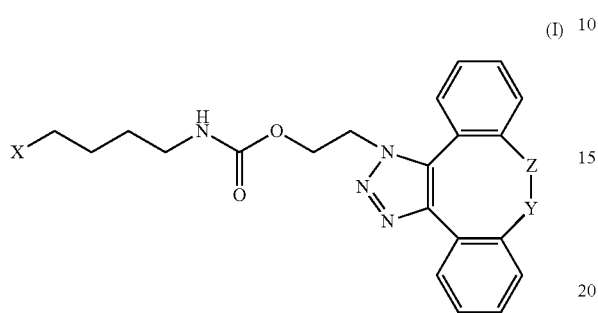
(I)

wherein:
Z is CH$_2$ and Y is

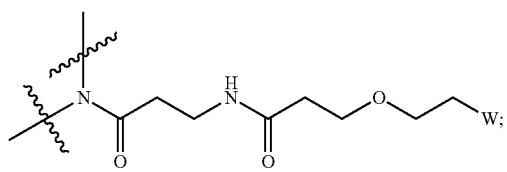

Y is CH$_2$ and Z is

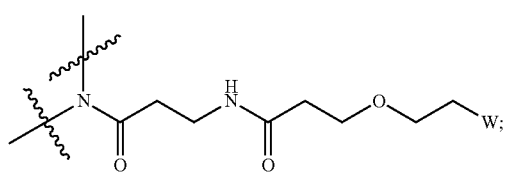

Z is CH$_2$ and Y is

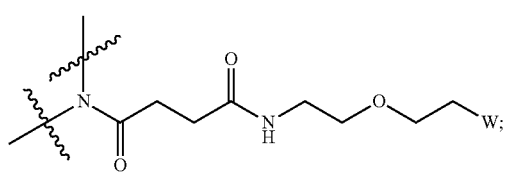

or
Y is CH$_2$ and Z is

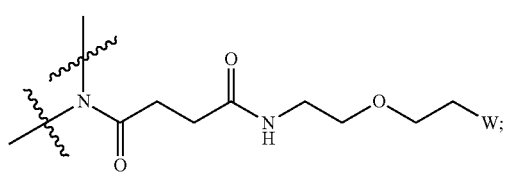

W is a PEG group having a molecular weight selected from about 5 kDa, about 10 kDa, about 15 kDa, about 20 kDa, about 25 kDa, about 30 kDa, about 35 kDa, about 40 kDa, about 45 kDa, about 50 kDa, and about 60 kDa;

X has the structure:

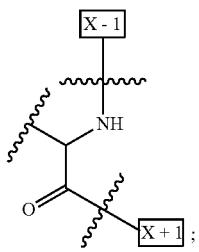

X−1 indicates the point of attachment to the preceding amino acid residue; and

X+1 indicates the point of attachment to the following amino acid residue;

wherein when the IL-15 conjugate comprises an amino acid sequence that is at least 95% identical to the amino acid sequence of SEQ ID NO: 1, the at least one amino acid residue replaced by the structure of Formula (I) is located in the IL-15 polypeptide at a position selected from S18, L25, E46, E53, N77, and S83, wherein the residue positions correspond to positions as set forth in SEQ ID NO: 1; and wherein when the IL-15 conjugate comprises an amino acid sequence that is at least 95% identical to the amino acid sequence of SEQ ID NO: 3, the at least one amino acid residue replaced by the structure of Formula (I) is located in the IL-15 polypeptide at a position selected from S19, L26, E47, E54, N78, and S84, wherein the residue positions correspond to positions as set forth in SEQ ID NO: 3.

2. The IL-15 conjugate of claim 1, wherein Z is CH$_2$ and Y is

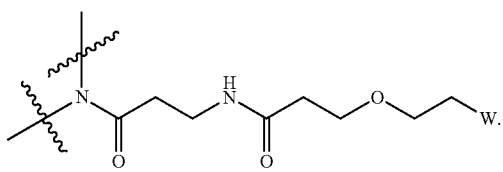

3. The IL-15 conjugate of claim 1, wherein Y is CH$_2$ and Z is

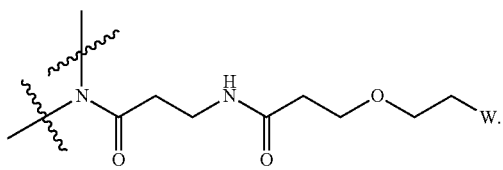

4. The IL-15 conjugate of claim 1, wherein Z is CH$_2$ and Y is

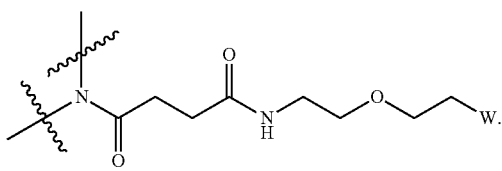

5. The IL-15 conjugate of claim 1, wherein Y is CH₂ and Z is

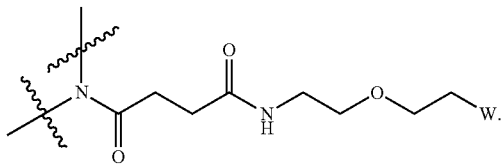

6. The IL-15 conjugate of claim 1, wherein the PEG group has a molecular weight selected from about 5 kDa, about 10 kDa, about 15 kDa, about 20 kDa, about 25 kDa, about 30 kDa, about 35 kDa, about 40 kDa, and about 45 kDa.

7. The IL-15 conjugate of claim 6, wherein the PEG group has a molecular weight of about 30 kDa or about 40 kDa.

8. The IL-15 conjugate of claim 1, wherein the IL-15 conjugate comprises the amino acid sequence of SEQ ID NO: 1 in which the at least one amino acid residue replaced by the structure of Formula (I) is located in the IL-15 polypeptide at a position selected from S18, L25, E46, E53, N77, and S83.

9. The IL-15 conjugate of claim 1, wherein the IL-15 conjugate comprises the amino acid sequence of SEQ ID NO: 3 in which the at least one amino acid residue replaced by the structure of Formula (I) is located in the IL-15 polypeptide at a position selected from S19, L26, E47, E54, N78, and S84.

10. The IL-15 conjugate of claim 1, wherein the structure of Formula (I) has the structure of Formula (II) or Formula (III):

wherein:

W is a PEG group having a molecular weight selected from about 5 kDa, about 10 kDa, about 15 kDa, about 20 kDa, about 25 kDa, about 30 kDa, about 35 kDa, about 40 kDa, about 45 kDa, about 50 kDa, and about 60 kDa;

X has the structure:

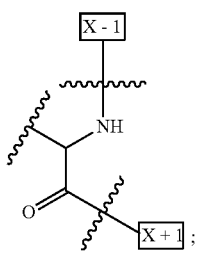

X−1 indicates the point of attachment to the preceding amino acid residue; and

X+1 indicates the point of attachment to the following amino acid residue.

11. The IL-15 conjugate of claim 1, wherein W is a linear PEG group.

12. The IL-15 conjugate of claim 11, wherein W is a methoxy PEG group.

13. The IL-15 conjugate of claim 1, wherein the structure of Formula (I) has the structure of Formula (IV) or Formula (V):

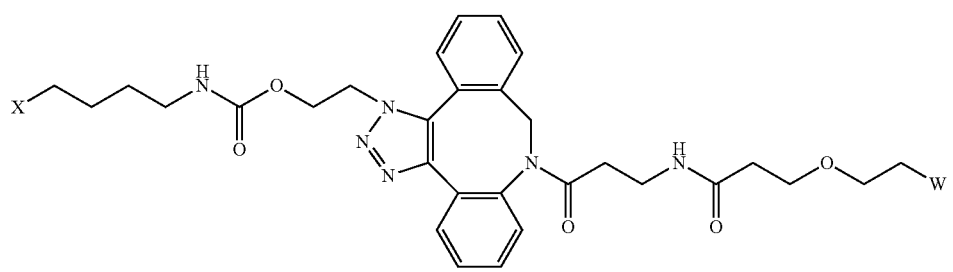

(II)

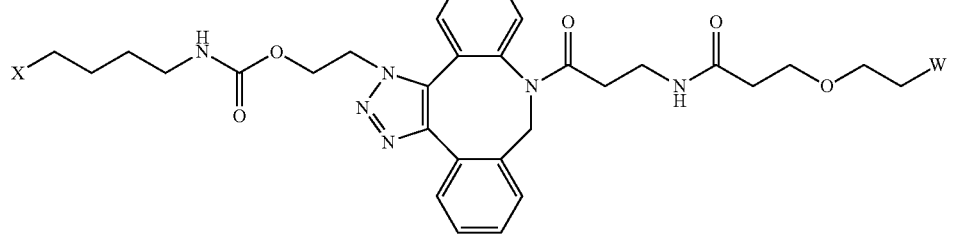

(III)

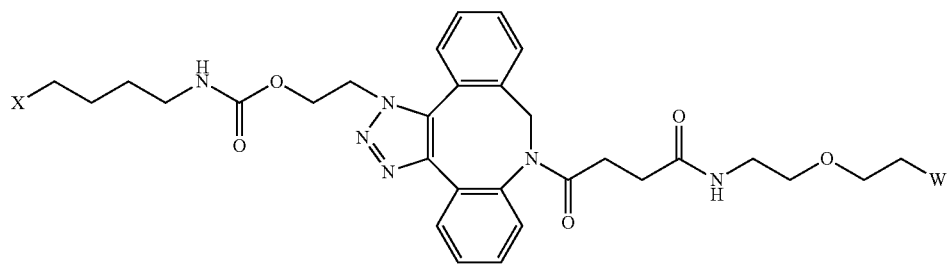

(IV)

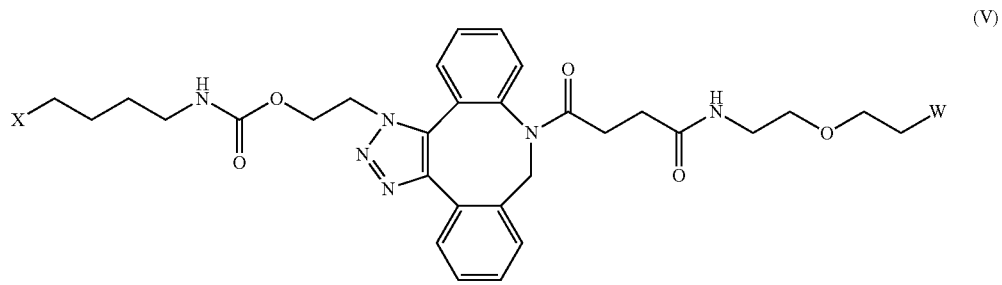

(V)

wherein:
W is a PEG group having a molecular weight selected from about 5 kDa, about 10 kDa, about 15 kDa, about 20 kDa, about 25 kDa, about 30 kDa, about 35 kDa, about 40 kDa, about 45 kDa, about 50 kDa, and about 60 kDa;
X has the structure:

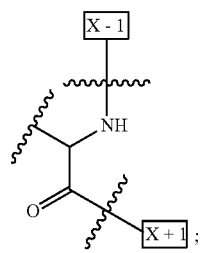

X−1 indicates the point of attachment to the preceding amino acid residue; and
X+1 indicates the point of attachment to the following amino acid residue.

14. The IL-15 conjugate of claim 10, wherein the IL-15 conjugate comprises:
the amino acid sequence of SEQ ID NO: 1 in which the at least one amino acid residue replaced by the structure of Formula (II) or Formula (III) is located in the IL-15 polypeptide at a position selected from S18, L25, E46, E53, N77, and S83; or
the amino acid sequence of SEQ ID NO: 3 in which the at least one amino acid residue replaced by the structure of Formula (II) or Formula (III) is located in the IL-15 polypeptide at a position selected from S19, L26, E47, ,E54, N78, and S84.

15. The IL-15 conjugate of claim 13, wherein the IL-15 conjugate comprises:
the amino acid sequence of SEQ ID NO: 1 in which the at least one amino acid residue replaced by the structure of Formula (IV) or Formula (V) is located in the IL-15 polypeptide at a position selected from S18, L25, E46, E53, N77, and S83; or
the amino acid sequence of SEQ ID NO: 3 in which the at least one amino acid residue replaced by the structure of Formula (IV) or Formula (V) is located in the IL-15 polypeptide at a position selected from S19, L26, E47, E54, N78, and S84.

16. The IL-15 conjugate of claim 1, wherein the structure of Formula (I) has the structure of Formula (VI) or Formula (VII):

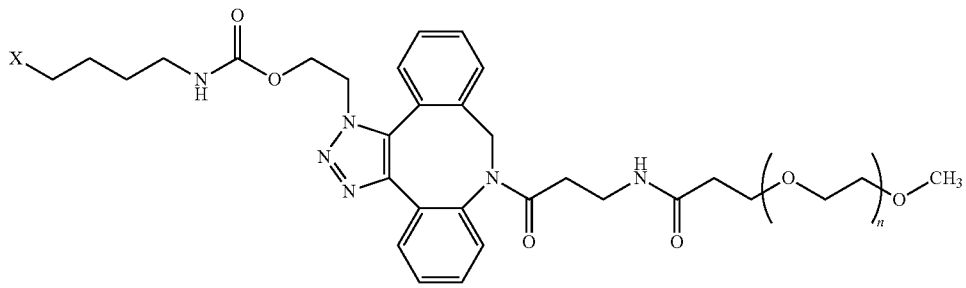

(VI)

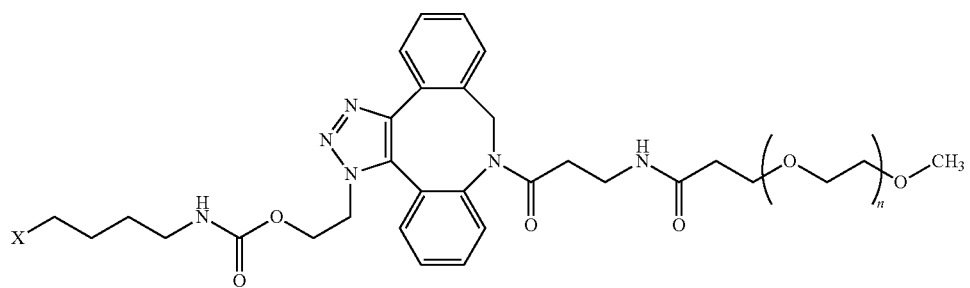

(VII)

wherein:
n is an integer such that the PEG group having the structure of —(OCH$_2$CH$_2$)$_n$—OCH$_3$ has a molecular weight selected from about 5 kDa, about 10 kDa, about 15 kDa, about 20 kDa, about 25 kDa, about 30 kDa, about 35 kDa, about 40 kDa, about 45 kDa, about 50 kDa, and about 60 kDa;

X has the structure:

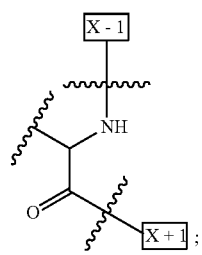

X−1 indicates the point of attachment to the preceding amino acid residue; and

X+1 indicates the point of attachment to the following amino acid residue.

17. The IL-15 conjugate of claim 16, wherein the IL-15 conjugate comprises:
the amino acid sequence of SEQ ID NO: 1 in which the at least one amino acid residue replaced by the structure of Formula (VI) or Formula (VII) is located in the IL-15 polypeptide at a position selected from S18, L25, E46, E53, N77, and S83; or
the amino acid sequence of SEQ ID NO: 3 in which the at least one amino acid residue replaced by the structure of Formula (VI) or Formula (VII) is located in the IL-15 polypeptide at a position selected from S19, L26, E47, E54, N78, and S84.

18. The IL-15 conjugate of claim 1, wherein the structure of Formula (I) has the structure of Formula (VIII) or Formula (IX):

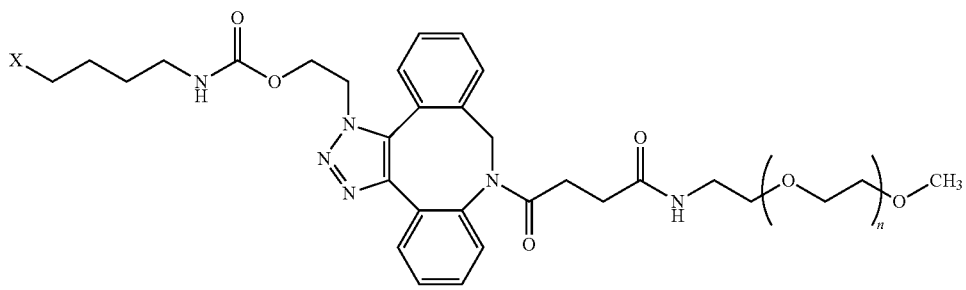

(VIII)

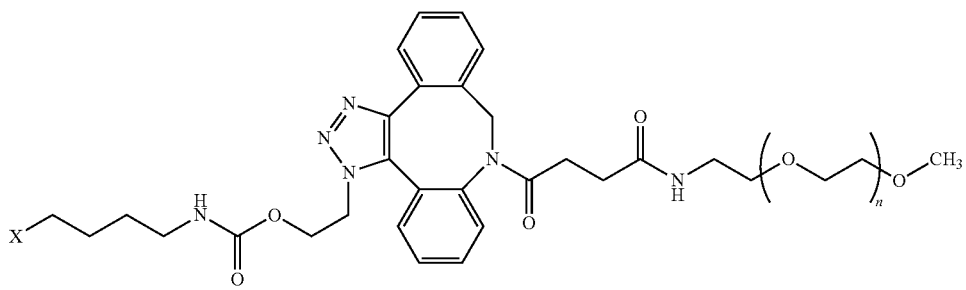

(IX)

wherein:
n is an integer such that the PEG group having the structure of —(OCH$_2$CH$_2$)$_n$—OCH$_3$ has a molecular weight selected from about 5 kDa, about 10 kDa, about 15 kDa, about 20 kDa, about 25 kDa, about 30 kDa, about 35 kDa, about 40 kDa, about 45 kDa, about 50 kDa, and about 60 kDa;

21. A pharmaceutical composition comprising an effective amount of the IL-15 conjugate of claim 1.

22. The pharmaceutical composition of claim 21, wherein the pharmaceutical composition comprises a mixture of IL-15 conjugates, wherein the mixture comprises (i) IL-15 conjugates in which the structure of Formula (I) has the structure of Formula (II) and (ii) IL-15 conjugates in which the structure of Formula (I) has the structure of Formula (III):

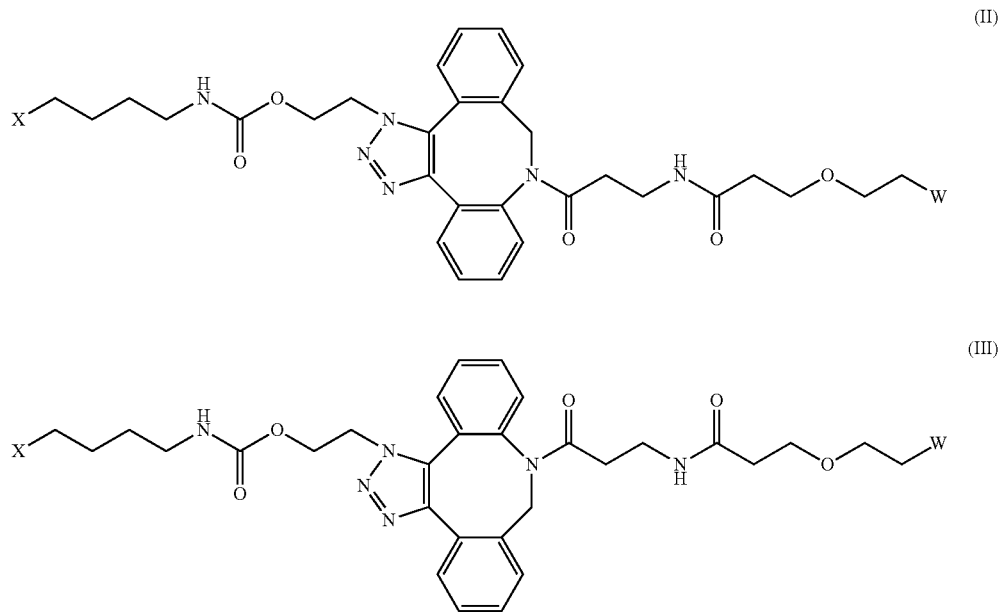

X has the structure:

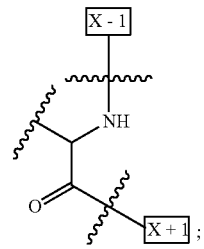

X−1 indicates the point of attachment to the preceding amino acid residue; and
X+1 indicates the point of attachment to the following amino acid residue.

19. The IL-15 conjugate of claim 1, which is a pharmaceutically acceptable salt, solvate, or hydrate.

20. The IL-15 conjugate of claim 18, wherein the IL-15 conjugate comprises:
the amino acid sequence of SEQ ID NO: 1 in which the at least one amino acid residue replaced by the structure of Formula (VIII) or Formula (IX) is located in the IL-15 polypeptide at a position selected from S18, L25, E46, E53, N77, and S83; or
the amino acid sequence of SEQ ID NO: 3 in which the at least one amino acid residue replaced by the structure of Formula (VI) or Formula (VII) is located in the IL-15 polypeptide at a position selected from S19, L26, E47, E54, N78, and S84.

wherein:
W is a PEG group having a molecular weight selected from about 5 kDa, about 10 kDa, about 15 kDa, about 20 kDa, about 25 kDa, about 30 kDa, about 35 kDa, about 40 kDa, about 45 kDa, about 50 kDa, and about 60 kDa;

X has the structure:

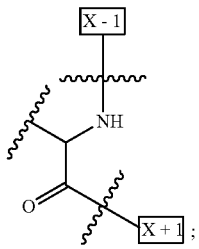

X−1 indicates the point of attachment to the preceding amino acid residue; and
X+1 indicates the point of attachment to the following amino acid residue.

23. The pharmaceutical composition of claim 21, wherein the pharmaceutical composition comprises a mixture of IL-15 conjugates, wherein the mixture comprises (i) IL-15 conjugates in which the structure of Formula (I) has the structure of Formula (IV) and (ii) IL-15 conjugates in which the structure of Formula (I) has the structure of Formula (V):

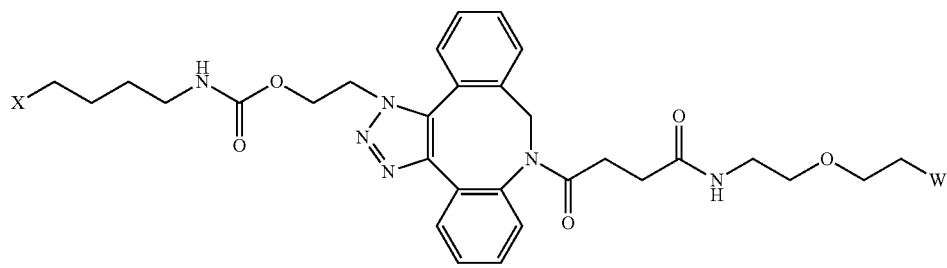

(IV)

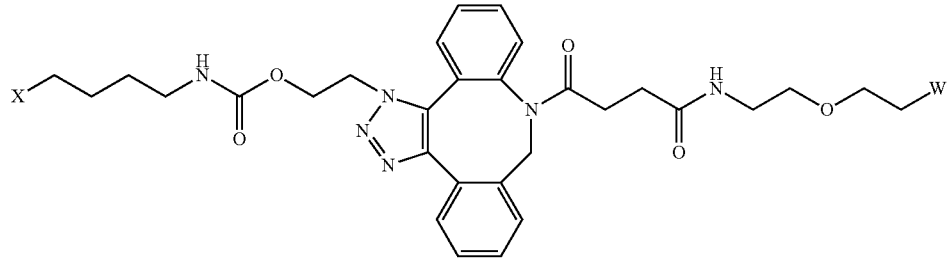

(V)

wherein:
W is a PEG group having a molecular weight selected from about 5 kDa, about 10 kDa, about 15 kDa, about 20 kDa, about 25 kDa, about 30 kDa, about 35 kDa, about 40 kDa, about 45 kDa, about 50 kDa, and about 60 kDa;

X has the structure:

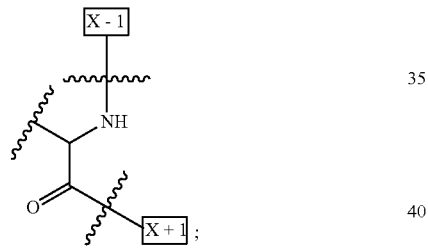

X−1 indicates the point of attachment to the preceding amino acid residue; and
X+1 indicates the point of attachment to the following amino acid residue.

24. The pharmaceutical composition of claim 21, wherein the pharmaceutical composition comprises a mixture of IL-15 conjugates, wherein the mixture comprises (i) IL-15 conjugates in which the structure of Formula (I) has the structure of Formula (VI) and (ii) IL-15 conjugates in which the structure of Formula (I) has the structure of Formula (VII):

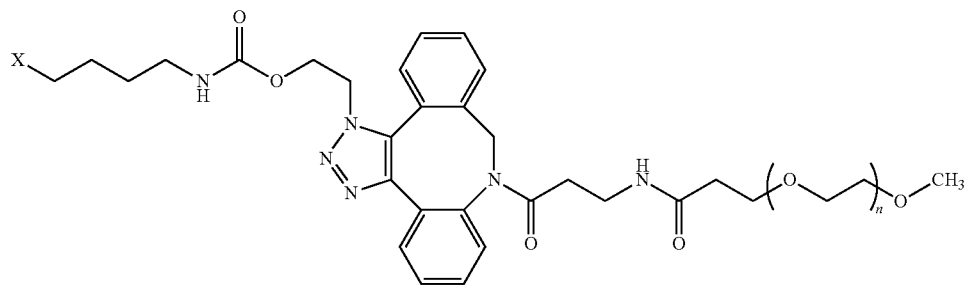

(VI)

-continued (VII)

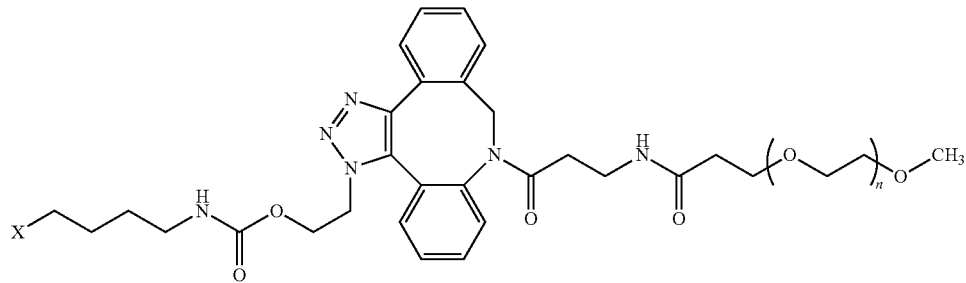

wherein:

n is an integer such that the PEG group having the structure of —(OCH$_2$CH$_2$)$_n$—OCH$_3$ has a molecular weight selected from about 5 kDa, about 10 kDa, about 15 kDa, about 20 kDa, about 25 kDa, about 30 kDa, about 35 kDa, about 40 kDa, about 45 kDa, about 50 kDa, and about 60 kDa;

X has the structure:

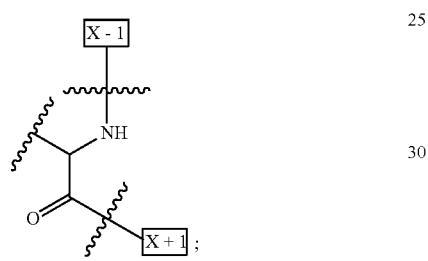

X−1 indicates the point of attachment to the preceding amino acid residue; and

X+1 indicates the point of attachment to the following amino acid residue.

25. The pharmaceutical composition of claim 21, wherein the pharmaceutical composition comprises a mixture of IL-15 conjugates, wherein the mixture comprises (i) IL-15 conjugates in which the structure of Formula (I) has the structure of Formula (VIII) and (ii) IL-15 conjugates in which the structure of Formula (I) has the structure of Formula (IX):

(VIII)

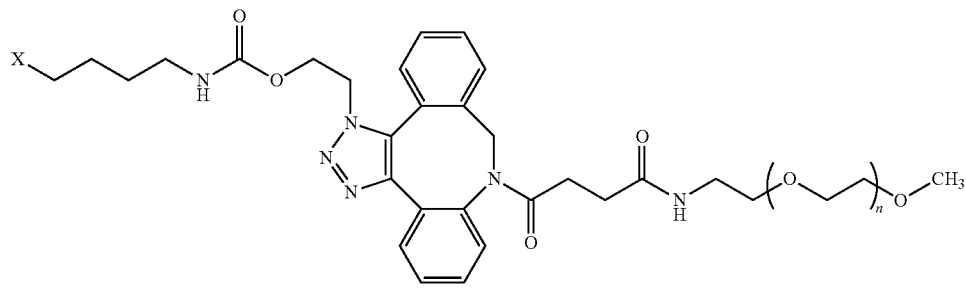

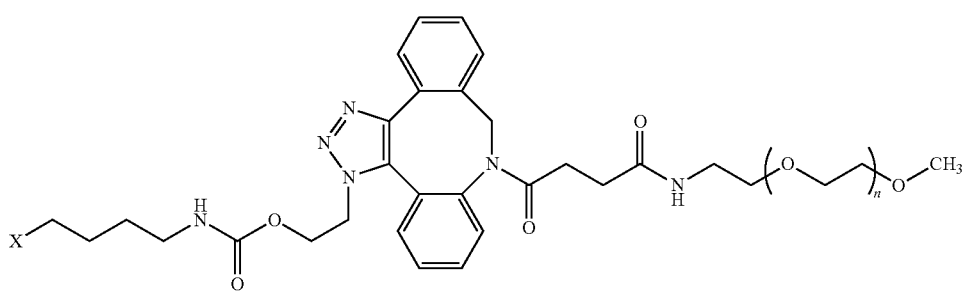

(IX)

wherein:
n is an integer such that the PEG group having the structure of —(OCH$_2$CH$_2$)$_n$—OCH$_3$ has a molecular weight selected from about 5 kDa, about 10 kDa, about 15 kDa, about 20 kDa, about 25 kDa, about 30 kDa, about 35 kDa, about 40 kDa, about 45 kDa, about 50 kDa, and about 60 kDa;
X has the structure:

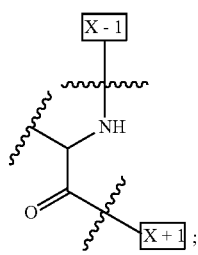

X−1 indicates the point of attachment to the preceding amino acid residue; and
X+1 indicates the point of attachment to the following amino acid residue.

26. The IL-15 conjugate of claim 1, wherein the IL-15 polypeptide comprises:
an amino acid sequence that is at least 98% identical to the amino acid sequence of SEQ ID NO: 1 in which the at least one amino acid residue replaced by the structure of Formula (I) is located in the IL-15 polypeptide at a position selected from S18, L25, E46, E53, N77, and S83; or
an amino acid sequence that is at least 98% identical to the amino acid sequence of SEQ ID NO: 3 in which the at least one amino acid residue replaced by the structure of Formula (I) is located in the IL-15 polypeptide at a position selected from S19, L26, E47, E54, N78, and S84.

27. The IL-15 conjugate of claim 10, wherein the IL-15 polypeptide comprises:
an amino acid sequence that is at least 98% identical to the amino acid sequence of SEQ ID NO: 1 in which the at least one amino acid residue replaced by the structure of Formula (II) or Formula (III) is located in the IL-15 polypeptide at a position selected from S18, L25, E46, E53, N77, and S83; or
an amino acid sequence that is at least 98% identical to the amino acid sequence of SEQ ID NO: 3 in which the at least one amino acid residue replaced by the structure of Formula (II) or Formula (III) is located in the IL-15 polypeptide at a position selected from S19, L26, E47, E54, N78, and S84.

28. The IL-15 conjugate of claim 13, wherein the IL-15 polypeptide comprises:
an amino acid sequence that is at least 98% identical to the amino acid sequence of SEQ ID NO: 1 in which the at least one amino acid residue replaced by the structure of Formula (IV) or Formula (V) is located in the IL-15 polypeptide at a position selected from S18, L25, E46, E53, N77, and S83; or
an amino acid sequence that is at least 98% identical to the amino acid sequence of SEQ ID NO: 3 in which the at least one amino acid residue replaced by the structure of Formula (IV) or Formula (V) is located in the IL-15 polypeptide at a position selected from S19, L26, E47, E54, N78, and S84.

29. The IL-15 conjugate of claim 16, wherein the IL-15 polypeptide comprises:
an amino acid sequence that is at least 98% identical to the amino acid sequence of SEQ ID NO: 1 in which the at least one amino acid residue replaced by the structure of Formula (VI) or Formula (VII) is located in the IL-15 polypeptide at a position selected from S18, L25, E46, E53, N77, and S83; or
an amino acid sequence that is at least 98% identical to the amino acid sequence of SEQ ID NO: 3 in which the at least one amino acid residue replaced by the structure of Formula (VI) or Formula (VII) is located in the IL-15 polypeptide at a position selected from S19, L26, E47, E54, N78, and S84.

30. The IL-15 conjugate of claim 18, wherein the IL-15 polypeptide comprises:
an amino acid sequence that is at least 98% identical to the amino acid sequence of SEQ ID NO: 1 in which the at least one amino acid residue replaced by the structure of Formula (VIII) or Formula (IX) is located in the IL-15 polypeptide at a position selected from S18, L25, E46, E53, N77, and S83; or
an amino acid sequence that is at least 98% identical to the amino acid sequence of SEQ ID NO: 3 in which the at least one amino acid residue replaced by the structure of Formula (VIII) or Formula (IX) is located in the IL-15 polypeptide at a position selected from S19, L26, E47, E54, N78, and S84.

31. The IL-15 conjugate of claim 17, wherein n in Formula (VI) or Formula (VII) is an integer such that the PEG group having the structure of —(OCH$_2$CH$_2$)$_n$—OCH$_3$ has a molecular weight of about 30 kDa or about 40 kDa.

32. The IL-15 conjugate of claim 20, wherein n in Formula (VIII) or Formula (IX) is an integer such that the PEG group having the structure of —(OCH$_2$CH$_2$)$_n$—OCH$_3$ has a molecular weight of about 30 kDa or about 40 kDa.

33. An IL-15 conjugate comprising the amino acid sequence of any one of SEQ ID NOs: 4-9 and 52-57, wherein X is N6-((2-azidoethoxy)-carbonyl)-L-lysine (AzK) covalently attached via a conjugating moiety comprising a dibenzocyclooctyne group to a PEG group having a molecular weight of about 30 kDa or about 40 kDa.

\* \* \* \* \*